US009440957B2

(12) United States Patent
Lelais et al.

(10) Patent No.: US 9,440,957 B2
(45) Date of Patent: Sep. 13, 2016

(54) COMPOUNDS AND COMPOSITIONS FOR MODULATING EGFR ACTIVITY

(71) Applicants: Gerald Lelais, San Diego, CA (US); Robert Epple, Solana Beach, CA (US); Thomas H. Marsilje, III, San Diego, CA (US); Pierre-Yves Michellys, San Marcos, CA (US); Matthew McNeill, San Clemente, CA (US); Yun Long, San Diego, CA (US); Wenshuo Lu, San Diego, CA (US); Bei Chen, San Diego, CA (US); Badry Bursulaya, Escondido, CA (US); Songchun Jiang, San Diego, CA (US)

(72) Inventors: Gerald Lelais, San Diego, CA (US); Robert Epple, Solana Beach, CA (US); Thomas H. Marsilje, III, San Diego, CA (US); Pierre-Yves Michellys, San Marcos, CA (US); Matthew McNeill, San Clemente, CA (US); Yun Long, San Diego, CA (US); Wenshuo Lu, San Diego, CA (US); Bei Chen, San Diego, CA (US); Badry Bursulaya, Escondido, CA (US); Songchun Jiang, San Diego, CA (US)

(73) Assignee: Novartis AG, Basel (CH)

( * ) Notice: Subject to any disclaimer, the term of this patent is extended or adjusted under 35 U.S.C. 154(b) by 11 days.

(21) Appl. No.: 14/405,773

(22) PCT Filed: Jun. 5, 2013

(86) PCT No.: PCT/US2013/044247
§ 371 (c)(1),
(2) Date: Dec. 4, 2014

(87) PCT Pub. No.: WO2013/184757
PCT Pub. Date: Dec. 12, 2013

(65) Prior Publication Data
US 2015/0197505 A1    Jul. 16, 2015

Related U.S. Application Data

(60) Provisional application No. 61/770,752, filed on Feb. 28, 2013.

(30) Foreign Application Priority Data

Jun. 6, 2012  (IN) .............................. 1741/DEL/12

(51) Int. Cl.
| A61K 31/55 | (2006.01) |
| C07D 401/14 | (2006.01) |
| C07D 403/04 | (2006.01) |
| C07D 403/14 | (2006.01) |
| C07D 405/14 | (2006.01) |
| C07D 409/14 | (2006.01) |
| C07D 411/14 | (2006.01) |
| C07D 413/14 | (2006.01) |
| C07D 417/14 | (2006.01) |
| A61K 31/4184 | (2006.01) |
| A61K 31/454 | (2006.01) |
| A61K 31/4545 | (2006.01) |
| A61K 31/551 | (2006.01) |
| A61K 31/553 | (2006.01) |
| A61K 45/06 | (2006.01) |
| C07D 401/04 | (2006.01) |
| C07D 413/04 | (2006.01) |
| C07D 471/04 | (2006.01) |
| C07D 513/04 | (2006.01) |

(52) U.S. Cl.
CPC ......... *C07D 401/14* (2013.01); *A61K 31/4184* (2013.01); *A61K 31/454* (2013.01); *A61K 31/4545* (2013.01); *A61K 31/55* (2013.01); *A61K 31/551* (2013.01); *A61K 31/553* (2013.01); *A61K 45/06* (2013.01); *C07D 401/04* (2013.01); *C07D 403/04* (2013.01); *C07D 403/14* (2013.01); *C07D 405/14* (2013.01); *C07D 413/04* (2013.01); *C07D 413/14* (2013.01); *C07D 417/14* (2013.01); *C07D 471/04* (2013.01); *C07D 513/04* (2013.01)

(58) Field of Classification Search
CPC .. A61K 31/55; C07D 401/14; C07D 403/04; C07D 403/14; C07D 405/14; C07D 409/14; C07D 411/14; C07D 413/14; C07D 417/14
USPC ...................................... 514/217.09; 540/603
See application file for complete search history.

(56) References Cited

U.S. PATENT DOCUMENTS 6,602,667 B1    8/2003  Walker et al.

FOREIGN PATENT DOCUMENTS

| EP | 1069124 B1 | 5/2004 |
| WO | WO00/08013 A2 | 2/2000 |
| WO | WO03/030902 A1 | 4/2003 |
| WO | WO03041708 A1 | 5/2003 |
| WO | WO2004014905 A1 | 2/2004 |
| WO | 2004078163 A3 | 9/2004 |
| WO | WO2007/022305 A3 | 2/2007 |
| WO | 2010030857 A2 | 3/2010 |
| WO | WO2011/071716 A3 | 6/2011 |
| WO | 2011091716 A1 | 8/2011 |
| WO | WO2011/099832 A1 | 8/2011 |
| WO | WO2012018668 A1 | 2/2012 |
| WO | WO2013/074518 A2 | 5/2013 |
| WO | WO2014/036016 A1 | 3/2014 |

*Primary Examiner* — Brenda Coleman
(74) *Attorney, Agent, or Firm* — Emily T. Wu; Genomics Institute of the Novartis Research Foundation

(57) ABSTRACT

The invention provides compounds and pharmaceutical compositions thereof, which are useful for modulating EGFR activity, as well as methods for using such compounds to treat, ameliorate or prevent a condition associated with abnormal or deregulated EGFR activity.

21 Claims, No Drawings

COMPOUNDS AND COMPOSITIONS FOR MODULATING EGFR ACTIVITY

CROSS-REFERENCE TO RELATED APPLICATIONS

This application is a 371 U.S. national phase application of international application number PCT/US2013/044247 filed Jun. 5, 2013, which claims the benefit of Indian provisional patent application serial number 1741/DEL/ 2012 filed Jun. 6, 2012; and of U.S. provisional application Ser. No. 61/770,752, filed Feb. 28, 2013; each of which is incorporated herein by reference in its entirety.

FIELD OF THE INVENTION

The invention relates to compositions and methods for modulating the activity of the epidermal growth factor receptor (EGFR, Erb-B1).

BACKGROUND OF THE INVENTION

The epidermal growth factor receptor (EGFR, Erb-B1) belongs to a family of proteins involved in the proliferation of normal and malignant cells. Overexpression of EGFR is found in over 70 percent of human cancers, including without limitation non-small cell lung carcinomas (NSCLC), breast cancers, gliomas, squamous cell carcinoma of the head and neck, and prostate cancer. The identification of EGFR as an oncogene has led to the development of anti-EGFR targeted molecules, such as gefitinib and erlotinib.

Despite the initial clinical benefits of gefitinib and erlotinib in NSCLC patients harboring EGFR mutations, many patients develop resistance. A secondary EGFR mutation, T790M, can render gefitinib and erlotinib ineffective inhibitors of EGFR kinase activity. Another major limitation of current EGFR inhibitors is the development of toxicity in normal tissues. Because ATP affinity of EGFR T790M is similar to wild type EGFR, the concentration of an irreversible EGFR inhibitor required to inhibit EGFR T790M may also effectively inhibit wild type EGFR. The class-specific toxicities of current EGFR kinase inhibitors, e.g., skin rash and diarrhea, are a result of inhibiting wild type EGFR in non-cancer tissues. These toxicities preclude dose escalation of current agents to plasma levels that can effectively inhibit EGFR T790M.

Accordingly, there continues to exist a need to develop novel EGFR inhibitors that is capable of giving an improved effect on EGFR tyrosine kinase mutants without the adverse side effects.

SUMMARY OF THE INVENTION

The invention provides compositions and methods for modulating the activity of the epidermal growth factor receptor (EGFR). In one aspect, the invention provides compounds which act as inhibitors of EGFR.

In a first embodiment, provided herein is a compound of Formula (1), a tautomer thereof, or a pharmaceutically acceptable salt thereof:

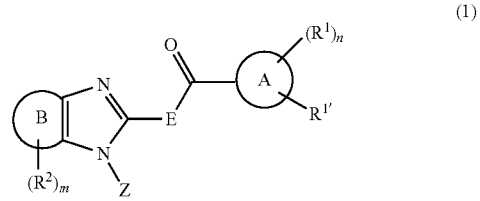

wherein Ring A is a 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Ring B is phenyl; a 5-6 membered heteroaryl comprising 1-3 heteroatoms selected from N, O and S; or a 5-6 membered heterocyclyl comprising 1-2 heteroatoms selected from N, O and S, and optionally substituted by oxo;

E is NH or $CH_2$;

$R^1$, $R^{1'}$ and $R^2$ are independently hydrogen; halo; cyano; $C_{1-6}$ alkyl; $C_{1-6}$ haloalkyl; 5-6 membered heteroaryl comprising 1-4 heteroatoms selected from N, O and S; phenyl, 5-6 membered heterocyclyl comprising 1-2 heteroatoms selected from N, O, S and P, and optionally substituted by oxo; $—X^1—C(O)OR^3$; $—X^1—O—C(O)R^3$; $—X^1—C(O)R^3$; $—X^1—C(O)NR^4R^5$; $—X^1—C(O)NR^4—X^3—C(O)OR^3$; $—X^1—C(O)NR^4—X^3—S(O)_{0-2}R^6$; $—X^1—NR^4R^5$; $—X^1NR^4—X^2—C(O)R^3$; $—X^1—NR^4—X^2—C(O)OR^3$; $—X^1—NR^4—X^2—C(O)NR^4R^5$; $—X^1—NR^4—X^3—S(O)_{0-2}R^6$; $—X^1—NR^4S(O)_2R^6$; $—X^1—OS(O)_2R^6$; $—X^1—OR^3$; $—X^1—O—X^4—OR^3$; $—X^1—O—X^4—S(O)_{0-2}R^6$; $—X^1—O—X^4—NR^4R^5$; $—X^1—S(O)_{0-2}R^6$; $—X^1—S(O)_{0-2}—X^3—NR^4R^5$; $—X^1—C(O)NR^4—X^3—P(O)R^{6a}R^{6b}$; $—X^1—NR^4—X^1—P(O)R^{6a}R^{6b}$; $—X^1—O—X^1—P(O)R^{6a}R^{6b}$; $—X^1—P(O)R^{6a}—X^1—NR^4R^5$; $—X^1—P(O)R^{6a}R^{6b}$ or $—X^1—S(O)_2NR^4R^5$; wherein each phenyl, heteroaryl, or heterocyclyl in $R^1$ or $R^2$ is unsubstituted or substituted by 1-3 groups selected from OH, halo, $C_{1-6}$ alkyl, $C_{1-6}$ haloalkyl and $C_{1-6}$ haloalkoxy;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$;

$R^6$ is $C_{1-6}$ alkyl or $C_{1-6}$ haloalkyl;

$R^{6a}$ and $R^{6b}$ are independently hydroxy, $C_{1-6}$ alkyl, $C_{1-6}$ haloalkyl, $C_{1-6}$ alkoxy, $C_{1-6}$ haloalkoxy, 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Z is

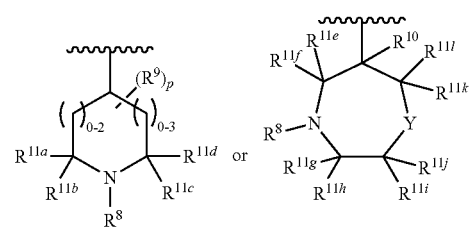

wherein Y is O or $NR^{19}$;

$R^8$ is
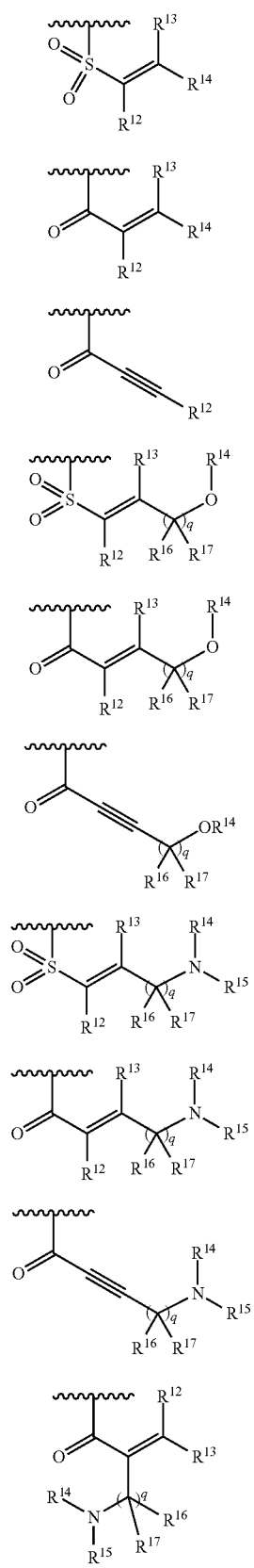
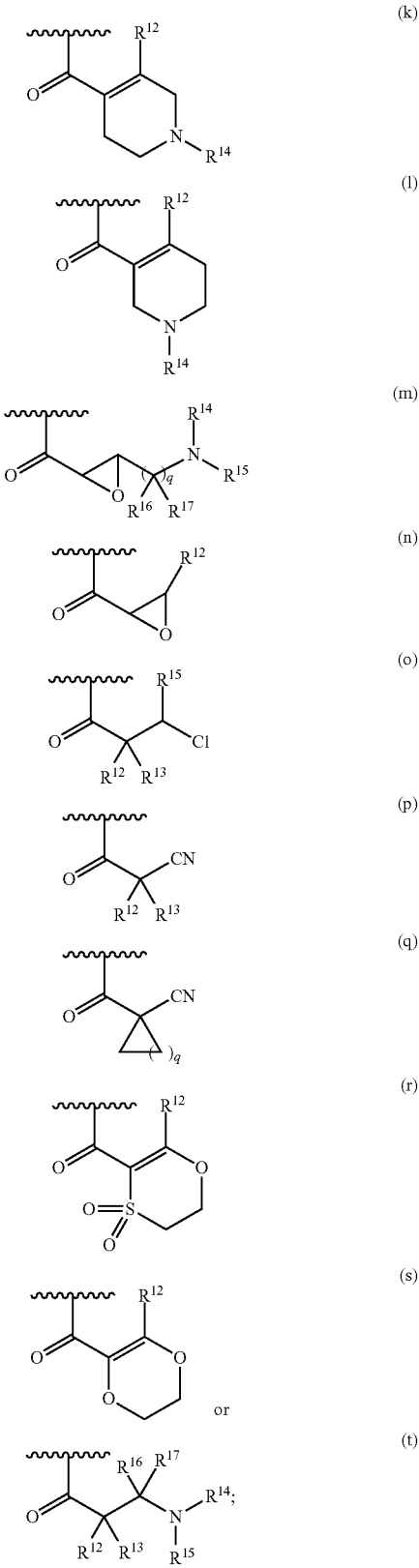
$R^9$ and $R^{10}$ are independently hydrogen, halo, $C_{1-6}$ alkyl, $C_{1-6}$ haloalkyl, OH, cyano, $C_{1-6}$ alkoxy, $C_{1-6}$ haloalkoxy;

$R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$ and $R^{11l}$ are independently hydrogen, $C_{1-6}$ alkyl or $C_{1-6}$ haloalkyl;

$R^{12}$ and $R^{13}$ are independently hydrogen, halo, cyano, $C_{1-6}$ alkyl or $C_{1-6}$ haloalkyl;

$R^{14}$ and $R^{15}$ are independently hydrogen, $C_{1-6}$ alkyl, -$L^1$-$R^{23}$, —$(CR^aR^b)_{2-3}$—$R^c$ or -$L^2$-$R^d$; or $R^{14}$ and $R^{15}$ together with N in $NR^{14}R^{15}$ may form a 4-7 membered ring containing 1-2 heteroatoms selected from N, O, S and P, and optionally substituted with 1-4 $R^{18}$ groups;

$R^{16}$ and $R^{17}$ are independently hydrogen or $C_{1-6}$ alkyl; or $R^{16}$ and $R^{17}$ together with the carbon to which they are attached may form a $C_{3-6}$ cycloalkyl;

$X^1$ and $X^2$ are independently a bond or $C_{1-6}$ alkyl;

$X^3$ is $C_{1-6}$ alkyl;

$X^4$ is $C_{2-6}$ alkyl;

$R^{19}$ hydrogen, $C_{1-6}$ alkyl, $COR^{20}$, $COOR^{20}$, $CONR^{20}R^{21}$ or $S(O)_2R^{20}$;

$R^{20}$ is $C_{1-6}$ alkyl, $C_{1-6}$ haloalkyl or cycloalkyl;

$R^{21}$ is hydrogen or $C_{1-6}$ alkyl; or $R^{20}$ and $R^{21}$ together with the N in $NR^{20}R^{21}$ may form a 4-7 membered ring containing 1-2 heteroatoms selected from N, O, S, P and optionally substituted with 1-4 $R^{22}$ groups;

$R^7$, $R^{18}$ and $R^{22}$ are independently oxo, halo, hydroxy, $C_{1-6}$ alkyl, $C_{1-6}$ haloalkyl, $C_{1-6}$ alkoxy or $C_{1-6}$ haloalkoxy;

$R^{23}$ is independently $C_{3-7}$ cycloalkyl, or a 4-10 membered heterocyclyl comprising 1-3 heteroatoms selected from N, O and S, and is optionally substituted with oxo; and $R^{23}$ is unsubstituted or substituted with $C_{1-6}$ alkyl, $C_{1-6}$ haloalkyl, -$L^3$-$R^e$ or -$L^4$-$R^f$;

$R^c$ and $R^e$ are independently halo, cyano, hydroxy, —$OR^{24}$, —$NRR^{25}$, —NR—$CO_2R^{24}$, —NR—$SO_2$—$R^{26}$, —NR—$COR^{26}$, —NR—$C(O)$—$NRR^{25}$, —OC(O)—$NRR^{25}$, or $C_{1-6}$ alkyl substituted with halo, $C_{1-6}$ alkoxy, hydroxy or cyano;

$R^d$ and $R^f$ are independently —$SO_2NRR^{25}$, —$CONRR^{25}$, —$C(O)OR^{24}$, —$SO_2R^{26}$ or $C(O)R^{26}$;

$R^{24}$ is $C_{1-6}$ alkyl, $C_{1-6}$haloalkyl, -$L^2$-$R^{23a}$ or —$(CR^aR^b)_{2-3}$—$N(R^aR^b)_2$;

$R^{25}$ is hydrogen, $C_{1-6}$ alkyl, $C_{1-6}$haloalkyl, -$L^2$-$R^{23b}$ or —$(CR_2)_{2-3}$—$N(R^aR^b)_2$;

$R^{26}$ is $C_{1-6}$ alkyl, $C_{1-6}$haloalkyl, -$L^2$-$R^{23c}$ or —$(CR^aR^b)_{1-3}$—$N(R^aR^b)_2$;

$R^{23a}$, $R^{23b}$ and $R^{23c}$ are independently selected from $R^{23}$;

R, $R^a$ and $R^b$ are independently hydrogen or $C_{1-6}$ alkyl;

$L^1$, $L^2$, $L^3$ and $L^4$ are independently a bond or —$(CR^aR^b)_{1-3}$; and n and m are independently 1-3; and p and q are 1-4;

or a pharmaceutically acceptable salt thereof.

In a second embodiment, provided herein is a compound of Formula (2) or a pharmaceutically acceptable salt thereof:

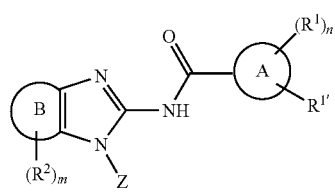
(2)

wherein Ring A is a 6-10 membered monocyclic or bicyclic aryl; a 5-10 membered heteroaryl comprising 1-4 heteroatoms selected from N, O and S; or a 5-6 membered heterocyclyl comprising 1-2 heteroatoms selected from N, O and S, and optionally substituted with oxo;

$R^1$ and $R^{1'}$ are independently hydrogen; halo; cyano; $C_{1-6}$ alkyl; $C_{1-6}$ haloalkyl; —$X^1$—$NR^4R^5$; —$X^1$—$OR^3$; —$X^1$—$S(O)_{0-2}R^6$; —$X^1$—$P(O)R^{6a}R^{6b}$; phenyl unsubstituted or substituted by $C_{1-6}$ alkyl; or a 5-6 membered heteroaryl comprising 1-4 heteroatoms selected from N, O and S;

$R^2$ is selected from hydrogen, halo; cyano; $C_{1-6}$ alkyl; $C_{1-6}$ haloalkyl; —$X^1$—$C(O)OR^3$; —$X^1$—$C(O)R^3$; —$X^1$—$C(O)NR^4R^5$; —$X^1$—$C(O)NR^4$—$X^3$—$C(O)OR^3$; —$X^1$—$C(O)NR^4$—$X^3$—$S(O)_{0-2}R^6$; —$X^1$—$NR^4R^5$; —$X^1NR^4$—$X^2$—$C(O)R^3$; —$X^1$—$NR^4$—$X^3$—$S(O)_{0-2}R^6$; —$X^1$—$OR^3$; —$X^1$—O—$X^4$—$OR^3$; —$X^1$—$S(O)_{0-2}R^6$; —$X^1$—O—$X^4$—$NR^4R^5$; or a 5-6 membered heteroaryl comprising 1-4 heteroatoms selected from N, O and S and is unsubstituted or substituted by $C_{1-6}$ alkyl;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$ groups;

$R^6$, $R^{6a}$ and $R^{6b}$ are $C_{1-6}$ alkyl;

Z is

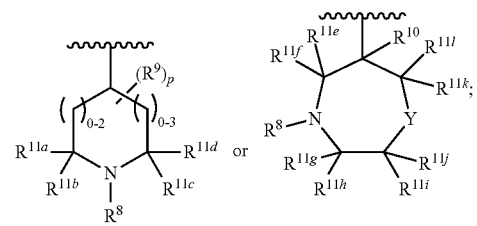

provided Z is a 4-7 membered heterocyclic ring when Z is

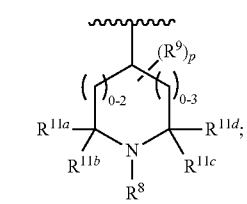

Y is O or $NR^9$;

$R^8$ is

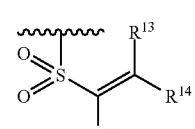
(a)

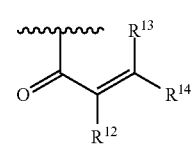
(b)

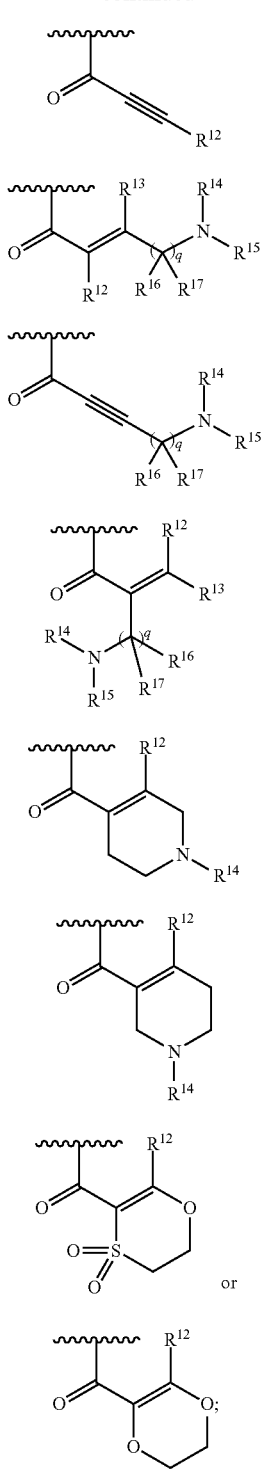

R⁹, R¹⁰, R¹¹ᵃ, R¹¹ᵇ, R¹¹ᶜ, R¹¹ᵈ, R¹¹ᵉ, R¹¹ᶠ, R¹¹ᵍ, R¹¹ʰ, R¹¹ⁱ, R¹¹ʲ, R¹¹ᵏ and R¹¹ˡ are hydrogen;

R¹², R¹³, R¹⁶ and R¹⁷ are independently hydrogen or $C_{1-6}$ alkyl;

R¹⁴ and R¹⁵ are independently hydrogen; $C_{1-6}$ alkyl; —C(O)O—($C_{1-6}$ alkyl); $C_{3-7}$ cycloalkyl unsubstituted or substituted with $C_{1-6}$ alkyl; or R¹⁴ and R¹⁵ together with N in NR¹⁴R¹⁵ may form may form a 4-7 membered ring containing 1-2 heteroatoms selected from N, O, S and P, and optionally substituted with 1-4 R¹⁸ groups;

R⁷ and R¹⁸ are independently oxo, halo, hydroxy, $C_{1-6}$ alkyl or $C_{1-6}$ alkoxy;

R¹⁹ hydrogen, COR²⁰ or COOR²⁰;

R²⁰ is $C_{1-6}$ alkyl;

p is 1;

m and q are independently 1-2; and

Ring B, X¹, X², X³ and X⁴ and n are as defined in any of the embodiments described herein.

In a third embodiment, provided herein is a compound of Formula (2A), (2B), (2C), (2D), (3A), (3B) or (3C) or a pharmaceutically acceptable salt thereof:

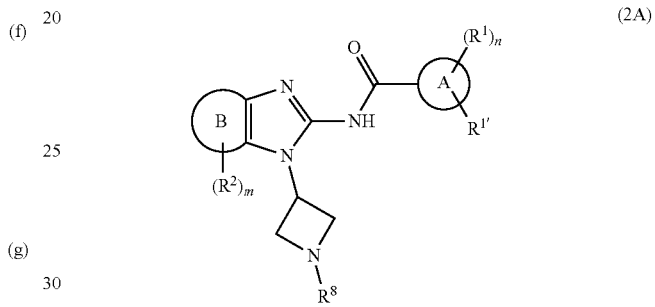

(2A)

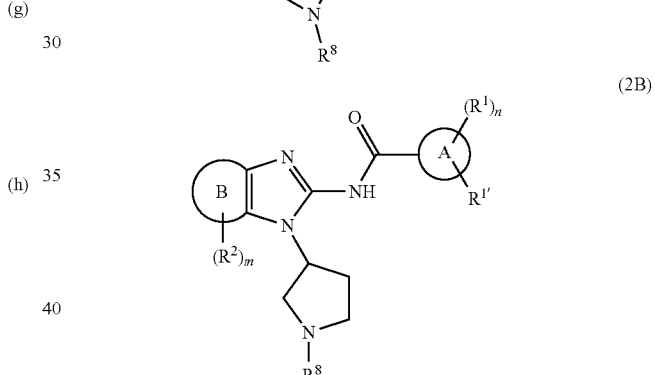

(2B)

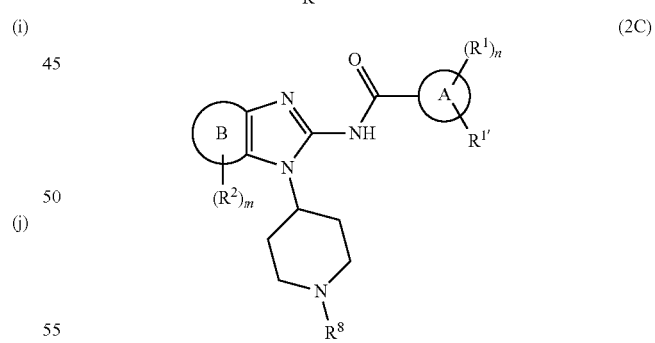

(2C)

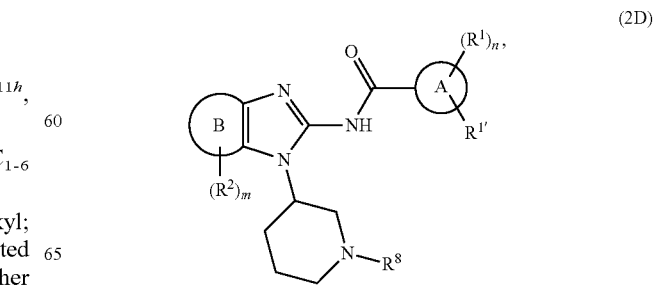

(2D)

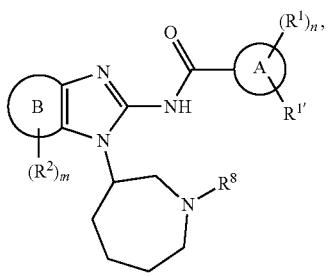

(3A)

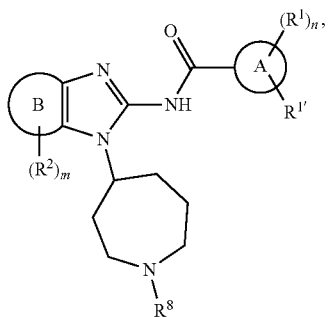

(3B)

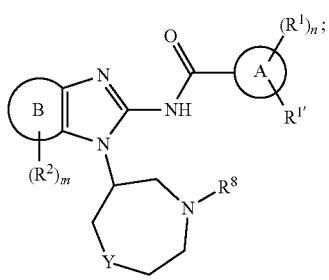

(3C)

or a pharmaceutically acceptable salt thereof;

wherein Y is O or $NR^{19}$; and $R^1$, $R^{1'}$, $R^2$, $R^8$, $R^{19}$, A, B, Y, m and n are as defined in any of the embodiments described herein.

In a fourth embodiment, provided herein is a compound of Formula (1), (2), (2A), (2B), (2C), (2D), (3A), (3B) or (3C) as described herein, or a pharmaceutically acceptable salt thereof, wherein Ring B together with the atoms to which it is attached forms a fused phenyl, pyridyl or piperidyl, each of which is unsubstituted or substituted by $(R^2)_m$; m is 1-2; and $R^2$ is as defined in any of the embodiments described herein.

In a fifth embodiment, provided herein is a compound of Formula (1), (2), (2A), (2B), (2C), (2D), (3A), (3B) or (3C) as described herein, or a pharmaceutically acceptable salt thereof, wherein Ring A is phenyl, pyridyl, pyrimidinyl, pyridazinyl, pyrazinyl, pyridin-2-onyl, oxazolyl, furanyl, thiazolyl, imidazole[2,1-b]thiazolyl, imidazo[1,2-a]pyridinyl, imidazo[1,5-a]pyridinyl or naphthyl, each of which is unsubstituted or substituted by $(R^1)_n$ and $R^{1'}$; wherein n is 1-3; and $R^1$ and $R^{1'}$ are as defined in any of the embodiments described herein.

In a sixth embodiment, provided herein is a compound of Formula (4) or a pharmaceutically acceptable salt thereof:

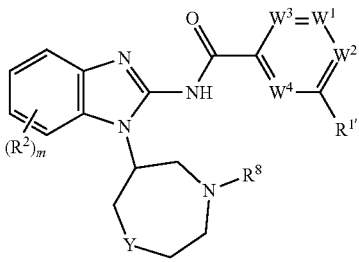

(4)

wherein $W^1$, $W^2$, $W^3$ and $W^4$ are independently $CR^1$ or N; and $R^1$, $R^{1'}$, $R^2$, $R^8$, Y and m are as defined in any of the embodiments described herein. In a particular embodiment, at least two of $W^1$, $W^2$, $W^3$ and $W^4$ are $CR^1$, and the others are N.

In a seventh embodiment, provided herein is a compound of Formula (5) or a pharmaceutically acceptable salt thereof:

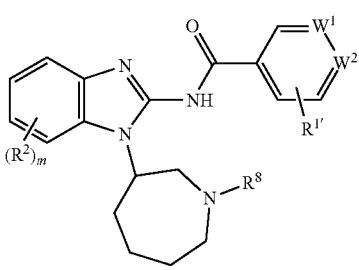

(5)

wherein $W^1$ and $W^2$ are independently $CR^1$ or N; and $R^1$, $R^{1'}$, $R^2$, $R^8$ and m are as defined in any of the embodiments described herein.

In a particular embodiment, provided herein is a compound of Formula (4) or (5) as described herein, or a pharmaceutically acceptable salt thereof, wherein: (i) $W^1$ is $CR^1$ and $W^2$ is N; (ii) $W^2$ is $CR^1$ and $W^1$ is N; (iii) $W^1$ and $W^2$ are $CR^1$; or (iv) $W^1$ and $W^2$ are N.

In an eighth embodiment, provided herein is a compound of Formula (1), (2), (2A), (2B), (2C), (2D), (3A), (3B), (3C), (4) or (5) as described herein, or a pharmaceutically acceptable salt thereof, wherein
$R^1$ and $R^{1'}$ are independently hydrogen; halo; cyano; $C_{1-6}$ alkyl; $C_{1-6}$ haloalkyl; —$X^1$—$NR^4R^5$; —$X^1$—$OR^3$; —$X^1$—$S(O)_{0-2}R^6$; phenyl unsubstituted or substituted by $C_{1-6}$ alkyl; tetrazolyl or pyrrolyl;
each $X^1$ is a bond or $CH_2$;
$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ form piperidinyl; and
$R^6$ is as defined in Formula (1) or (2).

In a ninth embodiment, provided herein is a compound of Formula (1), (2), (2A), (2B), (2C), (2D), (3A), (3B), (3C), (4) or (5) as described herein, or a pharmaceutically acceptable salt thereof, wherein
$R^{1'}$ is hydrogen, halo, cyano, $C_{1-6}$ alkyl, $C_{1-6}$ haloalkyl, tetrazolyl, pyrrolyl, —$X^1$—$NR^4R^5$, —$X^1$—$OR^3$, —$X^1$—$S(O)_{0-2}R^6$ or phenyl unsubstituted or substituted by $C_{1-6}$ alkyl;
$R^1$ is hydrogen, halo or $C_{1-6}$ alkyl;
$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ form piperidinyl;

$X^1$ is a bond or $CH_2$; and $R^6$ is as defined in Formula (1) or (2).

In a tenth embodiment, provided herein is a compound of Formula (1), (2), (2A), (2B), (2C), (2D), (3A), (3B), (3C), (4) or (5) as described herein, or a pharmaceutically acceptable salt thereof, wherein $R^1$ and $R^{1'}$ are independently hydrogen; methyl; t-butyl; trifluoromethyl; methoxy; ethoxy; trifluoromethoxy; difluoromethoxy; fluoro; chloro; cyano; dimethylamino; methylsulfonyl; dimethylphosphoryl; tetrazolyl; pyrrolyl; phenyl unsubstituted or substituted by methyl; or piperidinyl.

In an eleventh embodiment, provided herein is a compound of Formula (1), (2), (2A), (2B), (2C), (2D), (3A), (3B), (3C), (4) or (5) as described herein, or a pharmaceutically acceptable salt thereof, wherein $R^2$ is hydrogen; chloro; methyl; trifluoromethyl; methoxy; isoproproxy; cyano; hydroxymethyl; methoxymethyl; ethoxymethyl; methylsulfonyl; methylcarbonyl; carboxy; methoxycarbonyl; carbamoyl; dimethylaminomethyl; pyrrolidinylmethyl unsubstituted or substituted by 1-2 hydroxy, halo or methoxy; morpholinomethyl; azeditinylmethyl unsubstituted or substituted by 1-2 halo or methoxy; piperidinylmethyl; ((4-methyl-3-oxo-piperazin-1-yl)methyl); ((4-acetylpiperazin-1-yl)methyl); (1,1-dioxidothiomorpholine-4-carbonyl); pyrrolidinyl carbonyl unsubstituted or substituted by 1-2 hydroxy; pyrrolidinylethoxy; (1,1-dioxidothiomorpholino)methyl; or 1,2,4-oxadiazolyl unsubstituted or substituted by $C_{1-6}$ alkyl; alternatively, $R^2$ is $-CH_2-N(CH_3)-C(O)-CH_3$; $-CH_2-O-(CH_2)_2-OCH_3$; $-CH_2-N(CH_3)-(CH_2)_2-SO_2(CH_3)$; $-C(O)NH-(CH_2)_{1-2}-C(O)-OCH_3$; $-C(O)NH-(CH_2)_{1-2}-C(O)OH$; or $-C(O)NH-(CH_2)_2-SO_2(CH_3)$. In a particular embodiment, $R^2$ is halo.

In an twelfth embodiment, provided herein is a compound of Formula (1), (2), (2A), (2B), (2C), (2D), (3A), (3B), (3C), (4) or (5) as described herein, or a pharmaceutically acceptable salt thereof, wherein $R^8$ is

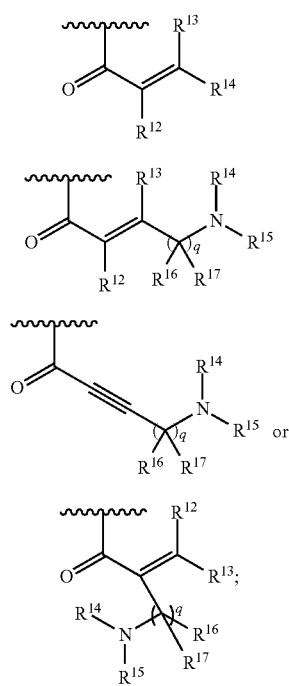

$R^{14}$ and $R^{15}$ are independently hydrogen, $C_{1-6}$ alkyl or $C_{3-7}$ cycloalkyl; or $R^{14}$ and $R^{15}$ together with N in $NR^{14}R^{15}$ may form an azetidinyl, piperidyl, pyrrolidinyl or morpholinyl; where said azetidinyl or pyrrolidinyl can be optionally substituted with 1-2 halo, methoxy or hydroxyl; and $R^{12}$, $R^{13}$, $R^{16}$, $R^{17}$ and q are as defined in any of the embodiments described herein.

In another embodiment, provided herein is a compound selected from:

N-{7-chloro-1-[(3R)-1-[4-(pyrrolidin-1-yl)but-2-enoyl]azepan-3-yl]-1H-1,3-benzodiazol-2-yl}-2-methylpyridine-4-carboxamide;

N-{7-chloro-1-[1-[4-(pyrrolidin-1-yl)but-2-enoyl]azepan-3-yl]-1H-1,3-benzodiazol-2-yl}-2-methylpyridine-4-carboxamide;

N-{7-chloro-1-[(3R)-1-[4-(3-fluoroazetidin-1-yl)but-2-enoyl]azepan-3-yl]-1H-1,3-benzodiazol-2-yl}-2-methylpyridine-4-carboxamide;

N-{7-chloro-1-[1-[4-(3-fluoroazetidin-1-yl)but-2-enoyl]azepan-3-yl]-1H-1,3-benzodiazol-2-yl}-2-methylpyridine-4-carboxamide;

N-{7-chloro-1-[(3R)-1-{4-[(3R)-3-fluoropyrrolidin-1-yl]but-2-enoyl}azepan-3-yl]-1H-1,3-benzodiazol-2-yl}-2-methylpyridine-4-carboxamide;

N-{7-chloro-1-[1-{4-[3-fluoropyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3S)-3-fluoropyrrolidin-1-yl]but-2-enoyl}azepan-3-yl]-1H-1,3-benzodiazol-2-yl}-2-methylpyridine-4-carboxamide;

N-{7-chloro-1-[1-{4-[3-fluoropyrrolidin-1-yl]but-2-enoyl}azepan-3-yl]-1H-1,3-benzodiazol-2-yl}-2-methylpyridine-4-carboxamide;

N-{7-chloro-1-[(3R)-1-[4-(3,3-difluoropyrrolidin-1-yl)but-2-enoyl]azepan-3-yl]-1H-1,3-benzodiazol-2-yl}-2-methylpyridine-4-carboxamide;

N-{7-chloro-1-[1-[4-(3,3-difluoropyrrolidin-1-yl)but-2-enoyl]azepan-3-yl]-1H-1,3-benzodiazol-2-yl}-2-methylpyridine-4-carboxamide;

N-{7-chloro-1-[(3R)-1-{4-[(3R)-3-methoxypyrrolidin-1-yl]but-2-enoyl}azepan-3-yl]-1H-1,3-benzodiazol-2-yl}-2-methylpyridine-4-carboxamide;

N-{7-chloro-1-[1-{4-[3-methoxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3S)-3-methoxypyrrolidin-1-yl]but-2-enoyl}azepan-3-yl]-1H-1,3-benzodiazol-2-yl}-2-methylpyridine-4-carboxamide;

N-{7-chloro-1-[1-{4-[3-methoxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3R)-3-hydroxypyrrolidin-1-yl]but-2-enoyl}azepan-3-yl]-1H-1,3-benzodiazol-2-yl}-2-methylpyridine-4-carboxamide;

N-{7-chloro-1-[1-{4-[3-hydroxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-[(2E)-4-[(3S)-3-hydroxypyrrolidin-1-yl]but-2-enoyl]azepan-3-yl]-1H-1,3-benzodiazol-2-yl}-2-methylpyridine-4-carboxamide;

N-{7-chloro-1-[1-[(2E)-4-[3-hydroxypyrrolidin-1-yl]but-2-enoyl]azepan-3-yl]-1H-1,3-benzodiazol-2-yl}-2-methylpyridine-4-carboxamide;

N-{7-chloro-1-[(3R)-1-[(2E)-4-(pyrrolidin-1-yl)but-2-enoyl]azepan-3-yl]-1H-1,3-benzodiazol-2-yl}pyridazine-4-carboxamide;

N-{7-chloro-1-[1-[(2E)-4-(pyrrolidin-1-yl)but-2-enoyl]azepan-3-yl]-1H-1,3-benzodiazol-2-yl}pyridazine-4-carboxamide;

2-methyl-N-{7-methyl-1-[(3R)-1-[(2E)-4-(pyrrolidin-1-yl)but-2-enoyl]azepan-3-yl]-1H-1,3-benzodiazol-2-yl}pyridine-4-carboxamide;

2-methyl-N-{7-methyl-1-[1-[(2E)-4-(pyrrolidin-1-yl)but-2-enoyl]azepan-3-yl]-1H-1,3-benzodiazol-2-yl}pyridine-4-carboxamide;

N-{1-[(3R)-1-[(2E)-4-[(3R)-3-fluoropyrrolidin-1-yl]but-2-enoyl]azepan-3-yl]-7-methyl-1H-1,3-benzodiazol-2-yl}-2-methylpyridine-4-carboxamide;

N-{1-[1-[(2E)-4-[3-fluoropyrrolidin-1-yl]but-2-enoyl]azepan-3-yl]-7-methyl-1H-1,3-benzodiazol-2-yl}-2-methylpyridine-4-carboxamide;

N-{7-chloro-1-[(3R)-1-[(2E)-4-[(3R)-3-fluoropyrrolidin-1-yl]but-2-enoyl]azepan-3-yl]-1H-1,3-benzodiazol-2-yl}pyridazine-4-carboxamide;

N-{7-chloro-1-[1-[(2E)-4-[3-fluoropyrrolidin-1-yl]but-2-enoyl]azepan-3-yl]-1H-1,3-benzodiazol-2-yl}pyridazine-4-carboxamide;

N-{1-[(3R)-1-[4-(azetidin-1-yl)but-2-enoyl]azepan-3-yl]-7-chloro-1H-1,3-benzodiazol-2-yl}-2-methylpyridine-4-carboxamide;

N-{1-[1-[4-(azetidin-1-yl)but-2-enoyl]azepan-3-yl]-7-chloro-1H-1,3-benzodiazol-2-yl}-2-methylpyridine-4-carboxamide;

N-{7-chloro-1-[(3R)-1-[4-(3-hydroxyazetidin-1-yl)but-2-enoyl]azepan-3-yl]-1H-1,3-benzodiazol-2-yl}-2-methylpyridine-4-carboxamide;

N-{7-chloro-1-[1-[4-(3-hydroxyazetidin-1-yl)but-2-enoyl]azepan-3-yl]-1H-1,3-benzodiazol-2-yl}-2-methylpyridine-4-carboxamide;

N-{7-chloro-1-[(3R)-1-[4-(3-methoxyazetidin-1-yl)but-2-enoyl]azepan-3-yl]-1H-1,3-benzodiazol-2-yl}-2-methylpyridine-4-carboxamide;

N-{7-chloro-1-[1-[(2E)-4-(3-methoxyazetidin-1-yl)but-2-enoyl]azepan-3-yl]-1H-1,3-benzodiazol-2-yl}-2-methylpyridine-4-carboxamide;

N-{7-chloro-1-[(3R)-1-[(2E)-4-(3,3-difluoroazetidin-1-yl)but-2-enoyl]azepan-3-yl]-1H-1,3-benzodiazol-2-yl}-2-methylpyridine-4-carboxamide;

N-{7-chloro-1-[1-[(2E)-4-(3,3-difluoroazetidin-1-yl)but-2-enoyl]azepan-3-yl]-1H-1,3-benzodiazol-2-yl}-2-methylpyridine-4-carboxamide;

N-{5-methyl-1-[(3S)-1-(prop-2-enoyl)piperidin-3-yl]-1H-1,3-benzodiazol-2-yl}-3-(trifluoromethyl)benzamide;

N-{5-methyl-1-[1-(prop-2-enoyl)piperidin-3-yl]-1H-1,3-benzodiazol-2-yl}-3-(trifluoromethyl)benzamide;

N-{7-chloro-1-[(3R)-1-[(2E)-4-(dimethylamino)but-2-enoyl]azepan-3-yl]-1H-1,3-benzodiazol-2-yl}-2-methylpyridine-4-carboxamide;

N-{7-chloro-1-[1-[(2E)-4-(dimethylamino)but-2-enoyl]azepan-3-yl]-1H-1,3-benzodiazol-2-yl}-2-methylpyridine-4-carboxamide;

N-{7-chloro-1-[(3R)-1-[(2E)-4-(dimethylamino)but-2-enoyl]azepan-3-yl]-1H-1,3-benzodiazol-2-yl}-2,6-dimethylpyridine-4-carboxamide;

N-{7-chloro-1-[1-[(2E)-4-(dimethylamino)but-2-enoyl]azepan-3-yl]-1H-1,3-benzodiazol-2-yl}-2,6-dimethylpyridine-4-carboxamide;

N-{1-[(3R)-1-[(2E)-4-(dimethylamino)but-2-enoyl]azepan-3-yl]-7-methyl-1H-1,3-benzodiazol-2-yl}-2-methylpyridine-4-carboxamide;

N-{1-[1-[(2E)-4-(dimethylamino)but-2-enoyl]azepan-3-yl]-7-methyl-1H-1,3-benzodiazol-2-yl}-2-methylpyridine-4-carboxamide;

N-{1-[(3R)-1-[(2E)-4-(dimethylamino)but-2-enoyl]azepan-3-yl]-7-methyl-1H-1,3-benzodiazol-2-yl}-2-(trifluoromethyl)pyridine-4-carboxamide;

N-{1-[1-[(2E)-4-(dimethylamino)but-2-enoyl]azepan-3-yl]-7-methyl-1H-1,3-benzodiazol-2-yl}-2-(trifluoromethyl)pyridine-4-carboxamide;

N-{7-chloro-6-methoxy-1-[(3R)-1-(prop-2-enoyl)azepan-3-yl]-1H-1,3-benzodiazol-2-yl}pyridazine-4-carboxamide;

N-{7-chloro-6-methoxy-1-[1-(prop-2-enoyl)azepan-3-yl]-1H-1,3-benzodiazol-2-yl}pyridazine-4-carboxamide;

N-{1-[(3R)-1-(ethenesulfonyl)azepan-3-yl]-7-methyl-1H-1,3-benzodiazol-2-yl}-3-(trifluoromethyl)benzamide;

N-{1-[1-(ethenesulfonyl)azepan-3-yl]-7-methyl-1H-1,3-benzodiazol-2-yl}-3-(trifluoromethyl)benzamide;

N-{1-[(3R)-1-(prop-2-enoyl)azepan-3-yl]-7-(pyrrolidin-1-ylmethyl)-1H-1,3-benzodiazol-2-yl}-3-(trifluoromethyl)benzamide;

N-{1-[1-(prop-2-enoyl)azepan-3-yl]-7-(pyrrolidin-1-ylmethyl)-1H-1,3-benzodiazol-2-yl}-3-(trifluoromethyl)benzamide;

N-{5-methyl-1-[1-(prop-2-enoyl)azepan-3-yl]-1H-1,3-benzodiazol-2-yl}-3-(trifluoromethyl)benzamide;

N-{7-chloro-1-[(3R)-1-[(2E)-4-(dimethylamino)but-2-enoyl]azepan-3-yl]-6-methoxy-1H-1,3-benzodiazol-2-yl}pyridazine-4-carboxamide;

N-{7-chloro-1-[1-[(2E)-4-(dimethylamino)but-2-enoyl]azepan-3-yl]-6-methoxy-1H-1,3-benzodiazol-2-yl}pyridazine-4-carboxamide;

N-(1-{1-[(2E)-4-(dimethylamino)but-2-enoyl]azepan-3-yl}-7-methyl-1H-1,3-benzodiazol-2-yl)-2-fluorobenzamide;

N-{1-[(3R)-1-[(2E)-4-(dimethylamino)but-2-enoyl]piperidin-3-yl]-7-methyl-1H-1,3-benzodiazol-2-yl}-2-methylpyridine-4-carboxamide;

N-{1-[1-[(2E)-4-(dimethylamino)but-2-enoyl]piperidin-3-yl]-7-methyl-1H-1,3-benzodiazol-2-yl}-2-methylpyridine-4-carboxamide;

N-(1-{1-[(2E)-4-(dimethylamino)but-2-enoyl]azepan-3-yl}-7-methyl-1H-1,3-benzodiazol-2-yl)-1,3-oxazole-5-carboxamide;

N-{-[(6R)-4-[(2E)-4-(dimethylamino)but-2-enoyl]-1,4-oxazepan-6-yl]-7-methyl-1H-1,3-benzodiazol-2-yl}-3-(trifluoromethyl)benzamide;

N-{1-[4-[(2E)-4-(dimethylamino)but-2-enoyl]-1,4-oxazepan-6-yl]-7-methyl-1H-1,3-benzodiazol-2-yl}-3-(trifluoromethyl)benzamide;

N-{1-[(6S)-4-[(2E)-4-(dimethylamino)but-2-enoyl]-1,4-oxazepan-6-yl]-7-methyl-1H-1,3-benzodiazol-2-yl}-3-(trifluoromethyl)benzamide;

N-{1-[4-[(2E)-4-(dimethylamino)but-2-enoyl]-1,4-oxazepan-6-yl]-7-methyl-1H-1,3-benzodiazol-2-yl}-3-(trifluoromethyl)benzamide;

N-{1-[1-(prop-2-enoyl)piperidin-3-yl]-1H-imidazol[4,5-c]pyridin-2-yl}-3-(trifluoromethyl)benzamide;

N-{3-[1-(prop-2-enoyl)piperidin-3-yl]-3H-imidazol[4,5-c]pyridin-2-yl}-3-(trifluoromethyl)benzamide;

N-{7-methyl-1-[1-(prop-2-enoyl)azepan-3-yl]-1H-1,3-benzodiazol-2-yl}-3-(trifluoromethyl)benzamide;

N-{7-methyl-1-[1-(prop-2-enoyl)azepan-3-yl]-1H-1,3-benzodiazol-2-yl}benzamide;

N-{1-[(3R)-1-(prop-2-enoyl)azepan-3-yl]-7-(trifluoromethyl)-1H-1,3-benzodiazol-2-yl}-3-(trifluoromethyl)benzamide;

N-{1-[1-(prop-2-enoyl)azepan-3-yl]-7-(trifluoromethyl)-1H-1,3-benzodiazol-2-yl}-3-(trifluoromethyl)benzamide;

N-{1-[(3R)-1-(prop-2-enoyl)azepan-3-yl]-1H-1,3-benzodiazol-2-yl}-3-(trifluoromethyl)benzamide;

N-{1-[1-(prop-2-enoyl)azepan-3-yl]-1H-1,3-benzodiazol-2-yl}-3-(trifluoromethyl)benzamide;
N-{7-methyl-1-[4-(prop-2-enoyl)-1,4-oxazepan-6-yl]-1H-1,3-benzodiazol-2-yl}-3-(trifluoromethyl)benzamide;
N-{7-chloro-1-[(3R)-1-(prop-2-enoyl)azepan-3-yl]-1H-1,3-benzodiazol-2-yl}pyridazine-4-carboxamide;
N-{7-chloro-1-[1-(prop-2-enoyl)azepan-3-yl]-1H-1,3-benzodiazol-2-yl}pyridazine-4-carboxamide;
N-{7-chloro-1-[(3R)-1-[(2E)-4-(dimethylamino)but-2-enoyl]azepan-3-yl]-1H-1,3-benzodiazol-2-yl}pyridazine-4-carboxamide;
N-{7-chloro-1-[1-[(2E)-4-(dimethylamino)but-2-enoyl]azepan-3-yl]-1H-1,3-benzodiazol-2-yl}pyridazine-4-carboxamide;
N-{7-chloro-1-[(3R)-1-(prop-2-enoyl)azepan-3-yl]-1H-1,3-benzodiazol-2-yl}-2-methylpyridine-4-carboxamide;
N-{7-chloro-1-[1-(prop-2-enoyl)azepan-3-yl]-1H-1,3-benzodiazol-2-yl}-2-methylpyridine-4-carboxamide;
N-{7-chloro-1-[(3R)-1-(prop-2-enoyl)azepan-3-yl]-1H-1,3-benzodiazol-2-yl}-3-(trifluoromethyl)benzamide;
N-{7-chloro-1-[1-(prop-2-enoyl)azepan-3-yl]-1H-1,3-benzodiazol-2-yl}-3-(trifluoromethyl)benzamide;
N-{1-[(3R)-1-(but-2-ynoyl)azepan-3-yl]-7-methyl-1H-1,3-benzodiazol-2-yl}-3-(trifluoromethyl)benzamide;
N-{1-[1-(but-2-ynoyl)azepan-3-yl]-7-methyl-1H-1,3-benzodiazol-2-yl}-3-(trifluoromethyl)benzamide;
N-{1-[(3R)-1-[(2E)-but-2-enoyl]azepan-3-yl]-7-methyl-1H-1,3-benzodiazol-2-yl}-3-(trifluoromethyl)benzamide;
N-{1-[1-[(2E)-but-2-enoyl]azepan-3-yl]-7-methyl-1H-1,3-benzodiazol-2-yl}-3-(trifluoromethyl)benzamide;
N-(1-{1-[(2E)-4-(dimethylamino)but-2-enoyl]azepan-3-yl}-7-methyl-1H-1,3-benzodiazol-2-yl)-3-fluorobenzamide;
N-(1-{1-[(2E)-4-(dimethylamino)but-2-enoyl]azepan-3-yl}-7-methyl-1H-1,3-benzodiazol-2-yl)-3,5-difluorobenzamide;
N-(1-{1-[(2E)-4-(dimethylamino)but-2-enoyl]azepan-3-yl}-7-methyl-1H-1,3-benzodiazol-2-yl)pyridine-3-carboxamide;
N-(1-{1-[(2E)-4-(dimethylamino)but-2-enoyl]azepan-3-yl}-7-methyl-1H-1,3-benzodiazol-2-yl)pyridazine-4-carboxamide;
N-{1-[(3R)-1-[(2E)-4-(dimethylamino)but-2-enoyl]azepan-3-yl]-7-methyl-1H-1,3-benzodiazol-2-yl}-3-(trifluoromethyl)benzamide;
N-{1-[1-[(2E)-4-(dimethylamino)but-2-enoyl]azepan-3-yl]-7-methyl-1H-1,3-benzodiazol-2-yl}-3-(trifluoromethyl)benzamide;
N-(1-{1-[(2E)-4-(dimethylamino)but-2-enoyl]azepan-3-yl}-7-methyl-1H-1,3-benzodiazol-2-yl)-4-fluorobenzamide;
N-(1-{1-[(2E)-4-(dimethylamino)but-2-enoyl]azepan-3-yl}-7-methyl-1H-1,3-benzodiazol-2-yl)-2,3-difluorobenzamide;
N-(1-{1-[(2E)-4-(dimethylamino)but-2-enoyl]azepan-3-yl}-7-methyl-1H-1,3-benzodiazol-2-yl)-2,4-difluorobenzamide;
N-(1-{1-[(2E)-4-(dimethylamino)but-2-enoyl]azepan-3-yl}-7-methyl-1H-1,3-benzodiazol-2-yl)-2,5-difluorobenzamide;
N-(1-{1-[(2E)-4-(dimethylamino)but-2-enoyl]azepan-3-yl}-7-methyl-1H-1,3-benzodiazol-2-yl)-3,4-difluorobenzamide;
3-chloro-N-(1-{1-[(2E)-4-(dimethylamino)but-2-enoyl]azepan-3-yl}-7-methyl-1H-1,3-benzodiazol-2-yl)-2-fluorobenzamide;
3-chloro-N-(1-{1-[(2E)-4-(dimethylamino)but-2-enoyl]azepan-3-yl}-7-methyl-1H-1,3-benzodiazol-2-yl)-2,4-difluorobenzamide;
N-(1-{1-[(2E)-4-(dimethylamino)but-2-enoyl]azepan-3-yl}-7-methyl-1H-1,3-benzodiazol-2-yl)-3,4,5-trifluorobenzamide;
N-(1-{1-[(2E)-4-(dimethylamino)but-2-enoyl]azepan-3-yl}-7-methyl-1H-1,3-benzodiazol-2-yl)pyridine-2-carboxamide;
N-(1-{1-[(2E)-4-(dimethylamino)but-2-enoyl]azepan-3-yl}-7-methyl-1H-1,3-benzodiazol-2-yl)pyridine-4-carboxamide;
N-(1-{1-[(2E)-4-(dimethylamino)but-2-enoyl]azepan-3-yl}-7-methyl-1H-1,3-benzodiazol-2-yl)pyrimidine-2-carboxamide;
N-(1-{1-[(2E)-4-(dimethylamino)but-2-enoyl]azepan-3-yl}-7-methyl-1H-1,3-benzodiazol-2-yl)pyrimidine-4-carboxamide;
N-(1-{1-[(2E)-4-(dimethylamino)but-2-enoyl]azepan-3-yl}-7-methyl-1H-1,3-benzodiazol-2-yl)pyrazine-2-carboxamide;
N-(1-{1-[(2E)-4-(dimethylamino)but-2-enoyl]azepan-3-yl}-7-methyl-1H-1,3-benzodiazol-2-yl)pyridazine-3-carboxamide;
N-(1-{1-[(2E)-4-(dimethylamino)but-2-enoyl]azepan-3-yl}-7-methyl-1H-1,3-benzodiazol-2-yl)benzamide;
N-(1-{1-[(2E)-4-(dimethylamino)but-2-enoyl]azepan-3-yl}-7-methyl-1H-1,3-benzodiazol-2-yl)-3-methylbenzamide;
3-cyano-N-(1-{1-[(2E)-4-(dimethylamino)but-2-enoyl]azepan-3-yl}-7-methyl-1H-1,3-benzodiazol-2-yl)benzamide;
3-chloro-N-(1-{1-[(2E)-4-(dimethylamino)but-2-enoyl]azepan-3-yl}-7-methyl-1H-1,3-benzodiazol-2-yl)benzamide;
N-(1-{1-[(2E)-4-(dimethylamino)but-2-enoyl]azepan-3-yl}-7-methyl-1H-1,3-benzodiazol-2-yl)-3-methoxybenzamide;
N-(1-{1-[(2E)-4-(dimethylamino)but-2-enoyl]azepan-3-yl}-7-methyl-1H-1,3-benzodiazol-2-yl)-6-methoxypyridine-3-carboxamide;
N-(1-{1-[(2E)-4-(dimethylamino)but-2-enoyl]azepan-3-yl}-7-methyl-1H-1,3-benzodiazol-2-yl)-6-(trifluoromethyl)pyridine-3-carboxamide;
N-(1-{1-[(2E)-4-(dimethylamino)but-2-enoyl]azepan-3-yl}-7-methyl-1H-1,3-benzodiazol-2-yl)-6-methylpyridine-3-carboxamide;
N-(1-{1-[(2E)-4-(dimethylamino)but-2-enoyl]azepan-3-yl}-7-methyl-1H-1,3-benzodiazol-2-yl)-2-methoxypyridine-4-carboxamide;
N-(1-{1-[(2E)-4-(dimethylamino)but-2-enoyl]azepan-3-yl}-7-methyl-1H-1,3-benzodiazol-2-yl)-1-methyl-2-oxo-1,2-dihydropyridine-4-carboxamide;
2-(dimethylamino)-N-(1-{1-[(2E)-4-(dimethylamino)but-2-enoyl]azepan-3-yl}-7-methyl-1H-1,3-benzodiazol-2-yl)pyridine-4-carboxamide;
N-(1-{1-[(2E)-4-(dimethylamino)but-2-enoyl]azepan-3-yl}-7-methyl-1H-1,3-benzodiazol-2-yl)imidazo[2,1-b][1,3]thiazole-6-carboxamide;
N-(1-{1-[(2E)-4-(dimethylamino)but-2-enoyl]azepan-3-yl}-7-methyl-1H-1,3-benzodiazol-2-yl)-3-methanesulfonylbenzamide;
N-(1-{1-[(2E)-4-(dimethylamino)but-2-enoyl]azepan-3-yl}-7-methyl-1H-1,3-benzodiazol-2-yl)-3-(1H-1,2,3,4-tetrazol-1-yl)benzamide;
N-(1-{1-[(2E)-4-(dimethylamino)but-2-enoyl]azepan-3-yl}-7-methyl-1H-1,3-benzodiazol-2-yl)-2-methylpyrimidine-4-carboxamide;

N-(1-{1-[(2E)-4-(dimethylamino)but-2-enoyl]azepan-3-yl}-7-methyl-1H-1,3-benzodiazol-2-yl)imidazo[1,2-a]pyridine-6-carboxamide;

N-(1-{1-[(2E)-4-(dimethylamino)but-2-enoyl]azepan-3-yl}-7-methyl-1H-1,3-benzodiazol-2-yl)furan-2-carboxamide;

N-(1-{1-[(2E)-4-(dimethylamino)but-2-enoyl]azepan-3-yl}-7-methyl-1H-1,3-benzodiazol-2-yl)-2-(piperidin-1-yl)pyridine-4-carboxamide;

N-(1-{1-[(2E)-4-(dimethylamino)but-2-enoyl]azepan-3-yl}-7-methyl-1H-1,3-benzodiazol-2-yl)-2-fluoropyridine-4-carboxamide;

N-(1-{1-[(2E)-4-(dimethylamino)but-2-enoyl]azepan-3-yl}-7-methyl-1H-1,3-benzodiazol-2-yl)-4,5-dimethylfuran-2-carboxamide;

N-(1-{1-[(2E)-4-(dimethylamino)but-2-enoyl]azepan-3-yl}-7-methyl-1H-1,3-benzodiazol-2-yl)-2-(1H-1,2,3,4-tetrazol-1-yl)pyridine-4-carboxamide;

2-tert-butyl-N-(1-{1-[(2E)-4-(dimethylamino)but-2-enoyl]azepan-3-yl}-7-methyl-1H-1,3-benzodiazol-2-yl)pyridine-4-carboxamide;

N-(1-{1-[(2E)-4-(dimethylamino)but-2-enoyl]azepan-3-yl}-7-methyl-1H-1,3-benzodiazol-2-yl)-2-methylpyridine-3-carboxamide;

N-(1-{1-[(2E)-4-(dimethylamino)but-2-enoyl]azepan-3-yl}-7-methyl-1H-1,3-benzodiazol-2-yl)imidazo[1,5-a]pyridine-7-carboxamide;

N-(1-{1-[(2E)-4-(dimethylamino)but-2-enoyl]azepan-3-yl}-7-methyl-1H-1,3-benzodiazol-2-yl)-2-methyl-1,3-thiazole-5-carboxamide;

N-(1-{1-[(2E)-4-(dimethylamino)but-2-enoyl]azepan-3-yl}-7-methyl-1H-1,3-benzodiazol-2-yl)-2-ethoxypyridine-4-carboxamide;

N-(1-{1-[(2E)-4-(dimethylamino)but-2-enoyl]azepan-3-yl}-7-methyl-1H-1,3-benzodiazol-2-yl)naphthalene-2-carboxamide;

N-{1-[(3R)-1-[(2E)-4-(dimethylamino)but-2-enoyl]azepan-3-yl]-7-methyl-1H-1,3-benzodiazol-2-yl}-5-(trifluoromethyl)pyridine-3-carboxamide;

N-{1-[1-[(2E)-4-(dimethylamino)but-2-enoyl]azepan-3-yl]-7-methyl-1H-1,3-benzodiazol-2-yl}-5-(trifluoromethyl)pyridine-3-carboxamide;

N-{1-[(3R)-1-[(2E)-4-(dimethylamino)but-2-enoyl]azepan-3-yl]-7-methyl-1H-1,3-benzodiazol-2-yl}-5-methylpyridine-3-carboxamide;

N-{1-[1-[(2E)-4-(dimethylamino)but-2-enoyl]azepan-3-yl]-7-methyl-1H-1,3-benzodiazol-2-yl}-5-methylpyridine-3-carboxamide;

N-{1-[(3R)-1-[(2E)-4-(dimethylamino)but-2-enoyl]azepan-3-yl]-7-methyl-1H-1,3-benzodiazol-2-yl}-5-fluoropyridine-3-carboxamide;

N-{1-[1-[(2E)-4-(dimethylamino)but-2-enoyl]azepan-3-yl]-7-methyl-1H-1,3-benzodiazol-2-yl}-5-fluoropyridine-3-carboxamide;

N-{1-[(3R)-1-[(2E)-4-(dimethylamino)but-2-enoyl]azepan-3-yl]-7-methyl-1H-1,3-benzodiazol-2-yl}-5-(1H-pyrrol-1-yl)pyridine-3-carboxamide;

N-{1-[1-[(2E)-4-(dimethylamino)but-2-enoyl]azepan-3-yl]-7-methyl-1H-1,3-benzodiazol-2-yl}-5-(1H-pyrrol-1-yl)pyridine-3-carboxamide;

N-{1-[(3R)-1-[(2E)-4-(dimethylamino)but-2-enoyl]azepan-3-yl]-7-methyl-1H-1,3-benzodiazol-2-yl}-2-methoxypyridine-4-carboxamide;

N-{1-[1-[(2E)-4-(dimethylamino)but-2-enoyl]azepan-3-yl]-7-methyl-1H-1,3-benzodiazol-2-yl}-2-methoxypyridine-4-carboxamide;

N-{1-[(3R)-1-[(2E)-4-(dimethylamino)but-2-enoyl]azepan-3-yl]-7-methyl-1H-1,3-benzodiazol-2-yl}-2,6-dimethylpyridine-4-carboxamide;

N-{1-[1-[(2E)-4-(dimethylamino)but-2-enoyl]azepan-3-yl]-7-methyl-1H-1,3-benzodiazol-2-yl}-2,6-dimethylpyridine-4-carboxamide;

2-chloro-N-{1-[(3R)-1-[(2E)-4-(dimethylamino)but-2-enoyl]azepan-3-yl]-7-methyl-1H-1,3-benzodiazol-2-yl}pyridine-4-carboxamide;

2-chloro-N-{1-[1-[(2E)-4-(dimethylamino)but-2-enoyl]azepan-3-yl]-7-methyl-1H-1,3-benzodiazol-2-yl}pyridine-4-carboxamide;

2-chloro-N-{1-[(3R)-1-[(2E)-4-(dimethylamino)but-2-enoyl]azepan-3-yl]-7-methyl-1H-1,3-benzodiazol-2-yl}-6-methylpyridine-4-carboxamide;

2-chloro-N-{1-[1-[(2E)-4-(dimethylamino)but-2-enoyl]azepan-3-yl]-7-methyl-1H-1,3-benzodiazol-2-yl}-6-methylpyridine-4-carboxamide;

2-chloro-N-{1-[(3R)-1-[(2E)-4-(dimethylamino)but-2-enoyl]azepan-3-yl]-7-methyl-1H-1,3-benzodiazol-2-yl}-6-methoxypyridine-4-carboxamide;

2-chloro-N-{1-[1-[(2E)-4-(dimethylamino)but-2-enoyl]azepan-3-yl]-7-methyl-1H-1,3-benzodiazol-2-yl}-6-methoxypyridine-4-carboxamide;

N-{1-[(3R)-1-[(2E)-4-(dimethylamino)but-2-enoyl]azepan-3-yl]-7-methyl-1H-1,3-benzodiazol-2-yl}-2-phenylpyridine-4-carboxamide;

N-{1-[I-[(2E)-4-(dimethylamino)but-2-enoyl]azepan-3-yl]-7-methyl-1H-1,3-benzodiazol-2-yl}-2-phenylpyridine-4-carboxamide;

6-chloro-N-{1-[(3R)-1-[(2E)-4-(dimethylamino)but-2-enoyl]azepan-3-yl]-7-methyl-1H-1,3-benzodiazol-2-yl}pyridine-3-carboxamide;

6-chloro-N-{1-[1-[(2E)-4-(dimethylamino)but-2-enoyl]azepan-3-yl]-7-methyl-1H-1,3-benzodiazol-2-yl}pyridine-3-carboxamide;

5,6-dichloro-N-{1-[(3R)-1-[(2E)-4-(dimethylamino)but-2-enoyl]azepan-3-yl]-7-methyl-1H-1,3-benzodiazol-2-yl}pyridine-3-carboxamide;

5,6-dichloro-N-{1-[1-[(2E)-4-(dimethylamino)but-2-enoyl]azepan-3-yl]-7-methyl-1H-1,3-benzodiazol-2-yl}pyridine-3-carboxamide;

N-{1-[(3R)-1-[(2E)-4-(dimethylamino)but-2-enoyl]azepan-3-yl]-7-methyl-1H-1,3-benzodiazol-2-yl}-5-methoxypyridine-3-carboxamide;

N-{1-[1-[(2E)-4-(dimethylamino)but-2-enoyl]azepan-3-yl]-7-methyl-1H-1,3-benzodiazol-2-yl}-5-methoxypyridine-3-carboxamide;

N-{1-[(3R)-1-[(2E)-4-(dimethylamino)but-2-enoyl]azepan-3-yl]-7-methyl-1H-1,3-benzodiazol-2-yl}-2-(2-methylphenyl)pyridine-4-carboxamide;

N-{1-[1-[(2E)-4-(dimethylamino)but-2-enoyl]azepan-3-yl]-7-methyl-1H-1,3-benzodiazol-2-yl}-2-(2-methylphenyl)pyridine-4-carboxamide;

6-methyl-N-{7-methyl-1-[(3R)-1-(prop-2-enoyl)azepan-3-yl]-1H-1,3-benzodiazol-2-yl}pyridazine-4-carboxamide;

6-methyl-N-{7-methyl-1-[1-(prop-2-enoyl)azepan-3-yl]-1H-1,3-benzodiazol-2-yl}pyridazine-4-carboxamide;

N-{1-[(3R)-1-[(2E)-4-(dimethylamino)but-2-enoyl]azepan-3-yl]-7-methyl-1H-1,3-benzodiazol-2-yl}-6-methylpyridazine-4-carboxamide;

N-{1-[1-[(2E)-4-(dimethylamino)but-2-enoyl]azepan-3-yl]-7-methyl-1H-1,3-benzodiazol-2-yl}-6-methylpyridazine-4-carboxamide;

N-{1-[(3R)-1-[(2E)-4-(dimethylamino)but-2-enoyl]azepan-3-yl]-7-methoxy-1H-1,3-benzodiazol-2-yl}pyridazine-4-carboxamide;

N-{1-[1-[(2E)-4-(dimethylamino)but-2-enoyl]azepan-3-yl]-7-methoxy-1H-1,3-benzodiazol-2-yl}pyridazine-4-carboxamide;

N-{7-methoxy-1-[(3R)-1-(prop-2-enoyl)azepan-3-yl]-1H-1,3-benzodiazol-2-yl}pyridazine-4-carboxamide;

N-{7-methoxy-1-[1-(prop-2-enoyl)azepan-3-yl]-1H-1,3-benzodiazol-2-yl}pyridazine-4-carboxamide;

N-{1-[(3R)-1-[(2E)-4-(dimethylamino)but-2-enoyl]azepan-3-yl]-7-(propan-2-yloxy)-1H-1,3-benzodiazol-2-yl}pyridazine-4-carboxamide;

N-{1-[1-[(2E)-4-(dimethylamino)but-2-enoyl]azepan-3-yl]-7-(propan-2-yloxy)-1H-1,3-benzodiazol-2-yl}pyridazine-4-carboxamide;

N-{1-[(3R)-1-(prop-2-enoyl)azepan-3-yl]-7-(propan-2-yloxy)-1H-1,3-benzodiazol-2-yl}pyridazine-4-carboxamide;

N-{1-[1-(prop-2-enoyl)azepan-3-yl]-7-(propan-2-yloxy)-1H-1,3-benzodiazol-2-yl}pyridazine-4-carboxamide;

N-{1-[(3R)-1-[4-(dimethylamino)but-2-ynoyl]azepan-3-yl]-7-methyl-1H-1,3-benzodiazol-2-yl}pyridazine-4-carboxamide;

N-{1-[1-[4-(dimethylamino)but-2-ynoyl]azepan-3-yl]-7-methyl-1H-1,3-benzodiazol-2-yl}pyridazine-4-carboxamide;

(R)—N-(7-methyl-1-(1-(2-methyl-4,4-dioxido-5,6-dihydro-1,4-oxathiine-3-carbonyl)azepan-3-yl)-1H-benzo[d]imidazol-2-yl)pyridazine-4-carboxamide;

N-(7-methyl-1-(1-(2-methyl-4,4-dioxido-5,6-dihydro-1,4-oxathiine-3-carbonyl)azepan-3-yl)-1H-benzo[d]imidazol-2-yl)pyridazine-4-carboxamide;

N-{1-[(3R)-1-[(5,6-dihydro-1,4-dioxin-2-yl)carbonyl]azepan-3-yl]-7-methyl-1H-1,3-benzodiazol-2-yl}pyridazine-4-carboxamide;

N-{1-[1-[(5,6-dihydro-1,4-dioxin-2-yl)carbonyl]azepan-3-yl]-7-methyl-1H-1,3-benzodiazol-2-yl}pyridazine-4-carboxamide;

N-{7-methyl-1-[(3R)-1-[2-(piperidin-1-ylmethyl)prop-2-enoyl]azepan-3-yl]-1H-1,3-benzodiazol-2-yl}pyridazine-4-carboxamide;

N-{7-methyl-1-[1-[2-(piperidin-1-ylmethyl)prop-2-enoyl]azepan-3-yl]-1H-1,3-benzodiazol-2-yl}pyridazine-4-carboxamide;

N-{7-methyl-1-[(3R)-1-[2-(pyrrolidin-1-ylmethyl)prop-2-enoyl]azepan-3-yl]-1H-1,3-benzodiazol-2-yl}pyridazine-4-carboxamide;

N-{7-methyl-1-[1-[2-(pyrrolidin-1-ylmethyl)prop-2-enoyl]azepan-3-yl]-1H-1,3-benzodiazol-2-yl}pyridazine-4-carboxamide;

N-{1-[(3R)-1-{2-[(diethylamino)methyl]prop-2-enoyl}azepan-3-yl]-7-methyl-1H-1,3-benzodiazol-2-yl}pyridazine-4-carboxamide;

N-{1-[1-{2-[(diethylamino)methyl]prop-2-enoyl}azepan-3-yl]-7-methyl-1H-1,3-benzodiazol-2-yl}pyridazine-4-carboxamide;

N-{7-methyl-1-[(3R)-1-[2-(morpholin-4-ylmethyl)prop-2-enoyl]azepan-3-yl]-1H-1,3-benzodiazol-2-yl}pyridazine-4-carboxamide;

N-{7-methyl-1-[1-[2-(morpholin-4-ylmethyl)prop-2-enoyl]azepan-3-yl]-1H-1,3-benzodiazol-2-yl}pyridazine-4-carboxamide;

N-{7-methyl-1-[(3R)-1-(prop-2-enoyl)azepan-3-yl]-1H-1,3-benzodiazol-2-yl}pyridazine-4-carboxamide;

N-{7-methyl-1-[1-(prop-2-enoyl)azepan-3-yl]-1H-1,3-benzodiazol-2-yl}pyridazine-4-carboxamide;

N-{1-[(3R)-1-[(2E)-4-(dimethylamino)but-2-enoyl]azepan-3-yl]-7-methyl-1H-1,3-benzodiazol-2-yl}pyridazine-4-carboxamide;

N-{1-[1-[(2E)-4-(dimethylamino)but-2-enoyl]azepan-3-yl]-7-methyl-1H-1,3-benzodiazol-2-yl}pyridazine-4-carboxamide;

methyl 1-[1-(prop-2-enoyl)azepan-3-yl]-2-{[3-(trifluoromethyl)benzene]amido}-1H-1,3-benzodiazole-7-carboxylate;

N-{5-methyl-1-[1-(prop-2-enoyl)piperidin-4-yl]-1H-1,3-benzodiazol-2-yl}-3-(trifluoromethyl)benzamide;

N-{5-methyl-1-[1-(prop-2-enoyl)pyrrolidin-3-yl]-1H-1,3-benzodiazol-2-yl}-3-(trifluoromethyl)benzamide;

N-{5-methyl-1-[1-(prop-2-enoyl)azetidin-3-yl]-1H-1,3-benzodiazol-2-yl}-3-(trifluoromethyl)benzamide;

N-{5-methyl-1-[1-(prop-2-enoyl)piperidin-3-yl]-1H-1,3-benzodiazol-2-yl}-3-(trifluoromethyl)benzamide;

N-{1-[1-(but-2-enoyl)azetidin-3-yl]-5-methyl-1H-1,3-benzodiazol-2-yl}-3-(trifluoromethyl)benzamide;

N-{1-[(3R)-1-[(2E)-4-(dimethylamino)but-2-enoyl]azepan-3-yl]-7-methyl-1H-1,3-benzodiazol-2-yl}-2-(trifluoromethoxy)pyridine-4-carboxamide;

N-{1-[1-[(2E)-4-(dimethylamino)but-2-enoyl]azepan-3-yl]-7-methyl-1H-1,3-benzodiazol-2-yl}-2-(trifluoromethoxy)pyridine-4-carboxamide;

2-(difluoromethoxy)-N-{1-[(3R)-1-[4-(dimethylamino)but-2-enoyl]azepan-3-yl]-7-methyl-1H-1,3-benzodiazol-2-yl}pyridine-4-carboxamide;

2-(difluoromethoxy)-N-{1-[1-[4-(dimethylamino)but-2-enoyl]azepan-3-yl]-7-methyl-1H-1,3-benzodiazol-2-yl}pyridine-4-carboxamide;

2-chloro-N-{1-[(3R)-1-[(2E)-4-(dimethylamino)but-2-enoyl]azepan-3-yl]-7-methyl-1H-1,3-benzodiazol-2-yl}-6-(trifluoromethoxy)pyridine-4-carboxamide;

2-chloro-N-{1-[1-[(2E)-4-(dimethylamino)but-2-enoyl]azepan-3-yl]-7-methyl-1H-1,3-benzodiazol-2-yl}-6-(trifluoromethoxy)pyridine-4-carboxamide;

N-{5-methyl-1-[(3R)-1-(prop-2-enoyl)piperidin-3-yl]-1H-1,3-benzodiazol-2-yl}-3-(trifluoromethyl)benzamide;

N-{5-methyl-1-[1-(prop-2-enoyl)piperidin-3-yl]-1H-1,3-benzodiazol-2-yl}-3-(trifluoromethyl)benzamide;

N-{7-methyl-1-[(3R)-1-(prop-2-enoyl)piperidin-3-yl]-1H-1,3-benzodiazol-2-yl}-3-(trifluoromethyl)benzamide;

N-{7-methyl-1-[1-(prop-2-enoyl)piperidin-3-yl]-1H-1,3-benzodiazol-2-yl}-3-(trifluoromethyl)benzamide;

N-{5-methyl-1-[1-(prop-2-enoyl)azepan-4-yl]-1H-1,3-benzodiazol-2-yl}-3-(trifluoromethyl)benzamide;

N-{7-methyl-1-[(3R)-1-(prop-2-enoyl)piperidin-3-yl]-1H-1,3-benzodiazol-2-yl}benzamide;

N-{7-methyl-1-[1-(prop-2-enoyl)piperidin-3-yl]-1H-1,3-benzodiazol-2-yl}benzamide;

2-methyl-N-{7-methyl-1-[(3R)-1-(prop-2-enoyl)piperidin-3-yl]-1H-1,3-benzodiazol-2-yl}pyridine-4-carboxamide;

2-methyl-N-{7-methyl-1-[1-(prop-2-enoyl)piperidin-3-yl]-1H-1,3-benzodiazol-2-yl}pyridine-4-carboxamide;

methyl 1-[(3R)-1-(prop-2-enoyl)piperidin-3-yl]-2-{[3-(trifluoromethyl)benzene]amido}-1H-1,3-benzodiazole-5-carboxylate;

methyl 1-[1-(prop-2-enoyl)piperidin-3-yl]-2-{[3-(trifluoromethyl)benzene]amido}-1H-1,3-benzodiazole-5-carboxylate;

N-{7-methyl-1-[(3R)-1-(prop-2-enoyl)azepan-3-yl]-5-(pyrrolidin-1-ylmethyl)-1H-1,3-benzodiazol-2-yl}benzamide;

N-{7-methyl-1-[1-(prop-2-enoyl)azepan-3-yl]-5-(pyrrolidin-1-ylmethyl)-1H-1,3-benzodiazol-2-yl}benzamide;

N-[5-(morpholin-4-ylmethyl)-1-[(3R)-1-(prop-2-enoyl)piperidin-3-yl]-1H-1,3-benzodiazol-2-yl]-3-(trifluoromethyl)benzamide;

N-[5-(morpholin-4-ylmethyl)-1-[1-(prop-2-enoyl)piperidin-3-yl]-1H-1,3-benzodiazol-2-yl]-3-(trifluoromethyl)benzamide;

2,6-dimethyl-N-{7-methyl-1-[(3R)-1-(prop-2-enoyl)azepan-3-yl]-5-(pyrrolidin-1-ylmethyl)-1H-1,3-benzodiazol-2-yl}pyridine-4-carboxamide;

2,6-dimethyl-N-{7-methyl-1-[1-(prop-2-enoyl)azepan-3-yl]-5-(pyrrolidin-1-ylmethyl)-1H-1,3-benzodiazol-2-yl}pyridine-4-carboxamide;

N-{7-[(3-hydroxypyrrolidin-1-yl)methyl]-1-[(3R)-1-(prop-2-enoyl)azepan-3-yl]-1H-1,3-benzodiazol-2-yl}benzamide;

N-{7-[(3-hydroxypyrrolidin-1-yl)methyl]-1-[1-(prop-2-enoyl)azepan-3-yl]-1H-1,3-benzodiazol-2-yl}benzamide;

N-(1-(1-acryloylazepan-3-yl)-7-(1,1-dioxidothiomorpholine-4-carbonyl)-1H-benzo[d]imidazol-2-yl)benzamide;

N-(7-cyano-1-{1-[(2E)-4-(dimethylamino)but-2-enoyl]azepan-3-yl}-5-(hydroxymethyl)-1H-1,3-benzodiazol-2-yl)-3-(trifluoromethyl)benzamide;

N-{1-[(3R)-1-(prop-2-enoyl)piperidin-3-yl]-5-(pyrrolidin-1-ylmethyl)-1H-1,3-benzodiazol-2-yl}-3-(trifluoromethyl)benzamide;

N-{1-[1-(prop-2-enoyl)piperidin-3-yl]-5-(pyrrolidin-1-ylmethyl)-1H-1,3-benzodiazol-2-yl}-3-(trifluoromethyl)benzamide;

N-[5-(piperidin-1-ylmethyl)-1-[(3R)-1-(prop-2-enoyl)piperidin-3-yl]-1H-1,3-benzodiazol-2-yl]-3-(trifluoromethyl)benzamide;

N-[5-(piperidin-1-ylmethyl)-1-[1-(prop-2-enoyl)piperidin-3-yl]-1H-1,3-benzodiazol-2-yl]-3-(trifluoromethyl)benzamide;

N-{5-[(N-methylacetamido)methyl]-1-[(3R)-1-(prop-2-enoyl)piperidin-3-yl]-1H-1,3-benzodiazol-2-yl}-3-(trifluoromethyl)benzamide;

N-{5-[(N-methylacetamido)methyl]-1-[1-(prop-2-enoyl)piperidin-3-yl]-1H-1,3-benzodiazol-2-yl}-3-(trifluoromethyl)benzamide;

N-(5-{[(3R,4R)-3,4-dihydroxypyrrolidin-1-yl]methyl}-1-[(3R)-1-(prop-2-enoyl)piperidin-3-yl]-1H-1,3-benzodiazol-2-yl)-3-(trifluoromethyl)benzamide;

N-(5-{[3,4-dihydroxypyrrolidin-1-yl]methyl}-1-[1-(prop-2-enoyl)piperidin-3-yl]-1H-1,3-benzodiazol-2-yl)-3-(trifluoromethyl)benzamide;

N-[5-(hydroxymethyl)-1-[(3R)-1-(prop-2-enoyl)piperidin-3-yl]-1H-1,3-benzodiazol-2-yl]-3-(trifluoromethyl)benzamide;

N-[5-(hydroxymethyl)-1-[1-(prop-2-enoyl)piperidin-3-yl]-1H-1,3-benzodiazol-2-yl]-3-(trifluoromethyl)benzamide;

N-[5-(methoxymethyl)-1-[(3R)-1-(prop-2-enoyl)piperidin-3-yl]-1H-1,3-benzodiazol-2-yl]-3-(trifluoromethyl)benzamide;

N-[5-(methoxymethyl)-1-[1-(prop-2-enoyl)piperidin-3-yl]-1H-1,3-benzodiazol-2-yl]-3-(trifluoromethyl)benzamide;

N-[5-(ethoxymethyl)-1-[(3R)-1-(prop-2-enoyl)piperidin-3-yl]-1H-1,3-benzodiazol-2-yl]-3-(trifluoromethyl)benzamide;

N-[5-(ethoxymethyl)-1-[1-(prop-2-enoyl)piperidin-3-yl]-1H-1,3-benzodiazol-2-yl]-3-(trifluoromethyl)benzamide;

N-{5-[(2-methoxyethoxy)methyl]-1-[(3R)-1-(prop-2-enoyl)piperidin-3-yl]-1H-1,3-benzodiazol-2-yl}-3-(trifluoromethyl)benzamide;

N-{5-[(2-methoxyethoxy)methyl]-1-[1-(prop-2-enoyl)piperidin-3-yl]-1H-1,3-benzodiazol-2-yl}-3-(trifluoromethyl)benzamide;

N-{5-[(3,3-difluoropyrrolidin-1-yl)methyl]-1-[(3R)-1-(prop-2-enoyl)piperidin-3-yl]-1H-1,3-benzodiazol-2-yl}-3-(trifluoromethyl)benzamide;

N-{5-[(3,3-difluoropyrrolidin-1-yl)methyl]-1-[1-(prop-2-enoyl)piperidin-3-yl]-1H-1,3-benzodiazol-2-yl}-3-(trifluoromethyl)benzamide;

2-methyl-N-{7-methyl-1-[(3R)-1-(prop-2-enoyl)azepan-3-yl]-5-(pyrrolidin-1-ylmethyl)-1H-1,3-benzodiazol-2-yl}pyridine-4-carboxamide;

2-methyl-N-{7-methyl-1-[1-(prop-2-enoyl)azepan-3-yl]-5-(pyrrolidin-1-ylmethyl)-1H-1,3-benzodiazol-2-yl}pyridine-4-carboxamide;

N-(5-{[(2-methanesulfonylethyl)(methyl)amino]methyl}-7-methyl-1-[(3R)-1-(prop-2-enoyl)azepan-3-yl]-1H-1,3-benzodiazol-2-yl)benzamide;

N-(5-{[(2-methanesulfonylethyl)(methyl)amino]methyl}-7-methyl-1-[1-(prop-2-enoyl)azepan-3-yl]-1H-1,3-benzodiazol-2-yl)benzamide;

N-{5-[(2-methoxyethoxy)methyl]-7-methyl-1-[(3R)-1-(prop-2-enoyl)azepan-3-yl]-1H-1,3-benzodiazol-2-yl}benzamide;

N-{5-[(2-methoxyethoxy)methyl]-7-methyl-1-[1-(prop-2-enoyl)azepan-3-yl]-1H-1,3-benzodiazol-2-yl}benzamide;

N-{7-[(dimethylamino)methyl]-1-[(3R)-1-(prop-2-enoyl)azepan-3-yl]-1H-1,3-benzodiazol-2-yl}benzamide;

N-{7-[(dimethylamino)methyl]-1-[1-(prop-2-enoyl)azepan-3-yl]-1H-1,3-benzodiazol-2-yl}benzamide;

N-{7-[(2-methoxyethoxy)methyl]-1-[(3R)-1-(prop-2-enoyl)azepan-3-yl]-1H-1,3-benzodiazol-2-yl}benzamide;

N-{7-[(2-methoxyethoxy)methyl]-1-[1-(prop-2-enoyl)azepan-3-yl]-1H-1,3-benzodiazol-2-yl}benzamide;

N-[7-(hydroxymethyl)-1-[(3R)-1-(prop-2-enoyl)azepan-3-yl]-1H-1,3-benzodiazol-2-yl]benzamide;

N-[7-(hydroxymethyl)-1-[1-(prop-2-enoyl)azepan-3-yl]-1H-1,3-benzodiazol-2-yl]benzamide;

(R)—N-(1-(1-acryloylazepan-3-yl)-7-((1,1-dioxidothiomorpholino)methyl)-1H-benzo[d]imidazol-2-yl)benzamide;

N-(1-(1-acryloylazepan-3-yl)-7-((1,1-dioxidothiomorpholino)methyl)-1H-benzo[d]imidazol-2-yl)benzamide;

N-(7-{[(2-methanesulfonylethyl)(methyl)amino]methyl}-1-[(3R)-1-(prop-2-enoyl)azepan-3-yl]-1H-1,3-benzodiazol-2-yl)benzamide;

N-(7-{[(2-methanesulfonylethyl)(methyl)amino]methyl}-1-[1-(prop-2-enoyl)azepan-3-yl]-1H-1,3-benzodiazol-2-yl)benzamide;

methyl 3-({2-benzamido-1-[1-(prop-2-enoyl)azepan-3-yl]-1H-1,3-benzodiazol-7-yl}formamido)propanoate;

methyl 2-({2-benzamido-1-[1-(prop-2-enoyl)azepan-3-yl]-1H-1,3-benzodiazol-7-yl}formamido)acetate;

3-({2-benzamido-1-[1-(prop-2-enoyl)azepan-3-yl]-1H-1,3-benzodiazol-7-yl}formamido)propanoic acid;

2-({2-benzamido-1-[1-(prop-2-enoyl)azepan-3-yl]-1H-1,3-benzodiazol-7-yl}formamido)acetic acid;

N-[7-(3-methyl-1,2,4-oxadiazol-5-yl)-1-[1-(prop-2-enoyl)azepan-3-yl]-1H-1,3-benzodiazol-2-yl]benzamide;

1-(1-acryloylazepan-3-yl)-2-benzamido-N-(2-(methylsulfonyl)ethyl)-1H-benzo[d]imidazole-7-carboxamide;

N-(7-{[(3R,4R)-3,4-dihydroxypyrrolidin-1-yl]carbonyl}-1-[1-(prop-2-enoyl)azepan-3-yl]-1H-1,3-benzodiazol-2-yl)benzamide;

N-(7-{[3,4-dihydroxypyrrolidin-1-yl]carbonyl}-1-[1-(prop-2-enoyl)azepan-3-yl]-1H-1,3-benzodiazol-2-yl)benzamide;

N-[7-(3-methyl-1,2,4-oxadiazol-5-yl)-1-[4-(prop-2-enoyl)-1,4-oxazepan-6-yl]-1H-1,3-benzodiazol-2-yl]benzamide;

N-(1-{4-[(2E)-4-(dimethylamino)but-2-enoyl]-1,4-oxazepan-6-yl}-7-(3-methyl-1,2,4-oxadiazol-5-yl)-1H-1,3-benzodiazol-2-yl)benzamide;

N-{1-[(3R)-1-[(2E)-4-(dimethylamino)but-2-enoyl]piperidin-3-yl]-5-(hydroxymethyl)-1H-1,3-benzodiazol-2-yl}-3-(trifluoromethyl)benzamide;

N-{1-[1-[(2E)-4-(dimethylamino)but-2-enoyl]piperidin-3-yl]-5-(hydroxymethyl)-1H-1,3-benzodiazol-2-yl}-3-(trifluoromethyl)benzamide;

2-methyl-N-[7-methyl-5-(piperidin-1-ylmethyl)-1-[(3R)-1-(prop-2-enoyl)azepan-3-yl]-1H-1,3-benzodiazol-2-yl]pyridine-4-carboxamide;

2-methyl-N-[7-methyl-5-(piperidin-1-ylmethyl)-1-[1-(prop-2-enoyl)azepan-3-yl]-1H-1,3-benzodiazol-2-yl]pyridine-4-carboxamide;

N-[5-(azetidin-1-ylmethyl)-7-methyl-1-[(3R)-1-(prop-2-enoyl)azepan-3-yl]-1H-1,3-benzodiazol-2-yl]-2-methylpyridine-4-carboxamide;

N-[5-(azetidin-1-ylmethyl)-7-methyl-1-[1-(prop-2-enoyl)azepan-3-yl]-1H-1,3-benzodiazol-2-yl]-2-methylpyridine-4-carboxamide;

N-(5-{[(3S)-3-hydroxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-hydroxypyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3S)-3-fluoropyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3R)-3-fluoropyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3S)-3-methoxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3R)-3-methoxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2-methylpyridine-4-carboxamide;

N-{5-[(3,3-difluoropyrrolidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3,3-difluoropyrrolidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3-fluoroazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3-fluoroazetidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3,3-difluoroazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3,3-difluoroazetidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3-methoxyazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3-methoxyazetidin-1-yl)methyl]-7-methyl-1-[1-(prop-2-enoyl)azepan-3-yl]-1H-1,3-benzodiazol-2-yl}-2-methylpyridine-4-carboxamide;

(R)—N-(1-(1-acryloylazepan-3-yl)-5-((1,1-dioxidothiomorpholino)methyl)-7-methyl-1H-benzo[d]imidazol-2-yl)-2-methylisonicotinamide;

N-(1-(1-acryloylazepan-3-yl)-5-((1,1-dioxidothiomorpholino)methyl)-7-methyl-1H-benzo[d]imidazol-2-yl)-2-methylisonicotinamide;

N-(5-{[(3S)-3-methoxypyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

N-(5-{[(3R)-3-methoxypyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

N-(5-{[(3S)-3-fluoropyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

N-(5-{[(3R)-3-fluoropyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

2,3-difluoro-N-(5-{[(3R)-3-methoxypyrrolidin-1-yl]methyl}-7-methyl-1-[(3R)-1-(prop-2-enoyl)azepan-3-yl]-1H-1,3-benzodiazol-2-yl)benzamide;

2,3-difluoro-N-(5-{[3-methoxypyrrolidin-1-yl]methyl}-7-methyl-1-[1-(prop-2-enoyl)azepan-3-yl]-1H-1,3-benzodiazol-2-yl)benzamide;

6-methyl-N-{7-methyl-1-[(3R)-1-(prop-2-enoyl)azepan-3-yl]-5-(pyrrolidin-1-ylmethyl)-1H-1,3-benzodiazol-2-yl}pyridazine-4-carboxamide;

6-methyl-N-{7-methyl-1-[1-(prop-2-enoyl)azepan-3-yl]-5-(pyrrolidin-1-ylmethyl)-1H-1,3-benzodiazol-2-yl}pyridazine-4-carboxamide;

N-{1-[(3R)-1-[(2E)-but-2-enoyl]azepan-3-yl]-5-{[(3S)-3-methoxypyrrolidin-1-yl]methyl}-7-methyl-1H-1,3-benzodiazol-2-yl}-2,6-dimethylpyridine-4-carboxamide;

N-{1-[1-[(2E)-but-2-enoyl]azepan-3-yl]-5-{[3-methoxypyrrolidin-1-yl]methyl}-7-methyl-1H-1,3-benzodiazol-2-yl}-2,6-dimethylpyridine-4-carboxamide;

N-{1-[(3R)-1-[(2E)-but-2-enoyl]azepan-3-yl]-5-{[(3R)-3-methoxypyrrolidin-1-yl]methyl}-7-methyl-1H-1,3-benzodiazol-2-yl}-2-methylpyridine-4-carboxamide;

N-{1-[1-[(2E)-but-2-enoyl]azepan-3-yl]-5-{[3-methoxypyrrolidin-1-yl]methyl}-7-methyl-1H-1,3-benzodiazol-2-yl}-2-methylpyridine-4-carboxamide;

N-{1-[(3R)-1-[(2E)-but-2-enoyl]azepan-3-yl]-7-methyl-5-(pyrrolidin-1-ylmethyl)-1H-1,3-benzodiazol-2-yl}-2-methylpyridine-4-carboxamide;

N-{1-[1-[(2E)-but-2-enoyl]azepan-3-yl]-7-methyl-5-(pyrrolidin-1-ylmethyl)-1H-1,3-benzodiazol-2-yl}-2-methylpyridine-4-carboxamide;

N-{1-[(3R)-1-[(2E)-but-2-enoyl]azepan-3-yl]-5-{[(3S)-3-fluoropyrrolidin-1-yl]methyl}-7-methyl-1H-1,3-benzodiazol-2-yl}-2,6-dimethylpyridine-4-carboxamide;
N-{1-[1-[(2E)-but-2-enoyl]azepan-3-yl]-5-{[3-fluoropyrrolidin-1-yl]methyl}-7-methyl-1H-1,3-benzodiazol-2-yl}-2,6-dimethylpyridine-4-carboxamide;
N-{1-[(3R)-1-[(2E)-but-2-enoyl]azepan-3-yl]-5-{[(3S)-3-fluoropyrrolidin-1-yl]methyl}-7-methyl-1H-1,3-benzodiazol-2-yl}-2-methylpyridine-4-carboxamide;
N-{1-[1-[(2E)-but-2-enoyl]azepan-3-yl]-5-{[3-fluoropyrrolidin-1-yl]methyl}-7-methyl-1H-1,3-benzodiazol-2-yl}-2-methylpyridine-4-carboxamide;
methyl 1-[1-(prop-2-enoyl)piperidin-3-yl]-2-{[3-(trifluoromethyl)benzene]amido}-1H,4H,5H,6H,7H-imidazo[4,5-c]pyridine-5-carboxylate;
N-{5-methanesulfonyl-1-[1-(prop-2-enoyl)piperidin-3-yl]-1H,4H,5H,6H,7H-imidazo[4,5-c]pyridin-2-yl}-3-(trifluoromethyl)benzamide;
N-{5-acetyl-1-[1-(prop-2-enoyl)piperidin-3-yl]-1H,4H,5H,6H,7H-imidazo[4,5-c]pyridin-2-yl}-3-(trifluoromethyl)benzamide;
methyl 3-[1-(prop-2-enoyl)piperidin-3-yl]-2-{[3-(trifluoromethyl)benzene]amido}-3H,4H,5H,6H,7H-imidazo[4,5-c]pyridine-5-carboxylate;
N-{5-methanesulfonyl-3-[1-(prop-2-enoyl)piperidin-3-yl]-3H,4H,5H,6H,7H-imidazo[4,5-c]pyridin-2-yl}-3-(trifluoromethyl)benzamide;
N-{5-acetyl-3-[1-(prop-2-enoyl)piperidin-3-yl]-3H,4H,5H,6H,7H-imidazo[4,5-c]pyridin-2-yl}-3-(trifluoromethyl)benzamide;
N-{5-methyl-3-[1-(prop-2-enoyl)piperidin-3-yl]-3H,4H,5H,6H,7H-imidazo[4,5-c]pyridin-2-yl}-3-(trifluoromethyl)benzamide;
N-{1-[(3R)-1-[(2E)-but-2-enoyl]azepan-3-yl]-5-{[(3S)-3-methoxypyrrolidin-1-yl]methyl}-1H-1,3-benzodiazol-2-yl}-2,6-dimethylpyridine-4-carboxamide;
N-{1-[1-[(2E)-but-2-enoyl]azepan-3-yl]-5-{[(3S)-3-methoxypyrrolidin-1-yl]methyl}-1H-1,3-benzodiazol-2-yl}-2,6-dimethylpyridine-4-carboxamide;
N-(5-{[(3S)-3-methoxypyrrolidin-1-yl]methyl}-1-[(3R)-1-(prop-2-enoyl)azepan-3-yl]-1H-1,3-benzodiazol-2-yl)-2,6-dimethylpyridine-4-carboxamide;
N-(5-{[3-methoxypyrrolidin-1-yl]methyl}-1-[1-(prop-2-enoyl)azepan-3-yl]-1H-1,3-benzodiazol-2-yl)-2,6-dimethylpyridine-4-carboxamide;
N-{1-[(3R)-1-[(2E)-4-(dimethylamino)but-2-enoyl]azepan-3-yl]-7-methoxy-1H-1,3-benzodiazol-2-yl}-2-methylpyridine-4-carboxamide;
N-{1-[1-[(2E)-4-(dimethylamino)but-2-enoyl]azepan-3-yl]-7-methoxy-1H-1,3-benzodiazol-2-yl}-2-methylpyridine-4-carboxamide;
N-{7-chloro-1-[(3R)-1-[(2E)-4-(dimethylamino)but-2-enoyl]azepan-3-yl]-6-methoxy-1H-1,3-benzodiazol-2-yl}-2-methylpyridine-4-carboxamide;
N-{7-chloro-1-[1-[(2E)-4-(dimethylamino)but-2-enoyl]azepan-3-yl]-6-methoxy-1H-1,3-benzodiazol-2-yl}-2-methylpyridine-4-carboxamide;
N-{6-chloro-1-[(3R)-1-[(2E)-4-(dimethylamino)but-2-enoyl]azepan-3-yl]-5-methoxy-1H-1,3-benzodiazol-2-yl}-2-methylpyridine-4-carboxamide;
N-{6-chloro-1-[1-[(2E)-4-(dimethylamino)but-2-enoyl]azepan-3-yl]-5-methoxy-1H-1,3-benzodiazol-2-yl}-2-methylpyridine-4-carboxamide;
N-{6-chloro-1-[(3R)-1-[(2E)-4-(dimethylamino)but-2-enoyl]azepan-3-yl]-5-methoxy-1H-1,3-benzodiazol-2-yl}-2,6-dimethylpyridine-4-carboxamide;
N-{6-chloro-1-[1-[(2E)-4-(dimethylamino)but-2-enoyl]azepan-3-yl]-5-methoxy-1H-1,3-benzodiazol-2-yl}-2,6-dimethylpyridine-4-carboxamide;
1-[(3R)-1-(prop-2-enoyl)piperidin-3-yl]-2-{[3-(trifluoromethyl)benzene]amido}-1H-1,3-benzodiazole-5-carboxylic acid;
1-[1-(prop-2-enoyl)piperidin-3-yl]-2-{[3-(trifluoromethyl)benzene]amido}-1H-1,3-benzodiazole-5-carboxylic acid;
1-[(3R)-1-(prop-2-enoyl)piperidin-3-yl]-2-C-[3-(trifluoromethyl)benzene]-1H-1,3-benzodiazole-2,5-dicarboxamide;
1-[1-(prop-2-enoyl)piperidin-3-yl]-2-C-[3-(trifluoromethyl)benzene]-1H-1,3-benzodiazole-2,5-dicarboxamide;
1-[1-(prop-2-enoyl)azepan-3-yl]-2-{[3-(trifluoromethyl)benzene]amido}-1H-1,3-benzodiazole-7-carboxylic acid;
N-{7-methyl-1-[(6R)-4-(prop-2-enoyl)-1,4-oxazepan-6-yl]-1H-1,3-benzodiazol-2-yl}-3-(trifluoromethyl)benzamide;
N-{7-methyl-1-[(6S)-4-(prop-2-enoyl)-1,4-oxazepan-6-yl]-1H-1,3-benzodiazol-2-yl}-3-(trifluoromethyl)benzamide;
N-{1-[(3S)-1-[(2E)-4-(dimethylamino)but-2-enoyl]azepan-3-yl]-7-methyl-1H-1,3-benzodiazol-2-yl}-2-(trifluoromethyl)pyridine-4-carboxamide;
N-{1-[(3S)-1-[(2E)-4-(dimethylamino)but-2-enoyl]azepan-3-yl]-7-methyl-1H-1,3-benzodiazol-2-yl}-2-methyl-1,3-thiazole-5-carboxamide;
N-{1-[(3R)-1-[(2E)-4-(dimethylamino)but-2-enoyl]azepan-3-yl]-7-methyl-1H-1,3-benzodiazol-2-yl}-2-methyl-1,3-thiazole-5-carboxamide;
N-{1-[1-[(2E)-4-(dimethylamino)but-2-enoyl]azepan-3-yl]-7-methyl-1H-1,3-benzodiazol-2-yl}-2-methyl-1,3-thiazole-5-carboxamide;
N-{7-methyl-1-[(3S)-1-(prop-2-enoyl)azepan-3-yl]-1H-1,3-benzodiazol-2-yl}-3-(trifluoromethyl)benzamide; and
N-{7-methyl-1-[(3R)-1-(prop-2-enoyl)azepan-3-yl]-1H-1,3-benzodiazol-2-yl}-3-(trifluoromethyl)benzamide; or a pharmaceutically acceptable salt thereof.
(R)—N-(7-chloro-1-(1-(1-methyl-1,2,5,6-tetrahydropyridine-3-carbonyl)azepan-3-yl)-1H-benzo[d]imidazol-2-yl)-2-methylisonicotinamide;
(N-(7-chloro-1-(1-(1-methyl-1,2,5,6-tetrahydropyridine-3-carbonyl)azepan-3-yl)-1H-benzo[d]imidazol-2-yl)-2-methylisonicotinamide;
(R)—N-(7-chloro-1-(1-(1-methyl-1,2,3,6-tetrahydropyridine-4-carbonyl)azepan-3-yl)-1H-benzo[d]imidazol-2-yl)-2-methylisonicotinamide;
N-(7-chloro-1-(1-(1-methyl-1,2,3,6-tetrahydropyridine-4-carbonyl)azepan-3-yl)-1H-benzo[d]imidazol-2-yl)-2-methylisonicotinamide;
(R,E)-N-(7-chloro-1-(1-(4-(dimethylamino)-4-methylpent-2-enoyl)azepan-3-yl)-1H-benzo[d]imidazol-2-yl)-2-methylisonicotinamide;
N-(7-chloro-1-(1-(4-(dimethylamino)-4-methylpent-2-enoyl)azepan-3-yl)-1H-benzo[d]imidazol-2-yl)-2-methylisonicotinamide;
tert-butyl 4-acryloyl-6-(7-chloro-2-(2-methylisonicotinamido)-1H-benzo[d]imidazol-1-yl)-1,4-diazepane-1-carboxylate;
N-(1-(1-acryloyl-1,4-diazepan-6-yl)-7-chloro-1H-benzo[d]imidazol-2-yl)-2-methylisonicotinamide;
N-(1-(1-acetyl-4-acryloyl-1,4-diazepan-6-yl)-7-chloro-1H-benzo[d]imidazol-2-yl)-2-methylisonicotinamide;
(R)—N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;
N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;

(R,E)-N-(7-chloro-1-(1-(4-(dicyclopropylamino)but-2-enoyl)azepan-3-yl)-1H-benzo[d]imidazol-2-yl)-2-methylisonicotinamide;
N-(7-chloro-1-(1-(4-(dicyclopropylamino)but-2-enoyl)azepan-3-yl)-1H-benzo[d]imidazol-2-yl)-2-methylisonicotinamide;
(R)—N-(1-(1-acryloylazepan-3-yl)-7-methyl-5-((4-methyl-3-oxopiperazin-1-yl)methyl)-1H-benzo[d]imidazol-2-yl)-2,6-dimethylisonicotinamide;
N-(1-(1-acryloylazepan-3-yl)-7-methyl-5-((4-methyl-3-oxopiperazin-1-yl)methyl)-1H-benzo[d]imidazol-2-yl)-2,6-dimethylisonicotinamide;
(R)—N-(5-((4-acetylpiperazin-1-yl)methyl)-1-(1-acryloylazepan-3-yl)-7-methyl-1H-benzo[d]imidazol-2-yl)-2,6-dimethylisonicotinamide;
N-(5-((4-acetylpiperazin-1-yl)methyl)-1-(1-acryloylazepan-3-yl)-7-methyl-1H-benzo[d]imidazol-2-yl)-2,6-dimethylisonicotinamide;
(E)-N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
(R,E)-tert-butyl 4-(3-(7-chloro-2-(2-methylisonicotinamido)-1H-benzo[d]imidazol-1-yl)azepan-1-yl)-4-oxobut-2-enyl(methyl)carbamate;
tert-butyl 4-(3-(7-chloro-2-(2-methylisonicotinamido)-1H-benzo[d]imidazol-1-yl)azepan-1-yl)-4-oxobut-2-enyl(methyl)carbamate;
(R,E)-N-(7-chloro-1-(1-(4-(methylamino)but-2-enoyl)azepan-3-yl)-1H-benzo[d]imidazol-2-yl)-2-methylisonicotinamide;
N-(7-chloro-1-(1-(4-(methylamino)but-2-enoyl)azepan-3-yl)-1H-benzo[d]imidazol-2-yl)-2-methylisonicotinamide;
(R,E)-N-(7-chloro-1-(1-(4-(methylamino)but-2-enoyl)azepan-3-yl)-1H-benzo[d]imidazol-2-yl)-2,6-dimethylisonicotinamide;
N-(7-chloro-1-(1-(4-(methylamino)but-2-enoyl)azepan-3-yl)-1H-benzo[d]imidazol-2-yl)-2,6-dimethylisonicotinamide;
(R,E)-N-(1-(1-(4-(dimethylamino)but-2-enoyl)azepan-3-yl)-7-(trifluoromethyl)-1H-benzo[d]imidazol-2-yl)-2-methylisonicotinamide;
N-(1-(1-(4-(dimethylamino)but-2-enoyl)azepan-3-yl)-7-(trifluoromethyl)-1H-benzo[d]imidazol-2-yl)-2-methylisonicotinamide;
(R,E)-N-(1-(1-(4-(dimethylamino)but-2-enoyl)azepan-3-yl)-7-(trifluoromethyl)-1H-benzo[d]imidazol-2-yl)-2,6-dimethylisonicotinamide;
N-(1-(1-(4-(dimethylamino)but-2-enoyl)azepan-3-yl)-7-(trifluoromethyl)-1H-benzo[d]imidazol-2-yl)-2,6-dimethylisonicotinamide;
(R,E)-N-(7-chloro-1-(1-(4-(cyclopropylamino)but-2-enoyl)azepan-3-yl)-1H-benzo[d]imidazol-2-yl)-2-methylisonicotinamide;
N-(7-chloro-1-(1-(4-(cyclopropylamino)but-2-enoyl)azepan-3-yl)-1H-benzo[d]imidazol-2-yl)-2-methylisonicotinamide;
(R,E)-N-(1-(1-(4-(tert-butylamino)but-2-enoyl)azepan-3-yl)-7-chloro-1H-benzo[d]imidazol-2-yl)-2-methylisonicotinamide;
N-(1-(1-(4-(tert-butylamino)but-2-enoyl)azepan-3-yl)-7-chloro-1H-benzo[d]imidazol-2-yl)-2-methylisonicotinamide;
(R,E)-N-(7-chloro-1-(1-(4-(1-methylcyclopropylamino)but-2-enoyl)azepan-3-yl)-1H-benzo[d]imidazol-2-yl)-2-methylisonicotinamide;
N-(7-chloro-1-(1-(4-(1-methylcyclopropylamino)but-2-enoyl)azepan-3-yl)-1H-benzo[d]imidazol-2-yl)-2-methylisonicotinamide;
(R)—N-(1-(1-acryloylazepan-3-yl)-7-chloro-6-(2-(pyrrolidin-1-yl)ethoxy)-1H-benzo[d]imidazol-2-yl)-2-methylisonicotinamide;
N-(1-(1-acryloylazepan-3-yl)-7-chloro-6-(2-(pyrrolidin-1-yl)ethoxy)-1H-benzo[d]imidazol-2-yl)-2-methylisonicotinamide;
(R,E)-N-(1-(1-but-2-enoylazepan-3-yl)-7-chloro-6-(2-(pyrrolidin-1-yl)ethoxy)-1H-benzo[d]imidazol-2-yl)-2-methylisonicotinamide;
N-(1-(1-but-2-enoylazepan-3-yl)-7-chloro-6-(2-(pyrrolidin-1-yl)ethoxy)-1H-benzo[d]imidazol-2-yl)-2-methylisonicotinamide;
(R,E)-N-(1-(1-but-2-enoylazepan-3-yl)-7-chloro-6-(2-(pyrrolidin-1-yl)ethoxy)-1H-benzo[d]imidazol-2-yl)-2,6-dimethylisonicotinamide;
N-(1-(1-but-2-enoylazepan-3-yl)-7-chloro-6-(2-(pyrrolidin-1-yl)ethoxy)-1H-benzo[d]imidazol-2-yl)-2,6-dimethylisonicotinamide;
(S,E)-N-(7-chloro-1-(1-(4-(dimethylamino)but-2-enoyl)azepan-3-yl)-1H-benzo[d]imidazol-2-yl)-2-methylisonicotinamide;
N-(7-chloro-1-(1-(4-(dimethylamino)but-2-enoyl)azepan-3-yl)-1H-benzo[d]imidazol-2-yl)-2-methylisonicotinamide;
(S,E)-N-(7-chloro-1-(1-(4-(dimethylamino)but-2-enoyl)azepan-3-yl)-1H-benzo[d]imidazol-2-yl)-2,6-dimethylisonicotinamide;
N-(7-chloro-1-(1-(4-(dimethylamino)but-2-enoyl)azepan-3-yl)-1H-benzo[d]imidazol-2-yl)-2,6-dimethylisonicotinamide;
(S,E)-N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
(R,E)-N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
(S,E)-N-(7-chloro-1-(1-(4-(dimethylamino)but-2-enoyl)azepan-3-yl)-1H-benzo[d]imidazol-2-yl)-2-(dimethylphosphoryl)isonicotinamide;
N-(7-chloro-1-(1-(4-(dimethylamino)but-2-enoyl)azepan-3-yl)-1H-benzo[d]imidazol-2-yl)-2-(dimethylphosphoryl)isonicotinamide;
(R,E)-N-(7-chloro-1-(1-(4-(dimethylamino)but-2-enoyl)azepan-3-yl)-1H-benzo[d]imidazol-2-yl)-2-(dimethylphosphoryl)isonicotinamide; and
N-(7-chloro-1-(1-(4-(dimethylamino)but-2-enoyl)azepan-3-yl)-1H-benzo[d]imidazol-2-yl)-2-(dimethylphosphoryl)isonicotinamide;
or a pharmaceutically acceptable salt thereof.

In a particular embodiment, provided herein is a compound selected from:
(R,E)-N-(7-chloro-1-(1-(4-(pyrrolidin-1-yl)but-2-enoyl)azepan-3-yl)-1H-benzo[d]imidazol-2-yl)-2-methylisonicotinamide;
N-(7-chloro-1-(1-(4-(pyrrolidin-1-yl)but-2-enoyl)azepan-3-yl)-1H-benzo[d]imidazol-2-yl)-2-methylisonicotinamide;

(R,E)-N-(7-chloro-1-(1-(4-(3-fluoroazetidin-1-yl)but-2-enoyl)azepan-3-yl)-1H-benzo[d]imidazol-2-yl)-2-methylisonicotinamide;

N-(7-chloro-1-(1-(4-(3-fluoroazetidin-1-yl)but-2-enoyl)azepan-3-yl)-1H-benzo[d]imidazol-2-yl)-2-methylisonicotinamide;

(S)—N-(1-(1-acryloylpiperidin-3-yl)-5-methyl-1H-benzo[d]imidazol-2-yl)-3-(trifluoromethyl)benzamide;

N-(1-(1-acryloylpiperidin-3-yl)-5-methyl-1H-benzo[d]imidazol-2-yl)-3-(trifluoromethyl)benzamide;

(R,E)-N-(7-chloro-1-(1-(4-(dimethylamino)but-2-enoyl)azepan-3-yl)-1H-benzo[d]imidazol-2-yl)-2-methylisonicotinamide;

N-(7-chloro-1-(1-(4-(dimethylamino)but-2-enoyl)azepan-3-yl)-1H-benzo[d]imidazol-2-yl)-2-methylisonicotinamide;

(R,E)-N-(7-chloro-1-(1-(4-(dimethylamino)but-2-enoyl)azepan-3-yl)-1H-benzo[d]imidazol-2-yl)-2,6-dimethylisonicotinamide;

N-(7-chloro-1-(1-(4-(dimethylamino)but-2-enoyl)azepan-3-yl)-1H-benzo[d]imidazol-2-yl)-2,6-dimethylisonicotinamide;

(R,E)-N-(1-(1-(4-(dimethylamino)but-2-enoyl)azepan-3-yl)-7-methyl-1H-benzo[d]imidazol-2-yl)-2-methylisonicotinamide;

N-(1-(1-(4-(dimethylamino)but-2-enoyl)azepan-3-yl)-7-methyl-1H-benzo[d]imidazol-2-yl)-2-methylisonicotinamide;

(R,E)-N-(1-(1-(4-(dimethylamino)but-2-enoyl)azepan-3-yl)-7-methyl-1H-benzo[d]imidazol-2-yl)-2-(trifluoromethyl)isonicotinamide;

N-(1-(1-(4-(dimethylamino)but-2-enoyl)azepan-3-yl)-7-methyl-1H-benzo[d]imidazol-2-yl)-2-(trifluoromethyl)isonicotinamide;

(R)—N-(1-(1-acryloylazepan-3-yl)-7-chloro-6-methoxy-1H-benzo[d]imidazol-2-yl)pyridazine-4-carboxamide;

N-(1-(1-acryloylazepan-3-yl)-7-chloro-6-methoxy-1H-benzo[d]imidazol-2-yl)pyridazine-4-carboxamide;

N-(7-methyl-1-(1-(vinylsulfonyl)azepan-3-yl)-1H-benzo[d]imidazol-2-yl)-3-(trifluoromethyl)benzamide;

N-(1-(1-acryloylazepan-3-yl)-7-(pyrrolidin-1-ylmethyl)-1H-benzo[d]imidazol-2-yl)-3-(trifluoromethyl)benzamide;

tert-butyl 4-acryloyl-6-(7-chloro-2-(2-methylisonicotinamido)-1H-benzo[d]imidazol-1-yl)-1,4-diazepane-1-carboxylate;

N-(1-(1-acryloyl-1,4-diazepan-6-yl)-7-chloro-1H-benzo[d]imidazol-2-yl)-2-methylisonicotinamide;

N-(1-(1-acetyl-4-acryloyl-1,4-diazepan-6-yl)-7-chloro-1H-benzo[d]imidazol-2-yl)-2-methylisonicotinamide;

(R)—N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;

N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;

(R,E)-N-(7-chloro-1-(1-(4-(dicyclopropylamino)but-2-enoyl)azepan-3-yl)-1H-benzo[d]imidazol-2-yl)-2-methylisonicotinamide;

N-(7-chloro-1-(1-(4-(dicyclopropylamino)but-2-enoyl)azepan-3-yl)-1H-benzo[d]imidazol-2-yl)-2-methylisonicotinamide;

(R)-1-(1-acryloylpiperidin-3-yl)-2-(3-(trifluoromethyl)benzamido)-1H-benzo[d]imidazole-5-carboxylic acid;

1-(1-acryloylpiperidin-3-yl)-2-(3-(trifluoromethyl)benzamido)-1H-benzo[d]imidazole-5-carboxylic acid;

(R)-1-(1-acryloylpiperidin-3-yl)-2-(3-(trifluoromethyl)benzamido)-1H-benzo[d]imidazole-5-carboxamide;

1-(1-acryloylpiperidin-3-yl)-2-(3-(trifluoromethyl)benzamido)-1H-benzo[d]imidazole-5-carboxamide; and 1-(1-acryloylazepan-3-yl)-2-(3-(trifluoromethyl)benzamido)-1H-benzo[d]imidazole-7-carboxylic acid; or a pharmaceutically salt form thereof; particularly acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate; and more particularly, mesylate.

In another aspect, provided herein is a pharmaceutical composition comprising a compound of Formula (1), (2), (2A), (2B), (2C), (2D), (3A), (3B), (3C), (4) or (5), or a pharmaceutically acceptable salt thereof, and a pharmaceutically acceptable carrier.

In another aspect, provided herein is a combination comprising a compound of Formula (1), (2), (2A), (2B), (2C), (2D), (3A), (3B), (3C), (4) or (5), or a pharmaceutically acceptable salt thereof, and a chemotherapeutic agent.

In another aspect, provided herein is the use of a compound of Formula (1), (2), (2A), (2B), (2C), (2D), (3A), (3B), (3C), (4) or (5), or a pharmaceutically acceptable salt thereof, for inhibiting epidermal growth factor receptor (EGFR).

In another aspect, provided herein is the use of a compound of Formula (1), (2), (2A), (2B), (2C), (2D), (3A), (3B), (3C), (4) or (5), or a pharmaceutically acceptable salt thereof, in the manufacture of a medicament for treating a condition mediated by epidermal growth factor receptor (EGFR).

In another aspect, provided herein is the use of a compound of Formula (1), (2), (2A), (2B), (2C), (2D), (3A), (3B), (3C), (4) or (5), or a pharmaceutically acceptable salt thereof, for treating a condition mediated by epidermal growth factor receptor (EGFR).

In one embodiment, the EGFR is a mutant EGFR; for example, wherein the mutant EGFR comprises G719S, G719C, G719A, L858R, L861Q, an exon 19 deletion mutation or an exon 20 insertion mutation. In other embodiments, the mutant EGFR further comprises an EGFR T790M, T854A or D761Y resistance mutation; more particularly, the mutant EGFR comprises L858R or an exon 19 deletion, each of which may further comprise an EGFR T790M.

In another aspect, provided herein is the use of a compound of Formula (1), (2), (2A), (2B), (2C), (2D), (3A), (3B), (3C), (4) or (5), or a pharmaceutically acceptable salt thereof, for treating a condition mediated by EGFR, wherein the condition is selected from non-small cell lung cancer (NSCLC), head and neck cancer, colorectal cancer, breast cancer, pancreatic cancer, ovarian cancer, gastric cancer, glioma and prostate cancer.

In another aspect, provided herein is a method for inhibiting epidermal growth factor, comprising administering to a system or subject a therapeutically effective amount of a compound of Formula (1), (2), (2A), (2B), (2C), (2D), (3A), (3B), (3C), (4) or (5), or a pharmaceutically acceptable salt thereof.

Also provided herein is a method for treating a condition mediated by epidermal growth factor receptor, comprising administering to a system or subject in need of such treatment an effective amount of a compound of Formula (1), (2), (2A), (2B), (2C), (2D), (3A), (3B), (3C), (4) or (5), or a pharmaceutically acceptable salt thereof, In another aspect, provided herein are mutant specific EGFR inhibitors that are less effective against wild type EGFR.

DETAILED DESCRIPTION OF THE INVENTION

Definitions

The term "$C_{1-6}$ alkyl" as used herein denotes a saturated or unsaturated alkyl radical having from 1 up to 6 carbon atoms, the radicals being either linear or branched with single or multiple branching; for example, butyl, such as n-butyl, sec-butyl, isobutyl, tert-butyl; propyl, such as n-propyl or isopropyl; ethyl or methyl. In particular embodiments, the $C_{1-6}$ alkyl is a saturated alkyl radical, and where specified, may be unsubstituted or substituted, for example by halo (i.e., haloalkyl such as trifluoromethyl, and the like), hydroxy (hydroxyalkyl such as hydroxymethyl, hydroxyethyl, 2-hydroxy-2-propyl and the like) or cyano (cyanoalkyl such as cyanomethyl, cyanoethyl and the like).

The term "$C_{1-6}$alkoxy" as used herein refers to the group —$OR^a$, where $R^a$ is $C_{1-6}$ alkyl group as defined herein. Non-limiting examples of alkoxy groups, as used herein, include methoxy, ethoxy, n-propoxy, isopropoxy, n-butyloxy, t-butyloxy, pentyloxy, hexyloxy and the like.

The term "$C_{1-6}$ haloalkyl" refers to $C_{1-6}$ alkyl group as defined herein, substituted with one or more halo groups, which may be the same or different. The haloalkyl can be monohaloalkyl, dihaloalkyl or polyhaloalkyl, including perhaloalkyl. In certain embodiments, a haloalkyl group is trifluoromethyl.

The term "cycloalkyl" as used herein, refers to a saturated or unsaturated monocyclic hydrocarbon group. The terms "$C_{3-7}$cycloalkyl" or "$C_5$-6 cycloalkyl" as used herein refer to a cycloalkyl having from 3 up to 7 carbon atoms, or from 5 to 6 carbon atoms, respectively; for example, cyclopropyl, cyclobutyl, cyclopentyl, cyclohexyl or cycloheptyl.

As used herein, the term "aryl" refers to an aromatic hydrocarbon group having 6-10 carbon atoms in the ring portion, and can be a single or bicyclic aromatic ring. Non-limiting examples include phenyl, naphthyl or tetrahydronaphthyl.

The term "heteroaryl," as used herein, refers to a 5-10 membered heteroaromatic ring having 1 to 4 heteroatoms independently selected from nitrogen, oxygen and sulfur, which may be a 5-6 membered monocyclic ring or an 8-10 membered fused bicyclic ring where at least one of the rings is aromatic. Such bicyclic ring systems may be fused to one or more aryl, cycloalkyl, or heterocycloalkyl rings. Non-limiting examples of heteroaryl groups, as used herein, include 2- or 3-furyl; 1-, 2-, 4-, or 5-imidazolyl; 3-, 4-, or 5-isothiazolyl; 3-, 4-, or 5-isoxazolyl; 2-, 4-, or 5-oxazolyl; 4- or 5-1,2,3-oxadiazolyl; 2- or 3-pyrazinyl; 1-, 3-, 4-, or 5-pyrazolyl; 3-, 4-, 5- or 6-pyridazinyl; 2-, 3-, or 4-pyridyl; 2-, 4-, 5- or 6-pyrimidinyl; 1-, 2- or 3-pyrrolyl; 1- or 5-tetrazolyl; 2- or 5-1,3,4-thiadiazolyl; 2-, 4-, or 5-thiazolyl; 2- or 3-thienyl; 2-, 4- or 6-1,3,5-triazinyl; 1-, 3- or 5-1,2,4-triazolyl; 1-, 4- or 5-1,2,3-triazolyl; 2-, 4-, 5-, 6-, or 7-benzoxazolyl; 1-, 2-, 4-, 5-, 6-, or 7-benzimidazolyl; 2-, 4-, 5-, 6-, or 7-benzothiazolyl; 2-, 3-, 4-, 5-, 6-, 7-benzo[b]thienyl; 2-, 3-, 4-, 5-, 6-, 7-, 8-, 9-benzo[b]oxepine; 2-, 4-, 5-, 6-, 7-, or 8-benzoxazinyl; 1-, 2-, 3-, 4-, 5-, 6-, 7-, 8, or 9-carbazolyl; 3-, 4-, 5-, 6-, 7-, or 8-cinnolinyl; 2-, 4-, or 5-4H-imidazo[4,5-d]thiazolyl; 2-, 3-, 5-, or 6-imidazo[2,1-b]thiazolyl; 2-, 3-, 6-, or 7-imidazo[1,2-b][1,2,4]triazinyl; 1-, 3-, 4-, 5-, 6-, or 7-indazolyl; 1-, 2-, 3-, 5-, 6-, 7-, or 8-indolizinyl; 1-, 2-, 3-, 4-, 5-, 6-, or 7-indolyl; 1-, 2-, 3-, 4-, 5-, 6-, or 7-isoindolyl; 1-, 3-, 4-, 5-, 6-, 7-, or 8-isoquinoliyl; 2-, 3-, 4-, 5-, 6-, or 7-naphthyridinyl; 1-, 4-, 5-, 6-, 7-, or 8-phthalazinyl; 2-, 4-, 6-, or 7-pteridinyl; 2-, 6-, 7-, or 8-purinyl; 2-, 3-, 5-, 6-, or 7-furo[3,2-b]-pyranyl; 1-, 3-, or 5-1H-pyrazolo[4,3-d]-oxazolyl; 2-, 3-, 5-, or 8-pyrazino[2,3-d]pyridazinyl; 1-, 2-, 3-, 4-, 5-, or 8-5H-pyrido[2,3-d]-o-oxazinyl; 1-, 2-, 3-, 4-, 6-, 7-, 8-, or 9-quinolizinyl; 2-, 3-, 4-, 5-, 6-, 7-, or 8-quinolinyl; 2-, 3-, 4-, 5-, 6-, 7-, or 8-quinazolinyl; and 2-, 3-, 4-, or 5-thieno[2,3-b]furanyl.

As used herein, the terms "heterocyclyl" or "heterocyclic" refer to a saturated or unsaturated non-aromatic ring or ring system, e.g., which is a 4-, 5-, 6-, or 7-membered monocyclic, or 6-, 7-, 8-, 9-, 10-, 11-, or 12-membered bicyclic ring system and contains at least one heteroatom selected from O, S, P and N, where the N, S and P can also optionally be oxidized to various oxidation states. The heterocyclic group can be attached at a heteroatom or a carbon atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, azetidinyl, tetrahydropyran, dihydropyran, oxathiolane, dithiolane, 1,3-dioxane, 1,3-dithiane, oxathiane, thiomorpholine, and the like. Where specified, the term "heterocyclyl" further refers to heterocyclic groups that is substituted by oxo; for example, pyrrolidin-2-one, 1,6-dihydro-pyridin-2(3H)-one, pyridin-2-(3H)-one, and the like.

The term "heteroatoms," as used herein, refers to nitrogen (N), oxygen (O), sulfur (S) or phosphorus (P) atoms, wherein the N, S and P can optionally be oxidized to various oxidation states.

The term "acceptable" with respect to a compound, formulation, composition or ingredient, as used herein, means having no persistent detrimental effect on the general health of the subject being treated.

The term "administration" or "administering" of the subject compound means providing a compound of the invention, a pharmaceutically acceptable salt, a pharmaceutically acceptable solvate, or solvate thereof to a subject in need of treatment.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

As used herein, the term "inhibit", "inhibition" or "inhibiting" refers to the reduction or suppression of a given condition, symptom, or disorder, or disease, or a significant decrease in the baseline activity of a biological activity or process.

The term "pharmaceutically acceptable," as used herein, refers to a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "carrier," as used herein, refers to chemical compounds or agents that facilitate the incorporation of a compound described herein into cells or tissues. The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329; Remington: The Science and Practice of Pharmacy, $21^{st}$ Ed. Pharmaceutical Press 2011; and subsequent versions thereof). Except insofar as any conventional carrier is incompatible with the active ingredient, its use in the therapeutic or pharmaceutical compositions is contemplated.

The term "pharmaceutically acceptable salt," as used herein, refers to a formulation of a compound that does not cause significant irritation to an organism to which it is administered and does not abrogate the biological activity and properties of the compounds described herein.

The term "combination" as used herein means a product that results from the mixing or combining of more than one active ingredient and includes both fixed and non-fixed combinations of the active ingredients. The term "fixed combination" means that the active ingredients, by way of example, a compound of Formula (1), (2), (2A), (2B), (2C), (2D), (3A), (3B), (3C), (4) or (5), or a pharmaceutically acceptable salt thereof, and an additional therapeutic agent, are both administered to a patient simultaneously in the form of a single entity or dosage. The term "non-fixed combination" means that the active ingredients, by way of example, a compound of Formula (1), (2), (2A), (2B), (2C), (2D), (3A), (3B), (3C), (4) or (5) or a pharmaceutically acceptable salt thereof, and an additional therapeutic agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The terms "composition" or "pharmaceutical composition," as used herein, refers to a mixture of at least one compound, such as a compound Formula (1), (2), (2A), (2B), (2C), (2D), (3A), (3B), (3C), (4) or (5), or a pharmaceutically acceptable salt thereof, with at least one and optionally more than one other pharmaceutically acceptable chemical components, such as carriers, stabilizers, diluents, dispersing agents, suspending agents, thickening agents, and/or excipients.

The term "subject" or "patient," as used herein, encompasses mammals and non-mammals. Examples of mammals include, but are not limited to, humans, chimpanzees, apes, monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

As used herein, a subject is "in need of" a treatment if such subject would benefit biologically, medically or in quality of life from such treatment.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

The term "a therapeutically effective amount" of a compound of the present invention, as used herein, refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to: (a) at least partially alleviating, inhibiting, preventing and/or ameliorating a condition, or a disorder or a disease (i) mediated by EGFR kinase, (ii) associated with EGFR kinase activity, or (iii) characterized by activity (normal or abnormal) of EGFR kinases; (b) reducing or inhibiting the activity of EGFR kinase; or (c) reducing or inhibiting the expression of EGFR kinase. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of EGFR kinase; or at least partially reducing or inhibiting the expression of EGFR kinase.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

In addition, as used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

Unless specified otherwise, the term "compound(s) of the invention" or "compound(s) provided herein" refers to compounds of Formula (1) and subformulae thereof (Formula (2), (2A), (2B), (2C), (2D), (3A), (3B), (3C), (4) or (5)), a pharmaceutically acceptable salt thereof, a prodrug thereof, a stereoisomer thereof (including diastereoisomers and enantiomers), a tautomer thereof, an isotopically labeled compound thereof (including deuterium substitutions), as well as inherently formed moieties (e.g., polymorphs, solvates and/or hydrates).

As used herein, the term "a," "an," "the" and similar terms used in the context of the present invention (especially in the context of the claims) are to be construed to cover both the singular and plural unless otherwise indicated herein or clearly contradicted by the context.

The chemical naming protocol and structure diagrams used herein employ and rely on the chemical naming features as utilized by the ChemDraw program (available from CambridgeSoft Corp., Cambridge, Mass.). In particular, compound structures and names were derived using Chemdraw Ultra (Version 10.0) and/or ChemAxon Name Generator (JChem Version 5.3.1.0).

DESCRIPTION OF THE PREFERRED EMBODIMENTS

The invention provides compositions and methods for modulating the activity of the epidermal growth factor receptor (EGFR). In one aspect, the invention provides compounds which act as inhibitors of EGFR. Various embodiments of the invention are described herein.

In one aspect, provided herein is a compound of Formula (1), a tautomer thereof, or a pharmaceutically acceptable salt thereof:

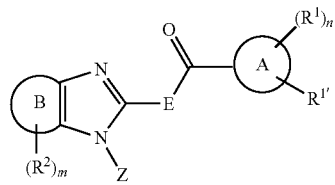

(1)

wherein Ring A is a 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Ring B is phenyl; a 5-6 membered heteroaryl comprising 1-3 heteroatoms selected from N, O and S; or a 5-6 membered heterocyclyl comprising 1-2 heteroatoms selected from N, O and S, and optionally substituted by oxo;

E is NH or $CH_2$;

$R^1$, $R^{1'}$ and $R^2$ are independently hydrogen; halo; cyano; $C_{1-6}$ alkyl; $C_{1-6}$ haloalkyl; 5-6 membered heteroaryl comprising 1-4 heteroatoms selected from N, O and S; phenyl, 5-6 membered heterocyclyl comprising 1-2 heteroatoms selected from N, O, S and P, and optionally substituted by oxo; $-X^1-C(O)OR^3$; $-X^1-O-C(O)R^3$; $-X^1-C(O)R^3$; $-X^1-C(O)NR^4R^5$; $-X^1-C(O)NR^4-X^3-C(O)OR^3$; $-X-C(O)NR^4-X^3-S(O)_{0-2}R^6$; $-X^1-NR^4R^5$; $-X^1NR^4-X^2-C(O)R^3$; $-X^1-NR^4-X^2-C(O)OR^3$; $-X^1-NR^4-X^2-C(O)NR^4R^5$; $-X^1-NR^4-X^3-S(O)_{0-2}R^6$; $-X^1-NR^4S(O)_2R^6$; $-X^1-OS(O)_2R^6$; $-X^1-OR^3$; $-X^1-O-X^4-OR^3$; $-X^1-O-X^4-S(O)_{0-2}R^6$; $-X^1-O-X^4-NR^4R^5$; $-X^1-S(O)_{0-2}R^6$; $-X^1-S(O)_{0-2}-X^3-NR^4R^5$; $-X^1-C(O)NR^4-X^3-P(O)R^{6a}R^{6b}$; $-X^1-NR^4-X^1-P(O)R^{6a}R^{6b}$; $-X^1-O-X^1-P(O)R^{6a}R^{6b}$; $-X^1-P(O)R^{6a}-X^1-NR^4R^5$; $-X^1-P(O)R^{6a}R^{6b}$ or $-X^1-S(O)_2NR^4R^5$; wherein each phenyl, heteroaryl, or heterocyclyl in $R^1$ or $R^2$ is unsubstituted or substituted by 1-3 groups selected from OH, halo, $C_{1-6}$ alkyl, $C_{1-6}$ haloalkyl and $C_{1-6}$ haloalkoxy;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$;

$R^6$ is $C_{1-6}$ alkyl or $C_{1-6}$ haloalkyl;

$R^{6a}$ and $R^{6b}$ are independently hydroxy, $C_{1-6}$ alkyl, $C_{1-6}$ haloalkyl, $C_{1-6}$ alkoxy, $C_{1-6}$ haloalkoxy, 6-10 membered monocyclic or bicyclic aryl; a 5-10 membered heteroaryl comprising 1-4 heteroatoms selected from N, O and S; or a 4-12 membered monocyclic or bicyclic heterocyclyl comprising 1-4 heteroatoms selected from N, O and S, and optionally substituted with oxo;

Z is

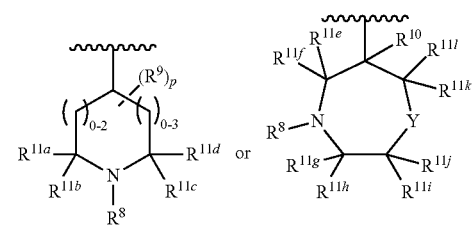

wherein Y is O or $NR^{19}$;

$R^8$ is
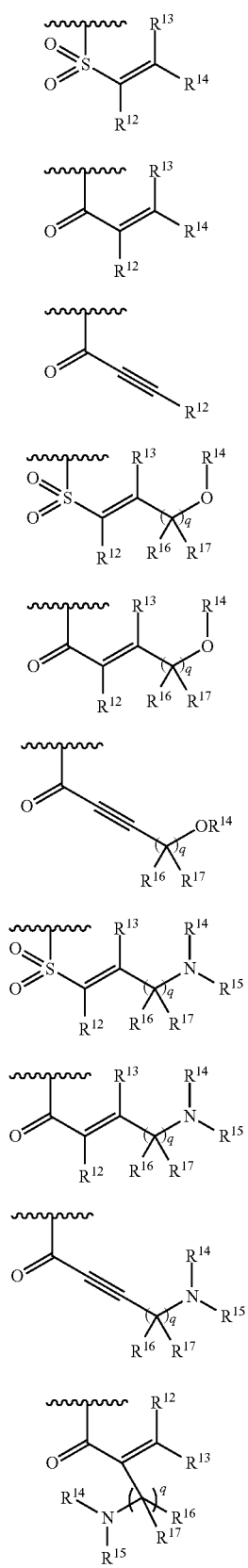
(a)
(b)
(c)
(d)
(e)
(f)
(g)
(h)
(i)
(j)
-continued
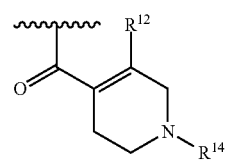 (k)
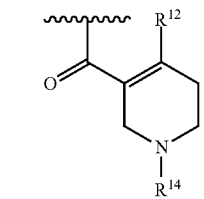 (l)
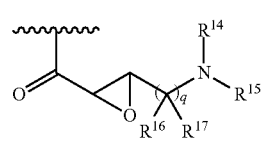 (m)
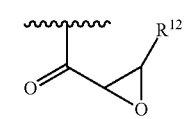 (n)
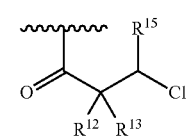 (o)
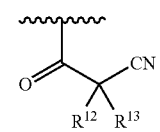 (p)
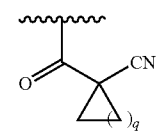 (q)
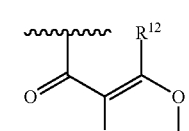 (r)
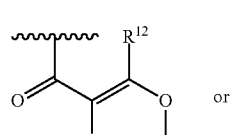 (s)
or
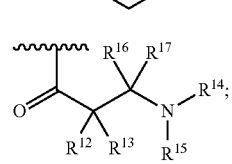 (t)
$R^9$ and $R^{10}$ are independently hydrogen, halo, $C_{1-6}$ alkyl, $C_{1-6}$ haloalkyl, OH, cyano, $C_{1-6}$ alkoxy, $C_{1-6}$ haloalkoxy;

$R^{11a}$, $R^{11b}$, $R^{11c}$, $R^{11d}$, $R^{11e}$, $R^{11f}$, $R^{11g}$, $R^{11g}$, $R^{11h}$, $R^{11i}$, $R^{11j}$, $R^{11k}$ and $R^{11l}$ are independently hydrogen, $C_{1-6}$ alkyl or $C_{1-6}$ haloalkyl;

$R^{12}$ and $R^{13}$ are independently hydrogen, halo, cyano, $C_{1-6}$ alkyl or $C_{1-6}$ haloalkyl;

$R^{14}$ and $R^{15}$ are independently hydrogen, $C_{1-6}$ alkyl, -$L^1$-$R^{23}$, —$(CR^aR^b)_{2-3}$—$R^c$ or -$L^2$-$R^d$; or $R^{14}$ and $R^{15}$ together with N in $NR^{14}R^{15}$ may form a 4-7 membered ring containing 1-2 heteroatoms selected from N, O, S and P, and optionally substituted with 1-4 $R^{18}$ groups;

$R^{16}$ and $R^{17}$ are independently hydrogen or $C_{1-6}$ alkyl; or $R^{16}$ and $R^{17}$ together with the carbon to which they are attached may form a $C_{3-6}$ cycloalkyl;

$X^1$ and $X^2$ are independently a bond or $C_{1-6}$ alkyl;

$X^3$ is $C_{1-6}$ alkyl;

$X^4$ is $C_{2-6}$ alkyl;

$R^{19}$ hydrogen, $C_{1-6}$ alkyl, $COR^{20}$, $COOR^{20}$, $CONR^{20}R^{21}$ or $S(O)_2R^{20}$;

$R^{20}$ is $C_{1-6}$ alkyl, $C_{1-6}$ haloalkyl or cycloalkyl;

$R^{21}$ is hydrogen or $C_{1-6}$ alkyl; or $R^{20}$ and $R^{21}$ together with the N in $NR^{20}R^{21}$ may form a 4-7 membered ring containing 1-2 heteroatoms selected from N, O, S, P and optionally substituted with 1-4 $R^{22}$ groups;

$R^7$, $R^{18}$ and $R^{22}$ are independently oxo, halo, hydroxy, $C_{1-6}$ alkyl, $C_{1-6}$ haloalkyl, $C_{1-6}$ alkoxy or $C_{1-6}$ haloalkoxy;

$R^{23}$ is independently $C_{3-7}$ cycloalkyl, or a 4-10 membered heterocyclyl comprising 1-3 heteroatoms selected from N, O and S, and is optionally substituted with oxo; and $R^{23}$ is unsubstituted or substituted with $C_{1-6}$ alkyl, $C_{1-6}$ haloalkyl, -$L^3$-$R^e$ or -$L^4$-$R^f$;

$R^c$ and $R^e$ are independently halo, cyano, hydroxy, —$OR^{24}$, —$NRR^{25}$, —$NR$—$CO_2R^{24}$, —$NR$—$SO_2$—$R^{26}$, —$NR$—$COR^{26}$, —$NR$—$C(O)$—$NRR^{25}$, —$OC(O)$—$NRR^{25}$, or $C_{1-6}$ alkyl substituted with halo, $C_{1-6}$ alkoxy, hydroxy or cyano;

$R^d$ and $R^f$ are independently —$SO_2NRR^{25}$, —$CONRR^{25}$, —$C(O)OR^{24}$, —$SO_2R^{26}$ or $C(O)R^{26}$ $R^{24}$ is $C_{1-6}$ alkyl, $C_{1-6}$haloalkyl, -$L^2$-$R^{23a}$ or —$(CR^aR^b)_{2-3}$—$N(R^aR^b)_2$;

$R^{25}$ is hydrogen, $C_{1-6}$ alkyl, $C_{1-6}$haloalkyl, -$L^2$-$R^{23b}$ or —$(CR_2)_{2-3}$—$N(R^aR^b)_2$;

$R^{26}$ is $C_{1-6}$ alkyl, $C_{1-6}$haloalkyl, -$L^2$-$R^{23c}$ or —$(CR^aR^b)_{1-3}$—$N(R^aR^b)_2$;

$R^{23a}$, $R^{23b}$ and $R^{23c}$ are independently selected from $R^{23}$;

R, $R^a$ and $R^b$ are independently hydrogen or $C_{1-6}$ alkyl;

$L^1$, $L^2$, $L^3$ and $L^4$ are independently a bond or —$(CR^aR^b)_{1-3}$; and n and m are independently 1-3; and p and q are 1-4;

or a pharmaceutically acceptable salt thereof.

In another embodiment, provided herein is a compound of Formula (2) or a pharmaceutically acceptable salt thereof:

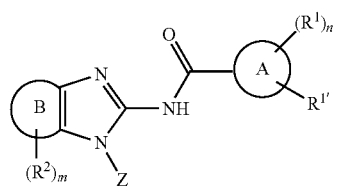

(2)

wherein Ring A is a 6-10 membered monocyclic or bicyclic aryl; a 5-10 membered heteroaryl comprising 1-4 heteroatoms selected from N, O and S; or a 5-6 membered heterocyclyl comprising 1-2 heteroatoms selected from N, O and S, and optionally substituted with oxo;

$R^1$ and $R^{1'}$ are independently hydrogen; halo; cyano; $C_{1-6}$ alkyl; $C_{1-6}$ haloalkyl; —$X^1$—$NR^4R^5$; —$X^1$—$OR^3$; —$X^1$—$S(O)_{0-2}R^6$; —$X^1$—$P(O)R^{6a}R^{6b}$; phenyl unsubstituted or substituted by $C_{1-6}$ alkyl; or a 5-6 membered heteroaryl comprising 1-4 heteroatoms selected from N, O and S;

$R^2$ is selected from hydrogen, halo; cyano; $C_{1-6}$ alkyl; $C_{1-6}$ haloalkyl; —$X^1$—$C(O)OR^3$; —$X^1$—$C(O)R^3$; —$X^1$—$C(O)NR^4R^5$; —$X^1$—$C(O)NR^4$—$X^3$—$C(O)OR^3$; —$X^1$—$C(O)NR^4$—$X^3$—$S(O)_{0-2}R^6$; —$X^1$—$NR^4R^5$; —$X^1NR^4$—$X^2$—$C(O)R^3$; —$X^1$—$NR^4$—$X^3$—$S(O)_{0-2}R^6$; —$X^1$—$OR^3$; —$X^1$—$O$—$X^4$—$OR^3$; —$X^1$—$S(O)_{0-2}R^6$; —$X^1$—$O$—$X^4$—$NR^4R^5$; or a 5-6 membered heteroaryl comprising 1-4 heteroatoms selected from N, O and S and is unsubstituted or substituted by $C_{1-6}$ alkyl;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, S and P, and optionally substituted with 1-4 $R^7$ groups;

$R^6$, $R^{6a}$ and $R^{6b}$ are $C_{1-6}$ alkyl;

Z is

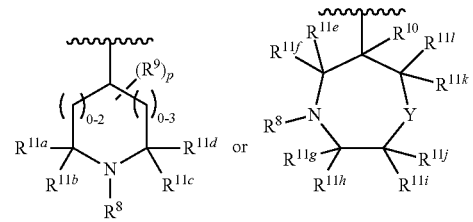

provided Z is a 4-7 membered heterocyclic ring when Z is

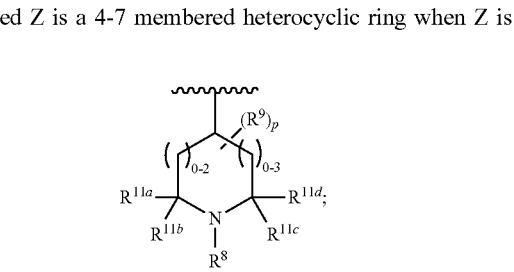

Y is O or $NR^{19}$;

$R^8$ is

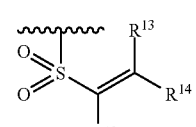

(a)

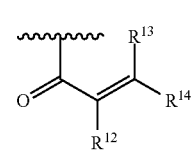

(b)

-continued

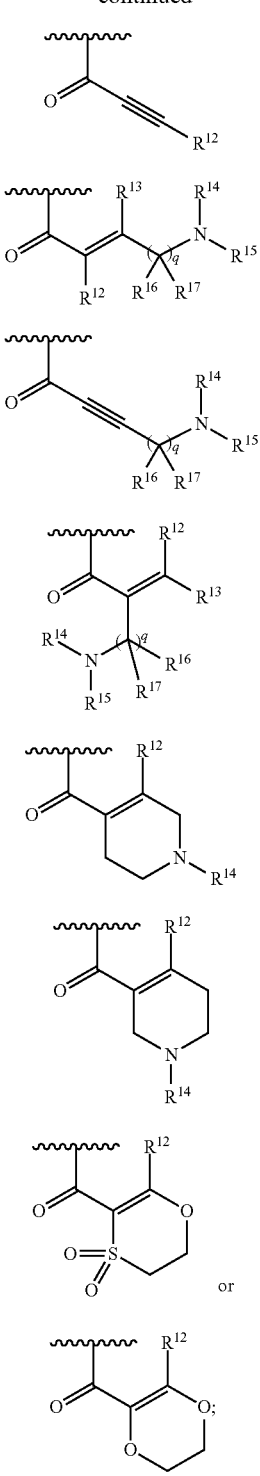

R[9], R[10], R[11a], R[11b], R[11c], R[11d], R[11e], R[11f], R[11g], R[11h], R[11i], R[11j], R[11k] and R[11l] are hydrogen;

R[2], R[13], R[16] and R[17] are independently hydrogen or $C_{1-6}$ alkyl;

R[14] and R[15] are independently hydrogen; $C_{1-6}$ alkyl; —C(O)O—($C_{1-6}$ alkyl); $C_{3-7}$ cycloalkyl unsubstituted or substituted with $C_{1-6}$ alkyl; or R[14] and R[15] together with N in NR[14]R[15] may form may form a 4-7 membered ring containing 1-2 heteroatoms selected from N, O, S and P, and optionally substituted with 1-4 R[18] groups;

R[7] and R[18] are independently oxo, halo, hydroxy, $C_{1-6}$ alkyl or $C_{1-6}$ alkoxy;

R[19] hydrogen, COR[20] or COOR[20];

R[20] is $C_{1-6}$ alkyl;

p is 1;

m and q are independently 1-2; and

Ring B, X[1], X[2], X[3] and X[4] and n are as defined in any of the embodiments described herein.

In another embodiment, provided herein is a compound of Formula (2A), (2B), (2C), (2D), (3A), (3B) or (3C) or a pharmaceutically acceptable salt thereof:

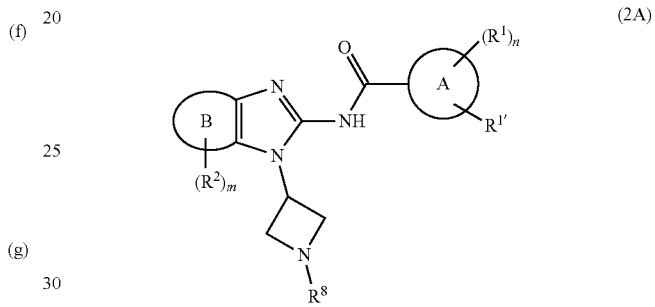
(2A)

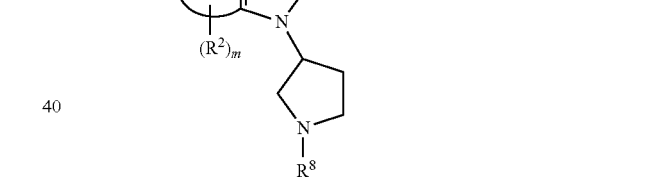
(2B)

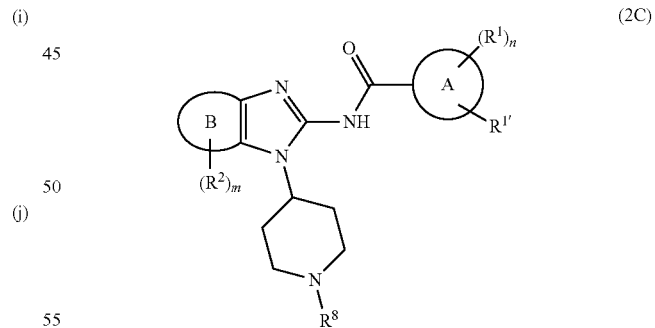
(2C)

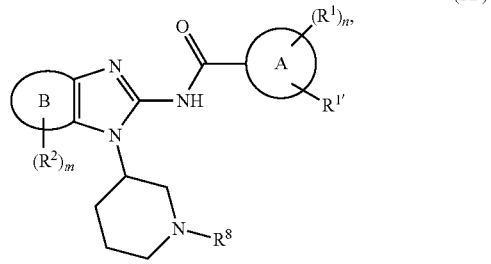
(2D)

-continued

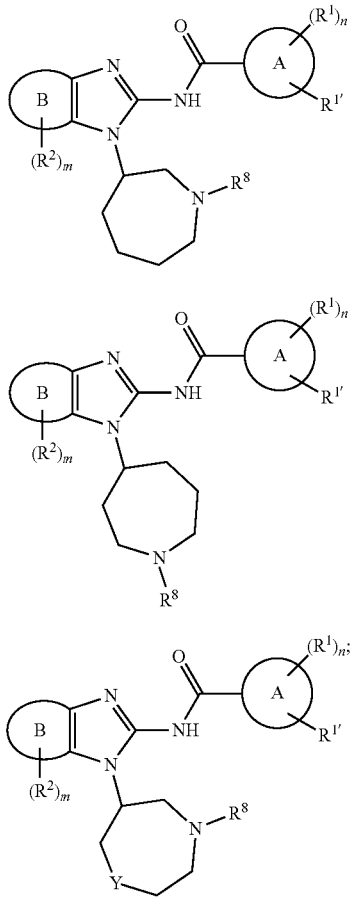

or a pharmaceutically acceptable salt thereof;

wherein Y is O or $NR^{19}$; and $R^1$, $R^{1'}$, $R^2$, $R^8$, $R^{19}$, A, B, Y, m and n are as defined in any of the embodiments described herein.

In yet another embodiment, provided herein is a compound of Formula (4) or a pharmaceutically acceptable salt thereof:

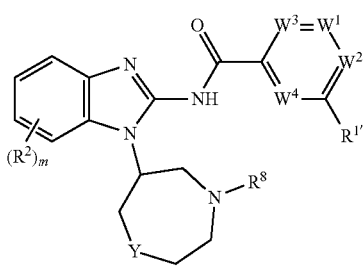

wherein $W^1$, $W^2$, $W^3$ and $W^4$ are independently $CR^1$ or N; and $R^1$, $R^{1'}$, $R^2$, $R^8$, Y and m are defined in any of the embodiments described herein. In a particular embodiment, at least two of $W^1$, $W^2$, $W^3$ and $W^4$ are $CR^1$, and the others are N.

In a further embodiment, provided herein is a compound of Formula (5) or a pharmaceutically acceptable salt thereof:

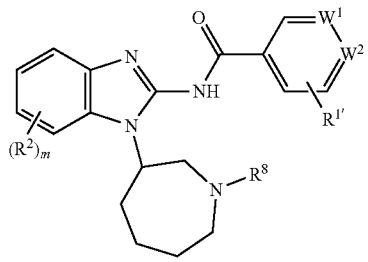

wherein $W^1$ and $W^2$ are independently $CR^1$ or N; and $R^1$, $R^{1'}$, $R^2$, $R^8$ and m are as defined in any of the embodiments described herein.

Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$ and $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the invention can generally be prepared by conventional techniques known to those skilled in the art or by processes analogous to those described in the accompanying Examples and Processes using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d^6$-acetone, $d^6$-DMSO.

Compounds of the invention, i.e. compounds of Formula (1), (2), (2A), (2B), (2C), (2D), (3A), (3B), (3C), (4) or (5), that contain groups capable of acting as donors and/or acceptors for hydrogen bonds may be capable of forming co-crystals with suitable co-crystal formers. These co-crystals may be prepared from the compounds of the invention by known co-crystal forming procedures. Such procedures include grinding, heating, co-subliming, co-melting, or contacting in solution a compound of the invention with the co-crystal former under crystallization conditions and isolating co-crystals thereby formed. Suitable co-crystal formers include those described in WO 2004/078163. Hence the invention further provides co-crystals comprising a compound of Formula (1), (2), (2A), (2B), (2C), (2D), (3A), (3B), (3C), (4) or (5).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention also provides for a method of inhibiting EGFR kinase activity in a cell comprising contacting the cell with an effective amount of an EGFR antagonist. In one embodiment, the administered amount is a therapeutically effective amount and the inhibition of EGFR kinase activity further results in the inhibition of the growth of the cell. In a further embodiment, the cell is a cancer cell.

Inhibition of cell proliferation is measured using methods known to those skilled in the art. For example, a convenient assay for measuring cell proliferation is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) J. Immunol. Meth. 160:81-88, U.S. Pat. No. 6,602,677. The assay may be conducted in 96- or 384-well format, making it amenable to automated high-throughput screening (HTS). See Cree et al (1995) AntiCancer Drugs 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU). Inhibition of cell proliferation may also be measured using colony formation assays known in the art.

Furthermore, the invention provides for methods of treating a condition mediated by EGFR in a subject suffering therefrom, comprising administering to the subject a therapeutically effective amount of an EGFR antagonist. In one embodiment, the condition is a cell proliferative disease.

Treatment of the cell proliferative disorder by administration of an EGFR antagonist results in an observable and/or measurable reduction in or absence of one or more of the following: reduction in the number of cancer cells or absence of the cancer cells; reduction in the tumor size; inhibition of cancer cell infiltration into peripheral organs including the spread of cancer into soft tissue and bone; inhibition of tumor metastasis; inhibition, to some extent, of tumor growth; and/or relief to some extent, one or more of the symptoms associated with the specific cancer; reduced morbidity and mortality, and improvement in quality of life issues. To the extent the EGFR antagonist may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB). In a specific embodiment, the administration of an EGFR antagonist decreases tumor burden (e.g., reduces size or severity of the cancer). In yet another specific embodiment, the administration of an EGFR antagonist kills the cancer.

Processes for Making Compounds of the Invention

Typically, a compound of Formula (1) can be prepared according to any one of the following schemes illustrated below, wherein A, B, $R^1$, $R^{1'}$, $R^2$, $R^8$, E, n and m are as defined in the Summary of the Invention, and Z* is the same as Z, except each N—$R^8$ moiety has been replaced with an N—H. In particular embodiments, E is NH. In any of the schemes below, it is understood that a radical as defined encompasses any protecting groups thereof. One of skill in the art will also appreciate that these methods are representative, and does not limit other methods for preparing the compounds of the present invention.

In one embodiment, a compound of Formula (1) can be prepared according to Scheme 1:

Scheme 1

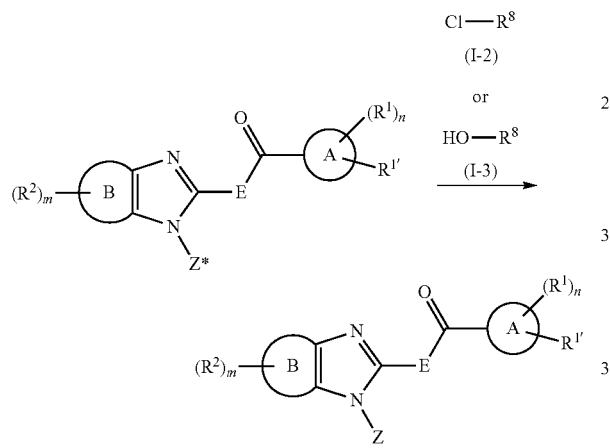

In Scheme 1, an intermediate of formula (I-1) is reacted with an intermediate of formula (I-2), in the presence of a base in a suitable solvent. Alternatively, a compound of Formula (1) can be prepared from the reaction of an intermediate of formula (I-1) with an intermediate of formula (I-3), in the presence of a coupling reagent and a base in a suitable solvent. The reaction proceeds in a temperature range of about −30° C. to about 50° C. Suitable bases include but are not limited to, DIEA, $K_2CO_3$, $NaHCO_3$, and the like.

In another embodiment, a compound of Formula (1) can be prepared according to Scheme 2, wherein A, $R^1$, $R^{1'}$, $R^2$, E, n and m are as defined in the Summary of the Invention, and B is aryl or a heteroaryl:

Scheme 2

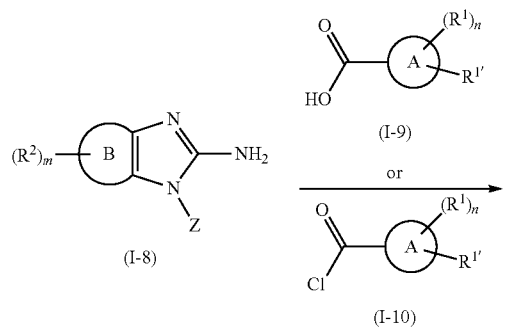

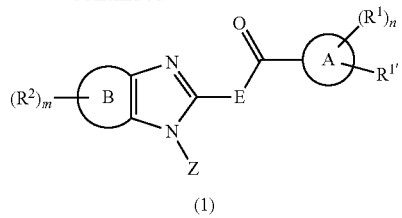

In Scheme 2, a compound of Formula (1) is prepared from the reaction of an intermediate of formula (I-8) with an intermediate of formula (I-9) in the presence of a coupling reagent and a base (for example, DIEA, triethylamine, $K_2CO_3$, $NaHCO_3$, and the like) in a suitable solvent. Alternatively, a compound of Formula (1) can be prepared from the reaction of an intermediate of formula (I-8) with an intermediate of formula (I-10) in the presence of base (for example, DIEA, $K_2CO_3$, $NaHCO_3$, and the like) in a suitable solvent. The reaction proceeds in a temperature range of about −30° C. to about 50° C.

Suitable coupling agents for use in the schemes described above include, but are not limited to, 2-(7-aza-1H-benzotriazole-1-yl)-1,1,3,3-tetramethyluronium hexafluorophosphate (HATU), O-benzotriazole-N,N,N',N'-tetramethyl-uronium-hexafluoro-phosphate (HBTU), 1-ethyl-3-(3-dimethylaminopropyl)carbodiimide hydrochloride/ hydroxybenzotriazole (EDCI/HOBt), and the like. Suitable solvents include but are not limited to, $CH_2Cl_2$, DMF, THF and the like.

The intermediate of Formula (I-8) can be prepared according to Scheme (3):

Scheme 3

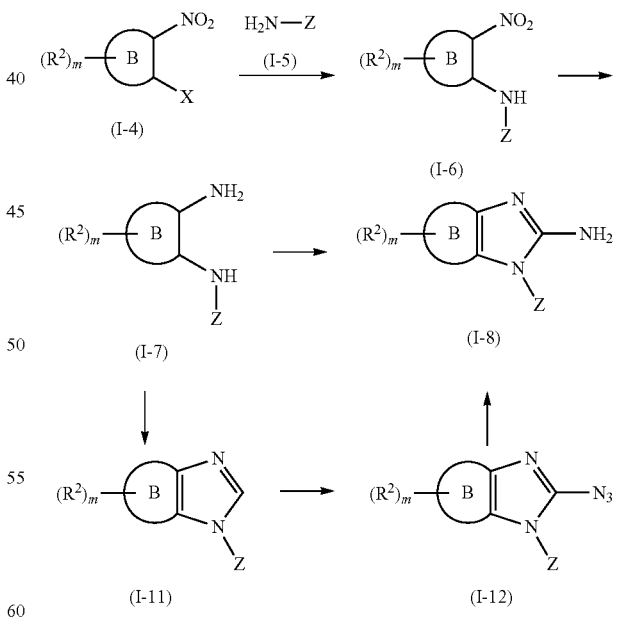

In Scheme 3, an intermediate of formula (I-4) (where X is a leaving group such as fluoro, chloro, bromo, methoxy, ethoxy and the like) is reacted with an intermediate of the formula (I-5) in the presence or absence of a base (for example, DIEA, triethylamine, $K_2CO_3$, $NaHCO_3$, and the like), either neat or in a suitable solvent such as DMF, DMA, N-methylpyrrolidine and the like, to generate an intermediate of formula (I-6). The reaction proceeds in a temperature range of about room temperature to about 150° C. An intermediate of formula (I-6) can further be converted to an intermediate of formula (I-7) by means of hydrogenation conditions known in the art (for example $H_2$, Pd/C, MeOH or $H_2$, Raney-Ni, MeOH and the like) or in the presence of a reducing agents such as iron, zinc and the like in a suitable solvent such as acetic acid or the like. An intermediate of formula (I-7) can then be converted to an intermediate of formula (I-8) in the presence of cyanogen bromide in a suitable solvent such as a mixture of water, MeCN and MeOH at a temperature ranging from about room temperature to about 60° C.

Alternatively, an intermediate of formula (I-11) can be prepared from the reaction of an intermediate of formula (I-7) with a condensation partner such as trimethyl orthoformate, triethyl orthoformate, 1,3,5-triazine, formamide, N,N-dimethylformamide dimethyl acetal, formic acid and the like in the presence or absence of an acid (for example AcOH, p-TSA, $H_2SO_4$, $HCO_2H$ and the like) either neat or in a suitable solvent such as DMF, DMA, MeOH, THF, toluene and the like. The reaction proceeds in a temperature range of about room temperature to about 150° C. An intermediate of formula (I-11) can further be deprotonated with a base such as BuLi, LDA, LHMDS and the like, and reacted with an azide source such as p-toluenesulfonyl azide, dodecylbenzenesulfonyl azide, methylsulfonylazide and the like in a suitable solvent such as toluene, THF and the like to form an intermediate of formula (I-12). The reaction proceeds in a temperature range of about −80° C. to about −20° C. An intermediate of formula (I-12) can further be reduced to an intermediate of formula (I-8) by reactions well known in the art (for example $H_2$, Pd/C, MeOH or $PPh_3$, $THF/H_2O$ or $Na_2S_2O_4/THF/H_2O$ and the like). The reaction proceeds in a temperature range of about −30° C. to about 60° C.

The invention also relates to those forms of the process in which a compound obtainable as an intermediate at any stage of the process is used as a starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. Compounds of the invention and intermediates can also be converted into each other according to methods generally known to those skilled in the art. Intermediates and final products can be worked up and/or purified according to standard methods, e.g. using chromatographic methods, distribution methods, (re-) crystallization, and the like.

In the reactions described, reactive functional groups, for example hydroxy, amino, imino, thio or carboxy groups, where these are desired in the final product, may be protected to avoid their unwanted participation in the reactions. A characteristic of protecting groups is that they can be removed readily (i.e. without the occurrence of undesired secondary reactions) for example by solvolysis, reduction, photolysis or alternatively under physiological conditions (e.g. by enzymatic cleavage). Conventional protecting groups may be used in accordance with standard practice (see e.g., T. W. Greene and P. G. M. Wuts in "Protective Groups in Organic Chemistry," 4$^{th}$ Ed., Wiley-Interscience, 2006, and subsequent versions thereof).

All the above-mentioned process steps mentioned herein before and hereinafter can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to 60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers. Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

The solvents from which those solvents that are suitable for any particular reaction may be selected include those mentioned specifically or, for example, water, esters, such as lower alkyl-lower alkanoates, for example ethyl acetate; ethers, such as aliphatic ethers, for example diethyl ether, or cyclic ethers, for example tetrahydrofuran or dioxane; liquid aromatic hydrocarbons, such as benzene or toluene; alcohols, such as methanol, ethanol or 1- or 2-propanol; nitriles, such as acetonitrile; halogenated hydrocarbons, such as methylene chloride or chloroform; acid amides, such as dimethylformamide or dimethyl acetamide; bases, such as heterocyclic or heteroaromatic nitrogen bases, for example pyridine or N-methylpyrrolidin-2-one; carboxylic acid anhydrides, such as lower alkanoic acid anhydrides, for example acetic anhydride; cyclic, linear or branched hydrocarbons, such as cyclohexane, hexane or isopentane, methycyclohexane; or mixtures of those solvents, for example aqueous solutions, unless otherwise indicated in the description of the processes. Such solvent mixtures may also be used in working up, for example by chromatography or partitioning.

The compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In one embodiment, the invention provides a compound of Formula (1), (2), (2A), (2B), (2C), (3A), (3B), (3C), (3D), (4) or (5) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington: The Science and Practice of Pharmacy," 21$^{st}$ Ed., Pharmaceutical Press 2011; and in "Pharmaceutical Salts: Properties, Selection, and Use," by Stahl and Wermuth, 2$^{nd}$ Rev. Ed., Wiley-VCH 2011, and subsequent versions thereof).

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. (See, "The Practice of Medicinal Chemistry," Ch. 31-32 Ed. Wermuth, Academic Press, San Diego, Calif., 2001, and subsequent versions thereof). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., alkyl esters, cycloalkyl esters, alkenyl esters, benzyl esters, mono- or di-substituted alkyl esters, such as the ω-(amino, mono- or di-alkylamino, carboxy, alkoxycarbonyl)-alkyl esters, the α-(alkanoyloxy, alkoxycarbonyl or di-alkylaminocarbonyl)-alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, "Design of Prodrugs," Elsevier (1985) and subsequent versions thereof). Hydroxy groups have been masked as esters and ethers. EP 039,051 (Sloan and Little) discloses Mannich-base hydroxamic acid prodrugs, their preparation and use.

Furthermore, the compounds of the present invention, including their salts, may also be obtained in the form of hydrates, or their crystals may, for example, include the solvent used for crystallization. Different crystalline forms may be present. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

General procedures for preparing a compound of the invention are described in the Examples, infra. All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl Science of Synthesis volumes 1-48, Georg Thieme Verlag, and subsequent versions thereof). All methods described herein can be performed in any suitable order unless otherwise indicated herein or otherwise clearly contradicted by context. The examples provided herein are offered to illustrate, but not to limit, the compounds of the invention, and the preparation of such compounds.

Pharmacology and Utility

The invention provides compounds and compositions that are able to modulate the activity of epidermal growth factor receptor (EGFR).

In one aspect, the invention provides a method of inhibiting epidermal growth factor receptor (EGFR) in a subject, comprising administering to the subject a therapeutically effective amount of a compound of the invention, or a pharmaceutically acceptable salt, ester, or prodrug thereof.

In another aspect, the invention provides the use of a compound of the invention for treating a condition mediated by EGFR. For example, the invention provides compounds and compositions for treating cancer, including but not limited to the following cancers: non-small cell lung cancer (NSCLC), head and neck cancer, colorectal cancer, breast cancer, pancreatic cancer, ovarian cancer, gastric cancer, glioma and prostate cancer.

Other cancers include but are not limited to: epidermoid, Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. A cancerous cell includes a cell afflicted by any one of the above-identified conditions.

Other cancers include but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In one embodiment, the invention provides compounds and compositions for treating lung cancer, non-small cell lung cancer, colorectal cancer, breast cancer, prostate cancer, liver cancer, pancreatic cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, a solid tumor, or a cancer comprising an EGFR activated tumor. The EGFR activated tumor can be from a mutation of EGFR; for example, from a mutation of EGFR located at G719S, G719C, G719A, L858R, L861Q, an exon 19 deletion mutation or an exon 20 insertion mutation. The EGFR activated tumor can also be from an amplification of EGFR, expression of EGFR, and/or ligand mediated activation of EGFR.

The invention also provides compounds and compositions for treating a condition that is resistant to EGFR targeted therapy. For example, the EGFR targeted therapy may comprise treatment with gefitinib, erlotinib, lapatinib, XL-647, HKI-272 (Neratinib), BIBW2992 (Afatinib), EKB-569 (Pelitinib), AV-412, canertinib, PF00299804, BMS 690514, HM781-36b, WZ4002, AP-26113, cetuximab, panitumumab, matuzumab, trastuzumab, or pertuzumab.

The invention also provides compounds and compositions for treating a condition that is resistant to ALK-targeted therapy. For example, the ALK targeted therapy may comprise treatment with crizotinib, SP-3026, AF802, X-396, or AP-26113.

In another embodiment, the invention provides compounds and compositions for treating a proliferative disease. For example, the compounds of the invention may be used to inhibit cell proliferative disease such as hyperplasias, dysplasias and pre-cancerous lesions. Examples of pre-cancerous lesions may occur in skin, esophageal tissue, breast and cervical intra-epithelial tissue. Inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition is observed, and may be referred to as prevention or chemoprevention.

In yet another embodiment, the invention provides compounds and compositions for treating an autoimmune disease, inflammatory disease, immunologically-mediated disease, bone disease, metabolic disease, neurological or neurodegenerative disease, cardiovascular disease, hormone related disease, allergy, or asthma.

Furthermore, the invention provides compounds and compositions for treating a condition selected from inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, angiogenesis including neoplasia, metastasis, a central nervous system disorder, a central nervous system disorder having an inflammatory or apoptotic component, Alzheimer's disease, Parkinson's disease, Huntington's disease, amyotrophic lateral sclerosis, spinal cord injury, and peripheral neuropathy, or Canine B-Cell Lymphoma. In a further embodiment, the condition is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

Further, the invention provides compounds and compositions for treating a neurodegenerative disease. Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjoegren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

In another aspect, the invention also provides a method of preventing resistance to gefitinib or erlotinib in a disease, comprising administering to a subject a therapeutically effective amount of a compound of the invention, or a pharmaceutically acceptable salt, ester, or prodrug thereof.

Administration and Pharmaceutical Compositions

In one aspect, the present invention provides a pharmaceutical composition comprising a compound of the invention and a pharmaceutically acceptable carrier, diluent or excipient. The pharmaceutical compositions can be formulated for oral, intravenous, intradermal, intramuscular, intraperitoneal, subcutaneous, intranasal, epidural, sublingual, intracerebral, intravaginal, intraventricular, intrathecal, epidural, transdermal, rectal, by inhalation, or topical administration.

In one embodiment, the pharmaceutical composition is formulated for oral administration. The pharmaceutical compositions can take the form of solutions, suspensions, emulsions, tablets, pills, pellets, capsules, capsules containing liquids, powders, suppositories, emulsions, aerosols, sprays, suspensions, or any other form suitable for use. The compositions can be formulated for immediate release, sustained release, or controlled release of the compounds of the invention.

Suitable pharmaceutical excipients include, for example, a) diluents (e.g., lactose, dextrose, sucrose, mannitol, sorbitol, cellulose and/or glycine); b) lubricants (e.g., silica, talcum, stearic acid, its magnesium or calcium salt and/or polyethyleneglycol); for tablets also c) binders (e.g., magnesium aluminum silicate, starch paste, gelatin, tragacanth, methylcellulose, sodium carboxymethylcellulose and or polyvinylpyrrolidone); if desired d) disintegrants, e.g., starches, agar, alginic acid or its sodium salt, or effervescent mixtures; and/or e) absorbents, colorants, flavors and sweeteners.

Additional suitable pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the compound of the invention is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Additional suitable pharmaceutical excipients include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, compositions in tablet or pill forms can be coated to delay disintegration and absorption in the gastrointestinal tract, thereby providing a sustained action over an extended period of time. Selectively permeable membranes surrounding an osmotically active substance driving a compound of the invention are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

In another embodiment, the compositions can be formulated for parenteral administration by various routes, including but not limited to, intravenous (including bolus injection), subcutaneous, intramuscular, and intra-arterial administration. Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In another embodiment, the compositions can be formulated for intranasal form via use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

In another embodiment, the compositions can be formulated for rectal or vaginal administration. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. Solid compositions of a similar type may also be employed as fillers in soft and hard-filled gelatin capsules using such excipients as lactose or milk sugar as well as high molecular weight polyethylene glycols and the like.

Compositions can be prepared according to conventional mixing, granulating or coating methods, respectively, and the present compositions can contain, in one embodiment, from about 0.1 percent to about 99 percent; and in another embodiment from about 1 percent to about 70 percent of the compound of the invention by weight or volume.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In another aspect, the pharmaceutical compositions further comprise one or more additional therapeutic agents. The compounds of the invention and the additional therapeutics agent(s) may act additively or synergistically.

In one embodiment, the compounds may be administered in combination with one or more therapeutic agents (e.g. small molecules, monoclonal antibodies, antisense RNA, and fusion proteins) that modulate protein kinase signaling involved in various disease states. Examples of such kinases may include, but are not limited to: serine/threonine specific kinases, phosphatidylinositol-3-kinases (PI3 kinases), Phosphatidylinositol-3 kinase-related kinases, mTOR, receptor tyrosine specific kinases and non-receptor tyrosine specific kinases. Serine/threonine kinases include mitogen activated protein kinases (MAPK), meiosis specific kinase (MEK), AKT, RAF PLK1, and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR/SF) (e.g, MET, RON, SEA, SEX); insulin receptor (e.g. Ins-R, IGFI-R, ALK, ROS); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGF alpha-R, PDG beta-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p 43, ARG); BTK (e.g. ITK/EMT, TEC); CSK, FAK, FPS, JAK, SRC, BMX, FER, CDK and SYK.

The compounds of the invention may also be administered in combination with one or more agents that modulate non-kinase biological targets or processes. Such targets include histone deacetylases (HDAC), DNA methyltransferase (DNMT), thrombin, TLR$^9$, hedgehog pathway, COX-2, Aromatase, heat shock proteins (e.g. HSP90), and proteosomes.

In another embodiment, the compounds of the invention may be combined with antineoplastic agents (e.g. small molecules, monoclonal antibodies, antisense RNA, and fusion proteins) that inhibit one or more biological targets such as vorinostat, erlotinib, gefitinib, lapatinib, sunitinib, dasatinib, sorafenib, MGCD265, Pazopanib, Regorafenib, Rapamycin, Temsirolimus (CCI-779), Ridaforolimus (MK8669), PF-04691502, DS-7423, Tanespimycin, GDC-0449, PF-04449913, IPI-926, XL139, TAK-441, MK-2206, GSK2110183, AZD6244, GDC-0941, XL765, CAL-101, BAY80-6946, XL147, PX-866, AMG 319, Volasertib, BMS-582664, motesanib, pasireotide, Romidepsin, Exemestane, letrozole, anastrozole, TemIntedanib, bortezomib, XL-518, GSK1120212, MSC1936369B, Selumetinib (AZD6244), PD-325901, BAY86-9766, RDEA119, TAK-733, RO4987655, EMD 1214063, AMG 208, XL880, AMG 337, tivantinib (ARQ 197), AZD6244, BMS-908662, BAY 43-9006, XL281, RO5126766, GSK2118436, Vemurafenib (RO5185426, PLX4032), MetMAb, Crizotinib, ASP-3026, AF802, X-396, AP-26113, CNF2024, RG108, BMS387032, Isis-3521, bevacizumab, trastuzumab, pertuzumab, MM-121, U3-1287 (AMG 888), cetuximab, panitumumab, zalutumumab, nimotuzumab, matuzumab, AV-299, PRO143966, IMC-A12, R1507, AVE-1642, Figitumumab, OSI-906, Intedanib, AMG 102, AMG 900, MLN8237, AG24322, PD325901, ZD6474 (vandetanib), PD184322, Obatodax, ABT737, XL-647, neratinib, afatinib, HM781-36B, AV-412, canertinib (CI-1033), Dacomitinib (PF00299804), or BMS 690514. Such combinations may enhance therapeutic efficacy over efficacy achieved by any of the agents alone and may prevent or delay the appearance of resistant mutational variants.

The compounds of the invention may also be administered in combination with a chemotherapeutic agent at various stages of the disease for the purposes of shrinking tumors, destroying remaining cancer cells left over after surgery, inducing remission, maintaining remission and/or alleviating symptoms relating to the cancer or its treatment. Examples of chemotherapeutic agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan, SN38, and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); interferons (interferon-α, interferon-β, interferon-γ); monoclonal antibodies (for example, Alemtuzumab, Gemtuzumab ozogamicin, Rituximab, Trastuzumab, Ibritumomab Tioxetan, Cetuximab, Panitumumab, Tositumomab, Bevacizumab, zalutumumab, nimotuzumab, matuzumab, pertuzumab, MM-121, U3-1287 (AMG 888), Figitumumab, AMG 102, IMC-A12, R1507, AVE-1642, MetMAb); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); glucocorticosteroids (dexamethasone); and retinoids (Bexarotene, Isotretinoin, Tretinoin (ATRA).

In certain embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In another aspect of the invention, the compounds of the invention are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent, such as agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (Schirrmacher et al. (1995) J. Cancer Res. Clin. Oncol. 121:487). In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells. The compounds of the invention can be used in conjunction with such techniques.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilizing antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumor necrosis factor a; an antibody therapy, such as a monoclonal antibody therapy; an antiviral agent, such as a nucleoside inhibitor (e.g. lamivudine) or an immune system modulator (e.g. interferon); an opioid analgesic; a local anesthetic; a stimulant, including caffeine; an $H_2$-antagonist (e.g. ranitidine); a proton pump inhibitor (e.g. omeprazole); an antacid (e.g. aluminum or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Other examples of therapeutic agents that may be combined with the compounds of this invention include, without limitation: treatments for Alzheimer's Disease such as ARICEPT® and EXCELON®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., AVONEX® and REBIF®, COPAXONE®, and mitoxantrone; treatments for asthma such as albuterol and SINGULAIR®; agents for treating schizophrenia such as ZYPREXA®, RISPERDAL®, SEROQUEL®, and haloperidol; anti-inflammatory agents such as corticosteroids, TNF blockers, interleukin 1 receptor antagonist (IL-iRA), azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin.

The pharmaceutical composition comprising a compound of the invention and one or more additional therapeutic agent may be provided as a combined preparation for simultaneous, separate or sequential use, by the same or different route of administration, in the treatment of a disease or condition mediated by EGFR kinase activity. Products provided as a combined preparation include a composition comprising a compound of the invention, and the other therapeutic agent(s) together in the same pharmaceutical composition; or a compound of the invention and the other therapeutic agent(s) in separate form, e.g. in the form of a kit.

In another aspect, the invention provides a kit comprising two or more separate pharmaceutical compositions, at least one of which contains a compound provided herein. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The therapeutically effective dosage of a compound, the pharmaceutical composition, or the combinations thereof, is dependent on the species of the subject, the body weight, age and individual condition, the disorder or disease or the severity thereof being treated, and can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg, alternatively from about 1 to about 50 mg/kg. In general, treatment regimens according to the present invention comprise administration to a patient in need of such treatment from about 10 mg to about 1000 mg of the compound(s) of this invention per day in single or multiple doses (such as two, three, or four times daily). Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

EXAMPLES

The following examples were offered to illustrate, but not to limit, the compounds of the present invention, and the preparation of such compounds.

Synthesis of Intermediates

Intermediate 1

(R)-tert-butyl 3-aminoazepane-1-carboxylate

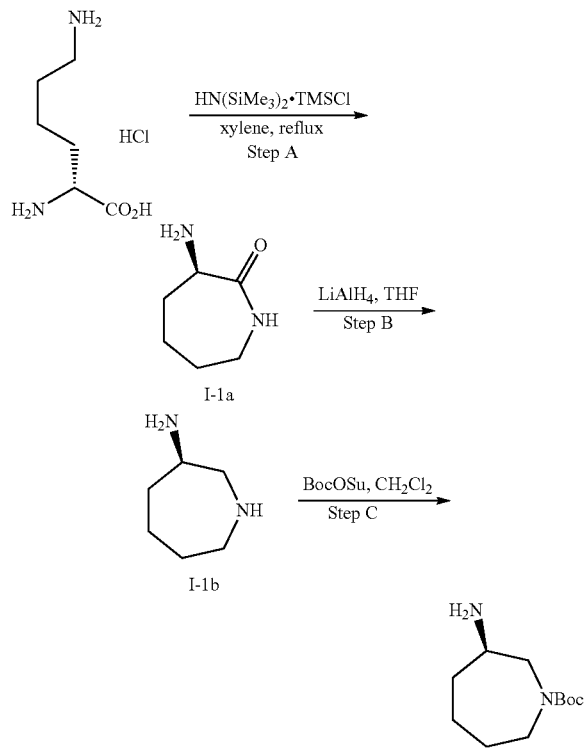

Intermediate 1

Step A:

To a solution of (R)-lysine HCl salt (100 g, 0.68 mol) in xylene (1 L) was added hexamethyldisilazane (1000 mL, 4.76 mol) and chlorotrimethylsilane (10 mL, 78.8 mmol). The mixture was heated to 120° C. for 24 h, then to 180° C. for 48 h. The solvent was then removed under reduced pressure and the crude material was purified by column chromatography (20:1 to 10:1 $CH_2Cl_2$/MeOH) to afford (R)-3-aminoazepan-2-one (I-1a).

$^1$H-NMR (400 MHz, $CDCl_3$): ∂ 6.55 (br s, 1H), 3.50-3.46 (m, 1H), 3.18-3.10 (m, 2H), 1.98-1.93 (m, 1H), 1.81-1.43 (m, 6H), 1.38-1.29 (m, 1H); MS calculated for $C_6H_{13}N_2O$ $(M+H^+)$ 129.09. found 129.1.

Step B:

To a suspension of $LiAlH_4$ (51.13 g, 1.345 mol) in THF (1 L) at 0° C. was added dropwise over 30 min a solution of I-1a (34.44 g, 0.269 mol) in THF (400 mL). The mixture was then stirred at room temperature overnight, cooled to 0° C., treated with $H_2O$ (52 ml) and 2M NaOH (52 mL) and stirred for 0.5 h. The resulting white precipitate was filtered through Celite and the filtrate evaporated under reduced pressure to afford (R)-azepan-3-amine (I-1b). The product was used in the next step without further purification. $^1$H-NMR (400 MHz, $CDCl_3$): ∂ 3.02-2.94 (m, 2H), 2.90-2.81 (m, 2H), 2.61-2.55 (m, 1H), 1.88-1.81 (m, 1H), 1.80-1.53 (m, 6H), 1.51-1.40 (m, 2H); MS calculated for $C_6H_{15}N_2$ $(M+H^+)$ 115.12. found 115.0.

Step C:

To a solution of I-1b (32.83 g, 0.288 mol) in $CH_2Cl_2$ (1300 mL) at −78° C. was added dropwise a solution of BocOSu (51.13 g, 1.345 mol) in $CH_2Cl_2$ (400 mL). The mixture was stirred at room temperature overnight, treated with $H_2O$ (400 mL) and the organic phase was separated and discarded. The aqueous layer was basified to pH~13 with solid NaOH and extracted with $CH_2Cl_2$. The combined organic layers were dried over $Na_2SO_4$ and concentrated under reduced pressure to afford the title compound (Intermediate 1) as a yellow oil. $^1$H-NMR (400 MHz, $CDCl_3$): ∂ 3.74-3.42 (m, 2H), 3.28-3.18 (m, 1H), 3.11-3.01 (m, 1H), 2.97-2.88 (m, 1H), 1.88-1.50 (m, 4H), 1.48 (s, 9H), 1.45-1.23 (m, 4H); MS calculated for $C_{11}H_{23}N_2O_2$ $(M+H^+)$ 215.17. found 215.1.

Intermediate 2

(S,E)-4-(3-hydroxypyrrolidin-1-yl)but-2-enoic acid hydrochloride

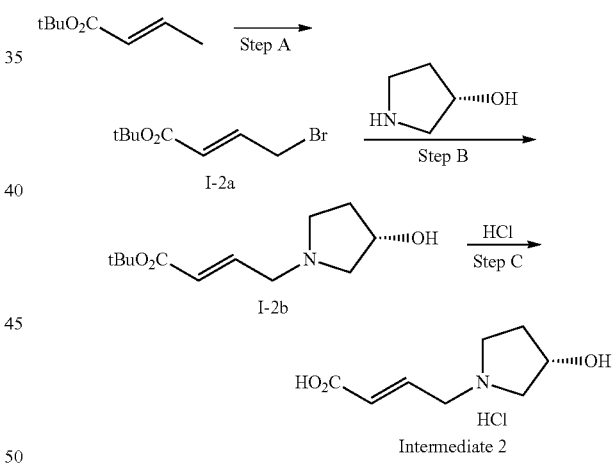

Intermediate 2

Step A:

To the mixture of (E)-tert-butyl but-2-enoate (10.0 g, 70.4 mmol) and NBS (12.5 g, 70.4 mmol) in $CCl_4$ (150 mL) was added benzoyl peroxide (510 mg, 2.11 mmol), and the reaction was refluxed for 12 h. The mixture was cooled to room temperature, and the solid was filtered off. The filtrate was concentrated in vacuo, and purified by column chromatography to afford (E)-tert-butyl 4-bromobut-2-enoate (I-2a). $^1$H-NMR (400 MHz, $CDCl_3$) δ 7.02-6.76 (m, 1H), 6.05-5.89 (m, 1H), 4.06-3.95 (m, 2H), 1.56-1.40 (m, 9H). MS calculated for $C_8H_{14}BrO_2$ $(M+H^+)$ 221.01. found: 221.0.

Step B:

A solution of I-2a (1.0 g, 4.55 mmol), (S)-pyrrolidin-3-ol HCl salt (561.7 mg, 4.55 mmol) and $NEt_3$ (1.27 mL, 9.1 mmol) in THF (35 mL) was stirred at room temperature overnight. The solid was filtered off, the filtrate was concentrated in vacuo, and purified by column chromatography to afford (S,E)-tert-butyl 4-(3-hydroxypyrrolidin-1-yl)but-2-enoate (I-2b). $^1$H-NMR (400 MHz, CDCl$_3$) δ 6.89 (dt, J=6.1, 15.7 Hz, 1H), 5.93 (d, J=15.6 Hz, 1H), 4.43-4.31 (m, 1H), 3.25 (dd, J=1.6, 6.1 Hz, 2H), 2.93 (d, J=5.2 Hz, 1H), 2.73 (d, J=9.7 Hz, 1H), 2.57 (dd, J=5.1, 10.1 Hz, 1H), 2.34 (d, J=6.3 Hz, 1H), 2.25-2.14 (m, 1H), 1.86 (d, J=7.0 Hz, 1H), 1.82-1.73 (m, 1H), 1.56 (s, 9H). MS calculated for C$_{12}$H$_{22}$NO$_3$ (M+H$^+$) 228.15. found: 228.1.

Step C:

A solution of I-2b (584 mg, 2.57 mmol) in 4N aq. HCl solution was stirred at room temperature for 4 h. The mixture was then concentrated and dried in vacuo to afford (S,E)-4-(3-hydroxypyrrolidin-1-yl)but-2-enoic acid (I-2) as a HCl salt.

$^1$H-NMR (400 MHz, MeOD) δ 6.88 (d, J=15.6 Hz, 1H), 6.26 (d, J=15.6 Hz, 1H), 4.58 (s, 1H), 4.03 (d, J=7.0 Hz, 2H), 3.74 (s, 1H), 3.52 (d, J=11.8 Hz, 1H), 3.46-3.36 (m, 1H), 3.19 (s, 1H), 2.45-2.28 (m, 1H), 2.14 (s, 1H), 2.10-1.95 (m, 1H). MS calculated for C$_8$H$_{14}$NO$_3$ (M+H$^+$) 172.09. found: 172.1.

The following intermediates were obtained following analogous procedures as described for the above Intermediate 2, using the appropriate starting materials.

| | Intermediate Structure | Physical Data ($^1$H NMR and MS) |
|---|---|---|
| I-3 | (S)-4-(3-hydroxypyrrolidin-1-yl)but-2-enoic acid · HCl | $^1$H-NMR (400 MHz, CDCl$_3$) δ 6.89 (dt, J = 6.2, 15.6 Hz, 1H), 5.92 (dt, J = 1.6,15.6 Hz, 1H), 4.37 (s, 1H), 3.24 (dd, J = 1.7, 6.2 Hz, 2H), 2.93 (td, J = 5.1, 8.6 Hz, 1H), 2.72 (d, J = 9.1 Hz, 1H), 2.56 (dd, J = 5.1, 10.1 Hz, 1H), 2.33 (td, J = 6.3, 8.9 Hz, 1H), 2.28-2.16 (m, 1H), 2.08 (s, 1H), 1.85-1.65 (m, 1H); MS calculated for C$_8$H$_{14}$NO$_3$ (M + H$^+$) 172.09, found: 172.1. |
| I-4 | (R)-4-(3-fluoropyrrolidin-1-yl)but-2-enoic acid · HCl | $^1$H-NMR (400 MHz, MeOD) δ 7.01-6.82 (m, 1H), 6.29 (dt, J = 1.3, 15.6 Hz, 1H), 5.48 (d, J = 52.2 Hz, 1H), 4.12 (d, J = 6.9 Hz, 2H), 3.83 (s, 2H), 3.32 (s, 2H), 2.41 (m, 3H); MS calculated for C$_8$H$_{13}$FNO$_2$ (M + H$^+$) 174.09, found: 174.1. |
| I-5 | (S)-4-(3-fluoropyrrolidin-1-yl)but-2-enoic acid · HCl | $^1$H-NMR (400 MHz, MeOD) δ 6.99-6.83 (m, 1H), 6.29 (d, J = 15.6 Hz, 1H), 5.49 (d, J = 51.8 Hz, 1H), 4.13 (s, 2H), 4.03-3.87 (m, 1H), 3.82 (s, 1H), 3.35 (d, J = 17.6 Hz, 2H), 2.35 (m, 3H); MS calculated for C$_8$H$_{13}$FNO$_2$ (M + H$^+$) 174.09, found: 174.1. |
| I-6 | (S)-4-(3-methoxypyrrolidin-1-yl)but-2-enoic acid · HCl | $^1$H-NMR (400 MHz, MeOD): δ 6.95-6.86 (m, 1H), 6.27 (d, J = 15.6 Hz, 1H), 3.35 (s, 3H), 4.22-4.17 (m, 1H), 4.10-4.04 (m, 2H), 3.79-3.68 (m, 2H), 3.30-3.19 (m, 2H) 2.43-2.30 (m, 1H), 2.21-2.07 (m, 1H); MS calculated for C$_9$H$_{16}$NO$_3$ (M + H$^+$) 186.12, found 186.1. |
| I-7 | (R)-4-(3-methoxypyrrolidin-1-yl)but-2-enoic acid · HCl | $^1$H-NMR (400 MHz, MeOD): δ 6.95-6.86 (m, 1H), 6.27 (d, J = 15.6 Hz, 1H), 3.35 (s, 3H), 4.22-4.17 (m, 1H), 4.10-4.04 (m, 2H), 3.79-3.68 (m, 2H), 3.30-3.19 (m, 2H) 2.43-2.30 (m, 1H), 2.21-2.07 (m, 1H); MS calculated for C$_9$H$_{16}$NO$_3$ (M + H$^+$) 186.12, found 186.1. |
| I-8 | 4-(pyrrolidin-1-yl)but-2-enoic acid · HCl | $^1$H-NMR (400 MHz, MeOD) δ 7.01-6.80 (m, 1H), 6.27 (d, J = 15.6 Hz, 1H), 4.04 (d, J = 6.9 Hz, 2H), 3.65 (m, 2H), 3.16 (m, 2H), 2.09 (m, 4H); MS calculated for C$_8$H$_{14}$NO$_2$ (M + H$^+$) 156.09, found: 156.1. |
| I-9 | 4-(3,3-difluoropyrrolidin-1-yl)but-2-enoic acid · HCl | $^1$H-NMR (400 MHz, MeOD) δ 6.87-6.82 (m, 1H), 6.27-6.22 (m, 1H), 4.03 (d, J = 6.8 Hz, 2H), 3.83 (t, J = 12.0 Hz, 2H), 3.66-3.61 (m, 2H), 2.67-2.60 (m, 2H); MS calculated for C$_8$H$_{12}$F$_2$NO$_2$ (M + H$^+$) 192.08, found: 192.1. |
| I-10 | 4-(azetidin-1-yl)but-2-enoic acid · HCl | $^1$H-NMR (400 MHz, MeOD) δ 6.83-6.65 (m, 1H), 6.22 (dd, J = 15.8, 22.1 Hz, 1H), 4.34-4.20 (m, 2H), 4.12 (dd, J = 9.6, 19.6 Hz, 2H), 4.03 (d, J = 6.6 Hz, 2H), 3.78 (d, J = 6.8 Hz, 1H), 2.66-2.41 (m, 2H); MS calculated for C$_7$H$_{12}$NO$_2$ (M + H$^+$) 142.08, found: 142.1. |

-continued

| Intermediate | Structure | Physical Data (¹H NMR and MS) |
|---|---|---|
| I-11 | 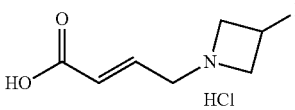 | ¹H-NMR (400 MHz, DMSO-d₆): δ 12.9-11.5 (br s, 2H), 6.69 (dt, J = 15.8, 6.4 Hz, 1H), ), 6.16 (d, J = 15.8 Hz, 1H), ), 5.39 (dm, J = 57.1 Hz, 1H), 4.47-4.38 (m, 2H), 4.29-4.20 (m, 2H), 4.06 (dd, J = 0.8, 6.3 Hz, 2H); MS calculated for $C_7H_{11}FNO_2$ (M + H⁺) 160.08, found 160.1. |
| I-12 | 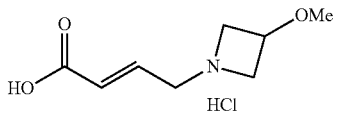 [SMILES: COC1CN(C/C=C/C(=O)O)C1 ; Cl] | ¹H-NMR (400 MHz, MeOD) δ 6.77 (ddd, J = 6.6, 12.7, 18.9 Hz, 1H), 6.21 (dd, J = 4.0, 15.7 Hz, 1H), 4.57 (dd, J = 6.5, 11.9 Hz, 1H), 4.32 (t, J = 7.5 Hz, 2H), 4.20 (d, J = 9.3 Hz, 1H), 4.08 (dd, J = 7.0, 10.3 Hz, 2H), 4.00 (dd, J = 5.4, 12.0 Hz, 1H), 3.35 (t, J = 8.1 Hz, 3H); MS calculated for $C_8H_{14}NO_3$ (M + H⁺) 172.09, found: 172.1. |
| I-13 | 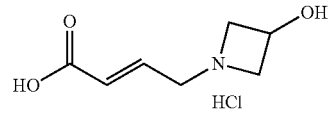 [SMILES: O=C(O)/C=C/CN1CC(O)C1 ; Cl] | ¹H-NMR (400 MHz, MeOD) δ 6.85-6.69 (m, 1H), 6.21 (dd, J = 5.9, 15.8 Hz, 1H), 4.77-4.60 (m, 1H), 4.58-4.45 (m, 1H), 4.30 (dd, J = 6.5, 12.0 Hz, 1H), 4.15-4.03 (m, 3H), 3.92 (dd, J = 4.5, 7.2 Hz, 1H), 3.22 (q, J = 7.3 Hz, 1H); MS calculated for $C_7H_{12}NO_3$ (M + H⁺) 158.08, found: 158.1. |
| I-14 | 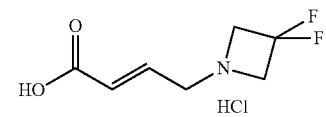 [SMILES: O=C(O)/C=C/CN1CC(F)(F)C1 ; Cl] | ¹H-NMR (400 MHz, MeOD) δ 6.82-6.75 (m, 1H), 6.22-6.18 (m, 1H), 4.72-4.69 (m, 4H), 4.09 (d, J = 6.8 Hz, 2H); MS calculated for $C_7H_{10}F_2NO_2$ (M + H⁺) 178.06, found: 178.1. |

Intermediate 15

(S)-tert-butyl 3-(2-amino-5-methyl-1H-benzo[d]imidazol-1-yl) piperidine-1-carboxylate

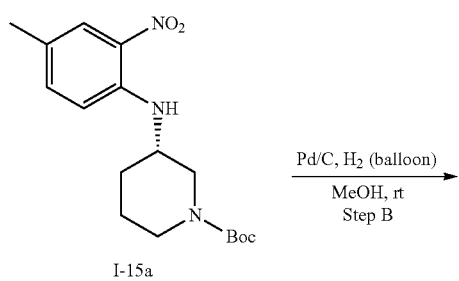

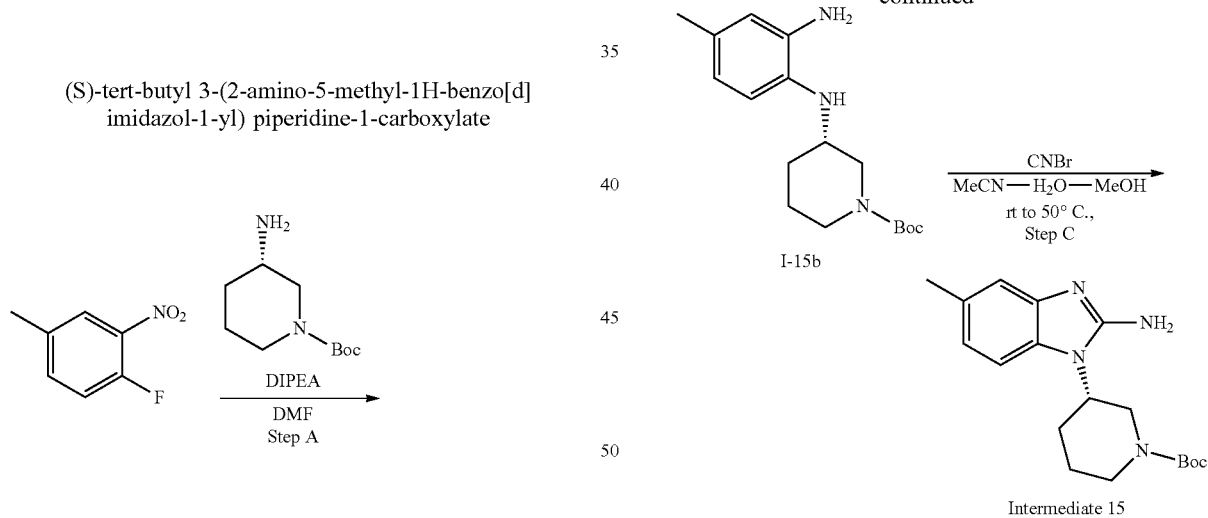

Step A:

A stirred solution of (S)-tert-butyl 3-aminopiperidine-1-carboxylate (0.500 g, 2.49 mmol), 1-fluoro-4-methyl-2-nitrobenzene (0.387 g, 2.49 mmol) and N,N-diisopropylethylamine (0.482 g, 3.74 mmol) in DMF under argon was heated to 110° C. for 6 h (reaction completion monitored by TLC). The mixture was diluted with water and extracted with EtOAc (3×100 mL). The combined organic layers were dried over anhydrous Na₂SO₄ and concentrated under reduced pressure to afford (S)-tert-butyl 3-((4-methyl-2-nitrophenyl)amino) piperidine-1-carboxylate (I-15a). MS calculated for $C_{17}H_{24}N_3O_4$ (M−H⁻) 334.18. found 334.0.

Step B:

To a stirred solution of I-15a (0.550 g, 1.64 mmol) in MeOH (35 mL) was added Pd/C (0.090 g) and the mixture was stirred at room temperature under hydrogen atmosphere (balloon) for 2 h (reaction completion monitored by TLC). The mixture was filtered through Celite, washed with MeOH and concentrated under reduced pressure to afford (S)-tert-butyl 3-((2-amino-4-methylphenyl)amino)piperidine-1-carboxylate (I-15b). MS calculated for $C_{17}H_{28}N_3O_2$ (M+H$^+$) 306.22. found 306.2.

Step C:

To a stirred solution of (S)-tert-butyl 3-((2-amino-4-methylphenyl)amino)piperidine-1-carboxylate (I-15b) (0.500 g, 1.63 mmol) in MeOH (20 mL) was added a solution of cyanogen bromide (0.208 g, 1.96 mmol) in 1:2 MeCN:H$_2$O (20 mL) for a period of 5 min. The mixture was heated to 50° C. for 2 h (reaction completion monitored by TLC), cooled to 0° C. and pH was adjusted to 10 by adding aqueous Na$_2$CO$_3$ solution. The mixture was stirred for 30 min at room temperature, the resulting solid was collected and dried under vacuum to afford the title compound (Intermediate 15). $^1$H-NMR (400 MHz, CDCl$_3$): ∂ 7.24 (s, 1H), 7.17 (d, J=7.6 Hz, 1H), 6.85 (d, J=8 Hz, 1H), 4.64 (br s, 2H), 4.17 (t, J=14.8 Hz, 2H), 3.99-3.93 (m, 1H), 3.32 (d, J=11.6 Hz, 1H), 2.79 (t, J=12.4 Hz, 1H), 2.41 (s, 3H), 2.38-2.37 (m, 1H), 2.34 (d, J=3.2 Hz, 1H), 1.91 (d, J=13.6 Hz, 3H), 1.69-1.61 (m, 1H), 1.47 (s, 9H); MS calculated for $C_{18}H_{27}N_4O_2$ (M+H$^+$) 331.21. found 331.0.

Intermediate 16

(S)—N-(5-methyl-1-(piperidin-3-yl)-1H-benzo[d]imidazol-2-yl)-3-(trifluoromethyl)benzamide

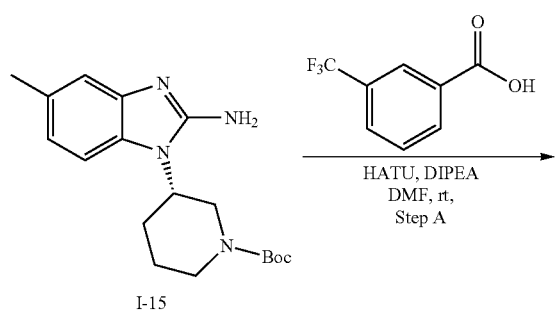

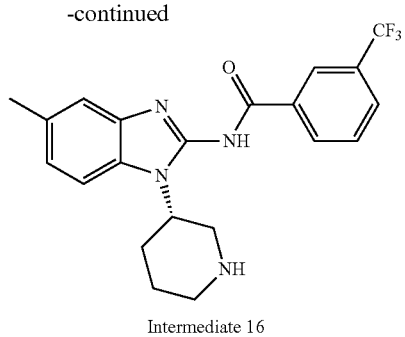

Intermediate 16

Step A:

To the stirred solution of I-15 (0.350 g, 1.06 mmol) in DMF (8 mL) were added sequentially 3-trifluoromethylbenzoic acid (0.221 g, 1.16 mmol), 2-(7-aza-1H-benzotriazole-1-yl)-1,1,3,3-tetramethyluronium hexafluorophosphate (0.483 g, 1.27 mmol) and N,N-diisopropylethylamine (0.410 g, 3.18 mmol). The mixture was stirred at room temperature for 16 h (reaction completion monitored by TLC), diluted with H$_2$O (50 mL) and EtOAc (50 mL). The organic layer was washed with saturated aqueous Na$_2$CO$_3$ solution and brine, dried over anhydrous Na$_2$SO$_4$, and concentrated under reduced pressure to afford (S)-tert-butyl 3-(5-methyl-2-(3-(trifluoromethyl)benzamido)-1H-benzo[d]imidazol-1-yl)piperidine-1-carboxylate (I-16a). $^1$H-NMR (400 MHz, CDCl$_3$): ∂ 12.47 (s, 1H), 8.58 (s, 1H), 8.46 (d, J=8.0 Hz, 1H), 7.73 (d, J=8.0 Hz, 1H), 7.56 (t, J=8.0 Hz, 1H), 7.28 (s, 1H), 7.15 (s, 1H), 7.09 (d, J=8.4 Hz, 1H), 4.60 (br s, 1H), 4.27 (br s, 2H), 2.9-2.84 (m, 2H), 2.45 (s, 3H), 2.08-1.96 (m, 2H), 1.93-1.90 (m, 1H), 1.50 (s, 9H); MS calculated for $C_{26}H_{30}F_3N_4O_3$ (M+H$^+$) 503.22. found 503.0.

Step B:

To a stirred solution of I-16a (0.300 g, 0.59 mmol) in CH$_2$Cl$_2$ (25 mL) at room temperature was added TFA (0.170 g, 1.49 mmol) and the mixture was stirred for 2 h (reaction completion monitored by TLC). The mixture was then concentrated under reduced pressure, the crude material was basified with saturated aqueous NaHCO$_3$ solution and extracted with CH$_2$Cl$_2$ (2×20 mL). The combined organic layers were washed with brine, dried over anhydrous Na$_2$SO$_4$ and concentrated under reduced pressure to afford the title compound (Intermediate 16) as a brown solid. $^1$H-NMR (400 MHz, CDCl$_3$): ∂ 8.59 (s, 1H), 8.49 (d, J=8 Hz, 1H), 7.73 (d, J=8 Hz, 1H), 7.58-7.54 (m, 1H), 7.33 (d, J=8.4 Hz, 1H), 7.14 (s, 1H), 7.08 (d, J=8.4 Hz, 1H), 4.78 (br s, 1H), 3.67 (t, J=11.2 Hz, 1H), 3.21 (t, J=9.2 Hz, 2H), 2.80-2.61 (m, 2H), 2.4 (s, 3H), 2.08-1.95 (m, 3H), 1.78-1.75 (m, 1H); MS calculated for $C_{21}H_{22}F_3N_4O$ (M+H$^+$) 403.17. found 403.0.

Intermediate 17 tert-butyl 3-(2-amino-1H-imidazo[4,5-c]pyridin-1-yl)piperidine-1-carboxylate

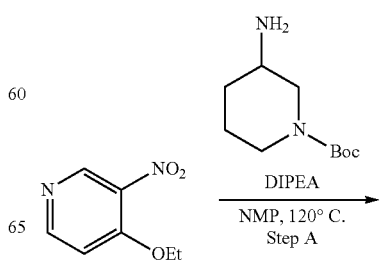

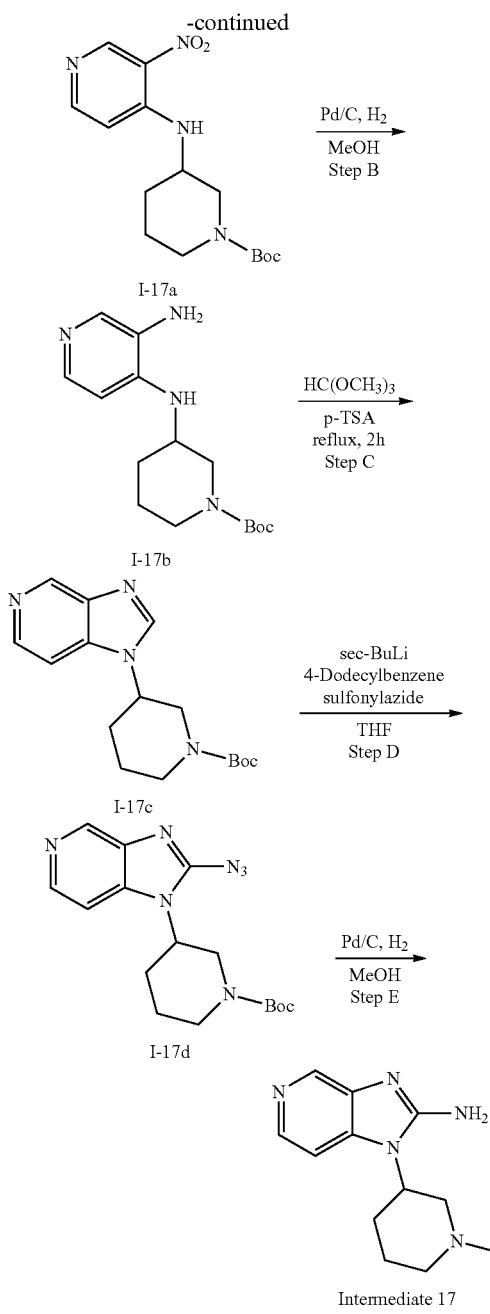

saturated aqueous NaHCO₃ and extracted with EtOAc (2×20 mL). The combined organic layers were dried over Na₂SO₄ and concentrated under reduced pressure. The crude material was purified by column chromatography to afford tert-butyl 3-(1H-imidazo[4,5-c]pyridin-1-yl)piperidine-1-carboxylate (I-17c) as a white solid.

Step D: To the stirred solution of I-17c (0.2 g, 0.66 mmol) in dry THF (4 mL) at −78° C. was added sec-butyl lithium (1.38 mL, 1.4M in cyclohexane) and the mixture was stirred at −78° C. for 50 min. Dodecylbenzenesulfonyl azide (0.28 g, 0.79 mmol) in THF (2 mL) was slowly added over 10 min and allowed to stir at −78° C. for 2 h (reaction completion monitored by TLC). The mixture quenched with saturated aqueous NH₄Cl solution and diluted with EtOAc (20 mL). The organic layer was separated, dried over anhydrous Na₂SO₄ and concentrated under reduced pressure to afford tert-butyl 3-(2-azido-1H-imidazo[4,5-c]pyridin-1-yl)piperidine-1-carboxylate (I-17d) as a liquid. ¹H-NMR (400 MHz, DMSO-d₆): ∂ 8.84 (s, 1H), 8.56 (s, 1H), 7.85 (m, 1H), 4.30-4.24 (m, 1H), 4.03-3.95 (m, 2H), 2.89-2.67 (m, 1H), 2.32-2.22 (m, 2H), 1.98-1.79 (m, 3H), 1.60-1.23 (m, 12H), 0.85-0.83 (m, 1H); MS calculated for $C_{16}H_{22}N_7O_2$ (M+H⁺) 344.18. found 344.2.

Step E:
To a stirred solution of I-17d (0.4 g) in MeOH (10 mL) was added Pd/C (0.1 g) and the mixture was stirred at room temperature under hydrogen atmosphere (balloon) for 2 h (reaction completion monitored by TLC). The mixture was filtered through Celite and concentrated under reduced pressure to afford the title compound (Intermediate 17). ¹H-NMR (400 MHz, DMSO-d₆): ∂ 8.37 (s, 1H), 7.99 (d, J=5.2 Hz, 1H), 7.50 (d, J=6.0 Hz, 1H), 6.78 (s, 2H), 4.31-4.25 (m, 1H), 3.98-3.95 (m, 2H), 3.40-3.32 (m, 1H), 2.90 (s, 1H), 2.23-2.19 (m, 1H), 1.89-1.79 (m, 2H), 1.58-1.49 (m, 2H), 1.40 (s, 9H), 1.33-1.22 (m, 2H); MS calculated for $C_{16}H_{24}N_5O_2$ (M+H⁺) 318.19. found 318.2.

Intermediate 18

N-(1-(piperidin-3-yl)-1H-imidazo[4,5-c]pyridin-2-yl)-3-(trifluoromethyl)benzamide

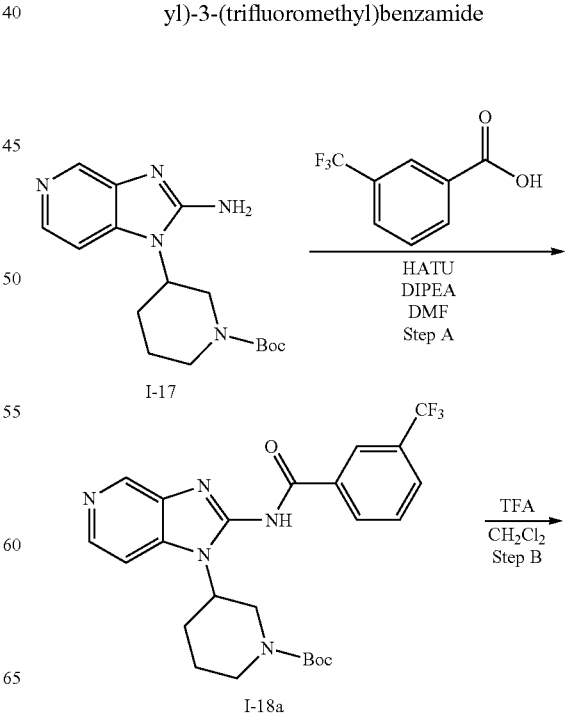

Steps A and B:
tert-butyl 3-((3-aminopyridin-4-yl)amino)piperidine-1-carboxylate (I-17b) was prepared from tert-butyl 3-((3-nitropyridin-4-yl)amino)piperidine-1-carboxylate (I-17a) following procedures analogous to I-15 Steps A and B. ¹H-NMR (400 MHz, DMSO-d₆): ∂ 7.65 (s, 1H), 7.57 (d, J=5.6 Hz, 1H), 6.42 (d, J=5.2 Hz, 1H), 5.07 (dd, J=7.2 Hz, 1H), 4.61 (s, 2H), 4.10-3.60 (m, 3H), 2.80 (s, 3H), 1.99-1.97 (m, 1H), 1.79-1.72 (m, 2H), 1.46-1.37 (m, 16H); MS calculated for $C_{15}H_{25}N_4O_2$ (M+H⁺) 293.20. found 293.3.

Step C:
A mixture of I-17b (1.5 g, 0.34 mmol), trimethylorthoformate (15 mL) and p-toluene sulfonic acid (0.025 g) was heated to reflux for 2 h (reaction completion monitored by TLC). The mixture was concentrated under reduced pressure. The residue was diluted with EtOAc, washed with

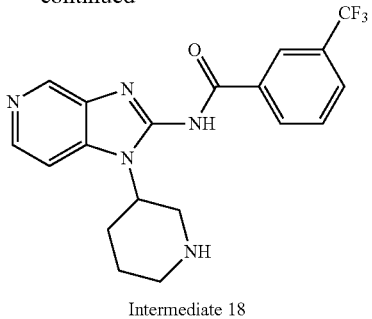

Intermediate 18

Steps A and B:

The title compound (Intermediate 18) as a white solid was prepared from I-17 in several steps following procedures analogous to I-16. MS calculated for $C_{19}H_{19}F_3N_5O$ (M+H$^+$) 390.15. found 390.0.

Intermediate 19 tert-butyl 3-(2-amino-3H-imidazo[4,5-c]pyridin-3-yl)piperidine-1-carboxylate

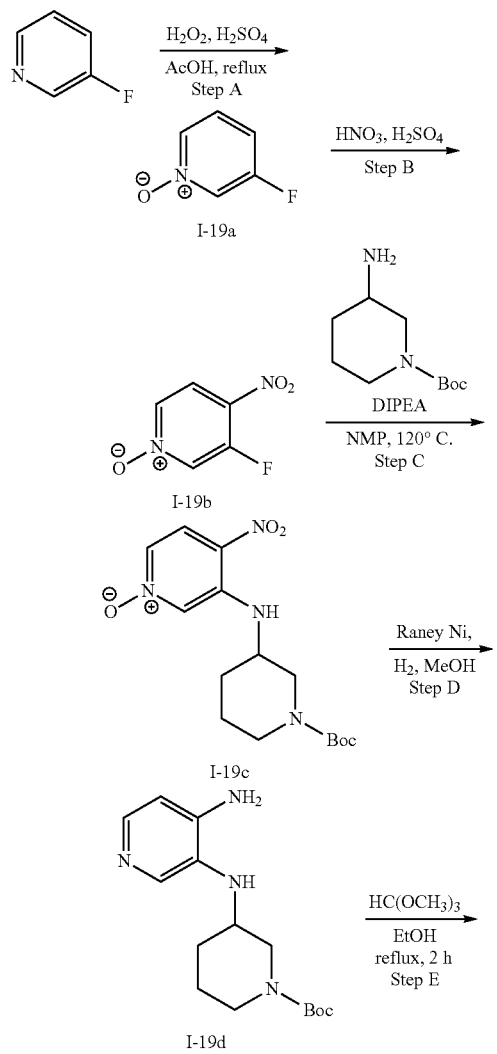

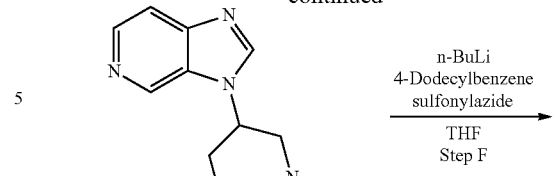

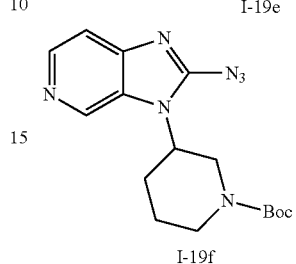

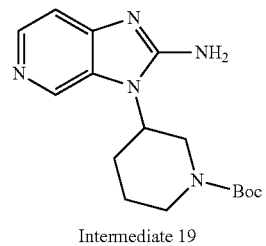

Intermediate 19

Step A:

To a stirred solution of 3-fluoropyridine (20 g, 206 mmol) in AcOH (120 mL) at 85° C. was added under nitrogen concentrated H$_2$SO$_4$ (1 mL). The mixture was then treated portion wise with H$_2$O$_2$ (30% in water, 48 mL, 422 mmol) and stirred at reflux for 24 h (reaction completion monitored by TLC). The mixture was quenched with solid Na$_2$SO$_3$, the solvent was removed under reduced pressure and the residue was dissolved in CH$_2$Cl$_2$ (500 mL). The mixture was neutralized with solid NaHCO$_3$ and stirred for 1 h. The mixture was filtered and concentrated under reduced pressure to afford crude 3-fluoropyridine 1-oxide (I-19a). $^1$H-NMR (400 MHz, CDCl$_3$): ∂ 8.16 (t, J=2.0 Hz, 1H), 8.11 (dd, J=2 and 26.8 Hz, 1H), 7.29-7.23 (m, 1H), 7.10-7.05 (m, 1H); MS calculated for C$_5$H$_5$FNO (M+H$^+$) 114.04. found 114.2.

Step B:

A solution of I-19a in concentrated H$_2$SO$_4$ (40 mL) was slowly treated over 15 min with a 2:3 HNO$_3$/H$_2$SO$_4$ mixture (73 mL). The mixture was then heated to 90° C. and stirred for 4 h. The mixture was cooled to room temperature, poured into ice and extracted with CH$_2$Cl$_2$ (3×300 mL). The combined organic phase was dried over Na$_2$SO$_4$ and concentrated under reduced pressure. The crude material was washed with pentane and stirred in CH$_2$Cl$_2$ (30 mL). The resulting yellow precipitate was collected to afford 3-fluoro-4-nitropyridine 1-oxide (I-19b). $^1$H-NMR (400 MHz, DMSO-d$_6$): ∂ 8.90 (dd, J=1.6, 6.0 Hz, 1H), 8.28 (dd, J=1.2, 6.0 Hz, 1H), 8.23 (dd, J=7.2, 2.0 Hz, 1H).

Step C:

3-((1-(tert-butoxycarbonyl)piperidin-3-yl)amino)-4-nitropyridine 1-oxide (I-19c) was prepared following procedures analogous to I-15 Step A. $^1$H-NMR (400 MHz, CDCl$_3$): ∂ 8.03 (d, J=7.2 Hz, 2H), 7.97 (d, J=1.6 Hz, 1H), 7.46 (dd, J=2 and 4 Hz, 1H), 3.74 (d, J=12.8 Hz, 1H), 3.51-3.43 (m, 5H), 2.17-1.97 (m, 1H), 1.80-1.73 (m, 2H), 1.65-1.62 (m, 2H), 1.46 (s, 10H); MS calculated for $C_{15}H_{21}N_4O_5$ (M–H$^-$) 337.15. found 337.4.

Step D:

To a stirred solution of I-19c (7.5 g, 22.1 mmol) in MeOH (450 mL) was added Raney-Ni (cat.) and AcOH (7 mL) and the mixture was stirred at room temperature under hydrogen atmosphere (balloon) for 2 h (reaction completion monitored by TLC). The mixture was filtered through Celite and concentrated under reduced pressure. The residue was dissolved in water, basified with 1M NaOH and extracted with Et$_2$O (2×100 mL). The combined organic phase was washed with brine, dried over anhydrous Na$_2$SO$_4$, and concentrated under reduced pressure to afford tert-butyl 3-((4-aminopyridin-3-yl)amino)piperidine-1-carboxylate (I-19d). MS calculated for $C_{15}H_{25}N_4O_2$ (M+H$^+$) 293.20. found 293.3.

Step E:

tert-butyl 3-(3H-imidazo[4,5-c]pyridin-3-yl)piperidine-1-carboxylate (I-19e) was prepared following procedures analogous to I-17, Step C. $^1$H-NMR (400 MHz, DMSO-d$_6$): ∂ 9.09 (s, 1H), 8.54 (s, 1H), 8.35 (d, J=6 Hz, 1H), 7.68 (d, J=4.8 Hz, 1H), 4.65-4.58 (m, 1H), 4.11 (br s, 1H), 3.86 (d, J=12.8 Hz, 1H), 3.05-2.98 (m, 1H), 2.20-2.19 (m, 2H), 1.84-1.81 (m, 1H), 1.65-1.37 (m, 10H).

Step F:

tert-butyl 3-(2-azido-3H-imidazo[4,5-c]pyridin-3-yl)piperidine-1-carboxylate (I-19f) was prepared following procedures analogous to I-17, Step D. $^1$H-NMR (400 MHz, DMSO-d$_6$): ∂ 9.08 (s, 1H0, 8.33 (d, J=5.2 Hz, 1H), 7.54 (d, J=5.6 Hz, 1H), 4.29-4.25 (m, 1H), 4.07-3.95 (m, 2H), 3.40 (br s, 1H), 2.35-2.25 (m, 1H), 2.01-1.99 (m, 1H), 1.83-1.80 (m, 1H), 1.61-1.48 (m, 1H0, 1.41 (s, 10H); MS calculated for $C_{16}H_{22}N_7O_2$ (M+H$^+$) 344.18. found 343.9.

Step G:

The title compound (Intermediate 19) was prepared following procedures analogous to I-17, Step E. $^1$H-NMR (400 MHz, DMSO-d$_6$): ∂ 8.67 (s, 1H), 8.05 (d, J=5.2 Hz, 1H), 7.09 (d, J=5.2 Hz, 1H), 6.95 (s, 2H), 4.32-4.26 (m, 1H), 3.97-3.95 (m, 2H), 3.43 (s, 1H), 2.96 (s, 1H), 2.25-2.21 (m, 1H), 1.90-1.79 (m, 2H), 1.58-1.41 (m, 11H); MS calculated for $C_{16}H_{24}N_5O_2$ (M+H$^+$) 318.19. found 318.3.

Intermediate 20

N-(3-(piperidin-3-yl)-3H-imidazo[4,5-c]pyridin-2-yl)-3-(trifluoromethyl)benzamide

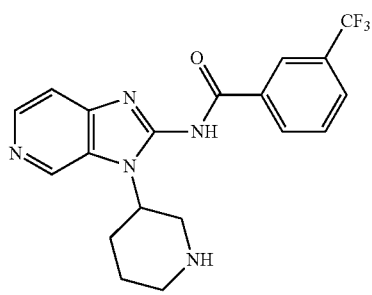 [SMILES: O=C(Nc1nc2ccncc2n1C1CCCNC1)c1cccc(C(F)(F)F)c1]

The title compound (Intermediate 20) was prepared from tert-butyl 3-(2-azido-3H-imidazo[4,5-c]pyridin-3-yl)piperidine-1-carboxylate (I-19) in several steps following procedures analogous to I-16. $^1$H-NMR (400 MHz, DMSO-d$_6$): ∂ 8.98 (s, 1H), 8.53-8.36 (m, 3H), 7.94-7.92 (m, 1H), 7.78-7.75 (m, 1H), 7.53-7.52 (m, 1H), 4.84-4.81 (m, 1H), 3.43-3.32 (m, 1H), 3.07-2.95 (m, 2H), 2.69-2.62 (m, 2H), 1.99-1.80 (m, 2H), 1.64-1.61 (m, 1H); MS calculated for $C_{19}H_{19}F_3N_5O$ (M+H$^+$) 390.15. found 390.0.

Intermediate 21

(R)-methyl 2-amino-1-(1-(tert-butoxycarbonyl)piperidin-3-yl)-1H-benzo[d]imidazole-5-carboxylate

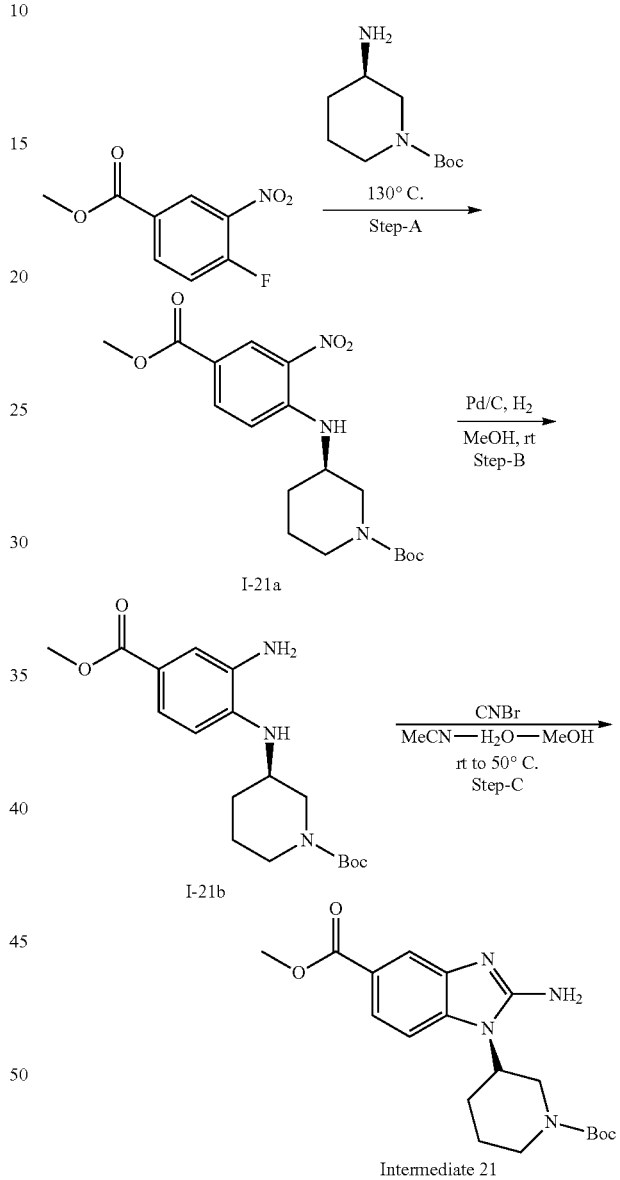

Intermediate 21

Step A:

A mixture of methyl 4-fluoro-3-nitrobenzoate (1.00 g, 5.02 mmol) and (R)-tert-butyl 3-aminopiperidine-1-carboxylate (1.00 g, 5.02 mmol) were heated to 130° C. for 3 h (reaction completion monitored by TLC). The mixture was cooled to room temperature, the resulting solid was collected and washed with n-hexanes to afford (R)-tert-butyl 3-((4-(methoxycarbonyl)-2-nitrophenyl)amino)piperidine-1-carboxylate (I-21a) as a red solid. $^1$H-NMR (400 MHz, CDCl$_3$): ∂ 8.89 (s, 1H), 8.40 (d, J=7.2 Hz, 1H), 8.06 (dd, J=2 and 6.8 Hz, 1H), 6.97 (d, J=8.8 Hz, 1H), 4.75 (d, J=13.6 Hz, 2H), 3.97-3.90 (m, 4H), 3.69-3.63 (m, 2H), 3.24-3.01 (m, 2H), 2.10-2.06 (m, 1H), 1.84-1.73 (m, 2H), 1.46 (s, 9H); MS calculated for $C_{18}H_{24}N_3O_6$ (M−H⁻) 378.17. found 378.4.

Steps B and C:

The title compound (Intermediate 21) was prepared from I-21a in several steps following procedures analogous to I-15, Steps B and C. MS calculated for $C_{19}H_{27}N_4O_4$ (M+H⁺) 375.20. found 375.2.

Intermediate 22

(R)-tert-butyl 3-(5-(hydroxymethyl)-2-(3-(trifluoromethyl)benzamido)-1H-benzo[d]imidazol-1-yl)piperidine-1-carboxylate

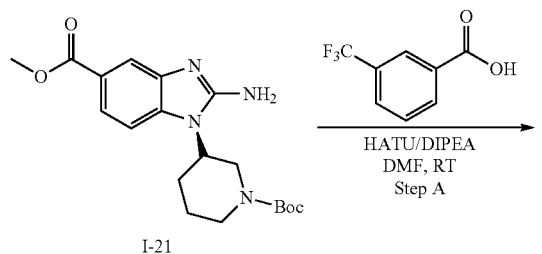

I-21

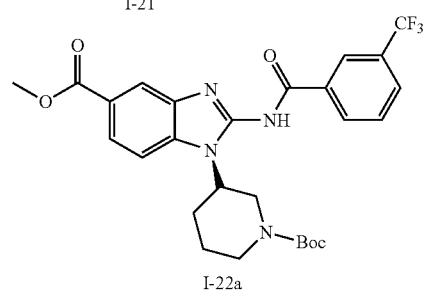

I-22a

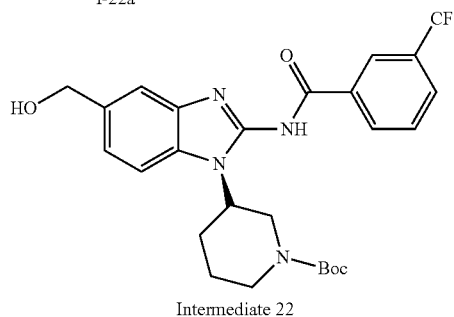

Intermediate 22

Step A:

(R)-methyl 1-(1-(tert-butoxycarbonyl)piperidin-3-yl)-2-(3-(trifluoromethyl)benzamido)-1H-benzo[d]imidazole-5-carboxylate (I-22a) was prepared from (R)-methyl 2-amino-1-(1-(tert-butoxycarbonyl)piperidin-3-yl)-1H-benzo[d]imidazole-5-carboxylate (I-21) following procedures analogous to I-16, Step A. ¹H-NMR (400 MHz, CDCl₃): ∂ 12.63 (br s, 1H), 8.58 (s, 1H), 8.47 (d, J=8 Hz, 1H), 8.03 (dd, J=1.2 and 4 Hz, 2H), 7.77-7.75 (m, 1H), 7.60-7.56 (m, 1H), 7.43-7.41 (m, 1H), 4.64 (br s, 1H), 4.29 (br s, 2H), 3.95 (s, 3H), 3.85-3.79 (m, 1H), 3.49 (s, 1H), 2.86-2.77 (m, 2H), 2.11-1.96 (m, 2H), 1.76-1.58 (m, 1H), 1.48 (s, 9H); MS calculated for $C_{27}H_{30}F_3N_4O_5$ (M+H⁺) 547.21. found 547.3.

Step B:

To a stirred solution of I-22a (1.00 g, 1.83 mmol) in THF (20 mL) at 0° C. was slowly added DIBAL-H (7.28 mL, 12.82 mmol) and the mixture was stirred for 2 h (reaction completion monitored by TLC). The mixture was diluted with water and extracted with EtOAc (2×50 mL), the combined organic layers were washed with brine, dried over anhydrous Na₂SO₄ and concentrated under reduced pressure. The crude material was purified by column chromatography (20% EtOAc/Hexanes) to afford the title compound (Intermediate 22); ¹H-NMR (400 MHz, DMSO-d₆): ∂ 12.90 (s, 1H), 8.48 (d, J=8.4 Hz, 2H), 7.9 (d, J=8 Hz, 1H), 7.75-7.7 (m, 2H), 7.56 (s, 1H), 7.20 (d, J=8.4 Hz, 1H), 4.82 (br s, 1H), 4.05-4.00 (m, 2H), 3.70 (br s, 1H), 2.90 (br s, 1H), 2.70-2.60 (m, 1H), 1.98-1.86 (m, 3H), 1.63-1.40 (m, 1H), 1.5 (s, 9H), 1.19 (s, 1H); MS calculated for $C_{26}H_{30}F_3N_4O_4$ (M+H⁺) 519.21. found 519.2.

Intermediate 23

(R)—N-(5-(morpholinomethyl)-1-(piperidin-3-yl)-1H-benzo[d]imidazol-2-yl)-3-(trifluoromethyl)benzamide

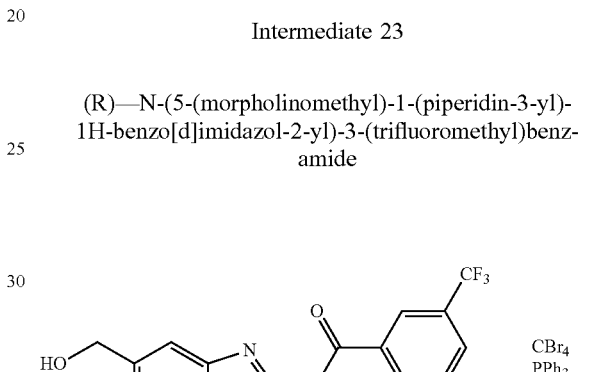

I-22

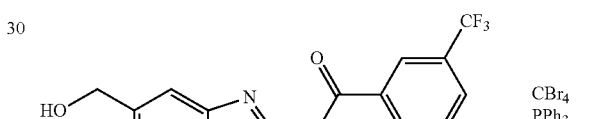

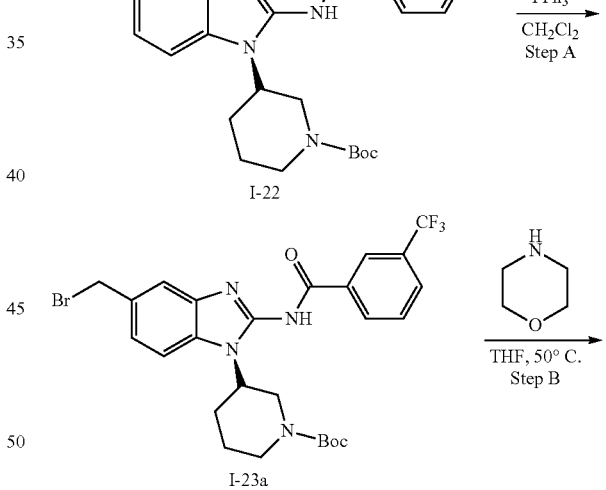

I-23a

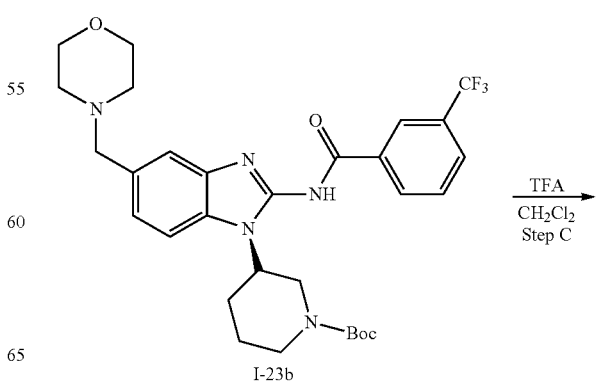

I-23b

-continued

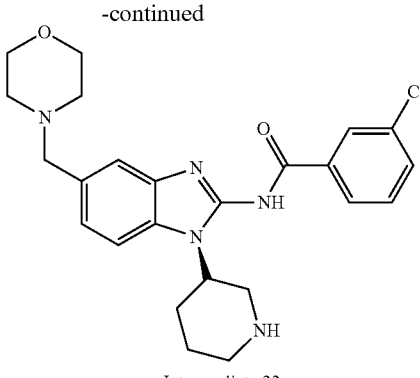

Intermediate 23

Step A:

To a stirred solution of I-22 (0.500 g, 0.96 mmol) in CH₂Cl₂ (30 mL) at 0° C. was added carbon tetrabromide (1.90 g, 5.79 mmol). The mixture was stirred for 15 min, PPh₃ (0.758 g, 2.89 mmol) was added and the mixture was further stirred for 45 min at 0° C. (reaction completion monitored by TLC). The mixture was diluted with water, extracted with CH₂Cl₂ (2×20 mL), the combined organic layers were washed with brine, dried over anhydrous Na₂SO₄ and concentrated under reduced pressure to afford (R)-tert-butyl 3-(5-(bromomethyl)-2-(3-(trifluoromethyl)benzamido)-1H-benzo[d]imidazol-1-yl) piperidine-1-carboxylate (I-23a). MS calculated for $C_{26}H_{27}BrF_3N_4O_3$ (M–H⁻) 579.13. found 579.3.

Step B:

To a stirred solution of I-23a (0.250 g, 0.43 mmol) in THF (10 mL) at 0° C. was added morpholine (0.120 g, 1.29 mmol) and the mixture was heated to 55° C. for 2 h (reaction completion monitored by TLC). The mixture was concentrated under reduced pressure and the crude material was purified by column chromatography to afford (R)-tert-butyl 3-(5-(morpholinomethyl)-2-(3-(trifluoromethyl)benzamido)-1H-benzo[d]imidazol-1-yl)piperidine-1-carboxylate (I-23b) as a light yellow solid; MS calculated for $C_{30}H_{37}F_3N_5O_4$ (M+H⁺) 588.27. found 588.4.

Step C:

The title compound (Intermediate 23) was prepared from I-23b following procedures analogous to I-16, Step B. MS calculated for $C_{25}H_{29}F_3N_5O_2$ (M+H⁺) 488.22. found 488.2.

Intermediate 24 tert-butyl 3-(2-amino-5-methyl-1H-benzo[d]imidazol-1-yl)azepane-1-carboxylate

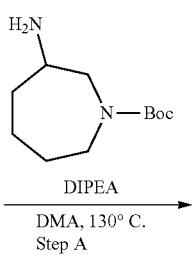

-continued

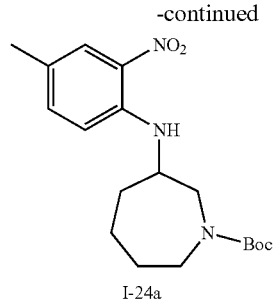

I-24a

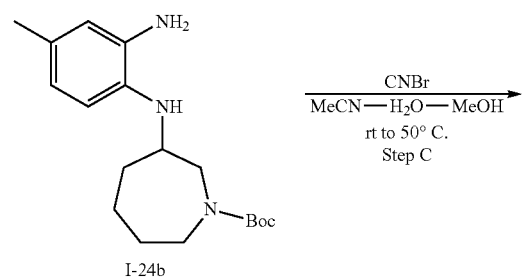

I-24b

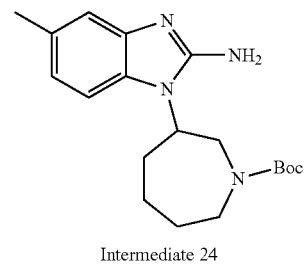

Intermediate 24

Step A, B and C:

The title compound (Intermediate 24) was prepared following procedures analogous to I-15, using the appropriate starting materials. ¹H-NMR (400 MHz, DMSO-d6): δ7.15-7.12 (m, 1H), 6.93 (s, 1H), 6.66 (d, J=7.6 Hz, 1H), 6.26 (s, 2H), 4.29 (br s, 1H), 3.81-3.75 (m, 1H), 3.55-3.36 (m, 3H), 2.29 (s, 3H), 2.08 (s, 2H), 1.86-1.68 (m, 5H), 1.40 (s, 9H); MS calculated for $C_{19}H_{29}N_4O_2$ (M+H⁺) 345.22. found 345.1.

Intermediate 25

N-(1-(azepan-3-yl)-5-methyl-1H-benzo[d]imidazol-2-yl)-3-(trifluoromethyl)benzamide

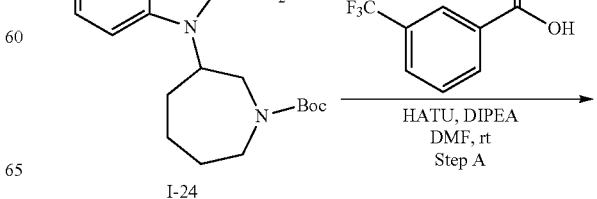

-continued

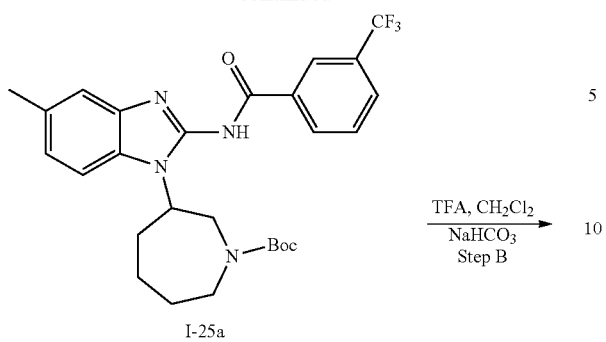

I-25a

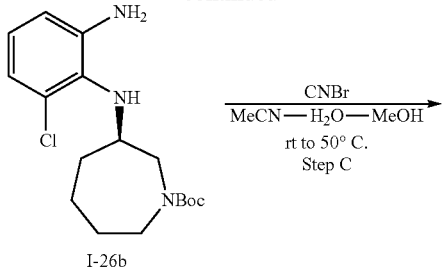

I-26b

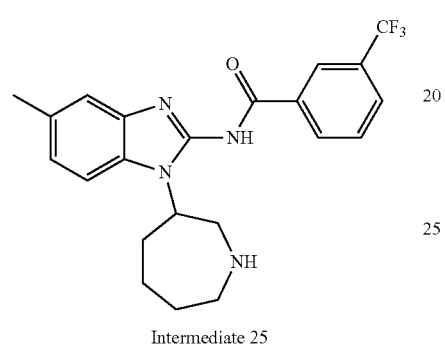

Intermediate 25

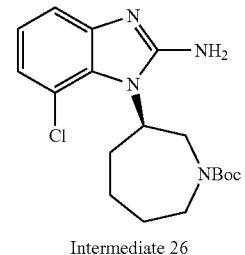

Intermediate 26

The title compound (Intermediate 25) was prepared from I-24 in several steps following procedures analogous to I-16, using the appropriate starting materials. $^1$H-NMR (400 MHz, DMSO-$d_6$): ∂ 12.85 (s, 1H), 9.1 (br s, 2H), 8.53 (d, J=8 Hz, 1H), 8.43 (s, 1H), 7.92 (d, J=7.6 Hz, 1H), 7.78-7.74 (m, 1H), 7.53 (d, J=8.4 Hz, 1H), 7.39 (s, 1H), 7.13 (d, J=8.4 Hz, 1H), 5.21 (br s, 1H), 4.03-3.97 (m, 1H), 3.57 (d, J=11.6 Hz, 1H), 2.40 (s, 3H), 2.08-2.01 (m, 4H), 1.97-1.72 (m, 1H); MS calculated $C_{22}H_{24}F_3N_4O$ (M+H$^+$) 417.18. found 417.2.

Intermediate 26

(R)-tert-butyl 3-(2-amino-7-chloro-1H-benzo[d]imidazol-1-yl)azepane-1-carboxylate

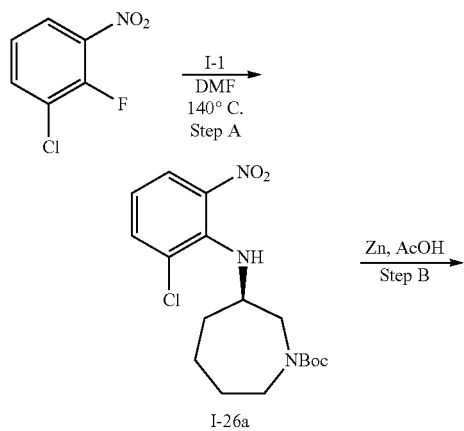

Step A:

(R)-tert-butyl 3-((2-chloro-6-nitrophenyl)amino)azepane-1-carboxylate (I-26a) was prepared following procedures analogous to I-15, Step A, using the appropriate starting materials. $^1$H-NMR (400 MHz, CDCl$_3$): ∂ 8.00-7.91 (m, 1H), 7.58-7.49 (m, 1H), 7.02-6.51 (m, 2H), 4.31-4.03 (m, 1H), 3.84-2.98 (m, 4H), 1.98-1.60 (m, 5H), 1.46-1.39 (m, 10H); MS calculated for $C_{17}H_{25}ClN_3O_4$ (M+H$^+$) 370.15. found 370.10.

Step B:

A mixture of I-26a (7.5 g, 19.5 mmol) and Zn (12.8 mg, 195 mmol) in AcOH (22 mL) was stirred at room temperature for 2 h. The reaction was basified with saturated aqueous Na$_2$CO$_3$ solution, filtered, and extracted with EtOAc (3×80 mL). The combined organic phase was washed with brine, dried with Na$_2$SO$_4$ and concentrated in vacuo to afford (R)-tert-butyl 3-((2-amino-6-chlorophenyl)amino)azepane-1-carboxylate (I-26b). MS calculated for $C_{17}H_{27}ClN_3O_2$ (M+H$^+$) 340.17. found 340.10. The crude was used in the next step without further purification.

Step C:

The title compound (Intermediate 26) was prepared from I-26b following procedures analogous to I-15, Step C. $^1$H-NMR (400 MHz, CDCl$_3$): ∂ 7.34-7.26 (m, 1H), 7.04-6.97 (m, 2H), 6.05-5.85 (m, 1H), 5.84-5.72 (m, 1H), 5.50-5.37 (m, 0.5H), 5.10-4.80 (m, 0.5H), 4.41-4.23 (m, 1H), 4.09-3.96 (m, 0.5H), 3.94-3.81 (m, 1H), 3.76-3.57 (m, 1H), 3.22-3.14 (m, 0.5H), 2.84-2.63 (m, 1H), 2.34-2.17 (m, 1H), 2.07-1.84 (m, 1H), 1.82-1.64 (m, 2H), 1.53 (s, 9H), 1.48-1.37 (m, 1H); MS calculated for $C_{18}H_{26}ClN_4O_2$ (M+H$^+$) 365.17. found 365.10.

Intermediate 27

(R)—N-(1-(azepan-3-yl)-7-chloro-1H-benzo[d]imidazol-2-yl)-2-methylisonicotinamide hydrochloride

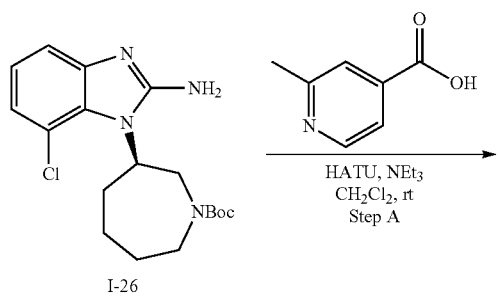

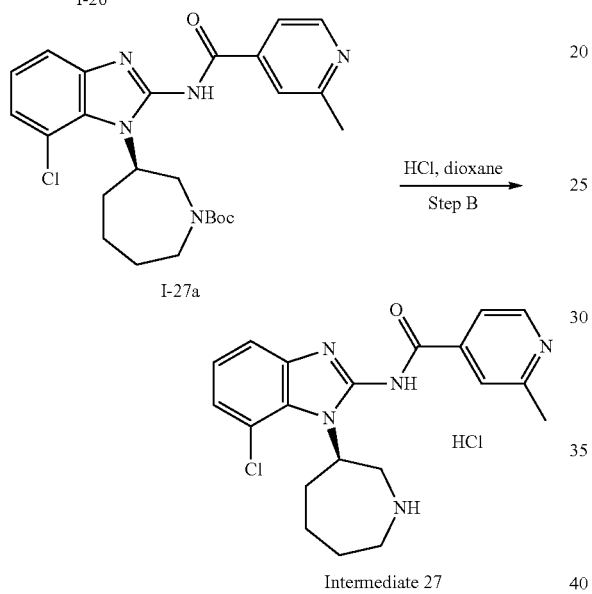

Step A:

A mixture of 2-methylisonicotinic acid (3.371 g, 24.6 mmol) and 2-(7-aza-1H-benzotriazole-1-yl)-1,1,3,3-tetramethyluronium hexafluorophosphate (9.345 g, 24.6 mmol) in CH$_2$Cl$_2$ (120 ml) was treated at room temperature with NEt$_3$ (4.1 mL, 29.4 mmol). The reaction was stirred for 1 hour before it was slowly added into a CH$_2$Cl$_2$ solution (45 ml) of I-26 (5.98 g, 16.4 mmol). Ten minutes later, more NEt$_3$ (4.1 mL, 29.4 mmol) was added and the mixture stirred for 2 h. The mixture was then diluted with CH$_2$Cl$_2$ (240 mL), washed with H$_2$O (2×80 mL), saturated aqueous NaHCO$_3$ solution (70 mL), and brine (70 mL). The organic phase was dried with Na$_2$SO$_4$, and concentrated under reduced pressure. The crude material was purified by column chromatography (55% EtOAc/hexanes) to afford (R)-tert-butyl 3-(7-chloro-2-(2-methylisonicotinamido)-1H-benzo[d]imidazol-1-yl)azepane-1-carboxylate (I-27a) as a light yellow foam. $^1$H-NMR (400 MHz, CDCl$_3$): ∂ 12.81 (br s, 1H), 8.65-8.62 (m, 1H), 7.95-7.85 (m, 2H), 7.27-7.11 (m, 3H), 5.64-5.51 (m, 1H), 4.56-4.44 (m, 1H), 4.07-3.92 (m, 1H), 3.79-3.71 (m, 0.5H), 3.41-3.35 (m, 0.5H), 3.29-3.23 (m, 1H), 2.71-2.59 (m, 1H), 2.65 (s, 3H), 2.22-2.00 (m, 3H), 1.93-1.80 (m, 1H), 1.51-1.45 (m, 1H), 1.50 (s, 3.5H), 1.41 (s, 5.5H); MS calculated for C$_{25}$H$_{31}$ClN$_5$O$_3$ (M+H$^+$) 484.20. found 484.20.

Step B:

A solution of I-27a (8.62 g, 16.4 mmol) in MeOH (67 mL) was treated with HCl in dioxane (4M, 67 mL) and the mixture was stirred at room temperature for 7 h. The mixture was then concentrated under reduced pressure to afford the title compound (Intermediate 27). The product was used in the next step without further purification. A sample was treated with 1M NaOH, extracted with EtOAc, dried with Na$_2$SO$_4$ and concentrated under reduced pressure to afford I-27 as a free base. $^1$H-NMR (400 MHz, CD$_3$CN): ∂ 8.49 (d, J=5.0 Hz, 1H), 7.81 (s, 1H), 7.72 (d, J=4.8 Hz, 1H), 7.50 (br d, J=7.52 Hz, 1H), 7.16-7.09 (m, 2H), 5.66-5.59 (m, 1H), 3.77 (dd, J=6.54, 14.3 Hz, 1H), 3.18 (dd, J=5.3, 14.3 Hz, 1H), 3.05-2.98 (m, 1H), 2.76-2.69 (m, 1H), 2.63-2.53 (m, 1H), 2.47 (s, 3H), 2.10-2.03 (m, 1H), 1.96-1.93 (m, 2H), 1.86-1.75 (m, 2H), 1.61-1.54 (m, 2H); MS calculated for C$_{20}$H$_{23}$ClN$_5$O (M+H$^+$) 384.15. found 384.20.

Intermediate 28

(R)-tert-butyl 3-(2-amino-7-chloro-6-methoxy-1H-benzo[d]imidazol-1-yl)azepane-1-carboxylate

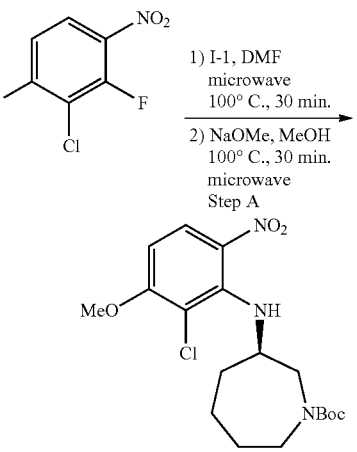

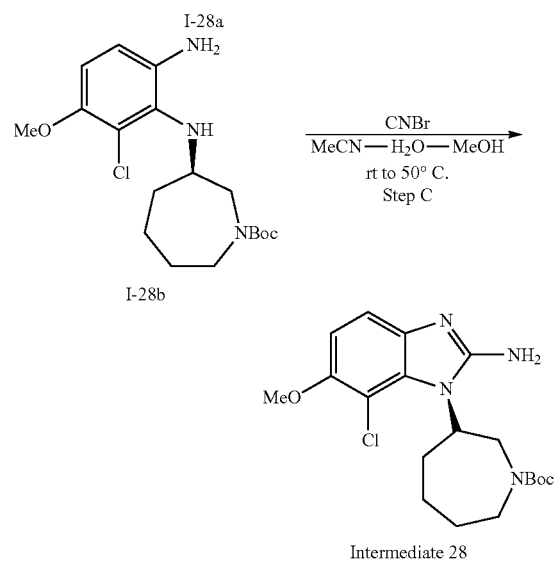

Step A:

To a solution of 2-chloro-1,3-difluoro-4-nitrobenzene (1.3548 g, 7 mmol) in DMF (10 mL) was added N,N- diisopropylethylamine (0.9951 g, 1.341 mL) and I-1 (1.575 g, 7.35 mmol). The mixture was subjected to microwave irradiation (100° C., 30 min), the solvent was evaporated and the crude was re-dissolved in a 0.5M sodium methoxide solution in MeOH (5 ml, 2.5 mmol). This mixture was re-subjected to microwave irradiation (100° C., 30 min). The mixture was then quenched with water and concentrated under reduced pressure. The crude material was purified by column chromatography (AcOEt in hexanes, 0% to 25%) to afford (R)-tert-butyl 3-((2-chloro-3-methoxy-6-nitrophenyl)amino)azepane-1-carboxylate (I-28a). MS calculated for $C_{18}H_{27}ClN_3O_5$ (M+H$^+$) 400.16. found 400.1.

Step B:

(R)-tert-butyl 3-((6-amino-2-chloro-3-methoxyphenyl)amino)azepane-1-carboxylate (I-28b) was prepared from I-28a following procedures analogous to I-26, Step B. MS calculated for $C_{18}H_{29}ClN_3O_3$ (M+H$^+$) 370.18. found 370.2.

Step C:

The title compound (Intermediate 28) was prepared from I-28b following procedures analogous to I-15, Step C. MS calculated for $C_{19}H_{28}ClN_4O_3$ (M+H$^+$) 395.18. found 395.2.

Intermediate 29

(R)—N-(1-(azepan-3-yl)-7-chloro-6-methoxy-1H-benzo[d]imidazol-2-yl)pyridazine-4-carboxamide hydrochloride Step A:

A solution of pyridazine-4-carboxylic acid (92.5 mg, 0.754) and 2-(7-aza-1H-benzotriazole-1-yl)-1,1,3,3-tetramethyluronium hexafluorophosphate (283 mg, 0.745 mmol) in 1:1 CH$_2$Cl$_2$/DMF (10 mL) was treated with NEt$_3$ (108 mg, 1.06 mmol) and stirred for 10 min. A solution of I-28 (224 mg, 0.56 mmol) in 1:1 CH$_2$Cl$_2$/DMF (10 mL) was then added and the mixture was stirred for 1 h (reaction completion monitored by LC/MS). The solvent was evaporated under reduced pressure and the residue was dissolved in CH$_2$Cl$_2$ (4 mL), treated with Na$_2$CO$_3$ (178 mg, 1.68 mmol) and stirred for 3 minutes. The mixture was then purified by column chromatography (MeOH in CH$_2$Cl$_2$, 0% to 10%) to afford (R)-tert-butyl 3-(7-chloro-6-methoxy-2-(pyridazine-4-carboxamido)-1H-benzo[d]imidazol-1-yl)azepane-1-carboxylate (I-29a). MS calculated for $C_{24}H_{30}ClN_6O_4$ (M+H$^+$) 501.19. found 501.2.

Step B:

The title compound (Intermediate 29) was prepared from I-29a following procedures analogous to I-27, Step B. MS calculated for $C_{19}H_{22}ClN_6O_2$ (M+H$^+$) 401.14, found 401.1.

Intermediate 30

(R)—N-(1-(azepan-3-yl)-7-chloro-1H-benzo[d]imidazol-2-yl)-2,6-dimethylisonicotinamide hydrochloride

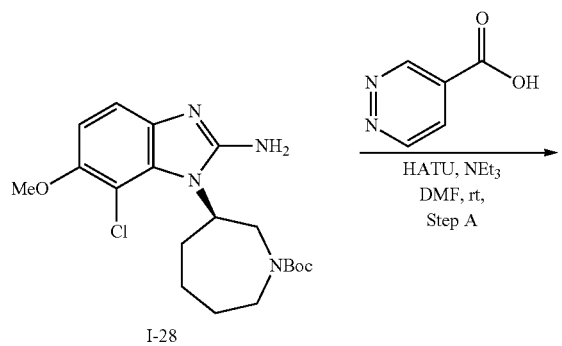

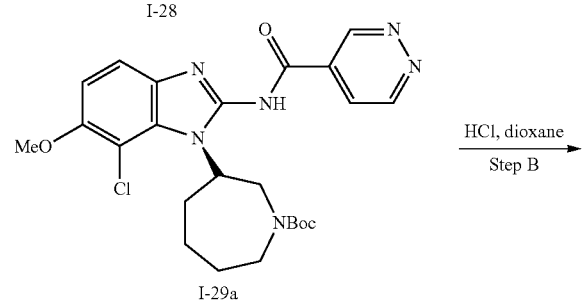

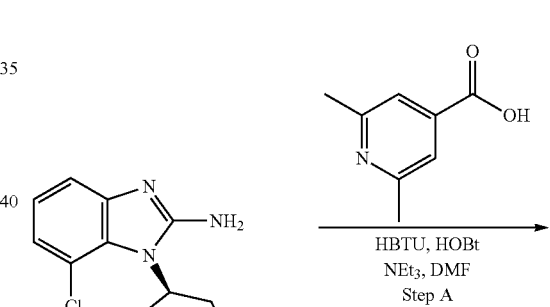

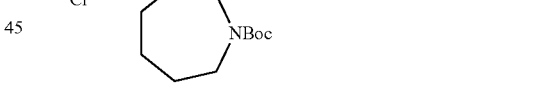

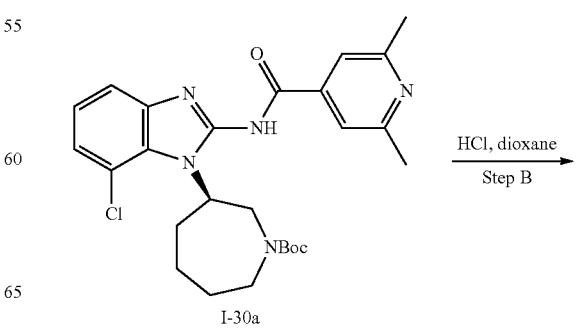

-continued

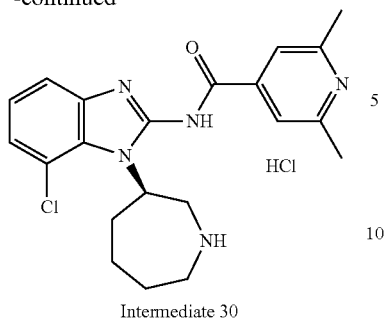

Intermediate 30

Step A:

A mixture of 2,6-dimethylisonicotinic acid (927 mg, 6.1 mmol) and O-benzotriazole-N,N,N',N'-tetramethyl-uronium-hexafluoro-phosphate (HBTU) (4.65 g, 12.3 mmol) in DMF (15 ml) was treated with hydroxybenzotriazole (HOBt) (1.82 g, 13.5 mmol) and stirred at room temperature for 10 min. The resulting mixture was then added to a solution of I-26 (1.12 g, 3.1 mmol) in DMF (4 mL), followed by addition of NEt$_3$ (1.7 mL, 12.3 mmol). The reaction was stirred overnight, quenched with H$_2$O (2 mL) and concentrated under reduced pressure. The crude was partitioned between EtOAc and 1N NaOH, and extracted with EtOAc. The combined organic phase was dried over Na$_2$SO$_4$, and concentrated under reduced pressure. The crude material was purified by column chromatography (0-100% EtOAc/Hexanes) to afford (R)-tert-butyl 3-(7-chloro-2-(2,6-dimethylisonicotinamido)-1H-benzo[d]imidazol-1-yl)azepane-1-carboxylate (I-30a). MS calculated for C$_{26}$H$_{33}$ClN$_5$O$_3$ (M+H$^+$) 498.22. found: 498.2.

Step B:

A solution of I-30a (951 mg, 1.9 mmol) in CH$_2$Cl$_2$ (20 mL) was treated with HCl in dioxane (4M, 20 mL) and the mixture was stirred at room temperature overnight. The yellow solid was filtered, washed with CH$_2$Cl$_2$ and dried to afford the title compound (Intermediate 30). MS calculated for C$_{21}$H$_{25}$ClN$_5$O (M+H$^+$) 398.17. found: 398.2.

Intermediate 31

(R)-tert-butyl 3-(2-amino-7-methyl-1H-benzo[d]imidazol-1-yl)azepane-1-carboxylate

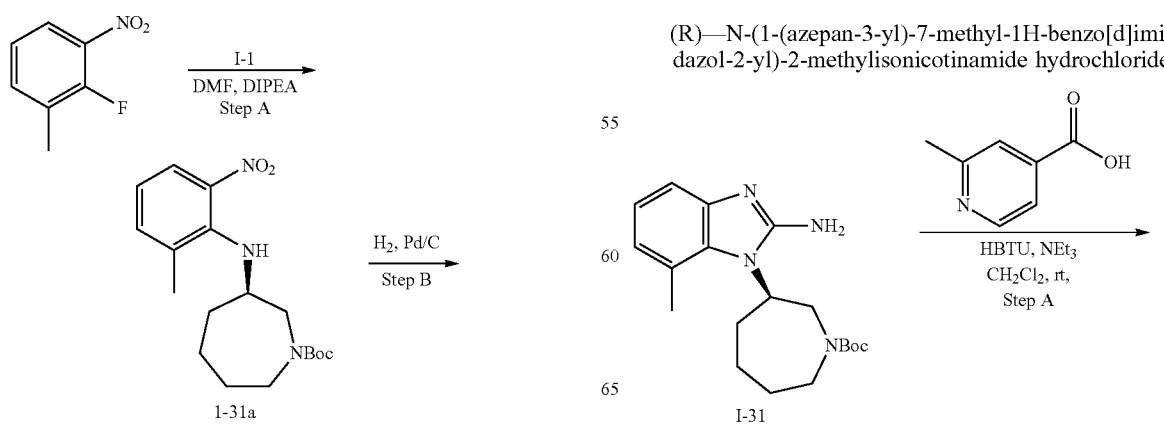

-continued

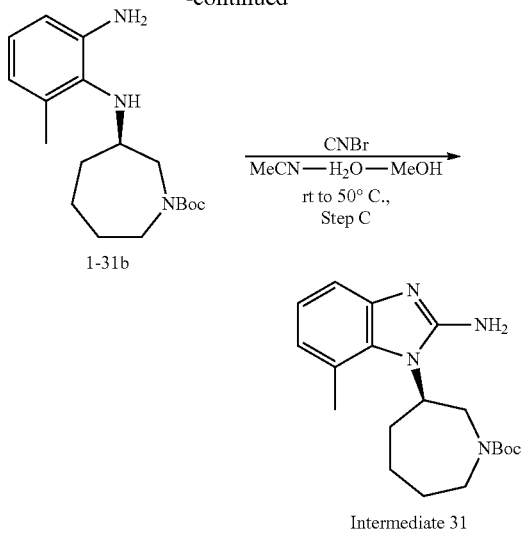

Step A:

(R)-tert-butyl 3-((2-methyl-6-nitrophenyl)amino)azepane-1-carboxylate (I-31a) was prepared following procedures analogous to I-15, Step A, using the appropriate starting materials. $^1$H-NMR (400 MHz, CDCl$_3$): ∂ 7.93-7.87 (m, 1H), 7.37-7.31 (m, 1H), 6.91-6.79 (m, 1.5H), 6.50-6.47 (m, 0.5H), 3.88-3.76 (m, 2H), 3.57-3.52 (m, 1H), 3.22-2.78 (m, 2H), 2.43-2.41 (m, 3H), 1.92-1.60 (m, 5H), 1.47-1.38 (m, 10H); MS calculated for C$_{18}$H$_{28}$N$_3$O$_4$ (M+H$^+$) 350.20. found 350.0.

Step B:

(R)-tert-butyl 3-((2-amino-6-methylphenyl)amino)azepane-1-carboxylate (I-31b) was prepared from I-31a following procedures analogous to I-15, Step B. MS calculated for C$_{18}$H$_{30}$N$_3$O$_2$ (M+H$^+$) 320.23. found 320.2.

Step C:

The title compound (Intermediate 31) was prepared from I-31b following procedures analogous to I-15, Step C. $^1$H-NMR (400 MHz, CDCl$_3$): ∂ 8.50 (br s, 1H), 7.27-7.24 (m, 1H), 7.18-7.14 (m, 1H), 7.00-6.97 (m, 1H), 5.10-5.05 (m, 1H), 4.32-4.26 (m, 1H), 3.99-3.92 (m, 1H), 3.78-3.72 (m, 1H), 2.99-2.87 (m, 1H), 2.68 (s, 3H), 2.30-2.23 (m, 1H), 2.13-2.08 (m, 1H), 1.87 (br s, 3H), 1.50 (s, 9H), 1.39-1.38 (m, 1H); MS calculated for C$_{19}$H$_{29}$N$_4$O$_2$ (M+H$^+$) 345.22. found 345.2.

Intermediate 32

(R)—N-(1-(azepan-3-yl)-7-methyl-1H-benzo[d]imidazol-2-yl)-2-methylisonicotinamide hydrochloride

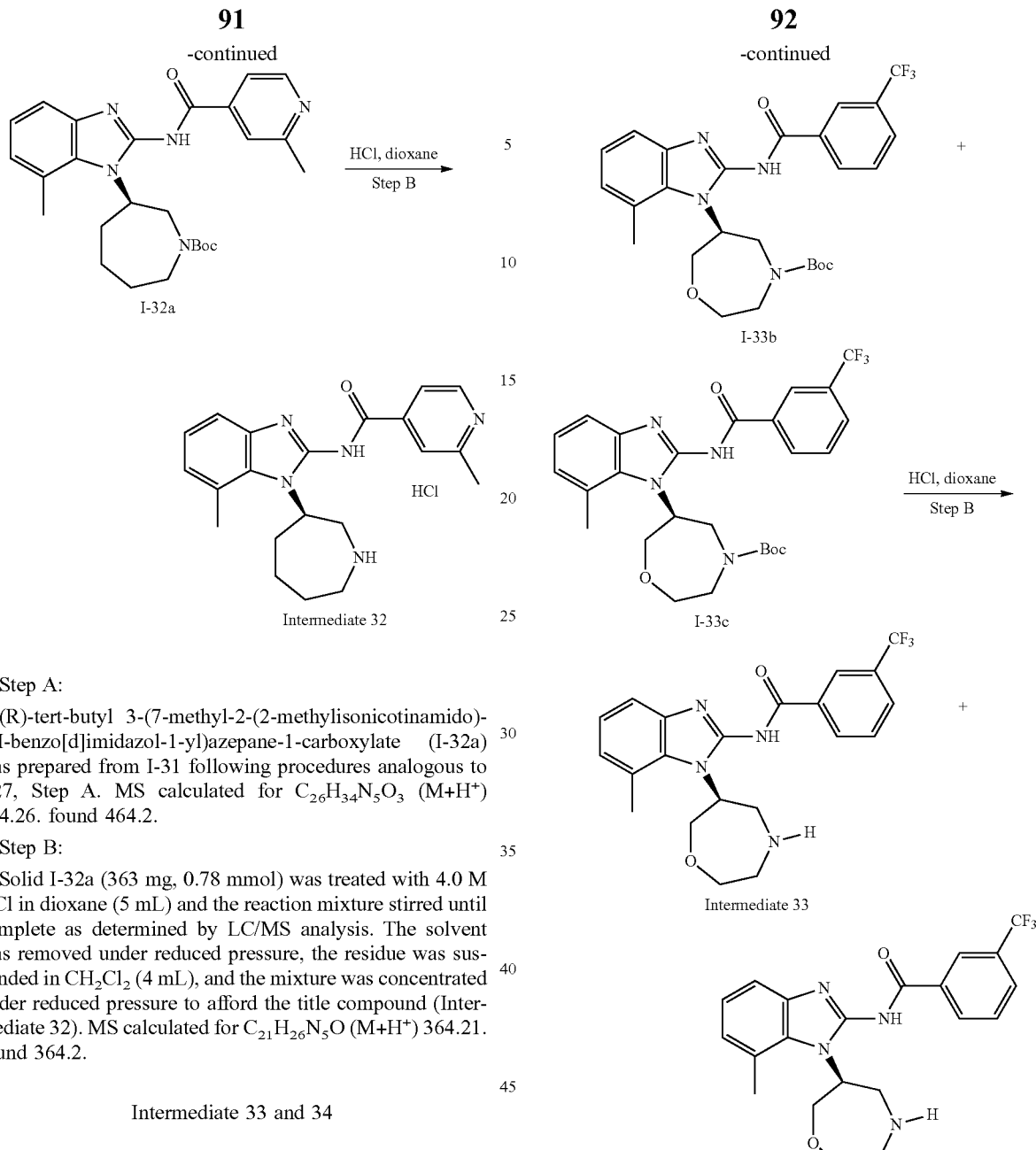

Step A:

(R)-tert-butyl 3-(7-methyl-2-(2-methylisonicotinamido)-1H-benzo[d]imidazol-1-yl)azepane-1-carboxylate (I-32a) was prepared from I-31 following procedures analogous to I-27, Step A. MS calculated for $C_{26}H_{34}N_5O_3$ (M+H$^+$) 464.26. found 464.2.

Step B:

Solid I-32a (363 mg, 0.78 mmol) was treated with 4.0 M HCl in dioxane (5 mL) and the reaction mixture stirred until complete as determined by LC/MS analysis. The solvent was removed under reduced pressure, the residue was suspended in $CH_2Cl_2$ (4 mL), and the mixture was concentrated under reduced pressure to afford the title compound (Intermediate 32). MS calculated for $C_{21}H_{26}N_5O$ (M+H$^+$) 364.21. found 364.2.

Intermediate 33 and 34

(R)— and (S)—N-(7-methyl-1-(1,4-oxazepan-6-yl)-1H-benzo[d]imidazol-2-yl)-3-(trifluoromethyl)benzamide

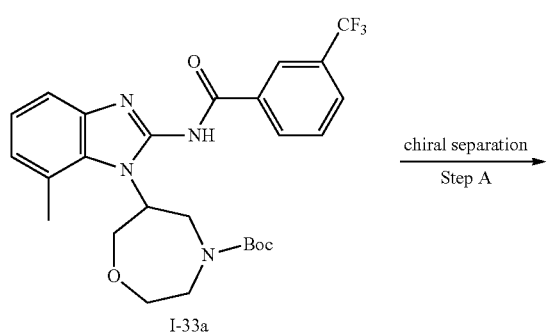

Step A:

A sample of racemate I-33a (prepared in several steps similarly to I-16a, using the appropriate starting materials) is subjected to chiral chromatography (ChiralPak AD-H) with isocratic elution (75/25 $CO_2$/iPrOH) using a Thar Technologies SFC Prep 80 system with SuperChrom v.5.3 software. The first eluting peak is (R)-tert-butyl 6-(7-methyl-2-(3-(trifluoromethyl)benzamido)-1H-benzo[d]imidazol-1-yl)-1,4-oxazepane-4-carboxylate (I-33b) and the second eluting peak is (S)-tert-butyl 6-(7-methyl-2-(3-(trifluoromethyl)benzamido)-1H-benzo[d]imidazol-1-yl)-1,4-oxazepane-4-carboxylate (I-33c). MS calculated for $C_{26}H_{30}F_3N_4O_4$ (M+H$^+$) 519.21. found 519.2.

Step B:

The title compounds (Intermediate 33 and Intermediate 34) were prepared from I-33b and I-33c respectively, fol-

Intermediate 35

(R)-tert-butyl 3-(2-amino-5-(hydroxymethyl)-7-methyl-1H-benzo[d]imidazol-1-yl)azepane-1-carboxylate

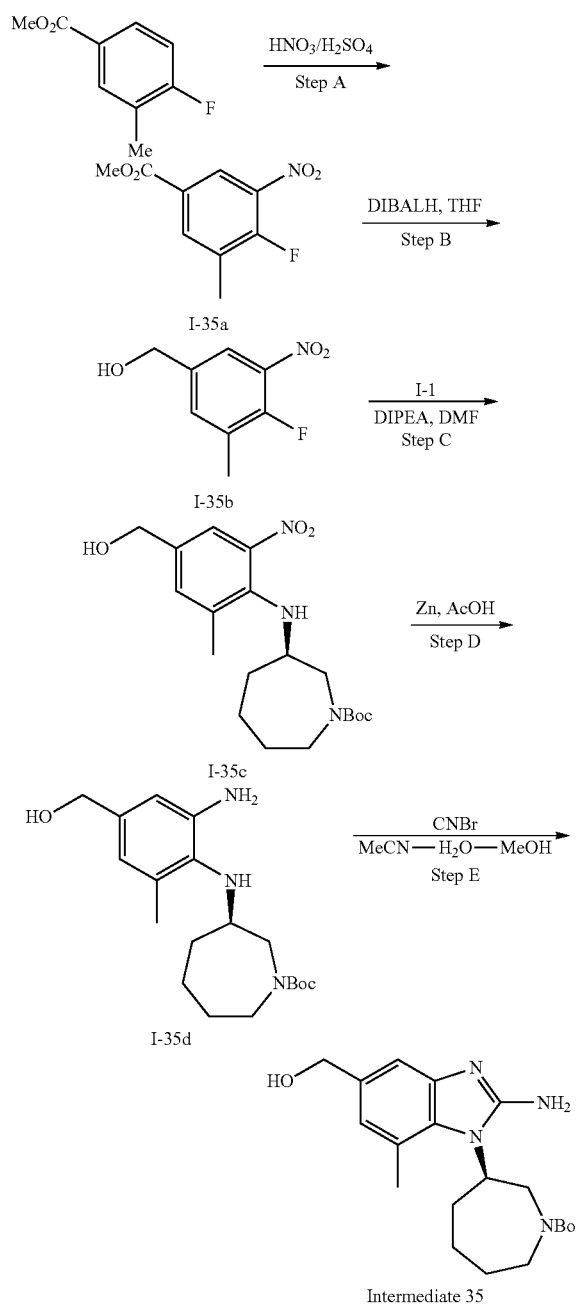

Intermediate 35

Step A:

Concentrated $H_2SO_4$ (17.5 mL) was slowly added to methyl 4-fluoro-3-methylbenzoate (12.8 g, 76 mmol) and the mixture was cooled to 0° C. A solution of fuming $HNO_3$ (69.5%, 11.6 mL) in concentrated $H_2SO_4$ (17.5 mL) was then added drop-wise over 10 min. The mixture was stirred for 80 min while slowly warming up to room temperature (reaction completion monitored by TLC). The mixture was slowly poured into ice, the aqueous layer was extracted with $CH_2Cl_2$ (3×200 mL), dried over anhydrous $Na_2SO_4$ and concentrated under reduced pressure. The crude was purified by column chromatography to afford methyl 4-fluoro-3-methyl-5-nitrobenzoate (I-35a) as a white solid. MS calculated for $C_9H_9FNO_4$ (M+H$^+$) 214.04. found 214.0.

Step B:

To a solution of I-35a (6.55 g, 30.73 mmol) in THF (50 mL) at −10° C. was slowly added DIBALH (92.2 mL of 1.0 M solution in hexanes) over 10 min. The mixture was stirred for 40 min at −10° C. (reaction completion monitored by TLC) and quenched with $Na_2SO_4·10H_2O$. The mixture was then treated with Rochelle's salt (19.4 g, 95 mmol) in water (300 mL), $CH_2Cl_2$ (400 mL) and EtOAc (200 ml) and stirred overnight. The organic phase was separated and the aqueous phase extracted with EtOAc (200 mL). The combined organic layers were dried over $Na_2SO_4$, and concentrated under reduced pressure. The crude was purified by column chromatography (EtOAc in Hexanes, 15% to 40%) to afford (4-fluoro-3-methyl-5-nitrophenyl)methanol (I-35b).

Step C:

A solution of I-35b (1.516 g, 8.20 mmol), (R)-tert-butyl 3-aminoazepane-1-carboxylate (1.844 g, 8.60 mmol) and N,N-diisopropylethylamine (1.16 g, 9.01 mmol) in DMF (30 mL) was subjected to microwave irradiation (140° C., 4.5 h). The solvent was evaporated and the residue was purified by column chromatography (EtOAc in Hexanes, 0% to 25%) to afford (R)-tert-butyl 3-((4-(hydroxymethyl)-2-methyl-6-nitrophenyl)amino)azepane-1-carboxylate (I-35c) as an orange oil. MS calculated for $C_{19}H_{30}N_3O_5$ (M+H$^+$) 380.21. found 380.2.

Steps D and E:

The title compound (Intermediate 35) was prepared from I-35c in several steps following procedures analogous to I-26, Steps B and C. MS calculated for $C_{20}H_{31}N_4O_3$ (M+H$^+$) 375.23. found 375.2.

Intermediate 36

(R)—N-(1-(azepan-3-yl)-7-methyl-5-(pyrrolidin-1-ylmethyl)-1H-benzo[d]imidazol-2-yl)benzamide hydrochloride

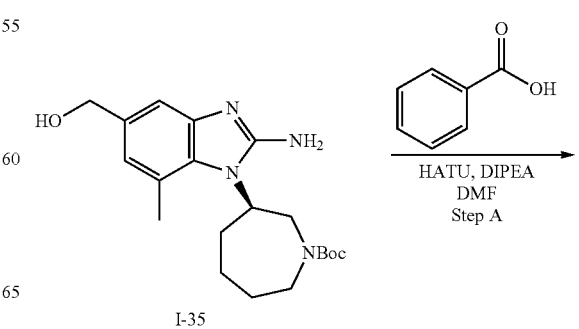

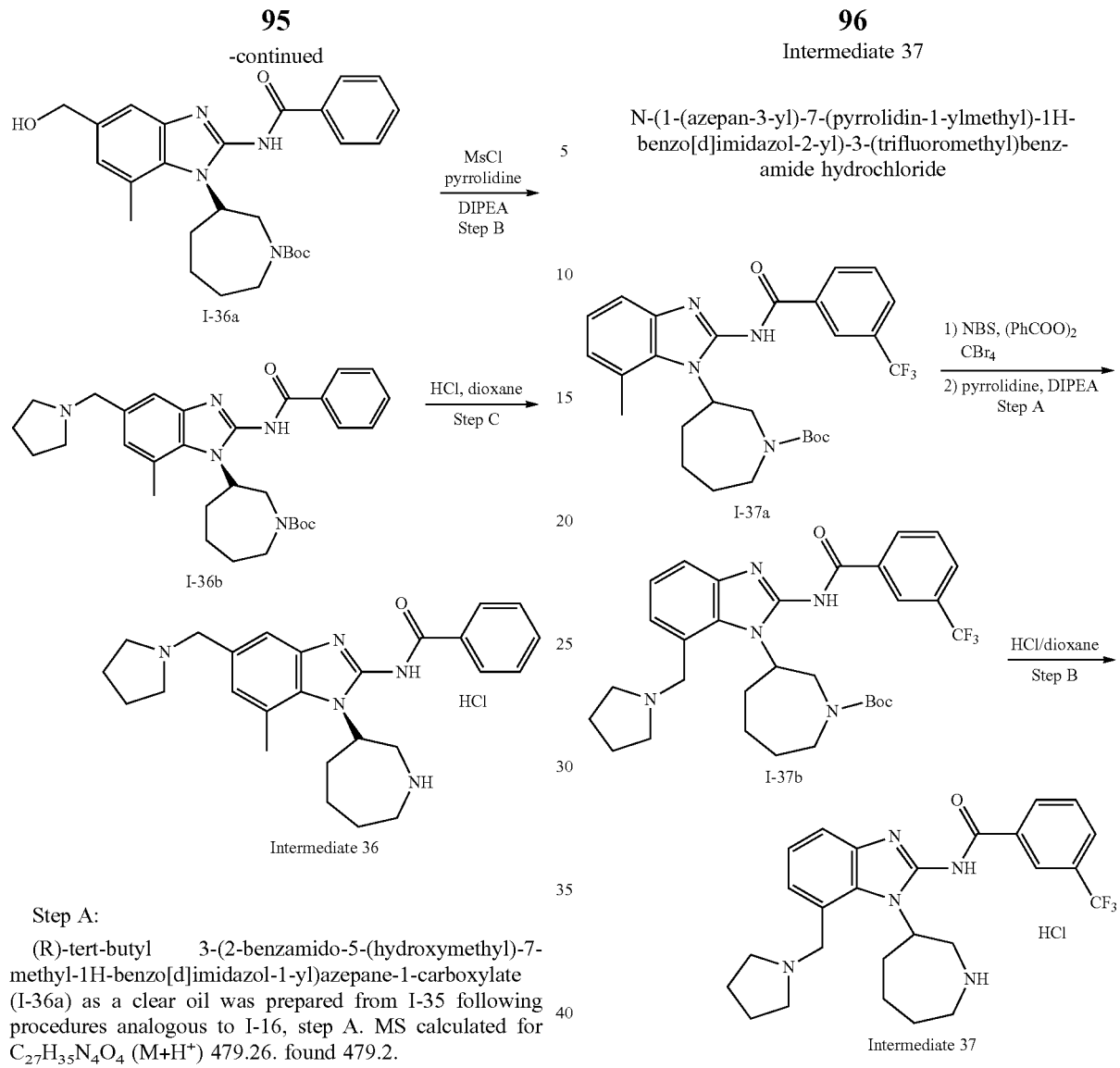

Intermediate 37

N-(1-(azepan-3-yl)-7-(pyrrolidin-1-ylmethyl)-1H-benzo[d]imidazol-2-yl)-3-(trifluoromethyl)benzamide hydrochloride Step A:

(R)-tert-butyl 3-(2-benzamido-5-(hydroxymethyl)-7-methyl-1H-benzo[d]imidazol-1-yl)azepane-1-carboxylate (I-36a) as a clear oil was prepared from I-35 following procedures analogous to I-16, step A. MS calculated for $C_{27}H_{35}N_4O_4$ (M+H$^+$) 479.26. found 479.2.

Step B:

To a solution of I-36a (540 mg, 1.128 mmol) in $CH_2Cl_2$ (65 mL) were added N,N-diisopropylethylamine (436 mg, 3.385 mmol) and mesyl chloride (388 mg, 3.385 mmol). The mixture was stirred at RT for 16 h. Pyrrolidine (401 mg, 5.64 mmol) was added and the mixture was stirred for 30 min. The solvent was evaporated and the residue was re-dissolved in DMA. More pyrrolidine ((401 mg, 5.64 mmol) was added and the mixture was subjected to microwave irradiation (80° C., 40 minutes). A few drops of water were added to quench the reaction and the mixture was concentrated under reduced pressure. The residue was dissolved in EtOAc (200 mL), washed with saturated aqueous $NaHCO_3$ solution and brine, dried over $Na_2SO_4$, and concentrated under reduced pressure. The crude material was purified by column chromatography (0-10% MeOH in $CH_2Cl_2$) to afford (R)-tert-butyl 3-(2-benzamido-7-methyl-5-(pyrrolidin-1-ylmethyl)-1H-benzo[d]imidazol-1-yl)azepane-1-carboxylate (I-36b). MS calculated for $C_{31}H_{42}N_5O_3$ (M+H$^+$) 531.32. found 532.3.

Step C:

The title compound (Intermediate 36) was prepared from I-36b following procedures analogous to I-27, Step B. MS calculated for $C_{26}H_{34}N_5O$ (M+H$^+$) 432.27. found 432.2.

Step A:

A solution of I-37a (45 mg, 0.087 mmol; prepared in several steps following procedures analogous to I-25, using the appropriate starting materials), NBS (23 mg, 0.131 mmol), benzoyl peroxide (3 mg, 0.012 mmol), and carbon tetrachloride (1 mL) in a 2 mL microwave reaction vessel was warmed to 100° C. by irradiation with a heat lamp for 6 h. The reaction mixture was cooled to room temperature and concentrated under reduced pressure. The residue was then suspended in acetonitrile (1 mL) and treated with pyrrolidine (0.014 mL, 0.174 mmol) and N,N-diisopropylethylamine (0.045 mL, 0.261 mL). The reaction mixture was stirred at room temperature until completed as determined by LC/MS analysis. The mixture was concentrated under reduced pressure to afford tert-butyl 3-(7-(pyrrolidin-1-ylmethyl)-2-(3-(trifluoromethyl)benzamido)-1H-benzo[d]imidazol-1-yl)azepane-1-carboxylate (I-37b). MS calculated for $C_{31}H_{39}F_3N_5O_3$ (M+H$^+$) 586.29. found 586.3.

Step B:

The title compound (Intermediate 37) was prepared following procedures analogous to I-32, Step B. MS calculated for $C_{26}H_{31}F_3N_5O$ (M+H$^+$) 486.24. found 486.2.

Intermediate 38

(R)—N-(1-(azepan-3-yl)-7-methyl-5-(pyrrolidin-1-methyl)-1H-benzo[d]imidazol-2-yl)-2,6-dimethyl-isonicotinamide hydrochloride

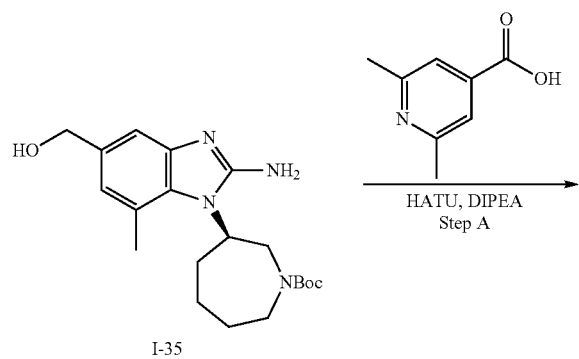

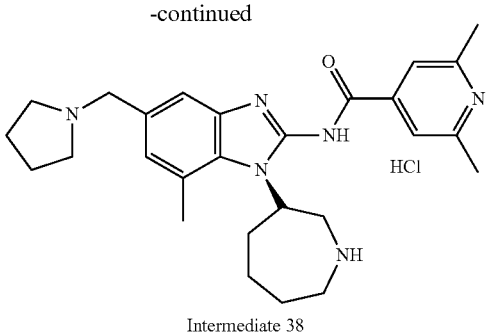

Intermediate 38

Step A:
(R)-tert-butyl 3-(2-(2,6-dimethylisonicotinamido)-5-(hydroxymethyl)-7-methyl-1H-benzo[d]imidazol-1-yl)azepane-1-carboxylate (I-38a) was prepared following procedures analogous to I-16.

Step B:
A suspension of I-38a (350 mg, 0.689 mmol) and IBX (386 mg, 1.379 mmol) in MeCN was heated to 90° C. in a sealed vessel for 1 h. The mixture was cooled to room temperature and filtered. The filtrate was concentrated to afford (R)-tert-butyl 3-(2-(2,6-dimethylisonicotinamido)-5-formyl-7-methyl-1H-benzo[d]imidazol-1-yl)azepane-1-carboxylate (I-38b). The compound was used in the next step without further purification.

Step C:
To a mixture of I-38b (350 mg, 0.689 mmol), pyrrolidine (146 mg, 2.067 mmol), and N,N-diisopropylethylamine (600 uL, 3.445 mmol) in $(CH_2Cl)_2$ (20 mL) was added $NaHB(OAc)_3$ (438 mg, 2.067 mmol). The mixture was then heated to 50° C. for 30 min., cooled to room temperature, filtered and concentrated. The crude was purified by column chromatography (0-90% [9:1:0.175N $CH_2Cl_2$/MeOH/$NH_3$]/$CH_2Cl_2$) to afford (R)-tert-butyl 3-(2-(2,6-dimethylisonicotinamido)-7-methyl-5-(pyrrolidin-1-ylmethyl)-1H-benzo[d]imidazol-1-yl)azepane-1-carboxylate (I-38c) as a yellow solid. MS calculated for $C_{32}H_{45}N_6O_3$ (M+H$^+$) 560.35. found 560.3.

Step D:
The title compound (Intermediate 38) was prepared from I-38c following procedures analogous to I-30, Step B. MS calculated for $C_{27}H_{37}N_6O$ (M+H$^+$) 461.30. found 461.3.

Intermediate 39

N-(1-((R)-azepan-3-yl)-7-((3-hydroxypyrrolidin-1-yl)methyl)-1H-benzo[d]imidazol-2-yl)benzamide

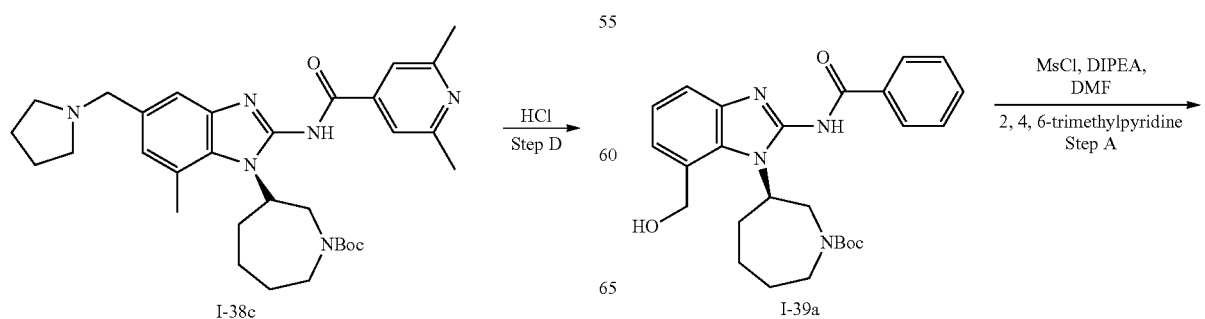

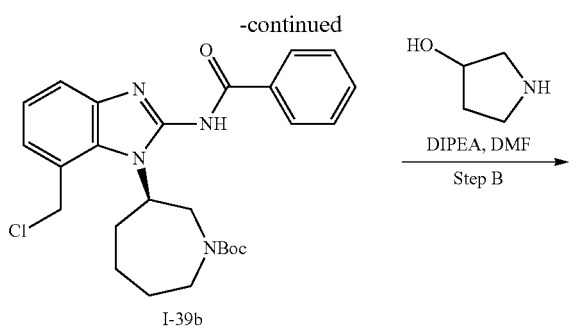

Step A:

To a solution of I-39a (227 mg, 0.488 mmol; prepared following procedures analogous to I-36a, using the appropriate starting materials) in CH$_2$Cl$_2$ (20 mL) at 0° C. were added N,N-diisopropylethylamine (152 mg, 1.175 mmol) and mesyl chloride (134 mg, 1.175 mmol). The mixture was stirred for 10 min, 2,4,6-trimethylpyridine (142.4 mg, 1.175 mmol) was added drop-wise and the reaction was stirred at room temperature for 2 h. More N,N-diisopropylethylamine (63 mg, 0.488 mmol) and mesyl chloride (56 mg, 0.488 mmol) were added and the mixture was stirred for 1 h at room temperature. The mixture was diluted with DMF (5 mL) and stirred overnight, quenched with ice and diluted with EtOAc (300 mL). The organic phase was washed with 0.2 N HCl (3×50 mL), saturated aqueous NaHCO$_3$ solution, and brine, dried over Na$_2$SO$_4$, and concentrated under reduced pressure. The crude material was purified by column chromatography (0-10% MeOH in CH$_2$Cl$_2$) to afford (R)-tert-butyl 3-(2-benzamido-7-(chloromethyl)-1H-benzo[d]imidazol-1-yl)azepane-1-carboxylate (I-39b). MS calculated for C$_{26}$H$_{32}$ClN$_4$O$_3$ (M+H$^+$) 483.21. found 483.0.

Step B:

A solution of I-39b (44 mg, 0.092 mmol) in DMF (2 mL) was treated with pyrrolidin-3-ol (16 mg, 0.184 mmol) and the mixture was stirred at 110° C. for 1 h. The solvent was evaporated under reduced pressure. The residue was dissolved with EtOAc (100 mL), washed with 0.2N HCl (2×20 mL), saturated aqueous NaHCO$_3$ solution and brine, dried over Na$_2$SO$_4$ and concentrated under reduced pressure. The crude material was purified by column chromatography (0-10% methanol in CH$_2$Cl$_2$) to afford (3R)-tert-butyl 3-(2-benzamido-7-((3-hydroxypyrrolidin-1-yl)methyl)-1H-benzo[d]imidazol-1-yl)azepane-1-carboxylate (I-39c). MS calculated for C$_{30}$H$_{40}$N$_5$O$_2$ (M+H$^+$) 534.30. found 534.3.

Step C:

The title compound (Intermediate 39) was prepared from I-39c following procedures analogous to I-27, Step B. MS calculated for C$_{25}$H$_{32}$N$_5$O$_2$ (M+H$^+$) 434.25. found 434.2.

Intermediate 40

N-(1-(azepan-3-yl)-7-(1,1-dioxidothiomorpholine-4-carbonyl)-1H-benzo[d]imidazol-2-yl)benzamide hydrochloride

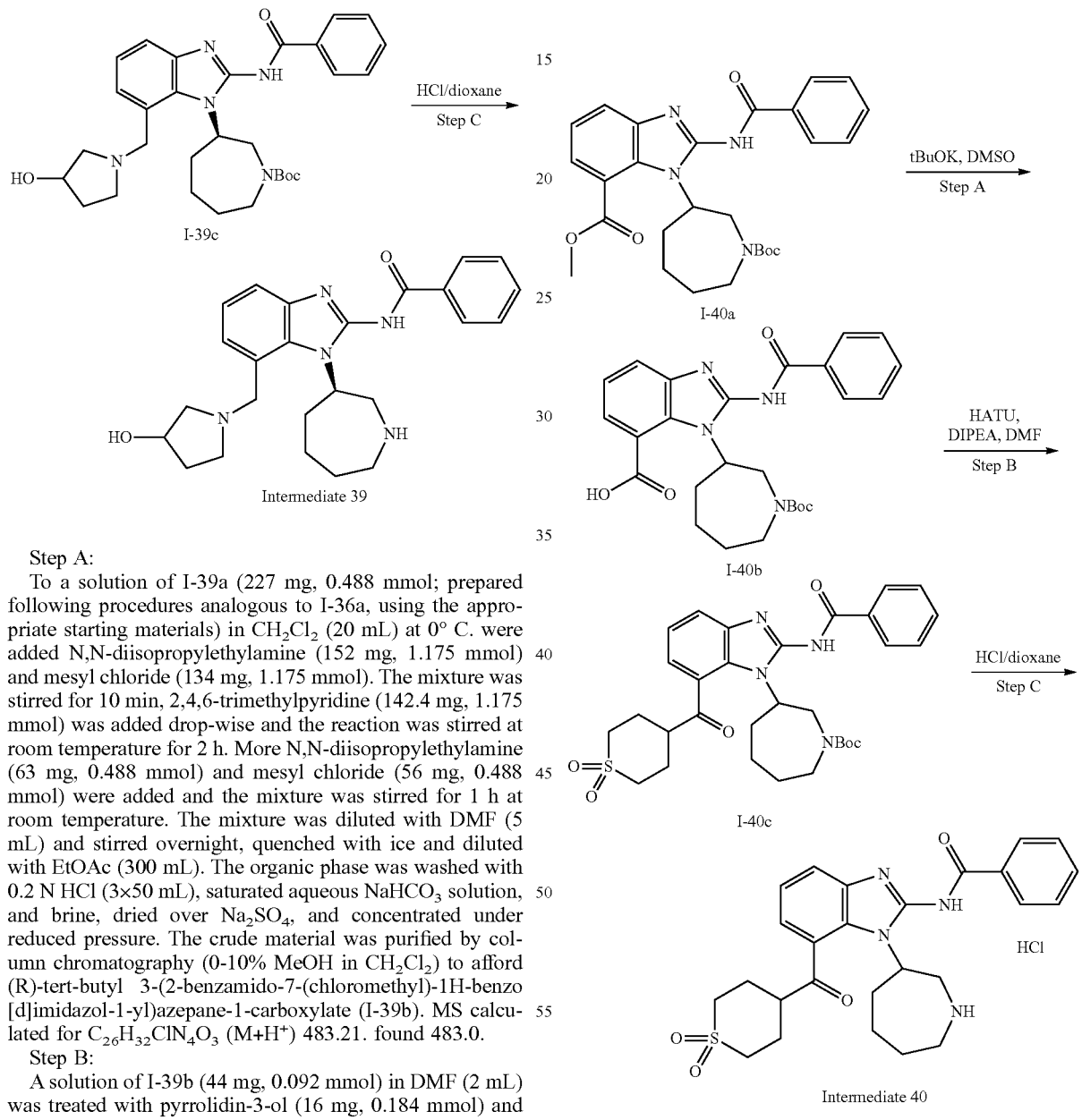

Step A:

To a solution of I-40a (49.3 mg, 0.1 mmol; prepared following procedures analogous to I-22a, using the appropriate starting materials) in DMSO (3 mL) was added potassium t-butoxide (112 mg, 1.0 mmol). The mixture was stirred at room temperature for 50 minutes, diluted with ice-water, acidified to pH=1 with 1N HCl, and extracted with EtOAc (3×50 mL). The combined organic layers were washed with brine and water, dried over $Na_2SO_4$ and concentrated under reduced pressure to afford 2-benzamido-1-(1-(tert-butoxycarbonyl)azepan-3-yl)-1H-benzo[d]imidazole-7-carboxylic acid (I-40b). MS calculated for $C_{26}H_{31}N_4O_5$ (M+H$^+$) 479.22. found 479.0.

Step B:

tert-butyl 3-(2-benzamido-7-(1,1-dioxidothiomorpholine-4-carbonyl)-1H-benzo[d]imidazol-1-yl)azepane-1-carboxylate (I-40c) was prepared from I-40a following procedures analogous to I-16. MS calculated for $C_{30}H_{38}N_5O_6S$ (M+H$^+$) 596.25. found 595.20.

Step C:

The title compound (Intermediate 40) was prepared from I-40c following procedures analogous to I-27, Step B. MS calculated for $C_{25}H_{30}N_5O_4S$ (M+H$^+$) 496.19. found 496.20.

Intermediate 41

2-amino-1-(1-(tert-butoxycarbonyl)azepan-3-yl)-7-cyano-1H-benzo[d]imidazole-5-carboxylate

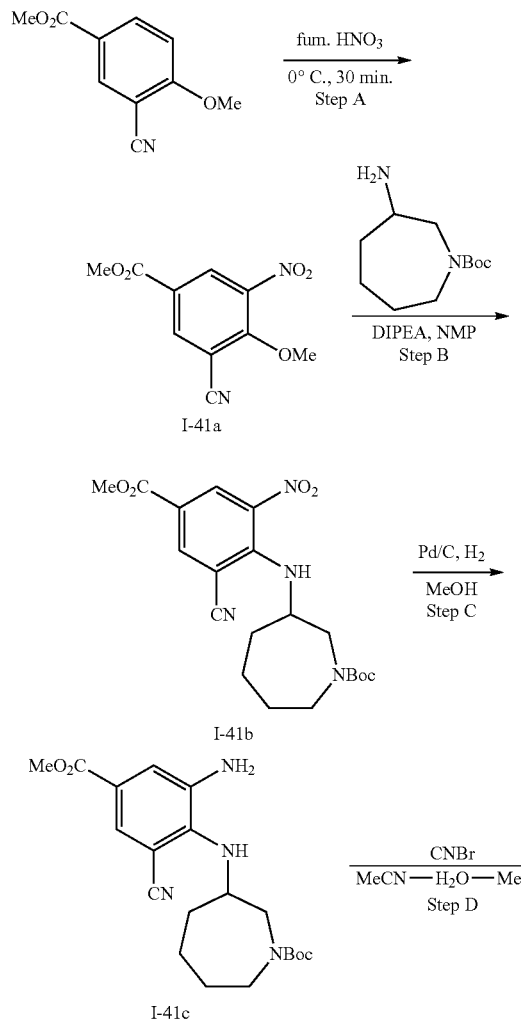

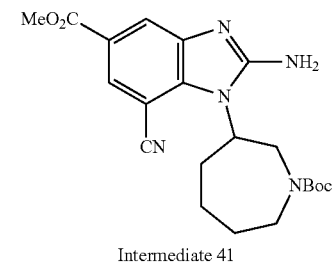

Intermediate 41

Step A:

To a stirred solution of methyl-3-cyano-4-methoxy benzoate (0.820 g) at 0° C. was slowly added fuming $HNO_3$ (15 mL) and the mixture was stirred at 5° C. for 30 min. The mixture was then poured in ice-cold water, the resulting solid was collected by filtration and dried under vacuum to afford methyl 3-cyano-4-methoxy-5-nitrobenzoate (I-41a); $^1$H-NMR (400 MHz, DMSO-d$_6$): ∂ 8.66 (d, J=2 Hz, 1H), 8.60 (d, J=2 Hz, 1H), 4.18 (s, 3H), 3.90 (s, 3H).

Steps B, C and D:

The title compound (Intermediate 41) was prepared in several steps from I-41a following procedures analogous to I-15. MS calculated for $C_{21}H_{28}N_5O_4$ (M+H$^+$) 414.21. found 414.3.

Intermediate 42

N-(1-(azepan-3-yl)-7-cyano-5-(hydroxymethyl)-1H-benzo[d]imidazol-2-yl)-3-(trifluoromethyl)benzamide hydrochloride

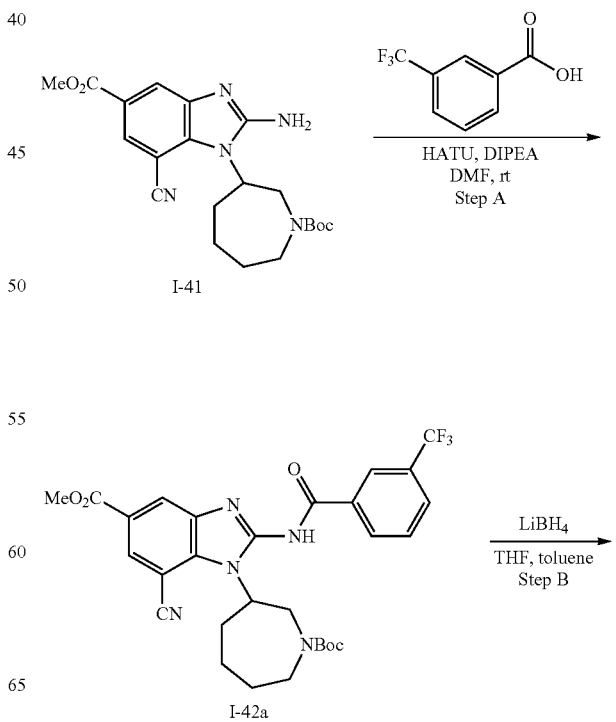

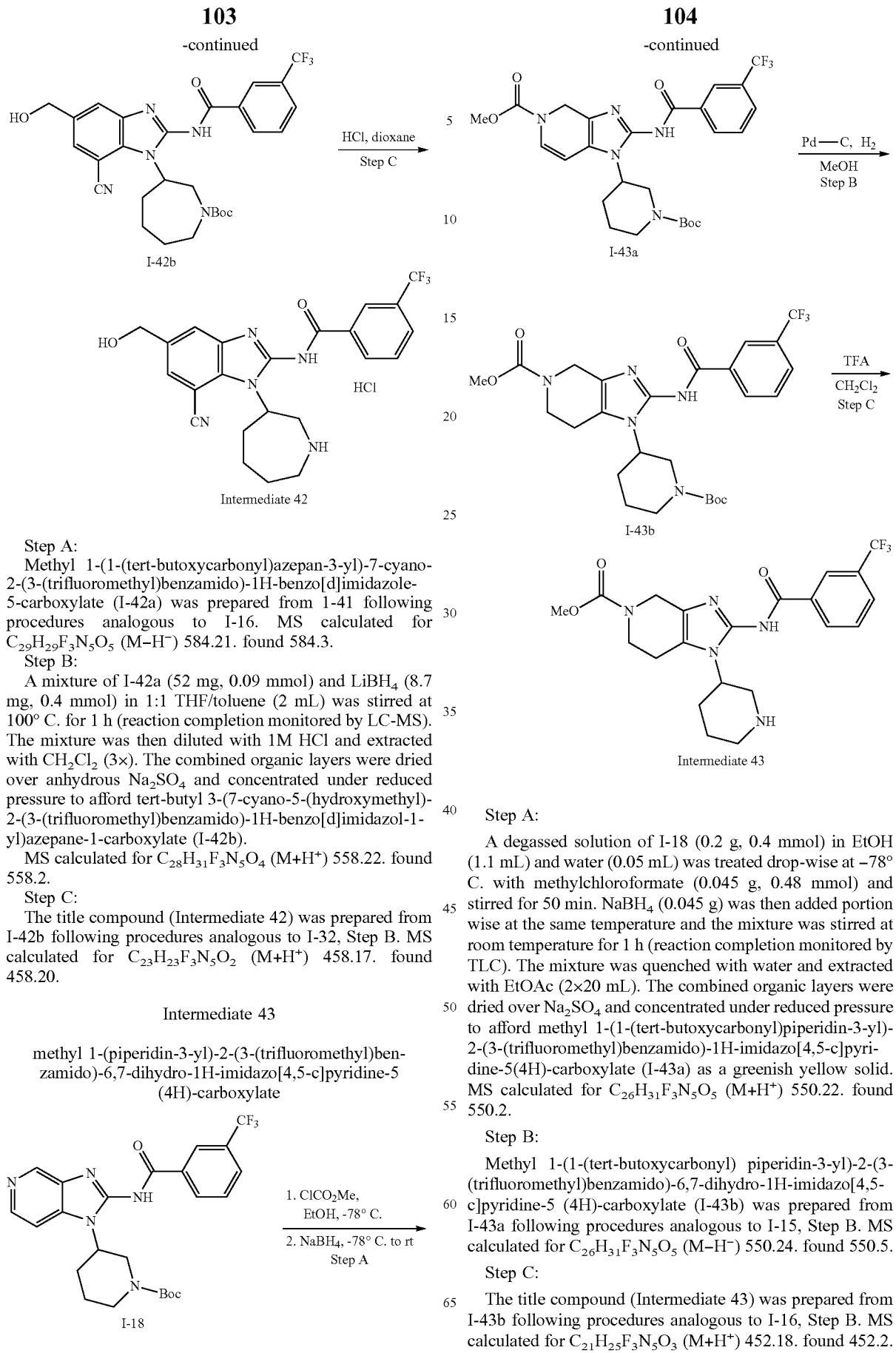

Step A:
Methyl 1-(1-(tert-butoxycarbonyl)azepan-3-yl)-7-cyano-2-(3-(trifluoromethyl)benzamido)-1H-benzo[d]imidazole-5-carboxylate (I-42a) was prepared from 1-41 following procedures analogous to I-16. MS calculated for $C_{29}H_{29}F_3N_5O_5$ (M−H⁻) 584.21. found 584.3.

Step B:
A mixture of I-42a (52 mg, 0.09 mmol) and LiBH$_4$ (8.7 mg, 0.4 mmol) in 1:1 THF/toluene (2 mL) was stirred at 100° C. for 1 h (reaction completion monitored by LC-MS). The mixture was then diluted with 1M HCl and extracted with CH$_2$Cl$_2$ (3×). The combined organic layers were dried over anhydrous Na$_2$SO$_4$ and concentrated under reduced pressure to afford tert-butyl 3-(7-cyano-5-(hydroxymethyl)-2-(3-(trifluoromethyl)benzamido)-1H-benzo[d]imidazol-1-yl)azepane-1-carboxylate (I-42b).

MS calculated for $C_{28}H_{31}F_3N_5O_4$ (M+H⁺) 558.22. found 558.2.

Step C:
The title compound (Intermediate 42) was prepared from I-42b following procedures analogous to I-32, Step B. MS calculated for $C_{23}H_{23}F_3N_5O_2$ (M+H⁺) 458.17. found 458.20.

Intermediate 43 methyl 1-(piperidin-3-yl)-2-(3-(trifluoromethyl)benzamido)-6,7-dihydro-1H-imidazo[4,5-c]pyridine-5(4H)-carboxylate Step A:
A degassed solution of I-18 (0.2 g, 0.4 mmol) in EtOH (1.1 mL) and water (0.05 mL) was treated drop-wise at −78° C. with methylchloroformate (0.045 g, 0.48 mmol) and stirred for 50 min. NaBH$_4$ (0.045 g) was then added portion wise at the same temperature and the mixture was stirred at room temperature for 1 h (reaction completion monitored by TLC). The mixture was quenched with water and extracted with EtOAc (2×20 mL). The combined organic layers were dried over Na$_2$SO$_4$ and concentrated under reduced pressure to afford methyl 1-(1-(tert-butoxycarbonyl)piperidin-3-yl)-2-(3-(trifluoromethyl)benzamido)-1H-imidazo[4,5-c]pyridine-5(4H)-carboxylate (I-43a) as a greenish yellow solid. MS calculated for $C_{26}H_{31}F_3N_5O_5$ (M+H⁺) 550.22. found 550.2.

Step B:
Methyl 1-(1-(tert-butoxycarbonyl) piperidin-3-yl)-2-(3-(trifluoromethyl)benzamido)-6,7-dihydro-1H-imidazo[4,5-c]pyridine-5 (4H)-carboxylate (I-43b) was prepared from I-43a following procedures analogous to I-15, Step B. MS calculated for $C_{26}H_{31}F_3N_5O_5$ (M−H⁻) 550.24. found 550.5.

Step C:
The title compound (Intermediate 43) was prepared from I-43b following procedures analogous to I-16, Step B. MS calculated for $C_{21}H_{25}F_3N_5O_3$ (M+H⁺) 452.18. found 452.2.

Intermediate 44

(R)—N-(1-(azepan-3-yl)-7-chloro-1H-benzo[d]imidazol-2-yl)pyridazine-4-carboxamide hydrochloride

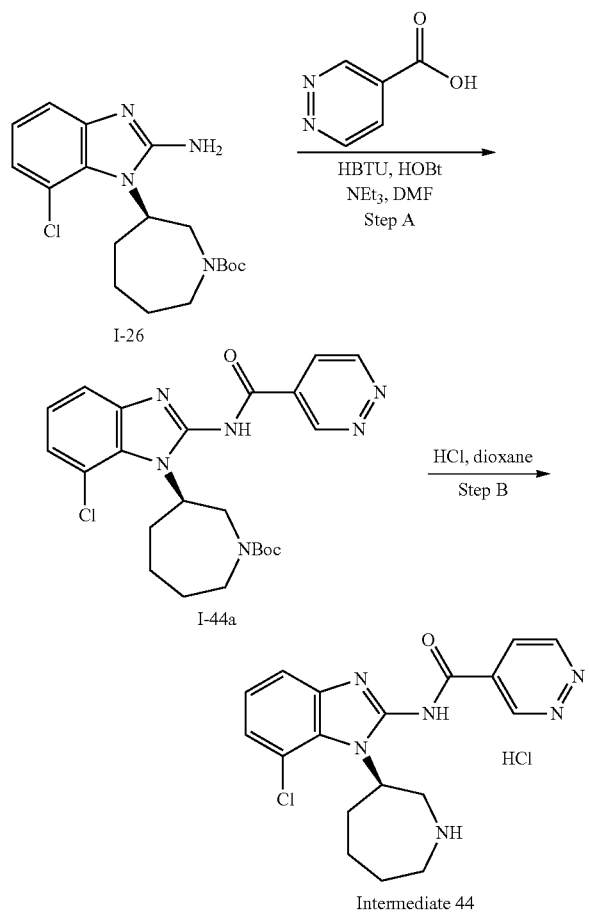

Steps A and B:
The title compound (Intermediate 44) was prepared in several steps from I-26 following procedures analogous to I-30. MS calculated for $C_{18}H_{20}ClN_6O$ (M+H$^+$) 371.13. found 371.1.

Intermediate 45

(R)—N-(1-(azepan-3-yl)-7-methyl-1H-benzo[d]imidazol-2-yl)-2-(trifluoromethyl)isonicotinamide hydrochloride

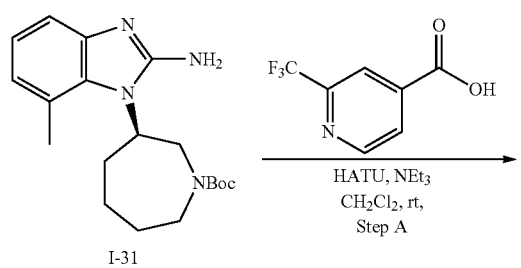

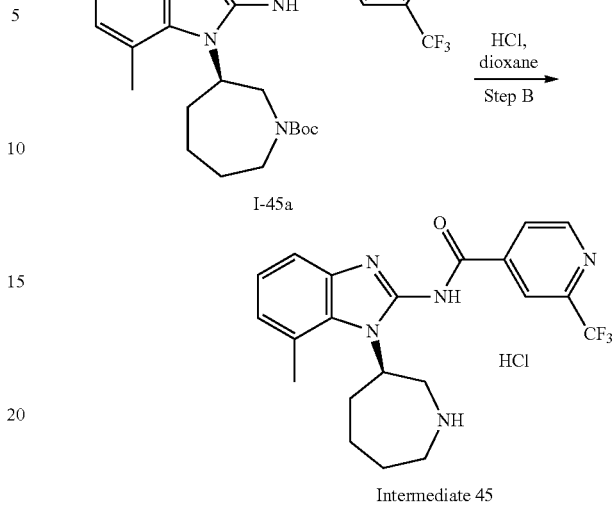

Step A:
(R)-tert-butyl 3-(7-methyl-2-(2-(trifluoromethyl)isonicotinamido)-1H-benzo[d]imidazol-1-yl)azepane-1-carboxylate (I-45a) was prepared from I-31 following procedures analogous to I-27, Step A. $^1$H-NMR (400 MHz, CDCl$_3$) ∂ 12.53 (s, 1H), 8.89 (d, J=4.6 Hz, 1H), 8.54 (d, J=7.1 Hz, 1H), 8.27 (d, J=4.6 Hz, 1H), 7.21 (dt, J=7.8, 21.3 Hz, 2H), 7.08 (t, J=9.2 Hz, 1H), 5.12-4.85 (m, 1H), 4.34 (dd, J=10.6, 13.6 Hz, 1H), 4.16-3.85 (m, 2H), 3.36-3.21 (m, 1H), 2.94-2.82 (m, 1H), 2.80 (s, 3H), 2.30-2.15 (m, 1H), 2.15-2.00 (m, 2H), 2.00-1.81 (m, 1H), 1.48 (s, 9H), 1.43-1.36 (m, 1H).
$^{19}$F-NMR (376 MHz, CDCl$_3$) ∂ −67.90 (s, 1H); MS calculated for $C_{26}H_{31}F_3N_5O_3$ (M+H$^+$) 518.23. found 518.2.

Step B:
The title compound (Intermediate 45) was prepared from I-45a following procedures analogous to I-32, Step B. $^1$H-NMR (400 MHz, DMSO) ∂ 9.40-9.09 (m, 2H), 8.99 (d, J=4.9 Hz, 1H), 8.37 (s, 1H), 8.34 (s, 1H), 7.50 (d, J=7.9 Hz, 1H), 7.18 (d, J=7.8 Hz, 1H), 7.11 (s, 1H), 5.33-5.14 (m, 1H), 4.40-4.23 (m, 1H), 3.71-3.69 (m, 1H), 3.38-3.18 (m, 2H), 2.79 (s, 3H), 2.69-2.57 (m, 1H), 2.29-2.12 (m, 1H), 2.10-1.89 (m, 3H), 1.89-1.72 (m, 1H). $^{19}$F-NMR (376 MHz, DMSO) ∂ −66.52 (s, 1H); MS calculated for $C_{21}H_{23}F_3N_5O$ (M+H$^+$) 418.18. found 418.2.

Intermediate 46

(R)—N-(1-(azepan-3-yl)-7-methyl-1H-benzo[d]imidazol-2-yl)-2,6-dimethylisonicotinamide hydrochloride

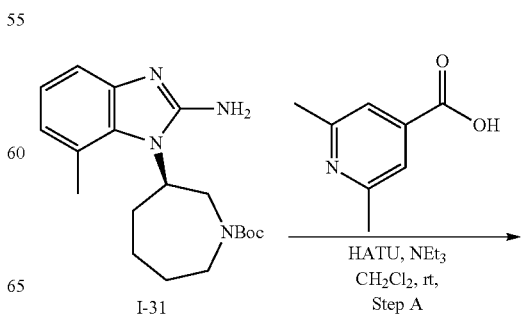

Intermediate 48

1-methyl-1,2,3,6-tetrahydropyridine-4-carboxylic acid hydrochloride

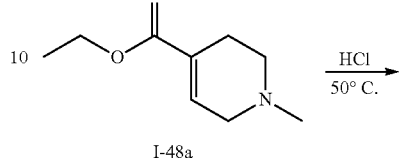

I-48a

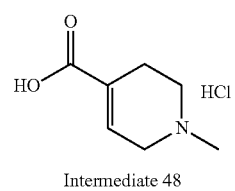

Intermediate 48

1-methyl-1,2,3,6-tetrahydropyridine-3-carboxylate (I-48a, 155 mg, 1.0 mmol) was diluted with concentrated HCl (2.0 mL), and the mixture was heated at 50° C. overnight. The reaction mixture was concentrated in vacuo to afford the title compound (Intermediate 48). MS calculated for $C_7H_{12}NO_2$ (M+H$^+$) 142.08. found: 142.2. The crude was used in the next step without further purification.

Intermediate 49

(E)-4-(dimethylamino)-4-methylpent-2-enoic acid hydrochloride

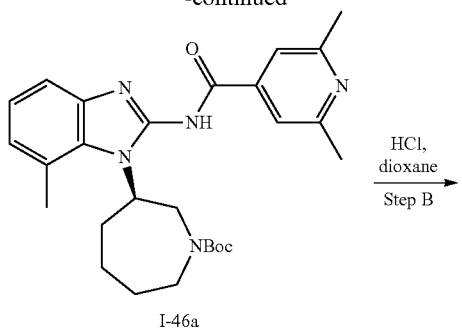

I-46a

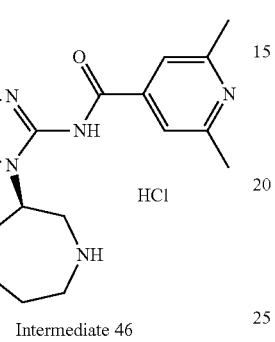

Intermediate 46

Step A:
(R)-tert-butyl 3-(2-(2,6-dimethylisonicotinamido)-7-methyl-1H-benzo[d]imidazol-1-yl)azepane-1-carboxylate (I-46a) was prepared from I-31 following procedures analogous to I-27, Step A. MS calculated for $C_{27}H_{36}N_5O_3$ (M+H$^+$) 478.27. found 478.3.

Step B:
The title compound (Intermediate 46) was prepared from I-46a following procedures analogous to I-32, Step B. $^1$H-NMR (400 MHz, DMSO) δ 7.69 (s, 2H), 7.44 (d, J=7.7 Hz, 1H), 7.11 (t, J=7.7 Hz, 1H), 7.07-6.99 (m, 1H), 4.91 (s, 1H), 3.79 (s, 1H), 3.20-3.04 (m, 1H), 2.94 (s, 1H), 2.86 (s, 1H), 2.71 (s, 3H), 2.70-2.68 (m, 2H), 2.52 (s, 6H), 2.06 (s, 1H), 1.84 (s, 2H), 1.72-1.56 (m, 1H); MS calculated for $C_{22}H_{28}N_5O$ (M+H$^+$) 378.22. found 378.3.

Intermediate 47

1-methyl-1,2,5,6-tetrahydropyridine-3-carboxylic acid hydrochloride

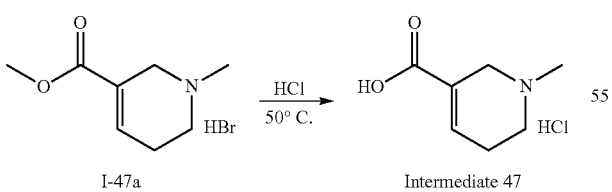

I-47a             Intermediate 47

1-methyl-1,2,5,6-tetrahydropyridine-3-carboxylate hydrobromide (I-47a, 235 mg, 1.0 mmol) was diluted with concentrated HCl (2.0 mL), and the mixture was heated at 50° C. overnight. The reaction mixture was concentrated in vacuo to afford the title compound (Intermediate 47). MS calculated for $C_7H_{12}NO_2$ (M+H$^+$) 142.08. found: 142.1. The crude was used in the next step without further purification.

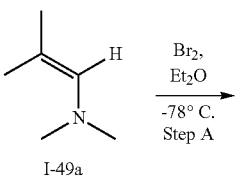

I-49a

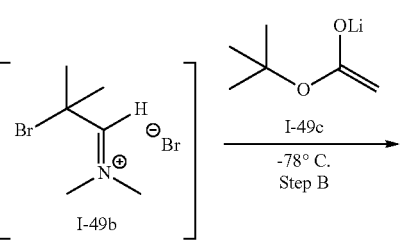

I-49b

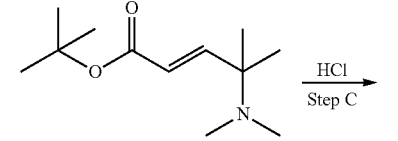

I-49d

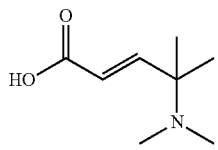

Intermediate 49

Step A and B:

To the solution of N,N-2-trimethylprop-1-en-1-amine (I-49a, 240 mg, 2.42 mmol) in anhydrous Et$_2$O (40 mL) at −78° C. was added dropwise Br$_2$ (0.12 mL, 2.42 mmol), whereupon I-49b precipitated as a thick, light yellow solid. This mixture was then warmed and kept at 0° C., and treated dropwise with a −78° C. solution of t-butyl lithioacetate, which was prepared in situ by dropwise addition of tert-butyl acetate (I-49c, 0.65 mL, 4.84 mmol) to a solution of LDA at −78° C. (prepared by dropwise addition of n-BuLi (3.02 mL, 4.84 mmol) to diisopropylamine (0.65 mL, 4.84 mmol) in Et$_2$O (10 mL) at −78° C.). During the addition, the precipitate dissolved, and a pale yellow solution was obtained. The reaction mixture was allowed to warm to room temperature, and stirred for another 1 h. The reaction mixture was partitioned between Et$_2$O and water and extracted with Et$_2$O. The combined organic layers were dried over Na$_2$SO$_4$ and concentrated under reduced pressure. The crude material was purified by column chromatography (0-10% MeOH in CH$_2$Cl$_2$) to afford (E)-tert-butyl 4-(dimethylamino)-4-methylpent-2-enoate (I-49d). MS calculated for C$_{12}$H$_{24}$NO$_2$ (M+H$^+$) 214.17. found: 214.2.

Step C:

Intermediate I-49d (133 mg, 0.62 mmol) was diluted with concentrated HCl (5.0 mL), and stirred at room temperature overnight. The reaction mixture was then concentrated in vacuo to afford the title compound (Intermediate 49). MS calculated for C$_8$H$_{16}$NO$_2$ (M+H$^+$) 158.11. found: 158.2. The crude was used in the next step without further purification.

Intermediate 50

2-(dimethylphosphoryl)-6-methylisonicotinic acid hydrochloride

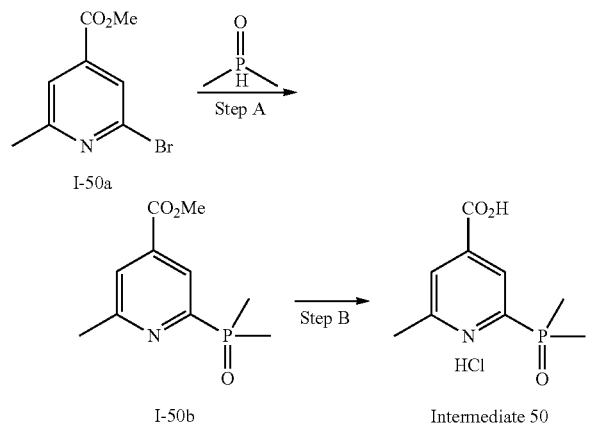

Step A:

Intermediate I-50b was prepared from Intermediate I-50a following a similar procedure as described in WO2009/143389. A solution of methyl 2-bromo-6-methylisonicotinate (I-50a, 690 mg, 3 mmol) in DMF (12 mL) was treated with dimethylphosphine oxide (515 mg, 6.6 mmol), palladium acetate (39 mg, 0.05 mmol), 4,5-Bis(diphenylphosphino)-9,9-dimethylxanthene (104 mg, 0.18 mmol) and potassium phosphate (700.5 mg, 3.3 mmol). The mixture was purged with nitrogen and subjected to microwave irradiation (20 min, 150° C.). The reaction mixture was concentrated and purified by column chromatography (9:1: 0.175N CH$_2$Cl$_2$/MeOH/NH$_3$ in CH$_2$Cl$_2$, 0% to 100%) to afford methyl 2-(dimethylphosphoryl)-6-methylisonicotinate (I-50b) as an off-white solid. $^1$H NMR (400 MHz, DMSO) ∂ 8.14 (s, 1H), 7.87 (s, 1H), 3.93 (s, 3H), 2.64 (s, 3H), 1.67 (d, J=13.6 Hz, 6H); MS calculated for C$_{10}$H$_{15}$NO$_3$P (M+H$^+$) 228.07. found 228.1.

Step B:

A solution of I-50b (539 mg, 2.37 mmol) in MeOH (0.5 mL) was treated with 10N NaOH (1 mL) and stirred at room temperature for 80 min. The mixture was then acidified with concentrated HCl, evaporated under reduced pressure and lyophilized. The crude was then triturated in MeOH and filtered to afford the title compound (Intermediate 50) as a white solid. $^1$H NMR (400 MHz, DMSO) ∂ 8.14 (s, 1H), 7.84 (s, 1H), 4.62 (br s, 2H), 2.63 (s, 3H), 1.67 (d, J=13.6 Hz, 6H); MS calculated for C$_9$H$_{13}$NO$_3$P (M+H$^+$) 214.06. found 214.1.

Intermediate 51

2-(dimethylphosphoryl)isonicotinic acid hydrochloride

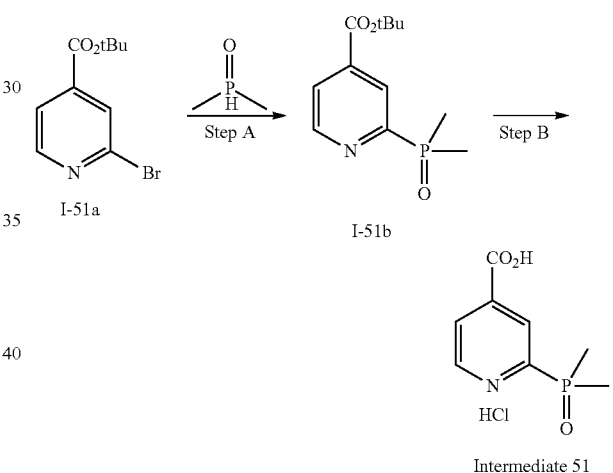

Step A:

tert-butyl 2-(dimethylphosphoryl)isonicotinate (I-51b) was prepared from I-51a following procedures analogous to I-50, Step A. $^1$H NMR (400 MHz, DMSO) ∂ 8.97 (d, J=4.9 Hz, 1H), 8.36-8.19 (m, 1H), 7.93 (dt, J=1.9, 4.9 Hz, 1H), 1.69 (d, J=13.7 Hz, 6H), 1.58 (s, 9H); MS calculated for C$_{12}$H$_{19}$NO$_3$P (M+H$^+$) 256.10. found 256.1.

Step B:

A solution of I-51b (511 mg, 2 mmol) in dichloromethane (4 mL) was treated with trifluoroacetic acid (4 mL) and stirred at room temperature for 5 hours. A solution of HCl in isopropanol (4N, 3 mL) was then added and the mixture was stirred at 55° C. for 2 hours (reaction completion monitored by LC/MS). The solvent was then evaporated and the crude was co-evaporated with HCl in isopropanol (3×) to afford the title compound (Intermediate 50) as a white solid. $^1$H NMR (400 MHz, DMSO) ∂ 8.98 (d, J=4.9 Hz, 1H), 8.33 (d, J=5.4 Hz, 1H), 7.96 (d, J=4.9 Hz, 1H), 6.24-4.44 (m, 2H), 1.69 (d, J=13.7 Hz, 6H); MS calculated for C$_8$H$_{11}$NO$_3$P (M+H$^+$) 200.04. found 200.1.

Intermediate 52

(R)—N-(1-(azepan-3-yl)-7-chloro-1H-benzo[d]imidazol-2-yl)-2-(dimethylphosphoryl)-6-methylisonicotinamide dihydrochloride

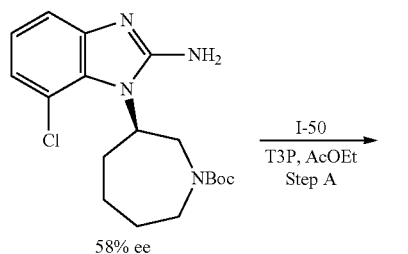

Step B:
Solid I-52a (314 mg, 0.56 mmol) was treated with HCl in isopropanol (5 mL) and stirred at room temperature for 4 hours, when dichloromethane (2 mL) was added and the mixture was further stirred at 50° C. for 4 hours (reaction completion monitored by LC/MS). The solvent was then evaporated and the crude material was dried under vacuum to afford the title compound (Intermediate 52) as a yellow solid. $^1$H NMR (400 MHz, DMSO) ∂ 9.89 (s, 1H), 9.55 (s, 1H), 8.45 (d, J=5.8 Hz, 1H), 7.99 (s, 1H), 7.60 (dd, J=1.1, 7.9 Hz, 1H), 7.44-7.10 (m, 2H), 5.88 (s, 1H), 4.82 (s, 1H), 4.35-4.30 (m, 1H), 3.78-3.74 (m, 1H), 3.28 (d, J=48.9 Hz, 2H), 2.70 (s, 3H), 2.60-2.50 (m, 1H), 2.20-1.95 (m, 4H), 1.88-1.57 (m, 7H); MS calculated for $C_{22}H_{28}ClN_5O_2P$ (M+H$^+$) 460.16. found 460.1.

Intermediate 53

(R)—N-(1-(azepan-3-yl)-7-chloro-1H-benzo[d]imidazol-2-yl)-2-(dimethylphosphoryl)isonicotinamide dihydrochloride

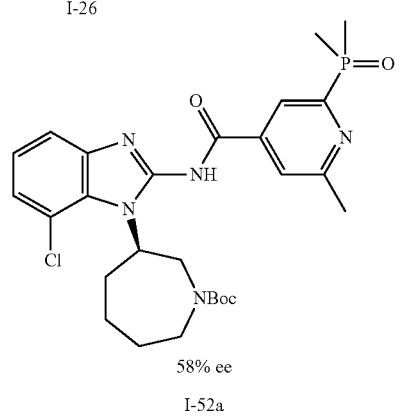

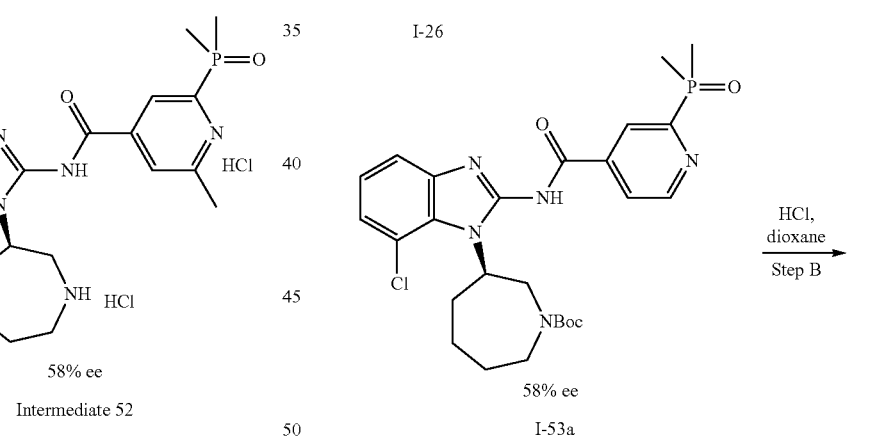

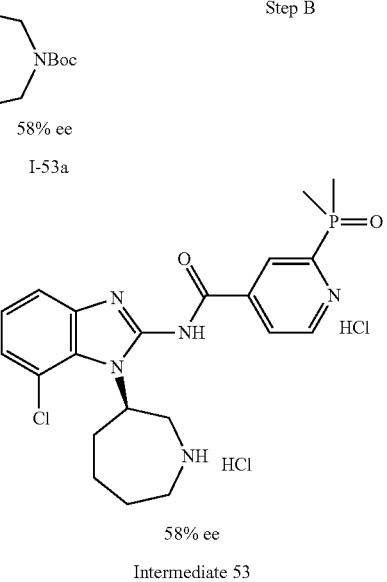

Steps A:
A mixture of I-26 (401 mg, 1.1 mmol) and I-50 (213 mg, 1 mmol) in ethyl acetate (2 mL) was treated with triethylamine (1.4 mL, 10 mmol) and a 50 w % solution of propane phosphonic acid anhydride in ethyl acetate (1.9 g, 3 mmol). The mixture was then stirred at 50° C. for 64 hours. The mixture was washed with saturated aqueous Na$_2$CO$_3$ (2×). The aqueous phase was re-extracted with ethyl acetate and the combined organics were washed with brine, dried over Na$_2$SO$_4$ and concentrated under reduced pressure. The crude was purified by column chromatography (9:1:0.175N CH$_2$Cl$_2$/MeOH/NH$_3$ in CH$_2$Cl$_2$, 0% to 100%) to afford (R)-tert-butyl 3-(7-chloro-2-(2-(dimethylphosphoryl)-6-methylisonicotinamido)-1H-benzo[d]imidazol-1-yl) azepane-1-carboxylate (I-52a) MS calculated for $C_{27}H_{36}ClN_5O_4P$ (M+H$^+$) 560.21. found 560.2.

Steps A and B:

The title compound (Intermediate 53) was prepared in several steps from I-26 and I-51 following procedures analogous to I-52. $^1$H NMR (400 MHz, DMSO) ∂ 9.85-9.80 (m, 1H), 9.60-9.51 (m, 1H), 8.97 (d, J=4.9 Hz, 1H), 8.62 (d, J=5.3 Hz, 1H), 8.17 (d, J=4.9 Hz, 1H), 7.60 (dd, J=1.1, 7.9 Hz, 1H), 7.44-7.15 (m, 2H), 5.91-5.82 (m, 1H), 5.63 (s, 1H), 4.38-4.29 (m, 1H), 3.76-3.71 (m, 1H), 3.40-3.19 (m, 2H), 2.70-2.51 (m, 2H), 2.20-1.93 (m, 4H), 1.87-1.68 (m, 7H); MS calculated for $C_{21}H_{26}ClN_5O_2P$ (M+H$^+$) 446.14. found 446.1.

Intermediate 54

1-benzyl 4-tert-butyl 6-amino-1,4-diazepane-1,4-dicarboxylate

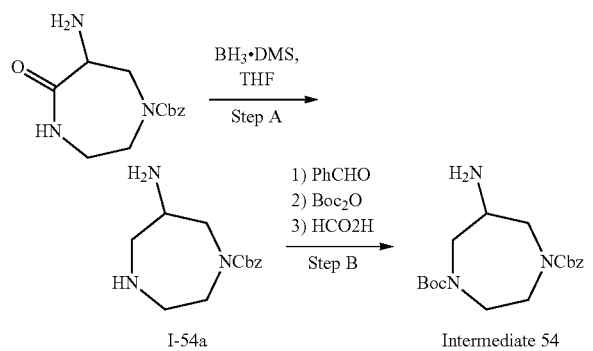

Step A:

A solution of benzyl 6-amino-5-oxo-1,4-diazepane-1-carboxylate (12.86 g, 47.4 mmol) in THF (158 mL) was treated dropwise with BH$_3$.DMS (22.5 mL, 237 mmol). The mixture was warmed to reflux and stirred for 15 hours. The mixture was then cooled to 0 OC, quenched by the slow addition of MeOH (50 mL; vigorous H$_2$ evolution observed) and treated over 10 min with concentrated HCl (12 mL). The reaction vessel was then heated to reflux for 8 hours. The volatiles were partially removed under reduced pressure and the mixture was basified to pH 11 with solid Na$_2$CO$_3$. The aqueous layer was extracted with CH$_2$Cl$_2$ (2×), the organic phase was dried (Na$_2$SO$_4$), and concentrated in vacuo to afford benzyl 6-amino-1,4-diazepane-1-carboxylate (I-54a). MS calculated for $C_{13}H_{20}N_3O_2$ (M+H$^+$) 250.15. found 250.1. The crude was used in the next step without further purification.

Step B:

Anhydrous sodium sulfate (5.92 g, 41.7 mmol) was suspended in a solution of I-54a (8.66 g, 34.7 mmol) in CH$_2$Cl$_2$. Benzaldehyde (4.4 mL, 43.4 mmol) was added and the mixture was stirred for 24 hours, resulting in a color change from colorless to bright yellow. The mixture was filtered, rinsed with CH$_2$Cl$_2$ (100 mL). The filtrate was treated with di-tert-butyl dicarbonate (9.10 g, 41.7 mmol) and triethylamine (9.7 mL, 69.5 mmol). The reaction mixture was stirred for 80 min and then treated with formic acid (38 mL, 868 mmol). The reaction color changed from bright yellow to cloudy orange. The mixture was stirred for 2 hours, diluted with 1.0 M HCl (50 mL) and extracted with CH$_2$Cl$_2$ (3×50 mL). The aqueous layer was made alkaline (~pH 10) with saturated Na$_2$CO$_3$ and extracted with CH$_2$Cl$_2$ (3×50 mL). The combined organic phase from all six extractions was then washed with 1.0 M NaHSO$_3$ (3×40 mL), dried over Na$_2$SO$_4$ and concentrated under reduced pressure to afford the title compound (Intermediate 54). $^1$H NMR (400 MHz, CD$_2$Cl$_2$) δ 7.39-7.34 (m, 5H), 7.34-7.23 (m, 2H), 4.65 (s, 2H), 3.69 (m, 1H), 3.53-3.21 (m, 1H), 3.21-2.96 (m, 1H), 2.96-2.77 (m, 3H), 2.73 (m, 1H), 2.66-2.54 (m, 1H), 2.47 (m, 1H), 1.78 (s, 9H); MS calculated for $C_{18}H_{28}N_3O_4$ (M+H$^+$) 350.20. found 350.1.

Intermediate 55

1-benzyl 4-tert-butyl 6-(2-amino-7-chloro-1H-benzo[d]imidazol-1-yl)-1,4-diazepane-1,4-dicarboxylate

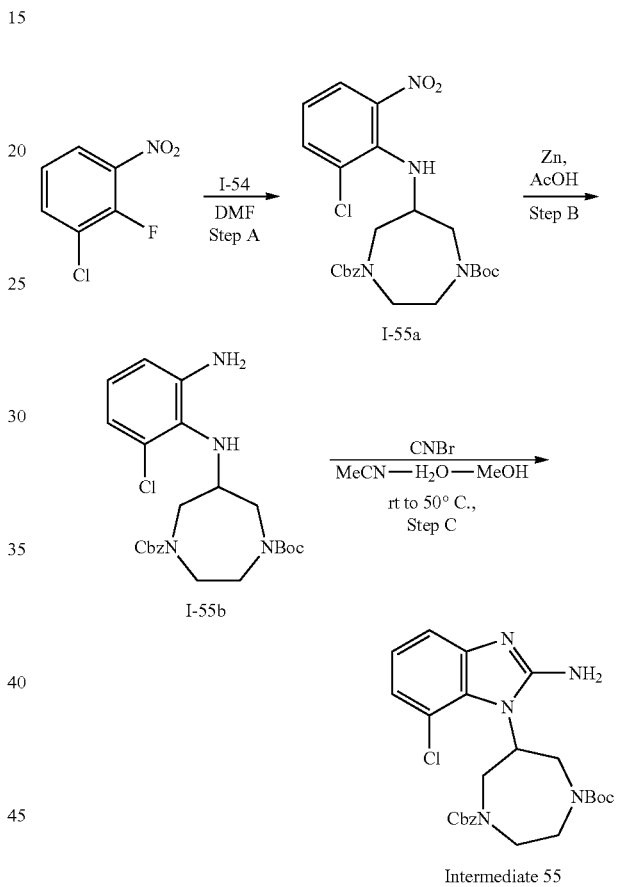

Step A:

1-benzyl 4-tert-butyl 6-((2-chloro-6-nitrophenyl)amino)-1,4-diazepane-1,4-dicarboxylate (I-55a) was prepared following procedures analogous to I-15, Step A, using the appropriate starting materials. $^1$NMR (400 MHz, CDCl$_3$) δ 7.91 (s, 1H), 7.52 (s, 1H), 7.33 (d, J=28.3 Hz, 5H), 7.11-6.88 (m, 1H), 6.88-6.69 (m, 1H), 5.31-4.95 (m, 2H), 4.82-4.34 (m, 1H), 3.77-3.55 (m, 4H), 3.54-3.14 (m, 4H), 1.47-1.38 (m, 9H);

MS calculated for $C_{24}H_{29}ClN_4NaO_6$ (M+Na$^+$) 527.17. found 527.2.

Step B:

1-benzyl 4-tert-butyl 6-((2-amino-6-chlorophenyl)amino)-1,4-diazepane-1,4-dicarboxylate (I-55b) was prepared from I-55a following procedures analogous to I-26, Step B. MS calculated for $C_{24}H_{32}ClN_4O_4$ (M+H$^+$) 475.20. found 475.2.

Step C:

The title compound (Intermediate 55) was prepared from I-55b following procedures analogous to I-15, Step C. $^1$H NMR (400 MHz, CD$_2$Cl$_2$) δ 7.59-7.08 (m, 6H), 7.08-6.91 (m, 2H), 5.98-5.79 (m, 1H), 5.62-5.35 (m, 2H), 5.27-4.99 (m, 2H), 4.51-3.90 (m, 4H), 3.90-3.67 (m, 2H), 3.56-2.75 (m, 2H), 1.49-1.34 (m, 9H). MS calculated for C$_{25}$H$_{31}$ClN$_5$O$_4$ (M+H$^+$) 500.20. found 500.2.

Intermediate 56 tert-butyl 6-(7-chloro-2-(2-methylisonicotinamido)-1H-benzo[d]imidazol-1-yl)-1,4-diazepane-1-carboxylate

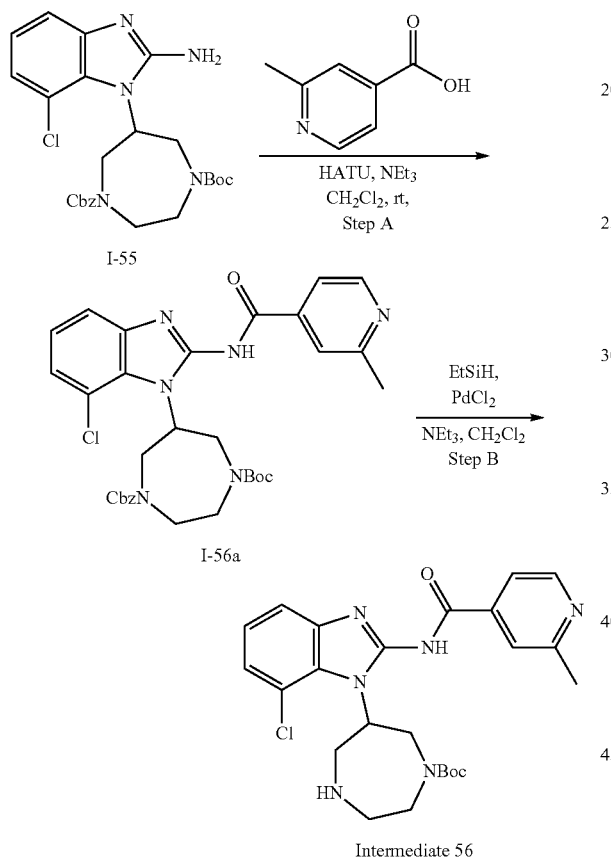

Step A:

1-benzyl 4-tert-butyl 6-(7-chloro-2-(2-methylisonicotinamido)-1H-benzo[d]imidazol-1-yl)-1,4-diazepane-1,4-dicarboxylate (I-56a) was prepared from 1-55 following procedures analogous to I-27, Step A. $^1$H NMR (400 MHz, DMSO) δ 8.62 (t, J=4.2 Hz, 1H), 7.87 (d, J=3.5 Hz, 1H), 7.80 (d, J=3.8 Hz, 1H), 7.63-7.53 (m, 1H), 7.49-7.33 (m, 3H), 7.33-7.24 (m, 4H), 7.24-7.06 (m, 1H), 5.68-5.50 (m, 1H), 5.20-5.00 (m, 2H), 4.51-4.22 (m, 2H), 4.22-4.08 (m, 3H), 4.06-3.96 (m, 1H), 3.45-3.37 (m, 1H), 3.29-3.16 (m, 1H), 2.58 (s, 3H), 1.45-1.30 (m, 9H); MS calculated for C$_{32}$H$_{36}$ClN$_6$O$_5$ (M+H$^+$) 619.24. found 619.2.

Step B:

A solution of I-56a (647 mg, 1.05 mmol) in CH$_2$Cl$_2$ (5 mL) was evacuated and backfilled with nitrogen (2×) and then treated with palladium(II) chloride (56 mg, 0.314 mmol). To the resulting brick red suspension was added triethylsilane (0.67 mL, 4.18 mmol) followed by NEt$_3$ (0.1 mL, 7.3 mmol) and the mixture was stirred for 30 min. The mixture was then partitioned between CH$_2$Cl$_2$ and saturated aqueous NH$_4$Cl solution, the layers separated, and the aqueous phase extracted with CH$_2$Cl$_2$ (2×). The combined organic phase was washed with brine, dried over Na$_2$SO$_4$, and concentrated under reduced pressure. The crude was purified by column chromatography (9:1:0.175 M CH$_2$Cl$_2$/MeOH/NH$_3$ in CH$_2$Cl$_2$, 30-75%) to afford the title compound (Intermediate 56). $^1$H NMR (400 MHz, DMSO) δ 8.63 (d, J=5.0 Hz, 1H), 7.85 (s, 1H), 7.82-7.71 (m, 1H), 7.57 (d, J=7.8 Hz, 1H), 7.31 (s, 1H), 7.25 (d, J=7.9 Hz, 1H), 5.55 (br s, 1H), 4.38 (br s, 1H), 3.95-3.83 (m, 1H), 3.83-3.70 (m, 1H), 3.63 (s, 1H), 3.27-2.96 (m, 3H), 2.96-2.85 (m, 1H), 2.58 (s, 3H), 1.38 (m, 9H); MS calculated for C$_{24}$H$_{30}$ClN$_6$O$_3$ (M+H$^+$) 485.20. found 485.2.

Intermediate 57

(R)-tert-butyl 3-(2-amino-7-chloro-6-(2-(pyrrolidin-1-yl)ethoxy)-1H-benzo[d]imidazol-1-yl)azepane-1-carboxylate

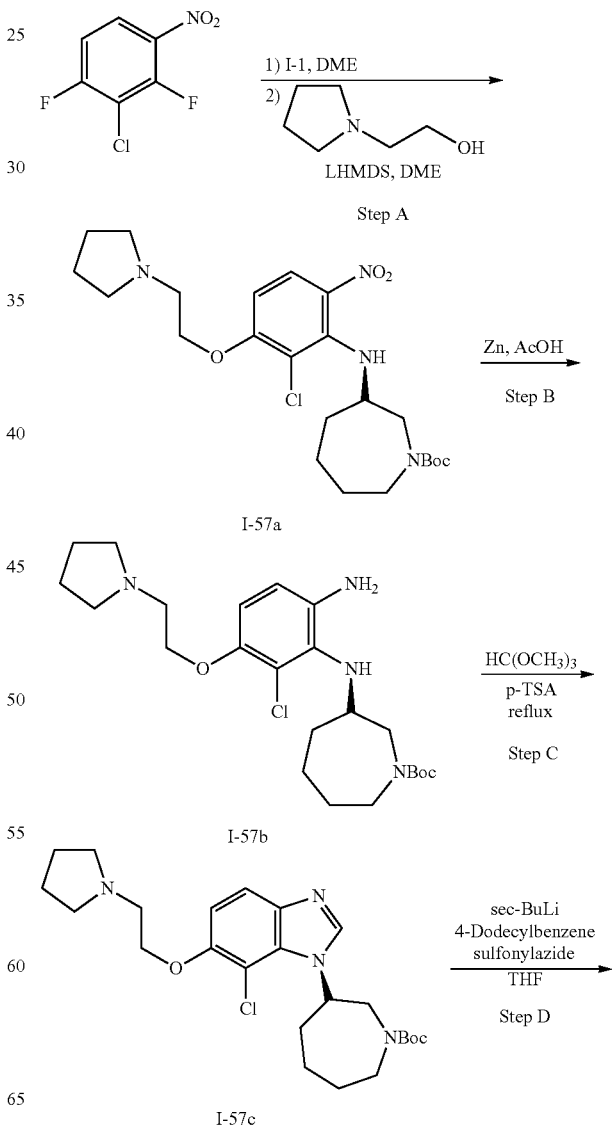

-continued

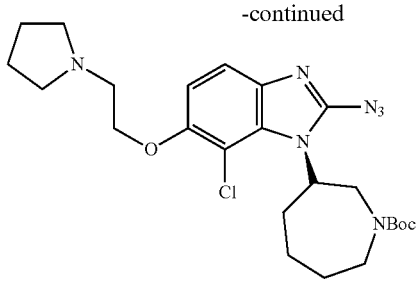

I-57d

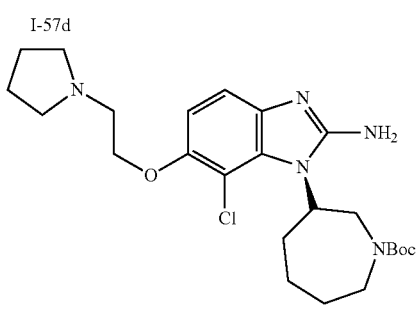

Intermediate 57

Step A:

To a solution of 2-chloro-1,3-difluoro-4-nitrobenzene (9 g, 46.5 mmol) in dimethoxyethane (93 mL) was added I-1 (10.96 g, 51.2 mmol). The mixture was heated under argon to 85° C. for 2 hours and then cooled to room temperature. In a separate flask, 2-(pyrrolidin-1-yl)ethanol (13.39 g, 116 mmol) in dimethoxyethane (30 mL) at 0° C. was treated with LHMDS (0.9M in methyl-cyclohexane, 134 mL, 121 mmol) and stirred at 0° C. for 15 min. The resulting suspension was then added at 0° C. to the first reaction mixture and then stirred at 85° C. for 30 min. After cooling to 0 OC, additional LHMDS (0.9 M in methyl-cyclohexane, 35 mL, 31.5 mmol) was added. The mixture was then stirred 10 minutes at room temperature and 40 minutes at 85° C., before being concentrated under reduced pressure and poured into ice water (300 mL). The aqueous phase was extracted with EtOAc (3×150 mL), the combined organic layer was dried with $Na_2SO_4$ and concentrated under reduced pressure. The crude was purified by column chromatography (0-10% MeOH in $CH_2Cl_2$) to afford (R)-tert-butyl 3-((2-chloro-6-nitro-3-(2-(pyrrolidin-1-yl)ethoxy)phenyl)amino)azepane-1-carboxylate (I-57a) as brown oil.

MS calculated for $C_{23}H_{36}ClN_4O_5$ (M+H$^+$) 483.23. found 483.2.

Step B:

(R)-tert-butyl 3-((6-amino-2-chloro-3-(2-(pyrrolidin-1-yl)ethoxy)phenyl)amino)azepane-1-carboxylate (I-57b) was prepared from I-57a following procedures analogous to I-26, Step B. MS calculated for $C_{23}H_{38}ClN_4O_3$ (M+H$^+$) 453.26. found 453.3.

Step C:

(R)-tert-butyl 3-(7-chloro-6-(2-(pyrrolidin-1-yl)ethoxy)-1H-benzo[d]imidazol-1-yl)azepane-1-carboxylate (I-57c) was prepared from I-57b following procedures analogous to I-17, Step C. MS calculated for $C_{24}H_{36}ClN_4O_3$ (M+H$^+$) 463.24. found 463.2.

Step D:

(R)-tert-butyl 3-(2-azido-7-chloro-6-(2-(pyrrolidin-1-yl) ethoxy)-1H-benzo[d]imidazol-1-yl)azepane-1-carboxylate (I-57d) was prepared from I-57c following procedures analogous to I-17, Step D. MS calculated for $C_{24}H_{35}ClN_7O_3$ (M+H$^+$) 504.24. found 504.2.

Step E:

A solution of I-57d (0.83 g, 1.65 mmol) in THF (18 mL) under nitrogen was cooled 0° C. and treated with trimethylphosphine (1M in THF, 17 mL, 17 mmol). The solution was stirred at 0° C. for 120 min. Then, 1M HCl was slowly added until pH 2 and the mixture was stirred for 22 hours at room temperature, before it was basified with 1N NaOH to pH 11. THF was evaporated under reduced pressure and the water phase was extracted with 3:1 chloroform/isopropanol (3×80 mL). The combined organic phase was washed with brine (40 mL), dried over $Na_2SO_4$, and concentrated under reduced pressure. The crude was purified by chiral SFC (methanol/liquid $CO_2$) to the title compound (Intermediate 57). MS calculated for $C_{24}H_{37}ClN_5O_3$ (M+H$^+$) 478.25. found 478.2.

Intermediate 58

(R)—N-(1-(azepan-3-yl)-7-chloro-6-(2-(pyrrolidin-1-yl)ethoxy)-1H-benzo[d]imidazol-2-yl)-2,6-dimethylisonicotinamide

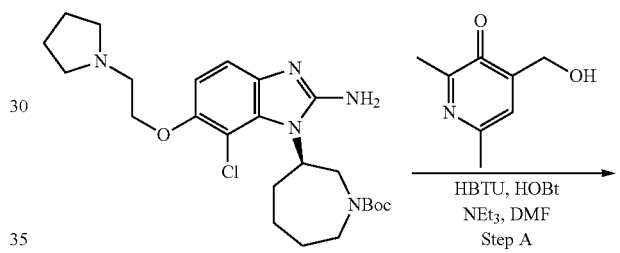

I-57

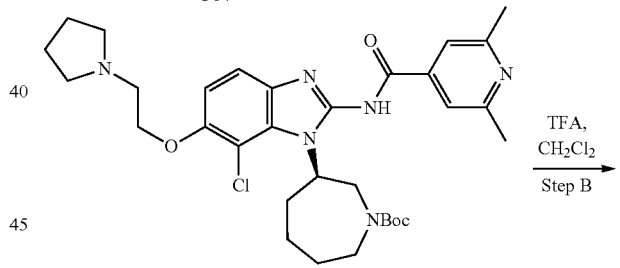

I-58a

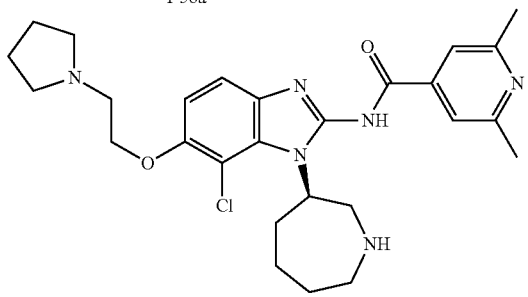

Intermediate 58

Step A (R)-tert-butyl 3-(7-chloro-2-(2,6-dimethylisonicotinamido)-6-(2-(pyrrolidin-1-yl)ethoxy)-1H-benzo[d]imidazol-1-yl)azepane-1-carboxylate (I-58a) was prepared from 1-57 following procedures analogous to I-30, Step A. MS calculated for $C_{32}H_{44}ClN_6O_4$ (M+H$^+$) 611.30. found 611.3.

Step B:

The title compound (Intermediate 58) was prepared from I-58a following procedures analogous to I-16, Step B. MS calculated for $C_{27}H_{36}ClN_6O_2$ (M+H⁺) 511.25. found 511.2.

Example 1

(R,E)-N-(7-chloro-1-(1-(4-(pyrrolidin-1-yl)but-2-enoyl)azepan-3-yl)-1H-benzo[d]imidazol-2-yl)-2-methylisonicotinamide

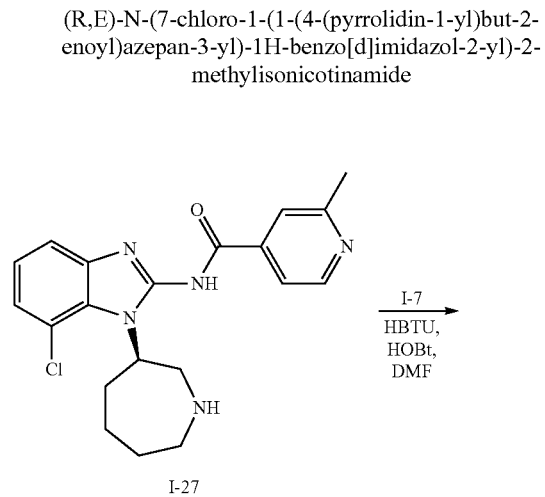

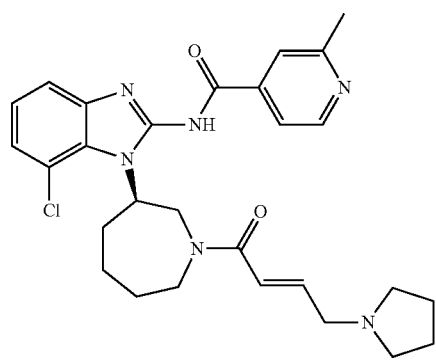

Example 1

To the mixture of I-7 (76.4 mg, 0.4 mmol) and 2-(7-aza-1H-benzotriazole-1-yl)-1,1,3,3-tetramethyluronium hexafluorophosphate (137.5 mg, 0.36 mmol) in DMF (2.0 mL) was added NEt₃ (0.11 mL, 0.8 mmol), and was stirred at room temperature for 10 min. The resulting mixture was added to a solution of I-27 (83.8 mg, 0.2 mmol) in DMF (1 mL), and the mixture was stirred at room temperature for 1 h. The reaction was quenched with H₂O (0.2 mL) and the mixture was purified by HPLC to afford the title compound (Example 1). ¹H NMR (400 MHz, MeOD) δ 8.58 (d, J=5.6 Hz, 1H), 8.15 (d, J=29.6 Hz, 2H), 7.41 (s, 1H), 7.22 (dd, J=8.9, 17.5 Hz, 2H), 6.87 (s, 1H), 6.70 (s, 1H), 5.69-5.44 (m, 1H), 4.76-4.48 (m, 1H), 4.23-4.06 (m, 1H), 3.96 (d, J=7.0 Hz, 2H), 3.84-3.60 (m, 2H), 3.59-3.25 (m, 2H), 3.12-2.82 (m, 2H), 2.65 (d, J=8.9 Hz, 3H), 2.03 (s, 7H), 1.50-1.29 (m, 1H), 1.19 (s, 2H), 0.80 (s, 1H). MS calculated for $C_{28}H_{34}ClN_6O_2$ (M+H⁺) 521.24. found: 521.2.

Example 2

(R,E)-N-(7-chloro-1-(1-(4-(3-fluoroazetidin-1-yl)but-2-enoyl)azepan-3-yl)-1H-benzo[d]imidazol-2-yl)-2-methylisonicotinamide

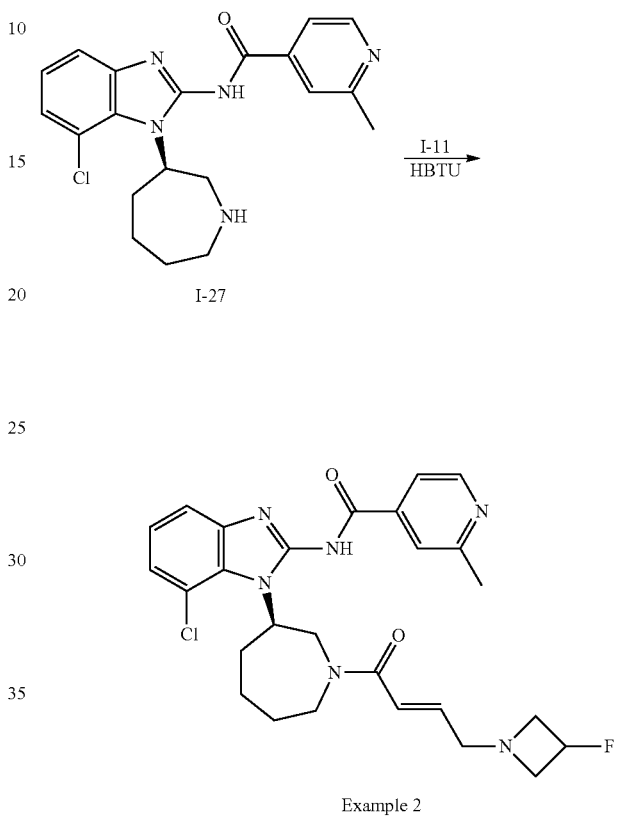

Example 2

To the mixture of I-11 (87.8 mg, 0.45 mmol) and O-benzotriazole-N,N,N',N'-tetramethyl-uronium-hexafluorophosphate (341 mg, 0.9 mmol) in DMF (2.0 mL) was added hydroxybenzotriazole (162 mg, 1.2 mmol) and stirred at room temperature for 10 min. The resulting mixture was added to a solution of I-27 (63 mg, 0.15 mmol) in DMF (1 mL), followed by addition of NEt₃ (0.2 mL, 1.43 mmol). The resulting mixture was stirred at room temperature for 1 h, quenched with H₂O (0.2 mL) and purified by HPLC to afford the title compound (Example 2). ¹H NMR (400 MHz, MeOD) δ 8.45 (d, J=4.4, 1H), 7.92 (d, J=10.0 Hz, 1H), 7.83 (s, 1H), 7.45-7.33 (m, 1H), 7.30-7.05 (m, 2H), 6.63 (s, 1H), 6.51 (d, J=16.0 Hz, 1H), 5.66-5.44 (m, 1H), 5.20-4.87 (m, 2H), 4.73-4.45 (m, 1H), 4.18-3.98 (m, 1H), 3.97-3.76 (m, 1H), 3.61 (s, 2H), 3.39 (s, 1H), 3.26 (dd, J=7.2, 20.0 Hz, 2H), 3.07 (d, J=5.2 Hz, 2H), 2.81-2.61 (m, 1H), 2.53 (s, 3H), 2.02 (s, 4H), 1.51-1.28 (m, 1H), 1.19 (s, 1H). MS calculated for $C_{27}H_{31}C_1FN_6O_2$ (M+H⁺) 525.21. found: 525.0.

Examples 3

The following compounds were prepared following analogous procedures as described in the above examples for Examples 1 and 2, using the appropriate starting materials.

| Ex. | Compound Structure | Physical Data (¹H NMR and MS) |
|---|---|---|
| 3-1 | 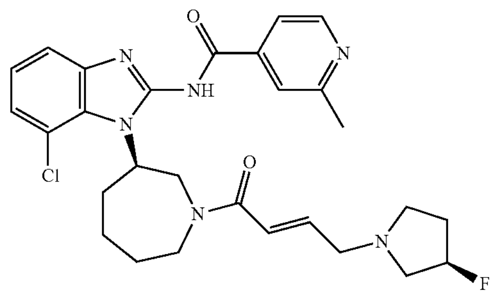 [SMILES: Cc1cc(C(=O)Nc2nc3cccc(Cl)c3n2[C@@H]2CCCCN(C(=O)/C=C/CN3CC[C@@H](F)C3)C2)ccn1] | ¹H NMR (400 MHz, MeOD) δ 8.76 (s, 1H), 8.41 (d, J = 30.4 Hz, 2H), 7.53 (s, 1H), 7.34 (dd, J = 7.9, 18.9 Hz, 2H), 7.01 (s, 1H), 6.91-6.71 (m, 1H), 5.82-5.27 (m, 3H), 4.83-4.56 (m, 1H), 4.35-4.17 (m, 2H), 4.14 (d, J = 6.9 Hz, 1H), 4.02-3.37 (m, 5H), 2.83 (d, J = 7.3 Hz, 3H), 2.56-2.25 (m, 2H), 2.27-1.88 (m, 4H), 1.59-1.40 (m, 1H), 1.27 (s, 1H). MS calc. for $C_{28}H_{33}ClFN_6O_2$ (M + H⁺) 539.23, found: 539.1. |
| 3-2 | 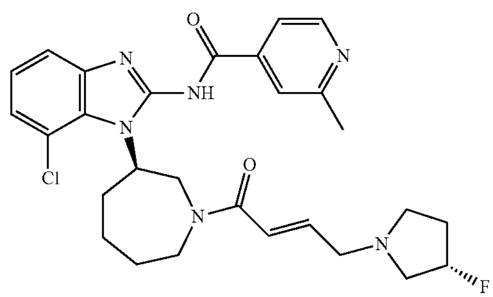 [SMILES: Cc1cc(C(=O)Nc2nc3cccc(Cl)c3n2[C@@H]2CCCCN(C(=O)/C=C/CN3CC[C@H](F)C3)C2)ccn1] | ¹H NMR (400 MHz, MeOD) δ 8.58 (d, J = 5.6 Hz, 1H), 8.15 (d, J = 29.3 Hz, 2H), 7.43 (s, 1H), 7.21 (dd, J = 7.9, 18.2 Hz, 2H), 6.89 (s, 1H), 6.71 (s, 1H), 5.68-5.14 (m, 3H), 4.71-4.51 (m, 1H), 4.26-4.08 (m, 1H), 4.03 (s, 2H), 3.92-3.71 (m, 2H), 3.69-3.48 (m, 2H), 3.47-3.24 (m, 2H), 2.65 (d, J = 8.8 Hz, 3H), 2.45-2.15 (m, 2H), 2.16-1.71 (m, 4H), 1.54-1.28 (m, 1H), 1.23-1.07 (m, 1H). MS calculated for $C_{28}H_{33}ClFN_6O_2$ (M + H⁺) 539.23, found: 539.1. |
| 3-3 | 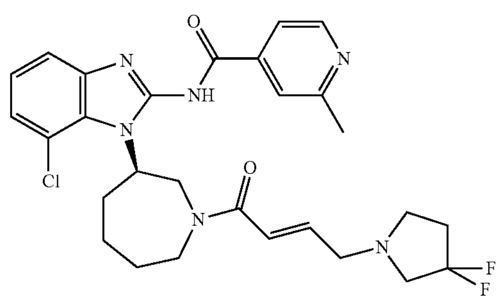 [SMILES: Cc1cc(C(=O)Nc2nc3cccc(Cl)c3n2[C@@H]2CCCCN(C(=O)/C=C/CN3CCC(F)(F)C3)C2)ccn1] | ¹H NMR (400 MHz, MeOD) δ 8.47 (s, 1H), 7.96 (d, J = 16.5 Hz, 1H), 7.92-7.81 (m, 1H), 7.51-7.35 (m, 1H), 7.19 (dd, J = 8.9, 19.4 Hz, 2H), 6.81-6.66 (m, 1H), 6.63 (s, 1H), 5.69-5.49 (m, 1H), 4.76-4.50 (m, 1H), 4.22-4.02 (m, 1H), 4.02-3.86 (m, 1H), 3.87-3.75 (m, 1H), 3.72-3.56 (m, 1H), 3.55-3.34 (m, 1H), 3.25 (s, 1H), 3.04 (s, 1H), 2.90 (s, 1H), 2.76 (s, 2H), 2.55 (d, J = 3.9 Hz, 3H), 2.46-2.30 (m, 1H), 2.29-2.14 (m, 1H), 2.02 (s, 4H), 1.48-1.32 (m, 1H), 1.19 (s, 1H). MS calculated for $C_{28}H_{32}ClF_2N_6O_2$ (M + H⁺) 557.22, found: 557.0. |
| 3-4 | 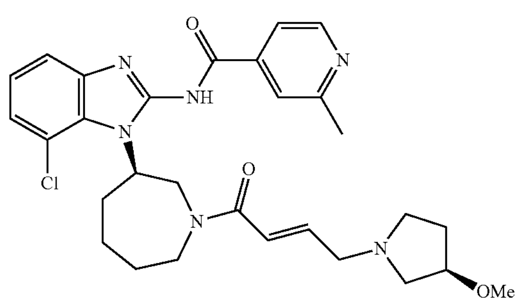 [SMILES: CO[C@@H]1CCN(C/C=C/C(=O)N2CCCC[C@@H](n3c(NC(=O)c4ccnc(C)c4)nc4cccc(Cl)c43)C2)C1] | ¹H NMR (400 MHz, MeOD) δ 8.62-8.45 (m, 1H), 8.10-7.97 (m, 1H), 8.00-7.87 (m, 1H), 7.60-7.39 (m, 1H), 7.43-7.10 (m, 2H), 7.03-6.59 (m, 2H), 5.81-5.59 (m, 1H), 4.83-4.59 (m, 1H), 4.37-3.61 (m, 5H), 3.65-3.40 (m, 2H), 3.35 (s, 1H), 3.26 (s, 2H), 3.26 (s, 3H), 2.99-2.73 (m, 2H), 2.65 (s, 2H), 2.30-1.82 (m, 4H), 1.64-1.42 (m, 1H), 1.30 (s, 1H), 0.96-0.84 (m, 1H). MS calculated for $C_{29}H_{36}ClN_6O_3$ (M + H⁺) 551.25, found: 551.1. |
| 3-5 | 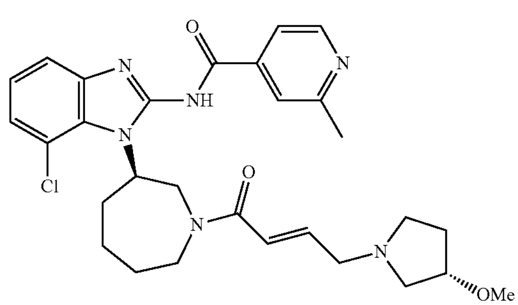 [SMILES: CO[C@H]1CCN(C/C=C/C(=O)N2CCCC[C@@H](n3c(NC(=O)c4ccnc(C)c4)nc4cccc(Cl)c43)C2)C1] | ¹H NMR (400 MHz, MeOD) δ 8.62-8.45 (m, 1H), 8.10-7.97 (m, 1H), 8.00-7.87 (m, 1H), 7.60-7.39 (m, 1H), 7.43-7.10 (m, 2H), 7.03-6.59 (m, 2H), 5.81-5.59 (m, 1H), 4.83-4.59 (m, 1H), 4.37-3.61 (m, 5H), 3.65-3.40 (m, 2H), 3.35 (s, 1H), 3.26 (s, 2H), 3.26 (s, 3H), 2.99-2.73 (m, 2H), 2.65 (s, 2H), 2.30-1.82 (m, 4H), 1.64-1.42 (m, 1H), 1.30 (s, 1H), 0.96-0.84 (m, 1H). MS calculated for $C_{29}H_{36}ClN_6O_3$ (M + H⁺) 551.25, found: 551.1. |

-continued

| Ex. | Compound Structure | Physical Data (¹H NMR and MS) |
|---|---|---|
| 3-6 | 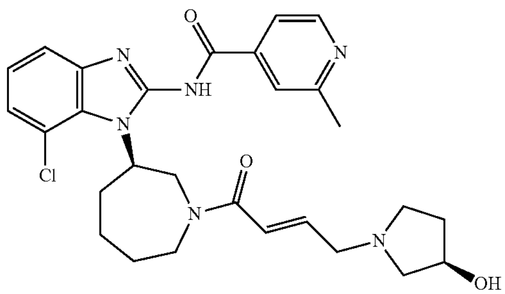 [SMILES: Cc1cc(C(=O)Nc2nc3cccc(Cl)c3n2[C@@H]2CCCCN(C(=O)/C=C/CN3CC[C@@H](O)C3)C2)ccn1] | ¹H NMR (400 MHz, MeOD) ¹H NMR (400 MHz, MeOD) δ 8.46 (s, 1H), 7.98-7.87 (m, 1H), 7.88-7.75 (m, 1H), 7.48-7.34 (m, 1H), 7.20 (s, 2H), 6.72-6.39 (m, 2H), 5.69-5.46 (m, 2H), 4.76-4.48 (m, 1H), 4.43-4.23 (m, 1H), 4.23-4.00 (m, 2H), 4.00-3.76 (m, 1H), 3.77-3.68 (m, 1H), 3.68-3.54 (m, 1H), 3.55-3.43 (m, 1H), 3.36 (s, 2H), 3.15-2.95 (m, 2H), 2.79 (s, 2H), 2.54 (s, 2H), 2.19-1.73 (m, 4H), 1.47-1.28 (m, 1H), 1.19 (s, 1H). MS calculated for $C_{28}H_{34}ClN_6O_3$ (M + H⁺) 537.23, found: 537.2. |
| 3-7 | 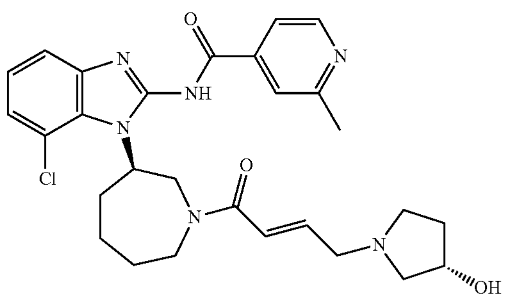 [SMILES: Cc1cc(C(=O)Nc2nc3cccc(Cl)c3n2[C@@H]2CCCCN(C(=O)/C=C/CN3CC[C@H](O)C3)C2)ccn1] | MS calculated for $C_{28}H_{34}ClN_6O_3$ (M + H⁺) 537.23, found: 537.3. |
| 3-8 | 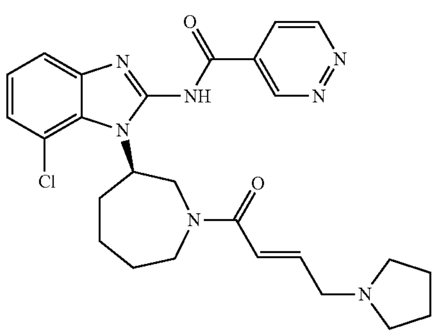 [SMILES: O=C(Nc1nc2cccc(Cl)c2n1[C@@H]1CCCCN(C(=O)/C=C/CN2CCCC2)C1)c1ccnnc1] | ¹H NMR (400 MHz, MeOD) δ 9.82-9.62 (m, 1H), 9.36-9.06 (m, 1H), 8.34-8.09 (m, 1H), 7.48-7.22 (m, 1H), 7.21-6.93 (m, 2H), 6.91-6.33 (m, 2H), 5.68-5.31 (m, 1H), 4.63-4.27 (m, 1H), 4.27-3.84 (m, 2H), 3.87-3.41 (m, 2H), 3.27(m, 1H), 3.11-2.83 (m, 1H), 2.52 (s, 2H), 2.37-2.13 (m, 2H), 1.91 (s, 2H), 1.77 (d, J = 18.8, 2H), 1.59 (s, 2H), 1.46-1.25 (m, 1H), 1.19 (s, 2H). MS calculated for $C_{26}H_{31}ClN_7O_2$ (M + H⁺) 508.21, found: 508.1. |
| 3-9 | 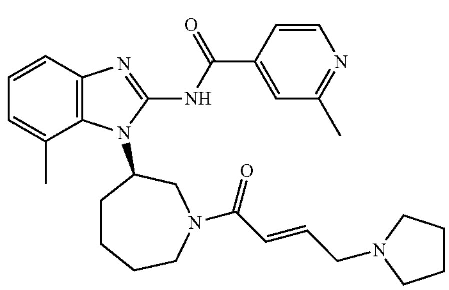 [SMILES: Cc1cc(C(=O)Nc2nc3cccc(C)c3n2[C@@H]2CCCCN(C(=O)/C=C/CN3CCCC3)C2)ccn1] | ¹H NMR (400 MHz, MeOD) δ 8.76-8.64 (m, 1H), 8.40-8.18 (m, 2H), 8.29-8.14 (m, 1H), 7.46-7.31 (m, 1H), 7.30-7.18 (m, 1H), 7.17-7.06 (m, 1H), 7.06-6.90 (m, 1H), 6.83-6.68 (m, 1H), 5.18-4.93 (m, 3H), 4.67-4.49 (m, 1H), 4.36-4.22 (m, 1H), 4.12-3.91 (m, 2H), 3.88-3.36 (m, 5H), 3.11-2.57 (m, 6H), 2.30-1.91 (m, 6H), 1.55-1.40 (m, 1H), 1.26-1.09 (m, 1H); MS calculated for $C_{29}H_{37}N_6O_2$ (M + H⁺) 501.29, found: 501.2. |
| 3-10 | 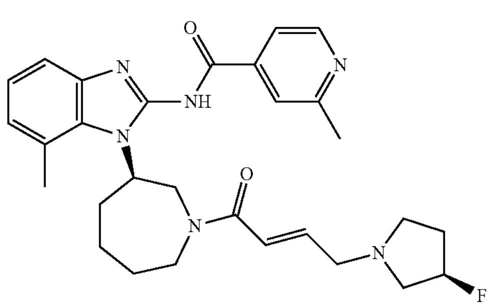 | ¹H NMR (400 MHz, MeOD) δ 8.67-8.44 (m, 1H), 8.12-7.72 (m, 2H), 7.62-7.43 (m, 1H), 7.42-7.05 (m, 2H), 6.97-6.61 (m, 2H), 5.42-5.04 (m, 2H), 4.75-4.46 (m, 2H), 4.38-3.89 (m, 2H), 3.87-3.41 (m, 3H), 3.26-3.09 (m, 2H), 2.77 (s, 2H), 2.65 (s, 1H), 2.41-2.03 (m, 3H), 1.99 (s, 3H), 1.65-1.39 (m, 2H), 1.30 (s, 4H), 0.98-0.84 (m, 1H); MS calculated for $C_{29}H_{36}FN_6O_2$ (M + H⁺) 519.28, found: 519.2. |

-continued

| Ex. | Compound Structure | Physical Data (¹H NMR and MS) |
|---|---|---|
| 3-11 | 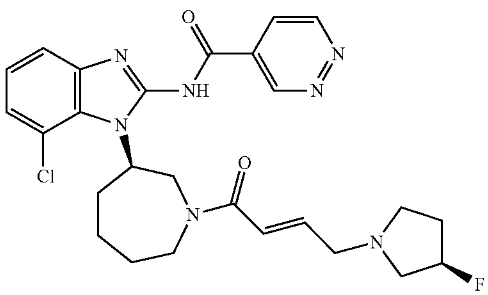 [SMILES: O=C(Nc1nc2cccc(Cl)c2n1[C@@H]1CCCCN(C(=O)/C=C/CN2CC[C@@H](F)C2)C1)c1ccnnc1] | ¹H NMR (400 MHz, MeOD) δ 9.72 (s, 1H), 9.28 (s, 1H), 8.21 (s, 1H), 7.58 (s, 1H), 7.49-7.32 (m, 1H), 7.29-7.10 (m, 2H), 6.84-6.66 (m, 1H), 6.61 (s, 1H), 5.71-5.41 (m, 1H), 5.24-4.88 (m, 1H), 4.74-4.42 (m, 1H), 4.27-4.03 (m, 1H), 4.01-3.71 (m, 1H), 3.55 (s, 1H), 3.27 (s, 1H), 3.09 (s, 1H), 2.95-2.78 (m, 1H), 2.67 (s, 3H), 1.93 (d, J = 104.5 Hz, 6H), 1.52-1.25 (m, 1H). MS calculated for $C_{26}H_{30}ClFN_7O_2$ (M + H⁺) 526.21, found: 526.1. |
| 3-12 | 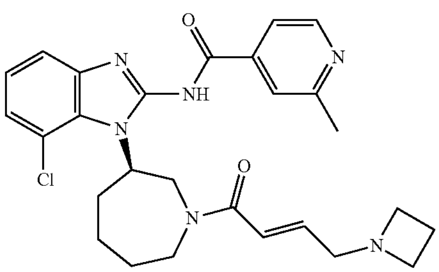 [SMILES: Cc1cc(C(=O)Nc2nc3cccc(Cl)c3n2[C@@H]2CCCCN(C(=O)/C=C/CN3CCC3)C2)ccn1] | MS calculated for $C_{27}H_{32}ClN_6O_2$ (M + H⁺) 507.22, found: 507.1. |
| 3-13 | 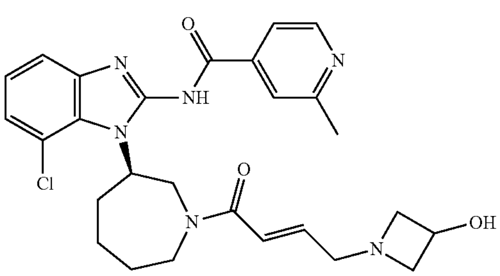 [SMILES: Cc1cc(C(=O)Nc2nc3cccc(Cl)c3n2[C@@H]2CCCCN(C(=O)/C=C/CN3CC(O)C3)C2)ccn1] | ¹H NMR (400 MHz, MeOD) δ 8.46 (s, 1H), 7.98-7.87 (m, 1H), 7.88-7.75 (m, 1H), 7.49-7.33 (m, 1H), 7.20 (s, 2H), 6.70-6.41 (m, 2H), 5.69-5.46 (m, 1H), 4.76-4.46 (m, 1H), 4.38-4.26 (m, 1H), 4.22-4.01 (m, 1H), 3.98-3.76 (m, 2H), 3.76-3.68 (m, 1H), 3.67-3.57 (m, 1H), 3.55-3.42 (m, 1H), 3.36 (m, 1H), 3.14-3.08 (m, 1H), 3.09-3.00 (m, 1H), 2.79 (s, 1H), 2.54 (s, 3H), 2.13-1.78 (m, 4H), 1.49-1.29 (m, 1H), 1.19 (s, 1H). MS calculated for $C_{27}H_{32}ClN_6O_3$ (M + H⁺) 523.21, found: 523.0. |
| 3-14 | 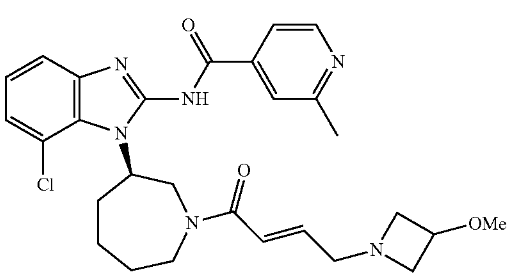 [SMILES: COC1CN(C/C=C/C(=O)N2CCCC[C@@H](n3c(NC(=O)c4ccnc(C)c4)nc4cccc(Cl)c43)C2)C1] | ¹H NMR (400 MHz, MeOD) δ 8.46 (s, 1H), 7.94 (s, 1H), 7.84 (s, 1H), 7.45-7.31 (m, 1H), 7.20 (s, 2H), 6.78-6.62 (m, 1H), 6.64-6.48 (m, 1H), 5.65-5.47 (m, 1H), 4.66-4.50 (m, 1H), 4.19-3.99 (m, 3H), 4.00-3.88 (m, 1H), 3.86-3.74 (m, 1H), 3.74-3.55 (m, 2H), 3.38 (s, 3H), 3.13 (s, 1H), 2.88-2.61 (m, 2H), 2.54 (s, 3H), 2.17-1.74 (m, 4H), 1.49-1.31 (m, 1H), 1.19 (s, 1H). MS calculated for $C_{28}H_{34}ClN_6O_3$ (M + H⁺) 537.23, found: 537.1. |
| 3-15 | 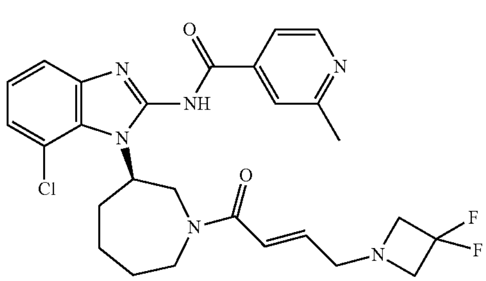 [SMILES: Cc1cc(C(=O)Nc2nc3cccc(Cl)c3n2[C@@H]2CCCCN(C(=O)/C=C/CN3CC(F)(F)C3)C2)ccn1] | ¹H NMR (400 MHz, MeOD) δ 8.52-8.36 (m, 1H), 7.98-7.87 (m, 1H), 7.88-7.79 (m, 1H), 7.47-7.36 (m, 1H), 7.30-7.09 (m, 2H), 6.70-6.58 (m, 1H), 6.57-6.45 (m, 1H), 5.70-5.47 (m, 1H), 4.68-4.48 (m, 1H), 4.22-4.01 (m, 1H), 4.01-3.70 (m, 2H), 3.61 (s, 2H), 3.37 (s, 2H), 3.18-3.00 (m, 1H), 2.97-2.63 (m, 2H), 2.54 (s, 3H), 2.16-1.74 (m, 4H), 1.48-1.31 (m, 1H), 1.19 (s, 1H). MS calculated for $C_{27}H_{30}ClF_2N_6O_2$ (M + H⁺) 543.20, found: 543.0. |

| Ex. | Compound Structure | Physical Data (¹H NMR and MS) |
|---|---|---|
| 3-16 | 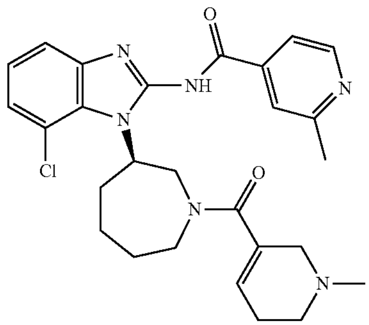 [SMILES: Cc1cc(C(=O)Nc2nc3cccc(Cl)c3n2[C@@H]2CCCCN(C(=O)C3=CCCN(C)C3)C2)ccn1] | ¹H NMR (400 MHz, MeOD) δ 8.46 (s, 1H), 7.92 (s, 1H), 7.84 (s, 1H), 7.39 (m, 1H), 7.19 (m, 2H), 6.02 (s, 1H), 5.57 (s, 1H), 5.39 (s, 1H), 4.60 (m, 1H), 4.11 (d, J = 12.9 Hz, 1H), 3.85 (m, 2H), 3.52 (dd, J = 14.6, 40.9 Hz, 2H), 3.29 (d, J = 16.8 Hz, 1H), 3.08 (m, 1H), 2.83 (m, 2H), 2.52 (m, 6H), 2.37 (s, 1H), 2.23 (s, 1H), 1.99 (m, 3H), 1.46 (m, 1H); MS calculated for $C_{27}H_{32}ClN_6O_2$ (M + H⁺) 507.22, found: 507.2. |
| 3-17 | 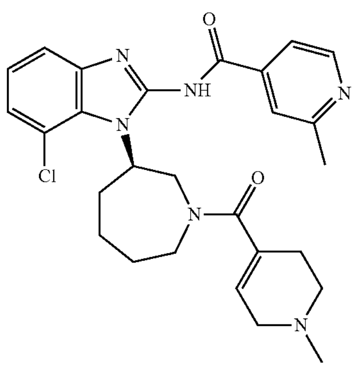 [SMILES: Cc1cc(C(=O)Nc2nc3cccc(Cl)c3n2[C@@H]2CCCCN(C(=O)C3=CCN(C)CC3)C2)ccn1] | ¹H NMR (400 MHz, MeOD) δ 8.47 (s, 1H), 7.94 (s, 1H), 7.85 (s, 1H), 7.41 (t, J = 8.5 Hz, 1H), 7.19 (m, 2H), 5.83 (d, J = 9.6 Hz, 1H), 5.56 (dt, J = 10.4, 14.1 Hz, 1H), 4.58 (m, 1H), 4.15 (d, J = 12.9 Hz, 1H), 3.85 (m, 2H), 3.51 (dd, J = 18.0, 28.7 Hz, 2H), 3.27 (s, 1H), 3.02 (dd, J = 17.8, 33.2 Hz, 2H), 2.63 (m, 2H), 2.55 (s, 3H), 2.45 (d, J = 17.7 Hz, 1H), 2.34 (d, J = 6.0 Hz, 3H), 2.06 (s, 3H), 1.92 (m, 2H); MS calculated for $C_{27}H_{32}ClN_6O_2$ (M + H⁺) 507.22, found: 507.2. |
| 3-18 | 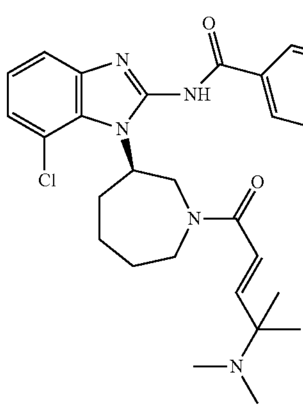 | ¹H NMR (400 MHz, MeOD) δ 8.45 (s, 1H), 7.92 (d, J = 12.9 Hz, 1H), 7.83 (s, 1H), 7.38 (s, 1H), 7.13 (d, J = 13.3 Hz, 2H), 6.81 (dt, J = 5.8, 11.8 Hz, 1H), 6.41 (m, 1H), 5.56 (d, J = 31.1 Hz, 1H), 4.57 (m, 0.5H), 4.19 (d, J = 12.0 Hz, 1H), 3.98 (m, 0.5 H), 3.82 (dd, J = 7.2, 15.4 Hz, 0.5H), 3.60 (dt, J = 7.7, 14.1 Hz, 0.5H), 3.32 (m, 1H), 2.71 (m, 1H), 2.54 (d, J = 3.7 Hz, 2H), 2.20 (s, 2H), 1.91 (m, 7H), 1.39 (m, 1H), 1.19 (d, J = 3.4 Hz, 3H), 0.95 (d, J = 24.0 Hz, 3H), 0.82 (d, J = 6.7 Hz, 1H); MS calculated for $C_{28}H_{36}ClN_6O_2$ (M + H⁺) 523.25, found: 523.1 |

Example 4

(S)—N-(1-(1-acryloylpiperidin-3-yl)-5-methyl-1H-benzo[d]imidazol-2-yl)-3-(trifluoromethyl)benzamide

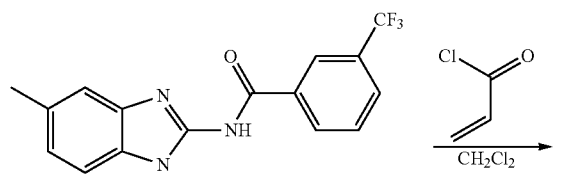

To a stirred solution of I-16 (0.150 g, 0.37 mmol) in $CH_2Cl_2$ (20 mL) at 0° C. was added acryloyl chloride in $CH_2Cl_2$ (0.050 g, 0.55 mmol) and the mixture was stirred for 30 min (reaction completion monitored by TLC). The mixture was diluted with water and extracted with $CH_2Cl_2$ (2×20 mL). The combined organic layers were washed with brine, dried over anhydrous $Na_2SO_4$ and concentrated under reduced pressure. The crude material was purified by column chromatography (50% EtOAc/Hexanes) to afford the title compound (Example 4). $^1$H-NMR (DMSO-$d_6$, 400 MHz): ∂ 12.84 (s, 1H), 8.46 (d, J=8 Hz, 2H), 7.89 (d, J=8 Hz, 1H), 7.75-7.63 (m, 2H), 7.39 (s, 1H), 7.09 (d, J=8.4 Hz, 1H), 6.95-6.79 (m, 1H), 6.19-6.13 (m, 1H), 5.75-5.59 (m, 1H), 4.79-4.56 (m, 2H), 4.23-4.06 (m, 2H), 3.70-3.65 (m, 1H), 3.27-3.21 (m, 1H), 2.85-2.66 (m, 2H), 2.39 (s, 3H), 2.00-1.91 (m, 2H), 1.64-1.5 (m, 1H); MS calculated for $C_{24}H_{24}F_3N_4O_2$ (M+H$^+$) 457.18. found 456.9.

Example 5

(R,E)-N-(7-chloro-1-(1-(4-(dimethylamino)but-2-enoyl)azepan-3-yl)-1H-benzo[d]imidazol-2-yl)-2-methylisonicotinamide

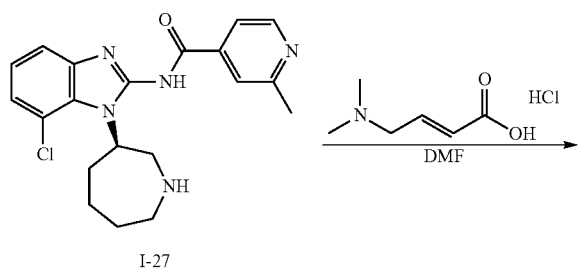

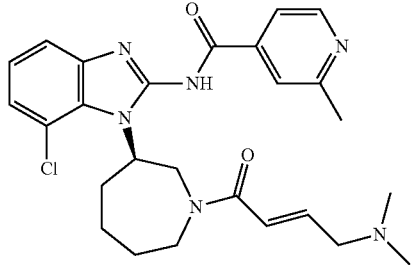

A mixture of (E)-4-(dimethylamino)but-2-enoic acid hydrochloride (58 mg, 0.35 mmol) and 1-ethyl-3-(3-dimethylaminopropyl)carbodiimide hydrochloride (67 mg, 0.35 mmol) in DMF (2 mL) was treated with hydroxybenzotriazole (54 mg, 0.35 mmol) and stirred at room temperature for 1 h. The resulting mixture was added to a solution of I-27 (100 mg, 0.22 mmol) in DMF (2 mL). Triethylamine (199 mg, 1.97 mmol) was then added and the mixture was stirred for 5 days. Water (2 mL) was added and the mixture was concentrated under reduced pressure. The residue was diluted with 1N NaOH (20 mL) and extracted with EtOAc (3×50 mL). The combined organic layers were washed with water (50 mL) and brine (2×50 mL), dried over $Na_2SO_4$, and concentrated under reduced pressure. The crude was purified by column chromatography (9:1:0.175N $CH_2Cl_2$/MeOH/$NH_3$ in $CH_2Cl_2$, 0% to 100%) to afford the title compound (Example 5).

$^1$H NMR (400 MHz, DMSO-$d_6$) δ 8.59 (d, J=4.8 Hz, 1H), 7.89 (s, 1H), 7.79 (d, J=4.8 Hz, 1H), 7.60 (d, J=7.5 Hz, 1H), 7.30-7.22 (m, 2H), 6.71-6.65 (m, 1H), 6.57-6.54 (m, 1H), 5.54 (br. s, 1H), 4.54 (br. s, 1H), 4.20 (br s, 1H), 3.95 (br s, 1H), 3.48 (br s, 1H), 2.98 (br s, 2H), 2.72 (d, J=12.0 Hz, 1H), 2.58 (s, 3H), 2.14 (br s, 6H), 2.05 (d, J=6.7 Hz, 3H), 1.88 (br s, 1H), 1.46 (d, J=11.3 Hz, 1H); MS calculated for $C_{26}H_{32}ClN_6O_2$ (M+H$^+$) 495.22. found 495.10. Melting point (114.6° C.).

(R,E)-N-(7-chloro-1-(1-(4-(dimethylamino)but-2-enoyl)azepan-3-yl)-1H-benzo[d]imidazol-2-yl)-2-methylisonicotinamide (1.0 g) was dissolved in acetone (30 mL) by heating to 55° C. to form a solution. Methanesulfonic acid (325 µL) was added to acetone (50 mL), and the methanesulfonic acid/acetone (22.2 mL) was added to the solution at 0.05 ml/min. Following precipitation, the resulting suspension was cooled to room temperature at 0.5° C./min, and crystals were collected by filtration, and dried for 4 hours at 40° C. under vacuum. The collected crystals (300 mg) were suspended in acetone/$H_2O$ (6 mL; v/v=95/5) by heating to 50° C. The suspension was kept slurrying for 16 hours, and cooled to room temperature at 0.5° C./min. The crystal was collected by filtration and dried for 4 hours at 40° C. under vacuum.

The structure of (R,E)-N-(7-chloro-1-(1-(4-(dimethylamino)but-2-enoyl)azepan-3-yl)-1H-benzo[d]imidazol-2-yl)-2-methylisonicotinamide mesylate was confirmed by Differential Scanning Calorimetry, X-Ray Powder Diffraction, and Elemental Analyses.

Melting point (170.1° C.). Theoretical calculated: % C (54.8); % H (5.9); % N (14.2); % O (13.5); % S (5.4); and % Cl (6.0); C:N ratio: 3.86. Found: % C (52.0); % H (5.8); % N (13.3); % Cl (5.9); C:N ratio: 3.91. Stoichiometry: 1.01.

Example 6

(R,E)-N-(7-chloro-1-(1-(4-(dimethylamino)but-2-enoyl)azepan-3-yl)-1H-benzo[d]imidazol-2-yl)-2,6-dimethylisonicotinamide

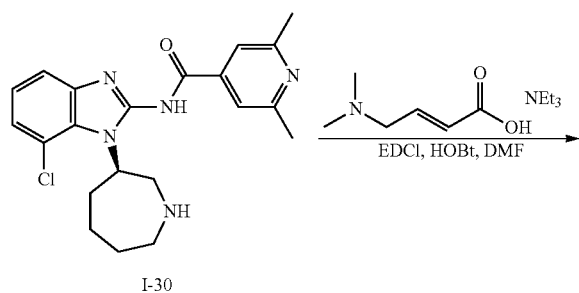

I-30

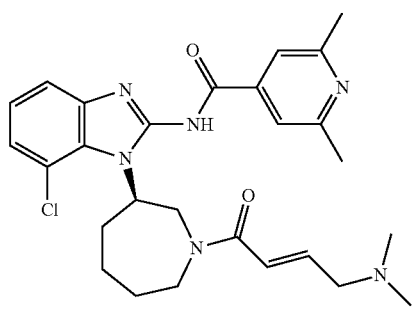

Example 6

To a mixture of (E)-4-(dimethylamino)but-2-enoic acid (370 mg, 2.9 mmol) and 1-ethyl-3-(3-dimethylaminopropyl)carbodiimide hydrochloride (730 mg, 3.8 mmol) in DMF (15 mL) was added hydroxybenzotriazole (516 mg, 3.8 mmol), and stirred at room temperature 10 min. The resulting mixture was then added to a suspension of I-30 in DMF (10 mL), followed by the addition of NEt$_3$ (1.86 mL, 13.4 mmol). The mixture was stirred at room temperature overnight, quenched with H$_2$O (2 mL) and concentrated under reduced pressure. The crude was partitioned between EtOAc and 1.0 N NaOH, and extracted with EtOAc. The combined organic layers were dried over Na$_2$SO$_4$ and concentrated in vacuo. The crude material was purified by column chromatography (0-10% MeOH/CH$_2$Cl$_2$) to afford the title compound (Example 6). $^1$H NMR (400 MHz, CD$_2$Cl$_2$) δ 12.69 (s, 1H), 8.75-8.48 (m, 1H), 8.06-7.70 (m, 2H), 7.49-7.06 (m, 2H), 6.88 (dt, J=4.4, 15.1 Hz, 1H), 6.58 (d, J=20.2 Hz, 1H), 5.64 (s, 1H), 4.94-4.26 (m, 2H), 4.23-3.96 (m, 1H), 3.97-3.29 (m, 2H), 3.21 (d, J=5.9 Hz, 1H), 3.03 (dd, J=18.8, 24.7 Hz, 1H), 2.79 (d, J=12.1 Hz, 1H), 2.64 (s, J=9.8 Hz, 6H), 2.36 (s, 3H), 2.28-1.83 (m, 6H), 1.53 (s, 1H). MS calculated for C$_{28}$H$_{34}$ClN$_6$O$_2$ (M+H$^+$) 509.24. found: 509.2.

Example 7

(R,E)-N-(1-(1-(4-(dimethylamino)but-2-enoyl)azepan-3-yl)-7-methyl-1H-benzo[d]imidazol-2-yl)-2-methylisonicotinamide

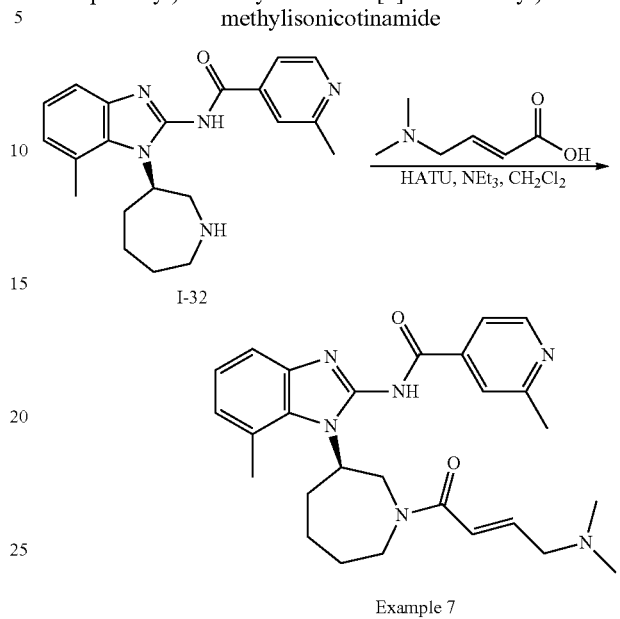

Example 7

A mixture of I-32 (313 mg, 0.78 mmol), (E)-4-(dimethylamino)but-2-enoic acid (139 mg, 1.02 mmol) and 2-(7-aza-1H-benzotriazole-1-yl)-1,1,3,3-tetramethyluronium hexafluorophosphate (453 mg, 1.18 mmol) in CH$_2$Cl$_2$ (7 mL) was treated with NEt$_3$ (0.66 mL, 4.70 mmol) and stirred at room temperature for 10 min. The mixture was then partitioned between half-saturated aqueous Na$_2$CO$_3$ solution and CH$_2$Cl$_2$ and the aqueous layer was extracted with CH$_2$Cl$_2$ (2×). The combined organic phase was dried over Na$_2$SO$_4$ and concentrated under reduced pressure. The crude was purified by column chromatography (9:1:0.175N CH$_2$Cl$_2$/MeOH/NH$_3$ in CH$_2$Cl$_2$, 0% to 60%) to afford the title compound (Example 7). $^1$H-NMR (400 MHz, DMSO) δ 8.61 (d, J=5.1 Hz, 1H), 7.92 (s, 1H), 7.81 (d, J=5.0 Hz, 1H), 7.46 (d, J=7.2 Hz, 1H), 7.14 (t, J=7.7, 1H), 7.04 (d, J=7.3 Hz, 1H), 6.67 (m, 2H), 4.92 (m, 1H), 4.35 (dd, J=10.7, 12.8 Hz, 1H), 4.16 (m, 1H), 3.95 (m, 1H), 3.60 (t, J=5.8 Hz, 1H), 3.07 (t, J=5.2 Hz, 1H), 2.84 (m, 1H), 2.75 (m, 1H), 2.70 (s, 3H), 2.57 (s, 3H), 2.10 (s, 6H), 1.91 (m, 4H), 1.34 (m, 1H). MS calculated for C$_{27}$H$_{35}$N$_6$O$_2$ (M+H$^+$) 475.27. found 475.2.

Example 8

(R,E)-N-(1-(1-(4-(dimethylamino)but-2-enoyl)azepan-3-yl)-7-methyl-1H-benzo[d]imidazol-2-yl)-2-(trifluoromethyl)isonicotinamide

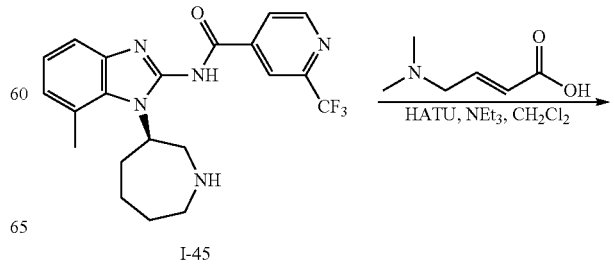

I-45

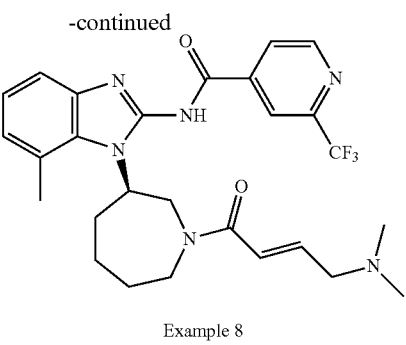

Example 8

The title compound (Example 8) was prepared from I-45 following procedures analogous to Example 7. $^1$H-NMR (400 MHz, MeOD) δ 8.88 (d, J=4.9 Hz, 1H), 8.56 (s, 1H), 8.34 (d, J=4.9 Hz, 1H), 7.41 (d, J=8.0 Hz, 1H), 7.20 (t, J=7.8 Hz, 1H), 7.12 (m, 1H), 6.86 (t, J=13.8 Hz, 1H), 6.78 (m, 1H), 5.12 (m, 1H), 4.54 (dd, J=10.8, 13.0 Hz, 1H), 4.27 (m, 1H), 4.02 (m, 1H), 3.65 (m, 3H), 2.92 (m, 1H), 2.78 (s, 3H), 2.67 (s, 6H), 2.22 (m, 1H), 2.08 (m, 3H), 1.49 (m, 1H). MS calculated for $C_{27}H_{32}F_3N_6O_2$ (M+H$^+$) 529.25. found 529.2.

Example 9

(R)—N-(1-(1-acryloylazepan-3-yl)-7-chloro-6-methoxy-1H-benzo[d]imidazol-2-yl)pyridazine-4-carboxamide

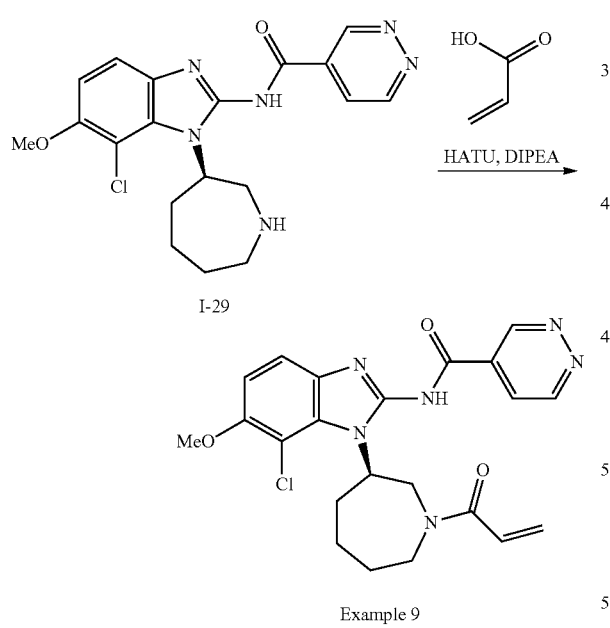

Example 9

Acrylic acid (21.6 mg, 0.30 mmol) and 2-(7-aza-1H-benzotriazole-1-yl)-1,1,3,3-tetramethyluronium hexafluorophosphate (114 mg, 0.30 mmol) were dissolved in DMF (2 mL). N,N-diisopropylethylamine (114 mg, 0.885 mmol) was added and the mixture was stirred for 10 min. A solution of I-29 (88 mg, 0.186 mmol) in DMF (1 mL) was then added and the mixture stirred for 1 h (reaction completion monitored by LC/MS). The mixture was concentrated under reduced pressure and the residue was diluted with showed that the reaction completed. Reaction mixture was stripped off solvents. The residue was dissolved in CH$_2$Cl$_2$ (2 mL), treated with K$_2$CO$_3$ (257 mg, 1.86 mmol) for 5 min and purified by column chromatography (MeOH in CH$_2$Cl$_2$, 0% to 10%) to afford a residue that was diluted with CH$_2$Cl$_2$ (150 mL) and washed with 0.2N HCl (3×20 mL), brine (20 mL), saturated aqueous NaHCO$_3$ aq, and water. The organic layer was then dried with Na$_2$SO$_4$, and concentrated under reduced pressure to afford the title compound (Example 9) as a light yellow solid. $^1$H-NMR (400 MHz, CD$_3$CN): δ 12.33 (br s, 1H), 9.71-9.67 (m, 1H), 9.27-9.24 (m, 1H), 8.09-8.05 (m, 1H), 7.38 (d, J=10.0 Hz, 0.4H), 7.36 (d, J=10.0 Hz, 0.6H), 6.98 (d, J=8.8 Hz, 0.4H), 6.97 (d, J=8.8 Hz, 0.6H), 6.68 (dd, J=10.4, 16.4 Hz, 0.6H), 6.66 (dd, J=10.4, 16.4 Hz, 0.4H), 6.18-6.12 (m, 1H), 5.62 (dd, J=10.4, 2.0 Hz, 0.6H), 5.49 (dd, J=10.4, 2.0 Hz, 0.6H), 5.64-5.57 (m, 1H), 4.65 (dd, J=14.8, 10.8 Hz, 0.4H), 4.45 (dd, J=14.8, 10.8 Hz, 0.6H), 4.16 (dd, J=14.8, 10.4 Hz, 0.4H), 4.00 (dd, J=14.8, 10.4 Hz, 0.6H), 3.96-3.69 (m, 1H), 3.84 (s, 1.2H), 3.83 (s, 1.8H), 3.62-3.56 (m, 0.6H), 3.36-3.30 (m, 0.4H), 2.70-2.54 (m, 1H), 2.08-1.88 (m, 4H), 1.43-1.31 (m, 1H). MS calculated for $C_{22}H_{24}ClN_6O_3$ (M+H$^+$) 455.15. found 455.1.

Example 10

N-(7-methyl-1-(1-(vinylsulfonyl)azepan-3-yl)-1H-benzo[d]imidazol-2-yl)-3-(trifluoromethyl)benzamide

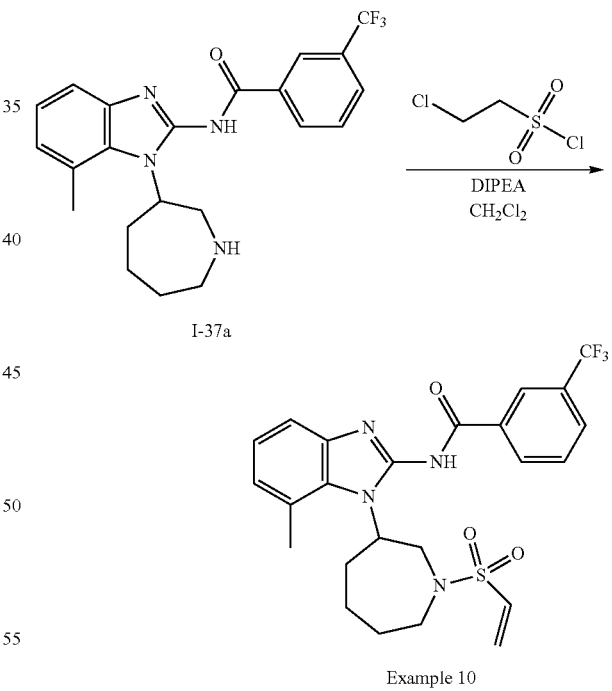

Example 10

A solution of I-37a (30 mg, 0.066 mmol) in CH$_2$Cl$_2$ (0.66 mL) was treated with N,N-diisopropylethylamine (0.046 mL, 0.265 mmol), followed by 2-chloroethanesulfonyl chloride (14 mg, 0.079 mmol). The reaction mixture was stirred at room temperature until completed as determined by LC/MS analysis. The crude reaction mixture was added directly to an ISCO dry loader and purified by column chromatography (0-30% [9:1:0.175N CH$_2$Cl$_2$/MeOH/NH$_3$]/CH$_2$Cl$_2$) to afford the title compound (Example 10) as a pale beige solid. $^1$H-NMR (400 MHz, CDCl$_3$) δ 12.55 (s, 1H), 8.58 (s, 1H), 8.38 (m, 1H), 7.70 (dd, J=7.5, 23.0, 1H), 7.57 (m, 1H), 7.15 (m, 1H), 7.11 (m, 1H), 6.98 (m, 1H), 6.24 (ddd, J=9.9, 60.0, 120.0, 1H), 5.10 (s, 1H), 4.49 (m, 1H), 3.74 (d, J=9.9, 1H), 3.20 (m, 1H), 3.06 (m, 1H), 2.81 (m, 1H), 2.79 (s, 3H), 1.64 (m, 1H). $^{19}$F-NMR (376 MHz, CDCl$_3$) δ −62.53; MS calculated for C$_{24}$H$_{26}$F$_3$N$_4$O$_3$S (M+H$^+$) 507.16. found 507.1.

Example 11

N-(1-(1-acryloyazepan-3-yl)-7-(pyrrolidin-1-ylmethyl)-1H-benzo[d]imidazol-2-yl)-3-(trifluoromethyl)benzamide

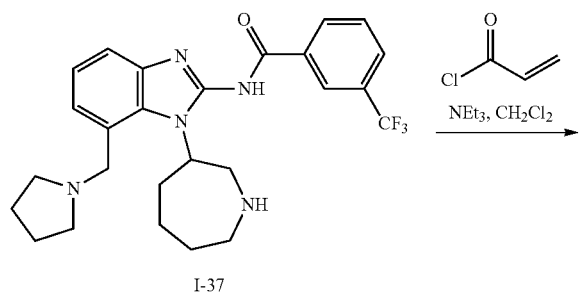

I-37

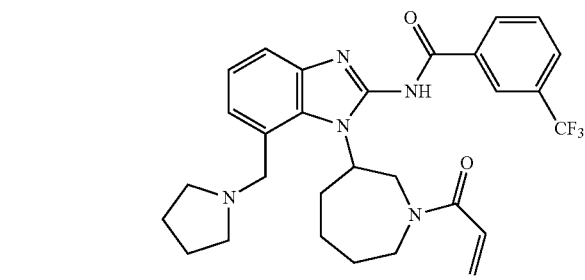

Example 11

The title compound as a pale beige solid was prepared following procedures analogous to Example 10, substituting acryloyl chloride for 2-chloroethanesulfonyl. $^1$H-NMR (400 MHz, CDCl$_3$) δ 12.61 (s, 1H), 8.67 (s, 1H), 8.43 (m, 1H), 7.74 (d, J=7.7 Hz, 1H), 7.59 (t, J=7.7 Hz, 1H), 7.28 (s, 1H), 7.21 (d, J=19.2 Hz, 1H), 7.15 (s, 2H), 6.65 (m, 1H), 6.36 (m, 1H), 5.74 (m, 1H), 5.38 (m, 1H), 4.92 (m, 1H), 4.46 (m, 1H), 4.25 (m, 1H), 3.97 (s, 1H), 3.58 (m, 1H), 2.85 (m, 1H), 2.41 (m, 3H), 2.21 (m, 2H), 2.02 (m, 4H), 1.69 (m, 4H). $^{19}$F-NMR (376 MHz, CDCl$_3$) δ −62.49; MS calculated for C$_{29}$H$_{33}$F$_3$N$_5$O$_2$ (M+H$^+$) 540.25. found 540.3.

Example 12 tert-butyl 4-acryloyl-6-(7-chloro-2-(2-methylisonicotinamido)-1H-benzo[d]imidazol-1-yl)-1,4-diazepane-1-carboxylate

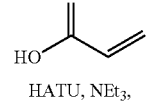

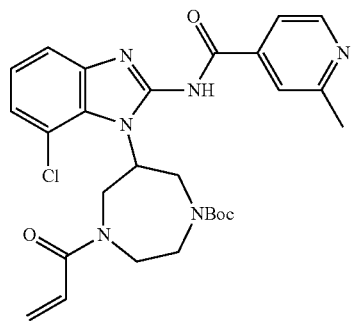

Example 12

The title compound was prepared following procedures analogous to Intermediate 27, step A, by substituting acrylic acid for 2-methylisonicotinic acid. $^1$H NMR (400 MHz, MeOD) δ 8.58 (d, J=5.1 Hz, 1H), 8.03-7.97 (m, 1H), 7.97-7.90 (m, 1H), 7.59-7.47 (m, 1H), 7.42-7.32 (m, 1H), 7.32-7.23 (m, 1H), 6.99-6.72 (m, 1H), 6.41-6.19 (m, 1H), 5.95-5.82 (m, 1H), 5.82-5.70 (m, 1H), 4.83-4.72 (m, 2H), 4.58-4.31 (m, 4H), 4.25-4.06 (m, 2H), 2.65 (s, 3H), 1.48-1.39 (m, 9H); MS calculated for C$_{27}$H$_{32}$ClN$_6$O$_4$ (M+H$^+$) 539.21. found 539.2.

Example 13

N-(1-(1-acryloyl-1,4-diazepan-6-yl)-7-chloro-1H-benzo[d]imidazol-2-yl)-2-methylisonicotinamide

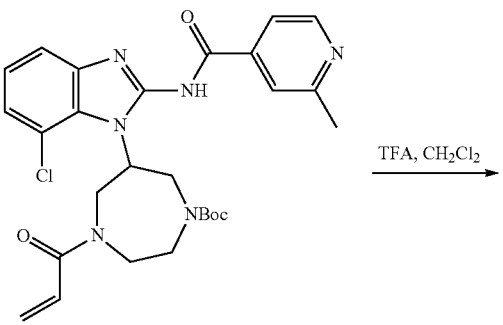

Example 12

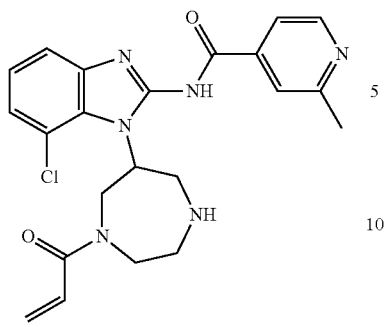

Example 13

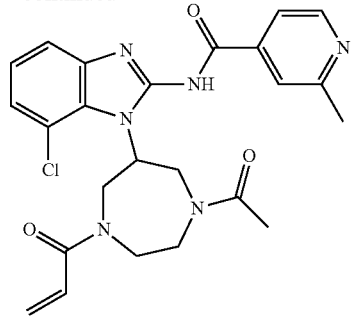

Example 14

A solution of Example 12 (150 mg, 0.278 mmol) in CH₂Cl₂ (2 mL) was treated with a 1:1 solution of 2,2,2-trifluoroacetic acid in CH₂Cl₂ (4 mL) and stirred for 90 min. The volatiles were removed under reduced pressure, the residue partitioned between CH₂Cl₂ and saturated aqueous Na₂CO₃, the layers separated, and the aqueous phase extracted with CH₂Cl₂ (2×). The combined organics were washed with brine, dried over Na2SO₄, and concentrated under reduced pressure to afford the title compound (Example 13). $^1$H NMR (400 MHz, MeOD) δ 8.58 (d, J=5.2 Hz, 1H), 7.96 (d, J=8.8 Hz, 1H), 7.88 (s, 1H), 7.60-7.47 (m, 1H), 7.31 (s, 1H), 7.30-7.21 (m, 1H), 6.83 (dd, J=10.6, 16.8 Hz, 1H), 6.31 (d, J=16.7 Hz, 1H), 6.17-5.85 (m, 1H), 5.78 (dd, J=10.5, 34.2 Hz, 1H), 4.79-4.39 (m, 1H), 4.37-4.12 (m, 1H), 4.12-3.56 (m, 1H), 3.55-3.34 (m, 1H), 3.25-2.97 (m, 3H), 2.96-2.82 (m, 1H), 2.65 (s, 3H); MS calculated for C₂₂H₂₄ClN₆O₂ (M+H⁺) 439.16. found 439.2.

A solution of Example 13 (30 mg, 0.068 mmol), N,N-dimethylaminopyridine (17 mg, 0.137 mmol), and N,N-diisopropylethylamine (0.024 mL, 0.137 mmol) in CH₂Cl₂ (0.75 mL) was treated at room temperature with acetic anhydride (0.01 mL, 0.103 mmol) and stirred for 5 min. The reaction was then added directly to a RediSep dry loader cartridge and purified by column chromatography (9:1:0.175 M CH₂Cl₂/MeOH/NH₃ in CH₂Cl₂, 0-50%) to afford the title compound (Example 14). $^1$H NMR (400 MHz, MeOD) δ 8.53-8.41 (m, 1H), 7.96-7.88 (m, 1H), 7.88-7.77 (m, 1H), 7.50-7.36 (m, 1H), 7.31-7.13 (m, 2H), 6.91-6.60 (m, 1H), 6.30-6.08 (m, 1H), 5.87-5.72 (m, 1H), 5.72-5.65 (m, 1H), 4.43-4.24 (m, 4H), 4.24-3.94 (m, 2H), 3.64-3.48 (m, 2H), 2.55 (s, 3H), 2.12-1.99 (m, 3H); MS calculated for C₂₄H₂₆ClN₆O₃ (M+H⁺) 481.17. found 481.2.

Example 15

(R)—N-(1-(1-acryloylazepan-3-yl)-7-chloro-6-(2-(pyrrolidin-1-yl)ethoxy)-1H-benzo[d]imidazol-2-yl)-2,6-dimethylisonicotinamide

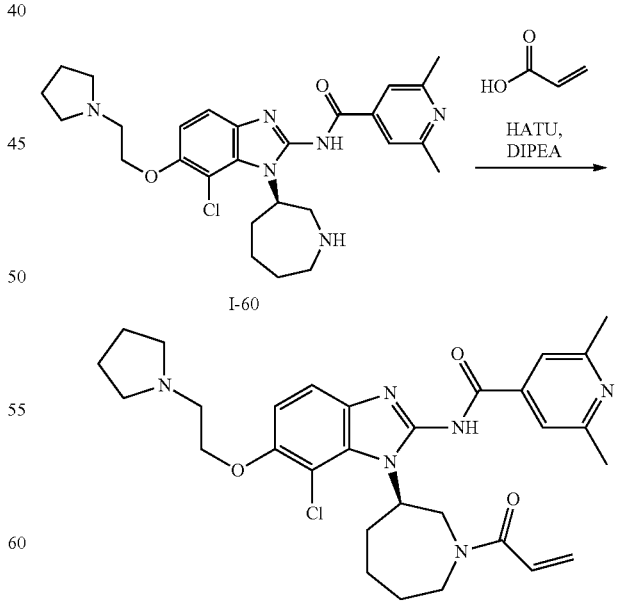

Example 14

N-(1-(1-acetyl-4-acryloyl-1,4-diazepan-6-yl)-7-chloro-1H-benzo[d]imidazol-2-yl)-2-methylisonicotinamide

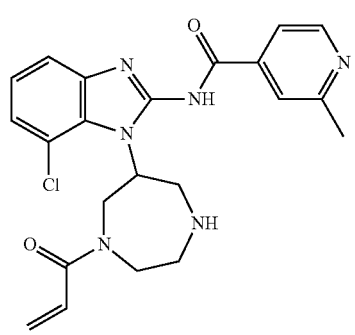

Example 13

The title compound was prepared following procedures analogous to Example 9. $^1$H-NMR (400 MHz, CD₂Cl₂): δ

7.64-7.54 (m, 2H), 7.16-7.09 (m, 1H), 6.90-6.83 (m, 1H), 6.64-6.54 (m, 1H), 6.34-6.21 (m, 1H), 5.65-5.46 (m, 2H), 4.81-4.69 (m, 1H), 4.62-4.45 (m, 1H), 4.35-4.19 (m, 1H), 4.14-4.03 (b m, 2H), 3.92-3.84 (m, 1H), 3.80-3.68 (m, 1H), 3.59-3.51 (m, 1H), 3.46-3.23 (m, 1H), 2.92-2.80 (b m, 2H), 2.75-2.63 (m, 1H), 2.55 (s, 3H), 2.47 (s, 4H), 2.18-1.81 (m, 4H), 1.70-1.35 (m, 6H). MS calculated for $C_{30}H_{38}ClN_6O_3$ (M+H$^+$) 565.26. found 565.3.

Example 16

(R,E)-N-(7-chloro-1-(1-(4-(dicyclopropylamino)but-2-enoyl)azepan-3-yl)-1H-benzo[d]imidazol-2-yl)-2-methylisonicotinamide

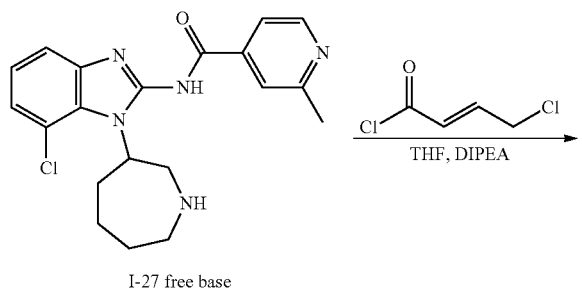

I-27 free base

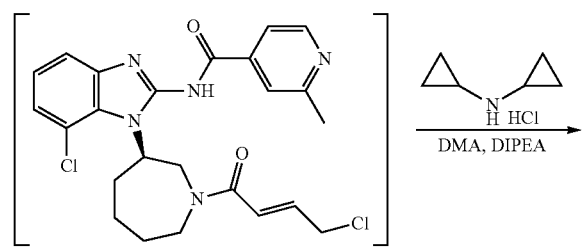

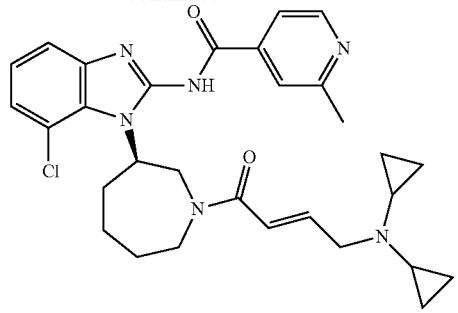

Example 16

A mixture of I-27 (free base, 340 mg, 0.89 mmol) and diisopropylethylamine (0.2 mL, 1.15 mmol) in THF (15 mL) was treated at 0° C. with (E)-4-chlorobut-2-enoyl chloride (136 mg, 0.98 mmol) and stirred at 0° C. for 10 min, when the reaction was deemed complete as determined by LC/MS (MS calculated for $C_{24}H_{26}Cl_2N_5O_2$ (M+H$^+$) 486.14. found 486.1). One seventh of the reaction mixture (2.2 mL) was diluted with DMA (2 mL), treated with diisopropylethylamine (0.16 mL, 0.91 mmol), followed by dicyclopropylamine hydrochloride (101.4 mg, 0.76 mmol) and subjected to microwave irradiation (100° C., 45 min). More diisopropylethylamine (0.16 mL, 0.91 mmol) and dicyclopropylamine hydrochloride (101.4 mg, 0.76 mmol) were added and the mixture was further subjected again to microwave irradiation (100° C., 45 min). The mixture was then passed through a HPLC-filter and purified by HPLC to afford the title compound. $^1$H NMR (400 MHz, CD$_2$Cl$_2$) δ 8.67-8.38 (m, 1H), 8.06-7.62 (m, 2H), 7.46-7.06 (m, 3H), 7.01-6.78 (m, 1H), 6.62-6.22 (m, 1H), 5.73-5.41 (m, 1H), 4.81-4.63 (m, 0.5H), 4.54-4.39 (m, 0.5H), 4.39-4.21 (m, 0.6H), 4.19-4.00 (m, 0.5H), 3.98-3.88 (m, 0.4H), 3.86-3.69 (m, 0.5H), 3.68-3.50 (m, 0.6H), 3.49-3.35 (m, 1H), 3.32-3.27 (m, 0.4H), 3.25-3.20 (m, 1H), 2.84-2.63 (m, 1H), 2.53 (s, 3H), 2.17-1.80 (m, 4H), 1.63-1.29 (m, 4H), 0.41-0.14 (m, 8H).

MS calculated for $C_{30}H_{36}ClN_6O_2$ (M+H$^+$) 547.25. found: 547.20.

Examples 17

The following compounds were prepared following analogous procedures as described in the above examples for Examples 4-16, using the appropriate starting materials.

| Ex. | Compound Structure | Physical Data ($^1$H NMR and MS) |
|---|---|---|
| 17-1 | 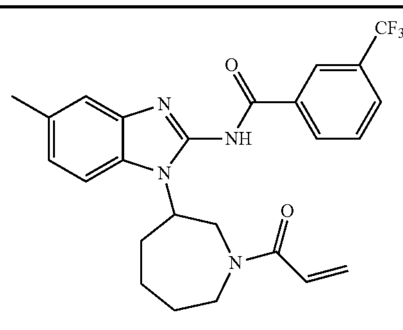 | $^1$H-NMR (400 MHz, DMSO-d$_6$): δ 12.81 (d, J = 19.6 Hz, 1H), 8.54 (s, 1H), 8.48-8.44 (m, 1H), 7.90-7.51 (m, 3H), 7.39 (d, J = 4.8 Hz, 1H), 7.10 (d, J = 7.6 Hz, 1H), 6.87-6.81 (m, 1H), 6.25-6.17 (m, 1H), 5.76-5.50 (m, 1H), 4.88 (br s, 1H), 4.16-4.03 (m, 2H), 3.90-3.63 (m, 1H), 3.37-3.22 (m, 1H), 2.40 (s, 3H), 2.05-1.85 (m, 4H), 1.43-1.40 (m, 1H); MS calculated for $C_{25}H_{26}F_3N_4O_2$ (M + H$^+$) 471.19, found 471.2. |

-continued

| Ex. | Compound Structure | Physical Data (¹H NMR and MS) |
|---|---|---|
| 17-2 | 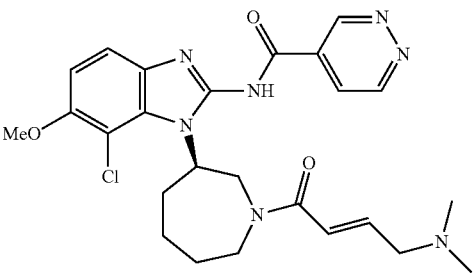 [SMILES: COc1ccc2nc(NC(=O)c3ccnnc3)n([C@@H]3CCCCN(C(=O)/C=C/CN(C)C)C3)c2c1Cl] | ¹H-NMR (400 MHz, methanol-d₄): δ 8.52 (d, J = 1.2 Hz, 0.5H), 8.51 (d, J = 1.2 Hz, 0.5H), 8.18 (dd, J = 1.2, 8.4 Hz, 1H), 7.46 (d, J = 8.8 Hz, 0.4H), 7.44 (d, J = 8.8 Hz, 0.6H), 7.33 (d, J = 8.4 Hz, 0.5H), 7.32 (d, J = 8.4 Hz, 0.5H), 7.11 (d, J = 8.8 Hz, 0.4H), 7.10 (d, J = 8.8 Hz, 0.6H), 6.84 (d, J = 15.0 Hz, 1H), 6.70 (dt, J = 6.8, 15.2 Hz, 1H), 5.84-5.76 (m, 1H), 4.82 (dd, J = 13.2, 10.4 Hz, 0.5H), 4.69 (dd, J = 13.2, 10.4 Hz, 0.5H), 4.25-4.04 (m, 1H), 3.96-3.94 (m, 1H), 3.79 (d, J = 6.8 Hz, 0.8H), 3.74 (d, J = 6.8 Hz, 1.2H), 3.55-3.48 (m, 1H), 3.14 (s, 1.5H), 3.01 (s, 1.5H), 2.78 & 2.75 (s & s, 6H), 2.82-2.72 (m, 1H), 2.50-1.93 (m, 4H), 1.58-1.25(m, 1H); MS calc. for $C_{25}H_{31}ClN_7O_3$ (M + H⁺) 512.21, found 512.2. |
| 17-3 | 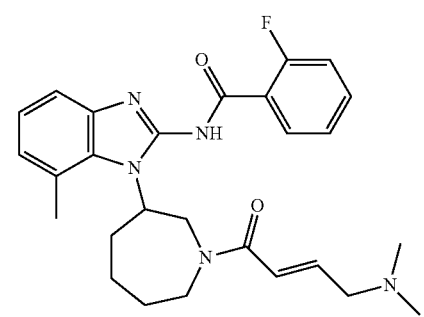 [SMILES: Cc1cccc2nc(NC(=O)c3ccccc3F)n(C3CCCCN(C(=O)/C=C/CN(C)C)C3)c12] | ¹H-NMR (400 MHz, CDCl₃) δ 12.59 (m, 1H), 8.08 (d, J = 7.6 Hz, 1H), 7.42 (m, 1H), 7.21 (m, 2H), 7.13 (t, J = 9.2 Hz, 3H), 6.97 (t, J = 20.5 Hz, 2H), 6.46 (d, J = 15.3 Hz, 1H), 5.00 (m, 1H), 4.42 (m, 2H), 3.92 (m, 1H), 3.45 (m, 1H), 3.00 (m, 3H), 2.76 (s, 3H), 2.29 (s, 6H), 2.02 (m, 3H), 1.35 (m, 1H). ¹⁹F-NMR (376 MHz, CDCl₃) δ −111.22. MS calc. for $C_{27}H_{33}FN_5O_2$ (M + H⁺) 478.25, found 478.3. |
| 17-4 | 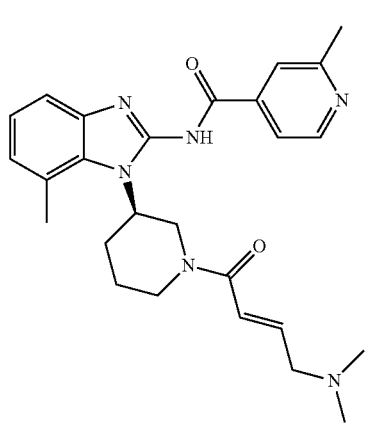 [SMILES: Cc1cc(C(=O)Nc2nc3cccc(C)c3n2[C@@H]2CCCN(C(=O)/C=C/CN(C)C)C2)ccn1] | ¹H-NMR (400 MHz, DMSO) δ 8.62 (d, J = 5.0 Hz, 1H), 7.88 (s, 1H), 7.84 (s, 1H), 7.47 (s, 1H), 7.14 (d, J = 7.8 Hz, 1H), 7.06 (s, 1H), 6.82 (m, 1H), 6.62 (m, 1H), 4.79 (m, 1H), 4.63 (m, 1H), 4.45 (m, 1H), 4.13 (m, 1H), 3.38 (d, J = 7.1 Hz, 2H), 3.15 (m, 3H), 2.67 (s, 4H), 2.58 (s, 3H), 2.33 (s, 4H), 2.00 (m, 2H), 1.60 (m, 1H); MS calculated for $C_{26}H_{33}N_6O_2$ (M + H⁺) 461.26, found 461.2. |
| 17-5 | 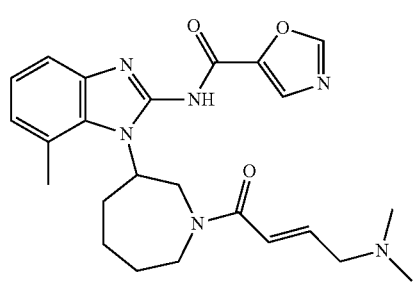 [SMILES: Cc1cccc2nc(NC(=O)c3cnco3)n(C3CCCCN(C(=O)/C=C/CN(C)C)C3)c12] | ¹H-NMR (400 MHz, MeOD) δ 8.36 (s, 1H), 7.74 (d, J = 14.3 Hz, 1H), 7.38 (d, J = 8.2 Hz, 1H), 7.18 (t, J = 7.8 Hz, 1H), 7.08 (d, J = 7.6 Hz, 1H), 6.94 (d, J = 15.2 Hz, 1H), 6.79 (m, 1H), 5.19 (d, J = 94.0 Hz, 1H), 4.61 (m, 1H), 4.28 (d, J = 9.7 Hz, 1H), 3.97 (s, 1H), 3.84 (s, 2H), 3.71 (s, 2H), 2.82 (s, 6H), 2.73 (d, J = 14.4 Hz, 3H), 2.11 (s, 4H), 1.46 (s, 1H). MS calc. for $C_{24}H_{31}N_6O_3$ (M + H+) 451.24, found 451.1. |

| Ex. | Compound Structure | Physical Data (¹H NMR and MS) |
|---|---|---|
| 17-6 | 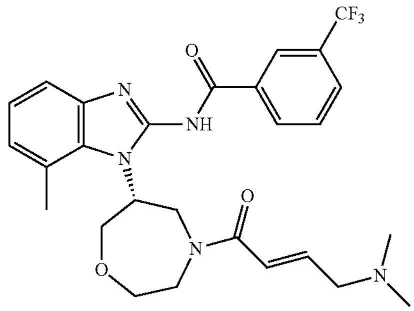 [SMILES: Cc1cccc2nc(NC(=O)c3cccc(C(F)(F)F)c3)n([C@H]3COCCN(C(=O)/C=C/CN(C)C)C3)c12] | ¹H-NMR (400 MHz, CDCl₃) δ 12.45 (m, 1H), 8.63 (m, 1H), 8.34 (m, 1H), 7.70 (m, 1H), 7.53 (m, 1H), 7.10 (m, 1H), 6.96 (m, 2H), 6.80 (m, 2H), 5.18 (m, 1H), 4.80 (m, 1H), 4.45 (m, 1H), 4.04 (m, 4H), 3.54 (m, 3H), 3.12 (m, 1H), 2.74 (s, 3H), 2.59 (s, 6H). ¹⁹F-NMR (376 MHz, CDCl₃) δ −62.41. MS calculated for $C_{27}H_{31}F_3N_5O_3$ (M + H⁺) 530.23, found 530.2. |
| 17-7 | 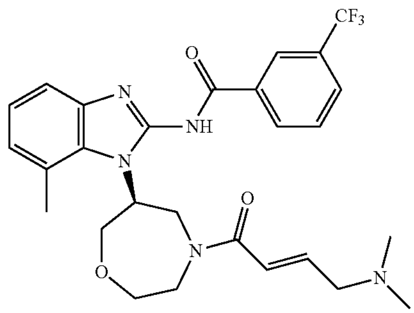 [SMILES: Cc1cccc2nc(NC(=O)c3cccc(C(F)(F)F)c3)n([C@@H]3COCCN(C(=O)/C=C/CN(C)C)C3)c12] | ¹H-NMR (400 MHz, MeOD) δ 8.81 (s, 1H), 8.48 (m, 1H), 7.81 (s, 1H), 7.68 (s, 1H), 7.39 (s, 1H), 7.18 (s, 1H), 7.10 (s, 1H), 6.83 (s, 1H), 5.33 (m, 2H), 5.09 (m, 2H), 4.21 (s, 3H), 3.88 (m, 2H), 3.52 (s, 3H), 2.79 (s, 3H), 2.44 (s, 6H). ¹⁹F-NMR (376 MHz, MeOD) δ −63.86. MS calculated for $C_{27}H_{31}F_3N_5O_3$ (M + H⁺) 530.23, found 530.2. |
| 17-8 | 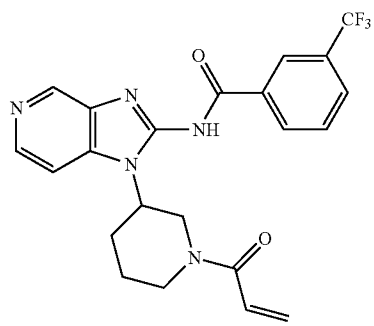 [SMILES: C=CC(=O)N1CCCC(n2c(NC(=O)c3cccc(C(F)(F)F)c3)nc3cnccc32)C1] | ¹H-NMR (400 MHz, DMSO-d₆): ∂ 13.07 (br s, 1H), 8.75 (s, 1H), 8.48 (br s, 2H), 8.39 (d, J = 5.4 Hz, 1H), 7.92 (d, J = 7.2 Hz, 1H), 7.90-7.80 (m, 1H), 7.78-7.74 (m, 1H), 6.93-6.78 (m, 1H), 6.18-6.14 (m, 1H), 5.76-5.61 (m, 1H), 4.78 (br s, 1H), 4.65-4.57 (m, 1H), 4.34-4.20 (m, 1H), 4.07-3.98 (m, 0.5H), 3.68-3.59 (m, 0.5H), 3.28-3.21 (m, 0.5H), 2.87-2.78 (m, 0.5H), 2.74-2.62 (m, 1H), 2.07-1.90 (m, 2H), 1.68-1.58 (m, 1H); MS calculated for $C_{22}H_{21}F_3N_5O_2$ (M + H⁺) 444.16, found 444.2. |
| 17-9 | 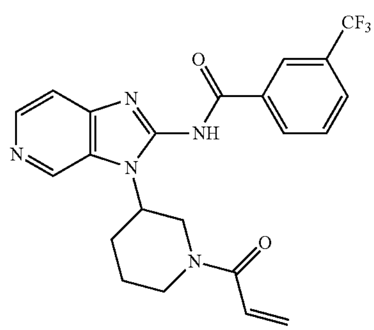 [SMILES: C=CC(=O)N1CCCC(n2c(NC(=O)c3cccc(C(F)(F)F)c3)nc3ccncc32)C1] | ¹H-NMR (400 MHz, DMSO-d₆): ∂ 13.11 (br s, 1H), 9.08 (s, 1H), 8.46 (d, J = 9.2 Hz, 2H), 8.39 (d, J = 5.2 Hz, 1H), 7.92 (d, J = 7.6 Hz, 1H), 7.77-7.73 (m, 1H), 7.54 (d, J = 5.6 Hz, 1H), 6.95-6.79 (m, 1H), 6.20-6.14 (m, 1H), 5.75-5.60 (m, 1H), 4.83 (s, 1H), 4.67-4.55 (m, 1H), 4.35-4.00 (m, 2H), 3.63-3.57 (m, 1H), 2.87-2.84 (m, 1H), 2.07-1.91 (m, 2H), 1.64-1.61 (m, 1H); MS calculated for $C_{22}H_{21}F_3N_5O_2$ (M + H⁺) 444.16, found 444.3. |
| 17-10 | 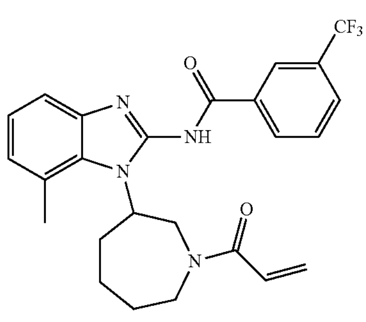 [SMILES: C=CC(=O)N1CCCCC(n2c(NC(=O)c3cccc(C(F)(F)F)c3)nc3cccc(C)c32)C1] | ¹H-NMR (DMSO-d₆, 400 MHz): ∂ 12.80 (br s, 1H), 8.52 (s, 1H), 8.42 (d, J = 8 Hz, 1H), 7.85-7.70 (m, 2H), 7.46 (d, J = 8 Hz, 1H), 7.13 (d, J = 8 Hz, 1H), 7.02 (d, J = 7.6 Hz, 1H), 6.82-6.75 (m, 1H), 6.15 (dd, J = 2.4 and 14 Hz, 1H), 5.66 (br s, 1H), 5.0 (br s, 1H), 4.25-4.22 (m, 2H), 4.0 (br s, 1H), 3.50 (br s, 1H), 2.7-2.65 (m, 4H), 2.10-1.89 (m, 4H), 1.42-1.39 (m, 1H); MS calculated for $C_{25}H_{26}F_3N_4O_2$ (M + H⁺) 471.19, found 471.3. |

| Ex. | Compound Structure | Physical Data (¹H NMR and MS) |
|---|---|---|
| 17-11 | 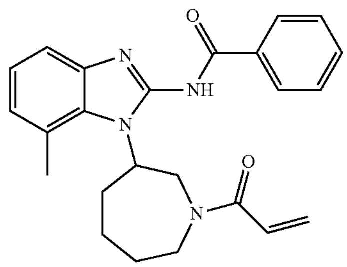 [SMILES: C=CC(=O)N1CCCCC(n2c(NC(=O)c3ccccc3)nc3cccc(C)c32)C1] | ¹H-NMR (400 MHz, DMSO-d$_6$): ∂ 12.91 (m, 1H), 8.22-8.20 (m, 2H), 7.54-7.43 (m, 4H), 7.13-6.80 (m, 3H), 6.24-6.20 (m, 1H), 5.75-5.72 (m, 1H), 4.90 (br s, 1H), 4.38-4.17 (m, 2H), 3.99-3.94 (m, 1H), 3.58-3.54 (m, 1H), 2.85-2.82 (m, 1H), 2.68 (s, 3H), 2.33-1.95 (m, 4H), 1.34-1.32 (m, 1H); MS calc. for $C_{24}H_{27}N_4O_2$ (M + H$^+$) 403.21, found 403.1. |
| 17-12 | 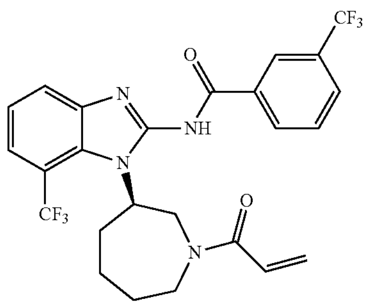 [SMILES: C=CC(=O)N1CCCC[C@@H](n2c(NC(=O)c3cccc(C(F)(F)F)c3)nc3cccc(C(F)(F)F)c32)C1] | ¹H-NMR (400 MHz, DMSO-d$_6$): ∂ 13.38 (s, 1H), 8.52-8.42 (m, 2H), 7.95-7.80 (m, 2H), 7.8-7.66 (m, 2H), 7.46-7.42 (m, 1H), 6.84-6.71 (m, 1H), 6.18-6.13 (m, 1H), 5.73-5.54 (m, 1H), 4.79-4.76 (m, 1H), 4.52-4.21 (m, 3H), 3.98-3.85 (m, 1H), 3.61-3.57 (m, 1H), 2.80-2.67 (m, 1H), 2.08-2.02 (m, 3H), 1.99 (s, 1H), 1.32-1.23 (m, 2H); MS calc. for $C_{25}H_{23}F_6N_4O_2$ (M + H$^+$) 525.16, found 525.1. |
| 17-13 | 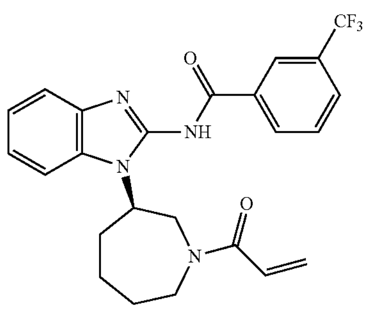 [SMILES: C=CC(=O)N1CCCC[C@@H](n2c(NC(=O)c3cccc(C(F)(F)F)c3)nc3ccccc32)C1] | ¹H-NMR (400 MHz, DMSO-d$_6$): ∂ 12.91 (d, J = 18.8 Hz, 1H), 8.55-8.45 (m, 2H), 7.91-7.89 (m, 1H), 7.76-7.58 (m, 3H), 7.30-7.24 (m, 2H), 6.89-6.81 (m, 1H), 6.26-6.17 (m, 1H), 5.77-5.74 (m, 1H), 5.54-5.51 (m, 1H), 4.91 (br s, 1H), 4.17-4.09 (m, 3H), 3.92-3.90 (m, 1H), 3.88-3.63 (m, 1H), 2.08-1.91 (m, 5H); MS calculated for $C_{24}H_{24}F_3N_4O_2$ (M + H$^+$) 457.18, found 457.2. |
| 17-14 | 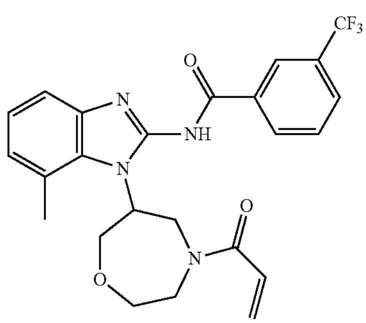 [SMILES: C=CC(=O)N1CCOCC(n2c(NC(=O)c3cccc(C(F)(F)F)c3)nc3cccc(C)c32)C1] | ¹H-NMR (400 MHz, CDCl$_3$) δ 12.53 (s, 1H), 8.80 (s, 1H), 8.42 (dd, J = 7.8, 15.8 Hz, 1H), 7.75 (d, J = 7.7 Hz, 1H), 7.60 (t, J = 7.7 Hz, 1H), 7.18 (m, 2H), 7.05 (m, 1H), 6.62 (dd, J = 10.5, 16.7 Hz, 1H), 6.41 (m, 1H), 5.79 (dd, J = 1.7, 10.5 Hz, 1H), 5.30 (m, 1H), 4.87 (m, 1H), 4.59 (dd, J = 4.1, 13.1 Hz, 1H), 4.41 (m, 1H), 4.13 (dt, J = 5.2, 11.2 Hz, 3H), 3.97 (m, 1H), 3.70 (m, 1H), 2.82 (s, 3H). ¹⁹F-NMR (376 MHz, CDCl$_3$) δ −62.57; MS calculated for $C_{24}H_{24}F_3N_4O_3$ (M + H$^+$) 473.17, found 473.2. |

| Ex. | Compound Structure | Physical Data (¹H NMR and MS) |
|---|---|---|
| 17-15 | 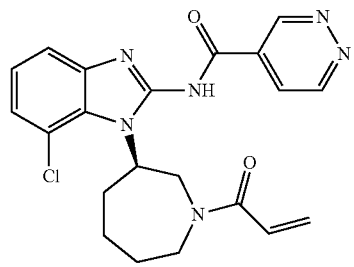 [SMILES: C=CC(=O)N1CCCC[C@@H](n2c(NC(=O)c3ccnnc3)nc3cccc(Cl)c32)C1] | ¹H-NMR (400 MHz, CDCl₃): δ 12.77-12.71 (m, 1H), 9.90 (dd, J = 1.2, 2.0 Hz, 0.6H), 9.88 (dd, J = 1.2, 2.0 Hz, 0.4H), 9.42 (dd, J = 1.2, 4.4 Hz, 0.6H), 9.41 (dd, J = 1.2, 4.4 Hz, 0.4H), 8.72 (dd, J = 2.0, 4.4 Hz, 0.6H), 8.65 (dd, J = 2.0, 4.4 Hz, 0.4H), 8.36-8.15 (m, 2H), 7.68 (dd, J = 4.4, 8.6 Hz, 0.6H), 7.37 (dd, J = 4.4, 8.6 Hz, 0.4H), 6.66 (dd, J = 10.4, 16.8 Hz, 0.6H), 6.65 (dd, J = 10.4, 16.8 Hz, 0.4H), 6.43 (dd, J = 16.8, 2.0 Hz, 0.4H), 6.40 (dd, J = 16.8, 2.0 Hz, 0.6H), 5.78 (dd, J = 2.0, 10.8 Hz, 0.6H), 5.70 (dd, J = 2.0, 10.8 Hz, 0.4H), 5.73-5.62 (m, 1H), 4.82-4.76 (m, 1H), 4.53-4.42 (m, 1H), 4.22-4.04 (m, 1H), 3.88-3.66 (m, 1H), 3.55-3.45 (m, 0.4H), 3.17-3.07 (m, 0.6H), 2.80-2.63 (m, 1H), 2.21-1.98 (m, 2H), 1.35-1.20 (m, 1H), 0.93-0.82 (m, 1H); MS calculated for $C_{21}H_{22}ClN_6O_2$ (M + H⁺) 425.14, found 425.2. |
| 17-16 | 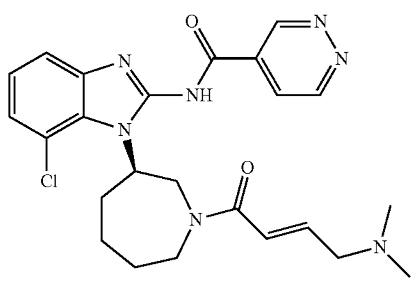 [SMILES: CN(C)C/C=C/C(=O)N1CCCC[C@@H](n2c(NC(=O)c3ccnnc3)nc3cccc(Cl)c32)C1] | ¹H-NMR (400 MHz, CDCl₃): δ 12.67 (br s, 1H), 9.82-9.80 (m, 1H), 9.32-9.30 (m, 1H), 8.09-8.05 (m, 1H), 7.27-7.11 (m, 2H), 6.94-6.82 (m, 2H), 6.49-6.47 (m, 1H), 5.61-5.54 (m, 1H), 4.73-4.33 (m, 2H), 4.10-3.95 (m, 1H), 3.80-3.53 (m, 1H), 3.44-3.37 (m, 1H), 3.20-2.86 (m, 2H), 2.75-2.48 (m, 1H), 2.29 & 2.15 (s & s, 6H), 2.10-1.82 (m, 2H), 1.50-1.12 (m, 2H); MS calculated for $C_{24}H_{29}ClN_7O_2$ (M + H⁺) 482.20, found 482.1. |
| 17-17 | 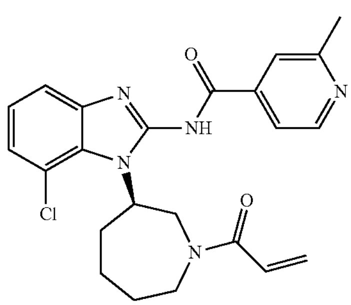 [SMILES: C=CC(=O)N1CCCC[C@@H](n2c(NC(=O)c3ccnc(C)c3)nc3cccc(Cl)c32)C1] | ¹H-NMR (400 MHz, CD₃OD): δ 8.46 (d, J = 5.2 Hz, 1H), 7.95-7.83 (m, 2H), 7.42-7.38 (m, 1H), 7.25-7.14 (m, 2H), 6.79-6.71 (m, 1H), 6.24-6.18 (m, 1H), 5.73-5.55 (m, 2H), 4.80-4.56 (m, 1H), 4.21-4.08 (m, 1H), 4.04-3.80 (m, 1H), 3.67-3.38 (m, 1H), 2.82-2.64 (m, 1H), 2.55 (s, 3H), 2.11-1.84 (m, 3H), 1.52-1.78 (m, 2H); MS calculated for $C_{23}H_{25}ClN_5O_2$ (M + H⁺) 438.16, found 438.1. |
| 17-18 | 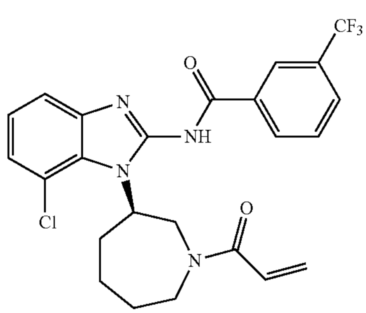 [SMILES: C=CC(=O)N1CCCC[C@@H](n2c(NC(=O)c3cccc(C(F)(F)F)c3)nc3cccc(Cl)c32)C1] | ¹H-NMR (400 MHz, DMSO-d₆): δ 13.17 (d, J = 6 Hz, 1H), 8.52-8.43 (m, 2H), 7.94-7.92 (m, 1H), 7.79-7.70 (m, 1H), 7.60-7.58 (m, 1H), 7.32-7.25 (m, 2H), 6.89-6.80 (m, 1H), 6.21-6.20 (m, 1H), 5.8-5.79 (m, 1H), 5.45-5.40 (m, 1H), 4.62-4.60 (m, 1H), 4.25 (m, 1H), 4.23-4.13 (m, 2H), 3.92-3.90 (m, 1H), 3.5-3.49 (m, 1H), 3.20-3.19 (m, 1H), 2.10-1.9 (m, 4H), 1.25-1.20 (m, 2H); MS calc. for $C_{24}H_{23}ClF_3N_4O_2$ (M + H⁺) 491.14, found 491.2. |

| Ex. | Compound Structure | Physical Data ($^1$H NMR and MS) |
|---|---|---|
| 17-19 | 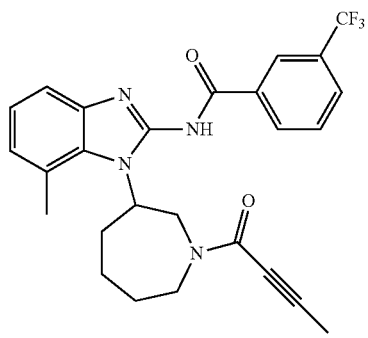 [SMILES: CC#CC(=O)N1CCCCC(n2c(NC(=O)c3cccc(C(F)(F)F)c3)nc3cccc(C)c32)C1] | $^1$H-NMR (400 MHz, CDCl$_3$) δ 12.59 (s, 1H), 8.64 (d, J = 10.3 Hz, 1H), 8.44 (d, J = 7.6 Hz, 1H), 7.78 (m, 1H), 7.62 (m, 1H), 7.19 (m, 2H), 7.04 (dd, J = 6.6, 14.2 Hz, 1H), 5.03 (m, 1H), 4.75 (m, 1H), 4.35 (m, 2H), 3.41 (m, 1H), 2.88 (m, 1H), 2.78 (d, J = 5.0 Hz, 3H), 2.27 (m, 1H), 2.13 (m, 1H), 2.08 (s, 3H), 2.03 (m, 1H), 1.45 (m, 2H); $^{19}$F-NMR (376 MHz, CDCl$_3$) δ −62.50; MS calc. for C$_{26}$H$_{26}$F$_3$N$_4$O$_2$ (M + H$^+$) 483.19, found 483.2. |
| 17-20 | 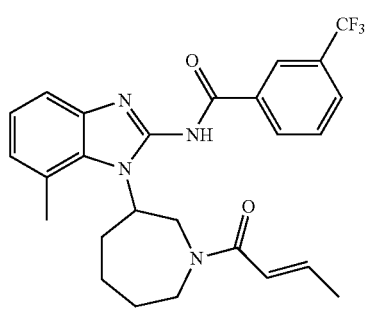 | $^1$H-NMR (400 MHz, CDCl$_3$) δ 12.61 (s, 1H), 8.65 (d, J = 19.1 Hz, 1H), 8.45 (d, J = 7.7 Hz, 1H), 7.77 (d, J = 7.3 Hz, 1H), 7.62 (t, J = 7.7 Hz, 1H), 7.19 (tt, J = 7.8, 15.2 Hz, 2H), 7.00 (m, 2H), 6.35 (m, 1H), 5.11 (s, 1H), 4.50 (dd, J = 3.6, 13.1 Hz, 1H), 4.39 (dd, J = 10.7, 13.1 Hz, 1H), 3.98 (dd, J = 7.2, 14.2 Hz, 1H), 3.61 (m, 1H), 2.98 (m, 1H), 2.81 (s, 3H), 2.19 (m, 1H), 2.06 (m, 3H), 1.94 (dd, J = 1.6, 6.8 Hz, 3H), 1.43 (ddd, J = 3.8, 12.1, 26.1 Hz, 1H). $^{19}$F-NMR (376 MHz, CDCl$_3$) δ −62.55; MS calculated for C$_{26}$H$_{28}$F$_3$N$_4$O$_2$ (M + H$^+$) 485.21, found 485.2. |
| 17-21 | 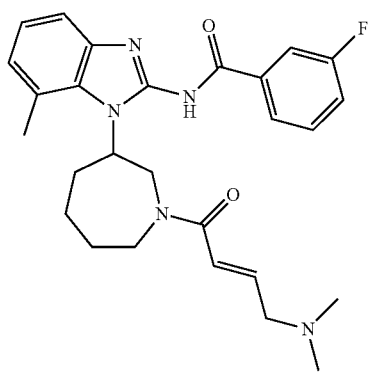 [SMILES: Cc1cccc2nc(NC(=O)c3cccc(F)c3)n(C3CCCCN(C(=O)/C=C/CN(C)C)C3)c12] | $^1$H-NMR (400 MHz, CDCl$_3$) δ 12.59 (m, 1H), 8.03 (m, 1H), 7.91 (m, 1H), 7.41 (m, 1H), 7.14 (m, 3H), 7.00 (m, 1H), 6.88 (m, 1H), 6.46 (d, J = 15.1 Hz, 1H), 4.93 (m, 1H), 4.39 (m, 1H), 4.03 (m, 1H), 3.50 (m, 1H), 3.11 (s, 1H), 2.92 (s, 1H), 2.71 (d, J = 43.6 Hz, 3H), 2.29 (d, J = 3.0 Hz, 6H), 2.11 (m, 2H), 2.05 (m, 3H), 1.40 (m, 2H). $^{19}$F-NMR (376 MHz, CDCl$_3$) δ −113.83. MS calculated for C$_{27}$H$_{33}$FN$_5$O$_2$ (M + H$^+$) 478.25, found 478.3. |
| 17-22 | 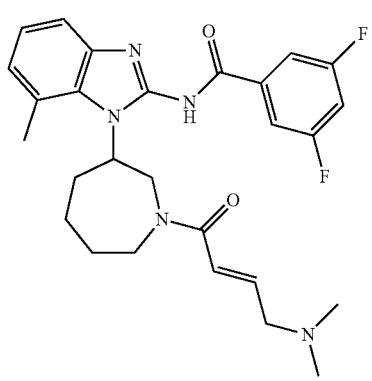 [SMILES: Cc1cccc2nc(NC(=O)c3cc(F)cc(F)c3)n(C3CCCCN(C(=O)/C=C/CN(C)C)C3)c12] | $^1$H-NMR (400 MHz, CDCl$_3$) δ 12.50 (m, 1H), 7.76 (m, 2H), 7.16 (m, 2H), 7.02 (m, 1H), 6.91 (m, 2H), 6.45 (m, 1H), 4.94 (m, 1H), 4.42 (m, 1H), 4.13 (m, 1H), 3.72 (m, 1H), 3.11 (s, 1H), 2.92 (m, 1H), 2.76 (s, 3H), 2.29 (s, 6H), 2.12 (s, 2H), 2.04 (s, 3H), 1.41 (m, 2H). $^{19}$F-NMR (376 MHz, CDCl$_3$) δ −110.32. MS calculated for C$_{27}$H$_{32}$F$_2$N$_5$O$_2$ (M + H$^+$) 496.24, found 496.3. |

| Ex. | Compound Structure | Physical Data (¹H NMR and MS) |
|---|---|---|
| 17-23 | 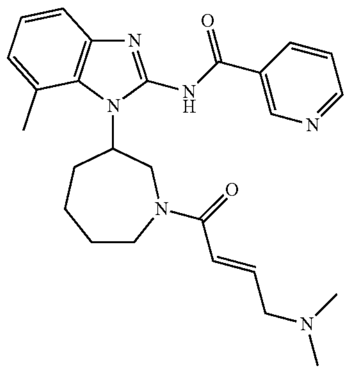 [SMILES: Cc1cccc2nc(NC(=O)c3cccnc3)n(C3CCCCN(C(=O)/C=C/CN(C)C)C3)c12] | ¹H-NMR (400 MHz, CDCl$_3$) δ 12.63 (s, 1H), 9.50 (dd, J = 0.8, 2.1 Hz, 1H), 8.70 (dd, J = 1.7, 4.8 Hz, 1H), 8.49 (dt, J = 1.9, 7.8 Hz, 1H), 7.41 (ddd, J = 0.8, 4.8, 7.9 Hz, 1H), 7.15 (m, 2H), 7.01 (m, 1H), 6.88 (t, J = 10.7, 1H), 6.58 (m, 1H), 4.98 (m, 1H), 4.41 (d, J = 10.1, 2H), 4.03 (m, 1H), 3.59 (m, 1H), 3.41 (m, 1H), 3.21 (m, 2H), 3.03 (m, 1H), 2.94 (m, 1H), 2.76 (s, 3H), 2.32 (d, J = 95.4 Hz, 6H), 2.07 (m, 3H). MS calculated for C$_{26}$H$_{33}$N$_6$O$_2$ (M + H$^+$) 461.26, found 461.2. |
| 17-24 | 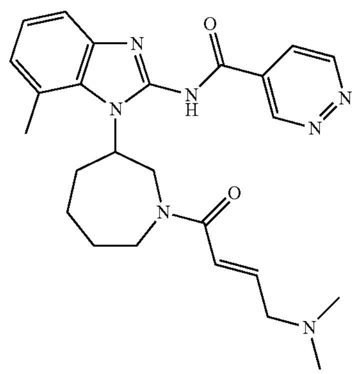 [SMILES: Cc1cccc2nc(NC(=O)c3ccnnc3)n(C3CCCCN(C(=O)/C=C/CN(C)C)C3)c12] | ¹H-NMR (400 MHz, CDCl$_3$) δ 12.56 (m, 1H), 9.91 (s, 1H), 9.38 (d, J = 5.1, 1H), 8.15 (dd, J = 2.0, 5.2, 1H), 7.19 (d, J = 11.6, 2H), 7.07 (s, 1H), 6.89 (s, 1H), 6.58 (m, 1H), 4.85 (m, 1H), 4.23 (m, 2H), 3.64 (m, 1H), 3.29 (m, 2H), 3.12 (m, 2H), 2.77 (s, 3H), 2.44 (s, 6H), 2.08 (m, 3H), 1.43 (m, 3H). MS calculated for C$_{25}$H$_{32}$N$_7$O$_2$ (M + H$^+$) 462.25, found 462.3. |
| 17-25 | 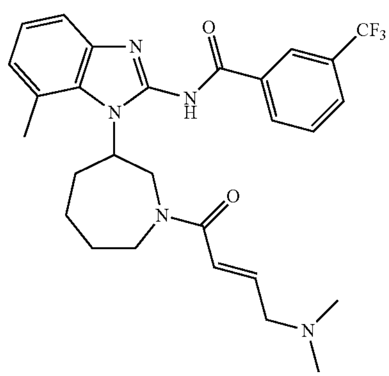 [SMILES: Cc1cccc2nc(NC(=O)c3cccc(C(F)(F)F)c3)n(C3CCCCN(C(=O)/C=C/CN(C)C)C3)c12] | ¹H-NMR (400 MHz, CDCl$_3$) δ 12.61 (s, 1H), 8.66 (s, 1H), 8.44 (d, J = 7.6 Hz, 1H), 7.77 (d, J = 7.2 Hz, 1H), 7.62 (t, J = 7.7 Hz, 1H), 7.18 (m, 2H), 7.03 (m, 1H), 6.92 (dt, J = 6.1, 15.2 Hz, 1H), 6.59 (d, J = 15.2 Hz, 1H), 5.10 (m, 1H), 4.46 (m, 2H), 4.01 (dt, J = 7.3, 14.4 Hz, 1H), 3.66 (m, 1H), 3.25 (s, 2H), 2.97 (s, 1H), 2.80 (s, 3H), 2.41 (s, 6H), 2.08 (m, 3H), 1.58 (m, 2H). ¹⁹F-NMR (376 MHz, CDCl$_3$) δ −62.82. MS calculated for C$_{28}$H$_{33}$F$_3$N$_5$O$_2$ (M + H$^+$) 528.25, found 528.2. |
| 17-26 | 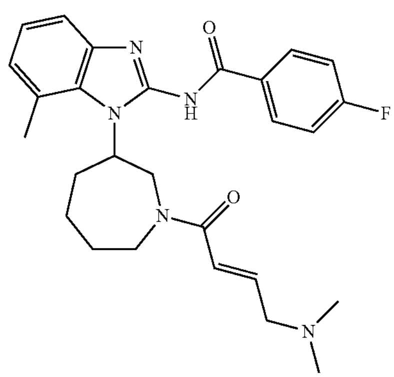 [SMILES: Cc1cccc2nc(NC(=O)c3ccc(F)cc3)n(C3CCCCN(C(=O)/C=C/CN(C)C)C3)c12] | ¹H-NMR (400 MHz, CDCl$_3$) δ 12.65 (s, 1H), 8.28 (m, 2H), 7.13 (m, 4H), 6.94 (m, 2H), 6.48 (m, 1H), 4.90 (m, 1H), 4.45 (t, J = 20.7 Hz, 1H), 4.38 (s, 1H), 3.77 (d, J = 124.3 Hz, 1H), 3.05 (dd, J = 3.9, 60.8 Hz, 2H), 2.86 (m, 1H), 2.71 (d, J = 41.2 Hz, 3H), 2.30 (s, 6H), 2.05 (m, 4H), 1.42 (m, 2H). ¹⁹F-NMR (376 MHz, CDCl$_3$) δ −109.69. MS calculated for C$_{27}$H$_{33}$FN$_5$O$_2$ (M + H$^+$) 478.25, found 478.3. |

| Ex. | Compound Structure | Physical Data (¹H NMR and MS) |
|---|---|---|
| 17-27 | 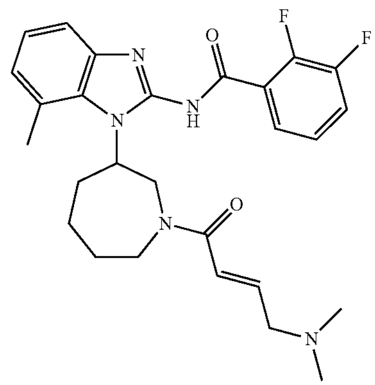 [SMILES: Cc1cccc2nc(NC(=O)c3cccc(F)c3F)n(C3CCCCN(C(=O)/C=C/CN(C)C)C3)c12] | ¹H-NMR (400 MHz, CDCl₃) δ 12.70 (m, 1H), 7.84 (t, J = 7.0, 1H), 7.31 (m, 1H), 7.19 (m, 3H), 7.06 (m, 2H), 6.86 (m, 1H), 4.97 (m, 1H), 4.53 (m, 1H), 4.37 (m, 1H), 4.01 (m, 1H), 3.83 (m, 2H), 3.63 (m, 1H), 2.88 (s, 6H), 2.77 (s, 3H), 2.08 (m, 4H), 1.36 (m, 2H). ¹⁹F-NMR (376 MHz, CDCl₃) δ −70.75, −137.84. MS calculated for $C_{27}H_{32}F_2N_5O_2$ (M + H⁺) 496.24, found 496.3. |
| 17-28 | 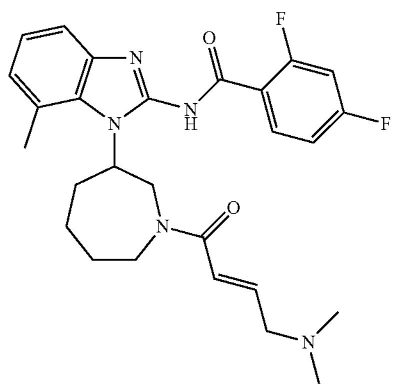 [SMILES: Cc1cccc2nc(NC(=O)c3ccc(F)cc3F)n(C3CCCCN(C(=O)/C=C/CN(C)C)C3)c12] | MS calculated for $C_{27}H_{32}F_2N_5O_2$ (M + H⁺) 496.24, found 496.3. |
| 17-29 | 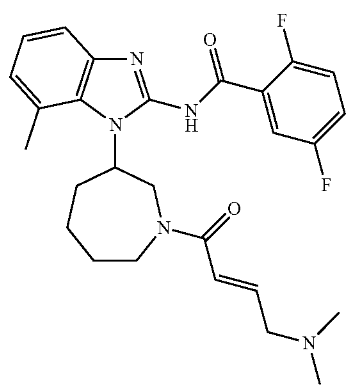 [SMILES: Cc1cccc2nc(NC(=O)c3cc(F)ccc3F)n(C3CCCCN(C(=O)/C=C/CN(C)C)C3)c12] | MS calculated for $C_{27}H_{32}F_2N_5O_2$ (M + H⁺) 496.24, found 496.3. |
| 17-30 | 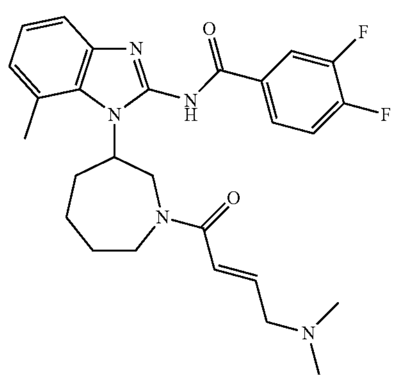 [SMILES: Cc1cccc2nc(NC(=O)c3ccc(F)c(F)c3)n(C3CCCCN(C(=O)/C=C/CN(C)C)C3)c12] | MS calculated for $C_{27}H_{32}F_2N_5O_2$ (M + H⁺) 496.24, found 496.3. |

| Ex. | Compound Structure | Physical Data ($^1$H NMR and MS) |
|---|---|---|
| 17-31 | 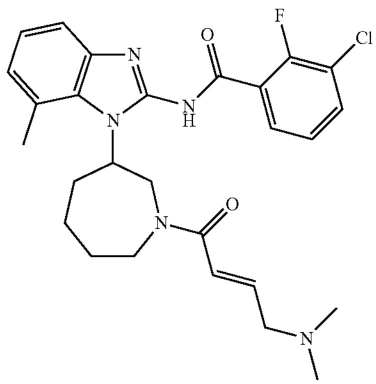 [SMILES: Cc1cccc2nc(NC(=O)c3cccc(Cl)c3F)n(C3CCCCN(C(=O)/C=C/CN(C)C)C3)c12] | $^1$H-NMR (400 MHz, CDCl$_3$) δ 7.94 (m, 1H), 7.55 (m, 1H), 7.35 (m, 1H), 7.19 (m, 3H), 7.10 (m, 1H), 6.84 (m, 1H), 5.01 (m, 1H), 4.52 (m, 1H), 4.35 (m, 1H), 3.95 (m, 1H), 3.81 (m, 2H), 3.65 (m, 1H), 2.87 (s, 6H), 2.81 (s, 3H), 2.69 (m, 1H), 2.10 (m, 4H), 1.57 (m, 1H). $^{19}$F-NMR (376 MHz, CDCl$_3$) δ −70.92. MS calculated for C$_{27}$H$_{32}$ClFN$_5$O$_2$ (M + H$^+$) 512.22, found 512.3. |
| 17-32 | 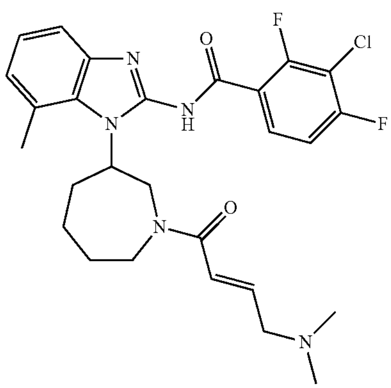 [SMILES: Cc1cccc2nc(NC(=O)c3ccc(F)c(Cl)c3F)n(C3CCCCN(C(=O)/C=C/CN(C)C)C3)c12] | $^1$H-NMR (400 MHz, CDCl$_3$) δ 7.99 (m, 1H), 7.33 (m, 1H), 7.11 (m, 4H), 6.85 (m, 1H), 5.04 (m, 1H), 4.58 (m, 1H), 4.29 (m, 1H), 4.01 (m, 1H), 3.80 (m, 2H), 3.65 (m, 1H), 2.85 (s, 6H), 2.81 (s, 3H), 2.69 (m, 1H), 2.06 (m, 4H), 1.36 (m, 1H). $^{19}$F-NMR (376 MHz, CDCl$_3$) δ −108.06, −108.77. MS calculated for C$_{27}$H$_{31}$ClF$_2$N$_5$O$_2$ (M + H$^+$) 530.21, found 530.3. |
| 17-33 | 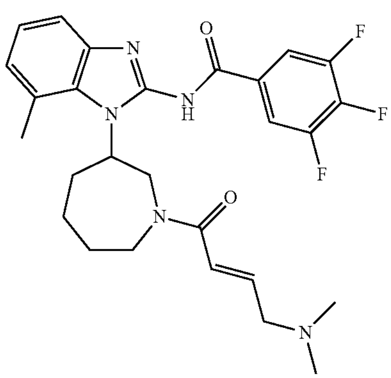 [SMILES: Cc1cccc2nc(NC(=O)c3cc(F)c(F)c(F)c3)n(C3CCCCN(C(=O)/C=C/CN(C)C)C3)c12] | $^1$H-NMR (400 MHz, CDCl$_3$) δ 7.87 (s, 2H), 7.12 (m, 4H), 6.86 (m, 1H), 4.97 (m, 1H), 4.40 (m, 2H), 4.01 (m, 1H), 3.81 (s, 2H), 3.66 (m, 1H), 2.87 (s, 6H), 2.81 (s, 3H), 2.67 (m, 1H), 2.26 (m, 1H), 2.07 (m, 3H), 1.44 (m, 1H). $^{19}$F-NMR (376 MHz, CDCl$_3$) δ −134.12, −156.13. MS calculated for C$_{27}$H$_{31}$F$_3$N$_5$O$_2$ (M + H$^+$) 514.24, found 514.3. |
| 17-34 | 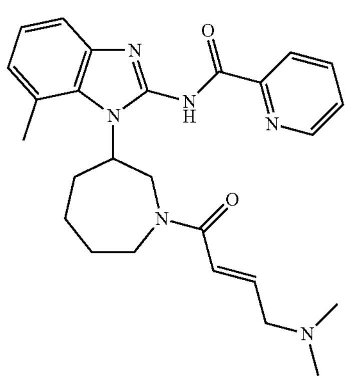 [SMILES: Cc1cccc2nc(NC(=O)c3ccccn3)n(C3CCCCN(C(=O)/C=C/CN(C)C)C3)c12] | $^1$H-NMR (400 MHz, CDCl$_3$) δ 12.31 (br, 1H), 9.86 (m, 1H), 8.61 (m, 2H), 8.47 (m, 1H), 7.56 (m, 2H), 7.31 (m, 2H), 7.17 (m, 1H), 5.86 (m, 1H), 5.27 (m, 1H), 4.57 (m, 1H), 4.39 (m, 2H), 3.59 (m, 1H), 3.21 (m, 1H), 3.03 (s, 6H), 2.82 (s, 3H), 2.63 (m, 1H), 2.10 (m, 3H), 1.40 (m, 2H). MS calculated for C$_{26}$H$_{33}$N$_6$O$_2$ (M + H$^+$) 461.26, found 461.3. |

| Ex. | Compound Structure | Physical Data (¹H NMR and MS) |
|---|---|---|
| 17-35 | 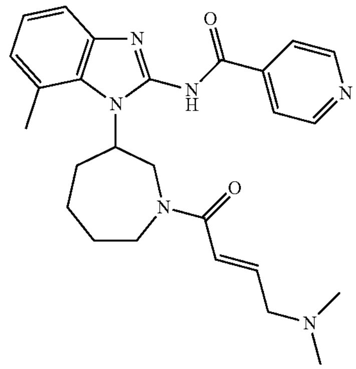 [SMILES: Cc1cccc2nc(NC(=O)c3ccncc3)n(C3CCCCN(C(=O)/C=C/CN(C)C)C3)c12] | MS calculated for $C_{26}H_{33}N_6O_2$ (M + H⁺) 461.26, found 461.3. |
| 17-36 | 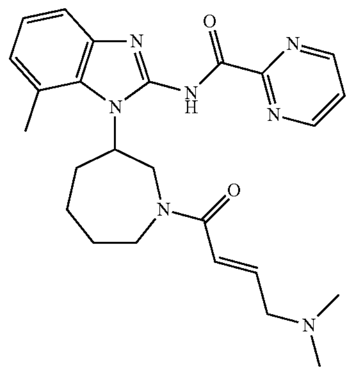 [SMILES: Cc1cccc2nc(NC(=O)c3ncccn3)n(C3CCCCN(C(=O)/C=C/CN(C)C)C3)c12] | MS calculated for $C_{25}H_{32}N_7O_2$ (M + H⁺) 462.25, found 462.3. |
| 17-37 | 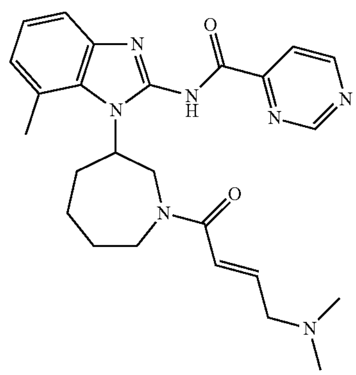 [SMILES: Cc1cccc2nc(NC(=O)c3ccncn3)n(C3CCCCN(C(=O)/C=C/CN(C)C)C3)c12] | ¹H-NMR (400 MHz, CDCl₃) δ 12.45 (m, 1H), 9.33 (d, J = 1.3, 1H), 8.85 (d, J = 5.0 Hz, 1H), 8.08 (dd, J = 1.4, 5.1 Hz, 1H), 7.17 (d, J = 2.7 Hz, 1H), 7.10 (t, J = 7.8 Hz, 1H), 6.97 (d, J = 7.5 Hz, 1H), 6.85 (m, 1H), 6.51 (m, 1H), 5.02 (m, 1H), 4.37 (m, J = 9.9 Hz, 2H), 3.89 (m, 1H), 3.57 (m, 1H), 3.21 (m, 2H), 2.83 (m, 1H), 2.70 (s, 3H), 2.47 (s, 6H), 2.05 (m, 4H), 1.34 (m, 1H). MS calculated for $C_{25}H_{32}N_7O_2$ (M + H⁺) 462.25, found 462.3. |
| 17-38 | 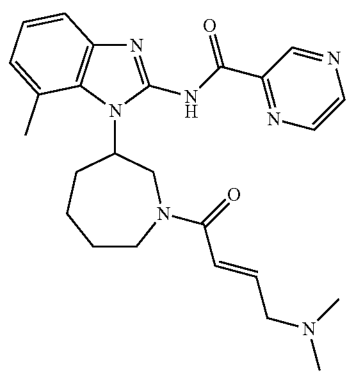 [SMILES: Cc1cccc2nc(NC(=O)c3cnccn3)n(C3CCCCN(C(=O)/C=C/CN(C)C)C3)c12] | ¹H-NMR (400 MHz, CDCl₃) δ 12.62 (s, 1H), 9.53 (t, J = 6.2 Hz, 1H), 8.76 (dd, J = 1.5, 2.4 Hz, 1H), 8.66 (dd, J = 2.4, 7.6 Hz, 1H), 7.24 (m, 1H), 7.17 (t, J = 7.8 Hz, 1H), 7.04 (m, 1H), 6.91 (m, 1H), 6.53 (m, 1H), 5.08 (s, 1H), 4.42 (d, J = 10.1 Hz, 2H), 3.91 (s, 1H), 3.62 (d, J = 13.7 Hz, 1H), 3.11 (m, 2H), 2.86 (m, 1H), 2.78 (s, 3H), 2.38 (s, 6H), 2.07 (m, 3H), 1.43 (m, 2H). MS calculated for $C_{25}H_{32}N_7O_2$ (M + H⁺) 462.25, found 462.3. |

| Ex. | Compound Structure | Physical Data ($^1$H NMR and MS) |
|---|---|---|
| 17-39 | 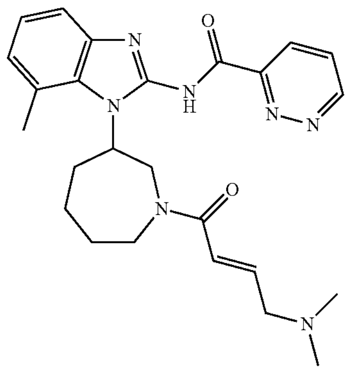 [SMILES: Cc1cccc2nc(NC(=O)c3cccnn3)n(C3CCCCN(C(=O)/C=C/CN(C)C)C3)c12] | $^1$H-NMR (400 MHz, CDCl$_3$) δ 12.46 (m, 1H), 9.28 (m, 1H), 8.32 (m, 1H), 7.60 (dd, J = 4.9, 8.4 Hz, 1H), 7.22 (m, 1H), 7.16 (t, J = 7.7 Hz, 1H), 7.04 (m, 1H), 6.89 (dt, J = 6.1, 15.2 Hz, 1H), 6.53 (m, 1H), 5.10 (m, 1H), 4.59 (m, 1H), 4.41 (dd, J = 3.1, 13.0 Hz, 1H), 3.88 (m, 1H), 3.57 (m, 1H), 3.17 (br d, J = 4.4 Hz, 2H), 2.92 (m, 1H), 2.78 (s, 3H), 2.34 (s, 6H), 2.06 (m, 4H), 1.42 (m, 1H). MS calculated for C$_{25}$H$_{32}$N$_7$O$_2$ (M + H$^+$) 462.25, found 462.3. |
| 17-40 | 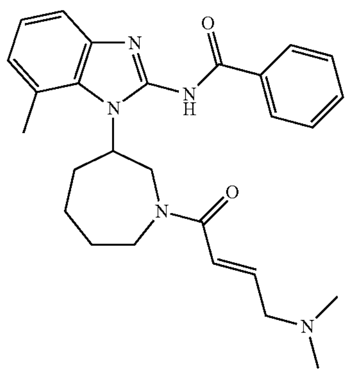 | $^1$H-NMR (400 MHz, MeOD) δ 8.24 (m, 2H), 7.50 (dd, J = 7.3, 12.3 Hz, 3H), 7.36 (d, J = 7.9 Hz, 1H), 7.16 (t, J = 7.9 Hz, 1H), 7.11 (m, J = 7.6 Hz, 1H), 6.78 (m, 2H), 5.07 (s, 2H), 4.60 (d, J = 21.8 Hz, 1H), 4.34 (d, J = 13.0 Hz, 1H), 4.00 (s, 1H), 3.68 (s, 1H), 2.97 (s, 1H), 2.75 (d, J = 11.6 Hz, 3H), 2.31 (d, J = 82.4 Hz, 6H), 2.11 (s, 3H), 1.46 (s, 1H), 1.37 (d, J = 6.6, 2H). MS calculated for C$_{27}$H$_{34}$N$_5$O$_2$ (M + H$^+$) 460.26, found 460.3. |
| 17-41 | 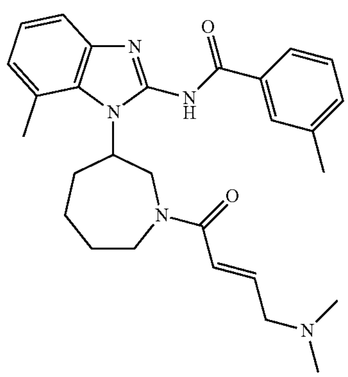 [SMILES: Cc1cccc(C(=O)Nc2nc3cccc(C)c3n2C2CCCCN(C(=O)/C=C/CN(C)C)C2)c1] | $^1$H-NMR (400 MHz, MeOD) δ 8.07 (m, 2H), 7.35 (d, J = 6.2 Hz, 3H), 7.15 (t, J = 7.9 Hz, 1H), 7.06 (t, J = 7.8 Hz, 1H), 6.78 (m, 2H), 5.01 (d, J = 54.2 Hz, 2H), 4.59 (s, 1H), 4.33 (d, J = 13.2 Hz, 1H), 4.01 (s, 1H), 3.70 (d, J = 14.7 Hz, 2H), 2.95 (s, 1H), 2.74 (d, J = 12.5 Hz, 3H), 2.43 (d, J = 6.4 Hz, 3H), 2.29 (s, J = 81.3 Hz, 6H), 2.10 (s, 3H), 1.46 (m, 1H), 1.37 (d, J = 6.6 Hz, 2H). MS calculated for C$_{28}$H$_{36}$N$_5$O$_2$ (M + H$^+$) 474.28, found 474.3. |
| 17-42 | 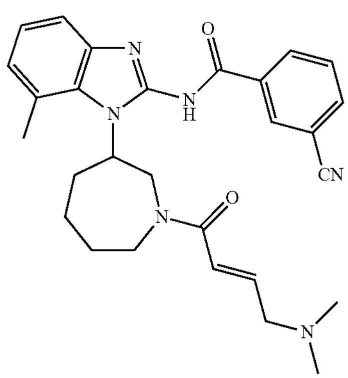 [SMILES: Cc1cccc2nc(NC(=O)c3cccc(C#N)c3)n(C3CCCCN(C(=O)/C=C/CN(C)C)C3)c12] | $^1$H-NMR (400 MHz, MeOD) δ 8.59 (m, 1H), 8.49 (d, J = 7.9 Hz, 1H), 7.87 (d, J = 7.6, 1H), 7.68 (t, J = 7.8 Hz, 1H), 7.38 (d, J = 8.1 Hz, 1H), 7.18 (t, J = 7.8 Hz, 1H), 7.08 (m 1H), 6.98 (d, J = 15.1 Hz, 1H), 6.81 (m, 1H), 5.12 (m, 1H), 4.68 (m, 1H), 4.27 (m, 1H), 3.93 (m, 3H), 3.74 (m, 2H), 3.23 (q, J = 7.4 Hz, 1H), 2.91 (s, 6H), 2.75 (s, J = 16.7 Hz, 3H), 2.22 (m, 1H), 2.11 (d, J = 13.3 Hz, 3H), 1.50 (s, 1H). MS calculated for C$_{28}$H$_{33}$N$_6$O$_2$ (M + H$^+$) 485.26, found 485.3. |

| Ex. | Compound Structure | Physical Data (¹H NMR and MS) |
| --- | --- | --- |
| 17-43 | 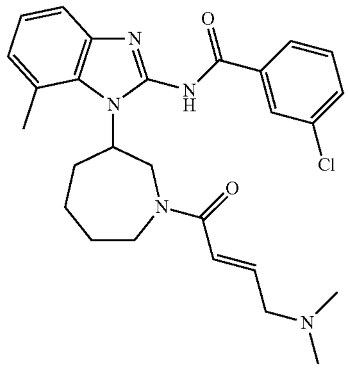 [SMILES: Cc1cccc2nc(NC(=O)c3cccc(Cl)c3)n(C3CCCCN(C(=O)/C=C/CN(C)C)C3)c12] | MS calculated for $C_{27}H_{33}ClN_5O_2$ (M + H⁺) 494.22, found 494.2. |
| 17-44 | 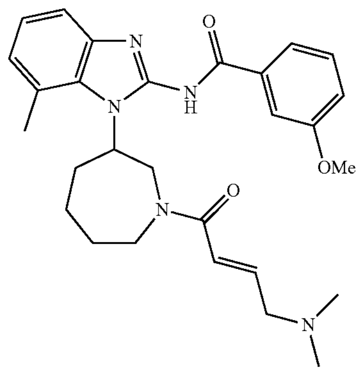 [SMILES: COc1cccc(C(=O)Nc2nc3cccc(C)c3n2C2CCCCN(C(=O)/C=C/CN(C)C)C2)c1] | ¹H-NMR (400 MHz, CDCl₃) δ 12.69 (s, 1H), 7.85 (m, 2H), 7.37 (t, J = 7.9 Hz, 1H), 7.14 (m, 2H), 7.06 (m, 1H), 7.00 (m, 1H), 6.92 (m, 1H), 6.46 (d, J = 15.2 Hz, 1H), 5.00 (m, 1H), 4.44 (m, 1H), 4.04 (m, 1H), 3.90 (s, 3H), 3.55 (m, 1H), 3.10 (d, J = 5.9 Hz, 1H), 2.95 (m, 2H), 2.76 (s, 3H), 2.29 (s, 6H), 2.04 (m, 3H), 1.41 (m, 1H), 1.29 (m, 2H). MS calculated for $C_{28}H_{36}N_5O_3$ (M + H⁺) 490.27, found 490.3. |
| 17-45 | 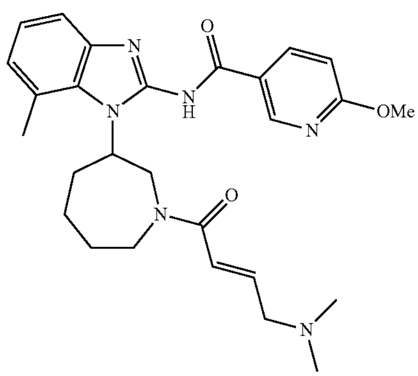 [SMILES: COc1ccc(C(=O)Nc2nc3cccc(C)c3n2C2CCCCN(C(=O)/C=C/CN(C)C)C2)cn1] | ¹H-NMR (400 MHz, MeOD) δ 9.05 (s, 1H), 8.45 (m, 1H), 7.37 (m, 1H), 7.17 (m, 1H), 7.06 (m, 1H), 6.92 (m, 1H), 6.83 (m, 1H), 6.72 (m, 1H), 5.07 (m, 1H), 4.58 (m, 1H), 4.32 (m, 1H), 4.12 (m, 1H), 4.00 (s, 3H), 3.71 (m, 2H), 3.48 (m, 1H), 3.13 (m, 1H), 2.91 (m, 1H), 2.75 (s, 3H), 2.42 (s, 6H), 2.11 (m, 2H), 1.49 (m, 1H), 1.32 (m, 1H). MS calculated for $C_{27}H_{35}N_6O_3$ (M + H⁺) 491.27, found 491.2. |
| 17-46 | 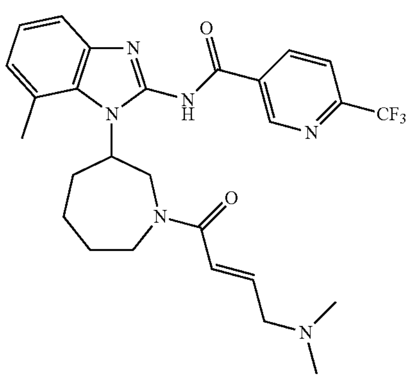 [SMILES: Cc1cccc2nc(NC(=O)c3ccc(C(F)(F)F)nc3)n(C3CCCCN(C(=O)/C=C/CN(C)C)C3)c12] | ¹H-NMR (400 MHz, DMSO) δ 9.46 (s, 1H), 8.68 (m, 1H), 8.07 (d, J = 8.1 Hz, 1H), 7.49 (m, 1H), 7.16 (t, J = 7.7 Hz, 1H), 7.07 (t, J = 6.6 Hz, 1H), 6.66 (m, 2H), 4.86 (m, 1H), 4.29 (dd, J = 10.5, 12.9 Hz, 1H), 4.17 (m, 1H), 3.87 (m, 1H), 3.58 (m, 1H), 3.43 (m, 1H), 3.08 (t, J = 4.8 Hz, 1H), 2.77 (m, 2H), 2.70 (s, 3H), 2.18 (s, 6H), 2.05 (m, 2H), 1.91 (m, 1H), 1.35 (m, 1H). ¹⁹F-NMR (376 MHz, DMSO) δ −66.38. MS calculated for $C_{27}H_{32}F_3N_6O_2$ (M + H⁺) 529.25, found 529.2. |

| Ex. | Compound Structure | Physical Data (¹H NMR and MS) |
|---|---|---|
| 17-47 | 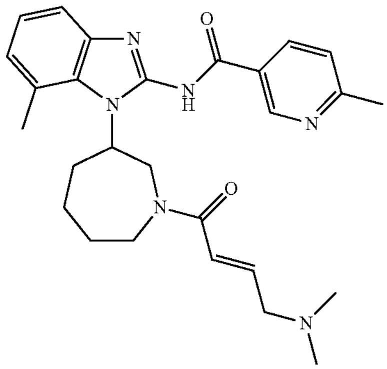 [SMILES: Cc1ccc(C(=O)Nc2nc3cccc(C)c3n2C2CCCCN(C(=O)/C=C/CN(C)C)C2)cn1] | MS calculated for $C_{27}H_{35}N_6O_2$ (M + H⁺) 475.27, found 475.2. |
| 17-48 | 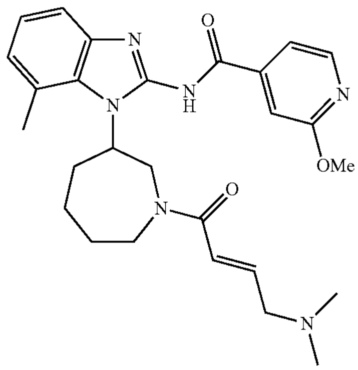 [SMILES: COc1cc(C(=O)Nc2nc3cccc(C)c3n2C2CCCCN(C(=O)/C=C/CN(C)C)C2)ccn1] | ¹H-NMR (400 MHz, MeOD) δ 8.25 (d, J = 3.3 Hz, 1H), 7.67 (s, 1H), 7.50 (d, J = 15.2 Hz, 1H), 7.38 (d, J = 9.0 Hz, 1H), 7.18 (t, J = 8.1 Hz, 1H), 7.08 (d, J = 7.7 Hz, 1H), 6.99 (d, J = 15.1 Hz, 1H), 6.76 (d, J = 7.2 Hz, 1H), 5.07 (s, 1H), 4.55 (s, 1H), 4.32 (d, J = 13.0 Hz, 1H), 3.99 (s, 1H), 3.97 (s, 3H), 3.93 (m, 1H), 3.71 (s, 2H), 3.23 (d, J = 7.4 Hz, 1H), 2.89 (s, 6H), 2.75 (s, 3H), 2.72 (s, 1H), 2.20 (m, 1H), 2.10 (m, 2H), 1.50 (m, 1H). MS calculated for $C_{27}H_{35}N_6O_3$ (M + H⁺) 491.27, found 491.2. |
| 17-49 | 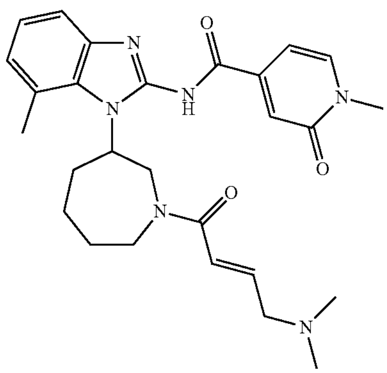 [SMILES: Cc1cccc2nc(NC(=O)c3ccn(C)c(=O)c3)n(C3CCCCN(C(=O)/C=C/CN(C)C)C3)c12] | ¹H-NMR (400 MHz, MeOD) δ 7.74 (d, J = 7.0 Hz, 1H), 7.36 (m, 2H), 7.18 (m, 1H), 7.08 (m, 2H), 6.84 (m, 1H), 6.68 (m, 1H), 5.04 (m, 2H), 4.50 (m, 1H), 4.33 (d, J = 12.8 Hz, 1H), 3.99 (m, 1H), 3.70 (m, 1H), 3.63 (s, 3H), 3.25 (d, J = 6.2 Hz, 1H), 3.10 (m, 1H), 2.87 (m, 1H), 2.75 (s, 3H), 2.34 (s, 6H), 2.09 (m, 3H), 1.45 (m, 1H). MS calculated for $C_{27}H_{35}N_6O_3$ (M + H⁺) 491.27, found 491.2. |
| 17-50 | 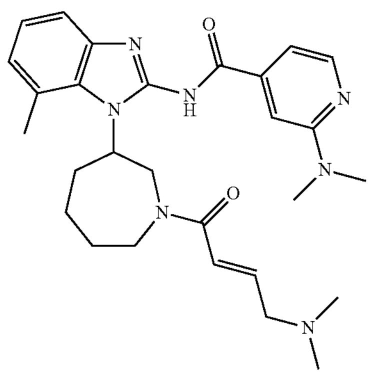 [SMILES: Cc1cccc2nc(NC(=O)c3ccnc(N(C)C)c3)n(C3CCCCN(C(=O)/C=C/CN(C)C)C3)c12] | ¹H-NMR (400 MHz, MeOD) δ 8.06 (d, J = 6.3 Hz, 1H), 7.77 (s, 1H), 7.57 (s, 1H), 7.42 (d, J = 7.6, 1H), 7.22 (t, J = 7.8 Hz, 1H), 7.12 (d, J = 7.4 Hz, 1H), 6.99 (d, J = 15.2 Hz, 1H), 6.76 (m, 1H), 5.10 (m, 1H), 4.42 (d, J = 61.8 Hz, 1H), 3.98 (m, 1H), 3.34 (s, 6H), 3.11 (d, J = 17.2 Hz, 1H), 2.93 (s, 6H), 2.78 (d, J = 10.7 Hz, 3H), 2.12 (s, 3H), 1.48 (m, 1H), 1.37 (dd, J = 3.3, 6.7 Hz, 2H). MS calculated for $C_{28}H_{38}N_7O_2$ (M + H⁺) 504.30, found 504.2. |

| Ex. | Compound Structure | Physical Data ($^1$H NMR and MS) |
|---|---|---|
| 17-51 | 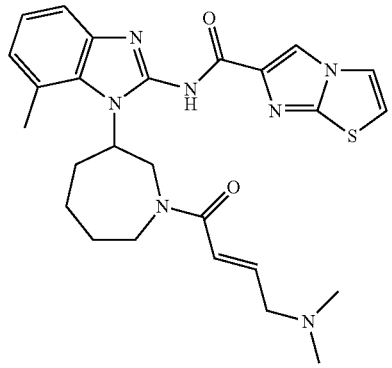 [SMILES: Cc1cccc2nc(NC(=O)c3cn4ccsc4n3)n(C3CCCCN(C(=O)/C=C/CN(C)C)C3)c12] | $^1$H-NMR (400 MHz, MeOD) δ 8.27 (d, J = 22.4 Hz, 1H), 7.86 (d, J = 4.5 Hz, 1H), 7.31 (s, 1H), 7.24 (s, 1H), 7.14 (t, J = 7.9 Hz, 1H), 7.05 (s, 1H), 6.82 (s, 1H), 6.72 (s, 1H), 4.95 (s, 2H), 4.46 (m, 1H), 4.00 (m, 1H), 3.68 (m, 1H), 3.48 (s, 1H), 3.23 (s, 1H), 3.06 (d, J = 61.8 Hz, 1H), 2.88 (m, 1H), 2.73 (d, J = 13.6 Hz, 3H), 2.26 (m, 6H), 2.01 (m, 2H), 1.49 (m, 1H), 1.29 (s, 1H). MS calculated for $C_{26}H_{32}N_7O_2S$ (M + H$^+$) 506.23, found 506.1. |
| 17-52 | 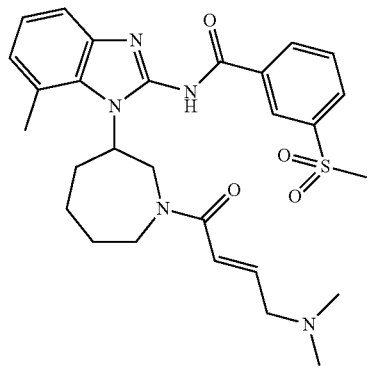 [SMILES: Cc1cccc2nc(NC(=O)c3cccc(S(C)(=O)=O)c3)n(C3CCCCN(C(=O)/C=C/CN(C)C)C3)c12] | $^1$H-NMR (400 MHz, MeOD) δ 8.94 (t, J = 1.6 Hz, 1H), 8.51 (d, J = 7.8 Hz, 1H), 8.10 (d, J = 8.2 Hz, 1H), 7.76 (t, J = 7.8 Hz, 1H), 7.39 (m, 1H), 7.17 (t, J = 7.8 Hz, 1H),<br>7.09 (t, J = 7.1, 1H), 6.83 (m, 1H), 6.73 (m, 1H), 5.11 (m, 1H), 4.93 (m, 1H), 4.57 (m, 1H), 4.37 (d, J = 13.1 Hz, 1H), 4.05 (m, 1H), 3.76 (m, 1H), 3.18 (s, 3H), 2.92 (m, 1H), 2.77 (s, 3H), 2.39 (s, 6H), 2.12 (m, 4H), 1.45 (m, 1H), 1.37 (d, J = 6.6 Hz, 1H).<br>MS calculated for $C_{28}H_{36}N_5O_4S$ (M + H$^+$) 538.24, found 538.2. |
| 17-53 | 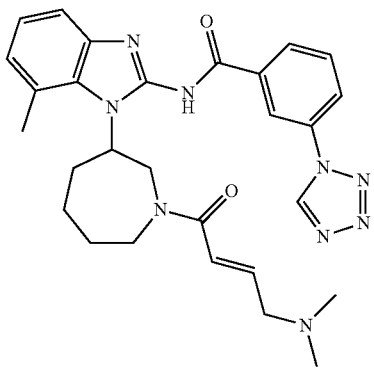 [SMILES: Cc1cccc2nc(NC(=O)c3cccc(-n4cnnn4)c3)n(C3CCCCN(C(=O)/C=C/CN(C)C)C3)c12] | $^1$H-NMR (400 MHz, DMSO) 10.22 (s, 1H), 10.04 (br s, 1H), 8.77 (m, 1H), 8.31 (m, 1H), 8.09 (ddd, J = 0.9, 2.2, 8.0 Hz, 1H), 7.80 (t, J = 7.9 Hz, 1H), 7.48 (d, J = 7.8 Hz, 1H), 7.14 (t, J = 7.7 Hz, 1H), 7.05 (t, J = 6.0 Hz, 1H), 6.89 (d, J = 15.0 Hz, 1H), 6.69 (m, 1H), 4.86 (m, 1H), 4.39 (m, 1H), 4.14 (m, 1H), 3.96 (m, 1H), 3.63 (m, 3H), 2.88 (t, J = 12.0 Hz, 1H), 2.71 (s, 3H),<br>2.63 (s, 6H), 2.00 (m, 4H), 1.39 (m, 1H). MS calculated for $C_{28}H_{34}N_9O_2$ (M + H$^+$) 528.28, found 528.2. |
| 17-54 | 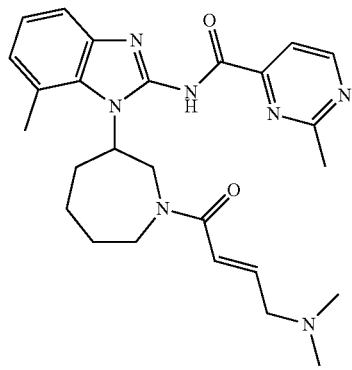 [SMILES: Cc1nccc(C(=O)Nc2nc3cccc(C)c3n2C2CCCCN(C(=O)/C=C/CN(C)C)C2)n1] | $^1$H-NMR (400 MHz, MeOD) δ 8.88 (d, J = 5.0 Hz, 1H), 8.08 (d, J = 4.9 Hz, 1H), 7.42 (d, J = 8.1 Hz, 1H), 7.21 (t, J = 7.8 Hz, 1H), 7.11 (d, J = 7.8 Hz, 1H), 7.01 (d, J = 15.1 Hz, 1H), 6.76 (m, 1H), 4.66 (t, J = 11.6 Hz, 1H), 4.31 (d, J = 12.9 Hz, 1H), 3.98 (m, 3H), 3.72 (m, 3H), 3.23 (q, J = 7.4 Hz, 2H), 2.93 (s, 6H), 2.80 (s, 3H), 2.77 (s, 3H), 2.12 (m, 3H). MS calculated for $C_{26}H_{34}N_7O_2$ (M + H$^+$) 476.27, found 476.3. |

| Ex. | Compound Structure | Physical Data (¹H NMR and MS) |
|---|---|---|
| 17-55 | 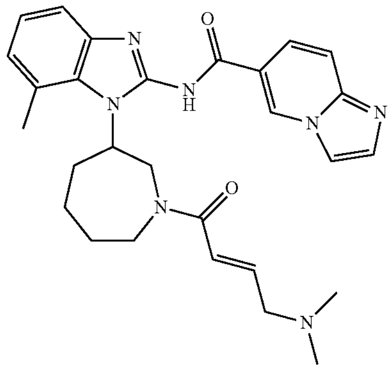 [SMILES: Cc1cccc2nc(NC(=O)c3ccc4nccn4c3)n(C3CCCCN(C(=O)/C=C/CN(C)C)C3)c12] | ¹H-NMR (400 MHz, MeOD) δ 8.51 (d, J = 7.1 Hz, 1H), 8.46 (s, 1H), 7.96 (s, 1H), 7.71 (s, 2H), 7.36 (d, J = 7.9 Hz, 1H), 7.16 (t, J = 8.5 Hz, 1H), 7.08 (t, J = 8.1 Hz, 1H), 6.80 (m, 2H), 5.08 (m, 1H), 4.56 (t, J = 11.8 Hz, 1H), 4.37 (d, J = 13.1 Hz, 1H), 4.00 (m, 1H), 3.74 (m, 1H), 3.41 (m, 3H), 3.04 (m, 2H), 2.76 (s, 3H), 2.44 (s, 6H), 2.10 (m, 2H), 1.51 (m, 1H). MS calculated for $C_{28}H_{34}N_7O_2$ (M + H⁺) 500.27, found 500.2. |
| 17-56 | 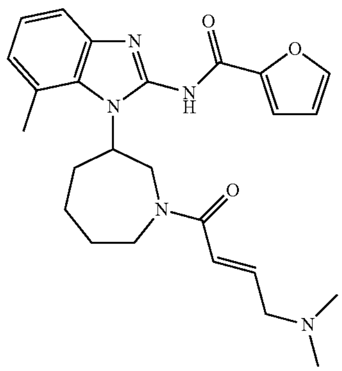 [SMILES: Cc1cccc2nc(NC(=O)c3ccco3)n(C3CCCCN(C(=O)/C=C/CN(C)C)C3)c12] | ¹H-NMR (400 MHz, MeOD) δ 7.69 (s, 1H), 7.34 (d, J = 8.1 Hz, 1H), 7.16 (m, 2H), 7.05 (d, J = 7.6 Hz, 1H), 6.78 (m, 2H), 6.59 (m, 1H), 4.59 (m, 1H), 4.29 (d, J = 13.1 Hz, 1H), 3.94 (m, 1H), 3.68 (m, 1H), 3.40 (m, 2H), 3.23 (m, 1H), 2.87 (dd, J = 11.7, 24.7 Hz, 1H), 2.74 (s, 3H), 2.46 (s, 6H), 2.11 (m, 4H), 1.44 (s, 1H). MS calculated for $C_{25}H_{32}N_5O_3$ (M + H⁺) 450.24, found 450.2. |
| 17-57 | 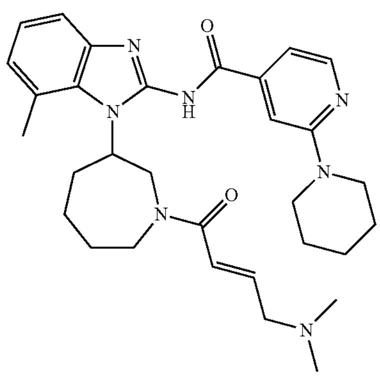 [SMILES: Cc1cccc2nc(NC(=O)c3ccnc(N4CCCCC4)c3)n(C3CCCCN(C(=O)/C=C/CN(C)C)C3)c12] | ¹H-NMR (400 MHz, MeOD) δ 8.18 (d, J = 5.2 Hz, 1H), 7.57 (s, 1H), 7.36 (m, 2H), 7.17 (t, J = 7.8 Hz, 1H), 7.09 (t, J = 8.1 Hz, 1H), 6.83 (m, 1H), 6.73 (d, J = 14.0 Hz, 1H), 5.05 (m, 2H), 4.51 (m, 1H), 4.33 (d, J = 12.8 Hz, 1H), 3.93 (m, 1H), 3.74 (m, 1H), 3.61 (m, 4H), 3.44 (m, 1H), 3.01 (m, 2H), 2.76 (s, 3H), 2.41 (s, 6H), 2.05 (m, 3H), 1.71 (br s, 6H), 1.46 (m, 1H). MS calculated for $C_{31}H_{42}N_7O_2$ (M + H⁺) 544.33, found 544.2. |
| 17-58 | 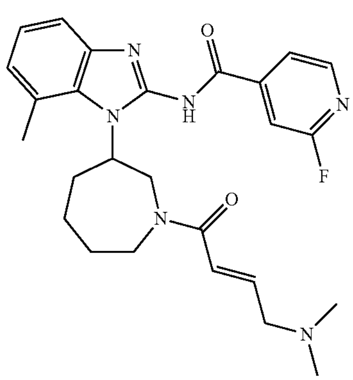 [SMILES: Cc1cccc2nc(NC(=O)c3ccnc(F)c3)n(C3CCCCN(C(=O)/C=C/CN(C)C)C3)c12] | ¹H-NMR (400 MHz, MeOD) δ 8.34 (d, J = 5.1 Hz, 1H), 8.02 (m, 1H), 7.73 (s, 1H), 7.39 (d, J = 7.9 Hz, 1H), 7.19 (m, 1H), 7.10 (t, J = 7.6 Hz, 1H), 6.85 (m, 1H), 6.68 (m, 1H), 5.10 (t, J = 11.0 Hz, 1H), 4.51 (dd, J = 10.7, 12.9 Hz, 1H), 4.31 (d, J = 13.0 Hz, 1H), 3.99 (m, 1H), 3.67 (m, 1H), 3.22 (d, J = 6.4 Hz, 2H), 2.87 (d, J = 11.7 Hz, 1H), 2.77 (s, 3H), 2.32 (s, 6H), 2.14 (s, 1H), 2.10 (d, J = 12.8 Hz, 3H), 1.50 (m, 1H). MS calculated for $C_{26}H_{32}FN_6O_2$ (M + H⁺) 479.25, found 479.2. |

| Ex. | Compound Structure | Physical Data (¹H NMR and MS) |
|---|---|---|
| 17-59 | 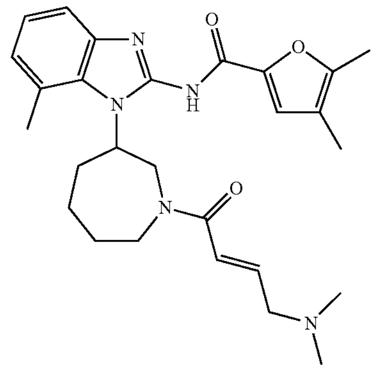 [SMILES: Cc1cc(C(=O)Nc2nc3cccc(C)c3n2C2CCCCN(C(=O)/C=C/CN(C)C)C2)oc1C] | ¹H-NMR (400 MHz, MeOD) δ 7.24 (m, 1H), 7.05 (m, 1H), 6.94 (t, J = 7.5 Hz, 1H), 6.87 (m, 1H), 6.70 (m, 2H), 4.52 (m, 1H), 4.12 (m, 1H), 3.87 (m, 1H), 3.54 (m, 2H), 3.26 (d, J = 4.4 Hz, 2H), 3.06 (m, 1H), 2.79 (m, 1H), 2.63 (s, 3H), 2.27 (s, J = 47.7 Hz, 6H), 2.17 (s, 3H), 2.03 (m, 3H), 1.93 (s, 3H), 1.39 (m, 1H). MS calculated for $C_{27}H_{36}N_5O_3$ (M + H⁺) 478.27, found 478.2. |
| 17-60 | 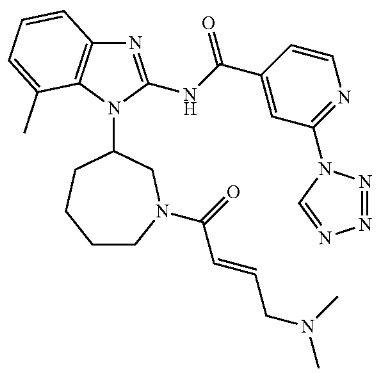 [SMILES: Cc1cccc2nc(NC(=O)c3ccnc(-n4cnnn4)c3)n(C3CCCCN(C(=O)/C=C/CN(C)C)C3)c12] | ¹H-NMR (400 MHz, DMSO) δ 10.28 (s, 1H), 8.83 (d, J = 5.0 Hz, 1H), 8.75 (s, 1H), 8.20 (d, J = 5.3 Hz, 1H), 7.50 (d, J = 7.7 Hz, 1H), 7.17 (t, J = 7.7, 1H), 7.08 (d, J = 7.4 Hz, 1H), 6.69 (m, 2H), 4.86 (m, 1H), 4.28 (m, 2H), 3.96 (m, 1H), 3.65 (m, 1H), 3.00 (br s, 2H), 2.80 (m, 1H), 2.72 (s, 3H), 2.20 (s, 6H), 2.03 (m, 3H), 1.89 (m, 1H), 1.39 (m, 1H). MS calculated for $C_{27}H_{33}N_{10}O_2$ (M + H⁺) 529.27, found 529.2. |
| 17-61 | 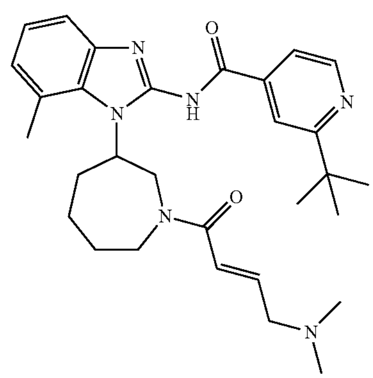 [SMILES: Cc1cccc2nc(NC(=O)c3ccnc(C(C)(C)C)c3)n(C3CCCCN(C(=O)/C=C/CN(C)C)C3)c12] | ¹H-NMR (400 MHz, MeOD) δ 8.52 (d, J = 5.1 Hz, 1H), 8.11 (m, 1H), 7.82 (m, 1H), 7.29 (d, J = 8.0 Hz, 1H), 7.08 (t, J = 7.8 Hz, 1H), 6.99 (d, J = 7.5 Hz, 1H), 6.73 (m, 1H), 6.59 (d, J = 15.2 Hz, 1H), 4.99 (t, J = 12.1 Hz, 1H), 4.42 (dd, J = 10.6, 12.9 Hz, 1H), 4.24 (d, J = 12.6 Hz, 1H), 3.91 (m, 1H), 3.55 (m, 1H), 3.12 (d, J = 6.3 Hz, 2H), 2.79 (m, 2H), 2.67 (s, 3H), 2.22 (s, 6H), 1.98 (m, 4H), 1.44 (m, 1H), 1.35 (s, 9H). MS calculated for $C_{30}H_{41}N_6O_2$ (M + H⁺) 517.32, found 517.2. |
| 17-62 | 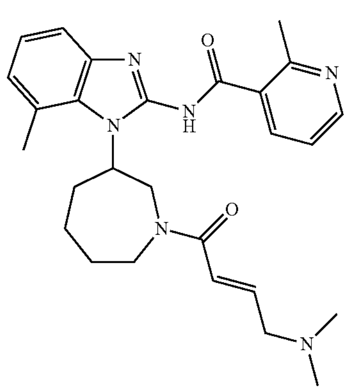 [SMILES: Cc1ncccc1C(=O)Nc1nc2cccc(C)c2n1C1CCCCN(C(=O)/C=C/CN(C)C)C1] | ¹H-NMR (400 MHz, MeOD) δ 8.46 (m, 1H), 8.32 (m, 1H), 7.38 (m, 2H), 7.17 (t, J = 7.8 Hz, 1H), 7.08 (t, J = 7.4 Hz, 1H), 6.82 (m, 1H), 6.64 (d, J = 15.2 Hz, 1H), 5.06 (t, J = 11.0 Hz, 1H), 4.49 (m, 1H), 4.29 (dd, J = 2.9, 12.9 Hz, 1H), 3.90 (m, 1H), 3.50 (m, 1H), 3.19 (dd, J = 1.4, 6.4 Hz, 2H), 2.82 (s, 3H), 2.78 (m, 1H), 2.75 (s, 3H), 2.30 (s, 6H), 2.04 (m, 3H), 1.84 (m, 1H), 1.42 (m, 1H). MS calculated for $C_{27}H_{35}N_6O_2$ (M + H⁺) 475.27, found 475.1. |

| Ex. | Compound Structure | Physical Data ($^1$H NMR and MS) |
|---|---|---|
| 17-63 | 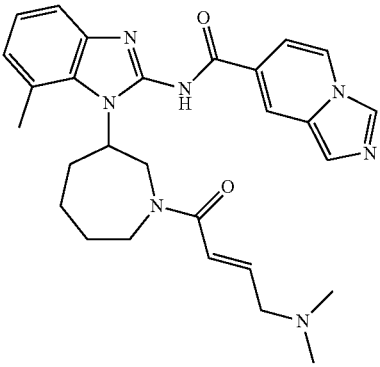 [SMILES: Cc1cccc2nc(NC(=O)c3ccn4cncc4c3)n(C3CCCCN(C(=O)/C=C/CN(C)C)C3)c12] | MS calculated for $C_{28}H_{34}N_7O_2$ (M + H$^+$) 500.27, found 500.2. |
| 17-64 | 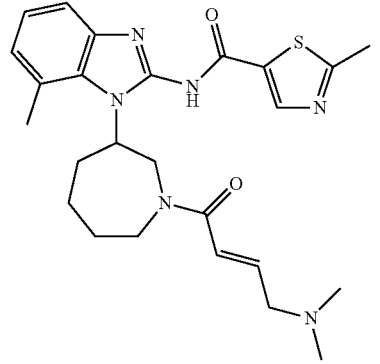 [SMILES: Cc1ncc(C(=O)Nc2nc3cccc(C)c3n2C2CCCCN(C(=O)/C=C/CN(C)C)C2)s1] | $^1$H-NMR (400 MHz, MeOD) δ 8.18 (s, 1H), 7.36 (d, J = 8.0 Hz, 1H), 7.17 (t, J = 7.8 Hz, 1H), 7.07 (d, J = 7.5 Hz, 1H), 6.84 (m, 1H), 6.69 (d, J = 15.2 Hz, 1H), 5.05 (m, 2H), 4.51 (m, 1H), 4.31 (d, J = 13.1 Hz, 1H), 4.03 (m, 1H), 3.68 (m, 1H), 3.16 (m, 2H), 2.85 (m, 1H), 2.75 (s, 6H), 2.32 (s, 6H), 2.08 (m, 3H), 1.42 (m, 1H). MS calculated for $C_{25}H_{33}N_6O_2S$ (M + H$^+$) 481.23, found 481.1. |
| 17-65 | 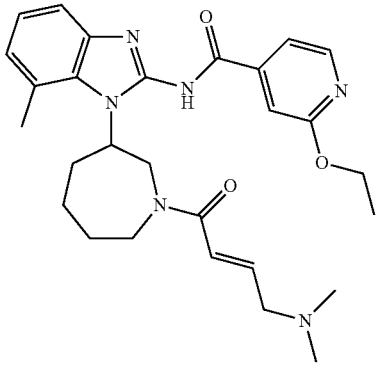 [SMILES: CCOc1cc(C(=O)Nc2nc3cccc(C)c3n2C2CCCCN(C(=O)/C=C/CN(C)C)C2)ccn1] | $^1$H-NMR (400 MHz, MeOD) δ 8.31 (m, 1H), 7.69 (m, 1H), 7.52 (m, 1H), 7.38 (m, 1H), 7.21 (m, 1H), 7.09 (m, 1H), 6.86 (m, 1H), 6.72 (m, 1H), 4.63 (s, 2H), 4.50 (m, 1H), 4.37 (m, 2H), 3.89 (m, 1H), 3.48 (m, 3H), 3.12 (m, 1H), 2.90 (m, 1H), 2.77 (s, 2H), 2.69 (m, 1H), 2.40 (s, 6H), 2.18 (m, 1H), 2.07 (m, 3H), 1.43 (t, J = 6.9, 3H). MS calculated for $C_{28}H_{37}N_6O_3$ (M + H$^+$) 505.28, found 505.1. |
| 17-66 | 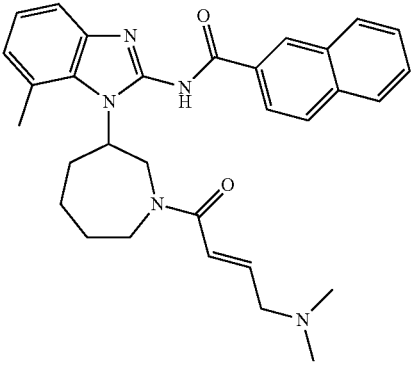 [SMILES: Cc1cccc2nc(NC(=O)c3ccc4ccccc4c3)n(C3CCCCN(C(=O)/C=C/CN(C)C)C3)c12] | $^1$H-NMR (400 MHz, MeOD) δ 8.79 (s, 1H), 8.31 (m, 1H), 7.96 (m, 3H), 7.57 (m, 2H), 7.39 (m, 1H), 7.18 (m, 1H), 7.08 (t, J = 8.0 Hz, 1H), 6.84 (m, 1H), 6.71 (d, J = 15.1 Hz, 1H), 5.08 (m, 1H), 4.68 (m, 1H), 4.36 (d, J = 10.3 Hz, 1H), 4.06 (m, 1H), 3.77 (m, 1H), 3.22 (d, J = 6.9 Hz, 1H), 3.05 (m, 1H), 2.78 (s, 3H), 2.32 (s, 6H), 2.08 (m, 4H). MS calculated for $C_{31}H_{36}N_5O_2$ (M + H$^+$) 510.28, found 510.1. |

| Ex. | Compound Structure | Physical Data (¹H NMR and MS) |
|---|---|---|
| 17-67 | 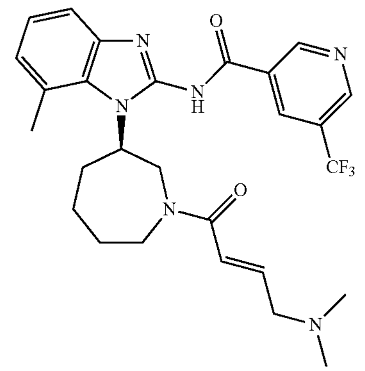 [SMILES: Cc1cccc2nc(NC(=O)c3cncc(C(F)(F)F)c3)n([C@@H]3CCCCN(C(=O)/C=C/CN(C)C)C3)c12] | ¹H-NMR (400 MHz, DMSO) δ 9.55 (s, 1H), 9.15 (s, 1H), 8.73 (s, 1H), 7.49 (d, J = 7.5 Hz, 1H), 7.16 (t, J = 7.7 Hz, 1H), 7.07 (t, J = 6.5 Hz, 1H), 6.63 (m, 2H), 4.96 (t, J = 10.7 Hz, 1H), 4.30 (m, 1H), 4.16 (d, J = 12.8 Hz, 1H), 3.94 (m, 1H), 3.52 (m, 1H), 3.06 (t, J = 4.9 Hz, 1H), 2.80 (m, 2H), 2.71 (s, 3H), 2.65 (s, 1H), 2.17 (s, 6H), 2.00 (m, 3H), 1.81 (m, 1H). ¹⁹F-NMR (376 MHz, DMSO) δ −60.99. MS calculated for $C_{27}H_{32}F_3N_6O_2$ (M + H⁺) 529.25, found 529.1. |
| 17-68 | 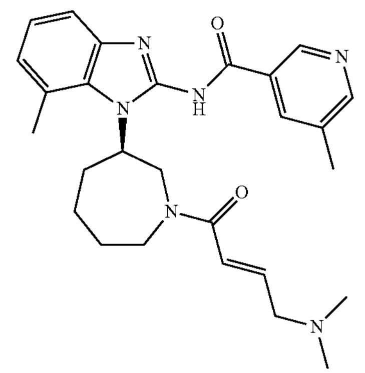 [SMILES: Cc1cncc(C(=O)Nc2nc3cccc(C)c3n2[C@@H]2CCCCN(C(=O)/C=C/CN(C)C)C2)c1] | ¹H-NMR (400 MHz, MeOD) δ 9.20 (s, 1H), 8.50 (s, 1H), 8.42 (s, 1H), 7.37 (d, J = 7.9 Hz, 1H), 7.17 (t, J = 7.8 Hz, 1H), 7.08 (t, J = 7.9 Hz, 1H), 6.82 (t, J = 6.4 Hz, 1H), 6.69 (d, J = 15.3 Hz, 1H), 5.03 (d, J = 50.2 Hz, 1H), 4.53 (m, 1H), 4.26 (dd, J = 12.0, 58.2 Hz, 1H), 4.02 (m, 1H), 3.64 (m, 1H), 3.16 (m, 2H), 2.92 (m, 1H), 2.76 (s, 3H), 2.46 (d, J = 3.7, 3H), 2.32 (s, 6H), 2.11 (m, 4H), 1.46 (m, 1H). MS calculated for $C_{27}H_{35}N_6O_2$ (M + H⁺) 475.27, found 475.1. |
| 17-69 | 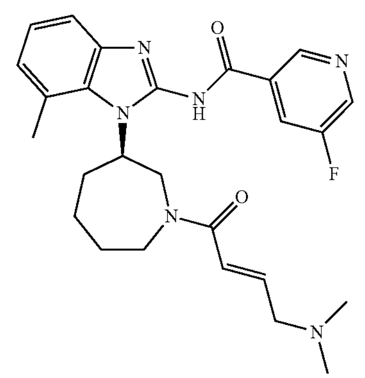 | MS calculated for $C_{26}H_{32}FN_6O_2$ (M + H⁺) 479.25, found 479.1. |
| 17-70 | 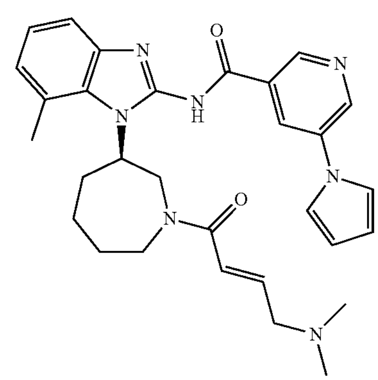 [SMILES: Cc1cccc2nc(NC(=O)c3cncc(-n4cccc4)c3)n([C@@H]3CCCCN(C(=O)/C=C/CN(C)C)C3)c12] | ¹H-NMR (400 MHz, MeOD) δ 9.24 (d, J = 14.7 Hz, 1H), 8.89 (d, J = 2.7 Hz, 1H), 8.64 (dd, J = 1.7, 2.6 Hz, 1H), 7.37 (m, 3H), 7.19 (t, J = 8.2 Hz, 1H), 7.09 (d, J = 8.0 Hz, 1H), 6.83 (m, 1H), 6.70 (m, 1H), 6.41 (m, 2H), 5.11 (t, J = 11.0, 1H), 4.54 (m, 1H), 4.35 (d, J = 12.7 Hz, 1H), 3.98 (m, 1H), 3.63 (m, 1H), 3.48 (s, 1H), 3.24 (d, J = 6.3 Hz, 1H), 2.94 (m, 1H), 2.77 (s, 3H), 2.34 (s, 6H), 2.04 (m, 4H), 1.47 (s, 1H). MS calculated for $C_{30}H_{36}N_7O_2$ (M + H⁺) 526.29, found 526.2. |

| Ex. | Compound Structure | Physical Data ($^1$H NMR and MS) |
|---|---|---|
| 17-71 | 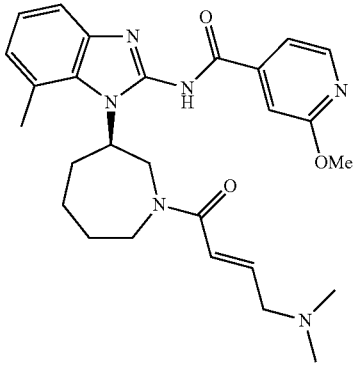 [SMILES: COc1cc(C(=O)Nc2nc3cccc(C)c3n2[C@@H]2CCCCN(C(=O)/C=C/CN(C)C)C2)ccn1] | $^1$H-NMR (400 MHz, DMSO) δ 8.32 (d, J = 5.2 Hz, 1H), 7.63 (d, J = 5.2 Hz, 1H), 7.44 (m, 2H), 7.14 (t, J = 7.7 Hz, 1H), 7.05 (t, J = 6.5 Hz, 1H), 6.63 (m, 2H), 4.91 (m, 1H), 4.47 (m, 1H), 4.16 (s, 1H), 3.95 (m, 1H), 3.91 (s, 3H), 3.54 (m, 1H), 3.08 (t, J = 4.8 Hz, 1H), 2.84 (m, 1H), 2.73 (m, 1H), 2.70 (s, 3H), 2.10 (s, 6H), 1.89 (m, 4H), 1.32 (m, 1H). MS calculated for $C_{27}H_{35}N_6O_3$ (M + H$^+$) 491.27, found 491.1. |
| 17-72 | 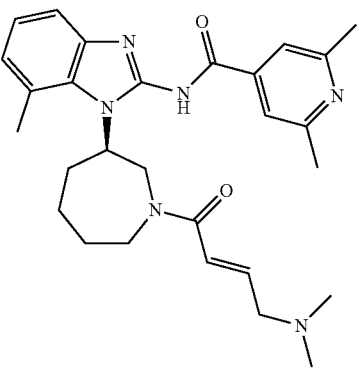 [SMILES: Cc1cc(C(=O)Nc2nc3cccc(C)c3n2[C@@H]2CCCCN(C(=O)/C=C/CN(C)C)C2)cc(C)n1] | $^1$H-NMR (400 MHz, MeOD) δ 7.82 (s, 2H), 7.37 (d, J = 7.9 Hz, 1H), 7.17 (t, J = 7.8 Hz, 1H), 7.09 (t, J = 8.1 Hz, 1H), 6.85 (m, 1H), 6.69 (d, J = 15.2 Hz, 1H), 5.10 (t, J = 10.7 Hz, 1H), 4.57 (m, 1H), 4.30 (d, J = 12.9 Hz, 1H), 3.99 (m, 1H), 3.64 (m, 1H), 3.22 (d, J = 6.0 Hz, 1H), 3.08 (m, 1H), 2.91 (m, 1H), 2.76 (s, 3H), 2.59 (s, 6H), 2.31 (s, 6H), 2.10 (m, 4H), 1.47 (m, 1H). MS calculated for $C_{28}H_{37}N_6O_2$ (M + H$^+$) 489.29, found 489.1. |
| 17-73 | 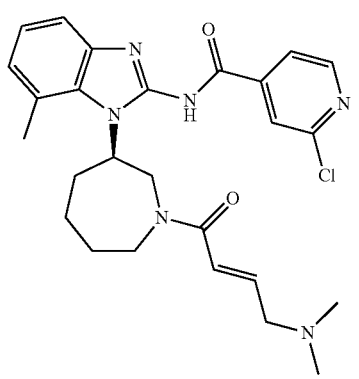 [SMILES: Cc1cccc2nc(NC(=O)c3ccnc(Cl)c3)n([C@@H]3CCCCN(C(=O)/C=C/CN(C)C)C3)c12] | MS calculated for $C_{26}H_{32}ClN_6O_2$ (M + H$^+$) 495.22, found 495.1. |
| 17-74 | 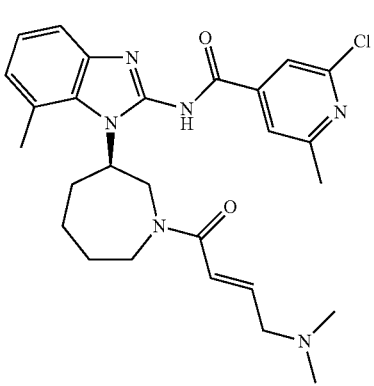 [SMILES: Cc1cc(C(=O)Nc2nc3cccc(C)c3n2[C@@H]2CCCCN(C(=O)/C=C/CN(C)C)C2)cc(Cl)n1] | MS calculated for $C_{27}H_{34}ClN_6O_2$ (M + H$^+$) 509.24, found 509.1. |

| Ex. | Compound Structure | Physical Data (¹H NMR and MS) |
|---|---|---|
| 17-75 | 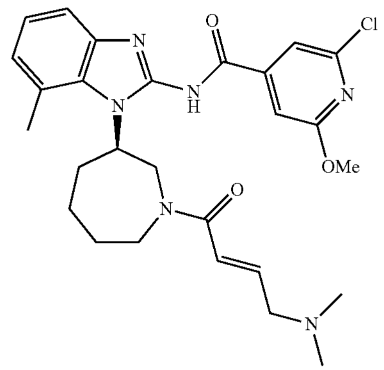 [SMILES: COc1cc(C(=O)Nc2nc3cccc(C)c3n2[C@@H]2CCCCN(C(=O)/C=C/CN(C)C)C2)cc(Cl)n1] | ¹H-NMR (400 MHz, MeOD) δ 7.69 (s, 1H), 7.39 (m, 2H), 7.18 (m, 1H), 7.09 (m, 1H), 6.85 (m, 1H), 6.71 (d, J = 14.2 Hz, 1H), 5.08 (m, 2H), 4.47 (t, J = 11.8 Hz, 1H), 4.30 (d, J = 13.0 Hz, 1H), 4.04 (m, 1H), 3.97 (s, 3H), 3.64 (m, 1H), 2.95 (m, 2H), 2.76 (s, 3H), 2.28 (s, 6H), 2.02 (m, 4H), 1.47 (m, 1H). MS calc. for $C_{27}H_{34}ClN_6O_3$ (M + H⁺) 525.23, found 525.1. |
| 17-76 | 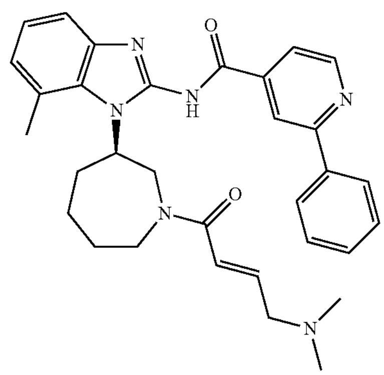 [SMILES: Cc1cccc2nc(NC(=O)c3ccnc(-c4ccccc4)c3)n([C@@H]3CCCCN(C(=O)/C=C/CN(C)C)C3)c12] | ¹H-NMR (400 MHz, MeOD) δ 8.75 (d, J = 5.0 Hz, 1H), 8.58 (s, 1H), 8.03 (m, 3H), 7.53 (m, 3H), 7.38 (d, J = 7.9 Hz, 1H), 7.19 (m, 1H), 7.08 (d, J = 7.5 Hz, 1H), 6.82 (m, 1H), 6.69 (m, 1H), 5.10 (t, J = 10.0 Hz, 1H), 4.96 (m, 1H), 4.54 (t, J = 11.8 Hz, 1H), 4.35 (d, J = 13.0 Hz, 1H), 3.98 (m, 1H), 3.63 (m, 1H), 3.12 (m, 1H), 2.93 (m, 1H), 2.76 (s, 3H), 2.27 (s, 6H), 2.03 (m, 4H), 1.46 (s, 1H). MS calc. for $C_{32}H_{37}N_6O_2$ (M + H⁺) 537.29, found 537.1. |
| 17-77 | 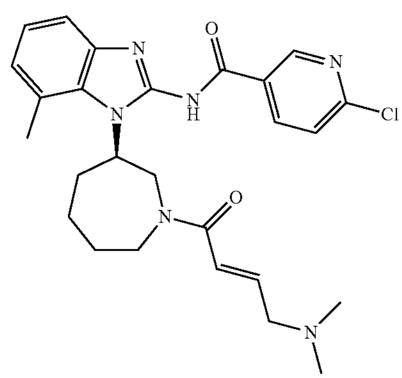 [SMILES: Cc1cccc2nc(NC(=O)c3ccc(Cl)nc3)n([C@@H]3CCCCN(C(=O)/C=C/CN(C)C)C3)c12] | ¹H-NMR (400 MHz, MeOD) δ 9.18 (d, J = 14.8 Hz, 1H), 8.53 (d, J = 8.3 Hz, 1H), 7.59 (d, J = 8.3 Hz, 1H), 7.37 (d, J = 8.0 Hz, 1H), 7.18 (t, J = 8.6 Hz, 1H), 7.08 (d, J = 7.7 Hz, 1H), 6.83 (dd, J = 6.4, 14.9 Hz, 1H), 6.74 (d, J = 14.2 Hz, 1H), 5.08 (s, 1H), 4.50 (t, J = 11.8 Hz, 1H), 4.32 (d, J = 12.7 Hz, 1H), 3.99 (m, 1H), 3.67 (m, 1H), 3.15 (m, 1H), 2.86 (m, 1H), 2.76 (s, 3H), 2.41 (s, 6H), 2.12 (s, 2H), 2.04 (m, 3H), 1.48 (m, 1H). MS calc. for $C_{26}H_{32}ClN_6O_2$ (M + H⁺) 495.22, found 495.1. |
| 17-78 | 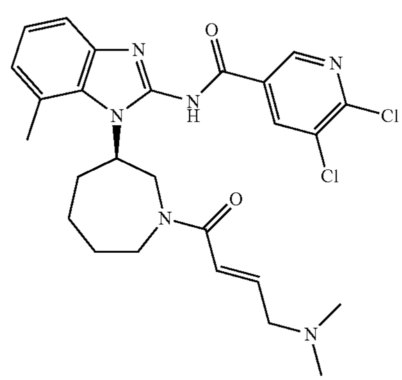 [SMILES: Cc1cccc2nc(NC(=O)c3cnc(Cl)c(Cl)c3)n([C@@H]3CCCCN(C(=O)/C=C/CN(C)C)C3)c12] | ¹H-NMR (400 MHz, MeOD) δ 9.09 (m, 1H), 8.63 (m, 1H), 7.38 (d, J = 8.1 Hz, 1H), 7.18 (t, J = 7.8 Hz, 1H), 7.09 (d, J = 7.7 Hz, 1H), 6.81 (s, 2H), 5.10 (s, 1H), 4.53 (m, 1H), 4.30 (d, J = 13.0 Hz, 1H), 3.97 (s, 1H), 3.71 (s, 1H), 3.53 (s, 2H), 3.14 (m, 1H), 2.85 (m, 1H), 2.76 (s, 3H), 2.57 (s, 6H), 2.21 (m, 1H), 2.10 (m, 2H), 1.49 (m, 1H). MS calculated for $C_{26}H_{31}Cl_2N_6O_2$ (M + H⁺) 529.18, found 529.0. |

| Ex. | Compound Structure | Physical Data (¹H NMR and MS) |
|---|---|---|
| 17-79 | 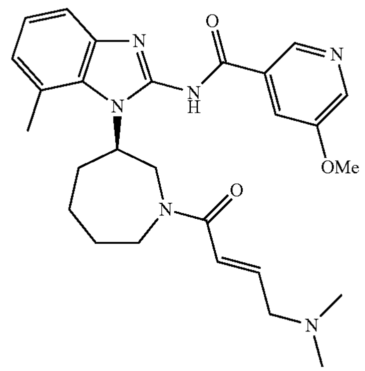 [SMILES: COc1cncc(C(=O)Nc2nc3cccc(C)c3n2[C@@H]2CCCCN(C(=O)/C=C/CN(C)C)C2)c1] | ¹H-NMR (400 MHz, MeOD) δ 9.02 (t, J = 1.7 Hz, 1H), 8.36 (d, J = 2.8 Hz, 1H), 8.13 (s, 1H), 7.38 (d, J = 8.0 Hz, 1H), 7.18 (t, J = 7.8 Hz, 1H), 7.09 (d, J = 7.5, 1H), 6.84 (m, 1H), 6.70 (d, J = 15.3 Hz, 1H), 5.10 (t, J = 11.0 Hz, 1H), 4.52 (m, 1H), 4.34 (d, J = 13.0 Hz, 1H), 4.03 (m, 1H), 3.98 (s, 3H), 3.64 (m, 1H), 3.25 (d, J = 6.3 Hz, 1H), 2.97 (m, 2H), 2.75 (d, J = 15.5 Hz, 3H), 2.34 (s, 6H), 2.13 (m, 4H), 1.48 (m, 1H). MS calculated for $C_{27}H_{35}N_6O_3$ (M + H⁺) 491.27, found 491.1. |
| 17-80 | 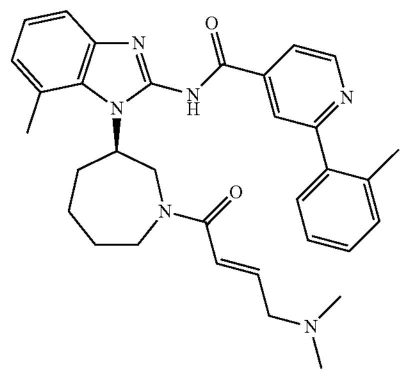 [SMILES: Cc1ccccc1-c1cc(C(=O)Nc2nc3cccc(C)c3n2[C@@H]2CCCCN(C(=O)/C=C/CN(C)C)C2)ccn1] | ¹H-NMR (400 MHz, MeOD) δ 8.76 (d, J = 5.2 Hz, 1H), 8.26 (m, 1H), 8.11 (d, J = 5.2 Hz, 1H), 7.42 (m, 2H), 7.34 (m, 3H), 7.19 (t, J = 7.8 Hz, 1H), 7.09 (d, J = 7.5 Hz, 1H), 6.81 (m, 1H), 6.68 (d, J = 15.2 Hz, 1H), 5.09 (t, J = 10.7 Hz, 1H), 4.50 (m, 1H), 4.33 (d, J = 12.7 Hz, 1H), 3.92 (m, 1H), 3.50 (m, 2H), 3.14 (m, 1H), 2.90 (m, 1H), 2.76 (s, 3H), 2.38 (s, 6H), 2.34 (s, 3H), 2.07 (m, 3H), 1.85 (m, 1H), 1.42 (m, 1H). MS calculated for $C_{33}H_{39}N_6O_2$ (M + H⁺) 551.31, found 551.1. |
| 17-81 | 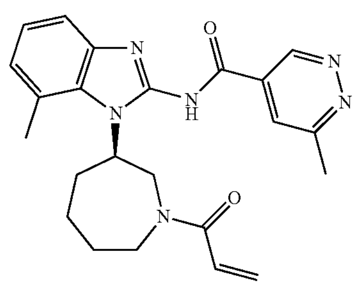 [SMILES: C=CC(=O)N1CCCC[C@@H](n2c(NC(=O)c3cnnc(C)c3)nc3cccc(C)c32)C1] | ¹H-NMR (400 MHz, MeOD) δ 9.68 (s, 1H), 8.22 (s, 1H), 7.40 (d, J = 7.9 Hz, 1H), 7.20 (t, J = 6.8 Hz, 1H), 7.11 (d, J = 7.4 Hz, 1H), 6.84 (dd, J = 12.3, 16.6 Hz, 1H), 6.30 (d, J = 16.8 Hz, 1H), 5.81 (d, J = 10.5 Hz, 1H), 5.12 (t, J = 10.7 Hz, 1H), 4.56 (t, J = 11.2 Hz, 1H), 4.31 (d, J = 12.3 Hz, 1H), 4.00 (m, 1H), 3.70 (m, 1H), 2.93 (m, 1H), 2.80 (s, 3H), 2.78 (s, 3H), 2.13 (m, 4H), 1.52 (m, 1H). MS calculated for $C_{23}H_{27}N_6O_2$ (M + H⁺) 419.21, found 419.0. |
| 17-82 | 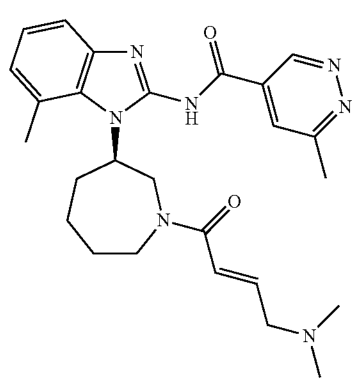 [SMILES: Cc1cc(C(=O)Nc2nc3cccc(C)c3n2[C@@H]2CCCCN(C(=O)/C=C/CN(C)C)C2)cnn1] | ¹H-NMR (400 MHz, MeOD) δ 9.69 (s, 1H), 8.22 (s, 1H), 7.41 (d, J = 8.0 Hz, 1H), 7.20 (t, J = 7.8 Hz, 1H), 7.11 (d, J = 1.5 Hz, 1H), 6.84 (m, 1H), 6.74 (d, J = 14.6 Hz, 1H), 5.12 (t, J = 11.0 Hz, 1H), 4.57 (m, 1H), 4.31 (d, J = 12.7 Hz, 1H), 4.00 (m, 1H), 3.70 (m, 1H), 3.46 (m, 2H), 2.93 (m, 1H), 2.80 (s, 3H), 2.78 (s, 3H), 2.31 (d, J = 73.1 Hz, 6H), 2.07 (m, 4H), 1.48 (m, 1H). MS calculated for $C_{26}H_{34}N_7O_2$ (M + H⁺) 476.27, found 476.0. |

| Ex. | Compound Structure | Physical Data (¹H NMR and MS) |
|---|---|---|
| 17-83 | 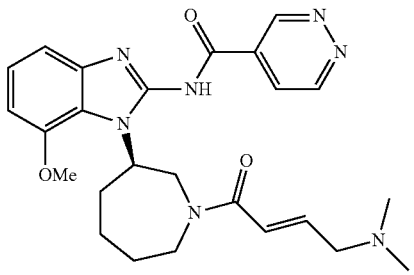 [SMILES: COc1cccc2nc(NC(=O)c3ccnnc3)n([C@@H]3CCCCN(C(=O)/C=C/CN(C)C)C3)c12] | ¹H-NMR (400 MHz, CDCl₃): ∂ 9.82 (d, J = 2.0 Hz, 0.6H), 9.78 (d, J = 2.0 Hz, 0.4H), 9.31 (br d, J = 5.2 Hz, 0.6H), 9.27 (br d, J = 5.2 Hz, 0.4H), 8.09 (dd, J = 5.2, 2.0 Hz, 0.6H), 8.06 (dd, J = 5.2, 2.0 Hz, 0.4H), 7.25-7.12 (m, 1H), 7.02-6.87 (m, 2H), 6.82-6.73 (m, 1H), 6.42 (dt, J = 15.2, 4.4, 4.4 Hz, 1H), 5.53-5.32 (m, 1H), 4.27-3.96 (m, 1H), 4.00-3.89 (m, 3H), 3.75-3.52 (m, 1H), 3.35-3.20 (m, 1H), 3.06 (br, 1.2H), 2.90 (br, 0.8H), 2.78-2.63 (m, 1H), 2.23 (s, 3H), 2.05 (s, 3H), 1.99-1.85 (m, 1H), 1.83-1.32 (m, 4H), 1.29-1.13 (m, 1H); MS calc. for $C_{25}H_{32}N_7O_3$ (M + H⁺) 478.25, found 478.2. |
| 17-84 | 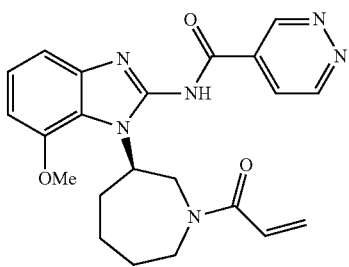 [SMILES: C=CC(=O)N1CCCC[C@@H](n2c(NC(=O)c3ccnnc3)nc3cccc(OC)c32)C1] | ¹H-NMR (400 MHz, CD₃CN): ∂ 12.3 (br s, 1H), 9.80-9.70 (m, 1H), 9.26-9.22 (m, 1H), 8.17-8.06 (m, 1H), 7.64-7.52 (m, 1H), 7.19-7.08 (m, 1H), 6.90-6.83 (m, 1H), 6.23-6.15 (m, 1H), 5.67-5.50 (m, 1H), 5.45-5.38 (m, 1H), 5.28-5.26 (m, 1H), 4.17-3.96 (m, 2H), 3.90-3.78 (m, 1H), 3.51-3.48 (m, 1H), 3.07 (s, 3H), 2.25-2.15 (m, 1H), 2.05-1.88 (m, 2H), 1.51-1.45 (m, 1H), 1.15-0.98 (m, 1H), 0.85-0.76 (m, 1H); MS calc. for $C_{22}H_{25}N_6O_3$ (M + H⁺) 421.19, found 421.2. |
| 17-85 | 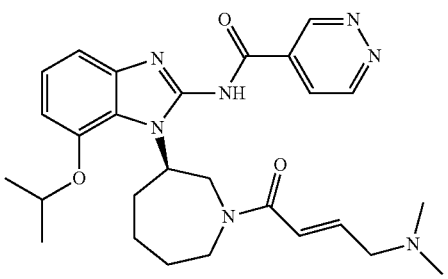 [SMILES: CC(C)Oc1cccc2nc(NC(=O)c3ccnnc3)n([C@@H]3CCCCN(C(=O)/C=C/CN(C)C)C3)c12] | ¹H-NMR (400 MHz, acetone-d6): ∂ 12.64 (br s, 1H), 9.74 (brd, J = 8.4 Hz, 1H), 9.28 (br d, J = 2.4 Hz, 1H), 8.26-8.04 (br m, 1H), 8.02-7.83 (br m, 1H), 7.27-7.12 (m, 1H), 6.99-6.86 (m, 1H), 6.81-6.70 (m, 1H), 6.60 (d, J = 15.2 Hz, 1H), 5.67-5.48 (m, 1H), 5.04-4.98 (m, 0.4H), 4.84-4.78 (m, 0.6H), 4.74-4.65 (m, 0.4H), 4.43-4.34 (m, 0.6H), 4.24-3.85 (m, 2H), 3.68-3.62 (m, 0.6H), 3.44-3.38 (m, 0.4H), 3.25-2.66 (br m, 8H), 2.28 (s, 1.2H), 2.25 (s, 1.8H), 2.06 (s, 1.2H), 2.02 (s, 1.8H), 1.90-1.95 (m, 1H), 1.53-1.50 (m, 2H), 1.49-1.48 (m, 3H); MS calculated for $C_{27}H_{36}N_7O_3$ (M + H⁺) 506.28, found 506.2. |
| 17-86 | 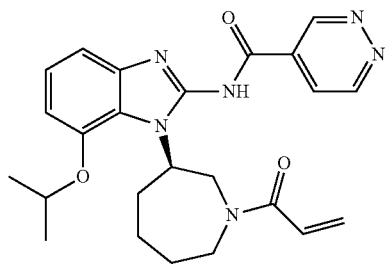 [SMILES: C=CC(=O)N1CCCC[C@@H](n2c(NC(=O)c3ccnnc3)nc3cccc(OC(C)C)c32)C1] | ¹H-NMR (400 MHz, CD₃CN): ∂ 12.32 (br s, 1H), 9.72-9.70 (m, 1H), 9.24 (d, J = 5.2 Hz, 0.6H), 9.21 (d, J = 5.2 Hz, 0.4H), 8.09 (dd, J = 1.6, 5.2 Hz, 0.6H), 8.06 (dd, J = 1.6, 5.2 Hz, 0.4H), 7.19-7.01 (m, 2H), 6.88-6.80 (m, 1H), 6.71-6.63 (m, 1H), 6.21-6.11 (m, 1H), 5.66-5.39 (m, 2H), 4.94-4.85 (m, 0.4H), 4.77-4.68 (m, 0.6H), 4.63-4.57 (m, 0.6H), 4.38-4.32 (m, 0.4H), 4.22-3.68 (m, 2H), 3.60-3.55 (m, 0.6H), 3.33-3.28 (m, 0.4H), 2.64-2.38 (m, 1H), 1.90-2.04 (m, 1H), 1.45-1.41 (m, 2H), 1.32-1.18 (m, 6H), 1.23-1.02 (m, 1H), 0.85-0.62 (m, 1H); MS calculated for $C_{24}H_{29}N_6O_3$ (M + H⁺) 449.22, found 449.2. |

| Ex. | Compound Structure | Physical Data (¹H NMR and MS) |
|---|---|---|
| 17-87 | 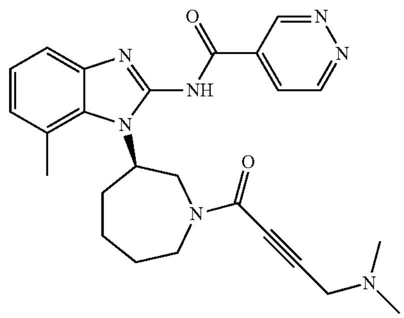 [SMILES: Cc1cccc2nc(NC(=O)c3ccnnc3)n([C@@H]3CCCCN(C(=O)C#CCN(C)C)C3)c12] | ¹H-NMR (400 MHz, CDCl₃): δ ¹H NMR (400 MHz, CDCl3) δ 12.53 (s, 1H), 9.83 (s, 1H), 9.42-9.23 (m, 1H), 8.07 (dd, J = 2.1, 5.2 Hz, 1H), 7.36-7.14 (m, 2H), 7.07-7.03 (m, 1H), 5.06-4.81 (m, 1H), 4.47-4.09 (m, 3H), 3.65-3.60 (m, 0.7H), 3.48 (s, 2H), 3.37-3.31 (m, 0.3H), 3.17-2.99 (m, 0.7H), 2.82-2.74 (m, 0.3H), 2.74 (s, 3H), 2.35 (s, 4.2H), 2.30-2.20 (m, 1H), 2.16-1.95 (m, 4H), 1.87(s, 1.8H), 1.50-1.40 (m, 1H); MS calculated for C₂₅H₃₀N₇O₂ (M + H⁺) 460.24, found 460.2. |
| 17-88 | 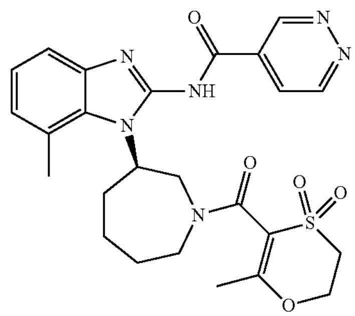 [SMILES: CC1=C(C(=O)N2CCCC[C@@H](n3c(NC(=O)c4ccnnc4)nc4cccc(C)c43)C2)S(=O)(=O)CCO1] | ¹H-NMR (400 MHz, CDCl₃): δ 12.44 (br s, 1H), 9.85 (s, 1H), 9.31(dd, J = 1.2, 5.2 Hz, 1H), 8.08 (d, J = 4.8, 2.0 Hz, 1H), 7.15-7.08 (m, 2H), 6.99 (d, J = 7.2 Hz, 1H), 5.08-4.94 (m, 1H), 4.75 (t, J = 5.7 Hz, 2H), 4.47-4.33(s, 2H), 4.15-4.02 (m, 1H), 3.59-3.21 (m, 3H), 2.70 (s, 3H), 2.66-2.53 (m, 1H), 2.29-1.65 (m, 5H), 1.89 (s, 1.5H), 1.64 (s, 1.5H); MS calculated for C₂₅H₂₉N₆O₅S (M + H⁺) 525.18, found 525.2. |
| 17-89 | 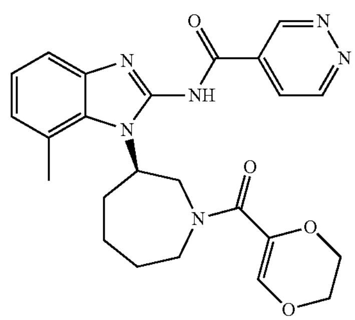 [SMILES: Cc1cccc2nc(NC(=O)c3ccnnc3)n([C@@H]3CCCCN(C(=O)C4=COCCO4)C3)c12] | ¹H-NMR (400 MHz, CDCl₃): δ 12.62 (s, 1H), 9.91 (s, 1H), 9.38 (d, J = 5.1, 0.8 Hz, 1H), 8.14 (dd, J = 2.0, 5.1Hz, 1H), 7.25-7.15 (m, 2H), 7.06 (d, J = 7.2 Hz, 1H), 6.89 (s, 1H), 5.18-4.95 (m, 1H), 4.78-3.74 (m, 6H), 3.70-3.2 (m, 2H), 2.85-2.57 (m, 1H), 2.73 (s, 3H), 2.28-1.99 (m, 4H), 1.58-1.40 (m, 1H); MS calculated for C₂₄H₂₇N₆O₄ (M + H⁺) 463.20, found 463.2. |
| 17-90 | 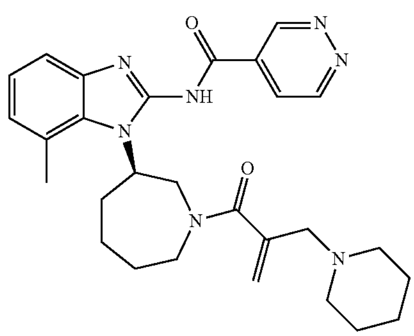 [SMILES: C=C(CN1CCCCC1)C(=O)N1CCCC[C@@H](n2c(NC(=O)c3ccnnc3)nc3cccc(C)c32)C1] | ¹H-NMR (400 MHz, CDCl₃): δ 12.56 (s, 1H), 9.95 (s, 1H), 9.39 (d, J = 5.0 Hz, 1H), 8.18-8.16 (m, 1H), 7.23-7.15 (m, 2H), 7.06 (d, J = 7.3 Hz, 1H), 5.39 (s, 1H), 5.20 (s, 1H), 5.13-5.09 (m, 1H), 4.47-4.03 (m, 2H), 3.95 - 3.87 (m, 1H), 3.60-2.90 (m, 3H), 2.78 (s, 3H), 2.77-2.65 (m, 1H), 2.52-2.40 (m, 4H), 2.23-2.16 (m, 1H), 2.10-1.87 (m, 4H), 1.67-1.45 (m, 6H); MS calculated for C₂₈H₃₆N₇O₂ (M + H⁺) 502.29, found 502.3. |
| 17-91 | 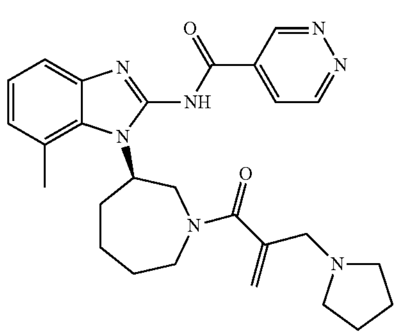 [SMILES: C=C(CN1CCCC1)C(=O)N1CCCC[C@@H](n2c(NC(=O)c3ccnnc3)nc3cccc(C)c32)C1] | ¹H NMR (400 MHz, CDCl₃): δ 12.62 (br s, 1H), 9.87-9.85 (m, 1H), 9.30 (d, J = 5.2 Hz, 1H), 8.09 (td, J = 2.1, 5.2 Hz, 1H), 7.15-7.07 (m, 2H), 6.97 (d, J = 7.2 Hz, 1H), 5.36 (s, 0.6H), 5.33 (d, J = 1.1 Hz, 0.4H), 5.18 (s, 0.4H), 5.10 (s, 0.6H), 5.06-4.96 (m, 1H), 4.38-4.28 (m, 1H), 4.07-3.85 (m, 1H), 3.61-2.84 (m, 4H), 2.70(s, 1.2H), 2.68 (s, 1.8H), 2.68-2.44 (m, 4H), 2.13-1.63 (m, 9H), 1.52-1.39 (m, 1H); MS calculated for C₂₇H₃₄N₇O₂ (M + H⁺) 488.27, found 488.2. |

| Ex. | Compound Structure | Physical Data ($^1$H NMR and MS) |
|---|---|---|
| 17-92 | 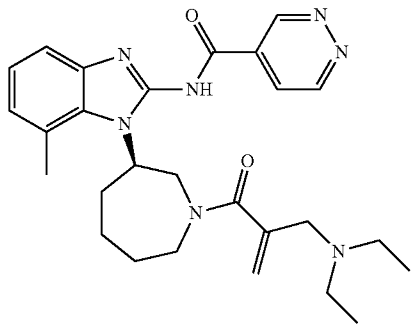 [SMILES: C=C(CN(CC)CC)C(=O)N1CCCC[C@@H](n2c(NC(=O)c3ccnnc3)nc3cccc(C)c32)C1] | $^1$H NMR (400 MHz, CDCl$_3$): δ 12.52 (br s, 1H), 9.97-9.68 (m, 1H), 9.31 (dd, J = 1.3, 5.2 Hz, 1H), 8.10-8.07 (m, 1H), 7.18-7.05 (m, 2H), 6.98 (d, J = 7.3, 1H), 5.29 (s, 0.6H), 5.24 (s, 0.4H), 5.10 (s, 0.6H), 5.07 (s, 0.4H), 5.12-4.97 (m, 1H), 4.43-4.25 (m, 1H), 4.07-3.76 (m, 1H), 3.53-3.25 (m, 2H), 2.93-2.86(m, 1H), 2.70(s, 3H), 2.69-2.32 (1H, 5H), 2.15-1.66 (m, 5H), 1.56-1.46 (m, 1H), 1.03 (t, J = 7.1 Hz, 1.8H), 0.96 (t, J = 7.1 Hz, 4.2H); MS calc. for C$_{27}$H$_{36}$N$_7$O$_2$ (M + H$^+$) 490.29, found 490.3. |
| 17-93 | 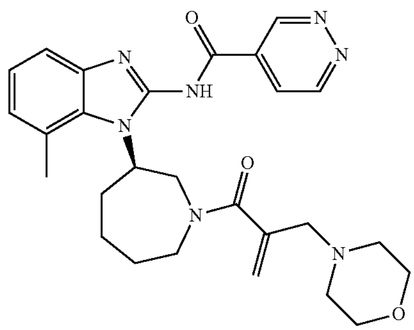 [SMILES: C=C(CN1CCOCC1)C(=O)N1CCCC[C@@H](n2c(NC(=O)c3ccnnc3)nc3cccc(C)c32)C1] | $^1$H-NMR (400 MHz, CDCl$_3$): δ 12.49 (s, 1H), 9.86 (dd, J = 1.6, 2.0 Hz, 1H), 9.31 (dd, J = 1.2, 5.2 Hz, 1H), 8.08 (dd, J = 2.0, 5.2 Hz, 1H), 7.15 (d, J = 7.2 Hz, 1H), 7.12-7.08 (m, 1H), 6.97(dd, J = 7.3 Hz, 1H), 5.37 (s, 1H), 5.18 (s, 1H), 5.08-5.00 (m, 1H), 4.40-4.02 (m, 2H), 3.63 (dd, J = 4.4, 4.6 Hz, 4H), 3.54-3.49 (m, 1H), 3.45 (d, J = 13.4 Hz, 1H), 2.93 (d, J = 13.5 Hz, 1H), 2.71-2.60 (m, 1H), 2.69 (s, 3H), 2.53-2.39 (m, 4H), 2.14-1.93 (m, 5H), 1.51-1.42 (m, 1H); MS calculated for C$_{27}$H$_{34}$N$_7$O$_3$ (M + H$^+$) 504.26, found 504.3. |
| 17-94 | 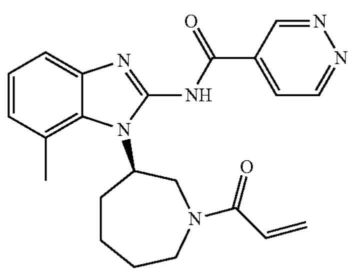 [SMILES: C=CC(=O)N1CCCC[C@@H](n2c(NC(=O)c3ccnnc3)nc3cccc(C)c32)C1] | $^1$H-NMR (400 MHz, CDCl$_3$) δ 12.59 (br. s, 1H), 9.93-9.89 (m, 1H), 9.40-9.38 (m, 1H), 8.17-8.13 (m, 1H), 7.29-7.17 (m, 2H), 7.11-7.07 (m, 1H), 6.68-6.58 (m, 1H), 6.51-6.36 (m, 1H), 5.78-5.70 (m, 1H), 5.13-5.07 (m, 1H), 4.50-4.46 (m, 1H), 4.35 (dd, J = 10.5, 13.6 Hz, 1H), 3.97-3.90 (m, 1H), 3.68-3.61 (m, 1H), 2.93-2.84 (m, 1H), 2.79 (s, 3H), 2.18-2.02 (m, 4H), 1.49-1.43 (m, 1H). MS calculated for C$_{22}$H$_{25}$N$_6$O$_2$ (M + H$^+$) 405.20, found 405.1. |
| 17-95 | 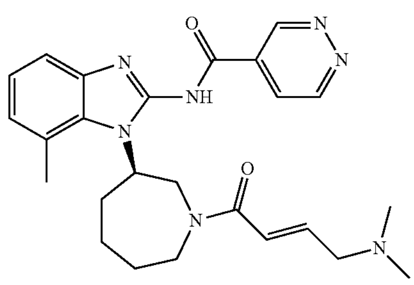 | $^1$H-NMR (400 MHz, CDCl$_3$) δ 12.57 (br. s, 1H), 9.92-9.88 (m, 1H), 9.38-9.37 (m, 1H), 8.16- 8.12 (m, 1H), 7.24-7.15 (m, 2H), 7.09-7.03 (m, 1H), 6.94-6.88 (m, 1H), 6.51-6.43 (m, 1H), 5.12-5.5.03 (m, 1H), 4.48- 4.43 (m, 1H), 4.35-4.29 (m, 1H), 3.96-3.89 (m, 1H), 3.66-3.59 (m, 1H), 3.17-3.07 (m, 2H), 2.96-2.82 (m, 1H), 2.77 (s, 3H), 2.30 (s, 6H), 2.20-2.02 (m, 4H), 1.49-1.43 (m, 1H). MS calculated for C$_{25}$H$_{32}$N$_7$O$_2$ (M + H$^+$) 462.25, found 462.2. |
| 17-96 | 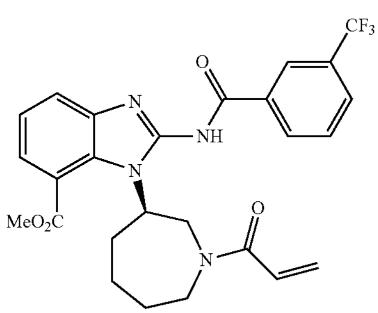 [SMILES: C=CC(=O)N1CCCC[C@@H](n2c(NC(=O)c3cccc(C(F)(F)F)c3)nc3cccc(C(=O)OC)c32)C1] | $^1$H-NMR (400 MHz, DMSO) δ 8.55-8.53 (m, 1H), 8.47-8.45 (m, 1H), 7.91 (d, J = 7.8 Hz, 1H), 7.82 (t, J = 7.6 Hz, 1H), 7.77 (t, J = 7.8 Hz, 1H), 7.58 (dd, J = 7.7, 19.0 Hz, 1H), 7.34 (t, J = 7.9 Hz, 1H), 6.85-6.63 (m, 1H), 6.16 (dd, J = 2.3, 16.7 Hz, 1H), 5.69-5.52 (m, 1H), 4.80-4.52 (m, 1.5H), 4.30 (t, J = 11.7 Hz, 0.5H), 4.16-3.95 (m, 1.5H), 3.89 (br s, 3.5H), 3.54-3.49 (m, 0.5H), 3.25-3.20 (m, 0.5H), 2.90-2.70 (m, 1H), 2.22-1.93 (m, 3H), 1.90-1.80 (m, 1H), 1.41-1.22 (m, 2H). MS calculated for C$_{26}$H$_{26}$F$_3$N$_4$O$_4$ (M + H$^+$) 515.18, found 515.1. |

| Ex. | Compound Structure | Physical Data (¹H NMR and MS) |
| --- | --- | --- |
| 17-97 | 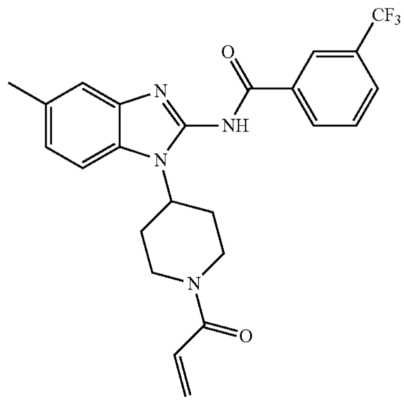 [SMILES: C=CC(=O)N1CCC(n2c(NC(=O)c3cccc(C(F)(F)F)c3)nc3cc(C)ccc32)CC1] | ¹H-NMR (DMSO-d$_6$, 400 MHz): ∂ 12.79 (s, 1H), 8.46-8.40 (m, 2H), 7.88 (d, J = 8.0 Hz, 1H), 7.70-7.63 (m, 1H), 7.51 (d, J = 8.4 Hz, 1H), 7.38 (s, 1H), 7.07 (d, J = 8.4 Hz, 1H), 6.96-6.89 (m, 1H), 6.22-6.18 (m, 1H), 5.75-5.69 (m, 1H), 5.04-4.97 (m, 1H), 4.73-4.65 (m, 1H), 4.34-4.29 (m, 1H), 3.30-3.28 (m, 1H), 2.87-2.81 (m, 1H), 2.68-2.54 (m, 2H), 2.40 (s, 3H), 2.00-1.93 (m, 2H); MS calculated for C$_{24}$H$_{24}$F$_3$N$_4$O$_2$ (M + H⁺) 457.19, found 457.3. |
| 17-98 | 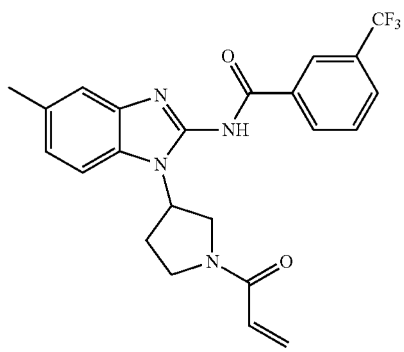 [SMILES: C=CC(=O)N1CCC(n2c(NC(=O)c3cccc(C(F)(F)F)c3)nc3cc(C)ccc32)C1] | ¹H-NMR (DMSO-d$_6$, 400 MHz): ∂ 12.83 (s, 1H), 8.51-8.48 (m, 1H), 8.42 (s, 1H), 7.88 (d, J = 8.0 Hz, 1H), 7.69-7.64 (m, 1H), 7.48-7.39 (m, 2H), 7.10 (d, J = 8.4 Hz, 1H), 6.78-6.54 (m, 1H), 6.26-6.17 (m, 1H), 5.78-5.60 (m, 2H), 4.27-4.22 (m, 0.5H), 4.13-4.00 (m, 1.5H), 3.95-3.86 (m, 1H), 3.79-3.73 (m, 0.5H), 3.58-3.51 (m, 0.5H), 2.83-2.71 (m, 1H), 2.40 (s, 3H), 2.38-2.25 (m, 1H); MS calculated for C$_{23}$H$_{22}$F$_3$N$_4$O$_2$ (M + H⁺) 443.16, found 442.8. |
| 17-99 | 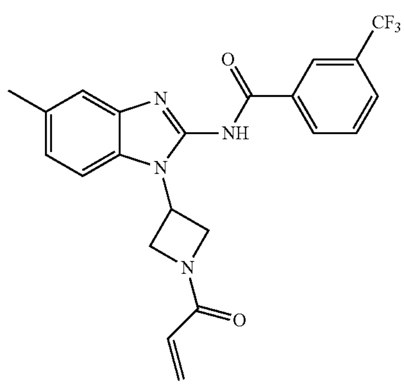 [SMILES: C=CC(=O)N1CC(n2c(NC(=O)c3cccc(C(F)(F)F)c3)nc3cc(C)ccc32)C1] | ¹H-NMR (DMSO-d$_6$, 400 MHz): ∂ 12.86 (s, 1H), 8.46-8.42 (m, 2H), 7.87 (d, J = 7.8 Hz, 1H), 7.63 (t, J = 7.8 Hz, 1H), 7.43 (d, J = 8.4 Hz, 1H), 7.40 (s, 1H), 7.13 (d, J = 7.8 Hz, 1H), 6.45 (dd, J = 10.2, 16.6 Hz, 1H), 6.24 (dd, J = 1.9, 17.1 Hz, 1H), 5.86-5.74 (m, 2H), 5.03-5.0 (m, 1H), 4.77-4.68 (m, 2H), 4.46 (t, J = 9.7 Hz, 1H), 2.40 (s, 3H); MS calculated for C$_{22}$H$_{20}$F$_3$N$_4$O$_2$ (M + H⁺) 429.15, found 429.0. |
| 17-100 | 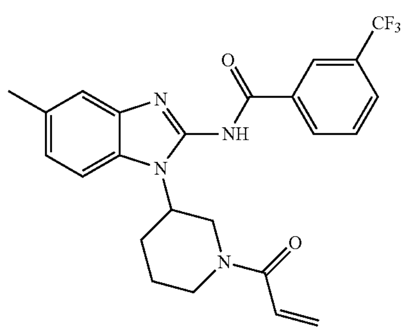 [SMILES: C=CC(=O)N1CCCC(n2c(NC(=O)c3cccc(C(F)(F)F)c3)nc3cc(C)ccc32)C1] | ¹H-NMR (DMSO-d$_6$, 400 MHz): ∂ 12.83 (s, 1H), 8.46 (d, J = 8.0 Hz, 2H), 7.89 (d, J = 8.0 Hz, 1H), 7.75-7.63 (m, 2H), 7.39 (s, 1H), 7.09 (d, J = 8.4 Hz, 1H), 6.95-6.79 (m, 1H), 6.20-6.13 (m, 1H), 5.78-5.59 (m, 1H), 4.79-4.56 (m, 2H), 4.23-4.06 (m, 2H), 3.70-3.65 (m, 0.5H), 3.27-3.21 (m, 0.5H), 2.85-2.66 (m, 1H), 2.39 (s, 3H), 2.00-1.91 (m, 2H), 1.64-1.5 (m, 1H); MS calculated for C$_{24}$H$_{24}$F$_3$N$_4$O$_2$ (M + H⁺) 457.18, found 457.3. |

| Ex. | Compound Structure | Physical Data (¹H NMR and MS) |
|---|---|---|
| 17-101 | 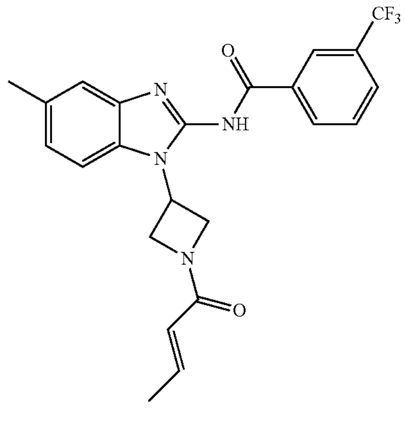 [SMILES: C/C=C/C(=O)N1CC(n2c(NC(=O)c3cccc(C(F)(F)F)c3)nc3cc(C)ccc32)C1] | ¹H-NMR (DMSO-d₆, 400 MHz): δ 12.86 (s, 1H), 8.46-8.42 (m, 2H), 7.87 (d, J = 7.8 Hz, 1H), 7.63 (t, J = 7.8 Hz, 1H), 7.42 (d, J = 8.4 Hz, 1H), 7.40 (s, 1H), 7.13 (d, J = 7.8 Hz, 1H), 6.84-675 (m, 1H), 6.16-6.12 (m, 1H), 5.86-5.74 (m, 1H), 4.99-4.94 (m, 1H), 4.73-4.62 (m, 2H), 4.45-4.40 (m, 1H), 2.40 (s, 3H), 1.88 (d, J = 1.0 Hz, 3H); MS calculated for $C_{23}H_{22}F_3N_4O_2$ (M + H⁺) 443.16, found 443.0. |
| 17-102 | 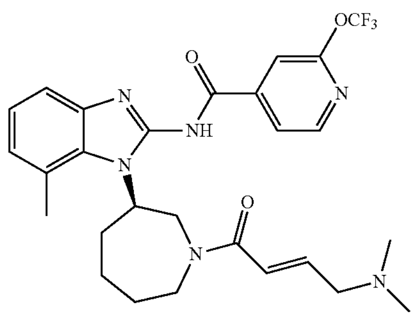 [SMILES: Cc1cccc2nc(NC(=O)c3ccnc(OC(F)(F)F)c3)n([C@@H]3CCCCN(C(=O)/C=C/CN(C)C)C3)c12] | ¹H-NMR (400 MHz, DMSO) δ 8.56 (d, J = 5.1 Hz, 1H), 8.05 (d, J = 5.1 Hz, 1H), 7.79 (s, 1H), 7.49 (d, J = 7.6 Hz, 1H), 7.16 (m, 1H), 7.07 (t, J = 6.2 Hz, 1H), 6.70 (m, 2H), 4.86 (m, 1H), 4.31 (dd, J = 10.7, 12.8 Hz, 1H), 4.15 (dd, J = 2.5, 12.7 Hz, 1H), 3.90 (m, 1H), 3.57 (dt, J = 5.5, 13.8 Hz, 1H), 3.07 (m, 1H), 2.74 (m, 2H), 2.70 (s, 3H), 2.38 (s, 6H), 1.93 (m, 4H), 1.36 (m, 1H). MS calculated for $C_{27}H_{32}F_3N_6O_3$ (M + H⁺) 545.24, found 545.2. |
| 17-103 | 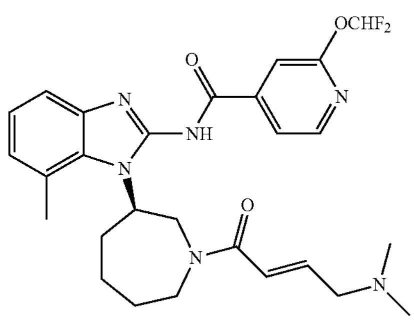 [SMILES: Cc1cccc2nc(NC(=O)c3ccnc(OC(F)F)c3)n([C@@H]3CCCCN(C(=O)/C=C/CN(C)C)C3)c12] | ¹H-NMR (400 MHz, CD₂Cl₂) δ 12.61 (s, 1H), 8.31 (d, J = 5.1 Hz, 1H), 7.88 (dd, J = 1.3, 5.2 Hz, 1H), 7.67 (m, 1H), 7.43 (t, J = 73.3 Hz, 1H), 7.24 (d, J = 7.3 Hz, 1H), 7.17 (t, J = 7.7 Hz, 1H), 7.06 (d, J = 7.3 Hz, 1H), 6.85 (m, 1H), 6.63 (d, J = 15.1 Hz, 1H), 5.03 (m, 1H), 4.36 (d, J = 7.8 Hz, 2H), 3.91 (m, 1H), 3.62 (m, 1H), 3.30 (br s, 2H), 2.88 (q, J = 11.9 Hz, 1H), 2.76 (s, 3H), 2.42 (s, 6H), 2.15 (m, 1H), 2.03 (m, 3H), 1.40 (m, 1H). ¹⁹F-NMR (376 MHz, CD₂Cl₂) δ −88.83. MS calculated for $C_{27}H_{33}F_2N_6O_3$ (M + H⁺) 527.25, found 527.2. |
| 17-104 | 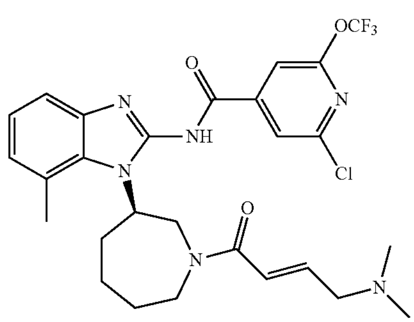 [SMILES: Cc1cccc2nc(NC(=O)c3cc(Cl)nc(OC(F)(F)F)c3)n([C@@H]3CCCCN(C(=O)/C=C/CN(C)C)C3)c12] | ¹H-NMR (400 MHz, DMSO) δ 8.05 (s, 1H), 7.75 (s, 1H), 7.50 (d, J = 7.2, 1H), 7.17 (m, 1H), 7.09 (t, J = 6.3, 1H), 6.71 (m, 1H), 6.64 (t, J = 13.2, 1H), 4.96 (m, 1H), 4.41 (m, 1H), 4.09 (dd, J = 3.1, 12.9, 1H), 3.89 (m, 1H), 3.49 (m, 1H), 2.98 (m, 2H), 2.72 (s, 1H), 2.68 (m, 3H), 2.17 (s, 6H), 2.02 (m, 2H), 1.94 (m, 1H), 1.81 (m, 1H), 1.35 (m, 1H). MS calculated for $C_{27}H_{31}ClF_3N_6O_3$ (M + H⁺) 579.20, found 579.2. |

| Ex. | Compound Structure | Physical Data (¹H NMR and MS) |
|---|---|---|
| 17-105 | 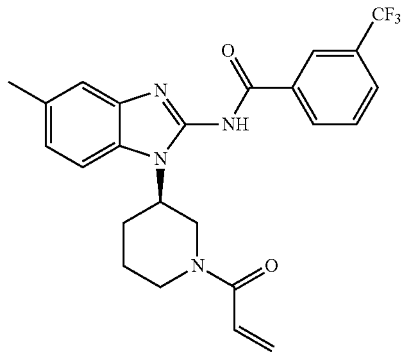 [SMILES: C=CC(=O)N1CCC[C@@H](n2c(NC(=O)c3cccc(C(F)(F)F)c3)nc3cc(C)ccc32)C1] | ¹H-NMR (400 MHz, DMSO-$d_6$): ∂ 12.84 (s, 1H), 8.46 (d, J = 8 Hz, 2H), 7.89 (d, J = 8 Hz, 1H), 7.75-7.63 (m, 2H), 7.39 (s, 1H), 7.09 (d, J = 8 Hz, 1H), 6.95-6.79 (m, 1H), 6.19-6.13 (m, 1H), 5.75-5.59 (m, 1H), 4.79-4.56 (m, 2H), 4.27-4.03 (m, 2H), 3.67 (t, J = 11.6 Hz, 1H), 3.28-3.21 (m, 1H), 1.64-1.61 (m, 1H); MS calculated for $C_{24}H_{24}F_3N_4O_2$ (M + H⁺) 457.18 found 456.8. |
| 17-106 | 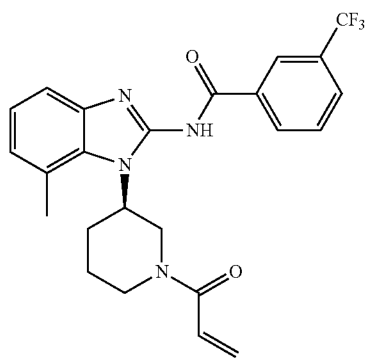 [SMILES: C=CC(=O)N1CCC[C@@H](n2c(NC(=O)c3cccc(C(F)(F)F)c3)nc3cccc(C)c32)C1] | ¹H-NMR (400 MHz, DMSO-$d_6$): ∂ 12.97 (br s, 1H), 8.51 (s, 1H), 8.46 (d, J = 8 Hz, 1H), 7.91 (d, J = 7.6 Hz, 1H), 7.78 (d, J = 7.2 Hz, 1H), 7.47 (d, J = 7.6 Hz, 1H), 7.15-7.12 (m, 1H), 7.04-7.02 (m, 2H), 6.17-6.10 (m, 1H), 5.79-5.70 (m, 1H), 4.74-4.64 (m, 3H), 4.31-4.0 (m, 1H), 3.3-3.15 (m, 1H), 2.66 (m, 3H), 2.10-1.95 (m, 2H), 1.59-1.6 (m, 1H); MS calculated for $C_{24}H_{24}F_3N_4O_2$ (M + H⁺) 457.18, found 457.20 |
| 17-107 | 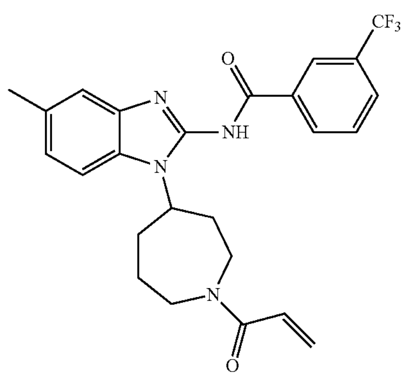 [SMILES: C=CC(=O)N1CCCC(n2c(NC(=O)c3cccc(C(F)(F)F)c3)nc3cc(C)ccc32)CC1] | ¹H-NMR (400 MHz, DMSO-$d_6$): ∂ 12.74 (s, 1H), 8.45-8.37 (m, 2H), 7.87 (d, J = 7.4 Hz, 1H), 7.67 (t, J = 7.8 Hz, 1H), 7.50 (d, J = 8.3 Hz, 1H), 7.38 (s, 1H), 7.08 (d, J = 8.3 Hz, 1H), 6.92-6.81 (m, 1H), 6.29-6.24 (m, 1H), 5.78-5.67 (m, 1H), 4.90 (br s, 1H), 3.92-3.43 (m, 4H), 2.60-2.56 (m, 2H), 2.39 (s, 3H), 2.10-1.78 (m, 4H), 1.25-1.21 (m, 1H); MS calculated for $C_{25}H_{26}F_3N_4O_2$ (M + H⁺) 471.19, found 471.0. |
| 17-108 | 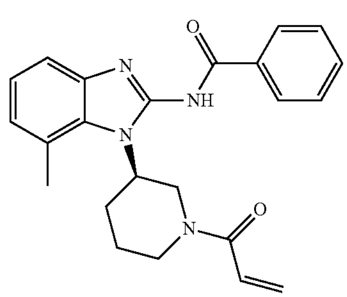 [SMILES: C=CC(=O)N1CCC[C@@H](n2c(NC(=O)c3ccccc3)nc3cccc(C)c32)C1] | ¹H-NMR (400 MHz, DMSO-$d_6$): ∂ 12.94 (s, 1H), 8.21 (d, J = 6 Hz, 2H), 7.45-7.43 (m, 4H), 7.13-6.91 (m, 3H), 6.20-6.13 (m, 1H), 5.75-5.65 (m, 1H), 4.71-4.45 (m, 3H), 4.24-4.07 (m, 1H), 2.74-2.63 (m, 4H), 2.07-1.95 (m, 2H), 1.59-1.56 (m, 2H); MS calculated for $C_{23}H_{25}N_4O_2$ (M + H⁺) 389.19, found 389.2. |

-continued

| Ex. | Compound Structure | Physical Data (¹H NMR and MS) |
|---|---|---|
| 17-109 | 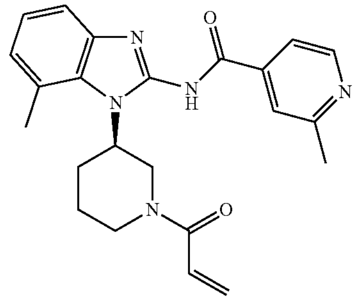 [SMILES: C=CC(=O)N1CCC[C@@H](n2c(NC(=O)c3ccnc(C)c3)nc3cccc(C)c32)C1] | ¹H-NMR (400 MHz, DMSO-d₆) δ 8.63 (d, J = 5.0 Hz, 1H), 7.90 (s, 1H), 7.86 (s, 1H), 7.48 (d, J = 7.9 Hz, 1H), 7.14 (t, J = 7.7 Hz, 1H), 7.05 (d, J = 7.4 Hz, 1H), 6.93 (m, 1H), 6.17 (s, 1H), 5.76 (s, 1H), 4.73 (s, 1H), 4.63 (m, 1H), 4.47 (m, 1H), 4.11 (m, 1H), 3.20 (m, 1H), 2.74 (m, 1H), 2.65 (d, J = 9.6, 3H), 2.59 (s, 3H), 2.08 (s, 1H), 1.93 (m, 1H), 1.60 (m, 1H); MS calculated for $C_{23}H_{26}N_5O_2$ (M + H⁺) 404.20, found 404.2. |
| 17-110 | 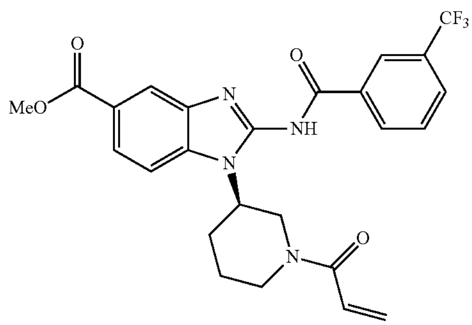 [SMILES: C=CC(=O)N1CCC[C@@H](n2c(NC(=O)c3cccc(C(F)(F)F)c3)nc3cc(C(=O)OC)ccc32)C1] | ¹H-NMR (400 MHz, DMSO-d₆): ∂ 13.10 (s, 1H), 8.48 (d, J = 7.8 Hz, 2H), 8.18 (s, 1H), 7.92-7.89 (m, 3H), 7.76 (d, J = 7.8 Hz, 1H), 6.96-6.79 (m, 1H), 6.20-6.13 (m, 1H), 5.77-5.61 (m, 1H), 4.85-72 (m, 1H), 4.63-4.55 (m, 1H), 4.40-4.20 (m, 1H), 4.18-4.07 (m, 0.5H), 3.88 (s, 3H), 3.75-3.68 (m, 0.5H), 3.27-3.21 (m, 1H), 2.88-2.68 (m, 1H), 2.06-1.91 (m, 2H), 1.69-1.59 (m, 1H); MS calculated for $C_{25}H_{24}F_3N_4O_4$ (M + H⁺) 501.17, found 501.2. |
| 17-111 | 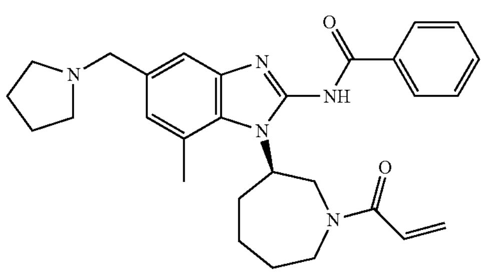 [SMILES: C=CC(=O)N1CCCC[C@@H](n2c(NC(=O)c3ccccc3)nc3cc(CN4CCCC4)cc(C)c32)C1] | ¹H-NMR (400 MHz, acetonitrile-d₃): ∂ 12.53 (s, 1H), 8.20-8.15 (m, 2H), 7.46-7.36 (m, 3H), 7.25 (s, 0.3H), 7.24 (s, 0.7H), 6.90 (s, 1H), 6.70-6.63 (m, 1H), 6.17 (dd, J = 2.0, 16.8 Hz, 0.3H ), 6.13 (dd, J = 2.0, 16.8 Hz, 0.7H), 5.61 (dd, J = 2.0, 10.4 Hz, 0.7H), 5.52 (dd, J = 2.0, 10.4 Hz, 0.3H), 4.91-4.68 (m, 1H), 4.33-4.28 (m, 1H), 4.21-4.16 (m, 1H), 3.93-3.79 (m, 1H), 3.54 (s, 2H), 3.54-3.28 (m, 1H), 2.86-2.63 (m, 2H), 2.61 & 2.55 (s & s, 3H), 2.42-2.37 (m, 2H), 2.02-1.84 (m, 5H), 1.68-1.64 (m, 4H), 1.39-1.27 (m, 1H); MS calculated for $C_{29}H_{36}N_5O_2$ (M + H⁺) 486.28, found 486.20. |
| 17-112 | 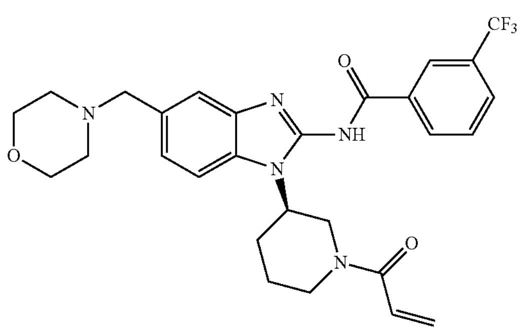 [SMILES: C=CC(=O)N1CCC[C@@H](n2c(NC(=O)c3cccc(C(F)(F)F)c3)nc3cc(CN4CCOCC4)ccc32)C1] | ¹H-NMR (400 MHz, DMSO-d₆): ∂ 12.87(s, 1H), 8.46 (d, J = 7.2 Hz, 2H), 7.89 (d, J = 7.6 Hz, 1H), 7.75-7.69 (m, 2H), 7.54 (s, 1H), 7.72 (s, 1H), 6.95-6.79 (m, 1H), 6.19-6.13 (m, 1H), 5.75-5.59 (m, 1H), 4.80-4.57 (m, 2H), 4.28-4.08 (m, 2H), 3.59-3.53 (m, 6H), 2.84-2.62 (m, 2H), 2.37-2.32 (m, 3H), 2.01-1.93 (m, 2H), 1.64-1.61 (m, 1H); MS calculated for $C_{28}H_{31}F_3N_5O_3$ (M + H⁺) 542.23, found 542.2. |
| 17-113 | 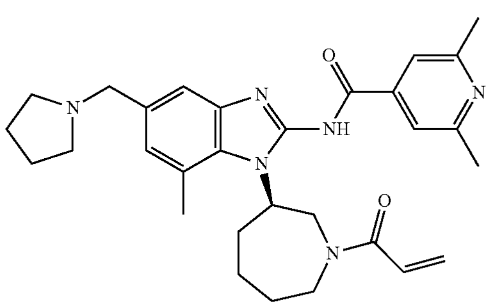 [SMILES: C=CC(=O)N1CCCC[C@@H](n2c(NC(=O)c3cc(C)nc(C)c3)nc3cc(CN4CCCC4)cc(C)c32)C1] | ¹H NMR (400 MHz, CDCl3) δ 7.70 (m, 2H), 7.50-7.39 (m, 1H), 7.20-7.14 (m, 1H), 6.59 (m, 1H), 6.50-6.43 (m, 0.3H), 6.36 (m, 0.7H), 5.74 (m, 1H), 5.08-4.97 (m, 1H), 4.40-4.35 (m, 2H), 4.30-4.19 (m, 1H), 4.10-3.86 (m, 2H), 3.69-3.55 (m, 2H), 2.98-2.86 (m, 1H), 2.76 (s, 3H), 2.62 (s, 6H), 2.15-1.91 (br, 5H), 1.48-1.30 (m, 8H); MS calculated for $C_{30}H_{39}N_6O_2$ (M + H⁺) 515.31, found 515.3. |

| Ex. | Compound Structure | Physical Data (¹H NMR and MS) |
|---|---|---|
| 17-114 | 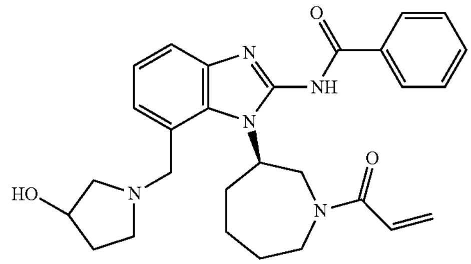 [SMILES: C=CC(=O)N1CCCC[C@@H](n2c(NC(=O)c3ccccc3)nc3cccc(CN4CCC(O)C4)c32)C1] | ¹H-NMR (CDCl₃, 400 MHz): δ 12.85 (br s, 1H), 8.31-8.28(m, 2H), 7.54-7.47 (m, 3H), 7.28-7.07(m, 3H), 6.71-6.61(m, 1H), 6.46-6.28(m, 1H), 5.82-5.61(m, 1H), 5.32(s, 1H), 5.43-5.12 (br m, 2H), 5.01-4.86 (m, 1H), 4.75-4.30 (m, 4H), 4.09-3.95(m, 1H), 3.90-3.51(m, 2H), 3.09-2.50 (m, 2H), 2.52-2.35(m, 1H), 2.2-1.99(m, 6H), 1.52-1.35(m, 1H); MS calculated for C₂₈H₃₄N₅O₃ (M + H⁺) 488.26, found 488.2. |
| 17-115 | 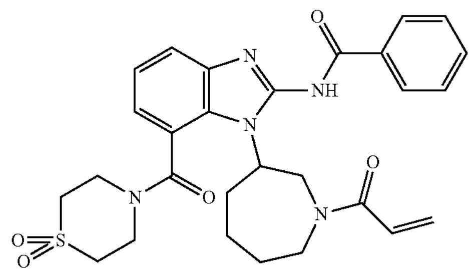 [SMILES: C=CC(=O)N1CCCCC(n2c(NC(=O)c3ccccc3)nc3cccc(C(=O)N4CCS(=O)(=O)CC4)c32)C1] | ¹H-NMR (400 MHz, CDCl₃): δ NMR (400 MHz,) δ 8.36-8.21 (m, 2H), 7.51 (m, 3H), 7.41 (dd, J = 1.6, 0.8 Hz, 1H), 7.26 (dd, J = 7.6 Hz, 1H), 7.08 (dd, J = 7.6, 0.8 Hz, 1H), 6.67-6.55 (m, 2H), 5.82 (dd, J = 2.6, 9.5, 1H), 4.68-4.36 (m, 4H), 4.28 (d, J = 11.7, 1H), 4.12-4.05 (m, 1H), 4.01-3.85 (m, 3H), 3.63-3.57 (m, 1H), 3.46-3.40 (m 1H), 3.14-3.06 (m, 1H), 2.99-2.94 (m, 1H), 2.75-2.66 (m, 1H), 2.29-2.01 (m, 5H), 1.37-1.26 (m, 1H); MS calculated for C₂₈H₃₂N₅O₅S (M + H⁺) 550.20, found 550.2. |
| 17-116 | 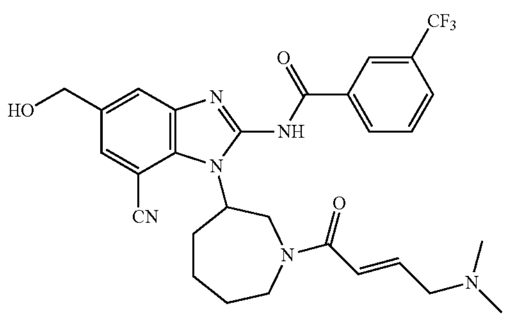 [SMILES: CN(C)C/C=C/C(=O)N1CCCCC(n2c(NC(=O)c3cccc(C(F)(F)F)c3)nc3cc(CO)cc(C#N)c32)C1] | ¹H-NMR (400 MHz, CDCl₃): δ 8.56 (br s, 1H), 8.38-8.30 (m, 1H), 7.83-7.75 (m, 1H), 7.68-7.65 (s, 0.3H), 7.60-7.56 (m, 2H), 7.43 (s, 0.7H), 7.05-6.92 (m, 1H), 6.58-6.47 (m, 1H), 5.32-5.22 (m, 1H), 4.83-4.74 (m, 2H), 4.65-4.48 (m, 2H), 4.20-4.05 (m, 0.4H), 3.93-3.82 (m, 0.6H), 3.75-3.67 (m, 0.8H), 3.55-3.49 (m, 0.2H), 3.20-3.12 (m, 2H), 3.02-2.55 (m, 2H), 2.17 (s, 3H), 2.17-2.01 (m, 2H); ¹⁹F-NMR (376 MHz, CDCl₃) δ −62.57. MS calculated for C₂₉H₃₂F₃N₆O₃ (M + H⁺) 569.24, found 569.3. |
| 17-117 | 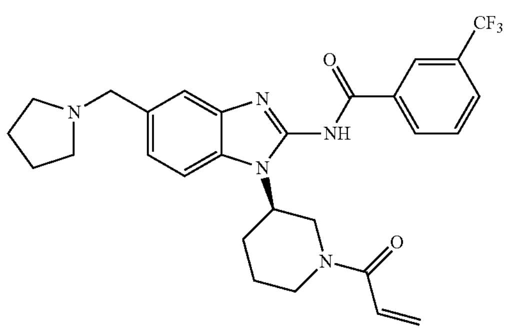 [SMILES: C=CC(=O)N1CCC[C@@H](n2c(NC(=O)c3cccc(C(F)(F)F)c3)nc3cc(CN4CCCC4)ccc32)C1] | ¹H-NMR (400 MHz, DMSO-d₆): δ 13.10 (s, 1H), 10.30 (S, 1H), 8.47(d, J = 7.2 Hz, 2H), 7.92-7.86 (m, 2H), 7.77-7.69 (m, 2H), 7.46 (br s, 1H), 6.96-6.78 (m, 1H), 6.19-6.15 (m, 1H), 5.76-5.60(m, 1H), 4.83-4.60 (m, 2H), 4.58 (s, 1H), 4.30-4.09 (m, 2H), 3.70 (s, 1H), 3.29 (br s, 2H), 2.86-2.67 (m, 2H), 2.02-1.94 (m, 6H), 1.65-1.62 (m, 1H); MS calculated for C₂₈H₃₁F₃N₅O₂ (M + H⁺) 526.24, found 526.1. |
| 17-118 | 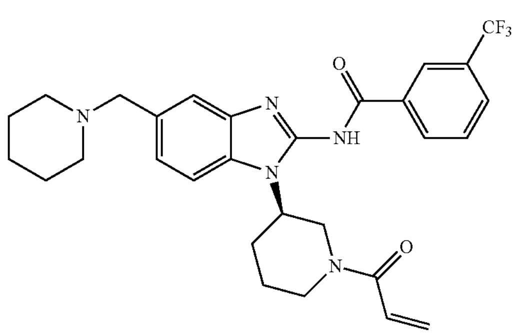 [SMILES: C=CC(=O)N1CCC[C@@H](n2c(NC(=O)c3cccc(C(F)(F)F)c3)nc3cc(CN4CCCCC4)ccc32)C1] | ¹H-NMR (400 MHz, DMSO-d₆): δ 12.86 (s, 1H), 8.46 (d, J = 6.8 Hz, 2H), 7.90-7.72 (m, 3H), 7.53 (s, 1H), 7.19 (d, J = 7.6 Hz, 1H), 6.95-6.79 (m, 1H), 6.15 (d, J = 16.4 Hz, 1H), 5.75-5.60 (m, 1H), 4.73-4.57 (m, 2H), 4.25-4.08 (m, 1H), 3.71-3.49 (m, 2H), 2.81-2.67 (m, 2H), 2.33 (s, 4H), 2.17-1.94 (m, 3H), 1.64-1.23 (m, 7H); MS calculated for C₂₉H₃₃F₃N₅O₂ (M + H⁺) 540.25, found 540.3. |

| Ex. | Compound Structure | Physical Data (¹H NMR and MS) |
|---|---|---|
| 17-119 | 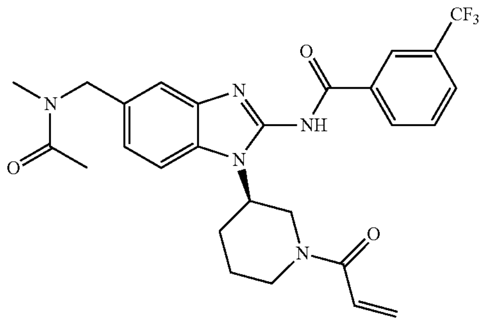 [SMILES: C=CC(=O)N1CCC[C@@H](n2c(NC(=O)c3cccc(C(F)(F)F)c3)nc3cc(CN(C)C(C)=O)ccc32)C1] | ¹H-NMR (400 MHz, DMSO-d$_6$): δ 12.88 (d, J = 8.8 Hz, 1H), 8.46 (d, J = 7.6 Hz, 2H), 7.89 (d, J = 7.2 Hz, 1H), 7.75-7.47 (m, 2H), 7.47 (s, 1H), 7.15-7.10 (m, 1H), 6.90-6.79 (m, 1H), 6.19-6.13 (m, 1H), 5.75-5.60 (m, 1H), 4.76-4.56 (m, 4H), 4.32-4.08 (m, 2H), 2.92 (s, 3H), 2.81 (s, 2H), 2.08 (s, 3H), 1.98-1.91 (m, 2H), 1.59 (s, 2H); MS calculated for C$_{27}$H$_{29}$F$_3$N$_5$O$_3$ (M + H$^+$) 528.21, found 528.3. |
| 17-120 | 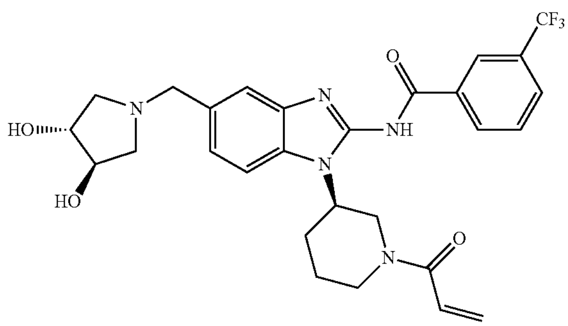 [SMILES: C=CC(=O)N1CCC[C@@H](n2c(NC(=O)c3cccc(C(F)(F)F)c3)nc3cc(CN4C[C@@H](O)[C@H](O)C4)ccc32)C1] | MS calculated for C$_{28}$H$_{31}$F$_3$N$_5$O$_4$ (M + H$^+$) 558.22, found 558.2. |
| 17-121 | 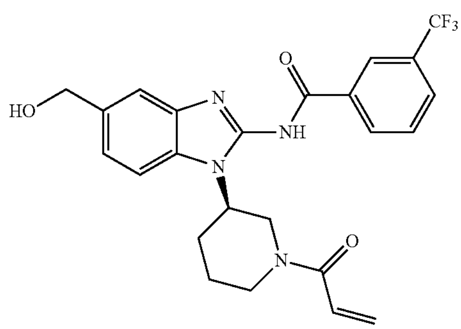 [SMILES: C=CC(=O)N1CCC[C@@H](n2c(NC(=O)c3cccc(C(F)(F)F)c3)nc3cc(CO)ccc32)C1] | ¹H-NMR (400 MHz, DMSO-d$_6$): δ 13.30 (s, 1H), 8.47 (d, J = 7.9 Hz, 2H), 7.89 (d, J = 7.8 Hz, 1H), 7.76-7.69 (m, 2H), 7.57 (s, 1H), 7.21 (d, J = 8.3 Hz, 1H), 6.99-6.79 (m, 1H), 6.20-6.13 (m, 1H), 5.84-5.60 (m, 1H), 5.32-5.24 (m, 1H), 4.77-4.74 (m, 1H), 4.60-56 (m, 2H), 4.31-4.03 (m, 2H), 3.75-3.56 (m, 1H), 2.78-2.70 (m, 2H), 2.05-1.90 (m, 2H), 1.71-1.59 (m, 1H); MS calculated for C$_{24}$H$_{24}$F$_3$N$_4$O$_3$ (M + H$^+$) 473.17, found 473.2. |
| 17-122 | 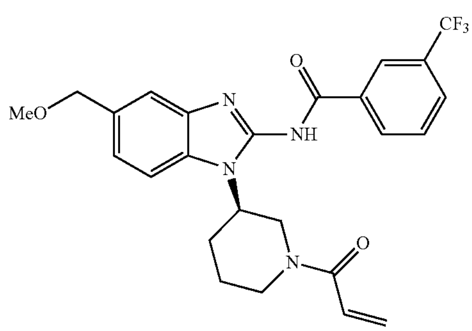 [SMILES: C=CC(=O)N1CCC[C@@H](n2c(NC(=O)c3cccc(C(F)(F)F)c3)nc3cc(COC)ccc32)C1] | ¹H-NMR (400 MHz, DMSO-d$_6$): δ 12.85 (s, 1H), 8.47 (d, J = 6.9 Hz, 2H), 7.88 (d, J = 7.3 Hz, 1H), 7.75-7.70 (m, 2H), 7.54 (s, 1H), 7.19 (d, J = 7.8 Hz, 1H), 6.95-6.80 (m, 1H), 6.19-6.13 (m, 1H), 5.75-5.59 (m, 1H), 4.75 (br. s, 1H), 4.60-4.56 (m, 1H), 4.48 (s, 2H), 4.28-4.20 (m, 1H), 4.09-3.66 (m, 1H), 3.32 (s, 3H), 2.85-2.67 (m, 2H), 2.01-1.82 (m, 2H), 1.65-1.59 (m, 1H); MS calculated for C$_{25}$H$_{26}$F$_3$N$_4$O$_3$ (M + H$^+$) 487.19, found 487.3. |

-continued

| Ex. | Compound Structure | Physical Data ($^1$H NMR and MS) |
|---|---|---|
| 17-123 | 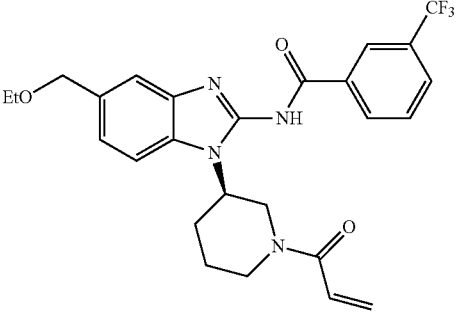 | $^1$H-NMR (400 MHz, DMSO-$d_6$): δ 12.91 (s, 1H), 8.47 (s, 2H), 7.89 (s, 1H), 7.74 (s, 2H), 7.56 (s, 1H), 7.22 (d, J = 6.8 Hz, 1H), 6.93-6.83 (m, 1H), 6.20-6.16 (m, 1H), 5.75-5.60 (m, 1H), 4.81-4.71 (m, 1H), 4.61-4.52 (m, 3H), 4.28-4.20 (m, 1H), 4.09-3.62 (m, 1H), 3.50 (d, J = 5.9 Hz, 2H), 2.83-2.71 (m, 2H), 2.09-1.94 (m, 2H), 1.65-1.59 (m, 1H), 1.22-1.16 (m, 3H); MS calculated for $C_{26}H_{28}F_3N_4O_3$ (M + H$^+$) 501.20, found 501.2. |
| 17-124 | 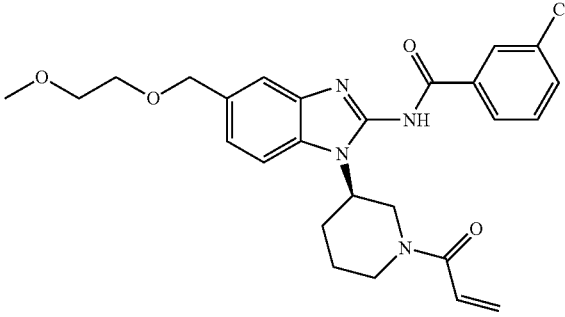 | $^1$H-NMR (400 MHz, DMSO-$d_6$): δ 12.97 (s, 1H), 8.46 (s, 2H), 7.87 (s, 1H), 7.72 (s, 1H), 7.60-7.54 (m, 2H), 7.21 (s, 1H), 6.98-6.78 (m, 1H), 6.18-6.14 (m, 1H), 5.72-5.58 (m, 1H), 4.80-4.71 (m, 1H), 4.54 (s, 2H), 4.23-4.18 (m, 1H), 4.10-3.60 (m, 1H), 4.09-3.62 (m, 1H), 3.55-2.48 (m, 4H), 2.83-2.71 (m, 2H), 2.01-1.92 (m, 2H), 1.65-1.60 (m, 1H), 1.32-1.21 (m, 3H); MS calculated for $C_{27}H_{30}F_3N_4O_4$ (M + H$^+$) 531.21, found 531.1. |
| 17-125 | 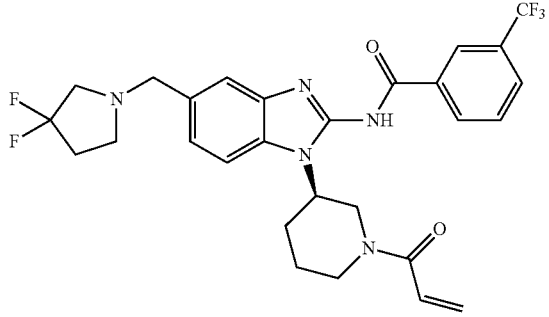 [SMILES: C=CC(=O)N1CCC[C@@H](n2c(NC(=O)c3cccc(C(F)(F)F)c3)nc3cc(CN4CCC(F)(F)C4)ccc32)C1] | MS calculated for $C_{28}H_{29}F_5N_5O_2$ (M + H$^+$) 562.22, found 562.3. |
| 17-126 | 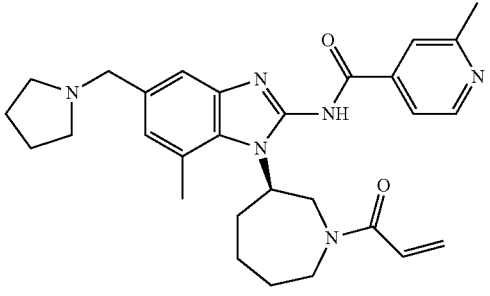 | $^1$H-NMR (400 MHz, acetonitrile-$d_3$): δ 12.33 (s, 1H), 8.50 (d, J = 5.2 Hz, 1H), 7.88 (s, 0.6H), 7.86 (s, 0.4H), 7.84 (s, 0.6H), 7.77 (d, J = 5.2 Hz, 1H), 7.24 (s, 0.6H), 6.93 (s, 1H), 6.66 (dd, J = 10.4, 16.4 Hz, 1H), 6.17(dd, J = 2.0, 16.8 Hz, 0.4H), 6.13 (dd, J = 2.0, 16.8 Hz, 0.6H), 5.63 (dd, J = 2.4, 10.4 Hz, 0.6H), 5.53 (dd, J = 2.4, 10.4 Hz, 0.4H), 4.92-4.71 (m, 1H), 4.33 (d, J = 10.8 Hz, 0.4H), 4.29 (d, J = 10.8 Hz, 0.6H), 4.19 (dd, J = 3.2, 13.2 Hz, 0.6H), 4.02 (dd, J = 3.2, 13.2 Hz, 0.4H), 4.00-3.93 (m, 0.4H), 3.86-3.79 (m, 0.6H), 3.55 (s, 2H), 3.54-3.49 (m, 0.6H), 3.33-3.28 (m, 0.4H), 2.84-2.74 (m, 1.2H), 2.70-2.60 (m, 0.8H), 2.63 (s, 2.1H), 2.56 (s, 0.9H), 2.51 (s, 2.1H), & 2.50 (s, 0.9H), 2.43-2.37 (m, 2H), 2.04-1.86 (m, 5H), 1.68-1.64(m, 4H), 1.39-1.28 (m, 1H); MS calculated for $C_{29}H_{37}N_6O_2$ (M + H$^+$) 501.29, found 501.3. |

| Ex. | Compound Structure | Physical Data ($^1$H NMR and MS) |
|---|---|---|
| 17-127 | 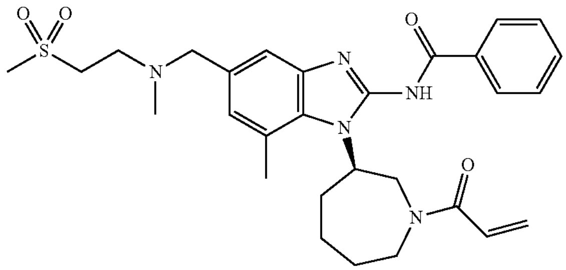 [SMILES: C=CC(=O)N1CCCC[C@@H](n2c(NC(=O)c3ccccc3)nc3cc(CN(C)CCS(C)(=O)=O)cc(C)c32)C1] | $^1$H-NMR (400 MHz, CDCl$_3$): δ 12.61(s, 1H), 8.22-8.17 (m, 2H), 7.46-7.38 (m, 3H), 7.05 (s, 0.3H), 6.99 (s, 0.7H), 6.86 (s, 0.3H), 6.84 (s, 0.7H), 6.58 (dd, J = 10.0, 17.2 Hz, 0.3H), 6.56 (dd, J = 10.4, 16.8 Hz, 0.7H), 6.39 (dd, J = 2.1, 6.4 Hz, 0.3H), 6.29 (dd, J = 2.0, 16.8 Hz, 0.7H), 5.67(dd, J = 2.0, 10.8 Hz, 0.7H), 5.64(dd, J = 2.0, 10.4 Hz, 0.3H), 4.99-4.91 (m, 0.7H), 4.74-4.65 (m, 0.3H), 4.40-4.33 (m, 1.6H), 4.15-4.08 (m, 0.4H), 3.98-3.83 (m, 1H), 3.58-3.50 (m, 0.7H), 3.50 (s, 2H), 3.40-3.34 (m, 0.3H), 3.11 (br t, J = 6.4 Hz, 2H), 2.96(s, 3H), 2.90 (br t, J = 6.4 Hz, 2H), 2.78-2.64 (m, 1H), 2.67 (s, 2.1H), 2.55(s, 0.9H), 2.18 (s, 0.9H), 2.15 (s, 2.1H), 2.06-1.94 (m, 4H), 1.43-1.28 (m, 0.7H), 1.21-1.08 (m, 0.3H); MS calculated for C$_{29}$H$_{38}$N$_5$O$_4$S (M + H$^+$) 552.26, found 552.2. |
| 17-128 | 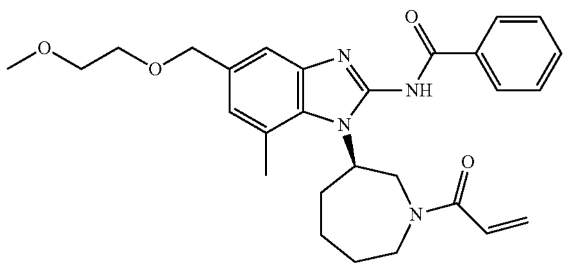 [SMILES: C=CC(=O)N1CCCC[C@@H](n2c(NC(=O)c3ccccc3)nc3cc(COCCOC)cc(C)c32)C1] | $^1$H-NMR (400 MHz, CDCl$_3$): δ 12.71 (s, 1H), 8.32-8.27 (m, 2H), 7.55-7.45 (m, 3H), 7.21(s, 0.3H), 7.17 (s, 0.7H), 6.65 (dd, J = 10.8, 16.8 Hz, 0.7H), 6.64 (dd, J = 10.8, 16.8 Hz, 0.3H), 6.48 (dd, J = 16.8, 2.0 Hz, 0.3H), 6.38 (dd, J = 16.8, 2.0 Hz, 0.7H), 5.76 (dd, J = 10.8, 2.0 Hz, 0.7H), 5.72 (dd, J = 10.8, 2 Hz, 0.3H), 5.10-4.98 (m, 0.7H), 4.82-4.74 (m, 0.3H), 4.602 (s, 2H), 4.51-4.33 (m, 1.8H), 4.27-4.17 (m, 0.2H), 4.04-3.92 (m, 1H), 3.68-3.58 (m, 4H), 3.43(s, 0.6H), 3.42(s, 2.4H), 3.04-2.95 (m, 1H), 2.82 (s, 1H), 2.77 (s, 2.1H), 2.65 (s, 0.9H), 2.26-1.96 (m, 5H), 1.53-1.37 (m, 0.7H), 0.94-0.88 (m, 0.3H); MS calculated for C$_{28}$H$_{35}$N$_4$O$_4$ (M + H$^+$) 491.26, found 491.2. |
| 17-129 | 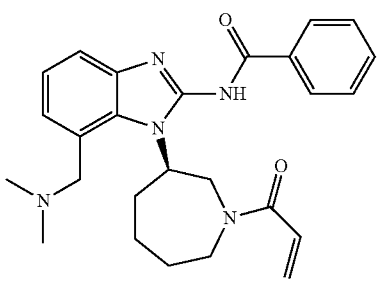 [SMILES: C=CC(=O)N1CCCC[C@@H](n2c(NC(=O)c3ccccc3)nc3cccc(CN(C)C)c32)C1] | $^1$H-NMR (400 MHz, CD$_3$OD): δ 8.28-8.25(m, 2H), 7.68(dd, J = 2.4, 8.8 Hz, 1H), 7.57-7.48 (m, 3H), 7.42-7.38 (m, 2H), 6.88 (dd, J = 10.8, 16.8 Hz, 0.3H), 6.89 (dd, J = 10.8, 16.8 Hz, 0.7H), 6.44 (dd, J = 1.6, 16.4 Hz, 0.3H), 6.43 (dd, J = 1.6, 16.4 Hz, 0.7H), 5.91 (dd, J = 1.6, 10.4 Hz, 0.3H), 5.89 (dd, J = 1.6 Hz, 10.4 Hz, 0.7H), 5.13 (d, J = 14.4 Hz, 0.3H), 5.06 (d, J = 14.4 Hz, 0.7H), 4.82 (d, J = 14.4 Hz, 0.3H), 4.71 (d, J = 14.4 Hz, 0.7H), 4.66-4.63 (m, 1H), 4.55-4.48 (m, 1H), 4.42-4.39 (m, 1H), 4.15-4.08 (m, 1H), 3.70-3.64 (m, 1H), 3.06 (s, 1.2H), 3.03(s, 4.8H), 2.28-2.08 (m, 5H), 1.60-1.45 (m, 1H); MS calculated for C$_{26}$H$_{32}$N$_5$O$_2$ (M + H$^+$) 446.25, found 446.2. |
| 17-130 | 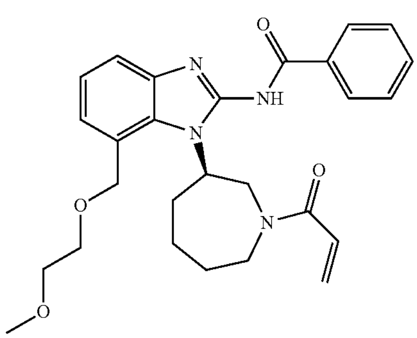 [SMILES: C=CC(=O)N1CCCC[C@@H](n2c(NC(=O)c3ccccc3)nc3cccc(COCCOC)c32)C1] | $^1$H-NMR (400 MHz, CDCl$_3$): δ 8.25-8.22 (m, 2H), 7.59-7.45 (m, 3H), 7.28-7.20 (m, 3H), 6.69 (dd, J = 10.4, 16. Hz, 0.4H), 6.66 (dd, J = 10.4, 16.4 Hz, 0.6H), 6.40 (dd, J = 1.6, 16.8 Hz, 0.4 H), 6.37 (dd, J = 1.6, 16.8 Hz, 0.6H), 5.83 (dd, J = 1.6, 10.4 Hz, 0.6H), 5.66 (dd, J = 1.6, 10.4 Hz, 0.4H), 5.42 (d, J = 12 Hz, 1H), 5.11-4.97 (m, 1H), 4.58 (d, J = 12 Hz, 1H), 4.46(d, J = 7.2 Hz, 1H), 4.03-3.86 (m, 1H), 3.80-3.67(m, 1H), 3.66-3.54 (m, 4H), 3.35(s, 2.1H), 3.34(s, 0.9H), 2.98-2.87(m, 1H), 2.20-1.98 (m, 5H), 1.62-1.44 (m, 1H); MS calculated for C$_{27}$H$_{33}$N$_4$O$_4$ (M + H$^+$) 477.24, found 477.2. |

| Ex. | Compound Structure | Physical Data (¹H NMR and MS) |
|---|---|---|
| 17-131 | 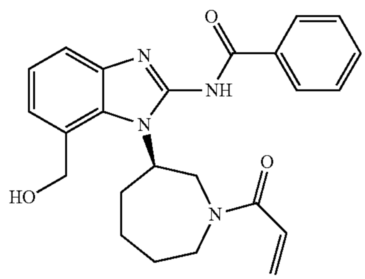 [SMILES: C=CC(=O)N1CCCC[C@@H](n2c(NC(=O)c3ccccc3)nc3cccc(CO)c32)C1] | ¹H-NMR (400 MHz, CD₃OD): δ 8.34-8.29 (m, 2H), 7.66-7.61 (m, 1H), 7.53-7.46 (m, 3H), 7.26-7.20 (m, 2H), 6.98 (dd, J = 10.4, 16.8 Hz, 0.3H), 6.85 (dd, J = 10.4, 16.8 Hz, 0.7H), 6.31 (dd, J = 2.4, 16.8 Hz, 0.7H), 6.26 (dd, J = 2.4, 16.8 Hz, 0.3H), 5.75 (dd, J = 2.4, 10.4 Hz, 0.7H), 5.56 (dd, J = 2.4, 10.4 Hz, 0.3H), 5.26 (d, J = 12.8 Hz, 1H), 5.25-5.16 (m, 1H), 4.99-4.18 (br s, 1H), 4.92 (d, J = 12.8 Hz, 1H), 4.54 (dd, J = 13.2, 10.8 Hz, 0.7H), 4.50 (dd, J = 13.2, 10.8 Hz, 0.3H), 4.37(dd, J = 12.8, 3.2 Hz, 0.7H), 4.20 (dd, J = 14, 4.0 Hz, 0.3H), 4.07-3.95 (m, 1H), 3.77-3.71 (m, 0.7H), 3.59-3.55 (m, 0.3H), 3.10-2.87 (m, 1H), 2.22-1.90 (m, 5H), 1.63-1.30 (m, 1H); MS calculated for C₂₄H₂₇N₄O₃ (M + H⁺) 419.20, found 419.2. |
| 17-132 | 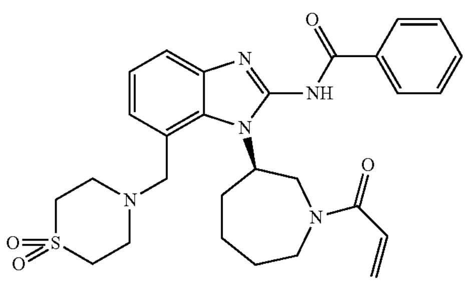 [SMILES: C=CC(=O)N1CCCC[C@@H](n2c(NC(=O)c3ccccc3)nc3cccc(CN4CCS(=O)(=O)CC4)c32)C1] | ¹H-NMR (400 MHz, CD₃OD): δ 8.17-8.12 (m, 2H), 7.42-7.36 (m, 3H), 7.13-7.05 (m, 3H), 6.75 (dd, J = 10.4, 16.4 Hz, 1H), 6.24 (d, J = 16.0 Hz, 0.25H), 6.22 (d, J = 16.0 Hz, 0.75H), 5.72(d, J = 10.4 Hz, 0.75H), 5.62 (d, J = 10.4 Hz, 0.25H), 5.26-4.98 (m, 1H), 4.53-4.30 (m, 3H), 4.22-3.94 (m, 1H), 3.78-3.46 (m, 2H), 2.96-2.89 (m, 8H), 2.18-1.96 (m, 4H), 1.33-1.00 (m, 2H); MS calculated for C₂₈H₃₄N₅O₄S (M + H⁺) 536.23, found 536.2. |
| 17-133 | 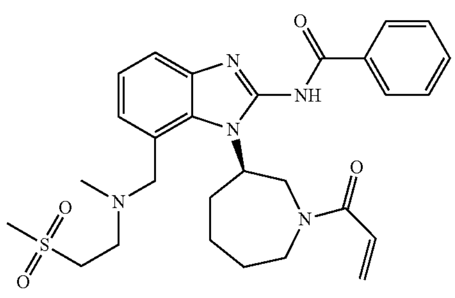 [SMILES: C=CC(=O)N1CCCC[C@@H](n2c(NC(=O)c3ccccc3)nc3cccc(CN(C)CCS(C)(=O)=O)c32)C1] | ¹H-NMR (400 MHz, CDCl₃): δ 12.82 (br s, 1H), 8.33-8.26 (m, 2H), 7.56-7.47 (m, 3H), 7.32-7.27 (m, 1H), 7.21-7.15 (m, 1H), 7.09-7.05 (m, 1H), 6.68 (dd, J = 10.8, 16.8 Hz, 0.7H), 6.62 (dd, J = 10.8, 16.8 Hz, 0.3H), 6.39 (dd, J = 16.8, 2.0 Hz, 0.3H), 6.35 (dd, J = 16.8, 2.0 Hz, 0.7H), 5.76 (dd, J = 2.0, 10.8 Hz, 0.7H), 5.63(dd, J = 2.0, 10.8 Hz, 0.3H), 5.22-5.12 (m, 1H), 4.64(d, J = 13.2 Hz, 1H), 4.51-4.35 (m, 2H), 4.07-3.84 (m, 1H), 3.71-3.61 (m, 1H), 3.43 (d, J = 13.2 Hz, 1H), 3.23-2.91 (m, 4H), 2.94 (s, 0.9H), 2.82 (s, 2.1H), 2.28 (s, 2.1H), 2.24 (s, 0.9H), 2.22-1.97 (m, 4H), 1.55-1.09 (m, 2H); MS calculated for C₂₈H₃₆N₅O₄S (M + H⁺) 538.24, found 538.2. |
| 17-134 | 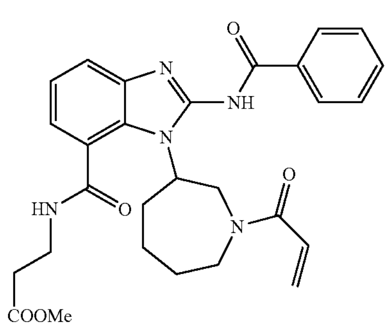 [SMILES: C=CC(=O)N1CCCCC(n2c(NC(=O)c3ccccc3)nc3cccc(C(=O)NCCC(=O)OC)c32)C1] | ¹H-NMR (400 MHz, CDCl₃): δ 12.99-12.85 (br s, 1H), 8.28-8.25 (m, 2H), 7.55-7.45 (m, 3H), 7.41-7.33 (m, 1H), 7.27-7.16 (m, 2H), 6.78 (dd, J = 10.4, 16.4 Hz, 0.3H), 6.63 (dd, J = 10.4, 16.4 Hz, 0.7H), 6.41 (dd, J = 2.0, 16.4 Hz, 0.3H), 6.33 (dd, J = 2.0, 16.4 Hz, 0.7H), 5.75 (dd, J = 10.4, 2.0 Hz, 0.7H), 5.64 (dd, J = 10.4, 2.0 Hz, 0.3H), 5.16-4.55 (m, 2H), 4.42-4.36 (m, 1H), 4.17-4.14 (m, 1H), 4.01-3.89 (m, 1H), 3.86-3.60 (m, 3H), 3.75(s, 0.9H), 3.74 (s, 2.1H), 2.77 (t, J = 6.4, 6.4 Hz, 1.4H), 2.71 (t, J = 6.4, 6.4 Hz, 0.6H), 2.30-1.88 (m, 5H), 1.46-1.36 (m, 1H), MS calc. for C₂₈H₃₂N₅O₅ (M + H⁺) 518.24, found 518.2. |

| Ex. | Compound Structure | Physical Data (¹H NMR and MS) |
|---|---|---|
| 17-135 | 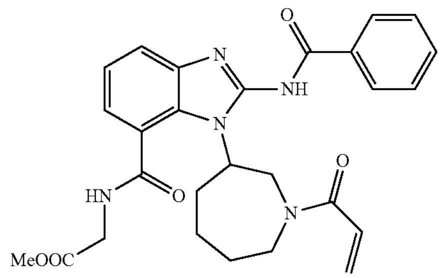 [SMILES: C=CC(=O)N1CCCCC(n2c(NC(=O)c3ccccc3)nc3cccc(C(=O)NCC(=O)OC)c32)C1] | ¹H-NMR (400 MHz, CDCl₃): δ 12.89 (br s, 1H), 8.26 (d, J = 7.9 Hz, 2H), 7.54-7.44 (m, 3H), 7.40-7.28 (m, 2H), 7.23-7.09 (m, 1H), 6.80 (dd, J = 10.5, 16.7 Hz, 0.3H), 6.61 (dd, J = 10.5, 16.7 Hz, 0.7H), 6.36 (dd, J = 1.6, 16.4 Hz, 0.3H), 6.25 (dd, J = 1.6, 16.4 Hz, 0.7H), 5.71 (dd, J = 1.6, 10.4 Hz, 0.7H), 5.59 (dd, J = 2.0, 10.4 Hz, 0.3H), 4.87-4.65 (m, 1H), 4.41-3.89 (m, 4H), 3.82(s, 0.9H), 3.79 (s, 2.1H), 3.66-3.58(m, 2H), 2.88-2.72 (m, 1H), 2.22-1.95 (m, 5H), 1.60-1.45 (m, 1H); MS calculated for C$_{27}$H$_{30}$N$_5$O$_5$ (M + H⁺) 504.22, found 504.2. |
| 17-136 | 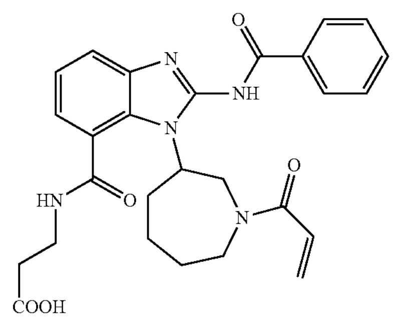 [SMILES: C=CC(=O)N1CCCCC(n2c(NC(=O)c3ccccc3)nc3cccc(C(=O)NCCC(=O)O)c32)C1] | ¹H-NMR (400 MHz, CDCl₃): δ 8.23-8.20 (m, 2H), 7.54-7.36 (m, 4H), 7.25-7.10 (m, 2H), 6.60 (dd, J = 10.4, 16.8 Hz, 1H), 6.29 (dd, J = 1.2, 16.8 Hz, 1H), 5.78 (d, J = 15.2 Hz, 1H), 4.79-4.68 (m, 1H), 4.48-4.43 (m, 1H), 4.23-4.20 (m, 1H), 3.95-3.78(m, 2H), 3.71-3.58 (m, 2H), 2.75-2.59 (m, 2H), 2.35-1.80 (m, 4H), 1.68-1.40 (m, 2H); MS calculated for C$_{27}$H$_{30}$N$_5$O$_5$ (M + H⁺) 504.22, found 504.2. |
| 17-137 | 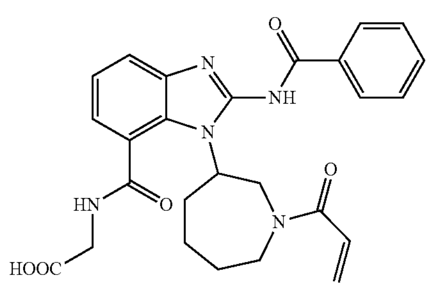 [SMILES: C=CC(=O)N1CCCCC(n2c(NC(=O)c3ccccc3)nc3cccc(C(=O)NCC(=O)O)c32)C1] | ¹H-NMR (400 MHz, CDCl₃): δ 8.16-8.14 (d, J = 7.6 Hz, 2H), 8.05 (br s, 1H), 7.92 (br s, 1H), 7.44-7.31(m, 4H), 7.26-7.16 (m, 1H), 7.05-6.95 (m, 1H), 6.86 (brs, 1H), 6.78 (dd, J = 10.8, 16.4 Hz, 0.3H), 6.29 (dd, J = 10.8, 16.4 Hz, 0.7H), 6.28-6.19 (m, 1H), 6.75 (d, J = 10.8 Hz, 0.7H), 5.58 (d, J = 10.8 Hz, 0.3H), 4.77-4.54 (m, 1H), 4.45-4.19 (m, 2H), 4.09-3.92 (m, 2H), 3.89-3.64 (m, 1H), 3.60-3.36 (m, 1H), 2.74-2.57 (m, 1H), 2.17-1.67 (m, 3H), 1.62-1.23 (m, 2H); MS calculated for C$_{26}$H$_{28}$N$_5$O$_5$ (M + H⁺) 490.20, found 490.1. |
| 17-138 | 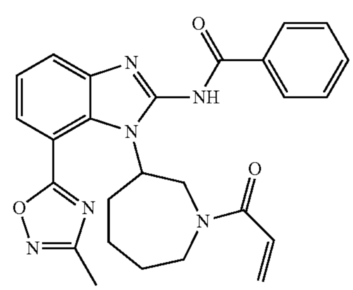 | ¹H NMR (400 MHz, CDCl₃) δ 8.25-8.22 (m, 2H), 7.75-7.68 (m, 1H), 7.62-7.32 (m, 5H), 6.53 (dd, J = 10.4, 16.8 Hz, 0.6H), 6.46 (dd, J = 10.4, 16.8 Hz, 0.4H), 6.27 (dd, J = 1.6, 16.8 Hz, 0.6H), 6.23 (dd, J = 1.6, 16.8 Hz, 0.4H), 5.71 (dd, J = 10.4, 1.6 Hz, 0.4H), 5.55 (dd, J = 10.4, 1.6 Hz, 0.6H), 5.10-4.83 (m, 1H), 4.41-4.14 (m, 1H), 4.00-3.70 (m, 1H), 3.62-3.47 (m, 1H), 2.92-2.71 (m, 1H), 2.54-2.42 (m, 1H), 2.47 (s, 1.9H), 2.46 (s, 1.1H), 2.19-1.85(m, 4H), 1.40-1.21(m, 1H); MS calculated for C$_{26}$H$_{27}$N$_6$O$_3$ (M + H⁺) 471.21, found 471.2. |

| Ex. | Compound Structure | Physical Data ($^1$H NMR and MS) |
|---|---|---|
| 17-139 | 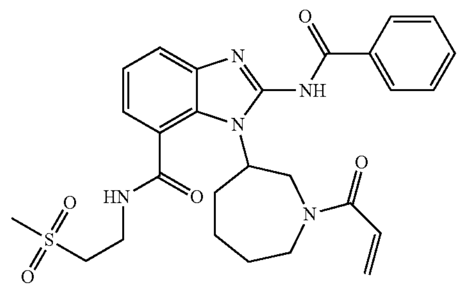 [SMILES: C=CC(=O)N1CCCCC(n2c(NC(=O)c3ccccc3)nc3cccc(C(=O)NCCS(C)(=O)=O)c32)C1] | $^1$H NMR (400 MHz, CD$_3$OD) δ 8.27-8.22 (m, 2H), 7.67-7.59 (m, 1H), 7.56-7.28 (m, 5H), 6.83 (dd, J = 10.4, 16.8 Hz, 1H), 6.31 (dd, J = 2.0, 16.8 Hz, 0.6H), 6.30 (dd, J = 2.0, 16.8 Hz, 0.4H), 5.79 (dd, J = 10.4, 2.0 Hz, 0.6H), 5.68 (dd, J = 10.4 Hz, 0.4H), 4.70-4.50 (m, 1H), 4.19-4.05 (m, 1H), 3.98-3.77 (m, 3H), 3.68-3.61 (m, 1H), 3.56-3.43(m, 2H), 3.09(s, 3H), 2.91-2.79 (m, 1H), 2.24-1.88 (m, 4H), 1.50-1.41 (m, 2H); MS calculated for C$_{27}$H$_{32}$N$_5$O$_5$S (M + H$^+$) 538.20, found 538.1. |
| 17-140 | 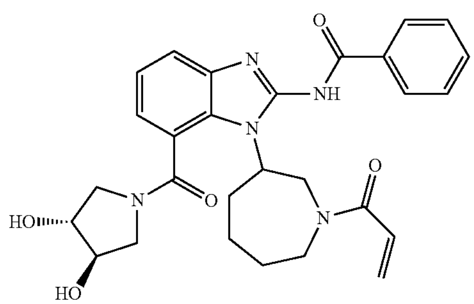 [SMILES: C=CC(=O)N1CCCCC(n2c(NC(=O)c3ccccc3)nc3cccc(C(=O)N4C[C@@H](O)[C@H](O)C4)c32)C1] | $^1$H-NMR (400 MHz, CDCl$_3$): δ 8.31-8.28 (m, 2H), 7.54-7.47 (m, 3H), 7.38-7.35 (m, 1H), 7.27-7.20 (m, 2H), 6.59 (dd, J = 10.8, 17.2 Hz, 1H), 6.31 (d, J = 16.8 Hz, 0.3H), 6.28 (d, J = 16.8 Hz, 0.7H), 5.80 (d, J = 10.8 Hz, 0.3H), 5.78 (d, J = 10.8 Hz, 0.7H), 4.77-4.68 (m, 1H), 4.61-4.45 (m, 1H), 4.39 (s, 1H), 4.34-4.25 (m, 1H), 4.19-4.10 (m, 2H), 4.07-3.98 (m, 1H), 3.91-3.72 (m, 2H), 3.62-3.56 (m, 1H), 3.53-3.49 (m, 1H), 2.85-2.72 (m, 1H), 2.31-2.26 (m, 1H), 2.23-2.01 (m, 4H), 2.07 (s, 2H), 1.47-1.33 (m, 1H); MS calculated for C$_{28}$H$_{32}$N$_5$O$_5$ (M + H$^+$) 518.23, found 518.2. |
| 17-141 | 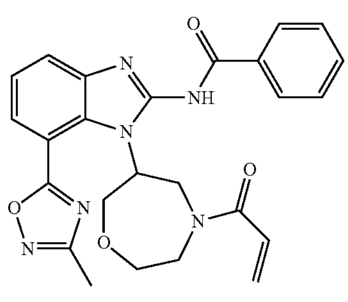 [SMILES: C=CC(=O)N1CCOCC(n2c(NC(=O)c3ccccc3)nc3cccc(-c4nc(C)no4)c32)C1] | MS calculated for C$_{25}$H$_{25}$N$_6$O$_4$ (M + H$^+$) 473.19, found 473.0. |
| 17-142 | 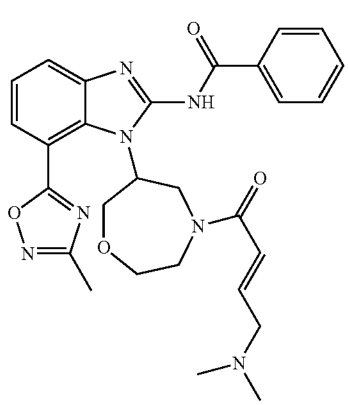 [SMILES: Cc1noc(-c2cccc3nc(NC(=O)c4ccccc4)n(C4COCCN(C(=O)/C=C/CN(C)C)C4)c23)n1] | $^1$H NMR (400 MHz, CDCl$_3$) δ 8.25-8.09 (m, 2H), 7.82-7.68 (m, 1H), 7.62-7.32 (m, 5H), 7.02-6.81 (m, 1H), 6.68-6.57 (m, 1H), 5.46-5.30 (m, 0.5H), 4.82-4.66 (m, 1.5H), 4.41-4.14 (m, 2H), 4.00-3.80 (m, 4H), 3.50-3.25 (m, 2H), 2.81 (s, 3H), 2.58-2.47 (m, 6H), 1.49-1.35 (m, 1H); MS calculated for C$_{28}$H$_{32}$N$_7$O$_4$ (M + H$^+$) 530.24, found 530.2. |

| Ex. | Compound Structure | Physical Data (¹H NMR and MS) |
|---|---|---|
| 17-143 | 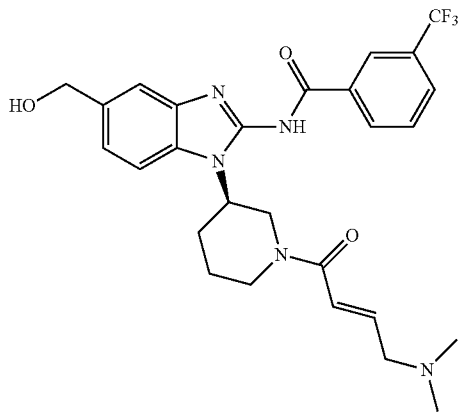 [SMILES: CN(C)C/C=C/C(=O)N1CCC[C@@H](n2c(NC(=O)c3cccc(C(F)(F)F)c3)nc3cc(CO)ccc32)C1] | MS calculated for $C_{27}H_{31}F_3N_5O_3$ (M + H⁺) 530.23, found 530.2. |
| 17-144 | 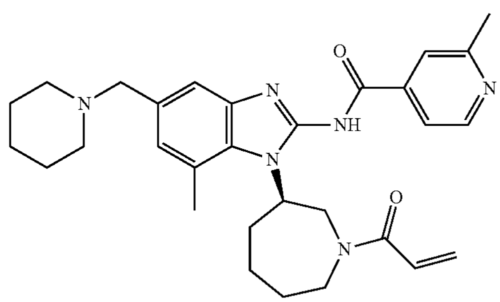 [SMILES: C=CC(=O)N1CCCC[C@@H](n2c(NC(=O)c3ccnc(C)c3)nc3cc(CN4CCCCC4)cc(C)c32)C1] | ¹H NMR (400 MHz, CDCl3) δ 8.57 (m, 1H), 7.91-7.70 (m, 2H), 7.17-7.10 (m, 1H), 7.00-6.86 (m, 1H), 6.56 (m, 1H), 6.46-6.21 (m, 1H), 5.73-5.54 (m, 1H), 5.03-4.77 (m, 1.6H), 4.79 (m, 0.4H), 4.31 (m, 1.6H), 4.19-4.08 (m, 0.4H), 3.98-3.73 (m, 2H), 3.53 (m, 2.5H), 3.43-3.29 (m, 0.5H), 2.91-2.73 (m, 1H), 2.73-2.62 (m, 2H), 2.63 (s, 2H), 2.30 (s, 3H), 2.20-1.66 (m, 6H), 1.57 (s, 3H), 1.47-1.25 (m, 2H); MS calculated for $C_{30}H_{39}N_6O_2$ (M + H⁺) 515.31, found 515.3. |
| 17-145 | 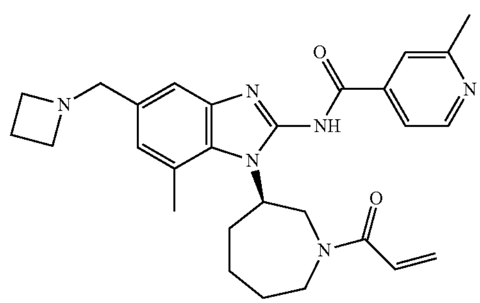 [SMILES: C=CC(=O)N1CCCC[C@@H](n2c(NC(=O)c3ccnc(C)c3)nc3cc(CN4CCC4)cc(C)c32)C1] | ¹H NMR (400 MHz, MeOD) δ 8.55 (d, J = 5.2, 1H), 8.01 (d, J = 15.3, 1H), 7.93 (dd, J = 5.6, 9.7, 1H), 7.36-7.27 (m, 1H), 7.03 (s, 1H), 6.84 (dt, J = 10.2, 16.8, 1H), 6.31 (td, J = 1.9, 16.4, 1H), 5.80 (dd, J = 1.9, 10.6, 0.6H), 5.70 (dd, J = 1.9, 10.5, 0.4H), 5.10-5.03 (m, 1H), 4.54-4.50 (m, 1H), 4.33-4.29 (m, 0.6H), 4.25-4.16 (m, 0.4H), 4.11-3.93 (m, 1H), 3.75-3.60 (m, 2H), 3.57-3.45 (m, 1H), 2.88-2.85 (m, 1H), 2.75 (s, 3H), 2.73-2.66 (m, 4H), 2.67 (s, 3H), 2.26-1.95 (m, 6H), 1.57-1.36 (m, 1H); MS calculated for $C_{28}H_{35}N_6O_2$ (M + H⁺) 487.27, found 487.3. |
| 17-146 | 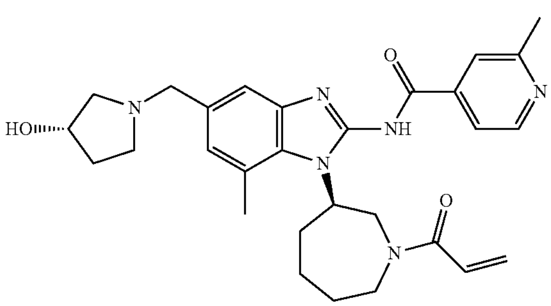 [SMILES: C=CC(=O)N1CCCC[C@@H](n2c(NC(=O)c3ccnc(C)c3)nc3cc(CN4CC[C@H](O)C4)cc(C)c32)C1] | ¹H NMR (400 MHz, CDCl3) δ 12.65 (s, 1H), 11.20 (s, 1H), 8.67-8.55 (m, 1H), 7.97-7.87 (m, 1H), 7.86-7.78 (m, 1H), 7.65-7.57 (m, 1H), 6.68-6.56 (m, 1H), 6.53-6.30 (m, 1H), 5.77-5.66 (m, 1H), 5.07-4.89 (m, 1H), 4.65-4.62 (m, 1H), 4.35-4.11 (m, 2H), 4.03-3.78 (m, 2H), 3.69-3.61 (m, 4H), 2.96-2.84 (m, 1H), 2.83-2.73 (m, 2H), 2.70-2.59 (m, 3H), 2.34-2.18 (m, 2H), 2.18-2.12 (m, 1H), 2.12-1.96 (m, 3H), 1.13-1.52 (m, 6H); MS calculated for $C_{29}H_{37}N_6O_3$ (M + H⁺) 517.28, found 517.3. |

| Ex. | Compound Structure | Physical Data (¹H NMR and MS) |
|---|---|---|
| 17-147 | 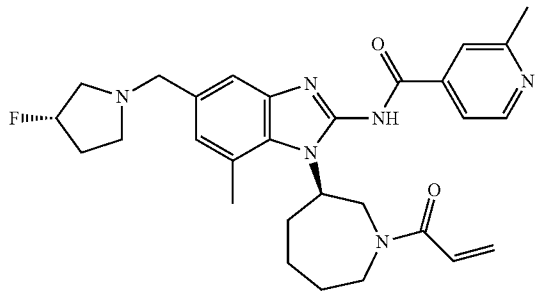 [SMILES: C=CC(=O)N1CCCC[C@@H](n2c(NC(=O)c3ccnc(C)c3)nc3cc(CN4CC[C@H](F)C4)cc(C)c32)C1] | ¹H NMR (400 MHz, MeOD) δ 8.56 (d, J = 5.2, 1H), 8.02 (d, J = 15.1, 1H), 7.93 (dd, J = 5.3, 9.9, 1H), 7.40 (d, J = 5.8, 1H), 7.11 (d, J = 12.8, 1H), 6.85 (dt, J = 11.0, 16.8, 1H), 6.31 (td, J = 1.9, 16.6, 1H), 5.81 (dd, J = 1.9, 10.6, 0.7H), 5.71 (dd, J = 1.9, 10.5, 0.3H), 5.32-5.25 (m, 1H), 5.19-5.02 (m, 1H), 4.97-4.91 (m, 1H), 4.60-4.51 (m, 1H), 4.35-4.25 (m, 1H), 4.13-3.92 (m, 1H), 3.88-3.60 (m, 3H), 3.05-2.80 (m, 3H), 2.80 (s, 2H), 2.72 (s, 2H), 2.64 (s, 3H), 2.54-2.50 (m, 1H), 2.32-2.18 (m, 2H), 2.08-2.01 (m, 3H), 1.55-1.42 (m, 1H); MS calc. for $C_{29}H_{36}FN_6O_2$ (M + H⁺) 519.28, found 519.3. |
| 17-148 | 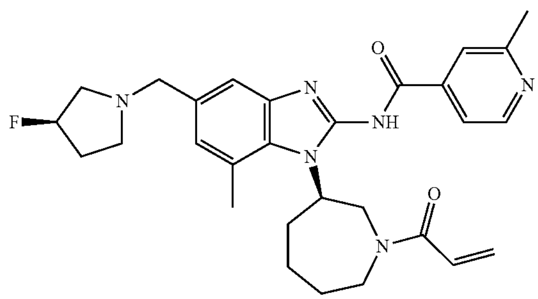 [SMILES: C=CC(=O)N1CCCC[C@@H](n2c(NC(=O)c3ccnc(C)c3)nc3cc(CN4CC[C@@H](F)C4)cc(C)c32)C1] | ¹H NMR (400 MHz, CDCl3) δ 8.52 (d, J = 5.1, 1H), 7.97 (d, J = 13.8, 1H), 7.93-7.83 (m, 1H), 7.35 (d, J = 11.4, 1H), 7.06 (s, 1H), 6.74 (dd, J = 10.6, 16.8, 1H), 6.42-6.22 (m, 1H), 5.83-5.67 (m, 1H), 5.29-4.99 (m, 2H), 4.94-4.88 (m, 1H), 4.56-4.41 (m, 1H), 4.36 (d, J = 10.2, 1H), 4.15-3.89 (m, 2H), 3.80-3.64 (m, 3H), 2.98-2.88 (m, 2H), 2.75 (s, 3H), 2.70-2.65 (m, 1H), 2.62(s, 3H), 2.57-2.34 (m, 1H), 2.34-1.89 (m, 5H), 1.48-1.40 (m, 1H); MS calc. for $C_{29}H_{36}FN_6O_2$ (M + H⁺) 519.28, found 519.3. |
| 17-149 | 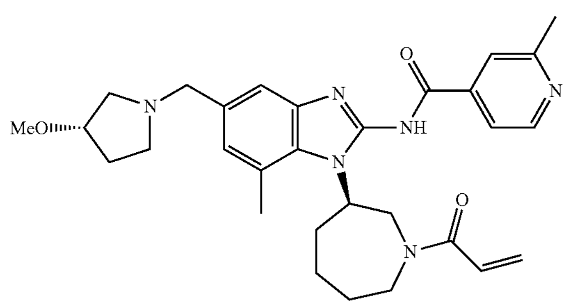 [SMILES: C=CC(=O)N1CCCC[C@@H](n2c(NC(=O)c3ccnc(C)c3)nc3cc(CN4CC[C@H](OC)C4)cc(C)c32)C1] | ¹H NMR (400 MHz, MeOD) δ 8.55 (d, J = 4.2, 1H), 8.02 (d, J = 15.0, 1H), 7.93 (dd, J = 5.3, 9.8, 1H), 7.46 (s, 1H), 7.18 (s, 1H), 6.85 (dt, J = 10.3, 16.8, 1H), 6.31 (td, J = 1.9, 16.5, 1H), 5.82 (dd, J = 1.9, 10.6, 0.6H), 5.71 (dd, J = 1.9, 10.5, 0.4H), 5.09-5.06 (m, 1H), 4.99-4.91 (m, 1H), 4.90 (s, 3H), 4.58-4.52 (m, 1H), 4.37-4.25 (m, 1H), 4.16-3.93 (m, 3H), 3.81-3.59 (m, 1H), 3.16-2.83 (m, 4H), 2.79 (s, 3H), 2.71 (s, 2H), 2.63 (s, 3H), 2.30-2.15 (m, 2H), 2.15-1.94 (m, 3H), 1.57-1.41 (m, 1H); MS calc. for $C_{30}H_{39}N_6O_3$ (M + H⁺) 531.30, found 531.3. |
| 17-150 | 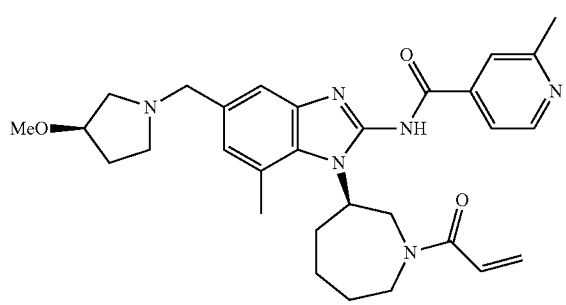 [SMILES: C=CC(=O)N1CCCC[C@@H](n2c(NC(=O)c3ccnc(C)c3)nc3cc(CN4CC[C@@H](OC)C4)cc(C)c32)C1] | ¹H NMR (400 MHz, CDCl3) δ 12.50 (s, 1H), 8.67-8.49 (m, 1H), 7.92-7.88 (m, 1H), 7.81-7.79 (m, 1H), 7.23-7.11 (m, 1H), 6.99 (s, 1H), 6.61-6.56 (m, 1H), 6.42- 6.32 (m, 1H), 5.77-5.60 (m, 1H), 5.10-4.87 (m, 2H), 4.49-4.28 (m, 2H), 3.93-3.87 (m, 2H), 3.62-3.57 (m, 4H), 3.25 (s, 3H), 2.91-2.83 (m, 1H), 2.72 (s, 3H), 2.62 (s, 3H), 2.78-2.39 (m, 3H), 2.14-2.01 (m, 4H), 1.45-1.35 (m, 2H); MS calc. for $C_{30}H_{39}N_6O_3$ (M + H⁺) 531.30, found 531.3. |

| Ex. | Compound Structure | Physical Data (¹H NMR and MS) |
|---|---|---|
| 17-151 | 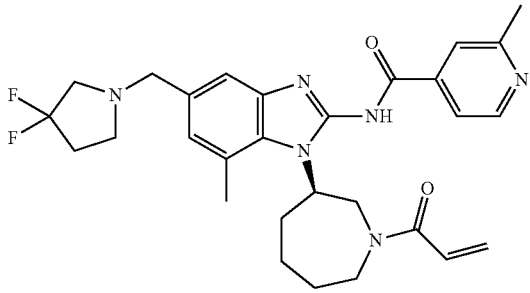 [SMILES: C=CC(=O)N1CCCC[C@@H](n2c(NC(=O)c3ccnc(C)c3)nc3cc(CN4CCC(F)(F)C4)cc(C)c32)C1] | ¹H NMR (400 MHz, MeOD) δ 8.45 (d, J = 5.2, 1H), 7.92 (d, J = 15.1, 1H), 7.88-7.72 (m, 1H), 7.33-7.22 (m, 1H), 6.99 (s, 1H), 6.74 (dt, J = 11.2, 16.8, 1H), 6.21 (td, J = 1.9, 16.7, 1H), 5.71 (dd, J = 1.8, 10.6, 0.6H), 5.61 (dd, J = 1.9, 10.5, 0.4H), 4.99-4.92 (m, 1H), 4.85-4.81 (m, 1H), 4.48-4.44 (m, 1H), 4.28-4.20 (m, 0.6H), 4.15-4.07 (m, 0.4H), 4.05-3.82 (m, 2H), 3.64-3.52 (m, 1H), 3.60 (s, 3H) 3.45-3.36 (m, 1H), 2.90-2.74 (m, 3H), 2.72-2.63 (m, 1H), 2.66(s, 2H), 2.54-2.49 (s, 3H), 2.31-2.05 (m, 3H), 2.05-1.92 (m, 3H), 1.44-1.27 (m, 1H); MS calc. for $C_{29}H_{35}F_2N_6O_2$ (M + H⁺) 537.27, found 537.3. |
| 17-152 | 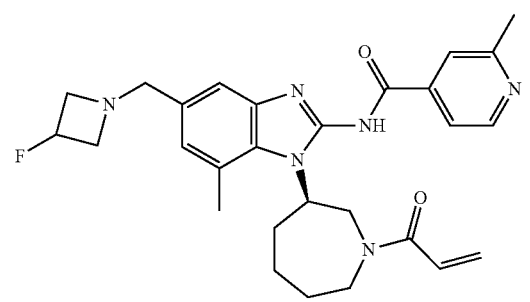 [SMILES: C=CC(=O)N1CCCC[C@@H](n2c(NC(=O)c3ccnc(C)c3)nc3cc(CN4CC(F)C4)cc(C)c32)C1] | ¹H NMR (400 MHz, MeOD) δ 8.55 (d, J = 4.1, 1H), 8.03 (d, J = 15.4, 1H), 7.94 (dd, J = 5.4, 10.5, 1H), 7.41-7.28 (m, 1H), 7.06 (s, 1H), 6.91-6.73 (m, 1H), 6.31-6.29 (m, 1H), 5.82-5.80 (m, 0.6H), 5.72-5.70 (m, 0.4H), 5.24-5.22 (m, 1H), 5.15-5.01 (m, 1H), 4.56-4.51 (m, 1H), 4.32-4.30 (m, 1H), 4.13-3.95 (m, 1H), 3.84-3.56 (m, 4H), 2.96-2.81 (m, 1H), 2.76 (s, 3H), 2.70 (s, 2H), 2.64 (s, 3H), 2.28-2.14 (m, 2H), 2.17-2.10 (m, 3H), 1.56-1.43 (m, 1H); MS calculated for $C_{28}H_{34}FN_6O_2$ (M + H⁺) 505.26, found 505.3. |
| 17-153 | 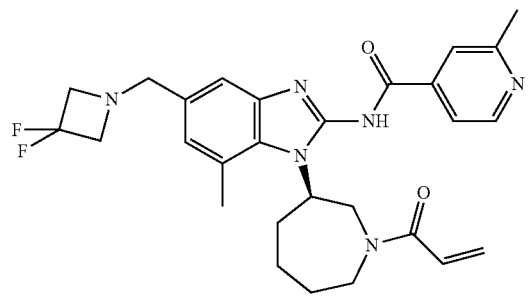 [SMILES: C=CC(=O)N1CCCC[C@@H](n2c(NC(=O)c3ccnc(C)c3)nc3cc(CN4CC(F)(F)C4)cc(C)c32)C1] | ¹H NMR (400 MHz, MeOD) δ 8.55 (d, J = 5.1, 1H), 8.02 (d, J = 15.1, 1H), 8.00-7.86 (m, 1H), 7.41-7.32 (m, 1H), 7.08 (s, 1H), 6.85 (dt, J = 10.0, 16.8, 1H), 6.31 (td, J = 1.9, 16.5, 1H), 5.81 (dd, J = 1.8, 10.6, 0.6H), 5.71 (dd, J = 1.9, 10.5, 0.4H), 5.10-5.02 (m, 1H), 4.98-4.91 (m, 1H), 4.55 (dd, J = 10.7, 13.0, 1H), 4.32-4.28 (m, 1H), 4.10-3.92 (m, 1H), 3.82 (s, 2H), 3.72-3.59 (m, 2H), 3.59-3.44 (m, 1H), 2.89-2.85 (m, 1H), 2.76 (s, 3H), 2.69 (s, 1H), 2.63 (s, 3H), 2.60(s, 1H), 2.28-2.16 (m, 1H), 2.14-1.97 (m, 2H), 1.52-1.37 (m, 1H); MS calc. for $C_{28}H_{33}F_2N_6O_2$ (M + H⁺) 523.26, found 523.2. |
| 17-154 | 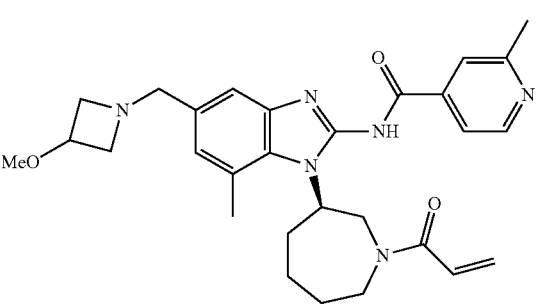 [SMILES: C=CC(=O)N1CCCC[C@@H](n2c(NC(=O)c3ccnc(C)c3)nc3cc(CN4CC(OC)C4)cc(C)c32)C1] | ¹H NMR (400 MHz, MeOD) δ 8.55 (d, J = 3.9, 1H), 8.02 (d, J = 15.3, 1H), 7.99-7.87 (m, 1H), 7.34 (d, J = 5.6, 1H), 7.05 (s, 1H), 6.85 (dt, J = 10.1, 16.8, 1H), 6.31 (td, J = 1.9, 16.5, 1H), 5.81 (dd, J = 1.9, 10.6, 0.6H), 5.71 (dd, J = 1.9, 10.5, 0.4H), 5.15-5.01 (m, 1H), 4.98-4.90 (m, 1H), 4.55 (dd, J = 10.6, 13.1, 1H), 4.35-4.18 (m, 1H), 4.13-3.92 (m, 2H), 3.83-3.67 (m, 1H), 3.77(s, 2H), 3.27 (s, 3H), 3.25-3.20 (m, 1H), 2.94-2.82 (m, 1H), 2.76 (s, 3H), 2.71 (s, 1H), 2.64 (s, 3H), 2.63 (s, 1H), 2.26-2.15 (m, 1H), 2.14-1.99 (m, 3H), 1.52-1.39 (m, 1H); MS calc. for $C_{29}H_{37}N_6O_3$ (M + H⁺) 517.28, found 517.2. |

| Ex. | Compound Structure | Physical Data (¹H NMR and MS) |
|---|---|---|
| 17-155 | 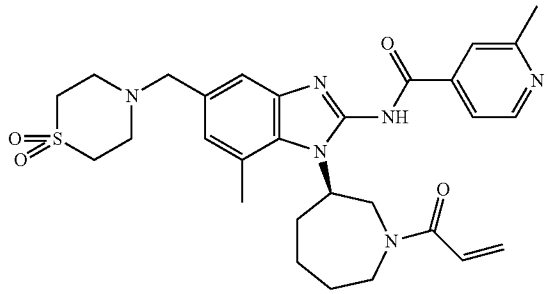 [SMILES: C=CC(=O)N1CCCC[C@@H](n2c(NC(=O)c3ccnc(C)c3)nc3cc(CN4CCS(=O)(=O)CC4)cc(C)c32)C1] | ¹H NMR (400 MHz, CDCl₃) δ 12.61 (s, 1H), 8.62 (m, 1H), 8.02-7.72 (m, 2H), 7.21-7.08 (m, 1H), 7.01-6.86 (m, 1H), 6.61 (m, 1H), 6.50-6.27 (m, 1H), 5.71 (m, 1H), 5.09-4.86 (m, 1.5H), 4.83-4.68 (m, 0.5 H), 4.48-4.29 (m, 1.5H), 4.26-4.14 (m, 0.5H), 4.01-3.81 (m, 1H), 3.65 (s, 2H), 3.74-3.50 (m, 1H), 3.06-2.94 (m, 8H), 2.79 (s, 2H), 2.67 (s, 3H), 2.28-1.96 (m, 3H), 1.65 (s, 3H); MS calc. for $C_{29}H_{37}N_6O_4S$ (M + H⁺) 565.25, found 565.2. |
| 17-156 | 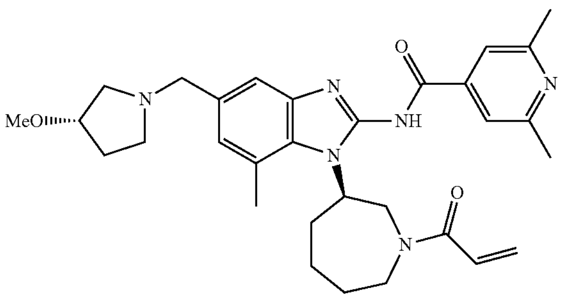 [SMILES: C=CC(=O)N1CCCC[C@@H](n2c(NC(=O)c3cc(C)nc(C)c3)nc3cc(CN4CC[C@H](OC)C4)cc(C)c32)C1] | ¹H NMR (400 MHz, CDCl₃) δ 12.44 (s, 1H), 7.71-7.56 (m, 2H), 7.17-7.07 (m, 1H), 7.04-6.92 (m, 1H), 6.63-6.49 (m, 1H), 6.46-6.24 (m, 1H), 5.77-5.60 (m, 1H), 5.11-4.87 (m, 2H), 4.46-4.30 (m, 2H), 4.26-4.14 (m, 1H), 4.00-3.81 (m, 2H), 3.78-3.42 (m, 3H), 3.22 (s, 3H), 3.10-2.98 (m, 1H), 2.88-2.82 (m, 1H), 2.76-2.62 (m, 1H), 2.67 (s, 3H), 2.62-2.45 (m, 3H), 2.55 (s, 3H) 2.18-1.87 (m, 4H), 1.78 (br, 1H), 1.45-1.29 (m, 2H); MS calculated for $C_{31}H_{41}N_6O_3$ (M + H⁺) 545.32, found 545.3. |
| 17-157 | 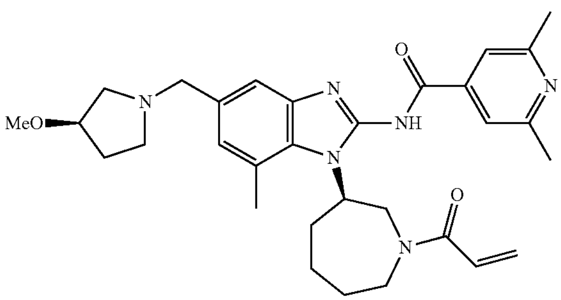 [SMILES: C=CC(=O)N1CCCC[C@@H](n2c(NC(=O)c3cc(C)nc(C)c3)nc3cc(CN4CC[C@@H](OC)C4)cc(C)c32)C1] | MS calculated for $C_{31}H_{41}N_6O_3$ (M + H⁺) 545.32, found 545.3. |
| 17-158 | 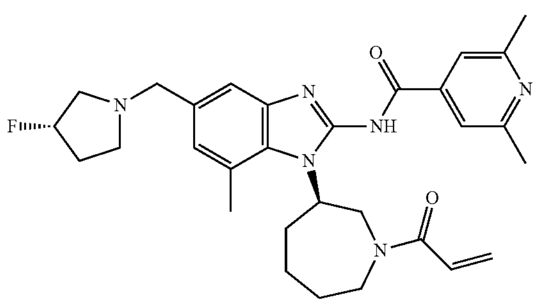 [SMILES: C=CC(=O)N1CCCC[C@@H](n2c(NC(=O)c3cc(C)nc(C)c3)nc3cc(CN4CC[C@H](F)C4)cc(C)c32)C1] | ¹H NMR (400 MHz, CDCl3) δ 12.56 (d, J = 19.2, 1H), 7.82-7.67 (m, 2H), 7.25-7.15 (m, 1H), 7.15-6.94 (m, 1H), 6.63 (dt, J = 15.3, 30.5, 1H), 6.56-6.30 (m, 1H), 5.85-5.66 (m, 1H), 5.36-5.21 (m, 1H), 5.12-4.95 (m, 2.6H), 4.82-4.74 (m, 0.4H), 4.53-4.37 (m, 1.6H), 4.29-4.21 (m, 0.4H), 4.05-3.87 (m, 1H), 3.78-3.49 (m, 1.6H), 3.70 (s, 2H), 3.49-3.29 (m, 0.4H), 3.04-2.67 (m, 3H), 2.77 (s, 3H), 2.67 (s, 3H), 2.54-2.44 (m, 1H), 2.34-1.97 (m, 6H), 1.89-1.80 (m, 1H), 1.55-1.36 (m, 1H); MS calculated for $C_{30}H_{38}FN_6O_2$ (M + H⁺) 533.30, found 533.3. |
| 17-159 | 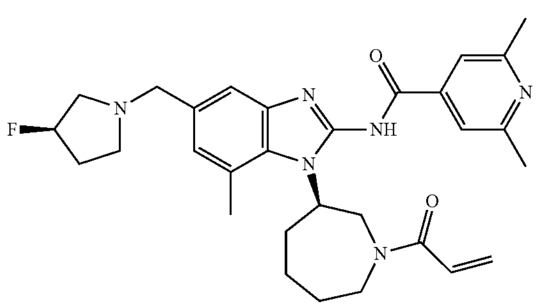 [SMILES: C=CC(=O)N1CCCC[C@@H](n2c(NC(=O)c3cc(C)nc(C)c3)nc3cc(CN4CC[C@@H](F)C4)cc(C)c32)C1] | ¹H NMR (400 MHz, CDCl3) δ 12.56 (s, 1H), 7.76-7.73 (m, 2H), 7.22-7.17 (m, 1H), 7.05-7.04 (m, 1H), 6.68-6.62 (m, 1H), 6.62-6.37 (m, 1H), 5.82-5.70 (m, 1H), 5.29 (br, 1H), 5.13-5.03 (m, 2H), 5.13-4.79 (m, 1H), 4.50-4.38 (m, 2H), 4.06-3.87 (m, 2H), 3.77-3.56 (m, 3H), 3.05-2.69 (m, 3H), 2.77 (s, 3H), 2.63 (s, 6H), 2.49-2.45 (m, 1H), 2.23-2.05 (m, 4H), 1.49-1.42 (m, 1H); MS calculated for $C_{30}H_{38}FN_6O_2$ (M + H⁺) 533.30, found 533.3. |

| Ex. | Compound Structure | Physical Data (¹H NMR and MS) |
|---|---|---|
| 17-160 | 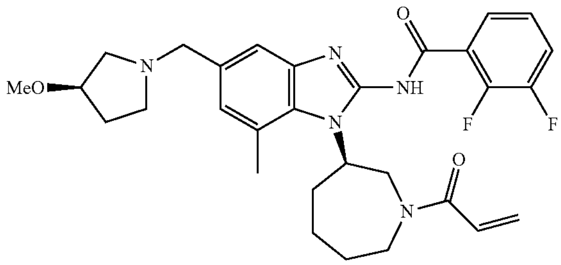 [SMILES: C=CC(=O)N1CCCC[C@@H](n2c(NC(=O)c3cccc(F)c3F)nc3cc(CN4CC[C@@H](OC)C4)cc(C)c32)C1] | ¹H NMR (400 MHz, CDCl3) δ 12.51 (d, J = 31.7, 1H), 7.92-7.74 (m, 1H), 7.31-7.25 (m, 1H), 7.21-6.90 (m, 3H), 6.69-6.51 (m, 1H), 6.45-6.32 (m, 1H), 5.78-5.60 (m, 1H), 5.08-4.86 (m, 1.6H), 4.76-4.64 (m, 0.4H), 4.45-4.38 (m, 1.6H), 4.25-4.19 (m, 0.4H), 4.07-3.77 (m, 2H), 3.77-3.49 (m, 2H), 3.28 (s, 3H), 2.95-2.90 (m, 1H), 2.82-2.66 (m, 1H), 2.72 (s, 3H), 2.66-2.41 (m, 2H), 2.30-1.79 (m, 5H), 1.55 (s, 2H), 1.47-1.19 (m, 2H); MS calculated for $C_{30}H_{36}F_2N_5O_3$ (M + H⁺) 552.27, found 552.3. |
| 17-161 | 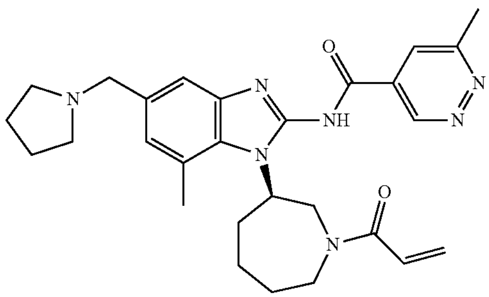 [SMILES: C=CC(=O)N1CCCC[C@@H](n2c(NC(=O)c3cnnc(C)c3)nc3cc(CN4CCCC4)cc(C)c32)C1] | ¹H NMR (400 MHz, CDCl3) δ 12.47 (s, 1H), 9.69 (dd, J = 1.7, 10.1, 1H), 8.02-7.86 (m, 1H), 7.22-7.15 (m, 1H), 7.08-6.94 (m, 1H), 6.66-6.52 (m, 1H), 6.43-6.27 (m, 1H), 5.80-5.61 (m, 1H), 5.11-4.93 (m, 1H), 4.52-4.12 (m, 2H), 3.87-3.82 (m, 1H), 3.76-3.50 (m, 2H), 2.91-2.76 (m, 1H), 2.79 (s, 3H), 2.72 (s, 2H), 2.63-2.56 (m, 1H), 2.57 (s, 3H), 2.24-1.92 (m, 5H), 1.85-1.70 (m, 5H), 1.54-1.27 (m, 1H); MS calculated for $C_{28}H_{36}N_7O_2$ (M + H⁺) 502.29, found 502.3. |
| 17-162 | 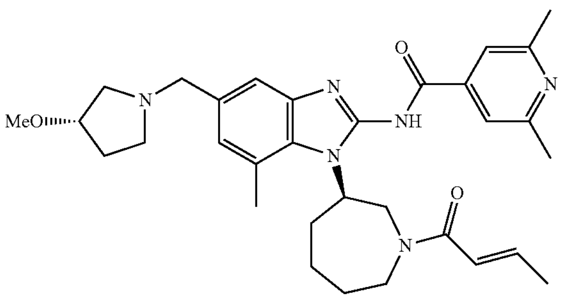 [SMILES: C/C=C/C(=O)N1CCCC[C@@H](n2c(NC(=O)c3cc(C)nc(C)c3)nc3cc(CN4CC[C@H](OC)C4)cc(C)c32)C1] | MS calculated for $C_{32}H_{43}N_6O_3$ (M + H⁺) 559.33, found 569.3. |
| 17-163 | 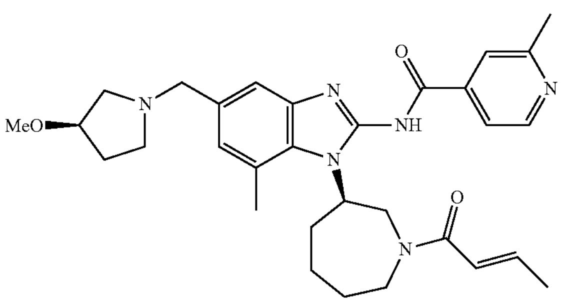 [SMILES: C/C=C/C(=O)N1CCCC[C@@H](n2c(NC(=O)c3ccnc(C)c3)nc3cc(CN4CC[C@@H](OC)C4)cc(C)c32)C1] | ¹H NMR (400 MHz, CDCl3) δ 12.52 (s, 1H), 8.60 (d, J = 5.1, 1H), 7.89 (s, 1H), 7.80 (t, J = 5.4, 1H), 7.21-7.15 (m, 1H), 7.04 (s, 1H), 6.99-6.82 (m, 1H), 6.28 (d, J = 1.7, 15.0, 1H), 5.05-4.76 (m, 2H), 4.42-4.29 (m, 2H), 4.04-3.61 (m, 5H), 3.61-3.44 (m, 1H), 3.26 (s, 3H), 3.22-3.07 (m, 1H), 3.03-2.54 (m, 4H), 2.72(s, 2H), 2.61(s, 3H), 2.29-1.97 (m, 2H), 1.97-1.85 (m, 3H), 1.52-1.31 (m, 3H); MS calculated for $C_{31}H_{41}N_6O_3$ (M + H⁺) 545.32, found 545.3. |
| 17-164 | 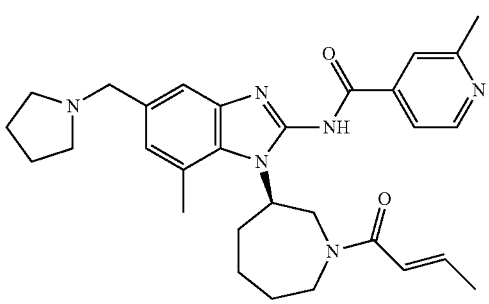 [SMILES: C/C=C/C(=O)N1CCCC[C@@H](n2c(NC(=O)c3ccnc(C)c3)nc3cc(CN4CCCC4)cc(C)c32)C1] | ¹H NMR (400 MHz, CDCl3) δ 12.66-12.44 (m, 1H), 8.63 (d, J = 5.0, 1H), 7.94 (s, 0.65H), 7.91 (s, 0.35H), 7.85-7.78 (m, 1H), 7.25-7.11 (m, 1H), 7.09-7.03 (m, 1H), 7.03-6.86 (m, 1H), 6.31 (d, J = 15.0, 1H), 5.11-4.97 (m, 1H), 4.97-4.76 (m, 1H), 4.50-4.27 (m, 2H), 4.12 (d, J = 7.1, 1H), 4.05-3.88 (m, 1H), 3.67 (s, 2H), 3.61-3.38 (m, 2H), 3.00-2.81 (m, 1H), 2.75 (s, 3H), 2.64 (s, 3H), 2.55 (s, 3H), 2.34-2.17 (m, 1H), 2.04 (s, 3H), 1.92 (d, J = 6.9, 2H), 1.82 (s, 3H), 1.55-1.32 (m, 1H), 1.25 (t, J = 7.2, 1H); MS calculated for $C_{30}H_{39}N_6O_2$ (M + H⁺) 515.31, found 515.3. |

| Ex. | Compound Structure | Physical Data (¹H NMR and MS) |
|---|---|---|
| 17-165 | 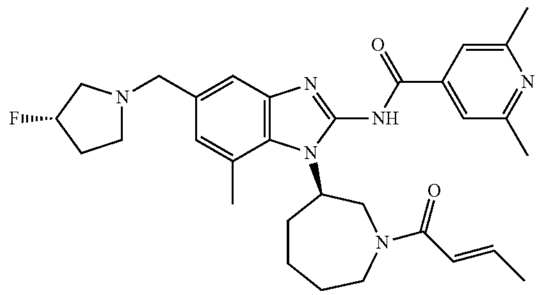 [SMILES: C/C=C/C(=O)N1CCCC[C@@H](n2c(NC(=O)c3cc(C)nc(C)c3)nc3cc(CN4CC[C@H](F)C4)cc(C)c32)C1] | ¹H NMR (400 MHz, CDCl3) δ ¹H NMR (400 MHz, CDCl3) δ 12.68-12.43 (m, 1H), 7.76 (d, J = 11.1, 2H), 7.28-7.13 (m, 1H), 7.13-7.03 (m, 1H), 7.03-6.90 (m, 1H), 6.35-6.31 (m, 1H), 5.32-5.12 (m, 2H), 5.12-4.73 (m, 2H), 4.42-4.38 (m, 3H), 4.12-3.84 (m, 2H), 3.84-3.68 (m, 2H), 3.68-3.52 (m, 1H), 3.05-2.79 (m, 3H), 2.78 (s, 3H), 2.65 (s, 6H), 2.19 (s, 2H), 2.17-2.02 (m, 2H), 1.95 (d, J = 6.8, 3H), 1.51-1.34 (m, 1H); MS calculated for $C_{31}H_{40}FN_6O_2$ (M + H⁺) 547.31, found 547.3. |
| 17-166 | 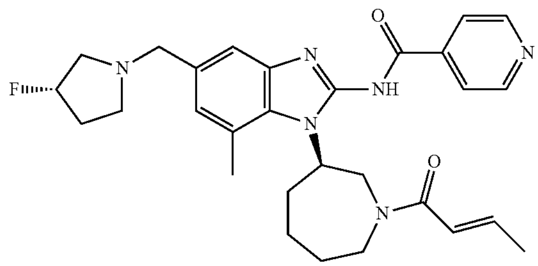 | ¹H NMR (400 MHz, CDCl3) δ 12.58 (s, 1H), 8.66 (d, J = 5.1, 1H), 7.95 (s, 1H), 7.87 (d, J = 5.2, 1H), 7.20( br, 1H), 7.06-7.01 (m, 1H), 6.97 (dd, J = 6.9, 15.0, 1H), 6.33 (dd, J = 1.7, 15.0, 1H), 5.22-5.10 (m, 1H), 4.99-4.90 (m, 1H), 4.53-4.28 (m, 1H), 4.14-4.08 (m, 2H), 4.06-3.91 (m, 2H), 3.73 (s, 2H), 3.69-3.33 (m, 2H), 3.05-2.94 (m, 3H), 2.79 (s, 3H), 2.67 (s, 3H), 2.19 (s, 2H), 2.20-2.18 (m, 1H) 2.15-2.02(m, 2H), 2.01-1.74 (d, 3H), 1.45-1.38 (m, 1H); MS calculated for $C_{30}H_{38}FN_6O_2$ (M + H⁺) 533.30, found 533.2. |
| 17-167 | 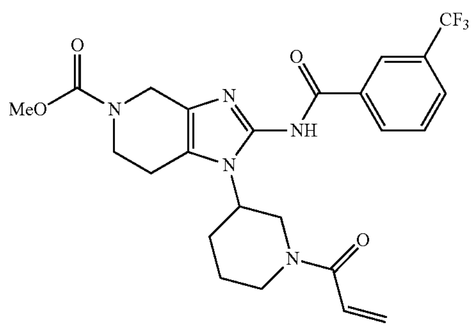 [SMILES: C=CC(=O)N1CCCC(n2c(NC(=O)c3cccc(C(F)(F)F)c3)nc3c2CCN(C(=O)OC)C3)C1] | ¹H-NMR (DMSO-d6, 400 MHz): ∂ 12.5 (br s, 1H), 8.51 (s, 1H), 8.36 (s, 1H), 7.68 (s, 2H), 7.53 (s, 2H), 7.46 (s, 2H), 6.62-6.60 (m, 1H), 6.33 (d, J = 16.8 Hz, 1H), 5.74 (s, 1H), 4.73 (s, 1H), 4.48-4.09 (m, 3H), 3.94-3.76 (m, 7H), 3.19 (s, 2H), 2.69 (s, 3H), 2.03 (s, 3H); MS calculated for $C_{24}H_{27}F_3N_5O_4$ (M + H⁺) 506.19, found 506.2. |
| 17-168 | 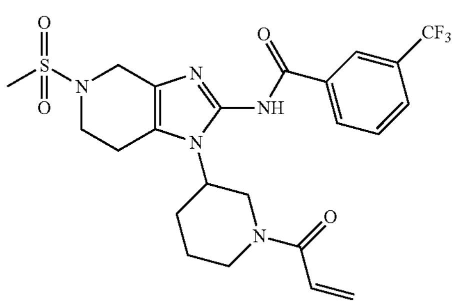 [SMILES: C=CC(=O)N1CCCC(n2c(NC(=O)c3cccc(C(F)(F)F)c3)nc3c2CCN(S(C)(=O)=O)C3)C1] | ¹H-NMR (400 MHz, DMSO-d6): ∂ 12.5 (s, 1H), 8.46-8.40 (m, 2H), 7.80 (d, J = 7.6 Hz, 1H), 7.68-7.64 (m, 1H), 6.88-6.81 (m, 1H), 6.14 (t, J = 15.6 Hz, 1H), 5.74-5.60 (m, 1H), 4.56 (s, 1H), 4.32-4.31 (m, 4H), 3.50-3.40 (m, 3H), 2.98 9s, 3H), 2.86 (s, 3H), 2.11-1.89 (m, 3H), 1.55-1.52 (m, 2H); MS calculated for $C_{23}H_{27}F_3N_5O_4S$ (M + H⁺) 526.17, found 526.1. |
| 17-169 | 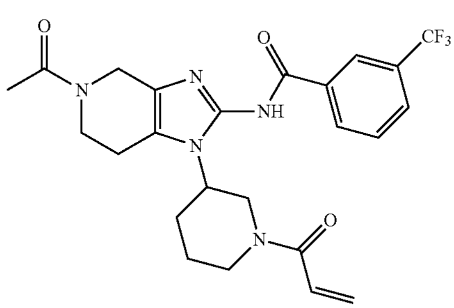 [SMILES: C=CC(=O)N1CCCC(n2c(NC(=O)c3cccc(C(F)(F)F)c3)nc3c2CCN(C(C)=O)C3)C1] | ¹H-NMR (400 MHz, DMSO-d6): ∂ 12.54 (s, 1H), 8.40 (s, 2H), 7.81 (s, 1H), 7.67 (s, 1H), 6.85 (s, 1H), 6.14 (s, 1H), 5.71-5.59 (m, 1H), 4.53-4.20 (m, 5H), 3.90-3.50 (m, 3H), 2.79-2.67 (m, 2H), 2.11-1.87 (m, 7H), 1.51-1.33 (m, 2H); MS calculated for $C_{24}H_{27}F_3N_5O_3$ (M + H⁺) 490.20, found 490.4. |

-continued

| Ex. | Compound Structure | Physical Data (¹H NMR and MS) |
|---|---|---|
| 17-170 | 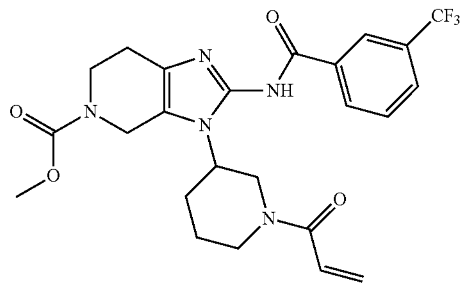 [SMILES: C=CC(=O)N1CCCC(n2c(NC(=O)c3cccc(C(F)(F)F)c3)nc3c2CN(C(=O)OC)CC3)C1] | ¹H-NMR (400 MHz, DMSO-$d_6$): ∂ 12.51 (s, 1H), 8.39 (s, 2H), 7.82 (d, J = 7.2 Hz, 1H), 7.67 (t, J = 7.2 Hz, 1H), 6.86 (d, J = 14 Hz, 1H), 6.14 (t, J = 13.2 Hz, 1H), 5.73-5.59 (m, 1H), 4.54-4.21 (m, 4H), 3.66 (s, 5H), 2.67-2.55 (m, 4H), 2.11-1.86 (m, 2H), 1.57 (s, 1H); MS calculated for $C_{24}H_{25}F_3N_5O_4$ (M − H⁻) 504.19, found 504.3. |
| 17-171 | 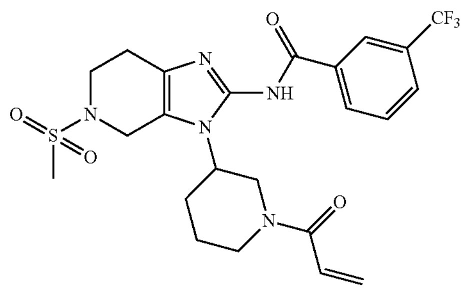 [SMILES: C=CC(=O)N1CCCC(n2c(NC(=O)c3cccc(C(F)(F)F)c3)nc3c2CN(S(C)(=O)=O)CC3)C1] | ¹H-NMR (400 MHz, DMSO-$d_6$): ∂ 12.55 (s, 1H), 8.40 (s, 2H), 7.82 (d, J = 7.2 Hz, 1H), 7.68 (t, J = 7.6 Hz, 1H), 6.87 (t, J = 8.4 Hz, 1H), 6.16 (d, J = 12.8 Hz, 1H), 5.75 (s, 1H), 4.58-4.23 (m, 5H), 3.55-3.36 (m, 3H), 3.02 (s, 3H), 2.69 (s, 3H), 2.11-1.86 (m, 2H), 1.59-1.56 (m, 1H); MS calculated for $C_{23}H_{27}F_3N_5O_4S$ (M + H⁺) 526.17, found 526.1 |
| 17-172 | 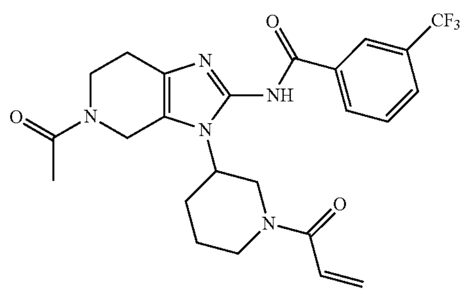 [SMILES: C=CC(=O)N1CCCC(n2c(NC(=O)c3cccc(C(F)(F)F)c3)nc3c2CN(C(C)=O)CC3)C1] | ¹H-NMR (400 MHz, CDCl$_3$): ∂ 8.51 (s, 1H), 8.36 (d, J = 7.2 Hz, 1H), 7.69 (d, J = 6.8 Hz, 1H), 7.53 (t, J = 7.6 Hz, 1H), 6.61-6.59 (m, 1H), 6.33 (d, J = 16.8 Hz, 1H), 5.76-5.74 (m, 1H), 4.81 (s, 2H), 4.42-4.39 (m, 2H), 4.12-3.65 (m, 4H), 2.70-2.64 (m, 4H), 2.22 (s, 3H), 2.15-2.09 (m, 1H); MS calculated for $C_{24}H_{27}F_3N_5O_3$ (M + H⁺) 490.20, found 490.4. |
| 17-173 | 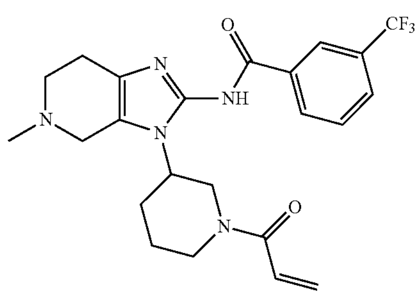 [SMILES: C=CC(=O)N1CCCC(n2c(NC(=O)c3cccc(C(F)(F)F)c3)nc3c2CN(C)CC3)C1] | ¹H-NMR (400 MHz, DMSO-$d_6$): ∂ 12.40 (s, 1H), 8.38 (s, 2H), 7.28-7.65 (m, 3H), 6.87-6.83 (m, 1H), 6.17-6.10 (m, 2H), 5.73-5.58 (m, 1H), 4.54-4.52 (m, 1H), 4.28-4.25 (m, 2H), 3.69-3.50 (m, 3H), 2.69-2.08 (m, 6H), 1.98-1.86 (m, 3H), 1.52-1.29 (m, 3H); MS calculated for $C_{23}H_{27}F_3N_5O_2$ (M + H⁺) 462.20, found 462.3. |
| 17-174 | 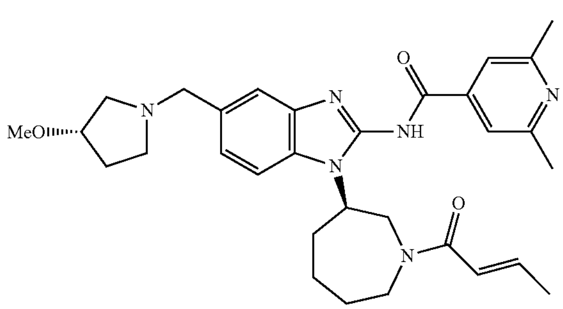 [SMILES: C/C=C/C(=O)N1CCCC[C@@H](n2c(NC(=O)c3cc(C)nc(C)c3)nc3cc(CN4CC[C@H](OC)C4)ccc32)C1] | ¹H NMR (400 MHz, CDCl$_3$) δ 12.39 (s, 1H), 7.74 (s, 1H), 7.72 (s, 1H), 7.41-7.36 (m, 2H), 7.26-7.23 (m, 1H), 7.10-6.91 (m, 1H), 6.49-6.23 (m, 1H), 4.81 (br, 1H), 4.38-4.02 (m, 2H), 4.02-3.58 (m, 5H), 3.27 (s, 3H), 2.85-2.69 (m, 3H), 2.60 (s, 3H), 2.58 (s, 3H), 2.21-1.39 (m, 12H); MS calculated for $C_{31}H_{41}N_6O_3$ (M + H⁺) 545.32, found 545.3. |

| Ex. | Compound Structure | Physical Data (¹H NMR and MS) |
|---|---|---|
| 17-175 | 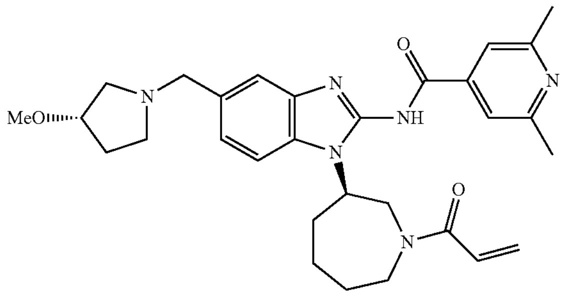 [SMILES: C=CC(=O)N1CCCC[C@@H](n2c(NC(=O)c3cc(C)nc(C)c3)nc3cc(CN4CC[C@H](OC)C4)ccc32)C1] | ¹H NMR (400 MHz, CDCl₃) δ 12.41 (s, 1H), 7.74 (s, 1H), 7.72 (s, 1H), 7.41-7.37 (m, 2H), 7.32-7.21 (m, 1H), 6.76 (dd, J = 10.3, 16.7 Hz, 0.4H), 6.65 (dd, J = 10.4, 16.7 Hz, 0.6H), 6.45 (ddd, J = 1.9, 16.7 Hz, 18.6, 1H), 5.71 (ddd, J = 1.9, 10.4, 50.8 Hz, 1H), 4.83 (br, 1H), 4.31-4.34 (m, 2H), 3.98-3.88 (m, 1H), 3.85-3.65 (m, 4H), 3.27 (s, 3H), 2.88-2.70 (m, 2H), 2.60 (s, 3H), 2.59 (s, 3H), 2.16-1.80 (m, 8H), 1.69-1.46 (m, 2H). ESMS calculated for C₃₀H₃₉N₆O₃ (M + H⁺) 531.30, found 531.2 |
| 17-176 | 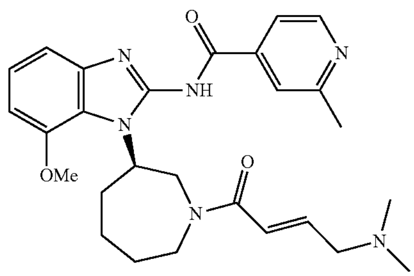 [SMILES: COc1cccc2nc(NC(=O)c3ccnc(C)c3)n([C@@H]3CCCCN(C(=O)/C=C/CN(C)C)C3)c12] | ¹H NMR (400 MHz, CDCl3) δ 12.52 (s, 1H), 8.50-8.45 (m, 1H), 7.92-7.74 (m, 2H), 7.20-7.09 (m, 1H), 6.99-6.89 (m, 1H), 6.81-6.69 (m, 2H), 6.59-6.39 (m, 1H), 5.45-5.30 (m, 1H), 4.64-4.58 (m, 0.45H), 4.38-4.28 (m, 0.55H), 4.15-4.01 (m, 1H), 3.97 (, 1.65H), 3.87 (s, 1.35H), 3.79-3.65 (m, 1H), 3.58-3.47 (m, 1H), 3.27-3.10 (m, 1H), 3.07-2.99 (m, 1H), 2.87-2.75 (m, 1H), 2.72-2.57 (m, 1H), 2.53 (s, 1.65H), 2.50 (s, 1.35H), 2.36-2.24 (m, 1H), 2.18 (s, 2H), 2.14-2.05 (m, 1H), 2.01 (s, 2H), 1.87 (2H), 1.94-1.88 (m, 1H), 1.49-1.32 (m, 1H); MS calculated for C₂₇H₃₅N₆O₃ (M + H⁺) 491.27, found 491.3. |
| 17-177 | 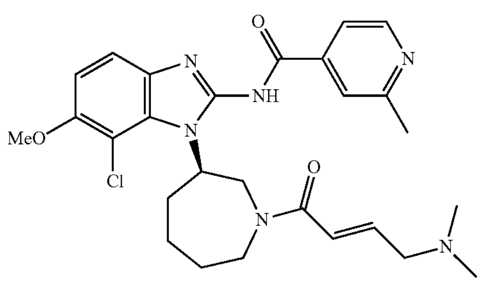 [SMILES: COc1ccc2nc(NC(=O)c3ccnc(C)c3)n([C@@H]3CCCCN(C(=O)/C=C/CN(C)C)C3)c2c1Cl] | ¹H-NMR (400 MHz, CD₂Cl₂): δ 12.56 (s, 1H), 8.51-8.49 (m, 1H), 7.84-7.72 (m, 2H), 7.18-7.13 (m, 1H), 6.91-6.72 (m, 2H), 6.43 (dd, J = 5.3, 15.1 Hz, 1H), 5.63-5.58 (m, 1H), 4.75-4.69 (m, 0.5H), 4.47-4.41 (m, 0.5H), 4.28-4.23 (m, 0.6H), 4.04-3.95 (m, 0.6H), 3.93-3.89 (m, 0.4H), 3.85 & 3.84 (s & s, 3H), 3.79-3.72 (m, 0.4H), 3.59-3.53 (m, 0.6H), 3.35-3.29 (m, 0.4H), 3.05 (br d, J = 5.4 Hz, 1H), 2.87 (br d, J = 5.7 Hz, 1H), 2.76-2.59 (m, 1H), 2.52 (s, 3H), 2.21 (s, 3H), 2.04 (s, 3H), 2.10-1.78 (m, 4H), 1.44-1.35 (m, 1H); MS calc. for C₂₇H₃₄ClN₆O₃ (M + H⁺) 525.23, found 525.2. |
| 17-178 | 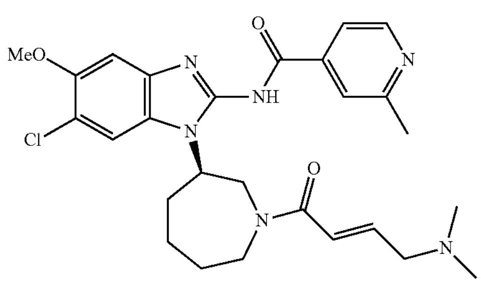 [SMILES: COc1cc2nc(NC(=O)c3ccnc(C)c3)n([C@@H]3CCCCN(C(=O)/C=C/CN(C)C)C3)c2cc1Cl] | ¹H-NMR (400 MHz, CD₂Cl₂): δ 12.48 (s, 1H), 8.51-8.49 (m, 1H), 7.86-7.76 (m, 2H), 7.42 (s, 0.6H), 7.33 (s, 0.4H), 6.93 (s, 0.4H), 6.89 (s, 0.6H), 6.85-6.73 (m, 1H), 6.60-6.53 (m, 1H), 4.76-4.58 (m, 1H), 4.11-4.01 (m, 2H), 3.85 & 3.83 (s & s, 3H), 3.77-3.70 (m, 1H), 3.64-3.58 (m, 1H), 3.27-3.22 (m, 1.4H), 2.87-2.80 (m, 0.6H), 2.53 & 2.52 (s & s, 3H), 2.34 (s, 3.6H), 2.08 (s, 2.4H), 2.05-1.76 (m, 4H), 1.48-1.40 (m, 2H); MS calculated for C₂₇H₃₄ClN₆O₃ (M + H⁺) 525.23, found 525.2. |
| 17-179 | 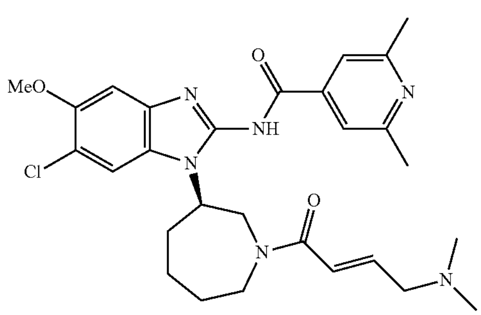 [SMILES: COc1cc2nc(NC(=O)c3cc(C)nc(C)c3)n([C@@H]3CCCCN(C(=O)/C=C/CN(C)C)C3)c2cc1Cl] | ¹H NMR (400 MHz, CD₂Cl₂): δ 12.45 (br s, 1H), 7.66 (s, 1.2H), 7.62 (s, 0.8H), 7.42 (s, 0.6H), 7.30 (s, 0.4H), 6.92 (0.4H), 6.88 (s, 0.6H), 6.85-6.72 (m, 1H), 6.44-6.40 (m, 1H), 4.72-4.57 (m, 1H), 4.13-4.05 (m, 2H), 3.84 & 3.82 (s & s, 3H), 3.79-3.69 (m, 1H), 3.60-3.55 (0.6H), 3.24-3.20 (0.4H), 3.03 (d, J = 6.0 Hz, 1H), 2.73-2.53 (m, 1H), 2.48 & 2.47 (s & s, 6H), 2.18 (s, 3.6 H), 1.95 (s, 2.4H), 2.04-1.78 (m, 4H), 1.48-1.39 (m, 2H); MS calculated for C₂₈H₃₆ClN₆O₃ (M + H⁺) 539.25, found 539.2. |

| Ex. | Compound Structure | Physical Data (¹H NMR and MS) |
|---|---|---|
| 17-180 | 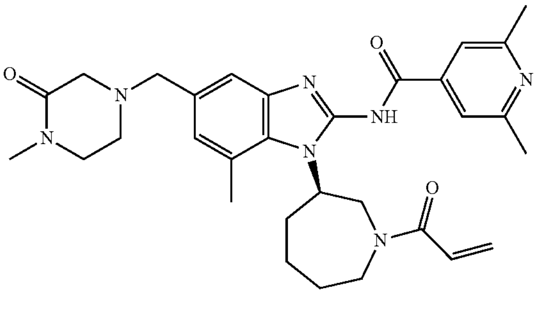 [SMILES: C=CC(=O)N1CCCC[C@@H](n2c(NC(=O)c3cc(C)nc(C)c3)nc3cc(CN4CCN(C)C(=O)C4)cc(C)c32)C1] | ¹H NMR (400 MHz, MeOD) δ 7.78 (s, 1H), 7.75 (s, 1H), 7.35-7.34 (m, 1H), 7.08-7.07 (m, 1H), 6.86-6.79 (m, 1H), 6.31-6.27 (m, 1H), 5.82-5.79 (m, 1H), 5.11-5.01 (m, 1H), 4.53- 4.51 (m, 1H), 4.29-4.26 (m, 1H), 4.19-3.93 (m, 1H), 3.62 (s, 2H), 3.54-3.45 (m, 1H), 3.37-3.32 (m, 2H), 3.11 (s, 2H), 3.04-2.99 (m, 1H), 2.95 (s, 3H), 2.92-2.79 (m, 1H), 2.71 (s, 3H), 2.58 (br, 2H), 2.26-2.15 (m, 1H), 2.06 (br, 2H), 1.50-1.35 (m, 1H), 1.28 (s, 3H), 1.29 (s, 3H); MS calculated for $C_{31}H_{40}N_7O_3$ (M + H⁺) 558.31, found 558.3. |
| 17-181 | 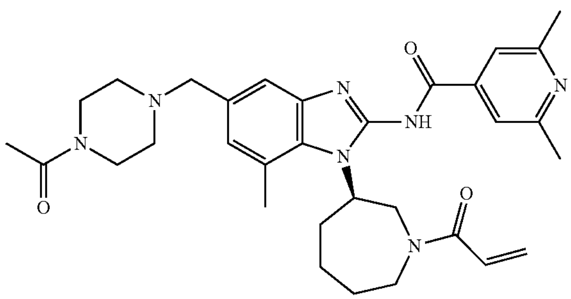 [SMILES: C=CC(=O)N1CCCC[C@@H](n2c(NC(=O)c3cc(C)nc(C)c3)nc3cc(CN4CCN(C(C)=O)CC4)cc(C)c32)C1] | ¹H NMR (400 MHz, MeOD) δ 7.77 (s, 1H), 7.74 (s, 1H), 7.33-7.31 (m, 1H), 7.07-7.04 (m, 1H), 6.86-4.79 (m, 1H), 6.23-6.27 (m, 1H), 5.82-5.79 (m, 1H), 5.08-5.01 (m, 1H), 4.55-4.49 (m, 1H), 4.27 (d, 1H), 4.04-3.93 (m, 1H), 3.71-3.62 (m, 2H), 3.59-3.52 (m, 4H), 3.20-3.17 (m, 1H), 2.88-2.84 (m, 1H), 2.73 (s, 2H), 2.68 (br, 1H), 2.57 (s, 3H), 2.47-2.42 (m, 2H), 2.21 (br, 1H), 2.16 (s, 2H), 2.08 (s, 3H), 2.05 (br, 2H), 1.36 (s, 3H), 1.35 (s, 3H); MS calculated for $C_{32}H_{42}N_7O_3$ (M + H⁺) 572.33, found 572.3. |
| 17-182 | 58% ee | ¹H NMR (400 MHz, CD₂Cl₂) δ 8.62 (dd, J = 5.8, 21.5 Hz, 1H), 8.02 (d, J = 5.8 Hz, 1H), 7.40-7.22 (m, 3H), 6.91-6.82 (m, 1H), 6.59-6.45 (m, 1H), 5.73-5.58 (m, 1H), 4.85 (dd, J = 10.7, 14.7 Hz, 0.5H), 4.56 (dd, J = 10.5, 13.0 Hz, 0.5H), 4.44 (dd, J = 3.9, 13.0 Hz, 0.5H), 4.27-4.15 (m, 0.5H), 4.06 (dd, J = 3.1, 14.6 Hz, 0.5H), 3.98-3.87 (m, 1H), 3.83-3.72 (m, 1H), 3.49-3.39 (m, 0.5H), 3.04 (dd, J = 6.0, 50.1 Hz, 2H), 2.90-2.74 (m, 1H), 2.70 (s, 3H), 2.28 (s, 3H), 2.21-1.99 (m, 5H), 1.77 (dd, J = 3.5, 13.5 Hz, 7H), 1.58-1.41 (m, 1H), MS calculated for $C_{28}H_{37}ClN_6O_3P$ (M + H⁺) 571.23, found 571.3. |
| 17-183 | 58% ee | ¹H NMR (400 MHz, MeOD) δ 9.04-8.87 (m, 1H), 8.87-8.74 (m, 1H), 8.34-8.09 (m, 1H), 7.52 (dd, J = 7.8, 11.4 Hz, 1H), 7.42-7.15 (m, 2H), 6.94-6.78 (m, 1H), 6.78-6.60 (m, 1H), 5.77-5.56 (m, 1H), 4.88-4.80 (m, 0.5H), 4.66-4.57 (m, 0.5H), 4.38 (d, J = 9.7 Hz, 0.5H), 4.28-4.15 (m, 1H), 4.06-3.86 (m, 1H), 3.86-3.69 (m, 1H), 3.55-3.39 (m, 0.5H), 3.15 (dd, J = 6.5, 50.0 Hz, 2H), 2.89-2.70 (m, 1H), 2.29 (d, J = 14.7 Hz, 3H), 2.25-2.01 (m, 5H), 1.86 (d, J = 13.7 Hz, 6H), 1.78-1.65 (m, 1H), 1.48 (s, 1H), MS calculated for $C_{27}H_{35}ClN_6O_3P$ (M + H⁺) 557.21, found 557.1. |

| Ex. | Compound Structure | Physical Data (¹H NMR and MS) |
|---|---|---|
| 17-184 | 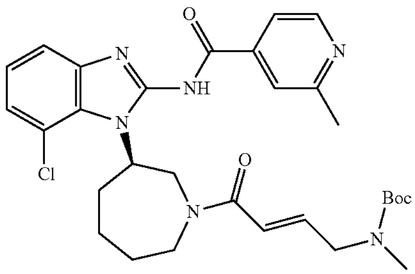 [SMILES: Cc1cc(C(=O)Nc2nc3cccc(Cl)c3n2[C@@H]2CCCCN(C(=O)/C=C/CN(C)C(=O)OC(C)(C)C)C2)ccn1] | ¹H NMR (400 MHz, CD$_2$Cl$_2$) δ 8.64 (t, J = 4.4 Hz, 1H), 7.96 (d, J = 9.9 Hz, 1H), 7.86 (t, J = 5.4 Hz, 1H), 7.41-7.16 (m, 3H), 6.88-6.73 (m, 1H), 6.47-6.30 (m, 1H), 5.71-5.57 (m, 1H), 4.85 (dd, J = 10.6, 14.7 Hz, 0.5H), 4.62-4.49 (m, 0.5H), 4.46-4.36 (m, 0.5H), 4.26-4.07 (m, 0.5H), 4.04 (s, 1.5H), 3.96-3.78 (m, 1.5H), 3.74-3.60 (m, 0.5H), 3.51-3.33 (m, 0.5H), 2.90 (s, 2H), 2.80-2.74 (m, 1H), 2.70-2.64 (m, 1H), 2.64 (s, 3H), 2.10 (m, 5H), 1.49 (s, 6H), 1.34 (s, 3H); MS calculated for C$_{30}$H$_{38}$ClN$_6$O$_4$ (M + H⁺) 581.26, found 581.2. |
| 17-185 | 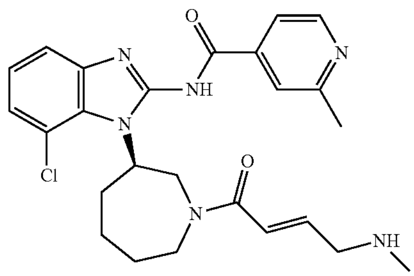 [SMILES: CNC/C=C/C(=O)N1CCCC[C@@H](n2c(NC(=O)c3ccnc(C)c3)nc3cccc(Cl)c32)C1] | ¹H NMR (400 MHz, CD$_2$Cl$_2$) δ 8.51 (dd, J = 5.0, 2.3 Hz, 1H), 7.84 (d, J = 9.2 Hz, 1H), 7.75 (t, J = 5.1 Hz, 1H), 7.30-7.05 (m, 3H), 6.88-6.78 (m, 1H), 6.43-6.38 (m, 1H), 5.68-5.58 (m, 1H), 4.75-4.69 (m, 0.5H), 4.45-4.39 (m, 0.5H), 4.29-4.26 (m, 0.5H), 4.03-3.86 (m, 1H), 3.85-3.70 (m, 0.5H), 3.57-3.51 (s, 0.6H), 3.35-3.31 (m, 0.4H), 3.29 (dd, J = 5.3, 1.7 Hz, 1H), 3.14-3.12 (m, 1H), 2.89-2.60 (m, 1H), 2.53 (s, 2H), 2.35 (s, 1.5H), 2.17 (s, 1.5H), 2.13-1.76 (m, 5H), 1.45-1.35 (m, 1H); MS calculated for C$_{25}$H$_{30}$ClN$_6$O$_2$ (M + H⁺) 481.20, found: 481.2. |
| 17-186 | 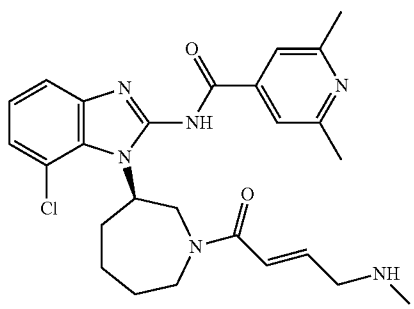 [SMILES: CNC/C=C/C(=O)N1CCCC[C@@H](n2c(NC(=O)c3cc(C)nc(C)c3)nc3cccc(Cl)c32)C1] | ¹H NMR (400 MHz, CD$_2$Cl$_2$) δ 7.63-7.55 (m, 2H), 7.25-7.08 (m, 3H), 6.88-6.70 (m, 1H), 6.47-6.28 (m, 1H), 5.60-5.41 (m, 1H), 4.80-4.67 (m, 0.5H), 4.51-4.37 (m, 0.5H), 4.32-4.15 (m, 0.5H), 4.09-3.97 (m, 0.5H), 3.95-3.85 (m, 0.5H), 3.84-3.68 (m, 0.5H), 3.61-3.47 (m, 1H), 3.33-3.25 (m, 1H), 3.20-3.05 (m, 1H), 2.79-2.62 (m, 1H), 2.50-2.29 (m, 6.5H), 2.27-1.78 (m, 6.5H), 1.49-1.29 (m, 1H); MS calculated for C$_{26}$H$_{32}$ClN$_6$O$_2$ (M + H⁺) 495.22, found: 495.25. |
| 17-187 | 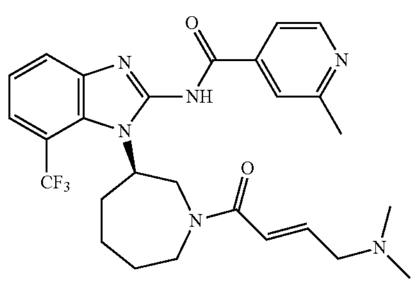 [SMILES: Cc1cc(C(=O)Nc2nc3cccc(C(F)(F)F)c3n2[C@@H]2CCCCN(C(=O)/C=C/CN(C)C)C2)ccn1] | ¹H NMR (400 MHz, CD$_2$Cl$_2$) δ 8.51 (s, 1H), 8.41-8.17 (m, 1H), 7.84 (d, J = 16.7 Hz, 1H), 7.79-7.70 (m, 1H), 7.59-7.50 (m, 2H), 7.35-7.23 (m, 1H), 6.78-6.66 (m, 1H), 6.39 (dd, J = 15.0 Hz, 0.6H), 6.29 (dd, J = 15.0 Hz, 0.4H), 4.88-4.77 (m, 0.6H), 4.68-4.51 (m, 1.4H), 4.29-4.12 (m, 1H), 3.90-3.44 (m, 3H), 2.98 (d, J = 5.33 Hz, 2H), 2.86-2.67 (m, 2H), 2.53 (s, 3H), 2.41-2.26 (m, 1H), 2.15 (s, 3H), 1.96 (s, 3H), 2.10-1.72 (m, 3H), 1.44-1.31(m, 1H). MS calculated for C$_{27}$H$_{32}$F$_3$N$_6$O$_2$ (M + H⁺) 529.25, found: 529.2. |
| 17-188 | 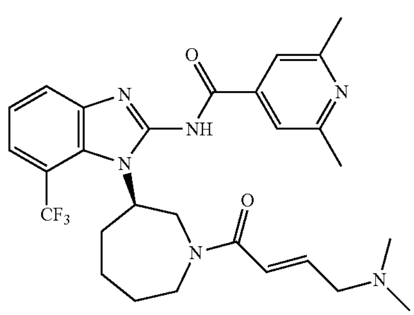 [SMILES: Cc1cc(C(=O)Nc2nc3cccc(C(F)(F)F)c3n2[C@@H]2CCCCN(C(=O)/C=C/CN(C)C)C2)cc(C)n1] | ¹H NMR (400 MHz, CD$_2$Cl$_2$) δ 7.65-7.47 (m, 4H), 7.36-7.20 (m, 1H), 6.80-6.64 (m, 1H), 6.45-6.22 (m, 1H), 4.91-4.77 (m, 0.6H), 4.67-4.52 (m, 1.4H), 4.25-4.12 (m, 1H), 3.91-3.79 (m, 1H), 3.75-3.55 (m, 1.2H), 3.52-3.37 (m, 0.7H), 3.04-2.97 (m, 1H), 2.89-2.69 (m, 2H), 2.47 (s, 3H), 2.17 (s, 3H), 2.00 (s, 3H), 2.10-1.73 (m, 3H), 1.44-1.32 (m, 1H); MS calculated for C$_{28}$H$_{34}$F$_3$N$_6$O$_2$ (M + H⁺) 543.26, found: 543.2. |

| Ex. | Compound Structure | Physical Data ($^1$H NMR and MS) |
|---|---|---|
| 17-189 | 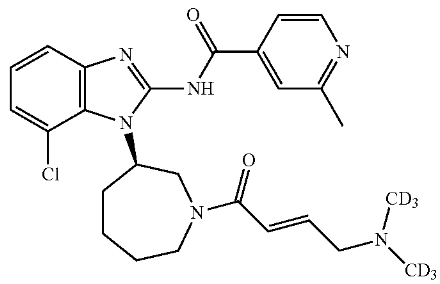 [SMILES: [2H]C([2H])([2H])N(C/C=C/C(=O)N1CCCC[C@@H](n2c(NC(=O)c3ccnc(C)c3)nc3cccc(Cl)c32)C1)C([2H])([2H])[2H]] | $^1$H NMR (400 MHz, CD$_2$Cl$_2$) δ 8.51-8.47 (m, 1H), 7.83 (d, J = 9.3 Hz, 1H), 7.78-7.70 (s, 1H), 7.25-7.08 (m, 3H), 6.78-6.69 (m, 1H), 6.42-6.37 (m, 1H), 5.59-5.42 (m, 1H), 4.77-4.68 (m, 0.5H), 4.47-4.36 (m, 0.5H), 4.34-4.21 (m, 0.5H), 4.13-3.96 (m, 0.5H), 3.96-3.86 (m, 0.5H), 3.82-3.68 (m, 1H), 3.62-3.47 (m, 1H), 3.36-3.24 (m, 0.5H), 2.98 (d, J = 5.9 Hz, 1H), 2.81 (d, J = 5.9 Hz, 1H), 2.78-2.59 (m, 1H), 2.53 (s, 3H), 2.03 (s, 4H), 1.43-1.29 (m, 1H); MS calculated for C$_{26}$H$_{26}$D$_6$ClN$_6$O$_2$ (M + H$^+$) 501.26, found: 501.3. |
| 17-190 | 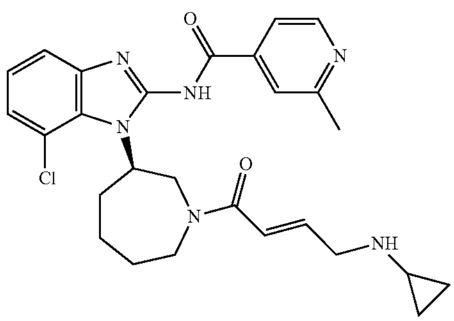 [SMILES: Cc1cc(C(=O)Nc2nc3cccc(Cl)c3n2[C@@H]2CCCCN(C(=O)/C=C/CNC3CC3)C2)ccn1] | $^1$H NMR (400 MHz, CD$_2$Cl$_2$) δ 8.52 (s, 1H), 7.83 (d, J = 7.3 Hz, 1H), 7.74 (s, 1H), 7.26-7.08 (m, 3H), 6.90-6.76 (m, 1H), 6.43-6.29 (m, 1H), 5.60-5.42 (m, 1H), 4.77-4.66 (m, 0.5H), 4.47-4.37 (m, 0.5H), 4.32-4.22 (m, 0.5H), 4.06-3.95 (m, 0.5H), 3.94-3.84 (m, 0.5H), 3.83-3.70 (m, 0.5H), 3.60-3.50 (m, 0.6H), 3.39 (d, J = 5.4 Hz, 1H), 3.35-3.27 (m, 0.4H), 3.25 (d, J = 5.2 Hz, 1H), 2.77-2.61 (m, 1H), 2.53 (s, 3H), 1.89 (s, 6H), 1.47-1.31 (m, 2H), 0.38-0.32 (m, 1H), 0.28-0.22 (m, 1H), 0.21-0.15 (m, 1H), 0.04-0.02 (m, 1H); MS calculated for C$_{27}$H$_{32}$ClN$_6$O$_2$ (M + H$^+$) 507.22, found: 507.2. |
| 17-191 | 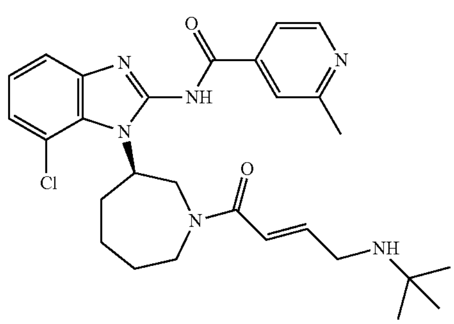 [SMILES: Cc1cc(C(=O)Nc2nc3cccc(Cl)c3n2[C@@H]2CCCCN(C(=O)/C=C/CNC(C)(C)C)C2)ccn1] | $^1$H NMR (400 MHz, CD$_2$Cl$_2$) δ 8.53-8.47 (m, 1H), 7.83 (d, J = 5.83 Hz, 1H), 7.79-7.70 (m, 1H), 7.28-7.09 (m, 3H), 6.94-6.78 (m, 1H), 6.51-6.34 (m, 1H), 5.60-5.43 (m, 1H), 4.77-4.68 (m, 0.5H), 4.46-4.34 (m, 0.5H), 4.34-4.21 (m, 0.7H), 4.08-3.96 (m, 0.5H), 3.96-3.85 (m, 0.3H), 3.85-3.69 (m, 0.5H), 3.59-3.47 (m, 0.7H), 3.34-3.26 (m, 1.3H), 3.17-3.12 (m, 1H), 2.79-2.57 (m, 1H), 2.53 (s, 3H), 1.89 (s, 6H), 1.50-1.28 (m, 1H), 1.03 (s, 5H), 0.85 (s, 4H); MS calculated for C$_{28}$H$_{36}$ClN$_6$O$_2$ (M + H$^+$) 523.25, found: 523.2. |
| 17-192 | 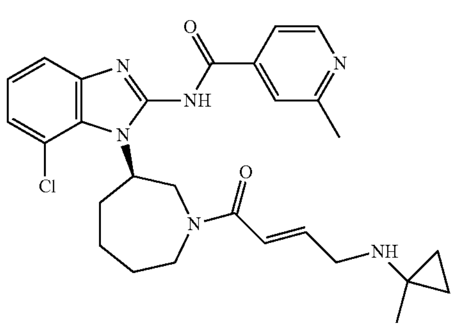 [SMILES: Cc1cc(C(=O)Nc2nc3cccc(Cl)c3n2[C@@H]2CCCCN(C(=O)/C=C/CNC3(C)CC3)C2)ccn1] | $^1$H NMR (400 MHz, CD$_2$Cl$_2$) δ 8.53-8.50 (m, 1H), 7.85-7.81 (m, 1H), 7.77-7.73 (m, 1H), 7.26-7.07 (m, 3H), 6.87-6.77 (m, 1H), 6.47-6.29 (m, 1H), 5.59-5.42 (m, 1H), 4.78-4.65 (m, 0.5H), 4.47-4.35 (m, 0.5H), 4.33-4.24 (m, 0.5H), 4.06-3.94 (m, 0.4H), 3.93-3.83 (m, 0.5H), 3.83-3.68 (m, 0.6H), 3.60-3.48 (m, 0.7H), 3.42-3.38 (m, 1H), 3.33-3.20 (m, 1.3H), 3.02-2.96 (m, 0.3H), 2.86-2.59 (m, 1.7H), 2.53 (s, 3H), 2.15-1.77 (m, 6H), 1.18 (s, 1.5H), 1.04 (s, 1.5H), 0.49-0.46 (m, 1H), 0.30-0.27 (m, 1H), 0.24-0.20 (m, 1H), 0.16-0.13 (m, 1H); MS calculated for C$_{28}$H$_{34}$ClN$_6$O$_2$ (M + H$^+$) 521.24, found: 521.3. |

| Ex. | Compound Structure | Physical Data (¹H NMR and MS) |
|---|---|---|
| 17-193 | 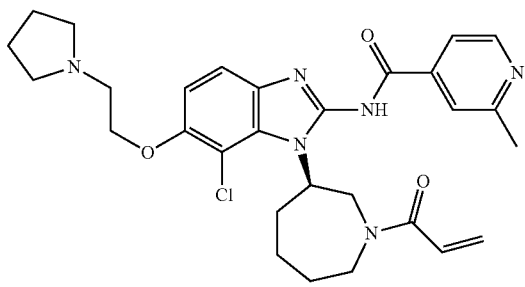 | ¹H NMR (400 MHz, CD$_2$Cl$_2$) δ 8.60-8.41 (m, 1H), 7.88-7.79 (m, 1H), 7.79-7.68 (m, 1H), 7.20-7.15 (m, 1H), 7.01-6.81 (m, 1H), 6.65-6.49 (m, 1H), 6.35-6.16 (m, 1H), 5.65-5.46 (m, 2H), 4.79-4.73 (m, 1H), 4.47-4.22 (m, 3H), 4.05-3.50 (m, 2H), 3.45-3.27 (m, 2H), 3.27-3.08 (m, 2H), 3.07-2.96 (m, 1H), 2.95-2.77 (m, 1H), 2.76-2.57 (m, 1H), 2.54 (s, 2H), 1.97-1.31 (m, 8H), 1.30-1.22 (m, 1H), 1.21-1.06 (m, 1H). MS calculated for C$_{29}$H$_{36}$ClN$_6$O$_3$ (M + H⁺) 551.25, found: 551.2. |
| 17-194 | 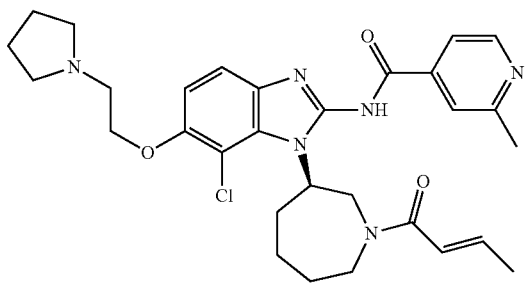 [SMILES: C/C=C/C(=O)N1CCCC[C@@H](n2c(NC(=O)c3ccnc(C)c3)nc3ccc(OCCN4CCCC4)c(Cl)c32)C1] | ¹H NMR (400 MHz, CD$_2$Cl$_2$) δ 8.50 (s, 1H), 7.82 (d, J = 6.63 Hz, 1H), 7.73 (s, 1H), 7.16-7.11 (m, 1H), 6.92-6.79 (m, 2H), 6.34-6.20 (m, 1H), 5.71-5.52 (m, 1H), 4.78-4.65 (m, 0.5H), 4.48-4.35 (m, 0.5H), 4.30-4.20 (m, 0.5H), 4.12-3.95 (m, 3H), 3.93-3.84 (m, 0.5H), 3.82-3.65 (m, 0.5H), 3.64-3.39 (m, 1H), 3.37-3.22 (m, 0.5H), 2.88-2.82 (m, 2H), 2.78-2.62 (m, 1H), 2.56 (s, 3H), 2.52 (s, 3H), 2.13-1.77 (m, 5H), 1.62-1.33 (m, 7H); MS calculated for C$_{30}$H$_{38}$ClN$_6$O$_3$ (M + H⁺) 565.26, found: 565.2. |
| 17-195 | 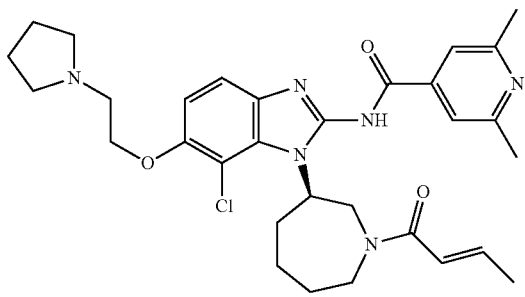 [SMILES: C/C=C/C(=O)N1CCCC[C@@H](n2c(NC(=O)c3cc(C)nc(C)c3)nc3ccc(OCCN4CCCC4)c(Cl)c32)C1] | ¹H NMR (400 MHz, CD2Cl2) δ 7.63 (d, J = 6.1 Hz, 2H), 7.16-7.10 (m, 1H), 6.93-6.75 (m, 2H), 6.28 (t, J = 14.3 Hz, 1H), 5.69-5.56 (m, 1H), 4.79-4.69 (m, 0.5H), 4.49-4.39 (m, 0.5H), 4.28-4.20 (m, 0.5 H), 4.12-4.01 (m, 3H), 3.94-3.85 (m, 0.5H), 3.82-3.69 (m, 0.5H), 3.60-3.49 (m, 1H), 3.33-3.24 (m, 0.5H), 2.87 (t, J = 5.7 Hz, 2H), 2.78-2.62 (m, 1H), 2.58 (s, 3H), 2.48 (s, 3H), 2.40-2.27 (m, 1H), 2.12-1.81 (m, 6H), 1.77-1.51 (m, 7H), 1.45-1.30 (m, 1H); MS calc. for C$_{31}$H$_{40}$ClN$_6$O$_3$ (M + H⁺) 579.28, found: 579.3. |
| 17-196 | 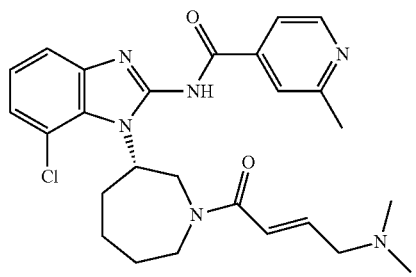 [SMILES: Cc1cc(C(=O)Nc2nc3cccc(Cl)c3n2[C@H]2CCCCN(C(=O)/C=C/CN(C)C)C2)ccn1] | ¹H NMR (400 MHz, CD$_2$Cl$_2$) δ 8.67-8.50 (m, 1H), 7.90 (dd, J = 10.3, 17.3 Hz, 1H), 7.86-7.76 (m, 1H), 7.42-7.10 (m, 3H), 6.94-6.72 (m, 1H), 6.62-6.35 (m, 1H), 5.73-5.48 (m, 1H), 4.83-4.77 (m, 0.5H), 4.59-4.42 (m, 0.5H), 4.40-4.36 (m, 0.5H), 4.19-3.92 (m, 1H), 3.88-3.81 (m, 0.5H), 3.68-3.61 (m, 0.5H), 3.46-3.35 (m, 0.5H), 3.07 (dd, J = 6.6, 15.3 Hz, 1H), 3.02-2.85 (m, 1H), 2.85-2.71 (m, 1H), 2.57 (s, 3H), 2.27 (s, 3H), 2.20-2.01 (m, 4H), 2.01-1.86 (m, 3H), 1.62-1.38 (m, 1H); MS calculated for C$_{26}$H$_{32}$ClN$_6$O$_2$ (M + H⁺) 495.22, found 495.10. |

| Ex. | Compound Structure | Physical Data ($^1$H NMR and MS) |
|---|---|---|
| 17-197 | 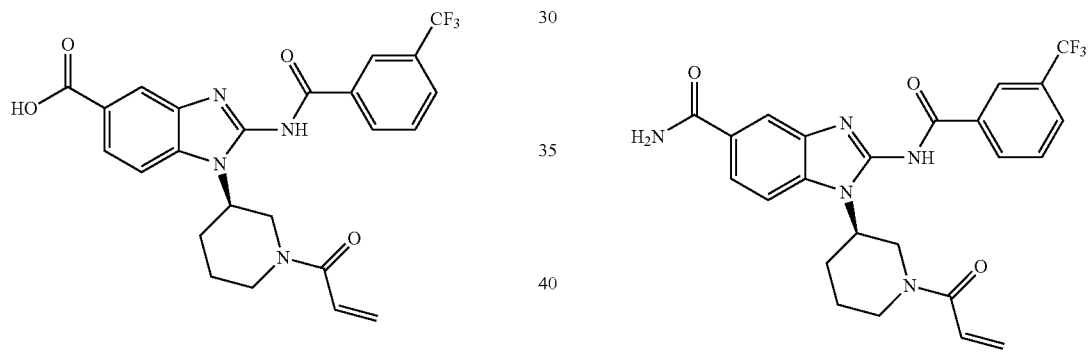 | $^1$H NMR (400 MHz, CD$_2$Cl$_2$) δ 7.77-7.66 (m, 2H), 7.38-7.10 (m, 3H), 6.94-6.75 (m, 1H), 6.50 (ddt, J = 1.4, 6.9, 15.2 Hz, 1H), 5.74-5.49 (m, 1H), 4.86 (ddd, J = 5.9, 8.5, 25.4 Hz, 0.5H), 4.61-4.48 (m, 0.5H), 4.43-4.30 (m, 0.5H), 4.22-4.09 (m, 0.5H), 4.01 (dd, J = 3.5, 14.7 Hz, 0.5H), 3.87 (dt, J = 8.6, 14.4 Hz, 0.5H), 3.73-3.53 (m, 0.5H), 3.44-3.28 (m, 0.5H), 3.16-3.05 (m, 1H), 2.93 (dd, J = 1.3, 6.0 Hz, 1H), 2.88-2.70 (m, 1H), 2.58 (s, 6H), 2.24 (s, 3H), 2.21-1.85 (m, 7H), 1.57-1.41 (m, 1H); MS calculated for C$_{27}$H$_{34}$ClN$_6$O$_2$ (M + H+) 509.24, found: 509.2. |

Example 18

(R)-1-(1-acryloylpiperidin-3-yl)-2-(3-(trifluoromethyl)benzamido)-1H-benzo[d]imidazole-5-carboxylic acid

Example 19

(R)-1-(1-acryloylpiperidin-3-yl)-2-(3-(trifluoromethyl)benzamido)-1H-benzo[d]imidazole-5-carboxamide A solution of Example 17-109 (50 mg, 0.1 mmol) and LiOH.H$_2$O (12 mg, 0.25 mmol) in 1:1 THF/H$_2$O (6 mL) was stirred at room temperature for 14 h (completion of reaction monitored by TLC). The mixture was diluted with water, adjusted to pH 3.5 with aqueous citric acid and extracted with CH$_2$Cl$_2$ (2×30 mL). The combined organic phase was washed with brine, dried over Na$_2$SO$_4$ and concentrated under reduced pressure. The crude material was purified by preparative TLC (10% MeOH in CH$_2$Cl$_2$) to afford the title compound (Example 18). $^1$H-NMR (400 MHz, DMSO-d$_6$): ∂ 13.08 (s, 1H), 8.48 (d, J=7.3 Hz, 2H), 8.18 (s, 1H), 7.93-7.87 (m, 3H), 7.76 (d, J=7.8 Hz, 1H), 6.96-6.79 (m, 1H), 6.22-6.13 (m, 1H), 5.77-5.61 (m, 1H), 4.85-72 (m, 1H), 4.63-4.55 (m, 1H), 4.40-4.20 (m, 1H), 4.18-4.07 (m, 0.5H), 3.75-3.68 (m, 0.5H), 3.27-3.21 (m, 1H), 2.88-2.68 (m, 1H), 2.06-1.90 (m, 2H), 1.71-1.59 (m, 1H); MS calculated for C$_{24}$H$_{22}$F$_3$N$_4$O$_4$ (M+H$^+$) 487.15. found 487.3.

To a solution of Example 18 (50 mg, 0.1 mmol) and NH$_4$Cl (7 mg, 0.11 mmol) in DMF (4 mL) were added hydroxybenzotriazole (15 mg, 0.11 mmol) and 1-ethyl-3-(3-dimethylaminopropyl)carbodiimide hydrochloride (21 mg, 0.11 mmol) and the mixture was stirred at room temperature for 14 h (completion of reaction monitored by TLC). The mixture was diluted with water and extracted with CH$_2$Cl$_2$ (3×20 mL). The combined organic phase was washed with water and brine, dried over Na$_2$SO$_4$ and concentrated under reduced pressure. The crude material was purified by column chromatography (10% MeOH in CH$_2$Cl$_2$) to afford the title compound (Example 19). $^1$H-NMR (400 MHz, DMSO-d$_6$): ∂ 13.0 (br s, 1H), 8.47 (d, J=7.2 Hz, 2H), 8.06-7.73 (m, 6H), 7.35 (s, 1H), 6.92-6.79 (m, 1H), 6.17-6.13 (m, 1H), 5.75-5.60 (m, 1H), 4.81-4.60 (m, 2H), 4.29-4.10 (m, 1H), 2.84-2.72 (m, 1H), 2.17-1.94 (m, 3H), 1.65 (s, 2H); MS calculated for C$_{24}$H$_{23}$F$_3$N$_5$O$_3$ (M+H$^+$) 486.17. found 486.3.

Example 20

1-(1-acryloylazepan-3-yl)-2-(3-(trifluoromethyl)benzamido)-1H-benzo[d]imidazole-7-carboxylic acid

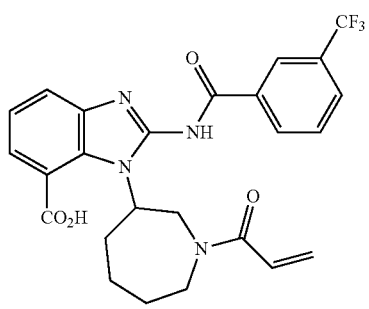 [SMILES: C=CC(=O)N1CCCCC(n2c(NC(=O)c3cccc(C(F)(F)F)c3)nc3cccc(C(=O)O)c32)C1]

The title compound (Example 20) was prepared following procedures analogous to Example 19, substituting Example 17-95 for Example 17-109. $^1$H-NMR (400 MHz, CDCl$_3$) δ 8.63 (d, J=11.0 Hz, 1H), 8.44 (d, J=7.7 Hz, 1H), 7.80 (dd, J=7.8, 14.9 Hz, 1H), 7.62 (dd, J=4.0, 10.7 Hz, 2H), 7.55-7.41 (m, 1H), 7.33-7.26 (m, 1H), 6.84-6.56 (m, 1H), 6.50-6.37 (m, 1H), 5.84-5.66 (m, 1H), 4.88-4.81 (m, 1H), 4.36-4.30 (m, 1H), 4.06-4.02 (m, 1H), 3.70-3.28 (m, 1H), 3.01 (d, J=11.6, 1H), 2.30-2.00 (m, 4H), 1.48-1.37 (m, 2H). MS calculated for C$_{25}$H$_{24}$F$_3$N$_4$O$_4$ (M+H$^+$) 501.17. found 501.2.

Examples 21

Method A

A sample of racemate or enantioenriched compound is subjected to chiral chromatography with isocratic elution using a Gilson purification system consisting of 306 pump, 806 manometric module, 119 UV/Vis detector, 215 auto sampler fraction collector and UniPoint v3.30 or Trilution v2.1 software. The eluting peaks are collected and reanalyzed accordingly.

Method B

A sample of racemate or enantioenriched compound is subjected to chiral chromatography with isocratic elution using a Thar Technologies SFC Prep 80 system with SuperChrom v.5.3 software. The eluting peaks are collected and reanalyzed accordingly.

By repeating the chiral separations described in Method A or B above, the following Examples are obtained. The eluted compounds in Examples 7A and 7B; 8A and 8B; 9A and 9B; and 10A and 10B were arbitrarily designated as Peak 1 and 2 respectively, without confirmation of absolute configuration. One skilled in the art can use any known methods to determine the absolute stereochemistry of the enantiomers.

| Example | Structure | Column | Mobile Phase | Method |
|---------|-----------|--------|--------------|--------|
| 21-1 | 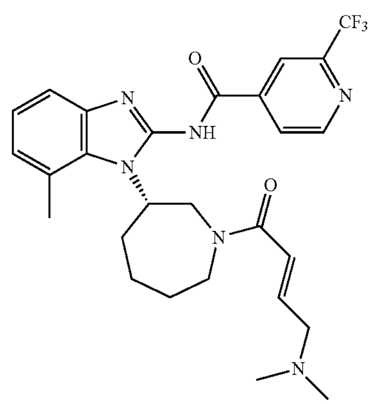 [SMILES: Cc1cccc2nc(NC(=O)c3ccnc(C(F)(F)F)c3)n([C@H]3CCCCN(C(=O)/C=C/CN(C)C)C3)c12] | ChiralCel OD-H | Hexane/iPrOH 95/5 to 80/20 | A Peak 1 |
| 21-2 | 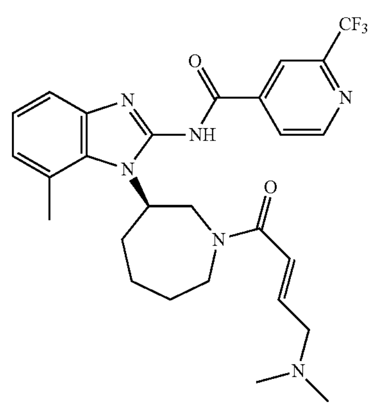 [SMILES: Cc1cccc2nc(NC(=O)c3ccnc(C(F)(F)F)c3)n([C@@H]3CCCCN(C(=O)/C=C/CN(C)C)C3)c12] | ChiralCel OD-H | Hexane/iPrOH 95/5 to 80/20 | A Peak 2 |

-continued

| Example | Structure | Column | Mobile Phase | Method |
|---|---|---|---|---|
| 21-3 | 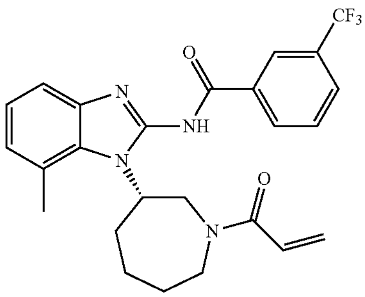 [SMILES: C=CC(=O)N1CCCC[C@H](n2c(NC(=O)c3cccc(C(F)(F)F)c3)nc3cccc(C)c32)C1] | ChiralCel OD-H | Hexane/iPrOH 80/20 | A Peak 1 |
| 21-4 | 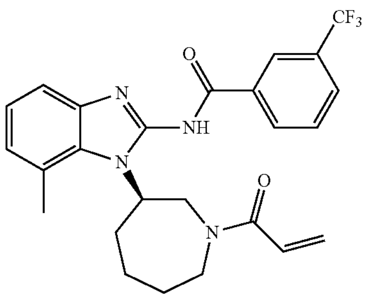 [SMILES: C=CC(=O)N1CCCC[C@@H](n2c(NC(=O)c3cccc(C(F)(F)F)c3)nc3cccc(C)c32)C1] | ChiralCel OD-H | Hexane/iPrOH 80/20 | A Peak 2 |
| 21-5 | 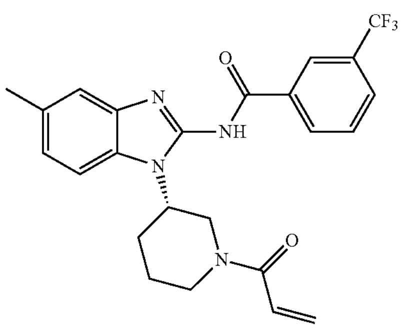 | ChiralCel OD-H | Hexane/iPrOH 75/25 | A Peak 1 |
| 21-6 | 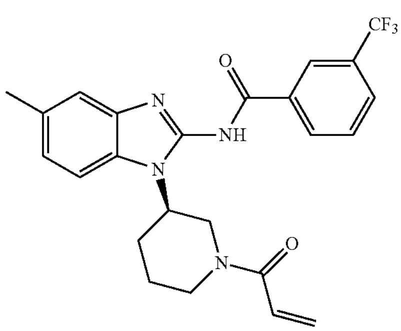 [SMILES: C=CC(=O)N1CCC[C@@H](n2c(NC(=O)c3cccc(C(F)(F)F)c3)nc3cc(C)ccc32)C1] | ChiralCel OD-H | Hexane/iPrOH 75/25 | A Peak 2 |
| 21-7A (Peak 1) 21-7B (Peak 2) | 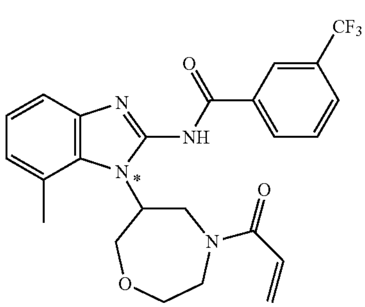 [SMILES: C=CC(=O)N1CCOCC(n2c(NC(=O)c3cccc(C(F)(F)F)c3)nc3cccc(C)c32)C1] | ChiralCel OD-H | Hexane/EtOH/ MeOH 90/5/5 | A |

-continued

| Example | Structure | Column | Mobile Phase | Method |
|---|---|---|---|---|
| 21-8A (Peak 1) 21-8B (Peak 2) | | ChiralCel OD-H | Hexane/(1:1 EtOH/MeOH) 85/15 | A |
| 21-9A (Peak 1) 21-9B (Peak 2) | | ChiralCel OD-H | $CO_2$/(MeOH + 0.5% $HNEt_2$) 85/15 | B |
| 21-10A (Peak 1) 21-10B (Peak 2) | | ChiralCel OD-H | Hexane/(1:1 EtOH/MeOH) 83/17 | A |

Assays

EGFR Biochemical Assays $IC_{50}$ Determinations.

All EGFR biochemical assays were carried out by HTRF method. The EGFR(L858R/T790M) enzyme were purchased from Carna (GST-a.a. 669-1210). The substrate peptide Biotin-TK-peptide was purchased from Cis-Bio. The reaction mixtures contained 1 μM peptide substrate, 10 μM ATP, and 0.036 nM EGFR(L858R/T790M) in the reaction buffer (50 mM HEPES pH 7.1, 10 mM $MgCl_2$, 0.01% BSA, 1 mM TCEP and 0.1 mM $Na_3VO_4$) at a final volume of 10 μL. All reactions were carried out at room temperature in white ProxiPlate™ 384-well Plus plates (PerkinElmer) and were quenched with 5 μL of 0.2 M EDTA at 60 min. Five L of the detection reagents (2.5 ng PT66K and 0.05 μg SAXL per well) were added, the plates were incubated at room temperature for 1 h and then read in EnVision reader. Compounds were diluted into assay mixture (final DMSO 0.5%), and $IC_{50}$ values were determined by 12-point (from 50 to 0.000282 μM) inhibition curves in duplicate under the assay conditions as described above. For no-preincubation condition, the compounds were added to the assay solution containing ATP and peptide, and the reaction was initiated by addition of enzyme. For pre-incubation conditions, the compounds were added to the assay solution containing enzyme and peptide, and pre-incubated at room temperature for desired period of time, then the reaction was initiated by addition of ATP.

EGFR Target Modulation in Engineered NIH/3T3 Cell Lines Tissue Culture.

NIH/3T3 cell lines expressing human EGFR (WT, L858R, and L858R/T790M) (obtained from Matthew Meyerson's Lab at DFCI) were maintained in 10% FBS/DMEM supplemented with 100 μg/ml Penicillin/Streptomycin (Hyclone #SV30010) and 2 μg/ml Puromycin. The cells were harvested with 0.05% Trypsin/EDTA (Hyclone #SH30236.01), re-suspended in 5% FBS/DMEM Pen/Strep without Puromycin and plated at 9,000 cells per well in 50 μl of media in a 384-well black plate with clear bottoms (Greiner #789068G). The cells were allowed to incubate overnight in a 37° C., 5% $CO_2$ humidified tissue culture incubator. A 12-point test compound curve was prepared by serial diluting a 10 μM stock 1:3 in DMSO in a 384-well compound plate (Greiner #789201L). The serial diluted compounds were transferred to the plate containing cells by using a 50 nl Pin Head device (Perkin Elmer) and the cells were placed back in the incubator for 3 hours. Only the EGFR WT-expressing cells were induced with 50 ng/ml EGF (Preprotech #AF-100-15) for 5 minutes before lysis. The media was removed and cells were lysed in 25 µl of Lysis buffer containing protease and phosphatase inhibitors (1% Triton X-100, 20 mM Tris, pH 7.5, 1 mM EDTA, 1 mM EGTA, 150 mM NaCl, 1× complete cocktail inhibitor (Roche #11 697 498 001), 1× Phosphatase Inhibitor Cocktail Set II and Set III (Sigma #P5726 and #P0044)). The plates were shaken at 4° C. for 5 minutes with foil top at maximum speed. An aliquot of 5 µl from each well was transferred to ProxiPlate™ 384-well Plus plates (PE #6008289). The plates were sealed with a foil top and frozen at −80° C. and thawed when needed.

AlphaLISA.

The frozen aliquots were thawed and briefly centrifuged. All antibodies and beads were diluted in 1× AlphaLISA HiBlock Buffer (PE #AL004C). Biotinylated anti-phospho-EGFR (Y1068) (Cell Signaling #4031) was incubated with the lysate for 1 hour at room temperature at 1 nM final concentration. Goat anti-total EGFR (R&D Systems #AF231) was added and allowed to equilibrate for 1 hour at room temperature at 1 nM final concentration. Then, 10 µl of mixed beads (AlphaScreen Streptavidin Donor Beads (PE #6760002S) and AlphaLISA anti-goat IgG Acceptor Beads (PE #AL107C)) was equilibrated for 1.5 hours before reading on EnVision plate reader using the built-in settings for AlphaScreen.

Data Analysis.

Cells untreated (L858R and L858R/T790M) or EGF-induced (WT) were set to 100% maximum response. For a negative control, 10 µM HKI-272 was used to normalize data to 0% of maximum response. With these parameters, the $IC_{50}$'s for each compound in each cell line was calculated using non-linear curve fitting analysis.

EGFR Target Modulation in H1975, H3255 and HCC827 Cell Lines Tissue Culture.

Cells were maintained in 10% FBS/RPMI supplemented with 100 µg/ml Penicillin/Streptomycin (Hyclone #SH30236.01). The cells were harvested with 0.25% Trypsin/EDTA (Hyclone #SH30042.1), re-suspended in 5% FBS/DMEM Pen/Strep and plated at 10,000 cells per well in 50 ul of media in a 384-well black plate with clear bottoms (Greiner #789068G). The cells were allowed to incubate overnight in a 37° C., 5% $CO_2$ humidified tissue culture incubator. A 12-point test compound curve was prepared by serial diluting a 10 uM stock 1:3 in DMSO in a 384-well compound plate (Greiner #789201L). The serial diluted compounds were transferred to the plate containing cells by using a 50 nl Pin Head device (Perkin Elmer) and the cells were placed back in the incubator for 3 hours.

Phospho-EGFR (Y1173) Target Modulation Assay.

The media was reduced to 20 ul using a Bio-Tek ELx 405 Select™ plate washer. Cells were lysed with 20 ul of 2× Lysis buffer containing protease and phosphatase inhibitors (2% Triton X-100, 40 mM Tris, pH 7.5, 2 mM EDTA, 2 mM EGTA, 300 mM NaCl, 2× complete cocktail inhibitor (Roche #11 697 498 001), 2× Phosphatase Inhibitor Cocktail Set II and Set III (Sigma #P5726 and #P0044)). The plates were shaken at 4° C. for 20 minutes. An aliquot of 25 ul from each well was transferred to pEGFR(Y1173) ELISA plates for analysis.

Phospho-EGFR (Y1173) ELISA.

Solid white high-binding ELISA plates (Greiner #781074) were coated with 5 ug/ml anti-EGFR capture antibody (R&D Systems #AF231) overnight in 50 mM carbonate/bicarbonate pH 9.5 buffer. Plates were blocked with 1% BSA (Sigma #A7030) in PBS for 1 hour at room temperature. Wash steps were carried out with a Bio-Tek ELx405 Select™ using 4 cycles of 100 ul TBS-T (20 mM Tris, 137 mM NaCl, 0.05% Tween-20) per well. Media was drained and cells were lysed in 40 ul Lysis buffer containing protease and phosphatase inhibitors (1% Triton X-100, 20 mM Tris, pH 7.5, 1 mM EDTA, 1 mM EGTA, 150 mM NaCl, 1× complete cocktail inhibitor (Roche #11 697 498 001), 1× Phosphatase Inhibitor Cocktail Set II and Set III (Sigma #P5726 and #P0044)). Lysis was allowed to occur for 20 minutes on ice. A 25 ul aliquot was added to each well of the blocked ELISA plate and incubated overnight at 4° C. with gentle shaking. A 1:500 anti-phospho-EGFR (Cell Signaling #4407) in 0.2% BSA/TBS-T was added and incubated for 1 hour at room temperature. After washing, 1:2,000 anti-rabbit-HRP (Cell Signaling #7074) in 0.2% BSA/TBS-T was added and incubated for 1 hour at room temperature. Chemiluminescent detection was carried out with SuperSignal ELISA Pico substrate (ThermoScientific #37069). Signal was read on EnVision plate reader using built-in UltraLUM setting.

Data Analysis.

Control cells treated with EGF were set to 100% maximum response. For a negative control, 10 uM CHV999 was used to normalize data to 0% of maximum response. With these parameters, the IC50's for each compound in each cell line was calculated using non-linear curve fitting analysis.

EGFR Target Modulation in HEKn (EGFR-WT) Cell Line Tissue Culture.

Human neonatal epithelial keratinocytes (Invitrogen #C-001-5C) were maintained in EpiLife media (Invitrogen #M-EPI-500-CA) supplemented with growth factors (Invitrogen #S-001-5). Cells were harvested with 0.05% Trypsin/EDTA (Hyclone #SH30236.01) and quenched with 5% FBS/EpiLife media. A density of 7500 cells in 50 ul of EpiLife media (no growth factors) was plated in each well of a 384-well solid black tissue culture plate (Greiner #789168G) and incubated overnight at 37° C., 5% $CO_2$ in a humidified tissue culture incubator. A 12-point test compound curve was prepared by serial diluting a 10 uM stock 1:3 in DMSO in a 384-well compound plate (Greiner #789201L). The serial diluted compounds were transferred to the plate containing cells by using a 50 nl Pin Head device (Perkin Elmer) and the cells were placed back in the incubator for 3 hours. Stimulation of EGFR autophosphorylation was carried out with 10 ng/ml EGF (Preprotech #AF-100-15) for 5 minutes in the tissue culture incubator.

Phospho-EGFR (Y1173) ELISA.

Solid white high-binding ELISA plates (Greiner #781074) were coated with 5 ug/ml anti-EGFR capture antibody (R&D Systems #AF231) overnight in 50 mM carbonate/bicarbonate pH 9.5 buffer. Plates were blocked with 1% BSA (Sigma #A7030) in PBS for 1 hour at room temperature. Wash steps were carried out with a Bio-Tek ELx405 Select™ using 4 cycles of 100 ul TBS-T (20 mM Tris, 137 mM NaCl, 0.05% Tween-20) per well. Media was drained and cells were lysed in 40 ul Lysis buffer containing protease and phosphatase inhibitors (1% Triton X-100, 20 mM Tris, pH 7.5, 1 mM EDTA, 1 mM EGTA, 150 mM NaCl, 1× complete cocktail inhibitor (Roche #11 697 498 001), 1× Phosphatase Inhibitor Cocktail Set II and Set III (Sigma #P5726 and #P0044)). Lysis was allowed to occur for 20 minutes on ice. A 25 ul aliquot was added to each well of the blocked ELISA plate and incubated overnight at 4° C. with gentle shaking. A 1:500 anti-phospho-EGFR (Cell Signaling #4407) in 0.2% BSA/TBS-T was added and incubated for 1 hour at room temperature. After washing, 1:2,000 anti-rabbit-HRP (Cell Signaling #7074) in 0.2% BSA/TBS-T was added and incubated for 1 hour at room temperature. Chemiluminescent detection was carried out with SuperSignal ELISA Pico substrate (ThermoScientific #37069). Signal was read on EnVision plate reader using built-in UltraLUM setting.

Data Analysis.

Control cells treated with EGF were set to 100% maximum response. For a negative control, 10 uM CHV999 was used to normalize data to 0% of maximum response. With these parameters, the IC50's for each compound in each cell line was calculated using non-linear curve fitting analysis.

EGFR Target Modulation in HaCaT (EGFR-WT) Cell Line Tissue Culture.

HaCaT cells were maintained in 10% FBS/RPMI supplemented with 100 µg/ml Penicillin/Streptomycin (Hyclone #SH30236.01). The cells were harvested with 0.25% Trypsin/EDTA (Hyclone #SH30042.1), re-suspended in 5% FBS/DMEM Pen/Strep and plated at 10,000 cells per well in 50 ul of media in a 384-well black plate with clear bottoms (Greiner #789068G). The cells were allowed to incubate overnight in a 37° C., 5% CO2 humidified tissue culture incubator. with A 12-point test compound curve was prepared by serial diluting a 10 uM stock 1:3 in DMSO in a 384-well compound plate (Greiner #789201L). The serial diluted compounds were transferred to the plate containing cells by using a 50 nl Pin Head device (Perkin Elmer) and the cells were placed back in the incubator for 3 hours. Stimulation of EGFR autophosphorylation was carried out with 10 ng/ml EGF (Preprotech #AF-100-15), prepared in 2% FBS/PBS for 5 minutes in the tissue culture incubator.

Phospho-EGFR (Y1173) ELISA.

Solid white high-binding ELISA plates (Greiner #781074) were coated with 5 ug/ml anti-EGFR capture antibody (R&D Systems #AF231) overnight in 50 mM carbonate/bicarbonate pH 9.5 buffer. Plates were blocked with 1% BSA (Sigma #A7030) in PBS for 1 hour at room temperature. Wash steps were carried out with a Bio-Tek ELx405 Select™ using 4 cycles of 100 ul TBS-T (20 mM Tris, 137 mM NaCl, 0.05% Tween-20) per well. Media was drained and cells were lysed in 40 ul Lysis buffer containing protease and phosphatase inhibitors (1% Triton X-100, 20 mM Tris, pH 7.5, 1 mM EDTA, 1 mM EGTA, 150 mM NaCl, 1× complete cocktail inhibitor (Roche #11 697 498 001), 1× Phosphatase Inhibitor Cocktail Set II and Set III (Sigma #P5726 and #P0044)). Lysis was allowed to occur for 20 minutes on ice. A 25 ul aliquot was added to each well of the blocked ELISA plate and incubated overnight at 4° C. with gentle shaking. A 1:500 anti-phospho-EGFR (Cell Signaling #4407) in 0.2% BSA/TBS-T was added and incubated for 1 hour at room temperature. After washing, 1:2,000 anti-rabbit-HRP (Cell Signaling #7074) in 0.2% BSA/TBS-T was added and incubated for 1 hour at room temperature. Chemiluminescent detection was carried out with SuperSignal ELISA Pico substrate (ThermoScientific #37069). Signal was read on EnVision plate reader using built-in UltraLUM setting.

Data Analysis.

Control cells treated with EGF were set to 100% maximum response. For a negative control, 10 uM CHV999 was used to normalize data to 0% of maximum response. With these parameters, the IC50's for each compound in each cell line was calculated using non-linear curve fitting analysis.

Biological Results

Table 1 sets forth the $IC_{50}$ determinations obtained from a EGFR biochemical assay as described above. In Table 1, Column A and B represent $IC_{50}$ determinations obtained from EGFR (L858R/T790M) without and with 90-minute pre-incubation, respectively. Representative compounds of the invention show an inhibition $IC_{50}$ in the range of <1 nM to 10 µM, more particularly in the range of <1 nM to 1 µM.

TABLE 1

| Example | IC50 (µM) Column A* | IC50 (µM) Column B** |
|---|---|---|
| 1 | 0.007 | <0.001 |
| 2 | 0.010 | <0.001 |
| 3-1 | 0.005 | <0.001 |
| 3-2 | 0.007 | <0.001 |
| 3-3 | 0.156 | 0.011 |
| 3-4 | 0.005 | <0.001 |
| 3-5 | 0.007 | <0.001 |
| 3-6 | 0.010 | <0.001 |
| 3-7 | 0.006 | <0.001 |
| 3-8 | 0.009 | <0.001 |
| 3-9 | 0.008 | <0.001 |
| 3-10 | 0.006 | <0.001 |
| 3-11 | 0.005 | <0.001 |
| 3-12 | 0.133 | 0.011 |
| 3-13 | 0.007 | <0.001 |
| 3-14 | 0.012 | <0.001 |
| 3-15 | 0.084 | 0.005 |
| 3-16 | 0.352 | 0.36 |
| 3-17 | 0.676 | 1.204 |
| 3-18 | 0.135 | 0.108 |
| 4, 21-5 | 0.410 | 0.071 |
| 5 | 0.008 | <0.001 |
| 6 | 0.010 | <0.001 |
| 7 | 0.002 | <0.001 |
| 8, 21-2 | <0.001 | <0.001 |
| 9 | 0.006 | <0.001 |
| 10 | 0.390 | 0.009 |
| 11 | 0.012 | <0.001 |
| 12 | 0.271 | 0.016 |
| 13 | 1.63 | 0.113 |
| 14 | 0.16 | 0.009 |
| 15 | 0.004 | <0.001 |
| 16 | 0.045 | 0.005 |
| 17-1 | 0.012 | <0.001 |
| 17-2 | 0.018 | 0.002 |
| 17-3 | 0.026 | <0.001 |
| 17-4 | 0.135 | 0.006 |
| 17-5 | 0.022 | 0.001 |
| 17-6 | 0.189 | 0.010 |
| 17-7 | 0.005 | <0.001 |
| 17-8 | 7.000 | 0.137 |
| 17-9 | 4.100 | 0.218 |
| 17-10 | 0.014 | <0.001 |
| 17-11 | <0.001 | <0.001 |
| 17-12 | 0.064 | 0.003 |
| 17-13 | 0.006 | <0.001 |
| 17-14 | 0.033 | 0.005 |
| 17-15 | 0.012 | <0.001 |
| 17-16 | 0.007 | <0.001 |
| 17-17 | 0.004 | <0.001 |
| 17-18 | 0.014 | <0.001 |
| 17-19 | 0.330 | 0.007 |
| 17-20 | 0.430 | 0.032 |
| 17-21 | 0.005 | <0.001 |
| 17-22 | 0.003 | <0.001 |
| 17-23 | 0.003 | <0.001 |
| 17-24 | 0.006 | <0.001 |
| 17-25 | <0.002 | <0.001 |
| 17-26 | 0.005 | <0.001 |
| 17-27 | 0.021 | 0.002 |
| 17-28 | 0.014 | <0.001 |
| 17-29 | 0.020 | <0.001 |
| 17-30 | 0.005 | <0.001 |
| 17-31 | 0.016 | <0.001 |
| 17-32 | 0.014 | <0.001 |
| 17-33 | 0.008 | <0.001 |
| 17-34 | 1.050 | 0.038 |
| 17-35 | 0.006 | <0.001 |
| 17-36 | 10.6 | 0.350 |
| 17-37 | 0.062 | 0.005 |
| 17-38 | 0.117 | 0.006 |

TABLE 1-continued

| Example | IC50 (μM) Column A* | IC50 (μM) Column B** |
|---|---|---|
| 17-39 | 0.120 | 0.007 |
| 17-40 | 0.007 | <0.001 |
| 17-41 | 0.008 | <0.001 |
| 17-42 | <0.002 | <0.001 |
| 17-43 | 0.006 | <0.001 |
| 17-44 | 0.007 | <0.001 |
| 17-45 | 0.006 | <0.001 |
| 17-46 | 0.092 | 0.005 |
| 17-47 | 0.009 | <0.001 |
| 17-48 | 0.007 | <0.001 |
| 17-49 | 0.029 | 0.001 |
| 17-50 | 0.009 | <0.001 |
| 17-51 | 1.950 | 0.048 |
| 17-52 | 0.002 | <0.001 |
| 17-53 | 0.002 | <0.001 |
| 17-54 | 0.090 | 0.005 |
| 17-55 | 0.007 | <0.001 |
| 17-56 | 0.020 | 0.002 |
| 17-57 | <0.001 | <0.001 |
| 17-58 | 0.005 | <0.001 |
| 17-59 | 0.105 | 0.006 |
| 17-61 | 0.004 | <0.001 |
| 17-62 | 0.140 | 0.006 |
| 17-63 | 0.003 | <0.001 |
| 17-64 | 0.020 | 0.001 |
| 17-65 | 0.004 | <0.001 |
| 17-66 | 0.005 | <0.001 |
| 17-67 | 0.003 | <0.001 |
| 17-68 | 0.003 | <0.001 |
| 17-69 | 0.002 | <0.001 |
| 17-70 | <0.001 | <0.001 |
| 17-71 | 0.002 | <0.001 |
| 17-72 | 0.004 | <0.001 |
| 17-73 | <0.001 | <0.001 |
| 17-74 | 0.003 | <0.001 |
| 17-75 | 0.017 | <0.001 |
| 17-76 | <0.001 | <0.001 |
| 17-77 | 0.003 | <0.001 |
| 17-78 | 0.006 | <0.001 |
| 17-79 | 0.005 | <0.001 |
| 17-80 | <0.001 | <0.001 |
| 17-81 | 0.002 | <0.001 |
| 17-82 | 0.007 | <0.001 |
| 17-83 | 0.020 | 0.001 |
| 17-84 | 0.049 | 0.003 |
| 17-85 | 0.038 | 0.003 |
| 17-86 | 0.040 | 0.004 |
| 17-87 | <0.001 | <0.001 |
| 17-88 | 0.390 | 0.040 |
| 17-89 | 1.010 | 2.320 |
| 17-90 | 0.199 | 0.013 |
| 17-91 | 0.198 | 0.007 |
| 17-92 | 0.213 | 0.012 |
| 17-93 | 0.390 | 0.059 |
| 17-94 | 0.002 | <0.001 |
| 17-95 | 0.002 | <0.001 |
| 17-96 | 0.106 | 0.011 |
| 17-97 | 0.204 | 0.400 |
| 17-98 | 0.840 | 0.058 |
| 17-99 | 1.220 | 0.097 |
| 17-101 | 0.990 | 0.193 |
| 17-102 | 0.002 | <0.001 |
| 17-103 | <0.001 | <0.001 |
| 17-104 | 0.018 | <0.001 |
| 17-105, 21-6 | 0.100 | 0.002 |
| 17-106 | 0.038 | 0.002 |
| 17-107 | 0.320 | 0.380 |
| 17-108 | 0.048 | 0.005 |
| 17-109 | 0.025 | <0.001 |
| 17-110 | 10.8 | 0.119 |
| 17-111 | 0.004 | <0.001 |
| 17-112 | 0.040 | 0.003 |
| 17-113 | 0.003 | <0.001 |
| 17-114 | 0.001 | <0.001 |
| 17-115 | 3.500 | 0.013 |
| 17-116 | 0.011 | <0.001 |
| 17-117 | 0.036 | 0.004 |
| 17-118 | 0.680 | 0.005 |
| 17-119 | 0.062 | 0.008 |
| 17-120 | 0.690 | 0.028 |
| 17-121 | 0.127 | <0.001 |
| 17-122 | 0.062 | <0.001 |
| 17-123 | 0.115 | 0.004 |
| 17-124 | 0.200 | 0.008 |
| 17-125 | 0.068 | 0.003 |
| 17-126 | 0.001 | <0.001 |
| 17-127 | 0.002 | <0.001 |
| 17-128 | 0.007 | <0.001 |
| 17-129 | 0.002 | <0.001 |
| 17-130 | 0.119 | 0.006 |
| 17-131 | 0.005 | <0.001 |
| 17-132 | 0.041 | 0.001 |
| 17-133 | 0.018 | 0.001 |
| 17-134 | 0.930 | 0.010 |
| 17-135 | 0.620 | 0.008 |
| 17-136 | 1.760 | 0.030 |
| 17-137 | 1.550 | 0.044 |
| 17-138 | 0.147 | 0.009 |
| 17-139 | 0.147 | 0.005 |
| 17-140 | 0.940 | 0.043 |
| 17-141 | 0.247 | 0.010 |
| 17-142 | 0.320 | 0.010 |
| 17-143 | 0.233 | 0.014 |
| 17-144 | 0.002 | <0.001 |
| 17-145 | 0.001 | <0.001 |
| 17-146 | 0.002 | <0.001 |
| 17-147 | 0.002 | <0.001 |
| 17-148 | 0.002 | <0.001 |
| 17-149 | 0.002 | <0.001 |
| 17-150 | 0.003 | <0.001 |
| 17-151 | 0.001 | <0.001 |
| 17-152 | 0.002 | <0.001 |
| 17-153 | 0.002 | <0.001 |
| 17-154 | 0.002 | <0.001 |
| 17-155 | 0.002 | <0.001 |
| 17-156 | 0.001 | <0.001 |
| 17-157 | 0.003 | <0.001 |
| 17-158 | 0.002 | <0.001 |
| 17-159 | 0.002 | <0.001 |
| 17-160 | 0.007 | <0.001 |
| 17-161 | 0.008 | <0.001 |
| 17-162 | 0.054 | 0.004 |
| 17-163 | 0.070 | 0.005 |
| 17-164 | 0.055 | 0.005 |
| 17-165 | 0.054 | 0.004 |
| 17-166 | 0.039 | 0.003 |
| 17-167 | 2.620 | 0.128 |
| 17-168 | 1.110 | 0.095 |
| 17-169 | 1.750 | 0.186 |
| 17-170 | 0.660 | 0.006 |
| 17-171 | 2.400 | 0.316 |
| 17-172 | 1.750 | 0.268 |
| 17-173 | 6.600 | 0.285 |
| 17-174 | 0.210 | 0.010 |
| 17-175 | 0.004 | <0.001 |
| 17-176 | 0.018 | <0.001 |
| 17-177 | 0.003 | <0.001 |
| 17-178 | 0.097 | 0.006 |
| 17-179 | 0.230 | 0.012 |
| 17-180 | 0.003 | <0.001 |
| 17-181 | 0.003 | <0.001 |
| 17-182 | 0.472 | 0.022 |
| 17-184 | 16.13 | 5.84 |
| 17-185 | 0.002 | <0.001 |
| 17-186 | 0.004 | <0.001 |
| 17-187 | 0.022 | 0.001 |
| 17-188 | 0.04 | 0.003 |
| 17-189 | 0.005 | <0.001 |
| 17-190 | 0.003 | <0.001 |
| 17-191 | 0.004 | <0.001 |
| 17-192 | 0.003 | <0.001 |
| 17-193 | 0.002 | <0.001 |
| 17-194 | 0.068 | 0.006 |
| 17-195 | 0.116 | 0.007 |

TABLE 1-continued

| Example | IC50 (μM) Column A* | IC50 (μM) Column B** |
|---|---|---|
| 17-196 | 0.374 | 0.025 |
| 17-197 | 1.666 | 0.117 |
| 18 | 2.590 | 0.041 |
| 19 | 0.218 | 0.010 |
| 20 | 0.110 | 0.005 |
| 21-1 | 0.171 | 0.012 |
| 21-3 | 0.700 | 0.098 |
| 21-4 | 0.006 | <0.001 |
| 21-7A | 2.010 | 0.560 |
| 21-7B | 0.008 | <0.001 |
| 21-8A | 0.620 | 0.033 |
| 21-8B | 0.006 | <0.001 |
| 21-9A | 32.35 | 3.7 |
| 21-9B | 0.894 | 0.024 |
| 21-10A | 6.05 | 0.572 |
| 21-10B | 0.222 | 0.014 |

*Column A - EGFR (L858R/T790M) with no pre-incubation
**Column B - EGFR (L858R/T790M) with 90 min pre-incubation Table 2 sets forth the $IC_{50}$ determinations obtained from EGFR target modulation in engineered NIH/3T3 cell lines. Compounds of the invention show an inhibition $IC_{50}$ for L858R/T790M and L858R in the range of 1 nM to 10 μM, more particularly in the range of 1 nM to 1 μM. Furthermore, compounds of the invention show an inhibition $IC_{50}$ for NIH3T3 EGFR WT cell lines in the range of 1 nM to 10 μM, and in some instances in the range of 1 nM to >10 μM.

TABLE 2

| Example | NIH3T3 IC50 (μM) EGFR (L858R/T790M) | NIH3T3 IC50 (μM) EGFR (L858R) | NIH3T3 IC50 (μM) EGFR (WT) |
|---|---|---|---|
| 1 | 0.004 | 0.004 | 0.152 |
| 2 | 0.011 | 0.008 | 0.183 |
| 3-1 | 0.004 | 0.003 | 0.235 |
| 3-2 | 0.006 | 0.006 | 0.303 |
| 3-3 | 0.174 | 0.157 | >7.6 |
| 3-4 | 0.005 | 0.003 | 0.058 |
| 3-5 | 0.006 | 0.006 | 0.259 |
| 3-6 | 0.032 | 0.018 | 0.114 |
| 3-7 | 0.021 | 0.009 | 0.890 |
| 3-12 | 0.123 | 0.050 | 1.130 |
| 3-13 | 0.022 | 0.014 | 0.410 |
| 3-14 | 0.012 | 0.011 | 0.780 |
| 3-15 | 0.148 | 0.111 | 7.300 |
| 5 | 0.011 | 0.015 | 0.259 |
| 6 | 0.002 | 0.004 | 0.340 |
| 7 | 0.001 | 0.001 | 0.019 |
| 8 | 0.001 | 0.001 | 0.021 |
| 9 | 0.002 | 0.008 | 0.101 |
| 10 | 0.037 | 0.340 | >10.0 |
| 11 | 0.002 | 0.002 | 0.120 |
| 17-1 | 0.011 | 0.081 | >10.0 |
| 17-2 | 0.015 | 0.018 | 0.380 |
| 17-3 | 0.015 | 0.034 | 0.860 |
| 17-4 | 0.058 | 0.062 | 1.400 |
| 17-5 | 0.011 | 0.008 | 0.172 |
| 17-6 | 0.244 | 0.700 | 6.000 |
| 17-7 | 0.003 | 0.015 | 0.550 |
| 17-8 | 0.370 | 5.500 | >10.0 |
| 17-9 | 0.194 | 8.600 | >10.0 |
| 17-10 | 0.003 | 0.007 | 1.650 |
| 17-11 | 0.002 | 0.015 | 1.540 |
| 17-12 | 0.008 | 0.052 | 4.400 |
| 17-13 | 0.001 | 0.008 | 0.430 |
| 17-14 | 0.003 | 0.016 | 1.080 |
| 17-15 | 0.006 | 0.017 | 0.204 |
| 17-16 | 0.017 | 0.015 | 0.282 |
| 17-17 | 0.005 | 0.008 | 0.211 |
| 17-18 | 0.004 | 0.020 | 2.480 |
| 17-19 | 0.044 | 0.330 | >10.0 |
| 17-20 | 0.073 | 0.750 | >10.0 |

TABLE 2-continued

| Example | NIH3T3 IC50 (μM) EGFR (L858R/T790M) | NIH3T3 IC50 (μM) EGFR (L858R) | NIH3T3 IC50 (μM) EGFR (WT) |
|---|---|---|---|
| 17-21 | 0.004 | 0.007 | 0.320 |
| 17-22 | 0.002 | 0.004 | 0.271 |
| 17-23 | 0.003 | 0.004 | 0.149 |
| 17-24 | 0.006 | 0.005 | 0.094 |
| 17-25 | <0.001 | 0.002 | 0.057 |
| 17-26 | 0.005 | 0.003 | 0.139 |
| 17-27 | 0.005 | 0.012 | 0.670 |
| 17-28 | 0.010 | 0.004 | 0.283 |
| 17-29 | 0.017 | 0.028 | 0.820 |
| 17-30 | 0.004 | 0.003 | 0.167 |
| 17-31 | 0.005 | 0.019 | 0.750 |
| 17-32 | 0.004 | 0.007 | 0.206 |
| 17-33 | 0.005 | 0.002 | 0.224 |
| 17-34 | 0.221 | 0.530 | >10.0 |
| 17-35 | 0.005 | 0.005 | 0.140 |
| 17-36 | 2.960 | 3.500 | >10.0 |
| 17-37 | 0.042 | 0.032 | 1.650 |
| 17-38 | 0.049 | 0.093 | 1.920 |
| 17-39 | 0.072 | 0.221 | 5.200 |
| 17-40 | 0.008 | 0.017 | 0.490 |
| 17-41 | 0.004 | 0.012 | 0.440 |
| 17-42 | 0.002 | 0.002 | 0.053 |
| 17-43 | 0.004 | 0.014 | 0.480 |
| 17-44 | 0.003 | 0.015 | 0.390 |
| 17-45 | 0.003 | 0.002 | 0.057 |
| 17-46 | 0.031 | 0.002 | 0.057 |
| 17-47 | 0.003 | 0.002 | 0.052 |
| 17-48 | 0.004 | 0.005 | 0.122 |
| 17-49 | 0.027 | 0.006 | 0.330 |
| 17-50 | 0.009 | 0.005 | 0.086 |
| 17-51 | 0.650 | 0.470 | 7.600 |
| 17-52 | <0.001 | 0.003 | 0.103 |
| 17-53 | 0.002 | 0.003 | 0.058 |
| 17-54 | 0.041 | 0.022 | 0.560 |
| 17-55 | 0.003 | 0.002 | 0.022 |
| 17-56 | 0.008 | 0.017 | 0.263 |
| 17-57 | 0.002 | <0.001 | 0.020 |
| 17-58 | 0.002 | 0.002 | 0.026 |
| 17-59 | 0.019 | 0.020 | 0.370 |
| 17-60 | 0.002 | 0.002 | 0.012 |
| 17-61 | 0.003 | <0.001 | 0.011 |
| 17-62 |  | 0.234 | 2.500 |
| 17-63 |  | 0.003 | 0.038 |
| 17-64 | 0.005 | 0.002 | 0.021 |
| 17-65 | 0.002 | 0.002 | 0.012 |
| 17-66 | 0.009 | 0.005 | 0.129 |
| 17-67 | 0.001 | 0.004 | 0.050 |
| 17-68 | 0.001 | 0.002 | 0.023 |
| 17-69 | <0.001 | 0.001 | 0.020 |
| 17-70 | <0.001 | 0.001 | 0.035 |
| 17-71 | 0.002 | 0.002 | 0.029 |
| 17-72 | 0.001 | 0.004 | 0.063 |
| 17-73 | <0.001 | 0.001 | 0.016 |
| 17-74 | 0.002 | 0.004 | 0.076 |
| 17-75 | 0.007 | 0.025 | 0.218 |
| 17-76 | <0.001 | <0.001 | 0.004 |
| 17-77 | 0.001 | 0.001 | 0.008 |
| 17-78 | 0.006 | 0.005 | 0.152 |
| 17-79 | 0.002 | 0.005 | 0.062 |
| 17-80 | <0.001 | <0.001 | 0.002 |
| 17-81 | 0.002 | 0.003 | 0.067 |
| 17-82 | 0.007 | 0.007 | 0.187 |
| 17-83 | 0.027 | 0.022 | 0.600 |
| 17-84 | 0.028 | 0.040 | 1.940 |
| 17-85 | 0.020 | 0.043 | 0.600 |
| 17-86 | 0.008 | 0.030 | 0.450 |
| 17-87 | <0.001 | <0.001 | 0.013 |
| 17-88 | 0.209 | 0.158 | 8.400 |
| 17-89 | 7.500 | 0.460 | 0.700 |
| 17-90 | 0.055 | 0.054 | 0.760 |
| 17-91 | 0.042 | 0.033 | 1.010 |
| 17-92 | 0.057 | 0.043 | 1.830 |
| 17-93 | 0.350 | 0.281 | 4.200 |
| 17-94 | <0.001 | 0.001 | 0.031 |
| 17-95 | 0.002 | 0.002 | 0.026 |
| 17-96 | 0.004 | 0.016 | 1.980 |

TABLE 2-continued

| Example | NIH3T3 IC50 (μM) EGFR (L858R/T790M) | NIH3T3 IC50 (μM) EGFR (L858R) | NIH3T3 IC50 (μM) EGFR (WT) |
|---|---|---|---|
| 17-100 | 0.026 | 0.340 | >10.0 |
| 17-102 | 0.002 | 0.001 | 0.047 |
| 17-103 | <0.001 | <0.001 | 0.019 |
| 17-104 | 0.020 | 0.023 | 0.610 |
| 17-105 | 0.012 | 0.149 | >10.0 |
| 17-106 | 0.007 | 0.124 | >10.0 |
| 17-108 | 0.021 | 0.306 | >10.0 |
| 17-109 | 0.028 | 0.032 | 0.880 |
| 17-110 | 0.460 | 4.700 | >10.0 |
| 17-111 | 0.001 | 0.003 | 0.047 |
| 17-112 | 0.006 | 0.040 | >10.0 |
| 17-113 | 0.001 | 0.001 | 0.081 |
| 17-114 | <0.001 | 0.002 | 0.143 |
| 17-115 | 0.165 | 1.600 | >10.0 |
| 17-116 | 0.008 | 0.019 | 0.470 |
| 17-117 | 0.006 | 0.050 | 6.400 |
| 17-118 | 0.005 | 0.156 | >10.0 |
| 17-119 | 0.008 | 0.051 | 5.000 |
| 17-120 | 0.860 | 8.200 | >10.0 |
| 17-121 | 0.016 | 0.259 | >10.0 |
| 17-122 | 0.020 | 0.176 | >10.0 |
| 17-123 | 0.017 | 0.174 | >10.0 |
| 17-124 | 0.023 | 0.271 | >10.0 |
| 17-125 | 0.013 | 0.087 | >7.6 |
| 17-126 | <0.001 | <0.001 | 0.024 |
| 17-127 | 0.001 | 0.004 | 0.099 |
| 17-128 | 0.002 | 0.006 | 0.186 |
| 17-129 | 0.002 | 0.002 | 0.045 |
| 17-130 | 0.016 | 0.094 | 1.410 |
| 17-131 | 0.002 | 0.010 | 0.311 |
| 17-132 | 0.012 | 0.047 | 2.870 |
| 17-133 | 0.006 | 0.041 | 1.290 |
| 17-134 | 0.073 | 0.630 | >10.0 |
| 17-135 | 0.045 | 0.400 | >10.0 |
| 17-136 | 6.500 | >10.0 | 8.200 |
| 17-137 | 7.900 | >10.0 | >10.0 |
| 17-138 | 0.067 | 0.450 | >10.0 |
| 17-139 | 0.043 | 0.305 | >9.1 |
| 17-140 | 0.181 | 1.640 | 7.900 |
| 17-141 | 0.097 | 0.680 | 7.800 |
| 17-142 | 0.090 | 0.340 | 5.200 |
| 17-143 | 0.046 | 0.313 | >10.0 |
| 17-144 | <0.001 | <0.001 | 0.029 |
| 17-145 | 0.001 | <0.001 | 0.026 |
| 17-146 | 0.004 | 0.003 | 0.137 |
| 17-147 | <0.001 | <0.001 | 0.025 |
| 17-148 | 0.002 | 0.001 | 0.083 |
| 17-149 | <0.001 | <0.001 | 0.015 |
| 17-150 | 0.001 | 0.001 | 0.042 |
| 17-151 | 0.001 | <0.001 | 0.014 |
| 17-152 | 0.001 | <0.001 | 0.032 |
| 17-153 | 0.001 | 0.001 | 0.037 |
| 17-154 | 0.001 | <0.001 | 0.010 |
| 17-155 | 0.002 | 0.002 | 0.065 |
| 17-161 | 0.009 | 0.006 | 0.281 |
| 17-167 | 0.140 | 4.800 | >10.0 |
| 17-168 | 0.072 | 0.600 | >2.77 |
| 17-169 | 0.140 | 1.750 | 8.200 |
| 17-170 | 0.010 | 0.390 | >10.0 |
| 17-171 | 0.160 | 1.860 | 9.900 |
| 17-172 | 0.173 | 1.400 | 8.700 |
| 17-173 | 0.840 | 0.670 | >10.0 |
| 18 | 6.300 | >10.0 | >10.0 |
| 19 | 0.026 | 0.226 | >10.0 |
| 20 | 0.820 | 3.300 | >10.0 |
| 21-1 | 0.120 | 2.230 | >10.0 |
| 21-3 | 0.450 | 2.200 | >10.0 |
| 21-4 | 0.002 | 0.004 | 0.239 |
| 21-7A | 0.490 | 3.200 | >10.0 |
| 21-7B | 0.002 | 0.012 | 0.650 |
| 21-8A | 0.138 | 0.211 | 0.980 |
| 21-8B | 0.002 | 0.001 | 0.016 |

Table 3 sets forth the $IC_{50}$ determinations obtained from EGFR target modulation in H1975 (EGFR L858/T790M), H3255 (EGFR L858R), HCC827 (Del E746-A750), HEKn (EGFR WT) and HaCaT (EGFR WT) cell lines. Compounds of the invention show an inhibition $IC_{50}$ in the range of 1 nM to 10 μM, more particularly in the range of 1 nM to 1 μM. Furthermore, compounds of the invention show an inhibition $IC_{50}$ for HEKn (EGFR WT) and/or HaCaT (EGFR WT) cell lines in the range of 0.01 μM to 10 μM, and in some instances in the range of 0.01 μM to >10 μM.

TABLE 3

| Example | H1975 IC50 (μM) | H3255 IC50 (μM) | HCC827 IC50 (μM) | HEKn (HaCaT) IC50 (μM) |
|---|---|---|---|---|
| 1 | 0.008 | 0.012 | 0.002 | 0.450 |
| 2 | 0.010 | 0.015 | <0.001 | 0.910 |
| 3-1 | 0.006 | 0.007 | | 0.340 |
| 3-2 | 0.009 | 0.011 | | 0.720 |
| 3-3 | 0.249 | 0.320 | 0.108 | 6.400 |
| 3-4 | 0.006 | 0.007 | <0.001 | 0.320 |
| 3-5 | 0.008 | 0.012 | <0.001 | 0.580 |
| 3-6 | 0.025 | 0.022 | 0.018 | 1.250 |
| 3-8 | 0.009 | 0.010 | 0.004 | 0.194 |
| 3-9 | 0.007 | 0.012 | 0.005 | 0.590 |
| 3-10 | 0.008 | 0.013 | | 0.620 |
| 3-11 | 0.007 | 0.009 | | 0.169 |
| 3-12 | 0.186 | 0.200 | | >10.0 |
| 3-13 | 0.019 | 0.012 | | 0.900 |
| 3-15 | 0.086 | 0.090 | 0.040 | 4.500 |
| 3-16 | 0.899 | 2.532 | | (>10.0) |
| 3-17 | 3.48 | 6.4 | | (>10.0) |
| 3-18 | 1.054 | 0.719 | 0.48 | (>10.0) |
| 5 | 0.013 | 0.030 | | 1.180 |
| 6 | 0.016 | 0.034 | 0.007 | 1.520 |
| 7 | 0.001 | 0.002 | | 0.074 |
| 8 | 0.001 | 0.002 | | 0.082 |
| 9 | 0.003 | 0.008 | | 0.152 |
| 12 | 0.05 | 0.111 | | (>10.0) |
| 13 | 0.113 | 0.312 | | (>10.0) |
| 14 | 0.027 | 0.071 | | (2.064) |
| 15 | 0.001 | 0.003 | 0.001 | (0.139) |
| 16 | 0.058 | 0.06 | | (1.099) |
| 17-1 | 0.005 | 0.033 | 0.014 | 0.730 |
| 17-2 | 0.076 | 0.170 | | 2.340 |
| 17-4 | 0.105 | 0.156 | | >10.0 |
| 17-12 | 0.010 | 0.147 | 0.030 | >10.0 |
| 17-15 | 0.006 | 0.022 | | 0.259 |
| 17-16 | 0.010 | 0.028 | | 0.295 |
| 17-17 | 0.003 | 0.008 | | 0.176 |
| 17-24 | 0.007 | 0.009 | | 0.225 |
| 17-25 | 0.002 | 0.026 | | 0.251 |
| 17-26 | 0.005 | 0.015 | | 0.190 |
| 17-27 | 0.012 | 0.088 | | 1.000 |
| 17-28 | 0.024 | 0.081 | | 0.370 |
| 17-29 | 0.093 | 0.290 | | 2.610 |
| 17-30 | 0.010 | 0.037 | | 0.313 |
| 17-33 | 0.005 | 0.065 | | 0.259 |
| 17-35 | 0.004 | 0.005 | | 0.285 |
| 17-37 | 0.128 | 0.135 | | >10.0 |
| 17-40 | 0.007 | 0.130 | | 0.760 |
| 17-42 | 0.002 | 0.013 | | 0.206 |
| 17-45 | 0.007 | 0.003 | | 0.142 |
| 17-46 | 0.132 | 0.005 | | 0.212 |
| 17-47 | 0.017 | 0.004 | | 0.186 |
| 17-48 | 0.010 | 0.007 | | 0.380 |
| 17-52 | 0.002 | 0.005 | | 0.320 |
| 17-53 | 0.002 | 0.004 | | 0.261 |
| 17-54 | 0.078 | 0.081 | | 4.900 |
| 17-58 | 0.003 | 0.009 | | 0.154 |
| 17-67 | 0.002 | 0.015 | | 0.249 |
| 17-68 | 0.002 | 0.008 | | 0.203 |
| 17-69 | 0.001 | 0.006 | | 0.071 |
| 17-70 | <0.001 | 0.007 | | 0.185 |
| 17-71 | 0.002 | 0.003 | | 0.134 |
| 17-72 | 0.003 | 0.012 | | 0.220 |
| 17-74 | 0.002 | 0.011 | | 0.261 |
| 17-75 | 0.026 | 0.085 | | 3.140 |
| 17-76 | <0.001 | 0.001 | | 0.014 |
| 17-77 | 0.002 | 0.001 | | 0.024 |
| 17-78 | 0.134 | 0.037 | | 1.680 |
| 17-79 | 0.002 | 0.007 | | 0.176 |

TABLE 3-continued

| Example | H1975 IC50 (μM) | H3255 IC50 (μM) | HCC827 IC50 (μM) | HEKn (HaCaT) IC50 (μM) |
|---|---|---|---|---|
| 17-80 | <0.001 | <0.001 | | 0.004 |
| 17-81 | 0.002 | 0.004 | | 0.162 |
| 17-82 | 0.010 | 0.029 | | 0.370 |
| 17-83 | 0.029 | 0.072 | | 2.330 |
| 17-84 | 0.037 | 0.137 | | 1.660 |
| 17-85 | 0.038 | 0.111 | | 2.080 |
| 17-86 | 0.012 | 0.057 | | 0.710 |
| 17-87 | 0.002 | <0.001 | | 0.037 |
| 17-94 | 0.001 | 0.002 | | 0.045 |
| 17-95 | 0.003 | 0.003 | | 0.127 |
| 17-103 | 0.001 | 0.002 | <0.001 | 0.098 |
| 17-105 | 0.027 | 0.243 | 0.207 | >10.0 |
| 17-106 | 0.009 | 0.083 | 0.153 | >10.0 |
| 17-108 | 0.014 | 0.044 | | >10.0 |
| 17-109 | 0.014 | 0.043 | | 1.680 |
| 17-111 | <0.001 | 0.008 | | 0.203 |
| 17-112 | 0.015 | 0.155 | 0.135 | >10.0 |
| 17-113 | 0.002 | 0.004 | <0.001 | 0.265 |
| 17-114 | <0.001 | 0.004 | | 0.100 |
| 17-117 | 0.013 | 0.290 | 0.243 | >10.0 |
| 17-118 | 0.640 | >10.0 | | >10.0 |
| 17-119 | 0.010 | 0.118 | 0.071 | >6.9 |
| 17-122 | 0.016 | 0.390 | 0.090 | >10.0 |
| 17-123 | 0.022 | 0.199 | 0.291 | >10.0 |
| 17-124 | 0.022 | 0.490 | | >10.0 |
| 17-126 | <0.001 | 0.002 | <0.001 | 0.065 |
| 17-129 | 0.001 | 0.004 | | 0.028 |
| 17-132 | 0.009 | 0.108 | | 2.850 |
| 17-142 | 0.105 | 0.640 | | >10.0 |
| 17-144 | <0.001 | 0.001 | <0.001 | 0.072 |
| 17-145 | 0.001 | 0.002 | <0.001 | 0.095 |
| 17-147 | <0.001 | 0.002 | <0.001 | 0.079 (0.044) |
| 17-148 | 0.001 | 0.002 | <0.001 | 0.077 (0.052) |
| 17-149 | <0.001 | 0.002 | <0.001 | 0.076 (0.048) |
| 17-150 | 0.002 | 0.003 | <0.001 | 0.129 (0.059) |
| 17-151 | <0.001 | 0.001 | <0.001 | 0.036 |
| 17-152 | 0.001 | 0.002 | <0.001 | 0.112 (0.046) |
| 17-153 | <0.001 | 0.002 | <0.001 | 0.061 |
| 17-154 | <0.001 | 0.002 | <0.001 | 0.079 (0.038) |
| 17-155 | 0.002 | 0.002 | <0.001 | 0.061 |
| 17-156 | <0.001 | 0.002 | <0.001 | 0.128 |
| 17-157 | 0.002 | 0.007 | 0.002 | 0.308 |
| 17-158 | <0.001 | 0.002 | | 0.082 (0.067) |
| 17-159 | <0.001 | 0.002 | | 0.070 (0.084) |
| 17-160 | 0.001 | 0.017 | | 0.237 |
| 17-161 | 0.008 | 0.009 | | 0.269 |
| 17-162 | 0.038 | 0.145 | 0.023 | 4.600 |
| 17-163 | 0.043 | 0.051 | 0.011 | 1.260 |
| 17-164 | 0.058 | 0.073 | 0.009 | 2.270 |
| 17-165 | 0.039 | 0.050 | 0.031 | 4.500 |
| 17-166 | 0.033 | 0.060 | 0.007 | 1.540 |
| 17-174 | 0.093 | 0.202 | | >10.0 (>10.0) |
| 17-175 | 0.002 | 0.004 | | 0.289 (0.522) |
| 17-176 | 0.014 | 0.020 | 0.004 | 0.870 |
| 17-177 | 0.004 | 0.004 | | 0.093 |
| 17-178 | 0.117 | 0.106 | 0.038 | 4.200 |
| 17-179 | 0.234 | 0.188 | | 5.400 |
| 17-180 | 0.001 | 0.001 | 0.001 | (0.092) |
| 17-181 | 0.001 | 0.001 | 0.001 | (0.077) |
| 17-182 | 0.77 | 0.422 | | (>10.0) |
| 17-184 | 3.74 | 4.84 | | (>10.0) |
| 17-185 | 0.001 | 0.002 | 0.001 | 0.044 (0.044) |
| 17-186 | 0.002 | 0.01 | 0.002 | 0.291 (0.213) |
| 17-187 | 0.013 | 0.014 | 0.002 | (0.475) |
| 17-188 | 0.016 | 0.039 | 0.01 | (0.87) |
| 17-189 | 0.003 | 0.005 | | (0.083) |
| 17-190 | 0.002 | 0.003 | | (0.047) |
| 17-191 | 0.002 | 0.003 | | (0.059) |
| 17-192 | 0.002 | 0.002 | | (0.037) |
| 17-193 | 0.001 | 0.002 | 0.001 | (0.044) |
| 17-194 | 0.041 | 0.067 | 0.016 | (0.576) |
| 17-195 | 0.036 | 0.181 | 0.045 | (7.12) |
| 17-196 | 0.277 | 0.295 | | (>10.0) |
| 17-197 | 0.935 | 2.0 | | (>10.0) |
| 19 | 0.168 | 2.020 | | >10.0 |
| 21-4 | 0.001 | 0.013 | | 0.285 |
| 21-8B | 0.004 | 0.002 | | 0.095 |
| 21-9A | >10 | 6.58 | | (>10.0) |
| 21-9B | 0.314 | 0.312 | | (>10.0) |
| 21-10A | >10 | 1.539 | | (>10.0) |
| 21-10B | 0.421 | 0.077 | | (6.09) |

It is understood that the examples and embodiments described herein are for illustrative purposes only and that various modifications or changes in light thereof will be suggested to persons skilled in the art and are to be included within the range and purview of this application and scope of the appended claims. All publications, patents, and patent applications cited herein are hereby incorporated by reference for all purposes.

The invention claimed is:

1. A compound having Formula (3A) or (3B) or a tautomer thereof:

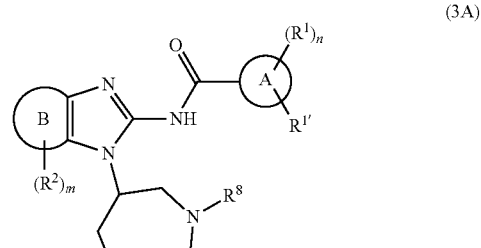

(3A)

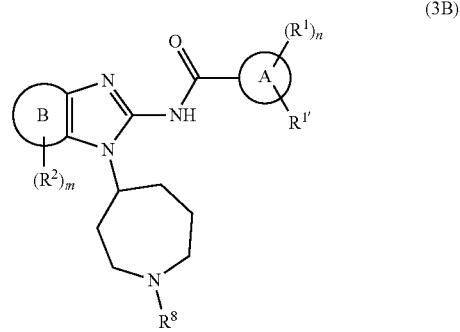

(3B)

wherein Ring A is a 5-10 membered heteroaryl comprising 1-4 heteroatoms selected from N, O and S;

Ring B is phenyl;

$R^1$ and $R^{1'}$ are independently hydrogen; halo; cyano; $C_{1-6}$ alkyl; $C_{1-6}$ haloalkyl; $-X^1-NR^4R^5$; $-X^1-OR^3$; $-X^1-S(O)_{0-2}R^6$; $-X^1-P(O)R^{6a}R^{6b}$; phenyl unsubstituted or substituted by $C_{1-6}$ alkyl; or a 5-6 membered heteroaryl comprising 1-4 heteroatoms selected from N, O and S;

$R^2$ is selected from hydrogen, halo; cyano; $C_{1-6}$ alkyl; $C_{1-6}$ haloalkyl; $-X^1-C(O)OR^3$; $-X^1-C(O)R^3$; $-X^1-C(O)NR^4R^5$; $-X^1-C(O)NR^4-X^3-C(O)OR^3$; $-X^1-C(O)NR^4-X^3-S(O)_{0-2}R^6$; $-X^1-NR^4R^5$; $-X^1-NR^4-X^2-C(O)R^3$; $-X^1-NR^4-X^3-S(O)_{0-2}R^6$; $-X^1-OR^3$; $-X^1-O-X^1-OR^3$; $-X^1-S(O)_{0-2}R^6$; $-X^1-O-X^4-NR^4R^5$; or a 5-6 membered heteroaryl comprising 1-4 heteroatoms selected from N, O and S and is unsubstituted or substituted by $C_{1-6}$ alkyl;

$X^1$ and $X^2$ are independently a bond or $C_{1-6}$ alkyl;

$X^3$ is $C_{1-6}$ alkyl;

$X^4$ is $C_{2-6}$ alkyl;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ may form a 4-7 membered ring containing 1-2 heteroatoms selected from N, O, and S, and optionally substituted with 1-4 $R^7$ groups;

$R^6$, $R^{6a}$ and $R^{6b}$ are $C_{1-6}$ alkyl;

$R^8$ is

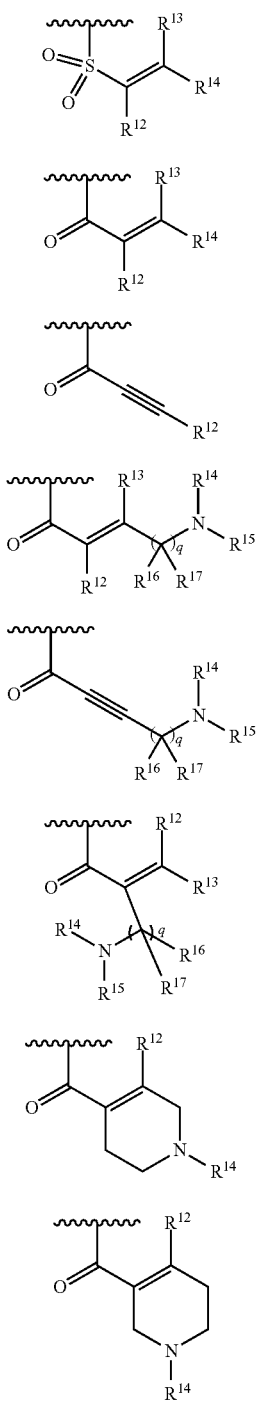

(a)

(b)

(c)

(d)

(e)

(f)

(g)

(h)

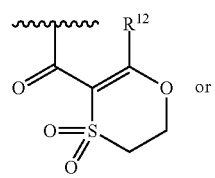

(i)

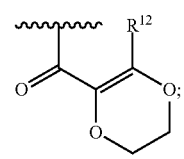

(j)

$R^{12}$, $R^{13}$, $R^{16}$ and $R^{17}$ are independently hydrogen or $C_{1-6}$ alkyl;

$R^{14}$ and $R^{15}$ are independently hydrogen; $C_{1-6}$ alkyl; —C(O)O—($C_{1-6}$ alkyl); $C_{3-7}$ cycloalkyl unsubstituted or substituted with $C_{1-6}$ alkyl; or $R^{14}$ and $R^{15}$ together with N in $NR^{14}R^{15}$ may form may form a 4-7 membered ring containing 1-2 heteroatoms selected from N, O and S, and optionally substituted with 1-4 $R^{18}$ groups;

$R^7$ and $R^{18}$ are independently oxo, halo, hydroxy, $C_{1-6}$ alkyl or $C_{1-6}$ alkoxy;

n is independently 1-3; and m and q are independently 1-2;

or a pharmaceutically acceptable salt thereof.

2. The compound of claim 1 or a pharmaceutically acceptable salt thereof, wherein: Ring A is pyridyl, pyrimidinyl, pyridazinyl, pyrazinyl, oxazolyl, furanyl, thiazolyl, imidazole[2,1-b][1,3]thiazolyl, imidazo[1,2-a]pyridinyl, imidazo[1,5-a]pyridinyl, each of which is unsubstituted or substituted by $(R^1)_n$ and $R^{1'}$; and $R^1$, $R^{1'}$ and n are as defined in claim 1.

3. The compound of claim 1 or a pharmaceutically acceptable salt thereof, wherein said compound is of Formula (5):

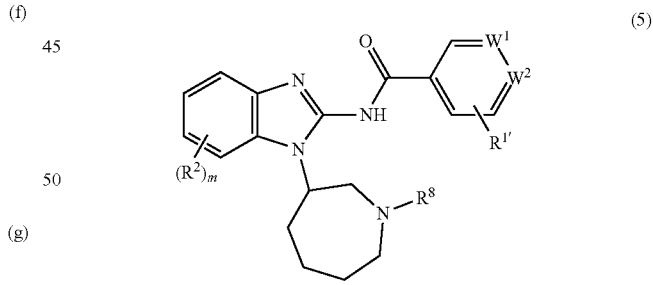

(5)

wherein one of $W^1$ and $W^2$ is $CR^1$ and the other is N; and $R^1$, $R^{1'}$, $R^2$, $R^8$ and m are as defined in claim 1.

4. The compound of claim 1 or a pharmaceutically acceptable salt thereof, wherein $R^1$ and $R^{1'}$ are independently hydrogen; halo; cyano; $C_{1-6}$ alkyl; $C_{1-6}$ haloalkyl; —$X^1$—$NR^4R^5$; —$X^1$—$OR^3$; —$X^1$—$S(O)_{0-2}R^6$; phenyl unsubstituted or substituted by $C_{1-6}$ alkyl; tetrazolyl or pyrrolyl; each $X^1$ is a bond or $CH_2$;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ form piperidinyl; and $R^6$ is as defined in claim 1.

5. The compound of claim 1 or a pharmaceutically acceptable salt thereof, wherein $R^1$ is hydrogen, halo, cyano, $C_{1-6}$ alkyl, $C_{1-6}$ haloalkyl, tetrazolyl, pyrrolyl, —$X^1$—$NR^4R^5$, —$X^1$—$OR^3$, —$X^1$—$S(O)_{0-2}R^6$ or phenyl unsubstituted or substituted by $C_{1-6}$ alkyl;

$R^{1'}$ is hydrogen, halo or $C_{1-6}$ alkyl;

$R^3$, $R^4$ and $R^5$ are independently hydrogen, $C_{1-6}$ alkyl or $C_{1-6}$ haloalkyl; or wherein $R^4$ and $R^5$ together with N in $NR^4R^5$ form piperidinyl;

$X^1$ is a bond or $CH_2$; and $R^6$ is as defined in claim 1.

6. The compound of claim 1 or a pharmaceutically acceptable salt thereof, wherein $R^1$ and $R^{1'}$ are independently hydrogen; methyl; t-butyl; trifluoromethyl; methoxy; ethoxy; trifluoromethoxy; difluoromethoxy; fluoro; chloro; cyano; dimethylamino; methylsulfonyl; dimethylphosphoryl; tetrazolyl; pyrrolyl; phenyl unsubstituted or substituted by methyl; or piperidin-1-yl.

7. The compound of claim 1 or a pharmaceutically acceptable salt thereof, wherein:

$R^2$ is hydrogen; chloro; methyl; trifluoromethyl; methoxy; isopropoxy; cyano; hydroxymethyl; methoxymethyl; ethoxymethyl; methylsulfonyl; methylcarbonyl; carboxy; methoxycarbonyl; carbamoyl; dimethylaminomethyl; pyrrolidin-1-ylmethyl unsubstituted or substituted by 1-2 hydroxy, halo or methoxy; morpholin-4-ylmethyl; azetidin-1-ylmethyl unsubstituted or substituted by 1-2 halo or methoxy; piperidin-1-ylmethyl; ((4-methyl-3-oxo-piperazin-1-yl)methyl); (1,1-dioxidothiomorpholine-4-carbonyl); pyrrolidin-1-yl carbonyl unsubstituted or substituted by 1-2 hydroxy; pyrrolidin-1-ylethoxy; (1,1-dioxido-thiomorpholin-4-yl)methyl; or 1,2,4-oxadiazolyl unsubstituted or substituted by $C_{1-6}$ alkyl;

alternatively, $R^2$ is —$CH_2$—$N(CH_3)$—$C(O)$—$CH_3$; —$CH_2$—O—$(CH_2)_2$—$OCH_3$;

—$CH_2$—$N(CH_3)$—$(CH_2)_2$—$SO_2(CH_3)$; —$C(O)NH$—$(CH_2)_{1-2}$—$C(O)$—$OCH_3$;

—$C(O)NH$—$(CH_2)_{1-2}$—$C(O)OH$; or —$C(O)NH$—$(CH_2)_2$—$SO_2(CH_3)$.

8. The compound of claim 1 or a pharmaceutically acceptable salt thereof, wherein $R^8$ is

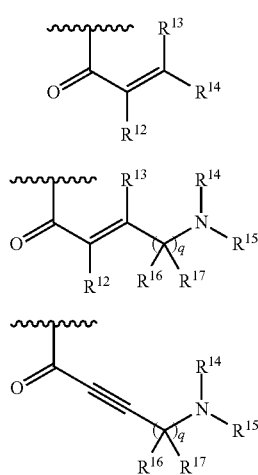

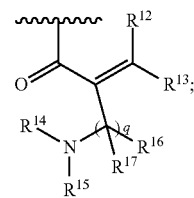

wherein $R^{14}$ and $R^{15}$ are independently hydrogen, $C_{1-6}$ alkyl or $C_{3-7}$ cycloalkyl; or $R^{14}$ and $R^{15}$ together with N in $NR^{14}R^{15}$ may form an azetidinyl, piperidyl, pyrrolidinyl or morpholinyl; where said azetidinyl or pyrrolidinyl can be optionally substituted with 1-2 halo, methoxy or hydroxyl; and $R^{12}$, $R^{13}$, $R^{16}$, $R^{17}$ and q are as defined in claim 1.

9. The compound of claim 1 or a pharmaceutically acceptable salt thereof, wherein said compound is selected from:

N-{7-chloro-1-[(3R)-1-[4-(pyrrolidin-1-yl)but-2-enoyl]azepan-3-yl]-1H-1,3-benzodiazol-2-yl}-2-methylpyridine-4-carboxamide;

N-{7-chloro-1-[1-[4-(pyrrolidin-1-yl)but-2-enoyl]azepan-3-yl]-1H-1,3-benzodiazol-2-yl}-2-methylpyridine-4-carboxamide;

N-{7-chloro-1-[(3R)-1-[4-(3-fluoroazetidin-1-yl)but-2-enoyl]azepan-3-yl]-1H-1,3-benzodiazol-2-yl}-2-methylpyridine-4-carboxamide;

N-{7-chloro-1-[1-[4-(3-fluoroazetidin-1-yl)but-2-enoyl]azepan-3-yl]-1H-1,3-benzodiazol-2-yl}-2-methylpyridine-4-carboxamide;

N-{7-chloro-1-[(3R)-1-{4-[(3R)-3-fluoropyrrolidin-1-yl]but-2-enoyl}azepan-3-yl]-1H-1,3-benzodiazol-2-yl}-2-methylpyridine-4-carboxamide;

N-{7-chloro-1-[1-{4-[3-fluoropyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3S)-3-fluoropyrrolidin-1-yl]but-2-enoyl}azepan-3-yl]-1H-1,3-benzodiazol-2-yl}-2-methylpyridine-4-carboxamide;

N-{7-chloro-1-[(3R)-1-[4-(3,3-difluoropyrrolidin-1-yl)but-2-enoyl]azepan-3-yl]-1H-1,3-benzodiazol-2-yl}-2-methylpyridine-4-carboxamide;

N-{7-chloro-1-[1-[4-(3,3-difluoropyrrolidin-1-yl)but-2-enoyl]azepan-3-yl]-1H-1,3-benzodiazol-2-yl}-2-methylpyridine-4-carboxamide;

N-{7-chloro-1-[(3R)-1-{4-[(3R)-3-methoxypyrrolidin-1-yl]but-2-enoyl}azepan-3-yl]-1H-1,3-benzodiazol-2-yl}-2-methylpyridine-4-carboxamide;

N-{7-chloro-1-[1-{4-[3-methoxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3S)-3-methoxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-{4-[(3R)-3-hydroxypyrrolidin-1-yl]but-2-enoyl}azepan-3-yl]-1H-1,3-benzodiazol-2-yl}-2-methylpyridine-4-carboxamide;

N-{7-chloro-1-[1-{4-[3-hydroxypyrrolidin-1-yl]but-2-enoyl}azepan-3-yl]-1H-1,3-benzodiazol-2-yl}-2-methylpyridine-4-carboxamide;

N-{7-chloro-1-[(3R)-1-[(2E)-4-[(3S)-3-hydroxypyrrolidin-1-yl]but-2-enoyl]azepan-3-yl]-1H-1,3-benzodiazol-2-yl}-2-methylpyridine-4-carboxamide;

N-{7-chloro-1-[1-[(2E)-4-[3-hydroxypyrrolidin-1-yl]but-2-enoyl]azepan-3-yl]-1H-1,3-benzodiazol-2-yl}-2-methylpyridine-4-carboxamide;

N-{7-chloro-1-[(3R)-1-[(2E)-4-(pyrrolidin-1-yl)but-2-enoyl]azepan-3-yl]-1H-1,3-benzodiazol-2-yl}pyridazine-4-carboxamide;

N-{7-chloro-1-[1-[(2E)-4-(pyrrolidin-1-yl)but-2-enoyl]azepan-3-yl]-1H-1,3-benzodiazol-2-yl}pyridazine-4-carboxamide;

2-methyl-N-{7-methyl-1-[(3R)-1-[(2E)-4-(pyrrolidin-1-yl)but-2-enoyl]azepan-3-yl]-1H-1,3-benzodiazol-2-yl}pyridine-4-carboxamide;

2-methyl-N-{7-methyl-1-[1-[(2E)-4-(pyrrolidin-1-yl)but-2-enoyl]azepan-3-yl]-1H-1,3-benzodiazol-2-yl}pyridine-4-carboxamide;

N-{1-[(3R)-1-[(2E)-4-[(3R)-3-fluoropyrrolidin-1-yl]but-2-enoyl]azepan-3-yl]-7-methyl-1H-1,3-benzodiazol-2-yl}-2-methylpyridine-4-carboxamide;

N-{1-[1-[(2E)-4-[3-fluoropyrrolidin-1-yl]but-2-enoyl]azepan-3-yl]-7-methyl-1H-1,3-benzodiazol-2-yl}-2-methylpyridine-4-carboxamide;

N-{7-chloro-1-[(3R)-1-[(2E)-4-[(3R)-3-fluoropyrrolidin-1-yl]but-2-enoyl]azepan-3-yl]-1H-1,3-benzodiazol-2-yl}pyridazine-4-carboxamide;

N-{7-chloro-1-[1-[(2E)-4-[3-fluoropyrrolidin-1-yl]but-2-enoyl]azepan-3-yl]-1H-1,3-benzodiazol-2-yl}pyridazine-4-carboxamide;

N-{1-[(3R)-1-[4-(azetidin-1-yl)but-2-enoyl]azepan-3-yl]-7-chloro-1H-1,3-benzodiazol-2-yl}-2-methylpyridine-4-carboxamide;

N-{1-[1-[4-(azetidin-1-yl)but-2-enoyl]azepan-3-yl]-7-chloro-1H-1,3-benzodiazol-2-yl}-2-methylpyridine-4-carboxamide;

N-{7-chloro-1-[(3R)-1-[4-(3-hydroxyazetidin-1-yl)but-2-enoyl]azepan-3-yl]-1H-1,3-benzodiazol-2-yl}-2-methylpyridine-4-carboxamide;

N-{7-chloro-1-[1-[4-(3-hydroxyazetidin-1-yl)but-2-enoyl]azepan-3-yl]-1H-1,3-benzodiazol-2-yl}-2-methylpyridine-4-carboxamide;

N-{7-chloro-1-[(3R)-1-[(2E)-4-(3-methoxyazetidin-1-yl)but-2-enoyl]azepan-3-yl]-1H-1,3-benzodiazol-2-yl}-2-methylpyridine-4-carboxamide;

N-{7-chloro-1-[1-[(2E)-4-(3-methoxyazetidin-1-yl)but-2-enoyl]azepan-3-yl]-1H-1,3-benzodiazol-2-yl}-2-methylpyridine-4-carboxamide;

N-{7-chloro-1-[(3R)-1-[(2E)-4-(3,3-difluoroazetidin-1-yl)but-2-enoyl]azepan-3-yl]-1H-1,3-benzodiazol-2-yl}-2-methylpyridine-4-carboxamide;

N-{7-chloro-1-[1-[(2E)-4-(3,3-difluoroazetidin-1-yl)but-2-enoyl]azepan-3-yl]-1H-1,3-benzodiazol-2-yl}-2-methylpyridine-4-carboxamide;

N-{7-chloro-1-[(3R)-1-[(2E)-4-(dimethylamino)but-2-enoyl]azepan-3-yl]-1H-1,3-benzodiazol-2-yl}-2-methylpyridine-4-carboxamide;

N-{7-chloro-1-[1-[(2E)-4-(dimethylamino)but-2-enoyl]azepan-3-yl]-1H-1,3-benzodiazol-2-yl}-2-methylpyridine-4-carboxamide;

N-{7-chloro-1-[(3R)-1-[(2E)-4-(dimethylamino)but-2-enoyl]azepan-3-yl]-1H-1,3-benzodiazol-2-yl}-2,6-dimethylpyridine-4-carboxamide;

N-{7-chloro-1-[1-[(2E)-4-(dimethylamino)but-2-enoyl]azepan-3-yl]-1H-1,3-benzodiazol-2-yl}-2,6-dimethylpyridine-4-carboxamide;

N-{1-[(3R)-1-[(2E)-4-(dimethylamino)but-2-enoyl]azepan-3-yl]-7-methyl-H-1,3-benzodiazol-2-yl}-2-methylpyridine-4-carboxamide;

N-{1-[1-[(2E)-4-(dimethylamino)but-2-enoyl]azepan-3-yl]-7-methyl-H-1,3-benzodiazol-2-yl}-2-methylpyridine-4-carboxamide;

N-{1-[(3R)-1-[(2E)-4-(dimethylamino)but-2-enoyl]azepan-3-yl]-7-methyl-H-1,3-benzodiazol-2-yl}-2-(trifluoromethyl)pyridine-4-carboxamide;

N-{1-[1-[(2E)-4-(dimethylamino)but-2-enoyl]azepan-3-yl]-7-methyl-H-1,3-benzodiazol-2-yl}-2-(trifluoromethyl)pyridine-4-carboxamide;

N-{7-chloro-6-methoxy-1-[(3R)-1-(prop-2-enoyl)azepan-3-yl]-1H-1,3-benzodiazol-2-yl}pyridazine-4-carboxamide;

N-{7-chloro-6-methoxy-1-[1-(prop-2-enoyl)azepan-3-yl]-1H-1,3-benzodiazol-2-yl}pyridazine-4-carboxamide;

N-{7-chloro-1-[(3R)-1-[(2E)-4-(dimethylamino)but-2-enoyl]azepan-3-yl]-6-methoxy-1H-1,3-benzodiazol-2-yl}pyridazine-4-carboxamide;

N-{7-chloro-1-[1-[(2E)-4-(dimethylamino)but-2-enoyl]azepan-3-yl]-6-methoxy-1H-1,3-benzodiazol-2-yl}pyridazine-4-carboxamide;

N-(1-{1-[(2E)-4-(dimethylamino)but-2-enoyl]azepan-3-yl}-7-methyl-H-1,3-benzodiazol-2-yl)-1,3-oxazole-5-carboxamide;

N-{7-chloro-1-[(3R)-1-(prop-2-enoyl)azepan-3-yl]-1H-1,3-benzodiazol-2-yl}pyridazine-4-carboxamide;

N-{7-chloro-1-[1-(prop-2-enoyl)azepan-3-yl]-1H-1,3-benzodiazol-2-yl}pyridazine-4-carboxamide;

N-{7-chloro-1-[(3R)-1-[(2E)-4-(dimethylamino)but-2-enoyl]azepan-3-yl]-1H-1,3-benzodiazol-2-yl}pyridazine-4-carboxamide;

N-{7-chloro-1-[1-[(2E)-4-(dimethylamino)but-2-enoyl]azepan-3-yl]-1H-1,3-benzodiazol-2-yl}pyridazine-4-carboxamide;

N-{7-chloro-1-[(3R)-1-(prop-2-enoyl)azepan-3-yl]-1H-1,3-benzodiazol-2-yl}-2-methylpyridine-4-carboxamide;

N-{7-chloro-1-[1-(prop-2-enoyl)azepan-3-yl]-1H-1,3-benzodiazol-2-yl}-2-methylpyridine-4-carboxamide;

N-(1-{1-[(2E)-4-(dimethylamino)but-2-enoyl]azepan-3-yl}-7-methyl-H-1,3-benzodiazol-2-yl)pyridine-3-carboxamide;

N-(1-{1-[(2E)-4-(dimethylamino)but-2-enoyl]azepan-3-yl}-7-methyl-H-1,3-benzodiazol-2-yl)pyridazine-4-carboxamide;

N-(1-{1-[(2E)-4-(dimethylamino)but-2-enoyl]azepan-3-yl}-7-methyl-H-1,3-benzodiazol-2-yl)pyridine-2-carboxamide;

N-(1-{1-[(2E)-4-(dimethylamino)but-2-enoyl]azepan-3-yl}-7-methyl-H-1,3-benzodiazol-2-yl)pyridine-4-carboxamide;

N-(1-{1-[(2E)-4-(dimethylamino)but-2-enoyl]azepan-3-yl}-7-methyl-H-1,3-benzodiazol-2-yl)pyrimidine-2-carboxamide;

N-(1-{1-[(2E)-4-(dimethylamino)but-2-enoyl]azepan-3-yl}-7-methyl-H-1,3-benzodiazol-2-yl)pyrimidine-4-carboxamide;

N-(1-{1-[(2E)-4-(dimethylamino)but-2-enoyl]azepan-3-yl}-7-methyl-H-1,3-benzodiazol-2-yl)pyrazine-2-carboxamide;

N-(1-{1-[(2E)-4-(dimethylamino)but-2-enoyl]azepan-3-yl}-7-methyl-H-1,3-benzodiazol-2-yl)pyridazine-3-carboxamide;

N-(1-{1-[(2E)-4-(dimethylamino)but-2-enoyl]azepan-3-yl}-7-methyl-H-1,3-benzodiazol-2-yl)-6-methoxypyridine-3-carboxamide;

N-(1-{1-[(2E)-4-(dimethylamino)but-2-enoyl]azepan-3-yl}-7-methyl-H-1,3-benzodiazol-2-yl)-6-(trifluoromethyl)pyridine-3-carboxamide;
N-(1-{1-[(2E)-4-(dimethylamino)but-2-enoyl]azepan-3-yl}-7-methyl-H-1,3-benzodiazol-2-yl)-6-methylpyridine-3-carboxamide;
N-(1-{1-[(2E)-4-(dimethylamino)but-2-enoyl]azepan-3-yl}-7-methyl-H-1,3-benzodiazol-2-yl)-2-methoxypyridine-4-carboxamide;
2-(dimethylamino)-N-(1-{1-[(2E)-4-(dimethylamino)but-2-enoyl]azepan-3-yl}-7-methyl-H-1,3-benzodiazol-2-yl)pyridine-4-carboxamide;
N-(1-{1-[(2E)-4-(dimethylamino)but-2-enoyl]azepan-3-yl}-7-methyl-H-1,3-benzodiazol-2-yl)imidazo[2,1-b][1,3]thiazole-6-carboxamide;
N-(1-{1-[(2E)-4-(dimethylamino)but-2-enoyl]azepan-3-yl}-7-methyl-H-1,3-benzodiazol-2-yl)-2-methylpyrimidine-4-carboxamide;
N-(1-{1-[(2E)-4-(dimethylamino)but-2-enoyl]azepan-3-yl}-7-methyl-H-1,3-benzodiazol-2-yl)imidazo[1,2-a]pyridine-6-carboxamide;
N-(1-{1-[(2E)-4-(dimethylamino)but-2-enoyl]azepan-3-yl}-7-methyl-H-1,3-benzodiazol-2-yl)furan-2-carboxamide;
N-(1-{1-[(2E)-4-(dimethylamino)but-2-enoyl]azepan-3-yl}-7-methyl-H-1,3-benzodiazol-2-yl)-2-(piperidin-1-yl)pyridine-4-carboxamide;
N-(1-{1-[(2E)-4-(dimethylamino)but-2-enoyl]azepan-3-yl}-7-methyl-H-1,3-benzodiazol-2-yl)-2-fluoropyridine-4-carboxamide;
N-(1-{1-[(2E)-4-(dimethylamino)but-2-enoyl]azepan-3-yl}-7-methyl-H-1,3-benzodiazol-2-yl)-4,5-dimethylfuran-2-carboxamide;
N-(1-{1-[(2E)-4-(dimethylamino)but-2-enoyl]azepan-3-yl}-7-methyl-H-1,3-benzodiazol-2-yl)-2-(1H-1,2,3,4-tetrazol-1-yl)pyridine-4-carboxamide;
2-tert-butyl-N-(1-{1-[(2E)-4-(dimethylamino)but-2-enoyl]azepan-3-yl}-7-methyl-H-1,3-benzodiazol-2-yl)pyridine-4-carboxamide;
N-(1-{1-[(2E)-4-(dimethylamino)but-2-enoyl]azepan-3-yl}-7-methyl-H-1,3-benzodiazol-2-yl)-2-methylpyridine-3-carboxamide;
N-(1-{1-[(2E)-4-(dimethylamino)but-2-enoyl]azepan-3-yl}-7-methyl-H-1,3-benzodiazol-2-yl)imidazo[1,5-a]pyridine-7-carboxamide;
N-(1-{1-[(2E)-4-(dimethylamino)but-2-enoyl]azepan-3-yl}-7-methyl-H-1,3-benzodiazol-2-yl)-2-methyl-1,3-thiazole-5-carboxamide;
N-(1-{1-[(2E)-4-(dimethylamino)but-2-enoyl]azepan-3-yl}-7-methyl-H-1,3-benzodiazol-2-yl)-2-ethoxypyridine-4-carboxamide;
N-{1-[(3R)-1-[(2E)-4-(dimethylamino)but-2-enoyl]azepan-3-yl]-7-methyl-H-1,3-benzodiazol-2-yl}-5-(trifluoromethyl)pyridine-3-carboxamide;
N-{1-[1-[(2E)-4-(dimethylamino)but-2-enoyl]azepan-3-yl]-7-methyl-H-1,3-benzodiazol-2-yl}-5-(trifluoromethyl)pyridine-3-carboxamide;
N-{1-[(3R)-1-[(2E)-4-(dimethylamino)but-2-enoyl]azepan-3-yl]-7-methyl-H-1,3-benzodiazol-2-yl}-5-methylpyridine-3-carboxamide;
N-{1-[1-[(2E)-4-(dimethylamino)but-2-enoyl]azepan-3-yl]-7-methyl-H-1,3-benzodiazol-2-yl}-5-methylpyridine-3-carboxamide;
N-{1-[(3R)-1-[(2E)-4-(dimethylamino)but-2-enoyl]azepan-3-yl]-7-methyl-H-1,3-benzodiazol-2-yl}-5-fluoropyridine-3-carboxamide;
N-{1-[1-[(2E)-4-(dimethylamino)but-2-enoyl]azepan-3-yl]-7-methyl-H-1,3-benzodiazol-2-yl}-5-fluoropyridine-3-carboxamide;
N-{1-[(3R)-1-[(2E)-4-(dimethylamino)but-2-enoyl]azepan-3-yl]-7-methyl-H-1,3-benzodiazol-2-yl}-5-(1H-pyrrol-1-yl)pyridine-3-carboxamide;
N-{1-[1-[(2E)-4-(dimethylamino)but-2-enoyl]azepan-3-yl]-7-methyl-H-1,3-benzodiazol-2-yl}-5-(1H-pyrrol-1-yl)pyridine-3-carboxamide;
N-{1-[(3R)-1-[(2E)-4-(dimethylamino)but-2-enoyl]azepan-3-yl]-7-methyl-H-1,3-benzodiazol-2-yl}-2-methoxypyridine-4-carboxamide;
N-{1-[1-[(2E)-4-(dimethylamino)but-2-enoyl]azepan-3-yl]-7-methyl-H-1,3-benzodiazol-2-yl}-2-methoxypyridine-4-carboxamide;
N-{1-[(3R)-1-[(2E)-4-(dimethylamino)but-2-enoyl]azepan-3-yl]-7-methyl-H-1,3-benzodiazol-2-yl}-2,6-dimethylpyridine-4-carboxamide;
N-{1-[1-[(2E)-4-(dimethylamino)but-2-enoyl]azepan-3-yl]-7-methyl-H-1,3-benzodiazol-2-yl}-2,6-dimethylpyridine-4-carboxamide;
2-chloro-N-{1-[(3R)-1-[(2E)-4-(dimethylamino)but-2-enoyl]azepan-3-yl]-7-methyl-H-1,3-benzodiazol-2-yl}pyridine-4-carboxamide;
2-chloro-N-{1-[1-[(2E)-4-(dimethylamino)but-2-enoyl]azepan-3-yl]-7-methyl-H-1,3-benzodiazol-2-yl}pyridine-4-carboxamide;
2-chloro-N-{1-[(3R)-1-[(2E)-4-(dimethylamino)but-2-enoyl]azepan-3-yl]-7-methyl-H-1,3-benzodiazol-2-yl}-6-methylpyridine-4-carboxamide;
2-chloro-N-{1-[1-[(2E)-4-(dimethylamino)but-2-enoyl]azepan-3-yl]-7-methyl-H-1,3-benzodiazol-2-yl}-6-methylpyridine-4-carboxamide;
2-chloro-N-{1-[(3R)-1-[(2E)-4-(dimethylamino)but-2-enoyl]azepan-3-yl]-7-methyl-H-1,3-benzodiazol-2-yl}-6-methoxypyridine-4-carboxamide;
2-chloro-N-{1-[1-[(2E)-4-(dimethylamino)but-2-enoyl]azepan-3-yl]-7-methyl-H-1,3-benzodiazol-2-yl}-6-methoxypyridine-4-carboxamide;
N-{1-[(3R)-1-[(2E)-4-(dimethylamino)but-2-enoyl]azepan-3-yl]-7-methyl-H-1,3-benzodiazol-2-yl}-2-phenylpyridine-4-carboxamide;
N-{1-[1-[(2E)-4-(dimethylamino)but-2-enoyl]azepan-3-yl]-7-methyl-H-1,3-benzodiazol-2-yl}-2-phenylpyridine-4-carboxamide;
6-chloro-N-{1-[(3R)-1-[(2E)-4-(dimethylamino)but-2-enoyl]azepan-3-yl]-7-methyl-H-1,3-benzodiazol-2-yl}pyridine-3-carboxamide;
6-chloro-N-{1-[1-[(2E)-4-(dimethylamino)but-2-enoyl]azepan-3-yl]-7-methyl-H-1,3-benzodiazol-2-yl}pyridine-3-carboxamide;
5,6-dichloro-N-{1-[(3R)-1-[(2E)-4-(dimethylamino)but-2-enoyl]azepan-3-yl]-7-methyl-1H-1,3-benzodiazol-2-yl}pyridine-3-carboxamide;
5,6-dichloro-N-{1-[1-[(2E)-4-(dimethylamino)but-2-enoyl]azepan-3-yl]-7-methyl-1H-1,3-benzodiazol-2-yl}pyridine-3-carboxamide;
N-{1-[(3R)-1-[(2E)-4-(dimethylamino)but-2-enoyl]azepan-3-yl]-7-methyl-H-1,3-benzodiazol-2-yl}-5-methoxypyridine-3-carboxamide;
N-{1-[1-[(2E)-4-(dimethylamino)but-2-enoyl]azepan-3-yl]-7-methyl-H-1,3-benzodiazol-2-yl}-5-methoxypyridine-3-carboxamide;
N-{1-[(3R)-1-[(2E)-4-(dimethylamino)but-2-enoyl]azepan-3-yl]-7-methyl-H-1,3-benzodiazol-2-yl}-2-(2-methylphenyl)pyridine-4-carboxamide;

N-{1-[1-[(2E)-4-(dimethylamino)but-2-enoyl]azepan-3-yl]-7-methyl-H-1,3-benzodiazol-2-yl}-2-(2-methylphenyl)pyridine-4-carboxamide;
6-methyl-N-{7-methyl-1-[(3R)-1-(prop-2-enoyl)azepan-3-yl]-1H-1,3-benzodiazol-2-yl}pyridazine-4-carboxamide;
6-methyl-N-{7-methyl-1-[1-(prop-2-enoyl)azepan-3-yl]-1H-1,3-benzodiazol-2-yl}pyridazine-4-carboxamide;
N-{1-[(3R)-1-[(2E)-4-(dimethylamino)but-2-enoyl]azepan-3-yl]-7-methyl-H-1,3-benzodiazol-2-yl}-6-methylpyridazine-4-carboxamide;
N-{1-[I-[(2E)-4-(dimethylamino)but-2-enoyl]azepan-3-yl]-7-methyl-H-1,3-benzodiazol-2-yl}-6-methylpyridazine-4-carboxamide;
N-{1-[(3R)-1-[(2E)-4-(dimethylamino)but-2-enoyl]azepan-3-yl]-7-methoxy-1H-1,3-benzodiazol-2-yl}pyridazine-4-carboxamide;
N-{1-[1-[(2E)-4-(dimethylamino)but-2-enoyl]azepan-3-yl]-7-methoxy-1H-1,3-benzodiazol-2-yl}pyridazine-4-carboxamide;
N-{7-methoxy-1-[(3R)-1-(prop-2-enoyl)azepan-3-yl]-1H-1,3-benzodiazol-2-yl}pyridazine-4-carboxamide;
N-{7-methoxy-1-[1-(prop-2-enoyl)azepan-3-yl]-1H-1,3-benzodiazol-2-yl}pyridazine-4-carboxamide;
N-{1-[(3R)-1-[(2E)-4-(dimethylamino)but-2-enoyl]azepan-3-yl]-7-(propan-2-yloxy)-1H-1,3-benzodiazol-2-yl}pyridazine-4-carboxamide;
N-{1-[1-[(2E)-4-(dimethylamino)but-2-enoyl]azepan-3-yl]-7-(propan-2-yloxy)-1H-1,3-benzodiazol-2-yl}pyridazine-4-carboxamide;
N-{1-[(3R)-1-(prop-2-enoyl)azepan-3-yl]-7-(propan-2-yloxy)-1H-1,3-benzodiazol-2-yl}pyridazine-4-carboxamide;
N-{1-[1-(prop-2-enoyl)azepan-3-yl]-7-(propan-2-yloxy)-1H-1,3-benzodiazol-2-yl}pyridazine-4-carboxamide;
N-{1-[(3R)-1-[4-(dimethylamino)but-2-ynoyl]azepan-3-yl]-7-methyl-H-1,3-benzodiazol-2-yl}pyridazine-4-carboxamide;
N-{1-[1-[4-(dimethylamino)but-2-ynoyl]azepan-3-yl]-7-methyl-H-1,3-benzodiazol-2-yl}pyridazine-4-carboxamide;
(R)—N-(7-methyl-1-(1-(2-methyl-4,4-dioxido-5,6-dihydro-1,4-oxathiine-3-carbonyl)azepan-3-yl)-1H-benzo[d]imidazol-2-yl)pyridazine-4-carboxamide;
N-(7-methyl-1-(1-(2-methyl-4,4-dioxido-5,6-dihydro-1,4-oxathiine-3-carbonyl)azepan-3-yl)-1H-benzo[d]imidazol-2-yl)pyridazine-4-carboxamide;
N-{1-[(3R)-1-[(5,6-dihydro-1,4-dioxin-2-yl)carbonyl]azepan-3-yl]-7-methyl-1H-1,3-benzodiazol-2-yl}pyridazine-4-carboxamide;
N-{1-[1-[(5,6-dihydro-1,4-dioxin-2-yl)carbonyl]azepan-3-yl]-7-methyl-1H-1,3-benzodiazol-2-yl}pyridazine-4-carboxamide;
N-{7-methyl-1-[(3R)-1-[2-(piperidin-1-ylmethyl)prop-2-enoyl]azepan-3-yl]-1H-1,3-benzodiazol-2-yl}pyridazine-4-carboxamide;
N-{7-methyl-1-[1-[2-(piperidin-1-ylmethyl)prop-2-enoyl]azepan-3-yl]-1H-1,3-benzodiazol-2-yl}pyridazine-4-carboxamide;
N-{7-methyl-1-[(3R)-1-[2-(pyrrolidin-1-ylmethyl)prop-2-enoyl]azepan-3-yl]-1H-1,3-benzodiazol-2-yl}pyridazine-4-carboxamide;
N-{7-methyl-1-[1-[2-(pyrrolidin-1-ylmethyl)prop-2-enoyl]azepan-3-yl]-1H-1,3-benzodiazol-2-yl}pyridazine-4-carboxamide;
N-{1-[(3R)-1-{2-[(diethylamino)methyl]prop-2-enoyl}azepan-3-yl]-7-methyl-H-1,3-benzodiazol-2-yl}pyridazine-4-carboxamide;
N-{1-[1-{2-[(diethylamino)methyl]prop-2-enoyl}azepan-3-yl]-7-methyl-H-1,3-benzodiazol-2-yl}pyridazine-4-carboxamide;
N-{7-methyl-1-[(3R)-1-[2-(morpholin-4-ylmethyl)prop-2-enoyl]azepan-3-yl]-1H-1,3-benzodiazol-2-yl}pyridazine-4-carboxamide;
N-{7-methyl-1-[1-[2-(morpholin-4-ylmethyl)prop-2-enoyl]azepan-3-yl]-1H-1,3-benzodiazol-2-yl}pyridazine-4-carboxamide;
N-{7-methyl-1-[(3R)-1-(prop-2-enoyl)azepan-3-yl]-1H-1,3-benzodiazol-2-yl}pyridazine-4-carboxamide;
N-{7-methyl-1-[1-(prop-2-enoyl)azepan-3-yl]-1H-1,3-benzodiazol-2-yl}pyridazine-4-carboxamide;
N-{1-[(3R)-1-[(2E)-4-(dimethylamino)but-2-enoyl]azepan-3-yl]-7-methyl-H-1,3-benzodiazol-2-yl}pyridazine-4-carboxamide;
N-{1-[1-[(2E)-4-(dimethylamino)but-2-enoyl]azepan-3-yl]-7-methyl-H-1,3-benzodiazol-2-yl}pyridazine-4-carboxamide;
N-{1-[(3R)-1-[(2E)-4-(dimethylamino)but-2-enoyl]azepan-3-yl]-7-methyl-H-1,3-benzodiazol-2-yl}-2-(trifluoromethoxy)pyridine-4-carboxamide;
N-{1-[1-[(2E)-4-(dimethylamino)but-2-enoyl]azepan-3-yl]-7-methyl-H-1,3-benzodiazol-2-yl}-2-(trifluoromethoxy)pyridine-4-carboxamide;
2-(difluoromethoxy)-N-{1-[(3R)-1-[4-(dimethylamino)but-2-enoyl]azepan-3-yl]-7-methyl-1H-1,3-benzodiazol-2-yl}pyridine-4-carboxamide;
2-(difluoromethoxy)-N-{1-[1-[4-(dimethylamino)but-2-enoyl]azepan-3-yl]-7-methyl-1H-1,3-benzodiazol-2-yl}pyridine-4-carboxamide;
2-chloro-N-{1-[(3R)-1-[(2E)-4-(dimethylamino)but-2-enoyl]azepan-3-yl]-7-methyl-H-1,3-benzodiazol-2-yl}-6-(trifluoromethoxy)pyridine-4-carboxamide;
2-chloro-N-{1-[1-[(2E)-4-(dimethylamino)but-2-enoyl]azepan-3-yl]-7-methyl-H-1,3-benzodiazol-2-yl}-6-(trifluoromethoxy)pyridine-4-carboxamide;
2,6-dimethyl-N-{7-methyl-1-[(3R)-1-(prop-2-enoyl)azepan-3-yl]-5-(pyrrolidin-1-ylmethyl)-1H-1,3-benzodiazol-2-yl}pyridine-4-carboxamide;
2,6-dimethyl-N-{7-methyl-1-[1-(prop-2-enoyl)azepan-3-yl]-5-(pyrrolidin-1-ylmethyl)-1H-1,3-benzodiazol-2-yl}pyridine-4-carboxamide;
2-methyl-N-{7-methyl-1-[(3R)-1-(prop-2-enoyl)azepan-3-yl]-5-(pyrrolidin-1-ylmethyl)-1H-1,3-benzodiazol-2-yl}pyridine-4-carboxamide;
2-methyl-N-{7-methyl-1-[1-(prop-2-enoyl)azepan-3-yl]-5-(pyrrolidin-1-ylmethyl)-1H-1,3-benzodiazol-2-yl}pyridine-4-carboxamide;
2-methyl-N-[7-methyl-5-(piperidin-1-ylmethyl)-1-[(3R)-1-(prop-2-enoyl)azepan-3-yl]-1H-1,3-benzodiazol-2-yl]pyridine-4-carboxamide;
2-methyl-N-[7-methyl-5-(piperidin-1-ylmethyl)-1-[1-(prop-2-enoyl)azepan-3-yl]-1H-1,3-benzodiazol-2-yl]pyridine-4-carboxamide;
N-[5-(azetidin-1-ylmethyl)-7-methyl-1-[(3R)-1-(prop-2-enoyl)azepan-3-yl]-1H-1,3-benzodiazol-2-yl]-2-methylpyridine-4-carboxamide;
N-[5-(azetidin-1-ylmethyl)-7-methyl-1-[1-(prop-2-enoyl)azepan-3-yl]-1H-1,3-benzodiazol-2-yl]-2-methylpyridine-4-carboxamide;
N-(5-{[(3S)-3-hydroxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-hydroxypyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3S)-3-fluoropyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3R)-3-fluoropyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[(3S)-3-methoxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2-methylpyridine-4-carboxamide;

N-(5-{[(3R)-3-methoxypyrrolidin-1-yl]methyl}-7-methyl-1-[(3R)-1-(prop-2-enoyl)azepan-3-yl]-1H-1,3-benzodiazol-2-yl)-2-methylpyridine-4-carboxamide;

N-{5-[(3,3-difluoropyrrolidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3,3-difluoropyrrolidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3-fluoroazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3-fluoroazetidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3,3-difluoroazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3,3-difluoroazetidin-1-yl)methyl]-7-methyl-1-[1-(prop-2-enoyl)azepan-3-yl]-1H-1,3-benzodiazol-2-yl}-2-methylpyridine-4-carboxamide;

N-{5-[(3-methoxyazetidin-1-yl)methyl]-7-methyl-1-[(3R)-1-(prop-2-enoyl)azepan-3-yl]-1H-1,3-benzodiazol-2-yl}-2-methylpyridine-4-carboxamide;

N-{5-[(3-methoxyazetidin-1-yl)methyl]-7-methyl-1-[1-(prop-2-enoyl)azepan-3-yl]-1H-1,3-benzodiazol-2-yl}-2-methylpyridine-4-carboxamide;

N-(5-{[(3S)-3-methoxypyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-methoxypyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

N-(5-{[(3R)-3-methoxypyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[(3S)-3-fluoropyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

N-(5-{[3-fluoropyrrolidin-1-yl]methyl}-7-methyl-1-[1-(prop-2-enoyl)azepan-3-yl]-1H-1,3-benzodiazol-2-yl)-2,6-dimethylpyridine-4-carboxamide;

N-(5-{[(3R)-3-fluoropyrrolidin-1-yl]methyl}-7-methyl-1-[(3R)-1-(prop-2-enoyl)azepan-3-yl]-1H-1,3-benzodiazol-2-yl)-2,6-dimethylpyridine-4-carboxamide;

6-methyl-N-{7-methyl-1-[(3R)-1-(prop-2-enoyl)azepan-3-yl]-5-(pyrrolidin-1-ylmethyl)-1H-1,3-benzodiazol-2-yl}pyridazine-4-carboxamide;

6-methyl-N-{7-methyl-1-[1-(prop-2-enoyl)azepan-3-yl]-5-(pyrrolidin-1-ylmethyl)-1H-1,3-benzodiazol-2-yl}pyridazine-4-carboxamide;

N-{1-[(3R)-1-[(2E)-but-2-enoyl]azepan-3-yl]-5-{[(3S)-3-methoxypyrrolidin-1-yl]methyl}-7-methyl-1H-1,3-benzodiazol-2-yl}-2,6-dimethylpyridine-4-carboxamide;

N-{1-[1-[(2E)-but-2-enoyl]azepan-3-yl]-5-{[3-methoxypyrrolidin-1-yl]methyl}-7-methyl-1H-1,3-benzodiazol-2-yl}-2,6-dimethylpyridine-4-carboxamide;

N-{1-[(3R)-1-[(2E)-but-2-enoyl]azepan-3-yl]-5-{[(3R)-3-methoxypyrrolidin-1-yl]methyl}-7-methyl-1H-1,3-benzodiazol-2-yl}-2-methylpyridine-4-carboxamide;

N-{1-[1-[(2E)-but-2-enoyl]azepan-3-yl]-5-{[3-methoxypyrrolidin-1-yl]methyl}-7-methyl-1H-1,3-benzodiazol-2-yl}-2-methylpyridine-4-carboxamide;

N-{1-[(3R)-1-[(2E)-but-2-enoyl]azepan-3-yl]-7-methyl-5-(pyrrolidin-1-ylmethyl)-1H-1,3-benzodiazol-2-yl}-2-methylpyridine-4-carboxamide;

N-{1-[1-[(2E)-but-2-enoyl]azepan-3-yl]-7-methyl-5-(pyrrolidin-1-ylmethyl)-1H-1,3-benzodiazol-2-yl}-2-methylpyridine-4-carboxamide;

N-{1-[(3R)-1-[(2E)-but-2-enoyl]azepan-3-yl]-5-{[(3S)-3-fluoropyrrolidin-1-yl]methyl}-7-methyl-1H-1,3-benzodiazol-2-yl}-2,6-dimethylpyridine-4-carboxamide;

N-{1-[1-[(2E)-but-2-enoyl]azepan-3-yl]-5-{[3-fluoropyrrolidin-1-yl]methyl}-7-methyl-1H-1,3-benzodiazol-2-yl}-2,6-dimethylpyridine-4-carboxamide;

N-{1-[(3R)-1-[(2E)-but-2-enoyl]azepan-3-yl]-5-{[(3S)-3-fluoropyrrolidin-1-yl]methyl}-7-methyl-1H-1,3-benzodiazol-2-yl}-2-methylpyridine-4-carboxamide;

N-{1-[1-[(2E)-but-2-enoyl]azepan-3-yl]-5-{[3-fluoropyrrolidin-1-yl]methyl}-7-methyl-1H-1,3-benzodiazol-2-yl}-2-methylpyridine-4-carboxamide;

N-{1-[(3R)-1-[(2E)-4-(dimethylamino)but-2-enoyl]azepan-3-yl]-7-methoxy-H-1,3-benzodiazol-2-yl}-2-methylpyridine-4-carboxamide;

N-{1-[1-[(2E)-4-(dimethylamino)but-2-enoyl]azepan-3-yl]-7-methoxy-1H-1,3-benzodiazol-2-yl}-2-methylpyridine-4-carboxamide;

N-{7-chloro-1-[(3R)-1-[(2E)-4-(dimethylamino)but-2-enoyl]azepan-3-yl]-6-methoxy-1H-1,3-benzodiazol-2-yl}-2-methylpyridine-4-carboxamide;

N-{7-chloro-1-[1-[(2E)-4-(dimethylamino)but-2-enoyl]azepan-3-yl]-6-methoxy-1H-1,3-benzodiazol-2-yl}-2-methylpyridine-4-carboxamide;

N-{6-chloro-1-[(3R)-1-[(2E)-4-(dimethylamino)but-2-enoyl]azepan-3-yl]-5-methoxy-1H-1,3-benzodiazol-2-yl}-2-methylpyridine-4-carboxamide;

N-{6-chloro-1-[1-[(2E)-4-(dimethylamino)but-2-enoyl]azepan-3-yl]-5-methoxy-1H-1,3-benzodiazol-2-yl}-2-methylpyridine-4-carboxamide;

N-{6-chloro-1-[(3R)-1-[(2E)-4-(dimethylamino)but-2-enoyl]azepan-3-yl]-5-methoxy-1H-1,3-benzodiazol-2-yl}-2,6-dimethylpyridine-4-carboxamide;

N-{6-chloro-1-[1-[(2E)-4-(dimethylamino)but-2-enoyl]azepan-3-yl]-5-methoxy-1H-1,3-benzodiazol-2-yl}-2,6-dimethylpyridine-4-carboxamide;

N-{1-[(3S)-1-[(2E)-4-(dimethylamino)but-2-enoyl]azepan-3-yl]-7-methyl-H-1,3-benzodiazol-2-yl}-2-(trifluoromethyl)pyridine-4-carboxamide;
N-{1-[(3S)-1-[(2E)-4-(dimethylamino)but-2-enoyl]azepan-3-yl]-7-methyl-H-1,3-benzodiazol-2-yl}-2-methyl-1,3-thiazole-5-carboxamide;
N-{1-[(3R)-1-[(2E)-4-(dimethylamino)but-2-enoyl]azepan-3-yl]-7-methyl-H-1,3-benzodiazol-2-yl}-2-methyl-1,3-thiazole-5-carboxamide;
N-{1-[1-[(2E)-4-(dimethylamino)but-2-enoyl]azepan-3-yl]-7-methyl-H-1,3-benzodiazol-2-yl}-2-methyl-1,3-thiazole-5-carboxamide;
(R)—N-(7-chloro-1-(1-(1-methyl-1,2,5,6-tetrahydropyridine-3-carbonyl)azepan-3-yl)-1H-benzo[d]imidazol-2-yl)-2-methylisonicotinamide;
(N-(7-chloro-1-(1-(1-methyl-1,2,5,6-tetrahydropyridine-3-carbonyl)azepan-3-yl)-1H-benzo[d]imidazol-2-yl)-2-methylisonicotinamide;
(R)—N-(7-chloro-1-(1-(1-methyl-1,2,3,6-tetrahydropyridine-4-carbonyl)azepan-3-yl)-1H-benzo[d]imidazol-2-yl)-2-methylisonicotinamide;
N-(7-chloro-1-(1-(1-methyl-1,2,3,6-tetrahydropyridine-4-carbonyl)azepan-3-yl)-1H-benzo[d]imidazol-2-yl)-2-methylisonicotinamide;
(R,E)-N-(7-chloro-1-(1-(4-(dimethylamino)-4-methylpent-2-enoyl)azepan-3-yl)-1H-benzo[d]imidazol-2-yl)-2-methylisonicotinamide;
N-(7-chloro-1-(1-(4-(dimethylamino)-4-methylpent-2-enoyl)azepan-3-yl)-1H-benzo[d]imidazol-2-yl)-2-methylisonicotinamide;
(R)—N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;
N-(1-(1-acryloylazepan-3-yl)-7-chloro-6-(2-(pyrrolidin-1-yl)ethoxy)-1H-benzo[d]imidazol-2-yl)-2,6-dimethylisonicotinamide;
(R,E)-N-(7-chloro-1-(1-(4-(dicyclopropylamino)but-2-enoyl)azepan-3-yl)-1H-benzo[d]imidazol-2-yl)-2-methylisonicotinamide;
N-(7-chloro-1-(1-(4-(dicyclopropylamino)but-2-enoyl)azepan-3-yl)-1H-benzo[d]imidazol-2-yl)-2-methylisonicotinamide;
(R)—N-(1-(1-acryloylazepan-3-yl)-7-methyl-5-((4-methyl-3-oxopiperazin-1-yl)methyl)-1H-benzo[d]imidazol-2-yl)-2,6-dimethylisonicotinamide;
N-(1-(1-acryloylazepan-3-yl)-7-methyl-5-((4-methyl-3-oxopiperazin-1-yl)methyl)-1H-benzo[d]imidazol-2-yl)-2,6-dimethylisonicotinamide;
(E)-N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;
(R,E)-tert-butyl 4-(3-(7-chloro-2-(2-methylisonicotinamido)-1H-benzo[d]imidazol-1-yl)azepan-1-yl)-4-oxobut-2-enyl(methyl)carbamate;
tert-butyl 4-(3-(7-chloro-2-(2-methylisonicotinamido)-1H-benzo[d]imidazol-1-yl)azepan-1-yl)-4-oxobut-2-enyl(methyl)carbamate;
(R,E)-N-(7-chloro-1-(1-(4-(methylamino)but-2-enoyl)azepan-3-yl)-1H-benzo[d]imidazol-2-yl)-2-methylisonicotinamide;
N-(7-chloro-1-(1-(4-(methylamino)but-2-enoyl)azepan-3-yl)-1H-benzo[d]imidazol-2-yl)-2-methylisonicotinamide;
(R,E)-N-(7-chloro-1-(1-(4-(methylamino)but-2-enoyl)azepan-3-yl)-1H-benzo[d]imidazol-2-yl)-2,6-dimethylisonicotinamide;
N-(7-chloro-1-(1-(4-(methylamino)but-2-enoyl)azepan-3-yl)-1H-benzo[d]imidazol-2-yl)-2,6-dimethylisonicotinamide;
(R,E)-N-(1-(1-(4-(dimethylamino)but-2-enoyl)azepan-3-yl)-7-(trifluoromethyl)-1H-benzo[d]imidazol-2-yl)-2-methylisonicotinamide;
N-(1-(1-(4-(dimethylamino)but-2-enoyl)azepan-3-yl)-7-(trifluoromethyl)-1H-benzo[d]imidazol-2-yl)-2-methylisonicotinamide;
(R,E)-N-(1-(1-(4-(dimethylamino)but-2-enoyl)azepan-3-yl)-7-(trifluoromethyl)-1H-benzo[d]imidazol-2-yl)-2,6-dimethylisonicotinamide;
N-(1-(1-(4-(dimethylamino)but-2-enoyl)azepan-3-yl)-7-(trifluoromethyl)-1H-benzo[d]imidazol-2-yl)-2,6-dimethylisonicotinamide;
(R,E)-N-(7-chloro-1-(1-(4-(cyclopropylamino)but-2-enoyl)azepan-3-yl)-1H-benzo[d]imidazol-2-yl)-2-methylisonicotinamide;
N-(7-chloro-1-(1-(4-(cyclopropylamino)but-2-enoyl)azepan-3-yl)-1H-benzo[d]imidazol-2-yl)-2-methylisonicotinamide;
(R,E)-N-(1-(1-(4-(tert-butylamino)but-2-enoyl)azepan-3-yl)-7-chloro-1H-benzo[d]imidazol-2-yl)-2-methylisonicotinamide;
N-(1-(1-(4-(tert-butylamino)but-2-enoyl)azepan-3-yl)-7-chloro-1H-benzo[d]imidazol-2-yl)-2-methylisonicotinamide;
(R,E)-N-(7-chloro-1-(1-(4-(1-methylcyclopropylamino)but-2-enoyl)azepan-3-yl)-1H-benzo[d]imidazol-2-yl)-2-methylisonicotinamide;
N-(7-chloro-1-(1-(4-(1-methylcyclopropylamino)but-2-enoyl)azepan-3-yl)-1H-benzo[d]imidazol-2-yl)-2-methylisonicotinamide;
(R)—N-(1-(1-acryloylazepan-3-yl)-7-chloro-6-(2-(pyrrolidin-1-yl)ethoxy)-1H-benzo[d]imidazol-2-yl)-2-methylisonicotinamide;
N-(1-(1-acryloylazepan-3-yl)-7-chloro-6-(2-(pyrrolidin-1-yl)ethoxy)-1H-benzo[d]imidazol-2-yl)-2-methylisonicotinamide;
(R,E)-N-(1-(1-but-2-enoylazepan-3-yl)-7-chloro-6-(2-(pyrrolidin-1-yl)ethoxy)-1H-benzo[d]imidazol-2-yl)-2-methylisonicotinamide;
N-(1-(1-but-2-enoylazepan-3-yl)-7-chloro-6-(2-(pyrrolidin-1-yl)ethoxy)-1H-benzo[d]imidazol-2-yl)-2-methylisonicotinamide;
(R,E)-N-(1-(1-but-2-enoylazepan-3-yl)-7-chloro-6-(2-(pyrrolidin-1-yl)ethoxy)-1H-benzo[d]imidazol-2-yl)-2,6-dimethylisonicotinamide;
N-(1-(1-but-2-enoylazepan-3-yl)-7-chloro-6-(2-(pyrrolidin-1-yl)ethoxy)-1H-benzo[d]imidazol-2-yl)-2,6-dimethylisonicotinamide;
(R,E)-N-(7-chloro-1-(1-(4-(dimethylamino)but-2-enoyl)azepan-3-yl)-1H-benzo[d]imidazol-2-yl)-2-methylisonicotinamide;
N-(7-chloro-1-(1-(4-(dimethylamino)but-2-enoyl)azepan-3-yl)-1H-benzo[d]imidazol-2-yl)-2-methylisonicotinamide;
(R,E)-N-(7-chloro-1-(1-(4-(dimethylamino)but-2-enoyl)azepan-3-yl)-1H-benzo[d]imidazol-2-yl)-2,6-dimethylisonicotinamide;
N-(7-chloro-1-(1-(4-(dimethylamino)but-2-enoyl)azepan-3-yl)-1H-benzo[d]imidazol-2-yl)-2,6-dimethylisonicotinamide;

(R,E)-N-(7-chloro-1-(1-(4-(dimethylamino)but-2-enoyl)azepan-3-yl)-1H-benzo[d]imidazol-2-yl)-2-(dimethylphosphoryl)-6-methylisonicotinamide;

N-(7-chloro-1-(1-(4-(dimethylamino)but-2-enoyl)azepan-3-yl) 1H-benzo[d]imidazol-2-yl)-2-(dimethylphosphoryl)isonicotinamide; and (R,E)-N-(7-chloro-1-(1-(4-(dimethylamino)but-2-enoyl)azepan-3-yl)-1H-benzo[d]imidazol-2-yl)-2-(dimethylphosphoryl)isonicotinamide.

10. The compound of claim 1 or a pharmaceutically acceptable salt thereof, wherein said compound is N-{7-chloro-1-[(3R)-1-[4-(pyrrolidin-1-yl)but-2-enoyl]azepan-3-yl]-1H-1,3-benzodiazol-2-yl}-2-methylpyridine-4-carboxamide;

(R,E)-N-(7-chloro-1-(1-(4-(dimethylamino)but-2-enoyl)azepan-3-yl)-1H-benzo[d]imidazol-2-yl)-2-methylisonicotinamide;

(R,E)-N-(7-chloro-1-(1-(4-(dimethylamino)but-2-enoyl)azepan-3-yl)-1H-benzo[d]imidazol-2-yl)-2,6-dimethylisonicotinamide;

N-{1-[(3R)-1-[(2E)-4-(dimethylamino)but-2-enoyl]azepan-3-yl]-7-methyl-H-1,3-benzodiazol-2-yl}-2-(trifluoromethyl)pyridine-4-carboxamide;

(R)—N-(1-(1-acryloylazepan-3-yl)-7-chloro-6-(2-(pyrrolidin-1-yl)ethoxy)-1H-benzo[d]imidazol-2-yl)-2,6-dimethylisonicotinamide; or (R,E)-N-(7-chloro-1-(1-(4-(methylamino)but-2-enoyl)azepan-3-yl)-1H-benzo[d]imidazol-2-yl)-2-methylisonicotinamide.

11. The compound of claim 1 or a pharmaceutically acceptable salt thereof, wherein said compound is (R,E)-N-(7-chloro-1-(1-(4-(dimethylamino)but-2-enoyl)azepan-3-yl)-1H-benzo[d]imidazol-2-yl)-2-methylisonicotinamide.

12. The compound of claim 11, wherein said compound is in the form of a salt selected from hydrochloric acid salt, mesylate, tosylate, bromide, maleate and nitrate.

13. A pharmaceutical composition comprising a compound of claim 1 or a pharmaceutically acceptable salt thereof, and a pharmaceutically acceptable carrier.

14. A pharmaceutical composition comprising a compound of claim 9 or a pharmaceutically acceptable salt thereof, and a pharmaceutically acceptable carrier.

15. A pharmaceutical composition comprising a compound of claim 10 or a pharmaceutically acceptable salt thereof, and a pharmaceutically acceptable carrier.

16. A pharmaceutical composition comprising a compound of claim 11 or a pharmaceutically acceptable salt thereof, and a pharmaceutically acceptable carrier.

17. A method for treating a condition mediated by epidermal growth factor receptor (EGFR), comprising administering to a subject in need of treatment an effective amount of a compound of claim 1 or a pharmaceutically acceptable salt thereof; wherein said condition mediated by EGFR is non-small cell lung cancer (NSCLC), head and neck cancer, colorectal cancer, breast cancer, pancreatic cancer, ovarian cancer, gastric cancer, glioma, prostate cancer or a solid tumor.

18. The method of claim 17, wherein said condition mediated by EGFR is non-small cell lung cancer (NSCLC).

19. The method of claim 17, wherein said condition mediated by EGFR is colorectal cancer.

20. The method of claim 17, wherein said EGFR is a mutant EGFR comprising G719S, G719C, G719A, L858R, L861Q, an exon 19 deletion mutation or an exon 20 insertion mutation.

21. The method of claim 20, wherein said EGFR is a mutant EGFR comprising an EGFR T790M, T854A or D761Y resistance mutation.

* * * * *